US008362044B2

(12) United States Patent
Hutchinson et al.

(10) Patent No.: US 8,362,044 B2
(45) Date of Patent: Jan. 29, 2013

(54) N,N-DISUBSTITUTED AMINOALKYLBIPHENYL ANTAGONISTS OF PROSTAGLANDIN D2 RECEPTORS

(75) Inventors: John Howard Hutchinson, San Diego, CA (US); Brian Andrew Stearns, Encinitas, CA (US); Jill Melissa Scott, San Diego, CA (US); Yen Pham Truong, San Diego, CA (US); Jeffrey Roger Roppe, Temecula, CA (US); Nicholas Simon Stock, San Diego, CA (US); Jeannie M. Arruda, San Diego, CA (US); Thomas Jon Seiders, San Diego, CA (US); Bowei Wang, Westfield, NJ (US); Deborah Volkots, La Jolla, CA (US)

(73) Assignee: Panmira Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 13/272,180

(22) Filed: Oct. 12, 2011

(65) Prior Publication Data

US 2012/0058123 A1    Mar. 8, 2012

Related U.S. Application Data

(63) Continuation of application No. 12/865,342, filed as application No. PCT/US2009/032499 on Jan. 29, 2009, now Pat. No. 8,067,445.

(60) Provisional application No. 61/025,597, filed on Feb. 1, 2008, provisional application No. 61/110,496, filed on Oct. 31, 2008.

(51) Int. Cl.
*A61K 31/4418* (2006.01)
*A61K 31/195* (2006.01)
(52) U.S. Cl. .......... 514/351; 514/563; 514/564
(58) Field of Classification Search .......... 514/351, 514/563, 564, 486, 565, 562, 488, 399, 269, 514/237.8, 25
See application file for complete search history.

(56) References Cited

U.S. PATENT DOCUMENTS

| 5,239,084 | A | 8/1993 | Guerry et al. |
| 5,334,598 | A | 8/1994 | Bagley et al. |
| 5,668,176 | A | 9/1997 | Bagley et al. |
| 5,827,868 | A | 10/1998 | Misra et al. |
| 6,617,351 | B1 | 9/2003 | Arnold et al. |
| 6,884,593 | B1 | 4/2005 | Hirai et al. |
| 7,005,440 | B1 | 2/2006 | Jayyosi et al. |
| 7,144,913 | B2 | 12/2006 | Wang et al. |
| 7,205,329 | B2 | 4/2007 | Chien et al. |
| 8,067,445 | B2 | 11/2011 | Hutchinson et al. |
| 8,168,678 | B2 | 5/2012 | Hutchinson et al. |
| 2001/0047027 | A1 | 11/2001 | Labelle et al. |
| 2002/0198251 | A1 | 12/2002 | Sundermann et al. |
| 2004/0214888 | A1 | 10/2004 | Matsura et al. |
| 2004/0220237 | A1 | 11/2004 | Fu et al. |
| 2005/0154044 | A1 | 7/2005 | Beaulieu et al. |
| 2005/0171143 | A1 | 8/2005 | Tanimoto et al. |
| 2005/0272756 | A1 | 12/2005 | Leblanc et al. |
| 2006/0040999 | A1 | 2/2006 | Ali et al. |
| 2006/0100425 | A1 | 5/2006 | Bennani et al. |
| 2006/0106081 | A1 | 5/2006 | Bennani et al. |
| 2007/0155726 | A1 | 7/2007 | Arzaiz et al. |
| 2008/0167378 | A1 | 7/2008 | Kohji et al. |
| 2008/0306109 | A1 | 12/2008 | Hynd et al. |
| 2009/0186293 | A1 | 7/2009 | Armer et al. |
| 2009/0186923 | A1 | 7/2009 | Armer et al. |
| 2009/0197959 | A1 | 8/2009 | Hutchinson et al. |
| 2010/0004331 | A1 | 1/2010 | Hutchinson et al. |
| 2010/0081673 | A1 | 4/2010 | Hutchinson et al. |
| 2010/0113503 | A1 | 5/2010 | Hutchinson et al. |
| 2010/0173313 | A1 | 7/2010 | Bain et al. |
| 2010/0280049 | A1 | 11/2010 | Stearns et al. |
| 2010/0298368 | A1 | 11/2010 | Stearns et al. |
| 2011/0021573 | A1 | 1/2011 | Hutchinson et al. |
| 2011/0034558 | A1 | 2/2011 | Brittain et al. |
| 2011/0039852 | A1 | 2/2011 | Hutchinson et al. |
| 2011/0098352 | A1 | 4/2011 | Hutchinson et al. |
| 2011/0245303 | A1 | 10/2011 | Hutchinson et al. |
| 2012/0059055 | A1 | 3/2012 | Hutchinson et al. |

FOREIGN PATENT DOCUMENTS

| EP | 1170594 A2 | 1/2002 |
| GB | 2460597 B | 4/2010 |
| GB | 2461629 B | 5/2010 |
| GB | 2463788 B | 12/2010 |
| JP | 2004-182657 A | 7/2004 |
| WO | WO-95-03044 | 2/1995 |
| WO | WO-99-11605 A1 | 3/1999 |
| WO | WO-03-006011 A1 | 1/2003 |
| WO | WO-2004-035543 A1 | 4/2004 |
| WO | WO-2004-058164 A2 | 7/2004 |
| WO | WO-2004-094372 | 11/2004 |
| WO | WO-2004-096777 A1 | 11/2004 |
| WO | WO-2005-040114 A1 | 5/2005 |
| WO | WO-2005-044260 A1 | 5/2005 |
| WO | WO-2005-051373 A1 | 6/2005 |
| WO | WO-2005-100298 A1 | 10/2005 |
| WO | WO-2005-105727 A1 | 10/2005 |
| WO | WO-2006-002099 | 1/2006 |
| WO | WO-2006-005909 A1 | 1/2006 |

(Continued)

OTHER PUBLICATIONS

Arima, M., and Fukuda, T., "Prostaglandin $D_2$ receptors DP and CRTH2 in the pathogenesis of asthma," *Curr. Mol. Med.* 8, 365-375 (2008).

(Continued)

*Primary Examiner* — Kristin Bianchi
(74) *Attorney, Agent, or Firm* — Wilson, Sonsini, Goodrich & Rosati

(57) ABSTRACT

Described herein are compounds that are antagonists of $PGD_2$ receptors. Also described are pharmaceutical compositions and medicaments that include the compounds described herein that are antagonists of $PGD_2$ receptors. Also described herein are methods of using such antagonists of $PGD_2$ receptors, alone and in combination with other compounds, for treating respiratory, cardiovascular, and other $PGD_2$-dependent or $PGD_2$-mediated conditions or diseases.

21 Claims, No Drawings

FOREIGN PATENT DOCUMENTS

| | | |
|---|---|---|
| WO | WO-2006-014357 A1 | 2/2006 |
| WO | WO-2006-018325 A1 | 2/2006 |
| WO | WO-2006-037982 A2 | 4/2006 |
| WO | WO-2006-052798 A2 | 5/2006 |
| WO | WO-2006-056854 A1 | 6/2006 |
| WO | WO-2006-070325 A2 | 7/2006 |
| WO | WO-2006-125596 AI | 11/2006 |
| WO | WO-2007-037187 A1 | 4/2007 |
| WO | WO-2007-039736 A1 | 4/2007 |
| WO | WO-2007-041494 | 4/2007 |
| WO | WO-2007-047378 | 4/2007 |
| WO | WO-2007-068894 A2 | 6/2007 |
| WO | WO-2007-088996 A1 | 8/2007 |
| WO | WO-2007-107772 A1 | 9/2007 |
| WO | WO-2007-144127 A1 | 12/2007 |
| WO | WO-2008-017989 A1 | 2/2008 |
| WO | WO-2008-024746 A1 | 2/2008 |
| WO | WO-2008-082567 A1 | 7/2008 |
| WO | WO-2008-137027 A2 | 11/2008 |
| WO | WO-2008-156780 A1 | 12/2008 |
| WO | WO-2009-004379 A1 | 1/2009 |
| WO | WO-2009-044147 A1 | 4/2009 |
| WO | WO-2009-063202 | 5/2009 |
| WO | WO-2009-063215 | 5/2009 |
| WO | WO-2009-089192 A1 | 7/2009 |
| WO | WO-2009-099901 A1 | 8/2009 |
| WO | WO-2009-099902 A1 | 8/2009 |
| WO | WO-2009-102893 A2 | 8/2009 |
| WO | WO-2009-108720 A2 | 9/2009 |
| WO | WO-2009-145989 A2 | 12/2009 |
| WO | WO-2010-003120 A2 | 1/2010 |
| WO | WO-2010-037054 A2 | 4/2010 |
| WO | WO-2010-037059 A2 | 4/2010 |
| WO | WO-2010-039977 A2 | 4/2010 |
| WO | WO-2010-042652 A2 | 4/2010 |
| WO | WO-2010-057118 A2 | 5/2010 |
| WO | WO-2011-014587 A2 | 2/2011 |
| WO | WO-2011-014588 A2 | 2/2011 |
| WO | WO-2011-017201 A2 | 2/2011 |

OTHER PUBLICATIONS

Brannan et al., "Inhibition of Mast Cell PGD2 Release Protects Against Mannitol-Induced Airway Narrowing," Eur Respir J, 2006, vol. 27, No. 5, pp. 944-950, ERS Journals Ltd.
Cossette et al., "Agonist and Antagonist Effects of 15R-Prostaglandin (PG) $D_2$ and 11-Methylene-$PGD_2$ on Human Eosinophils and Basophils," Journal of Pharmacology and Experimental Therapeutics, 2007, pp. 173-179, vol. 320, No. 1, American Society for Pharmacology and Experimental Therapeutics, USA.
Crosignani et al., "Discovery of a new class of potent, selective, and orally bioavailable CRTH2(DP2) receptor antagonists for the treatment of allergic inflammatory diseases" J Med Chem 51:2227-2243 (2008).
EP09709954.3 Search Report mailed Feb. 21, 2011.
Evans et al., "Seeing the future of bioactive lipid drug targets," Nature Chem Biol 6:476-479 (2010).
Golub et al., "Molecular Classification of Cancer: Class Discovery and Class Prediction by Gene Expression Monitoring," Science (1999), vol. 286, 531-537.
Hata, A.N. and Breyer, R.M., "Pharmacology and signaling of prostaglandin receptors: multiple roles in inflammation and immune modulation," Pharmacol Ther. Aug.;103(2):147-66 (2004).
Jatakanon et al., "Neutrophilic Inflammation in Severe Persistent Asthma," Am J Respir Crit Care Med 1999, pp. 1532-1539, vol. 160, National Heart and Lung Institute, London, UK.
Johnston et al., "Prostaglandin $D_2$-Induced Bronchoconstriction Is Mediated Only in Part by the Thromboxane Prostanoid Receptor," Eur Respir J, 1995, 8, pp. 411-415, ERS Journals Ltd, UK.
Kim et al., "Regulation of Immune Cells by Eicosanoid Receptors," TheScientificWorld Journal 7:1307-1328 (2007).
Kostenis, E. and Ulven, T., "Emerging roles of DP and CRTH2 in allergic inflammation," Trends Mol Med. Apr.;12(4):148-58 (2008).
Lala et al., "Role of Nitric Oxide in Tumor Progression: Lessons from Experimental Tumors," Cancer and Metastasis Reviews (1998), 17, 91-106.
Ly and Bacon, "Small-molecule CRTH2 antagonists for the treatment of allergic inflammation: an overview," Exp Opin Invest Drugs 14:769 (2005).
Medina, J. C. and Liu, J., "PGD2 Antagonists" Annual Reports in Medicinal Chemistry, vol. 41, 2006, pp. 221-235.
PCT/US09/32495 IPRP dated Aug. 3, 2010.
PCT/US09/32495 Written Opinion and Search Report dated Jun. 29, 2009.
PCT/US09/32499 IPRP dated Aug. 3, 2010.
PCT/US09/32499 Written Opinion and Search Report dated Jun. 29, 2009.
PCT/US09/33961 IPER and Written Opinion mailed Aug. 26, 2010.
PCT/US09/33961 Search Report mailed Aug. 11, 2009.
PCT/US09/35174 IPER and Written Opinion mailed Sep. 10, 2010.
PCT/US09/38291 Search Report and Written Opinion mailed Nov. 27, 2009.
PCT/US09/49621 Search Report and Written Opinion mailed Mar. 15, 2010.
PCT/US09/49631 Search Report and Written Opinion mailed Feb. 24, 2010.
PCT/US09/58655 Search Report and Written Opinion mailed May 10, 2010.
PCT/US09/58663 Search Report and Written Opinion mailed May 14, 2010.
PCT/US09/59256 Search Report and Written Opinion mailed Jun. 21, 2010.
PCT/US09/59891 Search Report and Written Opinion mailed May 24, 2010.
PCT/US09/64630 Search Report and Written Opinion mailed Jul. 19, 2010.
PCT/US10/43598 Search Report and Written Opinion mailed Apr. 22, 2011.
PCT/US10/43599 Search Report and Written Opinion mailed Apr. 28, 2011.
PCT/US10/43783 Search Report and Written Opinion mailed Apr. 22, 2011.
Pettipher et al., "Antagonists of the prostaglandin D2 receptor CRTH2," Drug News Perspect 21:317-322 (2008).
Pettipher et al., "The roles of the prostaglandin D(2) receptors DP(1) and CRTH2 in promoting allergic responses," Br J Pharmacol 153:S191 (2008).
Pettipher, R. et al., "Antagonism of the prostaglandin D2 receptors DP1 and CRTH2 as an approach to treat allergic diseases," Nature Drug Discovery 6:313-325 (2007).
Prieto et al., "Racemization in Suzuki couplings: a quantitative study using 4-hydroxyphenylglycine and tyrosine derivatives as probe molecules," J Org Chem 72(3):1047-1049 (2007).
Sagel et al., "Sputum Biomarkers of Inflammation in Cystic Fibrosis Lung Disease," Proc Am Thorac Soc, 2007, vol. 4, pp. 406-417, www.atsjournals.org.
Sandham et al., "7-Azaindole-3-acetic acid derivatives: potent and selective CRTH2 receptor antagonists," Bioorg Med Chem Lett 19:4794-4798 (2009).
Sandig et al., "Contrary prostaglandins: the opposing roles of PGD2 and its metabolites in leukocyte function," J Leukocyte Biology 81:372-382 (2007).
Science IP Structure Search dated Nov. 6, 2007 (2 parts).
Scott et al., "Discovery and optimization of a biphenylacetic acid series of prostaglandin D2 receptor DP2 antagonists with efficacy in a murine model of allergic rhinitis," Bioorg Med Chem Ltrs (2011), doi: 10.1016fj.bmc1.2011.01.024.
Shrader et al., "Factor VIIa inhibitors: Gaining selectivity within the trypsin family," Bioorg Med Chem Ltrs 16(6):1596-1600 (2006).
Srinivas et al., "Biaryl amino acid templates in place of D-Pro-L-Pro in cyclic beta-hairpin cationic antimicrobial peptidomimetics," Organic & Biomolecular Chemistry 5(19):3100-3105 (2007).
Stearns et al., "Novel tricyclic antagonists of the prostaglandin D2 receptor DP2 with efficacy in a murine model of allergic rhinitis," Bioorg Med Chem Ltrs 19:4647-4651 (2009).
Stebbins et al., "DP2 Receptor Antagonists: Novel Therapeutic Target for Copd," Mol Cell Pharmacol 2(3):89-96 (2010).

Stebbins et al., "Pharmacological Blockade of the DP2 Receptor Inhibits Cigarette Smoke-Induced Inflammation, Mucus Cell Metaplasia, and Epithelial Hyperplasia in the Mouse Lung," J Pharmacol Exp Ther 332(3):764-775 (2010).

Stebbins et al., "Therapeutic efficacy of AM156, a novel prostanoid DP2 receptor antagonist, in murine models of allergic rhinitis and house dust mite-induced pulmonary inflammation," Eur J Pharmacol 638:142-149 (2010).

Stock et al., "Sodium [2'-[(cyclopropanecarbonyl-ethyl-amino)-methyl]-4'-(6-ethoxy-pyridin-3-yl)-6-methoxy-biphenyl-3-yl]acetate (AM432): A potent, selective prostaglandin D2 receptor antagonist," Bioorg Med Chem Ltrs 21:1036-1040 (2011).

Sugimoto et al., "An Orally Bioavailable Small Molecule Antagonist of CRTH2, Ramatroban (Bay u3405), Inhibits Prostaglandin $D_2$-Induced Eosinophil Migration in Vitro," Journal of Pharmacology and Experimental Therapeutics, 2003, pp. 347-352, vol. 305, No. 1, American Society for Pharmacology and Experimental Therapeutics, USA.

Takeshita et al., "CRTH2 is a prominent effector in contact hypersensitivity-induced neutrophil inflammation," Intl Immunol 16(7):947-959 (2004).

Tirouvanziam, R., et al., "Profound functional and signaling changes in viable inflammatory neutrophils homing to cystic fibrosis airways," Proc. Nat. Acad. Sci. USA 105:4335-4339 (2008).

Ulven et al., "Minor Structural Modifications Cover the Dual TP/CRTH2," J Med Chem 48(4):897-900 (2005).

Ulven T et al,. "Targeting the prostaglandin D2 receptors DP and CRTH2 for treatment of inflammation", Curr. Top. Med. Chem. 2006;6(13):1427-44.

Wardlaw et al., "New Insights into the Relationship Between Airway Inflammation and Asthma," Clinical Science, 2002, pp. 201-211, vol. 103, The Biochemical Society and the Medical Research Society, GB.

Torisu et al. "Discovery of new chemical leads for prostaglandin $D_2$ receptor antagonists." *Bioorganic & Medicinal Chemistry Letters*, 2004, 14:4557-4562.

N,N-DISUBSTITUTED AMINOALKYLBIPHENYL ANTAGONISTS OF PROSTAGLANDIN D2 RECEPTORS

RELATED APPLICATIONS

This application is a continuation application of co-pending U.S. application Ser. No. 12/865,342 entitled "N,N-Disubstituted Aminoalkylbiphenyl Antagonists of Prostaglandin $D_2$ Receptors" filed on Jul. 29, 2010, which is a United States National Phase Application of International Application No. PCT/US2009/032499, entitled "N,N-Disubstituted Aminoalkylbiphenyl Antagonists of Prostaglandin $D_2$ Receptors" filed Jan. 29, 2009, which claims the benefit of U.S. provisional patent application No. 61/025,597 entitled "N,N-disubstituted aminoalkylbiphenyl antagonists of prostaglandin D2 receptors" filed on Feb. 1, 2008 and U.S. provisional patent application No. 61/110,496 entitled "N,N-disubstituted aminoalkylbiphenyl antagonists of prostaglandin D2 receptors" filed on Oct. 31, 2008, all of which are incorporated by reference in their entirety.

FIELD OF THE INVENTION

Described herein are compounds, methods of making such compounds, pharmaceutical compositions and medicaments comprising such compounds, and methods of using such compounds to treat, prevent or diagnose diseases, disorders or conditions associated with prostaglandin $D_2$.

BACKGROUND OF THE INVENTION

Prostaglandins are acidic lipids derived from the metabolism of arachidonic acid by the action of cyclooxygenase enzymes and downstream synthases. Prostaglandins have a diverse range of activities and have a well recognized role in pain and inflammation. Prostaglandin $D_2$ ($PGD_2$) is an acidic lipid mediator derived from the metabolism of arachidonic acid by cyclooxygenases and $PGD_2$ synthases. $PGD_2$ is produced by mast cells, macrophages and $T_H2$ lymphocytes in response to local tissue damage as well as allergic inflammation in diseases such as asthma, rhinitis, and atopic dermatitis. Exogenous $PGD_2$ applied to bronchial airways elucidates many characteristics of an asthmatic response suggesting that $PGD_2$ plays an important pro-inflammatory role in allergic diseases.

$PGD_2$ binds to a number of receptors, which include the thromboxane-type prostanoid (TP) receptor, $PGD_2$ receptor (DP, also known as $DP_1$) and chemoattractant receptor-homologous molecule expressed on Th2 cells (CRTH2; also known as $DP_2$). $DP_2$ is associated with promoting chemotaxis and activation of $T_H2$ lymphocytes, eosinophils and basophils. In particular, $PGD_2$ binds to $DP_2$, and mediates its effects through a $G_i$-dependant elevation in calcium levels and reduction of intracellular cyclic AMP. In $T_H2$ lymphocytes, IL4, IL5 and IL13 cytokine production is stimulated. These cytokines have been implicated in numerous biological actions including, by way of example only, immunoglobulin E production, airway response, mucous secretion, and eosinophil recruitment.

SUMMARY OF THE INVENTION

Presented herein are compounds, pharmaceutical compositions and medicaments, methods, for (a) diagnosing, preventing, or treating allergic and non-allergic inflammation, (b) mitigating adverse signs and symptoms that are associated with inflammation, and/or (c) controlling immunological, proliferative disorders. These disorders may arise from one or more of a genetic, iatrogenic, immunological, infectious, ontological, toxic, surgical, and/or traumatic etiology. In one aspect, the methods, compounds, pharmaceutical compositions, and medicaments described herein comprise antagonists of $PGD_2$ receptors. In one aspect, the methods, compounds, pharmaceutical compositions, and medicaments described herein comprise antagonists of $DP_2$.

In one aspect provided herein are compounds of Formula (I), Formula (II), Formula (III), Formula (IV), Formula (V), Formula (VI), Formula (VII), and Formula (VIII), pharmaceutically acceptable salts, pharmaceutically acceptable prodrugs, and pharmaceutically acceptable solvates thereof, which are antagonists of $DP_2$, and are used to treat mammals suffering from one or more $PGD_2$-dependent conditions or diseases, including, but not limited to, asthma, rhinitis, chronic obstructive pulmonary disease, pulmonary hypertension, interstitial lung fibrosis, arthritis, allergy, psoriasis, inflammatory bowel disease, adult respiratory distress syndrome, myocardial infarction, aneurysm, stroke, cancer, endotoxic shock, proliferative disorders and inflammatory conditions. In some embodiments, $PGD_2$-dependent conditions or diseases include those wherein an absolute or relative excess of $PGD_2$ is present and/or observed. In one aspect, the mammal is a human.

In one aspect is a compound having the structure of Formula (I), pharmaceutically acceptable salts, pharmaceutically acceptable solvates, or pharmaceutically acceptable prodrugs thereof:

Formula (I)

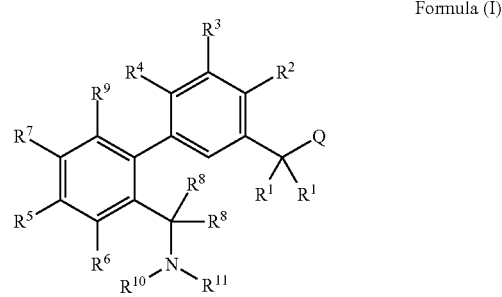

wherein,
Q is tetrazolyl or —C(=O)-$Q^1$;
$Q^1$ is —OH, —O($C_1$-$C_4$alkyl), —$NHSO_2R^{12}$, —N($R^{13}$)$_2$, —NH—OH, or —NH—CN;
each $R^1$ is independently selected from H, F, and —$CH_3$;
each of $R^2$, $R^3$, $R^4$, $R^5$, $R^6$, $R^7$ and $R^9$ is independently H, halogen, —CN, —$NO_2$, —OH, —$OR^{13}$, —$SR^{12}$, —S(=O)$R^{12}$, —S(=O)$_2R^{12}$, —NHS(=O)$_2R^{12}$, —C(=O)$R^{12}$, —OC(=O)$R^{12}$, —$CO_2R^{13}$, —$OCO_2R^{13}$, —CH($R^{13}$)$_2$, —N($R^{13}$)$_2$, —$NHCH_2CO_2R^{13}$, —$OCH_2CO_2R^{13}$, —$SCH_2CO_2R^{13}$, —C(=O)N($R^{13}$)$_2$, —OC(=O)N($R^{13}$)$_2$, —NHC(=O)NH($R^{13}$), —NHC(=O)$R^{12}$, —NHC(=O)$OR^{12}$, —C(OH)($R^{11}$)$_2$, $C_1$-$C_6$alkyl, $C_1$-$C_6$fluoroalkyl, $C_1$-$C_6$fluoroalkoxy, $C_1$-$C_6$alkoxy, $C_1$-$C_6$heteroalkyl, $C_3$-$C_{10}$cycloalkyl, a substituted or unsubstituted $C_2$-$C_{10}$heterocycloalkyl, a substituted or unsubstituted phenyl, a substituted or unsubstituted naphthyl, a substituted or unsubstituted monocyclic heteroaryl, or a substituted or unsubstituted bicyclic heteroaryl, —$OCH_2$—($C_3$-$C_6$cycloalkyl), —$OCH_2$-(substituted or unsubstituted phenyl), or —OCH$_2$-(substituted or unsubstituted monocyclic heteroaryl);

each R$^8$ is H;

R$^{10}$ is —C(=O)R$^{14}$, —C(=O)OR$^{15}$, —C(=O)N(R$^{16}$)$_2$, —C(=NR$^{19}$)N(R$^{16}$)$_2$, —S(=O)$_2$N(R$^{16}$)$_2$ or —S(=O)$_2$R$^{15}$;

R$^{14}$ is C$_1$-C$_6$alkyl, C$_1$-C$_6$fluoroalkyl, C$_1$-C$_6$heteroalkyl, C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_4$alkyl-(C$_3$-C$_{10}$cycloalkyl), —C$_1$-C$_4$alkyl-(a substituted or unsubstituted C$_2$-C$_{10}$heterocycloalkyl), —C$_1$-C$_4$alkyl-(a substituted or unsubstituted aryl), or —C$_1$-C$_4$alkyl-(a substituted or unsubstituted heteroaryl); or R$^{14}$ is L$^3$-X$^3$-Q$^3$;

L$^3$ is a C$_1$-C$_4$alkylene;

X$^3$ is a bond, —O—, —S—, —S(=O)—, —S(=O)$_2$—, or —NR$^{13}$—;

Q$^3$ is C$_1$-C$_6$alkyl, C$_1$-C$_6$fluoroalkyl, C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_4$alkyl-C$_3$-C$_{10}$cycloalkyl, —C$_1$-C$_4$alkyl-(a substituted or unsubstituted C$_2$-C$_{10}$heterocycloalkyl), —C$_1$-C$_4$alkyl-(a substituted or unsubstituted aryl), or —C$_1$-C$_4$alkyl-(a substituted or unsubstituted heteroaryl);

R$^{15}$ is C$_1$-C$_6$alkyl, C$_1$-C$_6$fluoroalkyl, C$_1$-C$_6$heteroalkyl, C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_4$alkyl-C$_3$-C$_{10}$cycloalkyl, —C$_1$-C$_4$alkyl-(substituted or unsubstituted C$_2$-C$_{10}$heterocycloalkyl), —C$_1$-C$_4$alkyl-(substituted or unsubstituted aryl), or —C$_1$-C$_4$alkyl-(substituted or unsubstituted heteroaryl);

each R$^{16}$ is independently H, —CN, C$_1$-C$_6$alkyl, C$_1$-C$_6$fluoroalkyl, C$_1$-C$_6$heteroalkyl, C$_3$-C$_{10}$cycloalkyl, substituted or unsubstituted C$_2$-C$_{10}$heterocycloalkyl, substituted or unsubstituted aryl, substituted or unsubstituted heteroaryl, —C$_1$-C$_4$alkyl-C$_3$-C$_{10}$cycloalkyl, —C$_1$-C$_4$alkyl-(substituted or unsubstituted C$_2$-C$_{10}$heterocycloalkyl), —C$_1$-C$_4$alkyl-(substituted or unsubstituted aryl), or —C$_1$-C$_4$alkyl-(substituted or unsubstituted heteroaryl); or two R$^{16}$ groups attached to the same N atom are taken together with the N atom to which they are attached to form a substituted or unsubstituted heterocycloalkyl;

R$^{19}$ is selected from among H, —S(=O)$_2$R$^{12}$, —S(=O)$_2$NH$_2$, —C(=O)R$^{12}$, —CN, and —NO$_2$;

R$^{11}$ is C$_1$-C$_6$alkyl, C$_1$-C$_6$heteroalkyl, C$_1$-C$_6$haloalkyl, C$_3$-C$_6$cycloalkyl, —C$_1$-C$_6$alkylene-OH, —C$_1$-C$_6$alkylene-O—(C$_1$-C$_4$alkyl), —C$_1$-C$_6$alkylene-S—(C$_1$-C$_4$alkyl), —C$_1$-C$_4$alkylene-S(=O)—(C$_1$-C$_4$alkyl), —C$_1$-C$_6$alkylene-S(=O)$_2$—(C$_1$-C$_4$alkyl), —C$_1$-C$_6$alkylene-NH$_2$, —C$_1$-C$_6$alkylene-N(CH$_3$)$_2$, —C$_1$-C$_6$alkylene-C(=O)—(C$_1$-C$_4$alkyl), —C$_1$-C$_6$alkylene-C(=O)OH, —C$_1$-C$_6$alkylene-C(=O)O(C$_1$-C$_4$alkyl), or —C$_1$-C$_6$alkylene-C(=O)NH$_2$.

R$^{12}$ is C$_1$-C$_6$alkyl, C$_1$-C$_6$heteroalkyl, C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted benzyl, a substituted or unsubstituted heteroaryl, —C$_1$-C$_4$alkyl-(substituted or unsubstituted C$_3$-C$_{10}$cycloalkyl), —C$_1$-C$_4$alkyl-(substituted or unsubstituted C$_2$-C$_{10}$heterocycloalkyl), —C$_1$-C$_4$alkyl-(substituted or unsubstituted aryl), or —C$_1$-C$_4$alkyl-(substituted or unsubstituted heteroaryl);

each R$^{13}$ is independently selected from H, C$_1$-C$_6$alkyl, C$_1$-C$_6$heteroalkyl, C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted benzyl, a substituted or unsubstituted heteroaryl, —C$_1$-C$_4$alkyl-(substituted or unsubstituted C$_3$-C$_{10}$cycloalkyl), —C$_1$-C$_4$alkyl-(substituted or unsubstituted C$_2$-C$_{10}$heterocycloalkyl), —C$_1$-C$_4$alkyl-(substituted or unsubstituted aryl), and —C$_1$-C$_4$alkyl-(substituted or unsubstituted heteroaryl); or two R$^{13}$ groups attached to the same N atom are taken together with the N atom to which they are attached to form an optionally substituted C$_2$-C$_{10}$heterocycloalkyl.

For any and all of the embodiments, substituents are selected from among from a subset of the listed alternatives. For example, in some embodiments, Q is —C(=O)-Q$^1$. In other embodiments, Q is tetrazolyl. In some embodiments, Q$^1$ is —OH, or —O(C$_1$-C$_4$alkyl). In other embodiments, Q$^1$ is —OH, —OCH$_3$, or —OCH$_2$CH$_3$. In yet other embodiments, Q$^1$ is —OH.

In some cases, R$^{11}$ is C$_1$-C$_6$alkyl, C$_1$-C$_6$heteroalkyl, C$_1$-C$_6$haloalkyl, C$_3$-C$_6$cycloalkyl, —C$_1$-C$_6$alkylene-C(=O)OH, —C$_1$-C$_6$alkylene-C(=O)O—C$_1$-C$_6$alkyl, or —C$_1$-C$_6$alkylene-C(=O)NH$_2$.

In one aspect, at least one of R$^2$ and R$^3$ is H. In one aspect, R$^2$ and R$^3$ are H. In another aspect, at least one of R$^2$, R$^3$ and R$^4$ is H. In another aspect, at least two of R$^2$, R$^3$ and R$^4$ is H.

In one aspect, at least two of R$^6$, R$^7$ and R$^9$ is H. In another aspect, R$^6$, R$^7$ and R$^9$ are H. In another aspect, at least two of R$^5$, R$^6$, R$^7$ and R$^9$ is H. In another aspect, at least three of R$^5$, R$^6$, R$^7$ and R$^9$ is H.

In one aspect, the compound of Formula (I) has the structure of Formula (II):

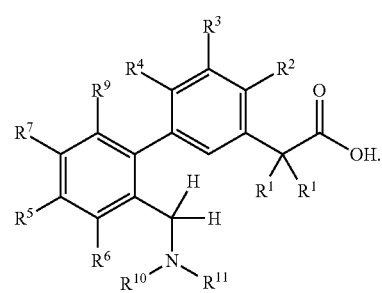

Formula (II)

In certain embodiments, each R$^1$ is H.

In some embodiments, each of R$^2$, R$^3$, R$^6$, R$^7$ and R$^9$ is independently selected from H, halogen, —CN, —OH, —OR$^{13}$, —SR$^{12}$, —S(=O)R$^{12}$, —S(=O)$_2$R$^{12}$, —C(=O)$_2$R$^{12}$, —C$_1$-C$_4$alkyl, C$_1$-C$_4$fluoroalkyl, C$_3$-C$_6$cycloalkyl, C$_1$-C$_4$fluoroalkoxy, C$_1$-C$_4$alkoxy, and C$_1$-C$_4$heteroalkyl. In some other embodiments, each of R$^2$, R$^3$, R$^6$, R$^7$ and R$^9$ is independently selected from H, halogen, —OH, C$_1$-C$_4$alkyl, C$_1$-C$_4$alkoxy, and C$_1$-C$_4$fluoroalkyl. In yet other embodiments, each of R$^2$, R$^3$, R$^6$, R$^7$ and R$^9$ is independently selected from H, halogen, —OH, —CH$_3$, —OCH$_3$, and —CF$_3$.

In some embodiments, R$^4$ is H, halogen, —CN, —NO$_2$, —OH, —OR$^{13}$, —SR$^{12}$, —S(=O)R$^{12}$, —S(=O)$_2$R$^{12}$, —C(=O)R$^{12}$, —OC(=O)R$^{12}$, —CO$_2$R$^{13}$, —OCO$_2$R$^{13}$, —CH(R$^{13}$)$_2$, —N(R$^{13}$)$_2$, —NHCH$_2$CO$_2$R$^{13}$, —OCH$_2$CO$_2$R$^{13}$, —SCH$_2$CO$_2$R$^{13}$, —C(=O)N(R$^{13}$)$_2$, C$_1$-C$_6$alkyl, C$_1$-C$_6$fluoroalkyl, C$_3$-C$_6$cycloalkyl, substituted or unsubstituted C$_2$-C$_5$heterocycloalkyl, C$_1$-C$_6$fluoroalkoxy, $C_1$-$C_6$alkoxy, $C_1$-$C_6$heteroalkyl, substituted or unsubstituted phenyl, substituted or unsubstituted monocyclic heteroaryl, —OCH$_2$—($C_3$-$C_6$cycloalkyl), —OCH$_2$-(substituted or unsubstituted phenyl), or —OCH$_2$-(substituted or unsubstituted monocyclic heteroaryl).

In some other embodiments, $R^4$ is H, F, Cl, Br, I, —CN, —OH, —$C_1$-$C_6$alkyl, $C_1$-$C_6$fluoroalkyl, $C_1$-$C_6$fluoroalkoxy, $C_1$-$C_6$alkoxy, $C_1$-$C_6$heteroalkyl, —OCH$_2$—CO$_2$R$^{13}$, —OCH$_2$—C(=O)R$^{12}$, —OCH$_2$—C(=O)N(R$^{13}$)$_2$, —OCH$_2$—$C_3$-$C_6$cycloalkyl, or —OCH$_2$-(substituted or unsubstituted phenyl).

In some embodiments, $R^5$ is H, halogen, —CN, —NO$_2$, —OH, —OR$^{13}$, —SR$^{12}$, —S(=O)R$^{12}$, —S(=O)$_2$R$^{12}$, —NHS(=O)$_2$R$^{12}$, —C(=O)R$^{12}$, —OC(=O)R$^{12}$, —CO$_2$R$^{13}$, —OCO$_2$R$^{13}$, —CH(R$^{13}$)$_2$, —N(R$^{13}$)$_2$, —NHCH$_2$CO$_2$R$^{13}$, —OCH$_2$CO$_2$R$^{13}$, —SCH$_2$CO$_2$R$^{13}$, —C(=O)N(R$^{13}$)$_2$, —OC(=O)N(R$^{13}$)$_2$, —NHC(=O)NH(R$^{13}$), —NHC(=O)R$^{12}$, —NHC(=O)OR$^{12}$, —C(OH)(R$^{13}$)$_2$, —$C_1$-$C_6$alkyl, $C_1$-$C_6$fluoroalkyl, $C_3$-$C_{10}$cycloalkyl, substituted or unsubstituted $C_2$-$C_{10}$heterocycloalkyl, $C_1$-$C_6$fluoroalkoxy, $C_1$-$C_6$alkoxy, $C_1$-$C_6$heteroalkyl, substituted or unsubstituted phenyl, substituted or unsubstituted naphthyl, substituted or unsubstituted monocyclic heteroaryl, substituted or unsubstituted bicyclic heteroaryl.

In some embodiments, $R^{10}$ is —C(=O)R$^{14}$, —C(=O)OR$^{15}$, or —C(=O)N(R$^{16}$)$_2$.

In some embodiments, $R^{14}$ is $C_1$-$C_6$alkyl, $C_1$-$C_6$fluoroalkyl, $C_1$-$C_6$heteroalkyl, or $C_3$-$C_6$cycloalkyl; or $R^{14}$ is $L^3$-$X^3$-$Q^3$; $L^3$ is a $C_1$-$C_4$alkylene; $X^3$ is a bond, —O—, —S—, —S(=O)—, —S(=O)$_2$—, or —NR$^{13}$—; $Q^3$ is $C_1$-$C_6$alkyl, $C_1$-$C_6$fluoroalkyl, $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_4$alkyl-$C_3$-$C_{10}$cycloalkyl, —$C_1$-$C_4$alkyl-(a substituted or unsubstituted $C_2$-$C_{10}$heterocycloalkyl), —$C_1$-$C_4$alkyl-(a substituted or unsubstituted aryl), or —$C_1$-$C_4$alkyl-(a substituted or unsubstituted heteroaryl).

In some embodiments, $R^{15}$ is $C_1$-$C_6$alkyl, $C_1$-$C_6$fluoroalkyl, $C_1$-$C_6$heteroalkyl, $C_3$-$C_{10}$cycloalkyl, a substituted or unsubstituted aryl, a substituted or unsubstituted heteroaryl, —$C_1$-$C_4$alkyl-$C_3$-$C_{10}$cycloalkyl, —$C_1$-$C_4$alkyl-(substituted or unsubstituted aryl), or —$C_1$-$C_4$alkyl-(substituted or unsubstituted heteroaryl);

In some embodiments, each $R^{16}$ is independently H, $C_1$-$C_6$alkyl, $C_1$-$C_6$fluoroalkyl, $C_1$-$C_6$heteroalkyl, $C_3$-$C_{10}$cycloalkyl, a substituted or unsubstituted aryl, a substituted or unsubstituted heteroaryl, —$C_1$-$C_4$alkyl-($C_3$-$C_{10}$cycloalkyl), —$C_1$-$C_4$alkyl-(substituted or unsubstituted aryl), or —$C_1$-$C_4$alkyl-(substituted or unsubstituted heteroaryl).

In some embodiments, $R^{14}$ is $C_1$-$C_6$alkyl, $C_1$-$C_6$fluoroalkyl, $C_1$-$C_6$heteroalkyl, or $C_3$-$C_6$cycloalkyl; or $R^{14}$ is $L^3$-$X^3$-$Q^3$; $L^3$ is —CH$_2$—, CH(CH$_3$)—, or —C(CH$_3$)$_2$—; $X^3$ is a —O—, —S—, —S(=O)—, —S(=O)$_2$—, or —NR$^{13}$—; $Q^3$ is $C_1$-$C_6$alkyl, $C_1$-$C_6$fluoroalkyl, $C_3$-$C_6$cycloalkyl, a substituted or unsubstituted phenyl, a substituted or unsubstituted monocyclic heteroaryl, —CH$_2$-(a substituted or unsubstituted phenyl), or —CH$_2$-(a substituted or unsubstituted monocyclic heteroaryl).

In some embodiments, $R^{15}$ is $C_1$-$C_6$alkyl, $C_1$-$C_6$fluoroalkyl, $C_1$-$C_6$heteroalkyl, $C_3$-$C_6$cycloalkyl, a substituted or unsubstituted phenyl, a substituted or unsubstituted monocyclic heteroaryl, —CH$_2$—$C_3$-$C_6$cycloalkyl, —CH$_2$-(substituted or unsubstituted phenyl), —CH(CH$_3$)-(substituted or unsubstituted phenyl), —CH$_2$-(substituted or unsubstituted monocyclic heteroaryl) or —CH(CH$_3$)-(substituted or unsubstituted monocyclic heteroaryl).

In some embodiments, each $R^{16}$ is independently H, $C_1$-$C_6$alkyl, $C_1$-$C_6$fluoroalkyl, $C_1$-$C_6$heteroalkyl, $C_3$-$C_6$cycloalkyl, a substituted or unsubstituted phenyl, a substituted or unsubstituted monocyclic heteroaryl, —CH$_2$—($C_3$-$C_6$cycloalkyl), —CH$_2$-(a substituted or unsubstituted phenyl), —CH(CH$_3$)-(a substituted or unsubstituted phenyl), —CH$_2$-(a substituted or unsubstituted monocyclic heteroaryl), or —CH(CH$_3$)-(a substituted or unsubstituted monocyclic heteroaryl).

In one aspect, $R^{10}$ is —C(=O)R$^{14}$.

In one aspect, the compound of Formula (I) has the structure of Formula (III):

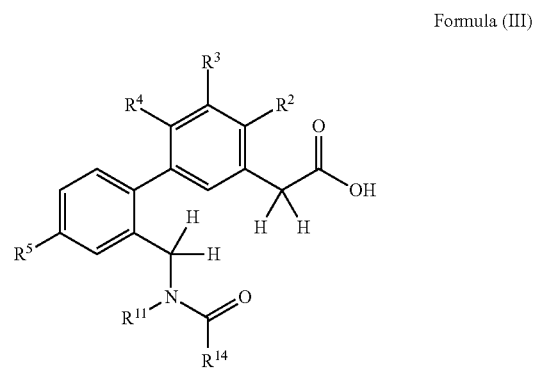

Formula (III)

In some embodiments, $R^{14}$ is $C_1$-$C_6$alkyl, $C_1$-$C_6$fluoroalkyl, or $C_3$-$C_6$cycloalkyl; or $R^{14}$ is $L^3$-$X^3$-$Q^3$; $L^3$ is —CH$_2$—, —CH(CH$_3$)—, or —C(CH$_3$)$_2$—; $X^3$ is —O—, —S—, —S(=O)—, or —S(=O)$_2$—; $Q^3$ is $C_1$-$C_6$alkyl, $C_1$-$C_6$fluoroalkyl, $C_3$-$C_6$cycloalkyl, a substituted or unsubstituted phenyl, or —CH$_2$-(a substituted or unsubstituted phenyl).

In other embodiments, $R^{14}$ is $C_1$-$C_6$alkyl, $C_1$-$C_6$fluoroalkyl, or $C_3$-$C_6$cycloalkyl. In other embodiments, $R^{14}$ is $L^3$-$X^3$-$Q^3$; $L^3$ is —CH$_2$—, —CH(CH$_3$)—, or —C(CH$_3$)$_2$—; $X^3$ is —O—, —S—, —S(=O)—, or —S(=O)$_2$—; $Q^3$ is a substituted or unsubstituted phenyl, or —CH$_2$-(a substituted or unsubstituted phenyl).

In one aspect, $R^{10}$ is —C(=O)OR$^{15}$.

In one aspect, the compound of Formula (I) has the structure of Formula (IV):

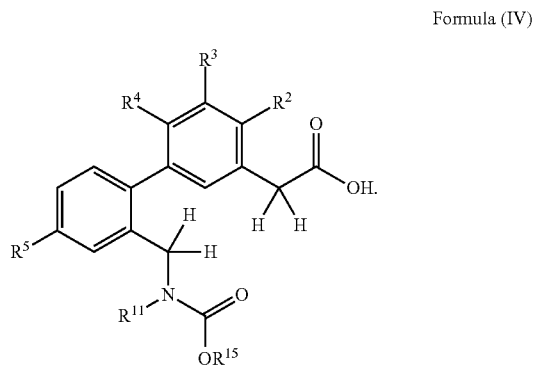

Formula (IV)

In one aspect, $R^{15}$ is $C_1$-$C_6$alkyl, —CH$_2$-(substituted or unsubstituted phenyl), —CH(CH$_3$)-(substituted or unsubstituted phenyl), —CH$_2$-(substituted or unsubstituted monocyclic heteroaryl) or —CH(CH$_3$)-(substituted or unsubstituted monocyclic heteroaryl).

In another aspect, $R^{15}$ is —$CH_2$-(substituted or unsubstituted phenyl), or —$CH(CH_3)$-(substituted or unsubstituted phenyl). In another aspect, $R^{15}$ is —$CH_2$-(substituted or unsubstituted phenyl).

In one aspect, $R^{10}$ is —$C(=O)N(R^{16})_2$.

In one aspect, the compound of Formula (I) has the structure of Formula (V):

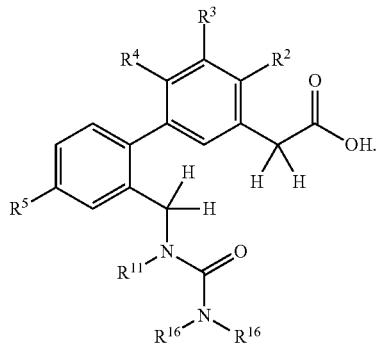

Formula (V)

In some embodiments, each $R^{16}$ is independently H, $C_1$-$C_6$alkyl, $C_3$-$C_6$cycloalkyl, a substituted or unsubstituted phenyl, a substituted or unsubstituted monocyclic heteroaryl, —$CH_2$-(a substituted or unsubstituted phenyl), —$CH(CH_3)$-(a substituted or unsubstituted phenyl), —$CH_2$-(a substituted or unsubstituted monocyclic heteroaryl), or —$CH(CH_3)$-(a substituted or unsubstituted monocyclic heteroaryl). In other embodiments, one $R^{16}$ is H and the other $R^{16}$ is —$CH_2$-(a substituted or unsubstituted phenyl), —$CH(CH_3)$-(a substituted or unsubstituted phenyl), —$CH_2$-(a substituted or unsubstituted monocyclic heteroaryl), or —$CH(CH_3)$-(a substituted or unsubstituted monocyclic heteroaryl). In yet other embodiments, one $R^{16}$ is H and the other $R^{16}$ is —$CH_2$-(a substituted or unsubstituted phenyl), or —$CH(CH_3)$-(a substituted or unsubstituted phenyl). In one aspect, one $R^{16}$ is H and the other $R^{16}$ is —$CH_2$-(a substituted or unsubstituted phenyl).

In one aspect, $R^{10}$ is —$S(=O)_2R^{15}$. In some embodiments, $R^{15}$ is $C_1$-$C_6$alkyl, $C_1$-$C_6$fluoroalkyl, $C_1$-$C_6$heteroalkyl, $C_3$-$C_6$cycloalkyl, an optionally substituted phenyl, an optionally substituted naphthyl, or an optionally substituted heteroaryl. In some other embodiments, $R^{15}$ is $C_1$-$C_6$alkyl, $C_3$-$C_6$cycloalkyl, an optionally substituted phenyl, an optionally substituted naphthyl, or an optionally substituted heteroaryl. In yet other embodiments, $R^{15}$ is $C_1$-$C_6$alkyl, or an optionally substituted phenyl.

In some embodiments, $R^{10}$ is —$C(=NR^{19})N(R^{16})_2$; each $R^{16}$ is independently H, —CN, $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted $C_2$-$C_{10}$heterocycloalkyl, an optionally substituted aryl, an optionally substituted heteroaryl, —$C_1$-$C_4$alkyl-(optionally substituted $C_3$-$C_{10}$cycloalkyl), —$C_1$-$C_4$alkyl-(optionally substituted $C_2$-$C_{10}$heterocycloalkyl), —$C_1$-$C_4$alkyl-(optionally substituted aryl), and —$C_1$-$C_4$alkyl-(optionally substituted heteroaryl); or two $R^{16}$ groups attached to the same N atom are taken together with the N atom to which they are attached to form an optionally substituted $C_2$-$C_6$heterocycloalkyl.

In some embodiments, $R^{10}$ is —$C(=NR^{19})NH(R^{16})$; $R^{16}$ is $C_1$-$C_6$alkyl, $C_1$-$C_6$fluoroalkyl, $C_1$-$C_6$heteroalkyl, $C_3$-$C_6$cycloalkyl, an optionally substituted phenyl, an optionally substituted heteroaryl, —$CH_2$—($C_3$-$C_6$cycloalkyl), —$CH_2$-(optionally substituted phenyl), or —$CH_2$-(optionally substituted heteroaryl); $R^{19}$ is —CN.

In one aspect, $R^2$ and $R^3$ are H.

In one aspect, $R^4$ is H, F, Cl, Br, I, —CN, —OH, $C_1$-$C_6$fluoroalkyl, $C_1$-$C_6$fluoroalkoxy, $C_1$-$C_6$alkoxy, or $C_1$-$C_6$heteroalkyl. In some embodiments, $R^4$ is H, F, Cl, Br, —OH, —$CH_3$, —$OCH_3$, —$CF_3$, or —$OCF_3$. In other embodiments, $R^4$ is —$OCH_3$.

In some embodiments, $R^5$ is F, Cl, Br, I, —CN, —$NO_2$, —OH, —$CH_3$, —$CH_2CH_3$, i-propyl, -tBu, —$CF_3$, —$CH_2CF_3$, —$OCH_3$, —$OCF_3$, —$C(CH_3)_2OH$, —$C(CH_2CH_3)_2OH$, —$S(=O)_2(C_1$-$C_6$alkyl), —$S(=O)_2$(substituted or unsubstituted phenyl), —$NHS(=O)_2(C_1$-$C_6$alkyl), —$NHS(=O)_2$(substituted or unsubstituted phenyl), —$NHS(=O)_2$(substituted or unsubstituted heteroaryl), —$C(=O)$-(substituted or unsubstituted phenyl), —$C(=O)CH_3$, —$CO_2H$, —$CO_2CH_3$, —$CO_2CH_2CH_3$, —$NH_2$, —$C(=O)NH_2$, —$C(=O)NH(CH_3)$, —$C(=O)NH(CH_2CH_3)$, —$C(=O)NH(tBu)$, —$C(=O)NH(iPr)$, —$C(=O)NH(CH_2CF_3)$, —$C(=O)NH(CH_2CH_2OCH_3)$, —$C(=O)NH$(substituted or unsubstituted phenyl), —$C(=O)NH$(substituted or unsubstituted monocyclic heteroaryl), —$NHC(=O)(C_1$-$C_6$alkyl), —$NHC(=O)$(substituted or unsubstituted phenyl), —$NHC(=O)$(substituted or unsubstituted monocyclic heteroaryl), —$NHC(=O)NH_2$, or —$NHC(=O)NH$(substituted or unsubstituted phenyl).

In some other embodiments, $R^5$ is F, Cl, Br, I, —CN, —$NO_2$, —OH, —$CH_3$, —$CH_2CH_3$, i-propyl, -tBu, —$CF_3$, —$CH_2CF_3$, —$OCH_3$, —$OCF_3$, —$C(CH_3)_2OH$, —$C(CH_2CH_3)_2OH$, —$S(=O)_2(C_1$-$C_6$alkyl), —$NHS(=O)_2(C_1$-$C_6$alkyl), —$C(=O)CH_3$, —$CO_2H$, —$CO_2CH_3$, —$CO_2CH_2CH_3$, —$C(=O)NH_2$, —$C(=O)NH(CH_3)$, —$C(=O)NH(CH_2CH_3)$, —$C(=O)NH(tBu)$, —$C(=O)NH(iPr)$, —$C(=O)NH(CH_2CF_3)$, —$C(=O)NH(CH_2CH_2OCH_3)$, or —$NHC(=O)(C_1$-$C_6$alkyl).

In one aspect, $R^5$ is F, Cl, Br, —OH, —$CH_3$, —$CH_2CH_3$, —$CF_3$, —$CH_2CF_3$, —$OCH_3$, —$OCF_3$, —$C(CH_3)_2OH$, —$S(=O)_2(C_1$-$C_6$alkyl), —$NHS(=O)_2(C_1$-$C_6$alkyl), —$CO_2H$, —$CO_2CH_3$, —$CO_2CH_2CH_3$, or —$NHC(=O)(C_1$-$C_6$alkyl). In another aspect, $R^5$ is F, Cl, Br, —OH, —$CH_3$, —$CF_3$, —$OCH_3$, or —$OCF_3$. In a particular embodiment, $R^5$ is —$CF_3$.

In some embodiments, $R^5$ is $C_3$-$C_{10}$cycloalkyl, substituted or unsubstituted $C_2$-$C_{10}$heterocycloalkyl, substituted or unsubstituted phenyl, substituted or unsubstituted naphthyl, substituted or unsubstituted monocyclic heteroaryl, or substituted or unsubstituted bicyclic heteroaryl, In other embodiments, $R^5$ is cyclopropyl, cyclobutyl, cyclopentyl, cyclohexyl, pyrrolidinyl, piperidinyl, morpholinyl, piperazinyl, thiomorpholinyl, or a substituted or unsubstituted group selected from phenyl, naphthyl, furanyl, thienyl, pyrrolyl, oxazolyl, thiazolyl, imidazolyl, pyrazolyl, isoxazolyl, isothiazolyl, oxadiazolyl, triazolyl, tetrazolyl, pyridinyl, pyridazinyl, pyrazinyl, pyrimidinyl, triazinyl, indolyl, benzofuranyl, benzothienyl, indazolyl, benzimidaolyl, benzthiazolyl, quinolinyl, isoquinolinyl, cinnolinyl, phthalazinyl, quinazolinyl, and quinoxalinyl.

In yet other embodiments, R⁵ is a substituted or unsubstituted group selected from phenyl, naphthyl, furanyl, thienyl, pyrrolyl, oxazolyl, thiazolyl, imidazolyl, pyrazolyl, isoxazolyl, isothiazolyl, oxadiazolyl, triazolyl, tetrazolyl, pyridinyl, pyridazinyl, pyrazinyl, pyrimidinyl, triazinyl, indolyl, benzofuranyl, benzothienyl, indazolyl, benzimidaolyl, benzthiazolyl, quinolinyl, isoquinolinyl, cinnolinyl, phthalazinyl, quinazolinyl, and quinoxalinyl. In one aspect, R⁵ is a substituted or unsubstituted group selected from pyrrolyl, oxazolyl, thiazolyl, imidazolyl, pyrazolyl, isoxazolyl, isothiazolyl, oxadiazolyl, triazolyl, tetrazolyl, pyridinyl, pyridazinyl, pyrazinyl, pyrimidinyl, triazinyl, indolyl, indazolyl, benzimidaolyl, benzthiazolyl, quinolinyl, isoquinolinyl, cinnolinyl, phthalazinyl, quinazolinyl, and quinoxalinyl. In another aspect, R⁵ is a substituted or unsubstituted group selected from pyrrolyl, oxazolyl, thiazolyl, pyrazolyl, isoxazolyl, isothiazolyl, pyridinyl, pyridazinyl, pyrazinyl, pyrimidinyl, quinolinyl, and isoquinolinyl.

In some embodiments, $R^{11}$ is $C_1$-$C_6$alkyl, $C_1$-$C_6$haloalkyl, or $C_3$-$C_6$cycloalkyl. In other embodiments, $R^{11}$ is —CH₃, —CH₂CH₃, —CF₃, —CH₂CF₃, cyclopropyl, cyclobutyl, or cyclopentyl. In yet other embodiments, $R^{11}$ is —CH₃, —CH₂CH₃, or —CH₂CF₃.

In one aspect, the compound of Formula (I) has the structure of Formula (VII).

In one aspect, described herein is a compound having the structure of Formula (VII), pharmaceutically acceptable salts, pharmaceutically acceptable solvates, or pharmaceutically acceptable prodrugs thereof:

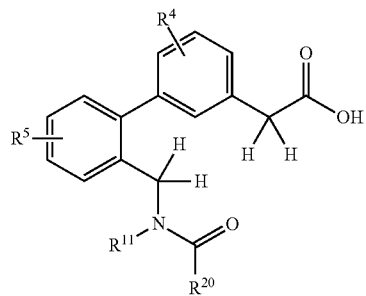

Formula (VII)

wherein,
R⁴ is H, halogen, —CN, —OH, $C_1$-$C_4$alkyl, $C_1$-$C_4$alkoxy, $C_1$-$C_4$fluoroalkyl, $C_1$-$C_4$fluoroalkoxy, or $C_1$-$C_4$heteroalkyl;
R⁵ is H, halogen, —CN, —NO₂, —OH, —OR¹³, —SR¹², —S(=O)R¹², —S(=O)₂R¹², —NHS(=O)₂R¹², —C(=O)R¹², —OC(=O)R¹², —CO₂R¹³, —OCO₂R¹³, —CH(R¹³)₂, —N(R¹³)₂, —C(=O)N(R¹³)₂, —OC(=O)N(R¹³)₂, —NHC(=O)NH(R¹³), —NHC(=O)R¹², —NHC(=O)OR¹², —C(OH)(R¹³)₂, —$C_1$-$C_6$alkyl, $C_1$-$C_6$fluoroalkyl, $C_1$-$C_6$fluoroalkoxy, $C_1$-$C_6$alkoxy, or $C_1$-$C_6$heteroalkyl;
R²⁰ is $C_1$-$C_4$alkyl, $C_3$-$C_6$cycloalkyl, —CH₂—O—$C_1$-$C_4$alkyl, —CH(CH₃)—O—$C_1$-$C_4$alkyl, —C(CH₃)₂—O—$C_1$-$C_4$alkyl, —CH₂O-(substituted or unsubstituted phenyl), —CH(CH₃)—O-(substituted or unsubstituted phenyl), —C(CH₃)₂—O-(substituted or unsubstituted phenyl), —CH₂OCH₂-(substituted or unsubstituted phenyl), —OC₁-C₄alkyl, —O—CH₂-(substituted or unsubstituted phenyl), —O—CH(CH₃)-(substituted or unsubstituted phenyl), —NR¹⁶—$C_1$-$C_4$alkyl, —NR¹⁶—$C_3$-$C_6$cycloalkyl, —NR¹⁶—CH₂-(substituted or unsubstituted phenyl), or —NR¹⁶—CH(CH₃)-(substituted or unsubstituted phenyl), wherein if the phenyl of R²⁰ is substituted, then the phenyl is substituted with 0, 1, or 2 R²¹ groups;
each R²¹ is independently selected from halogen, —OH, —OC₁-C₄alkyl, C₁-C₄alkyl, and —CF₃;
R¹⁶ is H or C₁-C₄alkyl;
R¹¹ is C₁-C₄alkyl, C₁-C₄fluoroalkyl, or C₃-C₆cycloalkyl;
R¹² is C₁-C₄alkyl, C₁-C₄heteroalkyl, or C₁-C₄fluoroalkyl;
each R¹³ is independently selected from H, C₁-C₄alkyl, C₁-C₄heteroalkyl, and C₁-C₄fluoroalkyl.

In one aspect, the compound of Formula (VII) has the structure of Formula (VIII):

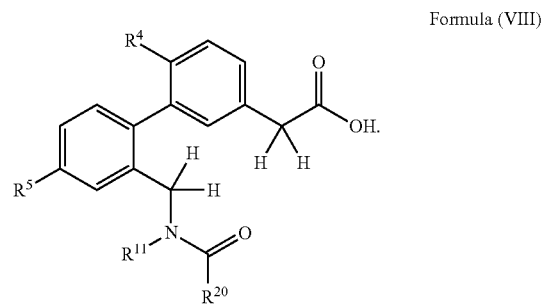

Formula (VIII)

In one aspect, $R^{11}$ is —CH₃, —CH₂CH₃, —CF₃, —CH₂CF₃, cyclopropyl, cyclobutyl, or cyclopentyl.

In some embodiments, R⁵ is H, halogen, —CN, —NO₂, —OH, —OR¹³, —SR¹², —S(=O)R¹², —S(=O)₂R¹², —NHS(=O)₂R¹², —C(=O)R¹², —OC(=O)R¹², —CO₂R¹³, —OCO₂R¹³, —N(R¹³)₂, —C(=O)N(R¹³)₂, —OC(=O)N(R¹³)₂, —NHC(=O)NH(R¹³), —NHC(=O)R¹², —NHC(=O)OR¹², —C(OH)(R¹³)₂, —C₁-C₄alkyl, C₁-C₄fluoroalkyl, C₁-C₄fluoroalkoxy, C₁-C₄alkoxy, or C₁-C₄heteroalkyl; R¹² is C₁-C₄alkyl; each R¹³ is independently selected from H, and C₁-C₄alkyl.

In some embodiments, R²⁰ is C₁-C₄alkyl, C₃-C₆cycloalkyl, —CH₂O—C₁-C₄alkyl, —CH₂O-(substituted or unsubstituted phenyl), —CH(CH₃)—O-(substituted or unsubstituted phenyl), —C(CH₃)₂—O-(substituted or unsubstituted phenyl), —CH₂OCH₂-(substituted or unsubstituted phenyl), —OC₁-C₄alkyl, —O—CH₂-(substituted or unsubstituted phenyl), —O—CH(CH₃)-(substituted or unsubstituted phenyl), —NR¹⁶C₁-C₄alkyl, —NR¹⁶—CH₂-(substituted or unsubstituted phenyl), or —NR¹⁶—CH (CH₃)-(substituted or unsubstituted phenyl), wherein if the phenyl of R²⁰ is substituted, then the phenyl is substituted with 0, 1, or 2 R²¹ groups.

In other embodiments, R²⁰ is —CH₃, —CH₂CH₃, cyclopropyl, cyclobutyl, cyclopentyl, cyclohexyl, —CH₂OCH₃, —CH₂O-(substituted or unsubstituted phenyl), —CH (CH₃)—O-(substituted or unsubstituted phenyl), —C(CH₃)₂—O-(substituted or unsubstituted phenyl), —CH₂OCH₂-(substituted or unsubstituted phenyl), wherein if the phenyl of R²⁰ is substituted, then the phenyl is substituted with 0, 1, or 2 R²¹ groups; each R²¹ is independently selected from F, Cl, Br, —OH, —OCH₃, —CH₃, and —CF₃.

In some embodiments, R⁴ is H, F, Cl, Br, —OH, —CH₃, —OCH₃, —CF₃, or —OCF₃.

In some embodiments, R⁵ is H, halogen, —CN, —NO₂, —OH, —S(=O)₂CH₃, —NHS(=O)₂CH₃, —C(=O)CH₃, —OC(=O)CH₃, —CO₂H, —CO₂CH₃, —CO₂CH₂CH₃, —NH$_2$, —C(=O)NH$_2$, —NHC(=O)CH$_3$, —CH$_3$, —CF$_3$, —OCF$_3$, —OCH$_3$, —CH$_2$OH, or —C(CH$_3$)$_2$OH.

In some embodiments, R$^4$ is H, F, Cl, Br, —CH$_3$, —OCH$_3$, —CF$_3$, or —OCF$_3$.

In other embodiments, R$^5$ is halogen, —CH$_3$, —CF$_3$, —OCF$_3$, or —OCH$_3$.

In some embodiments, R$^{20}$ is —CH$_3$, cyclopropyl, —CH$_2$OCH$_3$, —CH$_2$O-(substituted or unsubstituted phenyl), —CH$_2$OCH$_2$-(substituted or unsubstituted phenyl), wherein if the phenyl of R$^{20}$ is substituted, then the phenyl is substituted with 0, 1, or 2 R$^{21}$ groups; each R$^{21}$ is independently selected from F, Cl, Br, —OH, —OCH$_3$, —CH$_3$, and —CF$_3$.

In one aspect, R$^{20}$ is —OC$_1$-C$_4$alkyl, —O—CH$_2$-(substituted or unsubstituted phenyl), or —O—CH(CH$_3$)-(substituted or unsubstituted phenyl); wherein if the phenyl of R$^{20}$ is substituted, then the phenyl is substituted with 0, 1, or 2 R$^{21}$ groups; each R$^{21}$ is independently selected from F, Cl, Br, —OH, —OCH$_3$, —CH$_3$, and —CF$_3$.

In another aspect, R$^{20}$ is —O—CH$_2$-(substituted or unsubstituted phenyl), wherein if the phenyl of R$^{20}$ is substituted, then the phenyl is substituted with 0, 1, or 2 R$^{21}$ groups; each R$^{21}$ is independently selected from F, Cl, and Br.

In one aspect, the compound of Formula (VIII) has the following structure:

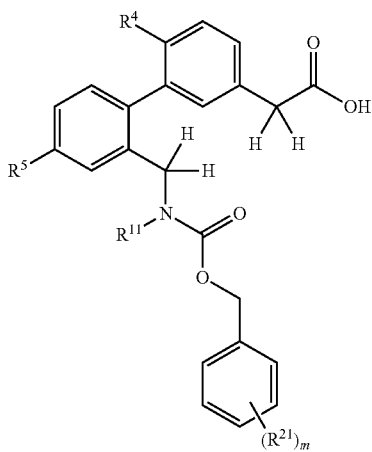

wherein, m is 0, 1, or 2.

In one aspect, R$^4$ is F, Cl, Br, —CH$_3$, —OCH$_3$, —CF$_3$, or —OCF$_3$.

In one aspect, R$^5$ is F, Cl, Br, —CH$_3$, —CF$_3$, —OCF$_3$, or —OCH$_3$.

In one aspect, R$^{11}$ is —CH$_3$, —CH$_2$CH$_3$, or —CH$_2$CF$_3$.

In some embodiments, R$^{20}$ is —NR$^{16}$C$_1$-C$_4$alkyl, —NR$^{16}$—CH$_2$-(substituted or unsubstituted phenyl), or —NR$^{16}$—CH(CH$_3$)-(substituted or unsubstituted phenyl), wherein if the phenyl of R$^{20}$ is substituted, then the phenyl is substituted with 0, 1, or 2 R$^{21}$ groups; each R$^{21}$ is independently selected from F, Cl, Br, —OH, —OCH$_3$, —CH$_3$, and —CF$_3$; R$^{16}$ is H, —CH$_3$, or —CH$_2$CH$_3$.

In one aspect, R$^{20}$ is —NH—CH$_2$-(substituted or unsubstituted phenyl), wherein if the phenyl of R$^{20}$ is substituted, then the phenyl is substituted with 0, 1, or 2 R$^{21}$ groups; each R$^{21}$ is independently selected from F, Cl, Br, —OH, —OCH$_3$, —CH$_3$, and —CF$_3$.

In one aspect, m is 0. In another aspect, m is 1. In another aspect, m is 2.

In one aspect, the compound of Formula (VIII) has the following structure:

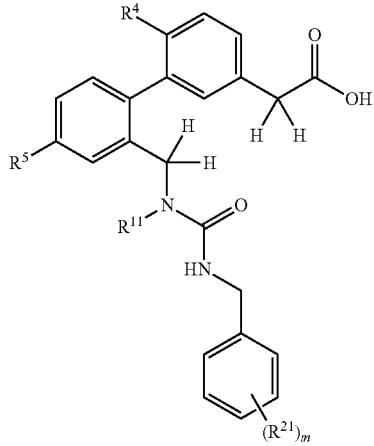

wherein, m is 0, 1, or 2.

In one aspect, R$^4$ is F, Cl, Br, —CH$_3$, —OCH$_3$, —CF$_3$, or —OCF$_3$.

In another aspect, R$^5$ is F, Cl, Br, —CH$_3$, —CF$_3$, —OCF$_3$, or —OCH$_3$.

In yet another aspect, R$^{11}$ is —CH$_3$, —CH$_2$CH$_3$, or —CH$_2$CF$_3$.

In one aspect, each R$^{21}$ is independently selected from F, Cl, Br, —OH, —OCH$_3$, —CH$_3$, and —CF$_3$.

In one aspect, R$^4$ is —OCH$_3$.
In one aspect, R$^5$ is —CF$_3$.
In another aspect, R$^{11}$ is —CH$_3$, or —CH$_2$CH$_3$.
In yet another aspect, each R$^{21}$ is independently selected from F, Cl, and Br.
In one aspect, m is 0; R$^4$ is —OCH$_3$; R$^5$ is —CF$_3$; R$^{11}$ is —CH$_2$CH$_3$.

In one aspect, described herein is a compound having the structure of Formula (VIII), pharmaceutically acceptable salts, pharmaceutically acceptable solvates, or pharmaceutically acceptable prodrugs thereof:

Formula (VIII)

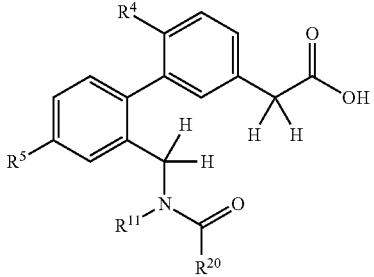

wherein,
R$^4$ is H, halogen, —CN, —OH, C$_1$-C$_4$alkyl, C$_1$-C$_4$alkoxy, C$_1$-C$_4$fluoroalkyl, C$_1$-C$_4$fluoroalkoxy, or C$_1$-C$_4$heteroalkyl;

R$^5$ is C$_3$-C$_{10}$cycloalkyl, a substituted or unsubstituted C$_2$-C$_{10}$heterocycloalkyl, a substituted or unsubstituted phenyl, a substituted or unsubstituted naphthyl, a substituted or unsubstituted monocyclic heteroaryl, or a substituted or unsubstituted bicyclic heteroaryl, wherein if R$^5$ is substituted, then R$^5$ is substituted with 1, or 2 R$^{21}$ groups $R^{20}$ is $C_1$-$C_4$alkyl, $C_3$-$C_6$cycloalkyl, —$CH_2$O—$C_1$-$C_4$alkyl, —$CH_2$O-(substituted or unsubstituted phenyl), —$CH(CH_3)$—O-(substituted or unsubstituted phenyl), —$C(CH_3)_2$—O-(substituted or unsubstituted phenyl), —$CH_2OCH_2$-(substituted or unsubstituted phenyl), —$OC_1$-$C_4$alkyl, —O—$CH_2$-(substituted or unsubstituted phenyl), —O—$CH(CH_3)$-(substituted or unsubstituted phenyl), —$NR^{16}C_1$-$C_4$alkyl, —$NR^{16}$—$CH_2$-(substituted or unsubstituted phenyl), or —$NR^{16}$—CH($CH_3$)-(substituted or unsubstituted phenyl), wherein if the phenyl of $R^{20}$ is substituted, then the phenyl is substituted with 1, or 2 $R^{21}$ groups;

each $R^{21}$ is independently selected from halogen, —OH, —$OC_1$-$C_4$alkyl, $C_1$-$C_4$alkyl, and —$CF_3$;

$R^{10}$ is H or $C_1$-$C_4$alkyl;

$R^{11}$ is $C_1$-$C_4$alkyl, $C_1$-$C_4$fluoroalkyl, or $C_3$-$C_6$cycloalkyl;

$R^{12}$ is $C_1$-$C_4$alkyl, $C_1$-$C_4$heteroalkyl, or $C_1$-$C_4$fluoroalkyl;

each $R^{13}$ is independently selected from H, $C_1$-$C_4$alkyl, $C_1$-$C_4$heteroalkyl, and $C_1$-$C_4$fluoroalkyl.

In one aspect, $R^4$ is H, F, Cl, Br, —OH, —$CH_3$, —$OCH_3$, —$CF_3$, or —$OCF_3$; $R^{11}$ is —$CH_3$, —$CH_2CH_3$, —$CF_3$, —$CH_2CF_3$, cyclopropyl, cyclobutyl, or cyclopentyl.

In one aspect, $R^5$ is cyclopropyl, cyclobutyl, cyclopentyl, cyclohexyl, pyrrolidinyl, piperidinyl, morpholinyl, piperazinyl, thiomorpholinyl, or a substituted or unsubstituted group selected from phenyl, naphthyl, furanyl, thienyl, pyrrolyl, oxazolyl, thiazolyl, imidazolyl, pyrazolyl, isoxazolyl, isothiazolyl, oxadiazolyl, triazolyl, tetrazolyl, pyridinyl, pyridazinyl, pyrazinyl, pyrimidinyl, triazinyl, indolyl, benzofuranyl, benzothienyl, indazolyl, benzimidaolyl, benzthiazolyl, quinolinyl, isoquinolinyl, cinnolinyl, phthalazinyl, quinazolinyl, and quinoxalinyl, where if $R^5$ is substituted, then $R^5$ is substituted with 1, or 2 $R^{21}$ groups.

In some embodiments, $R^5$ is a substituted or unsubstituted group selected from phenyl, naphthyl, pyrrolyl, oxazolyl, thiazolyl, imidazolyl, pyrazolyl, isoxazolyl, isothiazolyl, oxadiazolyl, triazolyl, tetrazolyl, pyridinyl, pyridazinyl, pyrazinyl, pyrimidinyl, triazinyl, indolyl, benzofuranyl, benzothienyl, indazolyl, benzimidaolyl, benzthiazolyl, quinolinyl, isoquinolinyl, cinnolinyl, phthalazinyl, quinazolinyl, and quinoxalinyl, where if $R^5$ is substituted, then $R^5$ is substituted with 1, or 2 $R^{21}$ groups.

In one aspect, $R^5$ is a substituted or unsubstituted group selected from pyrrolyl, oxazolyl, thiazolyl, imidazolyl, pyrazolyl, isoxazolyl, isothiazolyl, oxadiazolyl, triazolyl, tetrazolyl, pyridinyl, pyridazinyl, pyrazinyl, pyrimidinyl, triazinyl, indolyl, benzofuranyl, benzothienyl, indazolyl, benzimidaolyl, benzthiazolyl, quinolinyl, isoquinolinyl, where if $R^5$ is substituted, then $R^5$ is substituted with 1, or 2 $R^{21}$ groups; each $R^{21}$ is independently selected from F, Cl, Br, —OH, —$OCH_3$, —$CH_3$, and —$CF_3$.

In some embodiments, $R^{20}$ is —$CH_3$, —$CH_2CH_3$, cyclopropyl, cyclobutyl, cyclopentyl, cyclohexyl, —$CH_2OCH_3$, —$CH_2$O-(substituted or unsubstituted phenyl), —CH($CH_3$)—O-(substituted or unsubstituted phenyl), —$C(CH_3)_2$—O-(substituted or unsubstituted phenyl), —$CH_2OCH_2$-(substituted or unsubstituted phenyl), wherein if the phenyl of $R^{20}$ is substituted, then the phenyl is substituted with 0, 1, or 2 $R^{21}$ groups; each $R^{21}$ is independently selected from F, Cl, Br, —OH, —$OCH_3$, —$CH_3$, and —$CF_3$.

In one aspect, $R^{20}$ is —$CH_3$, cyclopropyl, —$CH_2OCH_3$, —$CH_2$O-(substituted or unsubstituted phenyl), —$CH_2OCH_2$-(substituted or unsubstituted phenyl), wherein if the phenyl of $R^{20}$ is substituted, then the phenyl is substituted with 1, or 2 $R^{21}$ groups; each $R^{21}$ is independently selected from F, Cl, Br, —OH, —$OCH_3$, —$CH_3$, and —$CF_3$.

In some embodiments, $R^{20}$ is —$OC_1$-$C_4$alkyl, —O—$CH_2$-(substituted or unsubstituted phenyl), or —O—CH($CH_3$)-(substituted or unsubstituted phenyl); wherein if the phenyl of $R^{20}$ is substituted, then the phenyl is substituted with 1, or 2 $R^{21}$ groups; each $R^{21}$ is independently selected from F, Cl, Br, —OH, —$OCH_3$, —$CH_3$, and —$CF_3$.

In other embodiments, $R^{20}$ is —O—$CH_2$-(substituted or unsubstituted phenyl), wherein if the phenyl of $R^{20}$ is substituted, then the phenyl is substituted with 1, or 2 $R^{21}$ groups; each $R^{21}$ is independently selected from F, Cl, and Br.

In some embodiments, $R^{20}$ is —$NR^{16}C_3$-$C_4$alkyl, —$NR^{16}$—$CH_2$-(substituted or unsubstituted phenyl), or —$NR^{16}$—CH($CH_3$)-(substituted or unsubstituted phenyl), wherein if the phenyl of $R^{20}$ is substituted, then the phenyl is substituted with 1, or 2 $R^{21}$ groups; each $R^{21}$ is independently selected from F, Cl, Br, —OH, —$OCH_3$, —$CH_3$, and —$CF_3$; $R^{16}$ is H, —$CH_3$, or —$CH_2CH_3$.

In other embodiments, $R^{20}$ is —NH—$CH_2$-(substituted or unsubstituted phenyl), wherein if the phenyl of $R^{20}$ is substituted, then the phenyl is substituted with 1, or 2 $R^{21}$ groups; each $R^{21}$ is independently selected from F, Cl, Br, —OH, —$OCH_3$, —$CH_3$, and —$CF_3$.

In one aspect, $R^4$ is F, Cl, Br, —$CH_3$, —$OCH_3$, —$CF_3$, or —$OCF_3$; $R^{11}$ is —$CH_3$, —$CH_2CH_3$, or —$CH_2CF_3$;

In yet other embodiments, $R^4$ is —$OCH_3$. In still further embodiments, $R^{11}$ is —$CH_3$, or —$CH_2CH_3$.

In one aspect, $R^5$ is a substituted or unsubstituted group selected from pyrrolyl, oxazolyl, thiazolyl, imidazolyl, pyrazolyl, isoxazolyl, isothiazolyl, pyridinyl, pyridazinyl, pyrazinyl, pyrimidinyl, quinolinyl, and isoquinolinyl, where if $R^5$ is substituted, then $R^5$ is substituted with 1, or 2 $R^{21}$ groups; each $R^{21}$ is independently selected from F, Cl, Br, —OH, —$OCH_3$, —$CH_3$, and —$CF_3$.

In one aspect, $R^{20}$ is —$R^{14}$, —$OR^{15}$, x or —$N(R^{16})_2$ as described herein. In one aspect, $R^{20}$ is —$R^{14}$ as described herein. In some embodiments, $R^{20}$ is —$OR^{15}$ as described herein. In some embodiments, $R^{20}$ is —$N(R^{16})_2$ as described herein.

Any combination of the groups described above for the various variables is contemplated herein. Throughout the specification, groups and substituents thereof are chosen by one skilled in the field to provide stable moieties and compounds.

Compounds of Formula (I), Formula (II), Formula (III), Formula (IV), Formula (V), Formula (VI), Formula (VII), and Formula (VIII), are antagonists of $DP_2$. In specific embodiments, the antagonist of $DP_2$ is selective for $DP_2$. In other embodiments, the antagonist of $DP_2$ is also an antagonist of $DP_1$. In some embodiments, the antagonist of $DP_2$ is also an antagonist of TP (thromboxane receptor).

In other embodiments, presented herein are compounds selected from active metabolites, solvates, pharmaceutically acceptable salts or pharmaceutically acceptable prodrugs of a compound of any of Formula (I), Formula (II), Formula (III), Formula (IV), Formula (V), Formula (VI), Formula (VII), or Formula (VIII).

In one aspect, provided herein is a pharmaceutical composition comprising a therapeutically effective amount of a compound provided herein. In some embodiments, the pharmaceutical composition includes at least one pharmaceutically acceptable excipient.

In certain embodiments, presented herein are methods for treating a $PGD_2$-dependent condition or disease in a patient comprising administering to the patient a therapeutically effective amount of an antagonist of $DP_2$ having the structure of any of Formula (I), Formula (II), Formula (III), Formula (IV), Formula (V), Formula (VI), Formula (VII), or Formula (VIII). In certain aspects, provided herein is a method for treating inflammation in a mammal comprising administering a therapeutically effective amount of a compound provided herein to the mammal in need.

In a specific aspect, provided herein is a method for treating asthma in a mammal comprising administering a therapeutically effective amount of a compound provided herein to the mammal in need. In a further or alternative embodiment, provided herein is a method for treating asthma in a mammal comprising administering a therapeutically effective amount of a compound provided herein, such as, for example, a compound of any of Formula (I), Formula (II), Formula (III), Formula (IV), Formula (V), Formula (VI), Formula (VII), or Formula (VIII) to the mammal in need.

In another aspect are compounds presented in Table 1 and Table 2 or pharmaceutically acceptable salts, pharmaceutically active metabolites, pharmaceutically acceptable prodrugs, and pharmaceutically acceptable solvates thereof, which antagonize $DP_2$ and are used to treat patients suffering from one or more $PGD_2$-dependent conditions or diseases, including, but not limited to, asthma, rhinitis, chronic obstructive pulmonary disease, pulmonary hypertension, interstitial lung fibrosis, arthritis, allergy, psoriasis, inflammatory bowel disease, adult respiratory distress syndrome, myocardial infarction, aneurysm, stroke, cancer, endotoxic shock, proliferative disorders and inflammatory conditions.

Compounds of Formula (I), Formula (II), Formula (III), Formula (IV), Formula (V), Formula (VI), Formula (VII), or Formula (VIII) are antagonists of $DP_2$. In still further or alternative embodiments such antagonists of $DP_2$ also antagonize other related $PGD_2$ receptors. Related $PGD_2$ receptors include, but are not limited to, $DP_1$ and TP.

In further or alternative embodiments, the compounds of Formula (I), Formula (II), Formula (III), Formula (IV), Formula (V), Formula (VI), Formula (VII), or Formula (VIII) are included into pharmaceutical compositions or medicaments used for treating a $PGD_2$-dependent or $PGD_2$ mediated condition or disease in a patient.

In another aspect, compounds of any of Formula (I), Formula (II), Formula (III), Formula (IV), Formula (V), Formula (VI), Formula (VII), or Formula (VIII) are used to treat or prevent inflammatory conditions. Inflammatory conditions include, but are not limited to, asthma, rhinitis, chronic obstructive pulmonary disease, pulmonary hypertension, interstitial lung fibrosis, atherosclerosis, aortic aneurysm, myocardial infarction, and stroke.

In another aspect, compounds of any of Formula (I), Formula (II), Formula (III), Formula (IV), Formula (V), Formula (VI), Formula (VII), or Formula (VIII) are used to treat or prevent immunological disorders. In one aspect the immunological disorders include, but are not limited to, allergy or to excessive or inappropriate response to an endogenous or exogenous antigen. In certain embodiments, the immunological disorder that is characterized by immune dysregulation that is not accompanied by inflammation.

In another aspect, compounds of any of Formula (I), Formula (II), Formula (III), Formula (IV), Formula (V), Formula (VI), Formula (VII), or Formula (VIII) are used to treat or prevent proliferative disorders. In one aspect the proliferative disorders include, but are not limited to, cancer and noncancerous disorders, including, but not limited to, those involving the skin or lymphatic tissues.

In another aspect, compounds of any of Formula (I), Formula (II), Formula (III), Formula (IV), Formula (V), Formula (VI), Formula (VII), or Formula (VIII) are used to treat or prevent pain.

In additional aspects, such conditions are iatrogenic and increases in, or abnormal localization of, $PGD_2$ is induced by other therapies or medical or surgical procedures. In other embodiments, the $PGD_2$-dependent or $PGD_2$ mediated condition or disease is caused by surgery.

In other aspects, the methods, compounds, pharmaceutical compositions, and medicaments described herein are used to prevent the cellular activity of $PGD_2$. In other aspects, such methods, compounds, pharmaceutical compositions, and medicaments comprise $DP_2$ antagonists disclosed herein for the treatment of asthma by modulating the activity of enzymes or proteins in a patient wherein such enzymes or proteins are involved in the $PGD_2$ pathway such as, by way of example, $DP_2$. In yet other aspects, the methods, compounds, pharmaceutical compositions, and medicaments described herein are used in combination with other medical treatments or surgical modalities.

In one aspect are methods for reducing/antagonizing the $PGD_2$ activation of $DP_2$ in a mammal comprising administering to the mammal at least once an effective amount of a compound having the structure of any of Formula (I), Formula (II), Formula (III), Formula (IV), Formula (V), Formula (VI), Formula (VII) or Formula (VIII).

In another aspect are methods for modulating, including reducing and/or antagonizing the activation of $DP_2$, directly or indirectly, in a mammal comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect, presented herein are methods for modulating, including reducing and/or antagonizing the activity of $PGD_2$ in a mammal, directly or indirectly, comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for treating $PGD_2$-dependent or $PGD_2$ mediated conditions or diseases, comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for treating inflammation comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for treating immunological abnormalities comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for treating respiratory diseases comprising administering to the mammal at least once an effective amount of at least one compound having the structure of any of Formula (I), Formula (II), Formula (III), Formula (IV), Formula (V), Formula (VI), Formula (VII) or Formula (VIII). In a further embodiment of this aspect, the respiratory disease is asthma. In a further embodiment of this aspect, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, neutrophilic asthma, isocapnic hyperventilation, child-onset asthma, adult-onset asthma, cough-variant asthma, occupational asthma, steroid-resistant asthma, seasonal asthma.

In another aspect are methods for treating respiratory diseases comprising administering to the mammal at least once an effective amount of at least one compound having the structure of any of Formula (I), Formula (II), Formula (III), Formula (IV), Formula (V), Formula (VI), Formula (VII) or Formula (VIII). In a further embodiment of this aspect, the respiratory disease is rhinitis. In a further embodiment of this aspect, the respiratory disease includes, but is not limited to, allergic (extrinsic) rhinitis, non-allergic (intrinsic) rhinitis, chronic rhinitis, allergen-induced rhinitis, aspirin-sensitive rhinitis, child-onset rhinitis, adult-onset rhinitis, occupational rhinitis, steroid-resistant rhinitis, seasonal rhinitis, perennial rhinitis, rhinosinusitis, and rhinopolyposis.

In another aspect are methods for treating chronic obstructive pulmonary disease comprising administering to the mammal at least once an effective amount of at least one compound having the structure of any of Formula (I), Formula (II), Formula (III), Formula (IV), Formula (V), Formula (VI), Formula (VII) or Formula (VIII). In a further embodiment of this aspect, chronic obstructive pulmonary disease includes, but is not limited to, chronic bronchitis and/or emphysema, pulmonary hypertension, interstitial lung fibrosis and/or airway inflammation and cystic fibrosis.

In another aspect are methods for preventing increased mucosal secretion and/or edema in a disease or condition comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for treating vasoconstriction, atherosclerosis and its sequelae, myocardial ischemia, myocardial infarction, aortic aneurysm, vasculitis, cardiac arrhythmia, and stroke comprising administering to the mammal an effective amount of a compound having the structure of any of Formula (I), Formula (II), Formula (III), Formula (IV), Formula (V), Formula (VI), Formula (VII) or Formula (VIII).

In another aspect are methods for treating organ reperfusion injury following organ ischemia and/or endotoxic shock comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for reducing the constriction of blood vessels in a mammal comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for lowering or preventing an increase in blood pressure of a mammal comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for preventing eosinophil and/or basophil and/or dendritic cell and/or neutrophil and/or monocyte or TH2 cell recruitment comprising administering to the mammal at least once an effective amount of at least one compound having the structure of any of Formula (I), Formula (II), Formula (III), Formula (IV), Formula (V), Formula (VI), Formula (VII) or Formula (VIII).

A further aspect are methods for the prevention or treatment of abnormal bone remodeling, loss or gain, including diseases or conditions as, by way of example, osteopenia, osteoporosis, Paget's disease, cancer, trauma, surgery, and other diseases comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for preventing ocular inflammation and allergic conjunctivitis, vernal keratoconjunctivitis, and papillary conjunctivitis comprising administering to the mammal at least once an effective amount of at least one having the structure of any of Formula (I), Formula (II), Formula (III), Formula (IV), Formula (V), Formula (VI), Formula (VII) or Formula (VIII).

In another aspect are methods for treating CNS disorders comprising administering to the mammal at least once an effective amount of at least one compound having the structure of any of Formula (I), Formula (II), Formula (III), Formula (IV), Formula (V), Formula (VI), Formula (VII) or Formula (VIII). CNS disorders include, but are not limited to, multiple sclerosis, Parkinson's disease, Alzheimer's or other degenerative disease, stroke, cerebral ischemia, retinal ischemia, post-surgical cognitive dysfunction, migraine, peripheral neuropathy/neuropathic pain, spinal cord injury, cerebral edema and head injury.

A further aspect are methods for the treatment of cancer comprising administering to the mammal at least once an effective amount of at least one compound having the structure of any of Formula (I), Formula (II), Formula (III), Formula (IV), Formula (V), Formula (VI), Formula (VII) or Formula (VIII). The type of cancer includes, but is not limited to, pancreatic cancer and other solid or hematological tumors.

In another aspect are methods for treating endotoxic shock and septic shock comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for treating rheumatoid arthritis and osteoarthritis comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for treating or preventing increased gastrointestinal diseases comprising administering to the mammal at least once an effective amount of at least one compound having the structure of any of Formula (I), Formula (II), Formula (III), Formula (IV), Formula (V), Formula (VI), Formula (VII) or Formula (VIII). Such diseases include, by way of example only, chronic gastritis, eosinophilic gastroenteritis, and gastric motor dysfunction.

A further aspect are methods for treating kidney diseases comprising administering to the mammal at least once an effective amount of at least one compound having the structure of any of Formula (I), Formula (II), Formula (III), Formula (IV), Formula (V), Formula (VI), Formula (VII) or Formula (VIII). Such diseases include, by way of example only, acute tubular necrosis, glomerulonephritis, cyclosporine nephrotoxicity, renal ischemia, and reperfusion injury.

In another aspect are methods for preventing or treating acute or chronic renal insufficiency comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for treating pain comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods to diminish the inflammatory aspects of acute infections within one or more solid organs or tissues such as the kidney with acute pyelonephritis.

In another aspect are methods for preventing or treating acute or chronic disorders involving recruitment or activation of eosinophils comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for preventing or treating acute or chronic erosive disease or motor dysfunction of the gastrointestinal tract caused by non-steroidal anti-inflammatory drugs (including selective or non-selective cyclooxygenase-1 or -2 inhibitors) comprising administering to the mammal at least once an effective amount of at least one compound having the structure of any of Formula (I), Formula (II), Formula (III), Formula (IV), Formula (V), Formula (VI), Formula (VII) or Formula (VIII).

A further aspect are methods for the prevention or treatment of rejection or dysfunction in a transplanted organ or tissue comprising administering to the mammal at least once an effective amount of at least one compound having the structure of any of Formula (I), Formula (II), Formula (III), Formula (IV), Formula (V), Formula (VI), Formula (VII) or Formula (VIII).

In another aspect are methods for treating inflammatory responses of the skin comprising administering to the mammal at least once an effective amount of at least one compound having the structure of any of Formula (I), Formula (II), Formula (III), Formula (IV), Formula (V), Formula (VI), Formula (VII) or Formula (VIII). Such inflammatory responses of the skin include, by way of example, dermatitis, contact dermatitis, eczema, urticaria, rosacea, and scarring. In another aspect are methods for reducing psoriatic lesions in the skin, joints, or other tissues or organs, comprising administering to the mammal an effective amount of a first compound having the structure of any of Formula (I), Formula (II), Formula (III), Formula (IV), Formula (V), Formula (VI), Formula (VII) or Formula (VIII).

A further aspect are methods for the treatment of cystitis, including, by way of example only, interstitial cystitis, comprising administering to the mammal at least once an effective amount of at least one compound having the structure of any of Formula (I), Formula (II), Formula (III), Formula (IV), Formula (V), Formula (VI), Formula (VII) or Formula (VIII).

A further aspect are methods for the treatment of Familial Mediterranean Fever comprising administering to the mammal at least once an effective amount of at least one compound having the structure of any of Formula (I), Formula (II), Formula (III), Formula (IV), Formula (V), Formula (VI), Formula (VII) or Formula (VIII).

In a further aspect are methods to treat hepatorenal syndrome comprising administering to the mammal at least once an effective amount of at least one compound having the structure of any of Formula (I), Formula (II), Formula (III), Formula (IV), Formula (V), Formula (VI), Formula (VII) or Formula (VIII).

In a further aspect are methods to modulate the immune response to endogenous or exogenous antigens.

In a further aspect are methods to treat acute or chronic allergic responses to exogenous substances that have been ingested such as foods (e.g., peanuts) or drugs (e.g., penicillin, non-steroidal anti-inflammatory drugs or the like).

In another aspect is the use of a compound of any of Formula (I), Formula (II), Formula (III), Formula (IV), Formula (V), Formula (VI), Formula (VII), or Formula (VIII) in the manufacture of a medicament for treating an inflammatory disease or condition in an animal in which the activity of at least one $PGD_2$-associated protein contributes to the pathology and/or symptoms of the disease or condition. In one embodiment of this aspect, the $PGD_2$ pathway protein is CRTH2. In another or further embodiment of this aspect, the inflammatory disease or conditions are respiratory, cardiovascular, or proliferative diseases.

In any of the aforementioned aspects are further embodiments in which: (a) the effective amount of the compound is systemically administered to the mammal; and/or (b) the effective amount of the compound is administered orally to the mammal; and/or (c) the effective amount of the compound is intravenously administered to the mammal; and/or (d) the effective amount of the compound administered by inhalation; and/or (e) the effective amount of the compound is administered by nasal administration; or and/or (f) the effective amount of the compound is administered by injection to the mammal; and/or (g) the effective amount of the compound is administered topically (dermal) to the mammal; and/or (h) the effective amount of the compound is administered by ophthalmic administration; and/or (i) the effective amount of the compound is administered rectally to the mammal.

In any of the aforementioned aspects are further embodiments in which the mammal is a human, including embodiments wherein the human has an asthmatic condition or one or more other condition(s) selected from the group consisting of allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, neutrophilic asthma, isocapnic hyperventilation, child-onset asthma, adult-onset asthma, cough-variant asthma, occupational asthma, steroid-resistant asthma, or seasonal asthma, or chronic obstructive pulmonary disease, or pulmonary hypertension or interstitial lung fibrosis. In any of the aforementioned aspects are further embodiments in which the mammal is an animal model for pulmonary inflammation, examples of which are provided herein.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In any of the aforementioned aspects involving the treatment of $PGD_2$ dependent diseases or conditions are further embodiments comprising administering at least one additional agent in addition to the administration of a compound having the structure of any of Formula (I), Formula (II), Formula (III), Formula (IV), Formula (V), Formula (VI), Formula (VII) or Formula (VIII). In various embodiments, each agent is administered in any order, including simultaneously. In certain embodiments, the at least one additional agent is, by way of example only, an anti-inflammatory agent, a different compound having the structure of any of Formula (I), Formula (II), Formula (III), Formula (IV), Formula (V), Formula (VI), Formula (VII), or Formula (VIII), a $DP_1$ receptor antagonist, a TP receptor antagonist, or a different $DP_2$ receptor antagonist.

In other embodiments, a compound of any of Formula (I), Formula (II), Formula (III), Formula (IV), Formula (V), Formula (VI), Formula (VII), or Formula (VIII) is combined with an additional agent that is a respiratory agent, including, but not limited to antihistamines (e.g., Zyrtec®), bronchodilators, LABAs (e.g., salmeterol), theophylline, IgE modulators (e.g., Xolair® and omalizumab), steroids (e.g., fluticasone).

In further or alternative embodiments, the anti-inflammatory agent is, by way of example only, a leukotriene pathway modulator such as a CysLT1 receptor antagonists (e.g., montelukast), a CysLT2 receptor antagonist, a 5-lipoxygenase inhibitor (e.g., zileuton), a 5-lipoxygenase-activating protein inhibitor (e.g., MK-0591, MK-886, DG-031 (BAY X1005), 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid, 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid), a LTA4 hydrolase inhibitor, a $LTC_4$ synthase inhibitor, a BLT1 receptor antagonist or a BLT2 receptor antagonist.

In any of the aforementioned aspects involving the treatment of proliferative disorders, including cancer, are further embodiments comprising administering at least one additional agent, including by way of example only alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues), interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In any of the aforementioned aspects involving the therapy of an immunogical disorder requiring immunosuppression or involving the therapy of transplanted organs or tissues or cells are further embodiments comprising administering at least one additional agent, including by way of example only azathioprine, a corticosteroid, cyclophosphamide, cyclosporin, dacluzimab, mycophenolate mofetil, OKT3, rapamycin, tacrolimus, or thymoglobulin.

In any of the aforementioned aspects involving the therapy of interstitial cystitis are further embodiments comprising administering at least one additional agent selected from e.g., dimethylsulfoxide, omalizumab, and pentosan polysulfate.

In any of the aforementioned aspects involving the therapy of disorders of bone are further embodiments comprising administering at least one additional agent such as, by way of example only, minerals, vitamins, bisphosphonates, anabolic steroids, parathyroid hormone or analogs, and cathepsin K inhibitors dronabinol.

In any of the aforementioned aspects involving the prevention or treatment of inflammation are further embodiments comprising: (a) monitoring inflammation in a mammal; (b) measuring bronchoconstriction in a mammal; (c) measuring eosinophil and/or basophil and/or dendritic cell and/or neutrophil and/or monocyte and/or lymphocyte recruitment in a mammal; (d) monitoring mucosal secretion in a mammal; (e) measuring mucosal edema in a mammal.

In any of the aforementioned aspects the $PGD_2$-dependent or $PGD_2$ mediated diseases or conditions include, but are not limited to, asthma, rhinitis, chronic obstructive pulmonary disease, pulmonary hypertension, interstitial lung fibrosis, arthritis, allergy, inflammatory bowel disease, adult respiratory distress syndrome, myocardial infarction, aneurysm, stroke, cancer, and endotoxic shock.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Prostaglandin $D_2$ ($PGD_2$) is an acidic lipid derived from the metabolism of arachidonic acid by cyclooxygenases and $PGD_2$ synthases. $PGD_2$ is produced by mast cells, macrophages and $T_H2$ lymphocytes in response to local tissue damage as well as in response allergic inflammation observed in diseases such as asthma, rhinitis, and atopic dermatitis. More specifically, exogenous $PGD_2$ applied to bronchial airways elicits many responses that are characteristic of acute asthma.

$PGD_2$ is a major mast cell product that acts via two receptors, the D-type prostanoid (DP, also known as $DP_1$) and the chemoattractant receptor-homologous molecule expressed on Th2 cells (CRTH2, also known as $DP_2$) receptors. $DP_2$ mediates the chemotaxis of eosinophils, basophils, and Th2 lymphocytes, and $DP_1$ receptor plays an important role in eosinophil trafficking. $DP_1$ antagonists do not inhibit the release of eosinophils when induced by the $DP_2$-selective agonists. However, eosinophils in human bone marrow specimens express $DP_1$ and $DP_2$ receptors at similar levels and human peripheral blood expresses both $DP_1$ and $DP_2$, but the $DP_1$ receptor is expressed at lower levels. In agreement with this, the chemotaxis of human peripheral blood eosinophils is inhibited by both $DP_1$ and $DP_2$ antagonists. Accordingly, $DP_1$, $DP_2$ and dual $DP_1/DP_2$ antagonists are useful in the treatment of allergic inflammation.

Activation of $DP_2$ is associated with chemotaxis and activation of $T_H2$ lymphocytes, eosinophils and basophils. In particular, $PGD_2$ binds to $DP_2$ and mediates many of its effects through a $G_i$-dependent elevation of intracellular calcium levels and reduction of cyclic AMP. In $T_H2$ lymphocytes, IL4, IL5 and IL13 cytokine production are also stimulated by $DP_2$ activation. These cytokines have been implicated in numerous biological actions including, by way of example only, immunoglobulin E production, airway response, mucous secretion, and eosinophil recruitment.

The terms CRTH2 and $DP_2$, refer to the same receptor and are used interchangeably herein. Likewise, another common name for DP is $DP_1$, and the two terms are used interchangeably herein.

Illustrative Biological Activity

Prostaglandins (PGs) are recognized physiological lipid acid mediators produced by the release of arachidonic acid from cell membrane phospholipids and converted to prostaglandins by the action of $COX_1$ and $COX_2$ cyclooxygenases and PG synthases. The cyclooxygenases sequentially convert arachidonic acid to cyclic endoperoxide prostaglandin $G_2$ ($PGG_2$) and subsequently, prostaglandin $H_2$ ($PGH_2$). Depending on the tissue, physiological signal, and/or synthase type, $PGH_2$ can be converted to numerous different prostaglandins, such as $PGE_2$, $PGD_2$, $PGF_2\alpha$, and $PGI_2$ as well as thromboxane $A_2$, another eicosanoid signaling molecule. These mediators then elicit a wide variety of physiological responses including vasoconstriction or dilation, platelet aggregation, calcium transport, pain sensitization, hormone release, inflammatory and immune response, and cellular growth.

Prostaglandin $D_2$ is a major metabolite produced from the $PGH_2$ intermediate via hematopoietic $PGD_2$ synthase or lipocalin $PGD_2$ synthase. In the brain and central nervous system, $PGD_2$ is produced and thought to function in pain perception and sleep regulation. In other tissues, $PGD_2$ is produced primarily in immunoglobulin E (IgE) activated mast cells and to a lesser extent, in macrophages, dendritic cells, T helper 2 ($T_H2$) lymphocytes and other leukocytes. In the cell, $PGD_2$ is rapidly metabolized and converted to other downstream effectors including $\Delta^{12}PGJ_2$, $9\alpha11\beta PGF_2$, 13,14-dihydro-15-keto-$PGD_2$, and 15-deoxy-$\Delta^{12,14}PGD_2$.

Mast-cell-derived $PGD_2$ is produced in high concentrations in response to an allergen challenge. Studies in preclinical species have observed the following features when $PGD_2$ is applied to in vivo preparations, or its overproduction is engineered by genetic manipulation:

Vasodilatation leading to erythema (flare) and -potentiation of oedema (wheal).

Recruitment of eosinophils and TH2 lymphocytes.

Modulation of TH2-cytokine production.

Bronchoconstriction.

Injection of $PGD_2$ into human skin has been shown to produce a long lasting erythema, to potentiate the effects of other mediators on induration and leukocyte infiltration in human skin and to enhance oedema formation in rat skin. It is most likely that these effects of $PGD_2$, like those of other vasodilator prostaglandins, are due to an increased blood flow to the inflamed lesion and are, therefore, most likely to be mediated predominantly by the $DP_1$ receptor. Although these observations make it clear that $DP_1$ mediates the vascular effects of $PGD_2$, the capacity of $PGD_2$ to promote the cellular changes associated with inflammation is not due to an action on $DP_1$.

The main receptors that are activated by $PGD_2$ or its metabolites and mediate its effects are $DP_1$, CRTH2 (or $DP_2$) and TP.

$DP_1$ (or DP) is a G-protein coupled seven-transmembrane receptor that, upon activation by $PGD_2$ binding, leads to an increase in intracellular cAMP levels. $DP_1$ is expressed in the brain, bronchial smooth muscle, vascular and airway smooth muscle, dendritic cells, and platelets and induces $PGD_2$ dependent bronchodilation, vasodilation, platelet aggregation inhibition, and suppression of cytokine production. Genetic analysis of $DP_1$ function using knock-out mice has shown that mice lacking DP do not develop asthmatic responses in an ovalbumin-induced asthma model. Analysis of selective DP antagonists in guinea pig allergic rhinitis models demonstrated dramatic inhibition of early nasal responses, as assessed by sneezing, mucosal plasma exudation and eosinophil infiltration. DP antagonism alleviates allergen-induced plasma exudation in the conjunctiva in a guinea pig allergic conjuctivitis model and antigen-induced esinophil infiltration into the lung in a guinea pig asthma model.

Much of the pro-inflammatory activity of $PGD_2$ is through interaction with $DP_2$ (or CRTH2). $DP_2$ is a G-protein coupled receptor and is typically highly expressed in $T_H2$ lymphocytes, eosinophils and basophils. $DP_2$ activation functions to directly activate and recruit $T_H2$ lymphocytes and eosinophils. Activated $T_H2$ lymphocytes produce and secrete inflammatory cytokines including IL4, IL5, and IL13. Despite binding $PGD_2$ with a similar affinity as $DP_1$, $DP_2$ is not structurally related to $DP_1$ and signals through a different mechanism—the effects of $DP_2$ are mediated through Gi-dependent elevation in intracellular calcium levels and reduction in intracellular levels of cyclic AMP. $DP_2$ activation is important in eosinophil recruitment in response to allergic challenge in such tissues as nasal mucosa, bronchial airways, and skin. The application of either $PGD_2$ or selective $DP_2$ agonists both exacerbate and enhance allergic responses in lung and skin. $DP_2$ activation appears to have a crucial role in mediating allergic responses, and thus the use of antagonists of $PGD_2$ activation of the $DP_2$ receptor are an attractive approach to treat the inflammatory component of allergic diseases such as asthma, rhinitis, and dermatitis.

TP receptors primarily function to antagonize $DP_1$ receptor's effects such as promoting bronchoconstriction, vasoconstriction, and platelet aggregation. While TP receptor's main ligand is thromboxane $A_2$, it also binds and is activated by the $PGD_2$ derivative, $9\alpha11\beta PGF_2$. TP is a Gq-coupled prostanoid receptor that binds thromboxane with high affinity, promoting platelet aggregation and constriction of both vascular and airway smooth muscle. $PGD_2$ activates the TP receptor in human bronchial muscle, probably through the formation of the 11-ketoreductase metabolite $9\alpha11\beta PGF2$. The bronchoconstrictor effects of TP dominate over the bronchodilator effects of $DP_1$ in the airways.

$DP_1$ and $DP_2$ have crucial, and complementary, roles in the physiological response of animals to $PGD_2$ and blockade of either one or both of these receptors may prove beneficial in alleviating allergic diseases or conditions triggered by $PGD_2$, such as, but not limited to, allergic rhinitis, asthma, dermatitis, and allergic conjunctivitis.

Compounds

Compounds described herein, including pharmaceutically acceptable salts, pharmaceutically acceptable prodrugs, and pharmaceutically acceptable solvates thereof, antagonize or modulate $DP_2$ and are used to treat patients suffering from $PGD_2$-dependent or $PGD_2$ mediated conditions or diseases, including, but not limited to, asthma, rhinitis, dermatitis, and inflammatory conditions.

In one aspect is a compound having the structure of Formula (I), pharmaceutically acceptable salts, pharmaceutically acceptable solvates, or pharmaceutically acceptable prodrugs thereof:

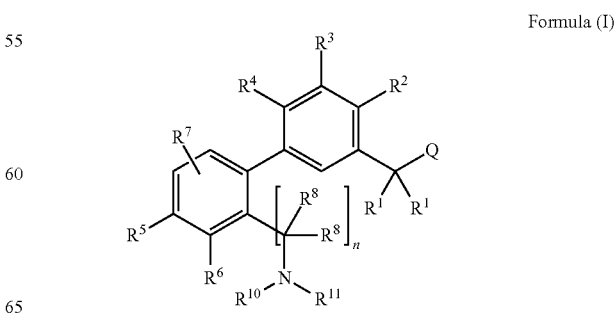

Formula (I)

wherein, n is 1, 2, 3 or 4;

Q is —C(=O)-Q$^1$, —SO$_2$NHC(=O)R$^{12}$, —CH$_2$OH, or tetrazolyl;

Q$^1$ is —OH, —OR$^{13}$, —NHSO$_2$R$^{12}$, —N(R$^{13}$)$_2$, —NH—OH, or —NH—CN;

each R$^1$ is independently selected from H, halogen, C$_1$-C$_4$alkyl, and C$_1$-C$_4$haloalkyl; or both R$^1$ groups taken together with the carbon atom to which they are attached form a C$_3$-C$_6$cycloalkyl;

each of R$^2$, R$^3$, R$^4$, R$^5$, R$^6$, and R$^7$ is independently H, halogen, —CN, —NO$_2$, —OH, —OR$^{13}$, —SR$^{12}$, —S(=O)R$^{12}$, —S(=O)$_2$R$^{12}$, —NHS(=O)$_2$R$^{12}$, —C(=O)R$^{12}$, —OC(=O)R$^{12}$, —CO$_2$R$^{13}$, —OCO$_2$R$^{13}$, —CH(R$^{13}$)$_2$, —N(R$^{13}$)$_2$, —NHCH$_2$CO$_2$R$^{13}$, —OCH$_2$CO$_2$R$^{13}$, —SCH$_2$CO$_2$R$^{13}$, —C(=O)N(R$^{13}$)$_2$, —OC(=O)N(R$^{13}$)$_2$, —NHC(=O)NH(R$^{13}$), —NHC(=O)R$^{12}$, —NHC(=O)OR$^{12}$, —C(OH)(R$^{13}$)$_2$, C$_1$-C$_6$alkyl, C$_1$-C$_6$fluoroalkyl, C$_1$-C$_6$fluoroalkoxy, C$_1$-C$_6$alkoxy, C$_1$-C$_6$heteroalkyl, an optionally substituted C$_3$-C$_{10}$cycloalkyl, an optionally substituted heterocycloalkyl, optionally substituted phenyl, optionally substituted monocyclic heteroaryl, or an optionally substituted group selected from among —C$_1$-C$_4$alkyl-C$_3$-C$_{10}$cycloalkyl, —C$_1$-C$_4$alkyl-heterocycloalkyl, —C$_1$-C$_4$alkyl-aryl, and —C$_1$-C$_4$alkyl-heteroaryl; or each of R$^2$, R$^3$, R$^4$, R$^5$, R$^6$, and R$^7$ is independently —X$^1$-L$^1$-Q$^2$, where, X$^1$ is a bond, —O—, —S—, —S(=O)—, —S(=O)$_2$—, or —NR$^{13}$—;

L$^1$ is a bond or a C$_1$-C$_4$alkylene;

Q$^2$ is —CO$_2$R$^{13}$, —C(=O)R$^{12}$, —C(=O)N(R$^{13}$)$_2$, —C(=O)NHSO$_2$R$^{12}$, an optionally substituted C$_3$-C$_{10}$cycloalkyl, an optionally substituted heterocycloalkyl, an optionally substituted aryl, or an optionally substituted heteroaryl;

each R$^8$ is each independently selected from H, halogen, C$_1$-C$_4$alkyl, and C$_1$-C$_4$haloalkyl; or both R$^8$ groups are taken together with the carbon atom to which they are attached to form a C$_3$-C$_6$cycloalkyl;

R$^{10}$ is —C(=O)R$^{14}$, —C(=O)OR$^{15}$, —C(=O)N(R$^{16}$)$_2$, —S(=O)$_2$N(R$^{16}$)$_2$ or —S(=O)$_2$R$^{15}$;

R$^{14}$ is C$_1$-C$_6$alkyl, C$_1$-C$_6$fluoroalkyl, C$_1$-C$_6$heteroalkyl, an optionally substituted C$_3$-C$_{10}$cycloalkyl, an optionally substituted heterocycloalkyl, an optionally substituted aryl, an optionally substituted heteroaryl, an optionally substituted —C$_1$-C$_4$alkyl-cycloalkyl, an optionally substituted —C$_1$-C$_4$alkyl-heterocycloalkyl, an optionally substituted —C$_1$-C$_4$alkyl-aryl or an optionally substituted —C$_1$-C$_4$alkyl-heteroaryl; or R$^{14}$ is L$^3$-X$^3$-Q$^3$;

L$^3$ is a C$_1$-C$_6$alkylene;

X$^3$ is a bond, —O—, —S—, —S(=O)—, —S(=O)$_2$—, or —NR$^{13}$—;

Q$^3$ is an optionally substituted C$_{1-6}$alkyl, C$_{1-6}$fluoroalkyl an optionally substituted C$_3$-C$_{10}$cycloalkyl, an optionally substituted heterocycloalkyl, an optionally substituted aryl, an optionally substituted heteroaryl, an optionally substituted C$_{1-4}$alkyl-C$_3$-C$_{10}$cycloalkyl, an optionally substituted C$_{1-4}$alkyl-heterocycloalkyl, an optionally substituted C$_{1-4}$alkyl-aryl, or an optionally substituted C$_{1-4}$alkyl-heteroaryl;

R$^{15}$ is C$_1$-C$_6$alkyl, C$_1$-C$_6$fluoroalkyl, C$_1$-C$_6$heteroalkyl, an optionally substituted C$_3$-C$_{10}$cycloalkyl, an optionally substituted heterocycloalkyl, an optionally substituted aryl, an optionally substituted heteroaryl, an optionally substituted —C$_1$-C$_4$alkyl-cycloalkyl, an optionally substituted —C$_1$-C$_4$alkyl-heterocycloalkyl, an optionally substituted —C$_1$-C$_4$alkyl-aryl or an optionally substituted —C$_1$-C$_4$alkyl-heteroaryl;

each R$^{16}$ is independently H, —CN, C$_1$-C$_6$alkyl, C$_1$-C$_6$fluoroalkyl, C$_1$-C$_6$heteroalkyl, an optionally substituted C$_3$-C$_{10}$cycloalkyl, an optionally substituted heterocycloalkyl, an optionally substituted aryl, an optionally substituted heteroaryl, an optionally substituted —C$_1$-C$_4$alkyl-cycloalkyl, an optionally substituted —C$_1$-C$_4$alkyl-heterocycloalkyl, an optionally substituted —C$_1$-C$_4$alkyl-aryl or an optionally substituted —C$_1$-C$_4$alkyl-heteroaryl; or two R$^{16}$ groups attached to the same N atom are taken together with the N atom to which they are attached to form an optionally substituted heterocycloalkyl;

R$^{11}$ is C$_1$-C$_6$alkyl, C$_1$-C$_6$heteroalkyl, C$_1$-C$_6$haloalkyl, (an optionally substituted monocyclic or bicyclic cycloalkyl), (an optionally substituted monocyclic or bicyclic heterocycloalkyl), an optionally substituted aryl, or an optionally substituted heteroaryl, C$_1$-C$_6$alkylene-R$^{17}$, —C$_1$-C$_6$alkylene-O—R$^{17}$, —C$_1$-C$_6$alkylene-S—R$^{17}$, —C$_1$-C$_6$alkylene-S(=O)—R$^{17}$, —C$_1$-C$_6$alkylene-S(=O)$_2$—R$^{17}$, —C$_1$-C$_6$alkylene-NR$^{13}$—R$^{17}$, —C$_1$-C$_6$alkylene-C(=O)—R$^{17}$, —C$_1$-C$_6$alkylene-C(=O)O—R$^{17}$—, —C$_1$-C$_6$alkylene-OC(=O)—R$^{17}$, —C$_1$-C$_6$alkylene-NR$^{13}$C(=O)—R$^{17}$ or —C$_1$-C$_6$alkylene-C(=O)NR$^{13}$—R$^{17}$;

R$^{17}$ is H, C$_1$-C$_6$alkyl, C$_1$-C$_6$heteroalkyl, C$_1$-C$_6$haloalkyl, an optionally substituted cycloalkyl, an optionally substituted heterocycloalkyl, an optionally substituted aryl, an optionally substituted benzyl, or an optionally substituted heteroaryl;

R$^{12}$ is C$_1$-C$_6$alkyl, C$_1$-C$_6$heteroalkyl, C$_1$-C$_6$fluoroalkyl, a substituted or unsubstituted cycloalkyl, a substituted or unsubstituted heterocycloalkyl, a substituted or unsubstituted aryl, a substituted or unsubstituted benzyl, a substituted or unsubstituted heteroaryl, a substituted or unsubstituted —C$_1$-C$_4$alkyl-cycloalkyl, a substituted or unsubstituted —C$_1$-C$_4$alkyl-heterocycloalkyl, a substituted or unsubstituted —C$_1$-C$_4$alkyl-aryl, or a substituted or unsubstituted —C$_1$-C$_4$alkyl-heteroaryl; and each R$^{13}$ is independently selected from H, C$_1$-C$_6$alkyl, C$_1$-C$_6$heteroalkyl, C$_1$-C$_6$fluoroalkyl, a substituted or unsubstituted cycloalkyl, a substituted or unsubstituted heterocycloalkyl, a substituted or unsubstituted aryl, a substituted or unsubstituted benzyl, a substituted or unsubstituted heteroaryl, a substituted or unsubstituted —C$_1$-C$_4$alkyl-cycloalkyl, a substituted or unsubstituted —C$_1$-C$_4$alkyl-heterocycloalkyl, a substituted or unsubstituted —C$_1$-C$_4$alkyl-aryl, and a substituted or unsubstituted —C$_1$-C$_4$alkyl-heteroaryl; or two R$^{13}$ groups attached to the same N atom are taken together with the N atom to which they are attached to form an optionally substituted heterocycloalkyl.

For any and all of the embodiments, substituents can be selected from among from a subset of the listed alternatives. For example, in some embodiments, n is 1 or 2. In other embodiments, n is 2, 3, or 4. In yet other embodiments, n is 3 or 4. In yet other embodiments, n is 1.

In some embodiments, when n is 1; R$^{14}$, R$^{15}$, or R$^{16}$ is an acyclic moiety; and R$^{11}$ is a —C$_1$-C$_6$alkylene-R$^{17}$ or —C$_1$-C$_6$alkylene-C(=O)—R$^{17}$; then R$^{17}$ is not a cyclic ring.

In some embodiments, when n is 1; and R$^{14}$ is a cyclic ring; then R$^{17}$ is not a cyclic ring.

In some embodiments, Q is —C(=O)-Q$^1$, —SO$_2$NHC(=O)R$^{12}$, or tetrazolyl. In other embodiments, Q is —C(=O)-Q$^1$, or tetrazolyl. In other embodiments, Q is selected from —CO$_2$H, —CO$_2$Me, —CO$_2$Et, —C(=O)NH$_2$, —C(=O)NHOH, —C(=O)NH—CN, tetrazolyl, —C(=O)—NHSO$_2$R$^{12}$, or

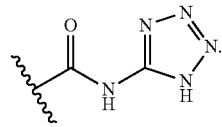 [SMILES: *C(=O)Nc1nnn[nH]1]

In some other embodiments, Q is selected from —CO$_2$H, —CO$_2$Me, —CO$_2$Et, —C(=O)NH$_2$, —C(=O)—NHSO$_2$CH$_3$, —C(=O)—NHSO$_2$CH$_2$CH$_3$. In other embodiments, Q is —C(=O)-Q$^1$. In yet some other embodiments, Q is —CO$_2$H.

In some embodiments, Q$^1$ is —OH, —OR$^{13}$, —NHSO$_2$R$^{12}$, or —N(R$^{13}$)$_2$. In some other embodiments, Q$^1$ is —OH, —OCH$_3$, —OCH$_2$CH$_3$, or —NHSO$_2$CH$_3$. In some other embodiments, Q$^1$ is —OH, —OCH$_3$, or —OCH$_2$CH$_3$.

In alternative embodiments, each R$^1$ is independently selected from H, F, C$_1$-C$_4$alkyl, and C$_1$-C$_4$haloalkyl; or both R$^1$ groups taken together with the carbon atom to which they are attached form a cyclopropyl, cyclobutyl or cyclohexyl.

In some embodiments, each R$^8$ is each independently selected from H, F, C$_1$-C$_4$alkyl, and C$_1$-C$_4$haloalkyl.

In one aspect, each R$^1$ is independently selected from H, F, and C$_1$-C$_4$alkyl; and each R$^8$ is each independently selected from H, F, and C$_1$-C$_4$alkyl. In some other embodiments, each R$^8$ is each independently selected from H, F, and —CH$_3$. In one aspect, each R$^8$ is H.

In another aspect, Q is —C(=O)-Q$^1$ and n is 1 and the compound of Formula (I) has the structure

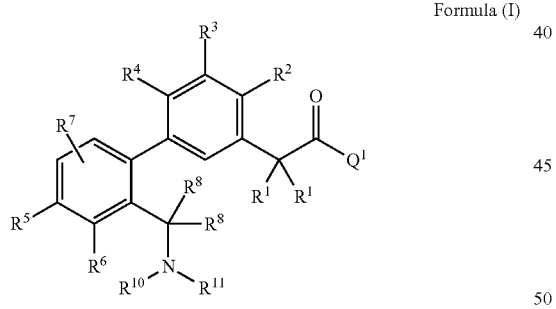

Formula (I)

wherein,
Q$^1$ is —OH, —OR$^{13}$, —NHSO$_2$R$^{12}$, —N(R$^{13}$)$_2$, —NH—OH, or —NH—CN;
each R$^1$ is independently selected from H, halogen, C$_1$-C$_4$alkyl, and C$_1$-C$_4$haloalkyl; or
both R$^1$ groups taken together with the carbon atom to which they are attached form a C$_3$-C$_6$cycloalkyl;
each of R$^2$, R$^3$, R$^4$, R$^5$, R$^6$, and R$^7$ is independently H, halogen, —CN, —NO$_2$, —OH, —OR$^{13}$, —SR$^{12}$, —S(=O)R$^{12}$, —S(=O)$_2$R$^{12}$, —NHS(=O)$_2$R$^{12}$, —C(=O)R$^{12}$, —OC(=O)R$^{12}$, —CO$_2$R$^{13}$, —OCO$_2$R$^{13}$, —CH(R$^{13}$)$_2$, —N(R$^{13}$)$_2$, —NHCH$_2$CO$_2$R$^{13}$, —OCH$_2$CO$_2$R$^{13}$, —SCH$_2$CO$_2$R$^{13}$, —C(=O)N(R$^{13}$)$_2$, —OC(=O)N(R$^{13}$)$_2$, —NHC(=O)NH(R$^{13}$), —NHC(=O)R$^{12}$, —NHC(=O)OR$^{12}$, —C(OH)(R$^{13}$)$_2$, C$_1$-C$_6$alkyl, C$_1$-C$_6$fluoroalkyl, C$_1$-C$_6$fluoroalkoxy, C$_1$-C$_6$alkoxy, C$_1$-C$_6$heteroalkyl, an optionally substituted C$_3$-C$_{10}$cycloalkyl, an optionally substituted heterocycloalkyl, optionally substituted phenyl, optionally substituted monocyclic heteroaryl, or an optionally substituted group selected from among —C$_1$-C$_4$alkyl-C$_3$-C$_{10}$cycloalkyl, —C$_1$-C$_4$alkyl-heterocycloalkyl, —C$_1$-C$_4$alkyl-aryl, and —C$_1$-C$_4$alkyl-heteroaryl; or
each of R$^2$, R$^3$, R$^4$, R$^5$, R$^6$, and R$^7$ is independently —X$^1$-L$^1$-Q$^2$, where,
X$^1$ is a bond, —O—, —S—, —S(=O)—, —S(=O)$_2$—, or —NR$^{13}$—;
L$^1$ is a bond or a C$_1$-C$_4$alkylene;
Q$^2$ is —CO$_2$R$^{13}$, —C(=O)R$^{12}$, —C(=O)N(R$^{13}$)$_2$, —C(=O)NHSO$_2$R$^{12}$, an optionally substituted C$_3$-C$_{10}$cycloalkyl, an optionally substituted heterocycloalkyl, an optionally substituted aryl, or an optionally substituted heteroaryl;
each R$^8$ is each independently selected from H, halogen, C$_1$-C$_4$alkyl, and C$_1$-C$_4$haloalkyl; or
both R$^8$ groups are taken together with the carbon atom to which they are attached to form a C$_3$-C$_6$cycloalkyl;
R$^{10}$ is —C(=O)R$^{14}$, —C(=O)OR$^{15}$, —C(=O)N(R$^{16}$)$_2$, —S(=O)$_2$N(R$^{16}$)$_2$ or —S(=O)$_2$R$^{15}$;
R$^{14}$ is C$_1$-C$_6$alkyl, C$_1$-C$_6$fluoroalkyl, C$_1$-C$_6$heteroalkyl, an optionally substituted C$_3$-C$_{10}$cycloalkyl, an optionally substituted heterocycloalkyl, an optionally substituted aryl, an optionally substituted heteroaryl, an optionally substituted —C$_1$-C$_4$alkyl-cycloalkyl, an optionally substituted —C$_1$-C$_4$alkyl-heterocycloalkyl, an optionally substituted —C$_1$-C$_4$alkyl-aryl or an optionally substituted —C$_1$-C$_4$alkyl-heteroaryl; or
R$^{14}$ is L$^3$-X$^3$-Q$^3$;
L$^3$ is a C$_1$-C$_6$alkylene;
X$^3$ is a bond, —O—, —S—, —S(=O)—, —S(=O)$_2$—, or —NR$^{13}$—;
Q$^3$ is an optionally substituted C$_{1-6}$alkyl, C$_{1-6}$fluoroalkyl an optionally substituted C$_3$-C$_{10}$cycloalkyl, an optionally substituted heterocycloalkyl, an optionally substituted aryl, an optionally substituted heteroaryl, an optionally substituted C$_{1-4}$alkyl-C$_3$-C$_{10}$cycloalkyl, an optionally substituted C$_{1-4}$alkyl-heterocycloalkyl, an optionally substituted C$_{1-4}$alkyl-aryl, or an optionally substituted C$_{1-4}$alkyl-heteroaryl;
R$^{15}$ is C$_1$-C$_6$alkyl, C$_1$-C$_6$fluoroalkyl, C$_1$-C$_6$heteroalkyl, an optionally substituted C$_3$-C$_{10}$cycloalkyl, an optionally substituted heterocycloalkyl, an optionally substituted aryl, an optionally substituted heteroaryl, an optionally substituted —C$_1$-C$_4$alkyl-cycloalkyl, an optionally substituted —C$_1$-C$_4$alkyl-heterocycloalkyl, an optionally substituted —C$_1$-C$_4$alkyl-aryl or an optionally substituted —C$_1$-C$_4$alkyl-heteroaryl;
each R$^{16}$ is independently H, —CN, C$_1$-C$_6$alkyl, C$_1$-C$_6$fluoroalkyl, C$_1$-C$_6$heteroalkyl, an optionally substituted C$_3$-C$_{10}$cycloalkyl, an optionally substituted heterocycloalkyl, an optionally substituted aryl, an optionally substituted heteroaryl, an optionally substituted —C$_1$-C$_4$alkyl-cycloalkyl, an optionally substituted —C$_1$-C$_4$alkyl-heterocycloalkyl, an optionally substituted —C$_1$-C$_4$alkyl-aryl or an optionally substituted —C$_1$-C$_4$alkyl-heteroaryl; or
two R$^{16}$ groups attached to the same N atom are taken together with the N atom to which they are attached to form an optionally substituted heterocycloalkyl;

$R^{11}$ is $C_1$-$C_6$alkyl, $C_1$-$C_6$heteroalkyl, $C_1$-$C_6$haloalkyl, (an optionally substituted monocyclic or bicyclic cycloalkyl), (an optionally substituted monocyclic or bicyclic heterocycloalkyl), an optionally substituted aryl, or an optionally substituted heteroaryl, $C_1$-$C_6$alkylene-$R^{17}$, —$C_1$-$C_6$alkylene-O—$R^{17}$, —$C_1$-$C_6$alkylene-S—$R^{17}$, —$C_1$-$C_6$alkylene-S(=O)—$R^{17}$, —$C_1$-$C_6$alkylene-S(=O)$_2$—$R^{17}$, —$C_1$-$C_6$alkylene-NR$^{13}$—$R^{17}$, —$C_1$-$C_6$alkylene-C(=O)—$R^{17}$, —$C_1$-$C_6$alkylene-C(=O)O—$R^{17}$—, —$C_1$-$C_6$alkylene-OC(=O)—$R^{17}$, —$C_1$-$C_6$alkylene-NR$^{13}$C(=O)—$R^{17}$ or —$C_1$-$C_6$alkylene-C(=O)NR$^{13}$—$R^{17}$;

$R^{17}$ is H, $C_1$-$C_6$alkyl, $C_1$-$C_6$heteroalkyl, $C_1$-$C_6$haloalkyl, an optionally substituted cycloalkyl, an optionally substituted heterocycloalkyl, an optionally substituted aryl, an optionally substituted benzyl, or an optionally substituted heteroaryl;

$R^{12}$ is $C_1$-$C_6$alkyl, $C_1$-$C_6$heteroalkyl, $C_1$-$C_6$fluoroalkyl, a substituted or unsubstituted cycloalkyl, a substituted or unsubstituted heterocycloalkyl, a substituted or unsubstituted aryl, a substituted or unsubstituted benzyl, a substituted or unsubstituted heteroaryl, a substituted or unsubstituted —$C_1$-$C_4$alkyl-cycloalkyl, a substituted or unsubstituted —$C_1$-$C_4$alkyl-heterocycloalkyl, a substituted or unsubstituted —$C_1$-$C_4$alkyl-aryl, or a substituted or unsubstituted —$C_1$-$C_4$alkyl-heteroaryl; and each $R^{13}$ is independently selected from H, $C_1$-$C_6$alkyl, $C_1$-$C_6$heteroalkyl, $C_1$-$C_6$fluoroalkyl, a substituted or unsubstituted cycloalkyl, a substituted or unsubstituted heterocycloalkyl, a substituted or unsubstituted aryl, a substituted or unsubstituted benzyl, a substituted or unsubstituted heteroaryl, a substituted or unsubstituted —$C_1$-$C_4$alkyl-cycloalkyl, a substituted or unsubstituted —$C_1$-$C_4$alkyl-heterocycloalkyl, a substituted or unsubstituted —$C_1$-$C_4$alkyl-aryl, and a substituted or unsubstituted —$C_1$-$C_4$alkyl-heteroaryl; or two $R^{13}$ groups attached to the same N atom are taken together with the N atom to which they are attached to form an optionally substituted heterocycloalkyl.

In one embodiment, the compound of Formula (I) has one of the following structures:

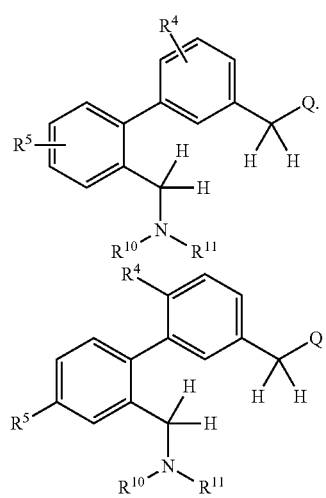

In one embodiment, the compound of Formula (I) has the structure of Formula (II):

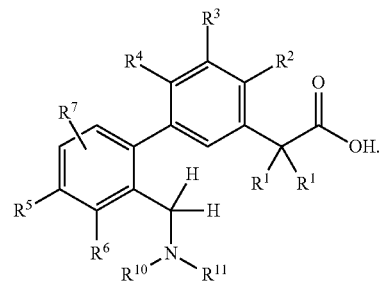

Formula (II)

In other embodiments, each $R^1$ is independently selected from H, F, and $C_1$-$C_4$alkyl. In some other embodiments, each $R^1$ is independently selected from H, F, and —$CH_3$. In some other embodiments, each $R^1$ is independently selected from H, and F. In yet some other embodiments, each $R^1$ is H.

In one aspect, each of $R^2$, $R^3$, $R^6$, and $R^7$ is independently H, halogen, —CN, —OH, —OR$^{13}$, —SR$^{12}$, —S(=O)R$^{12}$, —S(=O)$_2$R$^{12}$, —C(=O)R$^{12}$, —OC(=O)R$^{12}$, —CO$_2$R$^{13}$, —OCO$_2$R$^{13}$, —N(R$^{13}$)$_2$, —$C_1$-$C_6$alkyl, $C_1$-$C_6$fluoroalkyl, an optionally substituted $C_3$-$C_{10}$cycloalkyl, an optionally substituted heterocycloalkyl, $C_1$-$C_6$fluoroalkoxy, $C_1$-$C_6$alkoxy, $C_1$-$C_6$heteroalkyl, optionally substituted phenyl, or an optionally substituted monocyclic heteroaryl.

In one aspect, $R^4$ is H, halogen, —CN, —NO$_2$, —OH, —OR$^{13}$, —SR$^{12}$, —S(=O)R$^{12}$, —S(=O)$_2$R$^{12}$, —C(=O)R$^{12}$, —OC(=O)R$^{12}$, —CO$_2$R$^{13}$, —OCO$_2$R$^{13}$, —CH(R$^{13}$)$_2$, —N(R$^{13}$)$_2$, —NHCH$_2$CO$_2$R$^{13}$, —OCH$_2$CO$_2$R$^{13}$, —SCH$_2$CO$_2$R$^{13}$, —C(=O)N(R$^{13}$)$_2$, $C_1$-$C_6$alkyl, $C_1$-$C_6$fluoroalkyl, an optionally substituted $C_3$-$C_{10}$cycloalkyl, an optionally substituted heterocycloalkyl, $C_1$-$C_6$fluoroalkoxy, $C_1$-$C_6$alkoxy, $C_1$-$C_6$heteroalkyl, optionally substituted phenyl, optionally substituted monocyclic heteroaryl; or $R^4$ is —$X^1$-$L^1$-$Q^2$, where, $X^1$ is a bond, or —O—; $L^1$ is a bond or a $C_1$-$C_4$alkylene; $Q^2$ is —CO$_2$R$^{13}$, an optionally substituted $C_3$-$C_6$cycloalkyl, an optionally substituted aryl, or an optionally substituted heteroaryl.

In one aspect, $R^5$ is H, halogen, —CN, —NO$_2$, —OH, —OR$^{13}$, —SR$^{12}$, —S(=O)R$^{12}$, —S(=O)$_2$R$^{13}$, —NHS(=O)$_2$R$^{12}$, —C(=O)R$^{12}$, —OC(=O)R$^{12}$, —CO$_2$R$^{13}$, —OCO$_2$R$^{13}$, —CH(R$^{13}$)$_2$, —N(R$^{13}$)$_2$, —NHCH$_2$CO$_2$R$^{13}$, —OCH$_2$CO$_2$R$^{13}$, —SCH$_2$CO$_2$R$^{13}$, —C(=O)N(R$^{13}$)$_2$, —OC(=O)N(R$^{13}$)$_2$, —NHC(=O)NH(R$^{13}$), —NHC(=O)R$^{12}$, —NHC(=O)OR$^{12}$, —C(OH)(R$^{13}$)$_2$, —$C_1$-$C_6$alkyl, $C_1$-$C_6$fluoroalkyl, an optionally substituted $C_3$-$C_{10}$cycloalkyl, an optionally substituted heterocycloalkyl, $C_1$-$C_6$fluoroalkoxy, $C_1$-$C_6$alkoxy, $C_1$-$C_6$heteroalkyl, optionally substituted phenyl, optionally substituted monocyclic heteroaryl, or an optionally substituted group selected from among —$C_1$-$C_4$alkyl-$C_3$-$C_{10}$cycloalkyl, —$C_1$-$C_4$alkyl-heterocycloalkyl, —$C_1$-$C_4$alkyl-aryl, and —$C_1$-$C_4$alkyl-heteroaryl; or $R^5$ is independently —$X^1$-$L^1$-$Q^2$, where, $X^1$ is a bond, —O—, —S—, —S(=O)—, —S(=O)$_2$—, or —NR$^{13}$—; $L^1$ is a bond or a $C_1$-$C_4$alkylene; $Q^2$ is —CO$_2$R$^{13}$, —C(=O)R$^{12}$, —C(=O)N(R$^{13}$)$_2$, —C(=O)NHSO$_2$R$^{12}$, an optionally substituted $C_3$-$C_6$cycloalkyl, an optionally substituted aryl, or an optionally substituted heteroaryl.

In some embodiments, $R^{10}$ is —C(=O)R$^{14}$, —C(=O)N(R$^{16}$)$_2$, or —S(=O)$_2$R$^{15}$; $R^{14}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-aryl or an optionally substituted —$C_1$-$C_4$alkyl-heteroaryl; $R^{15}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-aryl or an optionally substituted —$C_1$-$C_4$alkyl-heteroaryl; each $R^{16}$ is independently H, $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-aryl or an optionally substituted —$C_1$-$C_4$alkyl-heteroaryl; or two $R^{16}$ groups attached to the same N atom are taken together with the N atom to which they are attached to form an optionally substituted heterocycloalkyl; $R^{11}$ is $C_1$-$C_6$alkyl, $C_1$-$C_6$heteroalkyl, $C_1$-$C_6$haloalkyl, —$C_1$-$C_6$alkylene-O—$R^{17}$, —$C_1$-$C_6$alkylene-S—$R^{17}$, —$C_1$-$C_6$alkylene-S(=O)—$R^{17}$, —$C_1$-$C_6$alkylene-S(=O)$_2$—$R^{17}$, —$C_1$-$C_6$alkylene-NR$^{13}$—$R^{17}$, —$C_1$-$C_6$alkylene-C(=O)O—$R^{17}$—, —$C_1$-$C_6$alkylene-OC(=O)—$R^{17}$, —$C_1$-$C_6$alkylene-NR$^{13}$C(=O)—$R^{17}$ or —$C_1$-$C_6$alkylene-C(=O)NR$^{13}$—$R^{17}$; $R^{17}$ is H, $C_1$-$C_6$alkyl, $C_1$-$C_6$heteroalkyl, $C_1$-$C_6$haloalkyl, an optionally substituted cycloalkyl, an optionally substituted heterocycloalkyl, an optionally substituted aryl, an optionally substituted benzyl, or an optionally substituted heteroaryl.

In other embodiments, $R^{10}$ is —C(=O)$R^{14}$, —C(=O)OR$^{15}$, —C(=O)N(R$^{16}$)$_2$, or —S(=O)$_2$R$^{15}$; $R^{14}$ is $C_1$-$C_6$alkyl, $C_1$-$C_6$fluoroalkyl, $C_1$-$C_6$heteroalkyl, an optionally substituted —$C_1$-$C_4$alkyl-aryl or an optionally substituted —$C_1$-$C_4$alkyl-heteroaryl; $R^{15}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-aryl or an optionally substituted —$C_1$-$C_4$alkyl-heteroaryl; each $R^{16}$ is independently H, $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-aryl or an optionally substituted —$C_1$-$C_4$alkyl-heteroaryl; $R^{11}$ is $C_1$-$C_6$alkyl, $C_1$-$C_6$heteroalkyl, $C_1$-$C_6$haloalkyl, (an optionally substituted monocyclic or bicyclic cycloalkyl), (an optionally substituted monocyclic or bicyclic heterocycloalkyl), an optionally substituted aryl, or an optionally substituted heteroaryl, —$C_1$-$C_6$alkylene-O—$R^{17}$, —$C_1$-$C_6$alkylene-S—$R^{17}$, —$C_1$-$C_6$alkylene-S(=O)—$R^{17}$, —$C_1$-$C_6$alkylene-S(=O)$_2$—$R^{17}$, —$C_1$-$C_6$alkylene-NR$^{13}$—$R^{17}$, —$C_1$-$C_6$alkylene-C(=O)O—$R^{17}$—, —$C_1$-$C_6$alkylene-OC(=O)—$R^{17}$, —$C_1$-$C_6$alkylene-NR$^{13}$C(=O)—$R^{17}$ or —$C_1$-$C_6$alkylene-C(=O)NR$^{13}$—$R^{17}$; $R^{17}$ is H, $C_1$-$C_6$alkyl, $C_1$-$C_6$heteroalkyl, $C_1$-$C_6$haloalkyl, an optionally substituted cycloalkyl, an optionally substituted heterocycloalkyl, an optionally substituted aryl, an optionally substituted benzyl, or an optionally substituted heteroaryl.

In some other embodiments, $R^{10}$ is —C(=O)$R^{14}$, —C(=O)OR$^{15}$, —C(=O)N(R$^{16}$)$_2$, or —S(=O)$_2$R$^{15}$; $R^{14}$ is $C_1$-$C_6$heteroalkyl, an optionally substituted —$C_1$-$C_4$alkyl-aryl or an optionally substituted —$C_1$-$C_4$alkyl-heteroaryl; $R^{15}$ is $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-aryl or an optionally substituted —$C_1$-$C_4$alkyl-heteroaryl; each $R^{16}$ is independently an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-aryl or an optionally substituted —$C_1$-$C_4$alkyl-heteroaryl; $R^{11}$ is $C_1$-$C_6$alkyl, $C_1$-$C_6$heteroalkyl, $C_1$-$C_6$haloalkyl, (an optionally substituted monocyclic or bicyclic cycloalkyl), (an optionally substituted monocyclic or bicyclic heterocycloalkyl), an optionally substituted aryl, or an optionally substituted heteroaryl, $C_1$-$C_6$alkylene-$R^{17}$, —$C_1$-$C_6$alkylene-O—$R^{17}$, —$C_1$-$C_6$alkylene-S—$R^{17}$, —$C_1$-$C_6$alkylene-S(=O)—$R^{17}$, —$C_1$-$C_6$alkylene-S(=O)$_2$—$R^{17}$, —$C_1$-$C_6$alkylene-NR$^{13}$—$R^{17}$, —$C_1$-$C_6$alkylene-C(=O)—$R^{17}$, —$C_1$-$C_6$alkylene-C(=O)O—$R^{17}$—, —$C_1$-$C_6$alkylene-OC(=O)—$R^{17}$, —$C_1$-$C_6$alkylene-NR$^{13}$C(=O)—$R^{17}$ or —$C_1$-$C_6$alkylene-C(=O)NR$^{13}$—$R^{17}$; $R^{17}$ is H, $C_1$-$C_6$alkyl, $C_1$-$C_6$heteroalkyl, $C_1$-$C_6$haloalkyl, an optionally substituted cycloalkyl, an optionally substituted heterocycloalkyl, an optionally substituted aryl, an optionally substituted benzyl, or an optionally substituted heteroaryl.

In some embodiments, $R^{10}$ is —C(=O)$R^{14}$, where, $R^{14}$ is an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-aryl or an optionally substituted —$C_1$-$C_4$alkyl-heteroaryl; $R^{11}$ is $C_1$-$C_6$alkyl, $C_1$-$C_6$heteroalkyl, $C_1$-$C_6$haloalkyl, $C_1$-$C_6$alkylene-$R^{17}$, —$C_1$-$C_6$alkylene-O—$R^{17}$, —$C_1$-$C_6$alkylene-S—$R^{17}$, —$C_1$-$C_6$alkylene-S(=O)—$R^{17}$, —$C_1$-$C_6$alkylene-S(=O)$_2$—$R^{17}$, —$C_1$-$C_6$alkylene-NR$^{13}$—$R^{17}$, —$C_1$-$C_6$alkylene-C(=O)—$R^{17}$, —$C_1$-$C_6$alkylene-C(=O)O—$R^{17}$—, or —$C_1$-$C_6$alkylene-C(=O)NR$^{13}$—$R^{17}$; $R^{17}$ is H, $C_1$-$C_6$alkyl, $C_1$-$C_6$heteroalkyl, $C_1$-$C_6$haloalkyl, an optionally substituted cycloalkyl, an optionally substituted heterocycloalkyl, an optionally substituted aryl, an optionally substituted benzyl, or an optionally substituted heteroaryl.

In some embodiments, $R^{10}$ is —C(=O)$R^{14}$; $R^{14}$ is $C_1$-$C_6$alkyl, $C_1$-$C_6$fluoroalkyl, $C_1$-$C_6$heteroalkyl, an optionally substituted —$C_1$-$C_4$alkyl-aryl or an optionally substituted —$C_1$-$C_4$alkyl-heteroaryl; $R^{11}$ is $C_1$-$C_6$heteroalkyl, (an optionally substituted monocyclic or bicyclic cycloalkyl), (an optionally substituted monocyclic or bicyclic heterocycloalkyl), an optionally substituted aryl, or an optionally substituted heteroaryl, —$C_1$-$C_6$alkylene-O—$R^{17}$, —$C_1$-$C_6$alkylene-S—$R^{17}$, —$C_1$-$C_6$alkylene-S(=O)—$R^{17}$, —$C_1$-$C_6$alkylene-S(=O)$_2$—$R^{17}$, —$C_1$-$C_6$alkylene-NR$^{13}$—$R^{17}$, —$C_1$-$C_6$alkylene-C(=O)O—$R^{17}$—, or —$C_1$-$C_6$alkylene-C(=O)NR$^{13}$—$R^{17}$; $R^{17}$ is H, $C_1$-$C_6$alkyl, $C_1$-$C_6$heteroalkyl, $C_1$-$C_6$haloalkyl, an optionally substituted cycloalkyl, an optionally substituted heterocycloalkyl, an optionally substituted aryl, an optionally substituted benzyl, or an optionally substituted heteroaryl.

In some embodiments, $R^{14}$ is $C_1$-$C_6$alkyl, $C_1$-$C_6$fluoroalkyl, $C_1$-$C_6$heteroalkyl, $C_3$-$C_6$cycloalkyl or -$L^3$-$X^3$-$Q^3$; $L^3$ is a $C_1$-$C_4$alkylene; $X^3$ is a bond, —O—, —S—, —S(=O)—, —S(=O)$_2$—, or —NR$^{13}$—; $Q^3$ is $C_1$-$C_6$alkyl, $C_1$-$C_6$fluoroalkyl, an optionally substituted phenyl, —$C_1$-$C_4$alkyl-(an optionally substituted phenyl). In some embodiments, $R^{14}$ is $C_1$-$C_4$alkyl, $C_1$-$C_4$fluoroalkyl, $C_1$-$C_4$heteroalkyl, $C_3$-$C_6$cycloalkyl or -$L^3$-$X^3$-$Q^3$. In some embodiments, $R^{14}$ is $C_1$-$C_4$alkyl, $C_3$-$C_6$cycloalkyl or -$L^3$-$X^3$-$Q^3$. In some embodiments, $R^{14}$ is $C_1$-$C_4$alkyl. In some embodiments, $R^{14}$ is $C_3$-$C_6$cycloalkyl. In some embodiments, $R^{14}$ is or -$L^3$-$X^3$-$Q^3$.

In some embodiments, $R^{10}$ is —C(=O)OR$^{15}$, or —C(=O)N(R$^{16}$)$_2$; $R^{15}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-aryl or an optionally substituted —$C_1$-$C_4$alkyl-heteroaryl; each $R^{16}$ is independently H, $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-aryl or an optionally substituted —$C_1$-$C_4$alkyl-heteroaryl; $R^{11}$ is $C_1$-$C_6$alkyl, $C_1$-$C_6$heteroalkyl, $C_1$-$C_6$haloalkyl, (an optionally substituted monocyclic or bicyclic cycloalkyl), (an optionally substituted monocyclic or bicyclic heterocycloalkyl), an optionally substituted aryl, or an optionally substituted heteroaryl, —$C_1$-$C_6$alkylene-O—$R^{17}$, —$C_1$-$C_6$alkylene-S—$R^{17}$, —$C_1$-$C_6$alkylene-N$R^{13}$—$R^{17}$, —$C_1$-$C_6$alkylene-C(=O)O—$R^{17}$—, or —$C_1$-$C_6$alkylene-C(=O)N$R^{13}$—$R^{17}$; $R^{17}$ is H, $C_1$-$C_6$alkyl, $C_1$-$C_6$heteroalkyl, $C_1$-$C_6$haloalkyl, an optionally substituted cycloalkyl, an optionally substituted heterocycloalkyl, an optionally substituted aryl, an optionally substituted benzyl, or an optionally substituted heteroaryl;

In one aspect, $R^{10}$ is —C(=O)O$R^{15}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-heterocycloalkyl, an optionally substituted —$C_1$-$C_4$alkyl-aryl or an optionally substituted —$C_1$-$C_4$alkyl-heteroaryl; $R^{11}$ is $C_1$-$C_6$alkyl, $C_1$-$C_6$heteroalkyl, $C_1$-$C_6$haloalkyl, (an optionally substituted monocyclic or bicyclic cycloalkyl), (an optionally substituted monocyclic or bicyclic heterocycloalkyl), an optionally substituted aryl, or an optionally substituted heteroaryl, —$C_1$-$C_6$alkylene-O—$R^{17}$, —$C_1$-$C_6$alkylene-S—$R^{17}$, —$C_1$-$C_6$alkylene-S(=O)—$R^{17}$, —$C_1$-$C_6$alkylene-S(=O)$_2$—$R^{17}$, —$C_1$-$C_6$alkylene-N$R^{13}$—$R^{17}$, —$C_1$-$C_6$alkylene-C(=O)O—$R^{17}$—, or —$C_1$-$C_6$alkylene-C(=O)N$R^{13}$—$R^{17}$; $R^{17}$ is H, $C_1$-$C_6$alkyl, $C_1$-$C_6$heteroalkyl, $C_1$-$C_6$haloalkyl, an optionally substituted cycloalkyl, an optionally substituted heterocycloalkyl, an optionally substituted aryl, an optionally substituted benzyl, or an optionally substituted heteroaryl.

In yet another aspect, $R^{10}$ is —C(=O)O$R^{15}$; $R^{15}$ is $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-aryl or an optionally substituted —$C_1$-$C_4$alkyl-heteroaryl; $R^{11}$ is $C_1$-$C_6$alkyl, $C_1$-$C_6$heteroalkyl, $C_1$-$C_6$haloalkyl, (an optionally substituted monocyclic or bicyclic cycloalkyl), (an optionally substituted monocyclic or bicyclic heterocycloalkyl), an optionally substituted aryl, or an optionally substituted heteroaryl, $C_1$-$C_6$alkylene-$R^{17}$, —$C_1$-$C_6$alkylene-O—$R^{17}$, —$C_1$-$C_6$alkylene-S—$R^{17}$, —$C_1$-$C_6$alkylene-S(=O)—$R^{17}$, —$C_1$-$C_6$alkylene-S(=O)$_2$—$R^{17}$, —$C_1$-$C_6$alkylene-N$R^{13}$—$R^{17}$, —$C_1$-$C_6$alkylene-C(=O)—$R^{17}$, —$C_1$-$C_6$alkylene-C(=O)O—$R^{17}$—, or —$C_1$-$C_6$alkylene-C(=O)N$R^{13}$—$R^{17}$; $R^{17}$ is H, $C_1$-$C_6$alkyl, $C_1$-$C_6$heteroalkyl, $C_1$-$C_6$haloalkyl, an optionally substituted cycloalkyl, an optionally substituted heterocycloalkyl, an optionally substituted aryl, an optionally substituted benzyl, or an optionally substituted heteroaryl.

In one aspect, $R^{15}$ is $C_1$-$C_4$alkyl, $C_3$-$C_6$cycloalkyl, —CH$_2$—$C_3$-$C_6$cycloalkyl, —CH$_2$-(an optionally substituted phenyl), or —CH(CH$_3$)-(an optionally substituted phenyl).

In some embodiments, $R^{10}$ is —C(=O)N($R^{16}$)$_2$. In some embodiments, each $R^{16}$ is independently H, $C_1$-$C_6$alkyl, $C_1$-$C_6$fluoroalkyl, $C_1$-$C_6$heteroalkyl, $C_3$-$C_{10}$cycloalkyl, a substituted or unsubstituted aryl, a substituted or unsubstituted heteroaryl, —$C_1$-$C_4$alkyl-($C_3$-$C_{10}$cycloalkyl), —$C_1$-$C_4$alkyl-(substituted or unsubstituted aryl), or —$C_1$-$C_4$alkyl-(substituted or unsubstituted heteroaryl). In other embodiments, each $R^{16}$ is independently H, $C_1$-$C_6$alkyl, $C_1$-$C_6$fluoroalkyl, $C_1$-$C_6$heteroalkyl, $C_3$-$C_6$cycloalkyl, a substituted or unsubstituted phenyl, a substituted or unsubstituted monocyclic heteroaryl, —CH$_2$—($C_3$-$C_6$cycloalkyl), —CH$_2$-(a substituted or unsubstituted phenyl), —CH(CH$_3$)-(a substituted or unsubstituted phenyl), —CH$_2$-(a substituted or unsubstituted monocyclic heteroaryl), or —CH(CH$_3$)-(a substituted or unsubstituted monocyclic heteroaryl). In other embodiments, each $R^{16}$ is independently H, $C_1$-$C_6$alkyl, $C_3$-$C_6$cycloalkyl, a substituted or unsubstituted phenyl, a substituted or unsubstituted monocyclic heteroaryl, —CH$_2$-(a substituted or unsubstituted phenyl), —CH(CH$_3$)-(a substituted or unsubstituted phenyl), —CH$_2$-(a substituted or unsubstituted monocyclic heteroaryl), or —CH(CH$_3$)-(a substituted or unsubstituted monocyclic heteroaryl). In other embodiments, one $R^{16}$ is H and the other $R^{16}$ is —CH$_2$-(a substituted or unsubstituted phenyl), —CH(CH$_3$)-(a substituted or unsubstituted phenyl), —CH$_2$-(a substituted or unsubstituted monocyclic heteroaryl), or —CH(CH$_3$)-(a substituted or unsubstituted monocyclic heteroaryl). In yet other embodiments, one $R^{16}$ is H and the other $R^{16}$ is —CH$_2$-(a substituted or unsubstituted phenyl), or —CH(CH$_3$)-(a substituted or unsubstituted phenyl). In yet other embodiments, one $R^{16}$ is H and the other $R^{16}$ is —CH$_2$-(a substituted or unsubstituted phenyl).

In one aspect, $R^{11}$ is $C_1$-$C_4$alkyl, $C_1$-$C_4$haloalkyl, or $C_3$-$C_6$cycloalkyl.

In some embodiments, each of $R^2$, $R^3$, $R^6$ and $R^7$ is independently H, halogen, —CN, —OH, —O$R^{13}$, $C_1$-$C_6$alkyl, $C_1$-$C_6$alkoxy, $C_1$-$C_6$fluoroalkyl, $C_1$-$C_6$fluoroalkoxy, or $C_1$-$C_6$heteroalkyl.

In some other embodiments, $R^5$ is H, F, Cl, Br, I, —CN, —NO$_2$, —OH, —O$R^{13}$, —S$R^{12}$, —S(=O)$R^{12}$, —S(=O)$_2$$R^{12}$, —NHS(=O)$_2$$R^{12}$, —C(=O)$R^{12}$, —OC(=O)$R^{12}$, —CO$_2$$R^{13}$, —OCO$_2$$R^{13}$, —N($R^{13}$)$_2$, —NHCH$_2$CO$_2$$R^{13}$, —OCH$_2$CO$_2$$R^{13}$, —SCH$_2$CO$_2$$R^{13}$, —C(=O)N($R^{13}$)$_2$, —OC(=O)N($R^{13}$)$_2$, —NHC(=O)$R^{12}$, —NHC(=O)N($R^{13}$)$_2$, —$C_1$-$C_6$alkyl, —$C_1$-$C_6$fluoroalkyl, $C_1$-$C_6$alkoxy, $C_1$-$C_6$fluoroalkoxy, $C_1$-$C_6$heteroalkyl, an optionally substituted $C_3$-$C_{10}$cycloalkyl, an optionally substituted heterocycloalkyl, optionally substituted phenyl, optionally substituted monocyclic heteroaryl, or an optionally substituted group selected from among —$C_1$-$C_4$alkyl-$C_3$-$C_{10}$cycloalkyl, —$C_1$-$C_4$alkyl-heterocycloalkyl, —$C_1$-$C_4$alkyl-aryl, and —$C_1$-$C_4$alkyl-heteroaryl.

In some other embodiments, each of $R^2$, $R^3$, $R^6$ and $R^7$ is independently H, halogen, —OH, $C_1$-$C_6$alkyl, $C_1$-$C_6$alkoxy, or $C_1$-$C_6$fluoroalkyl.

In some aspects, $R^5$ is H, F, Cl, Br, I, —CN, —NO$_2$, —OH—CH$_3$, —CH$_2$CH$_3$, i-propyl, -tBu, —CF$_3$, —CH$_2$CF$_3$, —OCH$_3$, —OCF$_3$, —S(=O)$_2$CH$_3$, —S(=O)$_2$(optionally substituted phenyl), —NHS(=O)$_2$($C_1$-$C_6$alkyl), —NHS(=O)$_2$(optionally substituted phenyl), —NHS(=O)$_2$(optionally substituted heteroaryl), —C(=O)-(optionally substituted phenyl), —C(=O)CH$_3$, —CO$_2$H, —CO$_2$CH$_3$, —CO$_2$CH$_2$CH$_3$, —NH$_2$, —C(=O)NH$_2$, —C(=O)NH(CH$_3$), —C(=O)NH(CH$_2$CH$_3$), —C(=O)NH (tBu), —C(=O)NH(iPr), —C(=O)NH(CH$_2$CF$_3$), —C(=O)NH(CH$_2$CH$_2$OCH$_3$), —C(=O)NH(optionally substituted phenyl), —C(=O)NH(optionally substituted monocyclic heteroaryl), —C(=O)NH(optionally substituted heterocycloalkyl), —NHC(=O)(C$_1$-C$_6$alkyl), —NHC(=O)(optionally substituted phenyl), —NHC(=O)(optionally substituted heteroaryl), —NHC(=O)NH$_2$, —NHC(=O)NH(optionally substituted phenyl), or an optionally substituted group selected from benzyl, cyclopentyl, cyclohexyl, pyrrolidinyl, piperidinyl, morpholinyl, piperazinyl, thiomorpholinyl, phenyl, pyridinyl, pyrazinyl, imidazolyl, pyrazolyl, 1-methylpyrazol-4-yl, isoxazolyl, oxazolyl, thiazolyl, imidazolyl and isoxazolyl.

In some embodiments, R$^5$ is H, F, Cl, Br, —CH$_3$, —CF$_3$, —C(=O)NH(CH$_2$CH$_3$), —NHC(=O)(CH$_2$CH$_3$), —SO$_2$CH$_3$, phenyl, 4-fluorophenyl, 2-methoxyphenyl, 3-methoxyphenyl, 4-methoxyphenyl, pyridin-2-yl, pyridin-3-yl, pyridin-4-yl, 5-amino-pyrazin-2-yl, pyrazol-1-yl, 1H-pyrazol-4-yl, 1-methyl-1H-pyrazol-4-yl, 3-methyl-3H-imidazol-4-yl, oxazolyl, or 2-methyl-3H-imidazol-4-yl.

In other embodiments, R$^4$ is H, F, Cl, Br, I, —CN, —OH, —OR$^{13}$, —C$_1$-C$_6$alkyl, C$_1$-C$_6$fluoroalkyl, C$_1$-C$_6$fluoroalkoxy, C$_1$-C$_6$alkoxy, C$_1$-C$_6$heteroalkyl; or R$^4$ is —X$^1$-L$^1$-Q$^2$, where, X$^2$ is —O—; L$^1$ is a C$_1$-C$_4$alkylene; Q$^2$ is —CO$_2$R$^{13}$, —C(=O)R$^{12}$, —C(=O)N(R$^{13}$)$_2$, optionally substituted C$_3$-C$_6$cycloalkyl, an optionally substituted aryl, or an optionally substituted heteroaryl.

In other aspects, R$^4$ is H, F, Cl, Br, —CN, —OH, —C$_1$-C$_6$alkyl, C$_1$-C$_6$fluoroalkyl, C$_1$-C$_6$fluoroalkoxy, C$_1$-C$_6$alkoxy, C$_1$-C$_6$heteroalkyl, —O—C$_1$-C$_4$alkylene-CO$_2$R$^{13}$, —O—C$_1$-C$_4$alkylene-C(=O)N(R$^{13}$)$_2$, —O—C$_1$-C$_4$alkylene-(optionally substituted C$_3$-C$_6$cycloalkyl), —O—C$_1$-C$_4$alkylene-(an optionally substituted aryl), or —O—C$_1$-C$_4$alkylene-(an optionally substituted heteroaryl).

In other embodiments, R$^4$ is H, F, Cl, —CF$_3$, —OH, —OCH$_3$, —OCH$_2$-cyclopropyl, —OCH$_2$CO$_2$H, or —OBn.

In one embodiment, the compound of Formula (I) has one of the following structures:

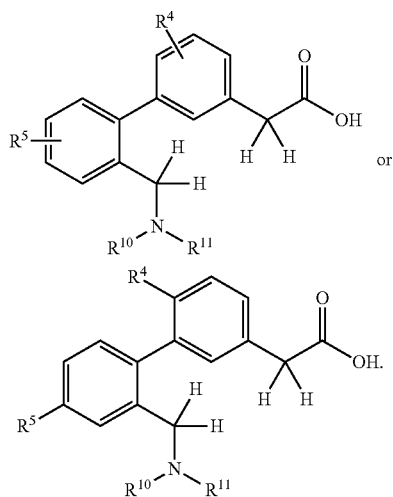

In some embodiments, the compounds of Formula (I) and Formula (II) have a structure of Formula (III), Formula (IV), Formula (V) or Formula (VI):

Formula (III)

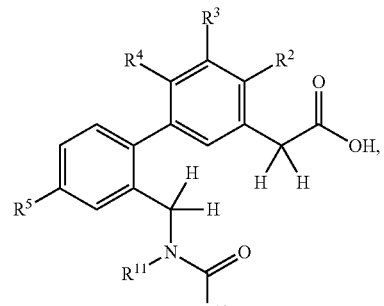

Formula (IV)

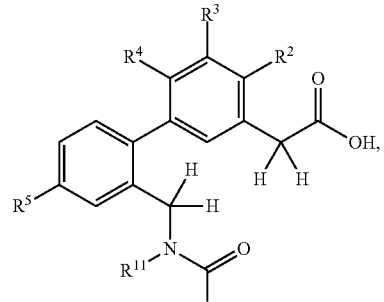

Formula (V)

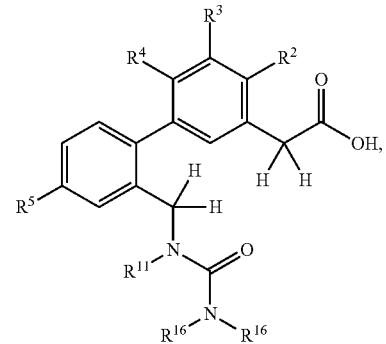

Formula (VI)

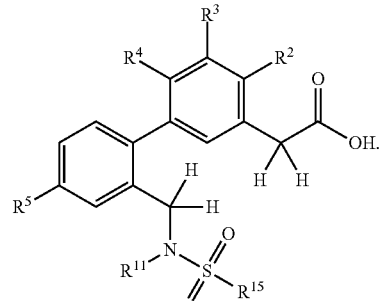

In some embodiments, the compounds described have a structure of Formula (III):

Formula (III)

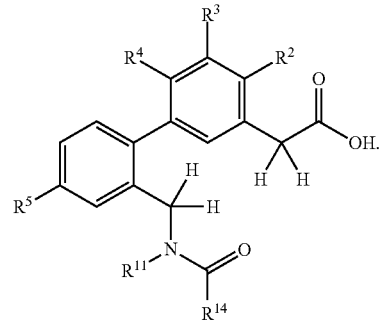

In some embodiments, $R^{14}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-heterocycloalkyl, an optionally substituted —$C_1$-$C_4$alkyl-aryl or an optionally substituted —$C_1$-$C_4$alkyl-heteroaryl; or $R^{14}$ is -$L^3$-$X^3$-$Q^3$; $L^3$ is a $C_1$-$C_6$alkylene; $X^3$ is a bond, —O—, —S—, —S(=O)—, —S(=O)$_2$—, or —$NR^{13}$—; $Q^3$ is an optionally substituted $C_{1-6}$alkyl, $C_{1-6}$fluoroalkyl an optionally substituted $C_3$-$C_{10}$cycloalkyl, an optionally substituted heterocycloalkyl, an optionally substituted aryl, an optionally substituted heteroaryl, an optionally substituted $C_1$-$C_4$alkyl-$C_3$-$C_{10}$cycloalkyl, an optionally substituted $C_1$-$C_4$alkyl-heterocycloalkyl, an optionally substituted $C_1$-$C_4$alkyl-aryl, or an optionally substituted $C_1$-$C_4$alkyl-heteroaryl.

In some embodiments, $R^{14}$ is $C_1$-$C_6$alkyl, $C_1$-$C_6$fluoroalkyl, or $C_1$-$C_6$heteroalkyl; or $R^{14}$ is -$L^3$-$X^3$-$Q^3$; $L^3$ is a $C_1$-$C_6$alkylene; $X^3$ is a bond, —O—, —S—, —S(=O)—, —S(=O)$_2$—, or —$NR^{13}$—; $Q^3$ is an optionally substituted $C_1$-$C_6$alkyl, $C_1$-$C_6$fluoroalkyl an optionally substituted $C_3$-$C_{10}$cycloalkyl, an optionally substituted heterocycloalkyl, an optionally substituted aryl, an optionally substituted heteroaryl, an optionally substituted $C_{1-4}$alkyl-$C_3$-$C_{10}$cycloalkyl, an optionally substituted $C_1$-$C_4$alkyl-heterocycloalkyl, an optionally substituted $C_1$-$C_4$alkyl-aryl, or an optionally substituted $C_1$-$C_4$alkyl-heteroaryl.

In other embodiments, $R^{14}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted aryl, an optionally substituted heteroaryl, an optionally substituted —$C_1$-$C_4$alkyl-aryl or an optionally substituted —$C_1$-$C_4$alkyl-heteroaryl.

In yet other embodiments, $R^{14}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted aryl, or an optionally substituted heteroaryl.

In yet other embodiments, $R^{14}$ is $C_1$-$C_6$alkyl, $C_1$-$C_6$fluoroalkyl, or $C_1$-$C_6$heteroalkyl. In other embodiments, $R^{14}$ is $C_1$-$C_6$alkyl.

In some embodiments, the compounds described have a structure of Formula (IV):

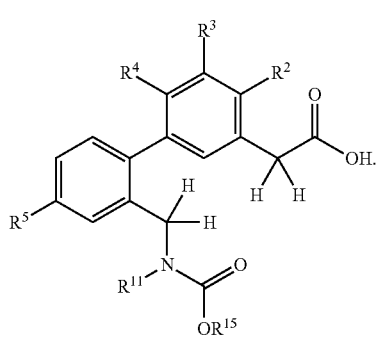

Formula (IV)

In some embodiments, $R^{15}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-heterocycloalkyl, an optionally substituted —$C_1$-$C_4$alkyl-aryl or an optionally substituted —$C_1$-$C_4$alkyl-heteroaryl.

In other embodiments, $R^{15}$ is $C_1$-$C_6$heteroalkyl, an optionally substituted $C_3$-$C_{10}$cycloalkyl, an optionally substituted aryl, an optionally substituted heteroaryl, an optionally substituted —$C_1$-$C_4$alkyl-cycloalkyl, an optionally substituted —$C_1$-$C_4$alkyl-aryl or an optionally substituted —$C_1$-$C_4$alkyl-heteroaryl.

In some embodiments, $R^{15}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted aryl, an optionally substituted heteroaryl, an optionally substituted —$C_1$-$C_4$alkyl-cycloalkyl, an optionally substituted —$C_1$-$C_4$alkyl-aryl, or an optionally substituted —$C_1$-$C_4$alkyl-heteroaryl.

In some embodiments, $R^{15}$ is an optionally substituted —$C_1$-$C_4$alkyl-cycloalkyl, an optionally substituted —$C_1$-$C_4$alkyl-aryl, or an optionally substituted —$C_1$-$C_4$alkyl-heteroaryl. In some embodiments, $R^{15}$ is an optionally substituted —$C_1$-$C_4$alkyl-phenyl.

In some embodiments, the compounds described have a structure of Formula (V):

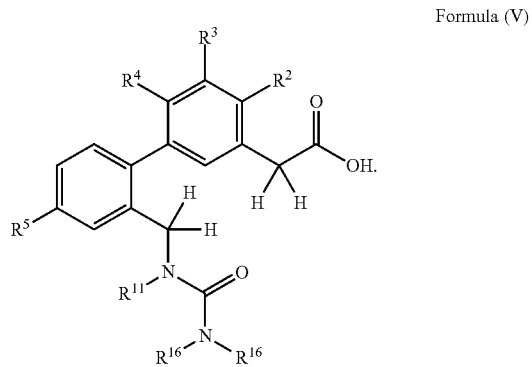

Formula (V)

In some embodiments, each $R^{16}$ is independently H, $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-heterocycloalkyl, an optionally substituted —$C_1$-$C_4$alkyl-aryl or an optionally substituted —$C_1$-$C_4$alkyl-heteroaryl; or two $R^{16}$ groups are taken together with the N atom to which they are attached to form an optionally substituted heterocycloalkyl. In some other embodiments, each $R^{16}$ is independently H, $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-heterocycloalkyl, an optionally substituted —$C_1$-$C_4$alkyl-aryl or an optionally substituted —$C_1$-$C_4$alkyl-heteroaryl. In some other embodiments, one $R^{16}$ is H or $C_1$-$C_6$alkyl and the other $R^{16}$ is an optionally substituted —$C_1$-$C_4$alkyl-phenyl.

In some embodiments, the compounds described have a structure of Formula (VI):

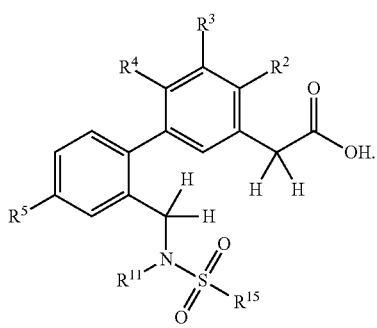

Formula (VI)

In some embodiments, $R^{15}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-heterocycloalkyl, an optionally substituted —$C_1$-$C_4$alkyl-aryl or an optionally substituted —$C_1$-$C_4$alkyl-heteroaryl. In other embodiments, $R^{15}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted aryl, or an optionally substituted heteroaryl.

In some embodiments, $R^{11}$ is $C_1$-$C_6$alkyl, $C_1$-$C_6$heteroalkyl, $C_1$-$C_6$haloalkyl, (an optionally substituted monocyclic or bicyclic cycloalkyl), (an optionally substituted monocyclic or bicyclic heterocycloalkyl), an optionally substituted aryl, or an optionally substituted heteroaryl, $C_1$-$C_6$alkylene-$R^{17}$, —$C_2$-$C_6$alkylene-O—$R^{17}$, —$C_2$-$C_6$alkylene-S—$R^{17}$, —$C_2$-$C_6$alkylene-S(=O)—$R^{17}$, —$C_1$-$C_6$alkylene-S(=O)$_2$—$R^{17}$, —$C_2$-$C_6$alkylene-NR$^{13}$—$R^{17}$, —$C_1$-$C_6$alkylene-C(=O)—$R^{17}$, —$C_1$-$C_6$alkylene-C(=O)O—$R^{17}$—, —$C_2$-$C_6$alkylene-OC(=O)—$R^{17}$, —$C_2$-$C_6$alkylene-NR$^{13}$C(=O)—$R^{17}$ or —$C_1$-$C_6$alkylene-C(=O)NR$^{13}$—$R^{17}$.

In some embodiments, $R^{11}$ is $C_1$-$C_6$heteroalkyl, (an optionally substituted monocyclic or bicyclic cycloalkyl), (an optionally substituted monocyclic or bicyclic heterocycloalkyl), an optionally substituted aryl, or an optionally substituted heteroaryl, —$C_2$-$C_6$alkylene-O—$R^{17}$, —$C_2$-$C_6$alkylene-S—$R^{17}$, —$C_2$-$C_6$alkylene-S(=O)—$R^{17}$, —$C_1$-$C_6$alkylene-S(=O)$_2$—$R^{17}$, —$C_2$-$C_6$alkylene-NR$^{13}$—$R^{17}$, —$C_1$-$C_6$alkylene-C(=O)O—$R^{17}$—, or —$C_1$-$C_6$alkylene-C(=O)NR$^{13}$—$R^{17}$.

In some embodiments, $R^{11}$ is $C_1$-$C_6$alkyl, $C_1$-$C_6$heteroalkyl, $C_1$-$C_6$haloalkyl, —$C_2$-$C_6$alkylene-O—$R^{17}$, —$C_2$-$C_6$alkylene-S—$R^{17}$, —$C_2$-$C_6$alkylene-S(=O)—$R^{17}$, —$C_1$-$C_6$alkylene-S(=O)$_2$—$R^{17}$, —$C_2$-$C_6$alkylene-NR$^{13}$—$R^{17}$, —$C_1$-$C_6$alkylene-C(=O)—$R^{17}$, —$C_1$-$C_6$alkylene-C(=O)O—$R^{17}$—, or —$C_1$-$C_6$alkylene-C(=O)NR$^{13}$—$R^{17}$; $R^{17}$ is H, $C_1$-$C_6$alkyl, $C_1$-$C_6$heteroalkyl, or $C_1$-$C_6$haloalkyl. In some embodiments, $R^{17}$ is H, $C_1$-$C_6$alkyl, $C_1$-$C_6$heteroalkyl, $C_1$-$C_6$haloalkyl, an optionally substituted cycloalkyl, an optionally substituted aryl, or an optionally substituted benzyl.

In some embodiments, $R^{11}$ is $C_1$-$C_6$alkyl, $C_1$-$C_6$heteroalkyl, $C_1$-$C_6$haloalkyl, (an optionally substituted monocyclic or bicyclic cycloalkyl), (an optionally substituted monocyclic or bicyclic heterocycloalkyl), an optionally substituted aryl, an optionally substituted heteroaryl, —$C_1$-$C_6$alkylene-(optionally substituted aryl), —$C_1$-$C_6$alkylene-O—$C_1$-$C_6$alkyl, —$C_1$-$C_6$alkylene-OH, —$C_1$-$C_6$alkylene-NH$_2$, —$C_1$-$C_6$alkylene-NH($C_1$-$C_6$alkyl), —$C_1$-$C_6$alkylene-N($C_1$-$C_6$alkyl)$_2$, —$C_1$-$C_6$alkylene-C(=O)OH, or —$C_1$-$C_6$alkylene-C(=O)NH$_2$.

In some embodiments, $R^{11}$ is $C_1$-$C_6$alkyl, $C_1$-$C_6$heteroalkyl, $C_1$-$C_6$haloalkyl, —$C_1$-$C_6$alkylene-(optionally substituted aryl), —$C_1$-$C_6$alkylene-O—$C_1$-$C_6$alkyl, —$C_1$-$C_6$alkylene-OH, —$C_1$-$C_6$alkylene-NH$_2$, —$C_1$-$C_6$alkylene-NH($C_1$-$C_6$alkyl), —$C_1$-$C_6$alkylene-N($C_1$-$C_6$alkyl)$_2$, —$C_1$-$C_6$alkylene-C(=O)OH, or —$C_1$-$C_6$alkylene-C(=O)NH$_2$.

In some embodiments, $R^{11}$ is (an optionally substituted monocyclic or bicyclic cycloalkyl), (an optionally substituted monocyclic or bicycle heterocycloalkyl), an optionally substituted aryl, or an optionally substituted heteroaryl.

In some embodiments, $R^{11}$ is $C_1$-$C_6$alkyl, $C_1$-$C_6$heteroalkyl, $C_1$-$C_6$haloalkyl, —$C_1$-$C_6$alkylene-C(=O)OH, —$C_1$-$C_6$alkylene-C(=O)O—$C_1$-$C_6$alkyl, or —$C_1$-$C_6$alkylene-C(=O)NH$_2$, (an optionally substituted monocyclic or bicyclic cycloalkyl), (an optionally substituted monocyclic or bicyclic heterocycloalkyl), an optionally substituted aryl, or an optionally substituted heteroaryl.

In some other embodiments, $R^{11}$ is $C_1$-$C_6$alkyl, $C_1$-$C_6$heteroalkyl, $C_1$-$C_6$haloalkyl, —$C_1$-$C_6$alkylene-C(=O)OH, —$C_1$-$C_6$alkylene-C(=O)O—$C_1$-$C_6$alkyl, or —$C_1$-$C_6$alkylene-C(=O)NH$_2$. In yet some other embodiments, $R^{11}$ is $C_1$-$C_6$alkyl, $C_1$-$C_6$heteroalkyl, or $C_1$-$C_6$haloalkyl. In yet some other embodiments, $R^{11}$ is $C_1$-$C_6$alkyl or $C_1$-$C_6$haloalkyl. In yet some other embodiments, $R^{11}$ is $C_1$-$C_6$alkyl. In one aspect, $R^{11}$ is $C_1$-$C_6$alkyl or $C_3$-$C_6$cycloalkyl.

In yet other cases, $R^{11}$ is $C_7$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_6$alkylene-$R^{17}$, —$C_1$-$C_6$alkylene-O—$R^{17}$, —$C_1$-$C_6$alkylene-S—$R^{17}$, —$C_1$-$C_6$alkylene-S(=O)—$R^{17}$, —$C_1$-$C_6$alkylene-S(=O)$_2$—$R^{17}$, —$C_1$-$C_6$alkylene-NR$^{13}$—$R^{17}$, —$C_1$-$C_6$alkylene-C(=O)—$R^{17}$, —$C_1$-$C_6$alkylene-C(=O)O—$R^{17}$—, —$C_1$-$C_6$alkylene-OC(=O)—$R^{17}$, —$C_1$-$C_6$alkylene-NR$^{13}$C(=O)—$R^{17}$ or —$C_1$-$C_6$alkylene-C(=O)NR$^{13}$—$R^{17}$; $R^{17}$ is a substituted or unsubstituted $C_3$-$C_{10}$cycloalkyl, substituted or unsubstituted $C_2$-$C_{10}$heterocycloalkyl, substituted or unsubstituted aryl, substituted or unsubstituted benzyl, or substituted or unsubstituted heteroaryl. In some other cases, $R^{11}$ is $C_7$-$C_{10}$cycloalkyl, substituted or unsubstituted $C_2$-$C_{10}$heterocycloalkyl, substituted or unsubstituted aryl, substituted or unsubstituted heteroaryl, or —$C_1$-$C_6$alkylene-$R^{17}$; $R^{17}$ is a substituted or unsubstituted $C_3$-$C_{10}$cycloalkyl, substituted or unsubstituted $C_2$-$C_{10}$heterocycloalkyl, substituted or unsubstituted aryl, substituted or unsubstituted benzyl, or substituted or unsubstituted heteroaryl.

In some other cases, $R^{11}$ is $C_7$-$C_{10}$cycloalkyl, substituted or unsubstituted $C_2$-$C_{10}$heterocycloalkyl, substituted or unsubstituted aryl, substituted or unsubstituted heteroaryl, or —$C_1$-$C_6$alkylene-$R^{17}$; $R^{17}$ is a substituted or unsubstituted $C_3$-$C_{10}$cycloalkyl, substituted or unsubstituted $C_2$-$C_{10}$heterocycloalkyl, substituted or unsubstituted aryl, substituted or unsubstituted benzyl, or substituted or unsubstituted heteroaryl.

In some embodiments, $R^{12}$ is $C_1$-$C_6$alkyl, $C_1$-$C_6$fluoroalkyl, $C_3$-$C_6$cycloalkyl, a substituted or unsubstituted $C_2$-$C_{10}$heterocycloalkyl, a substituted or unsubstituted phenyl, a substituted or unsubstituted benzyl, a substituted or unsubstituted monocyclic heteroaryl. In other embodiment, $R^{12}$ is $C_1$-$C_6$alkyl, $C_1$-$C_6$fluoroalkyl, a substituted or unsubstituted phenyl, a substituted or unsubstituted benzyl, a substituted or unsubstituted monocyclic heteroaryl. In some embodiments, $R^{12}$ is $C_1$-$C_6$alkyl, $C_1$-$C_6$fluoroalkyl, or a substituted or unsubstituted phenyl. In some embodiments, $R^{12}$ is $C_1$-$C_6$alkyl. In one aspect, $R^{12}$ is $C_1$-$C_4$alkyl or $C_1$-$C_4$fluoroalkyl. In one aspect, $R^{12}$ is $C_1$-$C_4$alkyl.

In some embodiments, each $R^{13}$ is independently selected from H, $C_1$-$C_6$alkyl, $C_1$-$C_6$fluoroalkyl, $C_3$-$C_6$cycloalkyl, a substituted or unsubstituted $C_2$-$C_{10}$heterocycloalkyl, a substituted or unsubstituted phenyl, a substituted or unsubstituted benzyl, a substituted or unsubstituted monocyclic heteroaryl. In some embodiments, each $R^{13}$ is independently selected from H, $C_1$-$C_6$alkyl, $C_1$-$C_6$fluoroalkyl, a substituted or unsubstituted phenyl, a substituted or unsubstituted benzyl, a substituted or unsubstituted monocyclic heteroaryl. In some embodiments, each $R^{13}$ is independently selected from H, $C_1$-$C_6$alkyl, $C_1$-$C_6$fluoroalkyl, a substituted or unsubstituted phenyl. In some embodiments, each $R^{13}$ is independently selected from H and $C_1$-$C_6$alkyl. In one aspect, each $R^{13}$ is independently selected from H, $C_1$-$C_4$alkyl, and $C_1$-$C_4$fluoroalkyl. In one aspect, each $R^{13}$ is independently selected from H and $C_1$-$C_4$alkyl.

In one aspect, $R^1$ is as defined in Table 1 and Table 2. In one aspect, $R^2$ is as defined in Table 1 and Table 2. In one aspect, $R^3$ is as defined in Table 1 and Table 2. In one aspect, $R^4$ is as defined in Table 1 and Table 2. In one aspect, $R^5$ is as defined in Table 1 and Table 2. In one aspect, $R^6$ is as defined in Table 1. In one aspect, $R^7$ is as defined in Table 1. In one aspect, $R^8$ is as defined in Table 1. In one aspect, $R^9$ is as defined in Table 1. In one aspect, $R^{10}$ is as defined in Table 1 and Table 2. In one aspect, $R^{11}$ is as defined in Table 1 and Table 2.

Any combination of the groups described above for the various variables is contemplated herein. Throughout the specification, groups and substituents thereof are chosen by one skilled in the field to provide stable moieties and compounds.

In one aspect, compounds described herein include, but are not limited to, those described in Table 1 and Table 2:

TABLE 1

| | $R^1, R^1{}'$ | $R^2$ | $R^3$ | $R^4$ | $R^5$ | $R^6$ | $R^7$ | $R^8$ | $R^9$ | $R^{11}$ | $R^{10}$ |
|---|---|---|---|---|---|---|---|---|---|---|---|
| 1-1 | H, H | H | H | OCH$_3$ | CF$_3$ | H | H | H | H | —CH$_3$ | —C(=O)—CH$_3$ |
| 1-2 | H, H | H | H | OCH$_3$ | CF$_3$ | H | H | H | H | —CH$_2$CH$_3$ | —C(=O)—CH$_3$ |
| 1-3 | H, H | H | H | OCH$_3$ | CF$_3$ | H | H | H | H | —CH$_2$—C(CH$_3$)$_3$ | —C(=O)—CH$_3$ |
| 1-4 | H, H | H | H | OCH$_3$ | CF$_3$ | H | H | H | H | —CH$_2$CF$_3$ | —C(=O)—CH$_3$ |
| 1-5 | H, H | H | H | OCH$_3$ | CF$_3$ | H | H | H | H | —CH$_2$CH$_2$—OH | —C(=O)—CH$_3$ |
| 1-6 | H, H | H | H | OCH$_3$ | CF$_3$ | H | H | H | H | —CH$_2$CH$_2$—OCH$_3$ | —C(=O)—CH$_3$ |
| 1-7 | H, H | H | H | OCH$_3$ | CF$_3$ | H | H | H | H | —CH$_2$CH$_2$—N(CH$_3$)$_2$ | —C(=O)—CH$_3$ |
| 1-8 | H, H | H | H | OCH$_3$ | CF$_3$ | H | H | H | H | —CH$_2$—CO$_2$H | —C(=O)—CH$_3$ |
| 1-9 | H, H | H | H | F | CF$_3$ | H | H | H | H | —CH$_2$—C(=O)—NH$_2$ | —C(=O)—CH$_3$ |
| 1-10 | H, H | H | H | F | CF$_3$ | H | H | H | H | —CH$_2$CH$_3$ | —C(=O)—CH$_3$ |
| 1-11 | H, H | H | H | OCH$_3$ | CF$_3$ | H | H | H | H | —CH$_2$CF$_3$ | —C(=O)—CH$_3$ |
| 1-12 | H, H | H | H | OCH$_3$ | CF$_3$ | H | H | H | H | Cyclopropyl | —C(=O)—CH$_3$ |
| 1-13 | H, H | H | H | OCH$_3$ | CF$_3$ | H | H | H | H | (S)-Indan-1-yl | —C(=O)—CH$_3$ |
| 1-14 | H, H | H | H | OCH$_3$ | CF$_3$ | H | H | H | H | (R)-Indan-1-yl | —C(=O)—CH$_3$ |
| 1-15 | H, H | H | H | OCH$_3$ | CF$_3$ | H | H | H | H | (1R,2S)-2-Hydroxy-indan-1-yl | —C(=O)—CH$_3$ |
| 1-16 | H, H | H | H | OCH$_3$ | CF$_3$ | H | H | H | H | (1R,2S)-2-Methoxy-indan-1-yl | —C(=O)—CH$_3$ |
| 1-17 | H, H | H | H | OCH$_3$ | CF$_3$ | H | H | H | H | Indan-2-yl | —C(=O)—CH$_3$ |
| 1-18 | H, H | H | H | OCH$_3$ | CF$_3$ | H | H | H | H | Ph | —C(=O)—CH$_3$ |
| 1-19 | H, H | H | H | OCH$_3$ | CF$_3$ | H | H | H | H | —CH$_2$Ph | —C(=O)—CH$_3$ |
| 1-20 | H, H | H | H | OCH$_3$ | CF$_3$ | H | H | H | H | —CH$_2$CH$_2$—Ph | —C(=O)—CH$_3$ |
| 1-21 | H, CH$_3$ | H | H | OCH$_3$ | CF$_3$ | H | H | H | H | —CH$_2$CH$_3$ | —C(=O)—CH$_3$ |
| 1-22 | H, H | H | H | OCH$_3$ | CF$_3$ | H | H | CH$_3$ | H | —CH$_2$CH$_3$ | —C(=O)—CH$_3$ |
| 1-23 | H, H | H | H | OCH$_3$ | CF$_3$ | H | H | H | H | —CH$_2$Ph | —C(=O)—OCH$_3$ |
| 1-24 | H, H | H | H | OCH$_3$ | CF$_3$ | H | H | H | H | —CH$_2$CH$_2$—Ph | —C(=O)—OCH$_3$ |
| 1-25 | H, H | H | H | OCH$_3$ | CF$_3$ | H | H | H | H | Indan-2-yl | —C(=O)—OCH$_3$ |
| 1-26 | H, H | H | H | OCH$_3$ | CF$_3$ | H | H | H | H | —CH$_3$ | —C(=O)—OCH$_3$ |
| 1-27 | H, H | H | H | F | CF$_3$ | H | H | H | H | —CH$_2$CH$_3$ | —C(=O)—OCH$_3$ |
| 1-28 | H, H | H | H | OCH$_3$ | CF$_3$ | H | H | H | H | —CH$_3$ | —C(=O)—CH$_3$ |
| 1-29 | H, H | H | H | OCH$_3$ | CF$_3$ | H | H | H | H | Cyclobutyl | —C(=O)—CH$_3$ |
| 1-30 | H, H | H | H | OCH$_3$ | CF$_3$ | H | H | H | H | Cyclopentyl | —C(=O)—CH$_3$ |
| 1-31 | H, H | H | H | OCH$_3$ | CF$_3$ | H | H | H | H | —CH$_2$CH$_3$ | —C(=O)—CF$_3$ |
| 1-32 | H, H | H | H | OCH$_3$ | CF$_3$ | H | H | H | H | —CH$_2$CH$_3$ | —C(=O)—CH$_3$ |
| 1-33 | H, H | H | H | OCH$_3$ | CF$_3$ | H | H | H | H | —CH$_3$ | —C(=O)-cyclopropyl |
| 1-34 | H, H | H | H | OCH$_3$ | CF$_3$ | H | H | H | H | Cyclobutyl | —C(=O)—OCH$_2$Ph |

TABLE 1-continued

| | $R^1$, $R^{1'}$ | $R^2$ | $R^3$ | $R^4$ | $R^5$ | $R^6$ | $R^7$ | $R^8$ | $R^9$ | $R^{11}$ | $R^{10}$ |
|---|---|---|---|---|---|---|---|---|---|---|---|
| 1-35 | H, H | H | H | OCH$_3$ | CF$_3$ | H | H | H | H | Cyclopentyl | —C(=O)—OCH$_2$Ph |
| 1-36 | H, H | H | H | OCH$_3$ | CF$_3$ | H | H | H | H | Cyclopropyl | —C(=O)—OCH$_2$Ph |
| 1-37 | H, H | H | H | OCH$_3$ | CO$_2$H | H | H | H | H | —CH$_2$CF$_3$ | —C(=O)—CH$_3$ |
| 1-38 | H, H | H | H | OCH$_3$ | CF$_3$ | H | H | H | H | —CH$_2$CH$_3$ | —C(=O)—OCH$_2$-(3,5-dichloro-phenyl) |
| 1-39 | H, H | H | H | OCH$_3$ | CF$_3$ | H | H | H | H | —CH$_2$CH$_3$ | —C(=O)—OCH$_2$-(2-chlorophenyl) |
| 1-40 | H, H | H | H | OCH$_3$ | CF$_3$ | H | H | H | H | —CH$_2$CH$_3$ | —C(=O)—OCH$_2$-(3,5-dichloro-phenyl) |
| 1-41 | H, H | H | H | OCH$_3$ | CF$_3$ | H | H | H | H | —CH$_2$CH$_3$ | —C(=O)—OCH$_2$-(4-fluoro-phenyl) |
| 1-42 | H, H | H | H | OCH$_3$ | CF$_3$ | H | H | H | H | —CH$_2$CH$_3$ | —C(=O)—OCH$_2$-(4-chloro-phenyl) |
| 1-43 | H, H | H | H | OCH$_3$ | CF$_3$ | H | H | H | H | —CH$_2$CH$_3$ | —C(=O)—OCH$_2$-(3-chlorophenyl) |
| 1-44 | H, H | H | H | OCH$_3$ | CF$_3$ | H | H | H | H | —CH$_2$CH$_3$ | —C(=O)—O—CH(CH$_3$)-(4-chlorophenyl) |
| 1-45 | H, H | H | H | OCH$_3$ | CF$_3$ | H | H | H | H | —CH$_2$CH$_3$ | —C(=O)—CH(CH$_3$)—(OPh) |
| 1-46 | H, H | H | H | OCH$_3$ | CF$_3$ | H | H | H | H | —CH$_2$CH$_3$ | —C(=O)—CH$_2$OCH$_3$ |
| 1-47 | H, H | H | H | OCH$_3$ | CF$_3$ | H | H | H | H | —CH$_2$CH$_3$ | —C(=O)—NH-(2-bromophenyl) |
| 1-48 | H, H | H | H | F | CF$_3$ | H | H | H | H | —CH$_2$CH$_3$ | —C(=O)—CH$_2$OPh |
| 1-49 | H, H | H | H | OCH$_3$ | Br | H | H | H | H | —CH$_2$CF$_3$ | —C(=O)—OCH$_2$Ph |
| 1-50 | H, H | H | H | OCH$_3$ | CF$_3$ | H | H | H | H | —CH$_2$CH$_3$ | —C(=O)—CH$_3$ |
| 1-51 | H, H | H | H | OCH$_3$ | NH—C(=O)—CH$_3$ | H | H | H | H | —CH$_2$CH$_3$ | —C(=O)—CH$_3$ |
| 1-52 | H, H | H | H | OCH$_3$ | Pyrazol-1-yl | H | H | H | H | o-Tolyl | —C(=O)—CH$_3$ |
| 1-53 | H, H | H | H | OCH$_3$ | CF$_3$ | H | H | H | H | Thiazol-2-yl | —C(=O)—CH$_3$ |
| 1-54 | H, H | H | H | CH$_3$ | CF$_3$ | H | H | H | H | 2-Methyl-pyrimidin-4-yl | —C(=O)—CH$_3$ |
| 1-55 | H, H | H | H | H | CF$_3$ | H | H | H | H | —CH$_2$CH$_3$ | —C(=O)—CH$_3$ |
| 1-56 | H, H | H | H | F | CF$_3$ | H | H | H | H | —CH$_3$ | —C(=O)—CH$_3$ |
| 1-57 | H, H | OCH$_3$ | H | CH$_3$ | CF$_3$ | H | H | H | H | —CH$_3$ | —C(=O)—CH$_3$ |
| 1-58 | H, H | H | H | Cyclopropyl | CF$_3$ | H | H | H | H | —CH$_3$ | —C(=O)—CH$_3$ |
| 1-59 | H, H | H | H | H | CF$_3$ | H | H | H | H | —CH$_3$ | —C(=O)—CH$_3$ |
| 1-60 | H, H | H | H | CH$_3$ | CF$_3$ | H | H | H | H | —CH$_3$ | —C(=O)—CH$_3$ |
| 1-61 | H, H | CH$_3$ | H | H | Br | H | H | H | H | —CH$_2$CH$_3$ | —C(=O)—CH$_3$ |
| 1-62 | H, H | H | H | OCH$_3$ | NH—C(=O)—CH$_3$ | H | H | H | H | —CH$_2$CH$_3$ | —C(=O)—CH$_3$ |
| 1-63 | H, H | H | H | OCH$_3$ | NH—C(=O)—OCH$_3$ | H | H | H | H | —CH$_3$ | —C(=O)—CH$_3$ |
| 1-64 | H, H | H | H | OCH$_3$ | NH—SO$_2$CH$_3$ | H | H | H | H | —CH$_3$ | —C(=O)—CH$_3$ |
| 1-65 | H, H | H | H | OCH$_3$ | SO$_2$CH$_3$ | H | H | H | H | —CH$_2$CH$_3$ | —C(=O)—CH$_3$ |
| 1-66 | H, H | H | H | OCH$_3$ | Pyrrolidin-1-yl | H | H | H | H | —CH$_2$CH$_3$ | —C(=O)—CH$_3$ |
| 1-67 | H, H | H | H | OCH$_3$ | Pyrazol-1-yl | H | H | H | H | —CH$_3$ | —C(=O)—CH$_3$ |
| 1-68 | H, H | H | H | OCH$_3$ | Cyclopropyl | H | H | H | H | —CH$_2$CH$_3$ | —C(=O)—CH$_3$ |

TABLE 1-continued

| | $R^1$, $R^1$ | $R^2$ | $R^3$ | $R^4$ | $R^5$ | $R^6$ | $R^7$ | $R^8$ | $R^9$ | $R^{11}$ | $R^{10}$ |
|---|---|---|---|---|---|---|---|---|---|---|---|
| 1-71 | H, H | H | H | OCH$_3$ | Phenyl | H | H | H | H | CH$_2$CH$_3$ | —C(=O)—CH$_3$ |
| 1-72 | H, H | H | H | OCH$_3$ | Oxazol-2-yl | H | H | H | H | CH$_2$CH$_3$ | —C(=O)—CH$_3$ |
| 1-73 | H, H | H | H | OCH$_3$ | 1H-Pyrazol-4-yl | H | H | H | H | CH$_2$CH$_3$ | —C(=O)—CH$_3$ |
| 1-74 | H, H | H | H | OCH$_3$ | Pyridin-2-yl | H | H | H | H | CH$_2$CH$_3$ | —C(=O)—CH$_3$ |
| 1-75 | H, H | H | H | OCH$_3$ | CF$_3$ | H | H | H | H | CH$_2$CH$_3$ | —C(=O)—O-(cyclopropyl) |
| 1-76 | H, H | H | H | OCH$_3$ | CF$_3$ | H | H | H | H | CH$_2$CH$_3$ | —C(=O)—NHCH$_3$ |
| 1-77 | H, H | H | H | OCH$_3$ | CF$_3$ | H | H | H | H | —CH$_3$ | —C(=O)-cyclopropyl |
| 1-78 | H, H | H | H | Cl | CF$_3$ | H | H | H | H | CH$_2$CH$_3$ | —C(=O)-cyclopropyl |
| 1-79 | H, H | H | H | OCH$_3$ | CF$_3$ | H | H | H | H | CH$_2$CH$_3$ | —C(=O)-cyclopentyl |
| 1-80 | H, H | H | H | OCH$_3$ | CF$_3$ | H | H | H | H | CH$_2$CH$_3$ | —C(=O)—CH$_3$ |
| 1-81 | H, H | H | H | OCH$_3$ | CF$_3$ | H | H | H | H | CH$_2$CH$_3$ | —C(=O)—Ph |
| 1-82 | H, H | H | H | Pyridin-2-yl | CF$_3$ | H | H | H | H | CH$_2$CH$_3$ | —C(=O)-pyridin-2-yl |
| 1-83 | H, H | H | H | OCH$_3$ | CF$_3$ | H | H | H | H | CH$_2$CH$_3$ | —C(=O)-(pyrazin-2-yl) |
| 1-84 | H, H | H | H | OCH$_3$ | CF$_3$ | H | H | H | H | CH$_2$CH$_3$ | —C(=O)-(1-methyl-1H-pyrazol-3-yl) |
| 1-85 | H, H | H | H | OCH$_3$ | H | H | H | H | H | CH$_2$CH$_3$ | —C(=O)—CH$_3$ |
| 1-86 | H, H | H | H | OCH$_3$ | H | H | Br | H | H | CH$_2$CH$_3$ | —C(=O)—CH$_3$ |
| 1-87 | H, H | H | H | OCH$_3$ | H | H | —NH—C(=O)—CH$_3$ | H | H | CH$_2$CH$_3$ | —C(=O)—CH$_3$ |
| 1-88 | H, H | H | H | OCH$_3$ | H | H | —NH—C(=O)—OCH$_3$ | H | H | CH$_2$CH$_3$ | —C(=O)—CH$_3$ |
| 1-89 | H, H | H | H | OCH$_3$ | H | H | —NH—SO$_2$CH$_3$ | H | H | CH$_2$CH$_3$ | —C(=O)—CH$_3$ |
| 1-90 | H, H | H | H | OCH$_3$ | H | —SO$_2$—CH$_3$ | Pyrrolidin-1-yl | H | H | CH$_2$CH$_3$ | —C(=O)—CH$_3$ |
| 1-91 | F, F | H | H | OCH$_3$ | H | H | Pyrazol-1-yl | H | H | CH$_2$CH$_3$ | —C(=O)—CH$_3$ |
| 1-92 | H, H | H | H | OCH$_3$ | CF$_3$ | H | H | H | H | CH$_2$CH$_3$ | —C(=O)—CH$_2$OCH$_2$Ph |
| 1-93 | H, H | H | H | OCH$_3$ | CF$_3$ | H | H | H | H | CH$_2$CH$_3$ | —C(=O)—CH$_2$O-(4-chlorophenyl) |
| 1-94 | H, H | H | H | OCH$_3$ | CF$_3$ | H | H | H | H | CH$_2$CH$_3$ | —C(=O)—N(CH$_2$CH$_3$)—(CH$_2$Ph) |
| 1-96 | H, H | H | H | OCH$_3$ | CF$_3$ | H | H | H | H | CH$_2$CH$_3$ | —C(=O)—NHCH$_2$Ph |
| 1-97 | H, H | H | H | OCH$_3$ | CF$_3$ | H | H | H | H | CH$_2$CH$_3$ | —C(=O)-(pyrrolidin-1-yl) |
| 1-98 | H, CH$_3$ | H | H | OCH$_3$ | CF$_3$ | H | H | H | H | CH$_2$CH$_3$ | —C(=O)—CH$_2$Ph |
| 1-99 | H, H | H | H | OCH$_3$ | CF$_3$ | H | H | H | H | CH$_2$CH$_3$ | —NH—CN |
| 1-100 | H, H | H | H | OCH$_3$ | CF$_3$ | H | H | H | H | CH$_2$CH$_2$—Ph | —SO$_2$—CH$_3$ |
| 1-101 | H, H | OCH$_3$ | H | OCH$_3$ | CF$_3$ | H | H | H | H | (1S,2R)-CH(CH$_3$)—CH(Ph)(OH) | —C(=O)—CH$_3$ |
| 1-104 | H, H | H | Cl | H | CF$_3$ | H | H | H | H | CH$_2$CH$_3$ | —C(=O)—OCH$_3$ |
| 1-107 | H, H | H | CF$_3$ | H | CF$_3$ | H | H | H | H | CH$_2$CH$_3$ | —C(=O)—OCH$_3$ |
| 1-108 | H, H | H | H | Cl | CF$_3$ | H | H | H | H | CH$_2$CH$_3$ | —C(=O)—OCH$_3$ |
| 1-109 | H, H | H | H | OCH$_3$ | CF$_3$ | H | H | H | H | CH$_2$CH$_3$ | —C(=O)—OCH$_3$ |
| 1-110 | H, H | H | H | OCH$_3$ | CF$_3$ | H | H | H | H | CH$_2$CH$_3$ | —C(=O)—OCH$_2$Ph |
| 1-111 | H, H | H | H | OCH$_3$ | CF$_3$ | H | H | H | H | CH$_2$CH$_3$ | —C(=N—CN)—NHCH$_2$Ph |

TABLE 1-continued

| | $R^1$, $R^1$ | $R^2$ | $R^3$ | $R^4$ | $R^5$ | $R^6$ | $R^7$ | $R^8$ | $R^9$ | $R^{11}$ | $R^{10}$ |
|---|---|---|---|---|---|---|---|---|---|---|---|
| 1-112 | H, H | H | H | OCH$_3$ | CF$_3$ | H | H | H | H | CH$_2$CH$_3$ | —C(=N—CN)—NHCH$_2$-(cyclohexyl) |
| 1-113 | H, H | H | H | OCH$_3$ | CF$_3$ | H | H | H | H | CH$_2$CH$_3$ | —C(=N—CN)—NHCH$_2$—C(CH$_3$)$_3$ |
| 1-114 | H, H | H | H | OCH$_3$ | CF$_3$ | H | H | H | H | CH$_2$CH$_3$ | —C(=N—CN)—NHCH$_2$-(4-methoxyphenyl) |
| 1-115 | CH$_3$, CH$_3$ | H | H | OCH$_3$ | CF$_3$ | H | H | H | H | CH$_2$CH$_3$ | —C(=O)—CH$_3$ |
| 1-116 | CH$_3$, CH$_3$ | H | H | OCH$_3$ | CF$_3$ | H | H | H | H | CH$_2$CH$_3$ | —C(=O)—OCH$_2$Ph |
| 1-117 | H, H | H | H | OCH$_3$ | CF$_3$ | H | H | H | H | CH$_2$CH$_3$ | —CH$_2$SPh |
| 1-118 | H, H | H | H | OCH$_3$ | CF$_3$ | H | H | H | H | CH$_2$CH$_3$ | —C(=O)—C(CH$_3$)$_2$—O-(4-chlorphenyl) |
| 1-119 | H, H | H | H | OCH$_3$ | CF$_3$ | H | H | H | H | CH$_2$CH$_3$ | —C(=O)—CH$_2$—SO—Ph |
| 1-120 | H, H | CF$_3$ | H | OCH$_3$ | CF$_3$ | H | H | H | H | CH$_2$CH$_3$ | —C(=O)—CH$_2$—SO—Ph |
| 1-121 | H, H | Cl | H | OCH$_3$ | CF$_3$ | H | H | H | H | CH$_2$CH$_3$ | —C(=O)—NHPh |
| 1-122 | H, H | H | H | OCH$_3$ | CF$_3$ | H | H | H | OCH$_3$ | CH$_2$CH$_3$ | —C(=O)—OCH$_2$Ph |
| 1-123 | H, H | H | H | H | CF$_3$ | H | H | H | OCH$_3$ | CH$_2$CH$_3$ | —C(=O)—OCH$_2$-(3,5-difluorophenyl) |
| 1-124 | H, H | H | H | H | H | H | H | H | H | CH$_2$CH$_3$ | —C(=O)—OCH$_2$Ph |
| 1-125 | H, H | H | F | H | CF$_3$ | H | H | H | H | CH$_2$CH$_3$ | —C(=O)—OCH$_2$Ph |
| 1-126 | H, H | H | H | H | CF$_3$ | H | H | H | H | CH$_2$CH$_3$ | —C(=O)—OCH$_2$Ph |
| 1-127 | H, H | H | H | H | CF$_3$ | H | H | H | H | CH$_2$CH$_3$ | —C(=O)—OCH$_2$Ph |
| 1-128 | H, H | H | H | —OCH$_2$—Ph | CF$_3$ | H | H | H | H | CH$_2$CH$_3$ | —C(=O)—OCH$_2$Ph |
| 1-129 | H, H | H | H | —OCH$_2$—CH$_3$ | CF$_3$ | H | H | H | H | CH$_2$CH$_3$ | —C(=O)—OCH$_2$Ph |
| 1-130 | H, H | H | H | —OCH$_2$-(cyclopropyl) | CF$_3$ | H | H | H | H | CH$_2$CH$_3$ | —C(=O)—OCH$_2$Ph |
| 1-131 | H, H | H | H | OCH$_3$ | CF$_3$ | H | H | H | H | CH$_2$CH$_3$ | —C(=O)-(1-(2,4-dichlorphenyl)-cycloprop-1-yl) |
| 1-132 | F, F | H | H | OCH$_3$ | CF$_3$ | H | H | H | H | CH$_2$CH$_3$ | —C(=O)—OCH$_2$Ph |
| 1-135 | H, H | H | Cl | OCH$_3$ | CF$_3$ | H | H | H | H | CH$_2$CH$_3$ | —C(=O)-(cyclopropyl) |
| 1-136 | H, H | H | CF$_3$ | H | CF$_3$ | H | H | H | H | CH$_2$CH$_3$ | —C(=O)-(cyclopropyl) |
| 1-137 | H, H | H | Cl | H | CF$_3$ | H | H | H | H | CH$_2$CH$_3$ | —C(=O)—CH$_3$ |
| 1-138 | H, H | H | CF$_3$ | H | CF$_3$ | H | H | H | H | CH$_2$CH$_3$ | —C(=O)—CH$_3$ |
| 1-139 | H, H | H | H | H | CF$_3$ | H | H | H | H | CH$_2$CH$_3$ | —C(=O)—NHCH$_2$-(pyridin-2-yl) |
| 1-140 | H, H | H | H | OCH$_3$ | CF$_3$ | H | H | H | H | CH$_2$CH$_3$ | —C(=O)—NHCH$_2$-(4-cyclopropyl) |
| 1-143 | H, H | H | H | OCH$_3$ | CF$_3$ | H | H | H | H | CH$_2$CH$_3$ | —C(=O)—NHCH$_2$-(cyclopropyl) |
| 1-144 | H, H | H | H | H | CF$_3$ | H | H | H | H | CH$_2$CH$_3$ | —C(=O)—OCH$_2$Ph |
| 1-145 | H, H | H | H | Ph | CF$_3$ | H | H | H | H | CH$_2$CH$_3$ | —C(=O)—OCH$_2$Ph |
| 1-146 | H, H | H | H | OCH$_3$ | CF$_3$ | H | H | H | H | CH$_2$CH$_3$ | C(=N—CN)—NHCH$_2$CH$_3$ |
| 1-147 | H, H | H | H | OCH$_3$ | CF$_3$ | H | H | H | H | CH$_2$CH$_3$ | —C(=N—CN)—NHCH$_2$-(cyclopropyl) |
| 1-148 | H, H | H | H | OCH$_3$ | CF$_3$ | H | H | H | H | CH$_2$CH$_3$ | —C(=N—CN)—NHCH$_2$-(pyridin-2-yl) |
| 1-149 | H, H | H | H | OCH$_3$ | CF$_3$ | H | H | H | H | CH$_2$CH$_3$ | —C(=O)—CH$_2$-(pyrazol-1-yl) |
| | H, H | H | H | OCH$_3$ | CF$_3$ | H | H | H | H | CH$_2$CH$_3$ | —C(=O)—CH$_2$-(2-methyl-imidazol-1-yl) |

TABLE 1-continued

| | $R^1$, $R^{1'}$ | $R^2$ | $R^3$ | $R^4$ | $R^5$ | $R^6$ | $R^7$ | $R^8$ | $R^9$ | $R^{10}$ | $R^{11}$ |
|---|---|---|---|---|---|---|---|---|---|---|---|
| 1-150 | H, H | H | H | OCH$_3$ | CF$_3$ | H | H | H | H | —C(=O)—CH$_2$-([1,2,4]triazol-1-yl) | —CH$_2$CH$_3$ |
| 1-151 | H, H | H | H | OCH$_3$ | CF$_3$ | H | H | H | H | —C(=O)—CH$_2$-(pyrrolidin-1-yl) | —CH$_2$CH$_3$ |
| 1-152 | H, H | H | H | OCH$_3$ | CF$_3$ | H | H | H | H | —C(=O)—NHCH$_2$-(3,4-dichlorophenyl) | —CH$_2$CH$_3$ |
| 1-153 | H, H | H | H | OCH$_3$ | NH—(C=O)—CH$_3$ | H | H | H | H | —C(=O)—OCH$_2$Ph | —CH$_2$CH$_3$ |
| 1-154 | H, H | H | H | OCH$_3$ | NH—C(=O)-(4-chlorophenyl) | H | H | H | H | —C(=O)—OCH$_2$Ph | —CH$_2$CH$_3$ |
| 1-155 | H, H | H | H | OCH$_3$ | NH—SO$_2$—CH$_3$ | H | H | H | H | —C(=O)—OCH$_2$Ph | —CH$_2$CH$_3$ |
| 1-156 | H, H | H | H | OCH$_3$ | NH—SO$_2$-(4-chlorophenyl) | H | H | H | H | —C(=O)—OCH$_2$Ph | —CH$_2$CH$_3$ |
| 1-157 | H, H | H | Cl | OCH$_3$ | CF$_3$ | H | H | H | H | —C(=O)—NHCH$_2$Ph | —CH$_2$CH$_3$ |
| 1-158 | H, H | H | CF$_3$ | OCH$_3$ | CF$_3$ | H | H | H | H | —C(=O)—NHCH$_2$Ph | —CH$_2$CH$_3$ |
| 1-159 | H, H | H | F | OCH$_3$ | CF$_3$ | H | H | H | H | —C(=O)—NHCH$_2$Ph | —CH$_2$CH$_3$ |
| 1-163 | H, H | H | CF$_3$ | H | CF$_3$ | H | H | H | H | —C(=O)—OCH$_3$ | —CH$_2$CH$_3$ |
| 1-164 | H, H | H | Cl | H | CF$_3$ | H | H | H | H | —C(=O)—OCH$_3$ | —CH$_2$CH$_3$ |
| 1-165 | H, H | H | H | OCH$_3$ | CF$_3$ | H | H | H | H | —C(=O)—NHCH$_2$-(3,5-dichlorophenyl) | —CH$_2$CH$_3$ |
| 1-168 | H, H | H | H | OCH$_3$ | H | H | CF$_3$ | H | H | —C(=O)—OCH$_2$-(4-fluorophenyl) | —CH$_2$CH$_3$ |
| 1-169 | H, H | H | H | OCH$_3$ | H | H | CH$_3$ | H | H | —C(=O)—OCH$_2$-(4-fluorophenyl) | —CH$_2$CH$_3$ |
| 1-170 | H, H | H | H | OCH$_3$ | H | H | CH$_3$ | H | H | —C(=O)—(cyclopropyl) | —CH$_2$CH$_3$ |
| 1-171 | H, H | H | H | OCH$_3$ | H | H | CH$_3$ | H | H | —C(=O)—(cyclopropyl) | —CH$_2$CH$_3$ |
| 1-172 | H, H | H | H | OCH$_3$ | H | H | H | H | H | —C(=O)—NHCH$_2$Ph | —CH$_2$CH$_3$ |
| 1-173 | H, H | H | H | OCH$_3$ | CF$_3$ | H | H | H | H | —C(=O)—NHCH$_2$Ph | —CH$_2$CH$_3$ |
| 1-174 | H, H | H | H | OCH$_3$ | CF$_3$ | H | H | H | H | —C(=O)—OCH$_2$-(4-chlorophenyl) | —CH$_2$CH$_3$ |
| 1-175 | H, H | H | H | OCH$_3$ | CF$_3$ | H | H | H | H | —C(=O)—OCH$_2$-(4-chlorophenyl) | —CH$_2$CH$_3$ |
| 1-176 | H, H | H | H | OCH$_3$ | CF$_3$ | H | H | H | H | —C(=O)—NHCH$_2$-(4-fluorophenyl) | —CH$_2$CH$_3$ |
| 1-177 | H, H | H | H | OCH$_3$ | CF$_3$ | H | H | H | H | —C(=O)—NHCH$_2$-(3-chlorophenyl) | —CH$_2$CH$_3$ |
| 1-178 | H, H | H | H | OCH$_3$ | CF$_3$ | H | H | H | H | —C(=O)—NHCH$_2$-(3,5-difluorophenyl) | —CH$_2$CH$_3$ |
| 1-179 | H, H | H | H | OCH$_3$ | CF$_3$ | H | H | H | H | (R)—C(=O)—NH—CH(CH$_3$)-(4-chlorophenyl) | —CH$_2$CH$_3$ |
| 1-180 | H, H | H | H | OCH$_3$ | CF$_3$ | H | H | H | H | (S)—C(=O)—NH—CH(CH$_3$)-(4-chlorophenyl) | —CH$_2$CH$_3$ |
| 1-181 | H, H | H | H | OCH$_3$ | CF$_3$ | H | H | H | H | —C(=O)—NHCH$_2$CH$_3$ | —CH$_2$CH$_3$ |
| 1-182 | H, H | H | H | OCH$_3$ | CF$_3$ | H | H | H | H | —C(=O)—NH-(cyclopropyl) | —CH$_2$CH$_3$ |
| 1-183 | H, H | H | H | OCH$_3$ | F | H | H | H | H | —C(=O)—OCH$_2$Ph | —CH$_2$CH$_3$ |
| 1-184 | H, H | H | H | OCH$_3$ | F | H | H | H | H | —C(=O)—CH$_3$ | —CH$_2$CH$_3$ |

TABLE 1-continued

| | $R^1$, $R^1$ | $R^2$ | $R^3$ | $R^4$ | $R^5$ | $R^6$ | $R^7$ | $R^8$ | $R^9$ | $R^{11}$ | $R^{10}$ |
|---|---|---|---|---|---|---|---|---|---|---|---|
| 1-185 | H, H | H | H | OCH$_3$ | F | H | H | H | H | CH$_2$CH$_3$ | —C(=O)—NHCH$_2$-(4-chlorophenyl) |
| 1-186 | H, H | H | H | OCH$_3$ | F | H | H | H | H | CH$_2$CH$_3$ | —C(=O)-(cyclopropyl) |
| 1-187 | H, H | H | H | OCH$_3$ | F | H | H | H | H | CH$_2$CH$_3$ | —C(=O)—NHCH$_2$Ph |
| 1-188 | H, H | H | CF$_3$ | H | CF$_3$ | H | H | H | H | CH$_2$CH$_3$ | —C(=O)—OCH$_2$-(4-chlorophenyl) |
| 1-189 | H, H | H | CF$_3$ | H | CF$_3$ | H | H | H | H | CH$_2$CH$_3$ | —C(=O)—OCH$_2$-(4-chlorophenyl) |
| 1-190 | H, H | H | CF$_3$ | H | CF$_3$ | H | H | H | H | CH$_2$CH$_3$ | —C(=O)—OCH$_2$-(4-fluorophenyl) |
| 1-191 | H, H | H | CF$_3$ | H | CF$_3$ | H | H | H | H | CH$_2$CH$_3$ | —C(=O)—OCH$_2$-(4-fluorophenyl) |
| 1-192 | H, H | H | Cl | H | CF$_3$ | H | H | H | H | CH$_2$CH$_3$ | —C(=O)—NHCH$_2$-(4-chlorophenyl) |
| 1-193 | H, H | H | CF$_3$ | H | H | H | H | H | H | CH$_2$CH$_3$ | —C(=O)—NHCH$_2$-(4-chlorophenyl) |
| 1-194 | H, H | H | H | OCH$_3$ | H | H | OCH$_3$ | H | H | CH$_2$CH$_3$ | —C(=O)—OCH$_2$-(4-chlorophenyl) |
| 1-195 | H, H | H | H | OCH$_3$ | H | H | OCH$_3$ | H | H | CH$_2$CH$_3$ | —C(=O)—NHCH$_2$-(4-fluorophenyl) |
| 1-196 | H, H | H | H | OCH$_3$ | H | H | OCH$_3$ | H | H | CH$_2$CH$_3$ | —C(=O)—OCH$_2$-(4-chlorophenyl) |
| 1-197 | H, H | H | H | OCH$_3$ | CF$_3$ | H | H | H | H | CH$_2$CH$_3$ | —C(=O)-(cyclopropyl) |
| 1-198 | H, H | H | H | H | CF$_3$ | H | H | H | H | CH$_2$CH$_3$ | —C(=O)—NHCH$_2$Ph |
| 1-199 | H, H | H | H | H | CF$_3$ | H | H | H | H | CH$_2$CH$_3$ | —C(=O)—NHCH$_2$-(pyridin-3-yl) |
| 1-200 | H, H | H | H | H | CF$_3$ | H | H | H | H | CH$_2$CH$_3$ | —C(=O)—NHCH$_2$-(pyridin-4-yl) |
| 1-201 | H, H | H | Cl | OCH$_3$ | CF$_3$ | H | H | H | H | CH$_2$CH$_3$ | —C(=O)—NHCH$_2$-(6-chloropyridin-3-yl) |
| 1-202 | H, H | H | CF$_3$ | H | CF$_3$ | H | H | H | H | CH$_2$CH$_3$ | —C(=O)—NHCH$_3$ |
| 1-203 | H, H | H | Cl | H | CF$_3$ | H | H | H | H | CH$_2$CH$_3$ | —C(=O)NHCH$_3$ |
| 1-204 | H, H | H | CF$_3$ | H | CF$_3$ | H | H | H | H | CH$_2$CH$_3$ | —C(=O)—Ph |
| 1-206 | H, H | H | H | OCH$_3$ | CF$_3$ | H | H | H | H | CH$_2$CH$_3$ | —C(=O)—Ph |
| 1-207 | H, H | H | H | OCH$_3$ | CF$_3$ | H | H | H | H | CH$_2$CH$_3$ | —C(=O)-(cyclobutyl) |
| 1-208 | H, H | H | H | OCH$_3$ | CF$_3$ | H | H | H | H | CH$_2$CH$_3$ | —C(=O)—CH$_2$Ph |
| 1-209 | H, H | H | H | OCH$_3$ | CF$_3$ | H | H | H | H | CH$_2$CH$_3$ | —C(=O)—CH$_2$CH$_2$Ph |
| 1-210 | H, H | H | H | OCH$_3$ | CF$_3$ | H | H | H | H | CH$_2$CH$_3$ | —C(=O)-(1-hydroxy-cycloprop-1-yl) |
| 1-211 | H, CH$_3$ | H | H | OCH$_3$ | CF$_3$ | H | H | H | H | CH$_2$CH$_3$ | —C(=O)—NH$_2$ |
| 1-212 | H, CH$_3$ | H | Cl | OCH$_3$ | CF$_3$ | H | H | H | H | CH$_2$CH$_3$ | —C(=O)—CH$_3$ |
| 1-213 | H, CH$_3$ | H | CF$_3$ | OCH$_3$ | CF$_3$ | H | H | H | H | CH$_2$CH$_3$ | —C(=O)-(cyclopropyl) |
| 1-214 | H, CH$_3$ | H | CF$_3$ | OCH$_3$ | CF$_3$ | H | H | H | H | CH$_2$CH$_3$ | —C(=O)—OCH$_2$Ph |
| 1-215 | H, CH$_3$ | H | H | OCH$_3$ | SO$_2$—CH$_3$ | H | H | H | H | CH$_2$CH$_3$ | —C(=O)—CH$_3$ |
| 1-217 | H, H | H | H | OCH$_3$ | C(CH$_3$)$_2$—(OH) | H | OCH$_3$ | H | H | CH$_2$CH$_3$ | —C(=O)-(cyclopropyl) |
| 1-218 | H, H | H | H | H | CF$_3$ | H | OCH$_3$ | H | H | CH$_2$CH$_3$ | —C(=O)—OCH$_2$Ph |
| 1-219 | H, H | H | Cl | H | H | H | OCH$_3$ | H | H | CH$_2$CH$_3$ | —C(=O)—NHCH$_2$Ph |

TABLE 1-continued

| | $R^1, R^1$ | $R^2$ | $R^3$ | $R^4$ | $R^5$ | $R^6$ | $R^7$ | $R^8$ | $R^9$ | $R^{11}$ | $R^{10}$ |
|---|---|---|---|---|---|---|---|---|---|---|---|
| 1-220 | H, H | H | H | OH | CF$_3$ | H | H | H | H | CH$_2$CH$_3$ | —C(=O)—NHCH$_2$Ph |
| 1-221 | H, H | H | Cl | H | H | H | OCH$_3$ | H | H | CH$_2$CH$_3$ | —C(=O)—CH$_2$O-(4-chlorophenyl) |
| 1-222 | H, CH$_3$ | H | Cl | OCH$_3$ | CF$_3$ | H | H | H | H | CH$_2$CH$_3$ | —C(=O)—NHCH$_2$Ph |
| 1-223 | H, CH$_3$ | H | Cl | H | CF$_3$ | H | H | H | H | CH$_2$CH$_3$ | —C(=O)—NHCH$_2$Ph |
| 1-224 | (R)—CH$_3$ | H | H | OCH$_3$ | CF$_3$ | H | H | H | H | CH$_2$CH$_3$ | —C(=O)—(cyclopropyl) |
| 1-225 | (S)—CH$_3$ | H | H | OCH$_3$ | CF$_3$ | H | H | H | H | CH$_2$CH$_3$ | —C(=O)—(cyclopropyl) |
| 1-226 | H, H | H | H | OCH$_3$ | COOH | H | H | H | H | CH$_2$CH$_3$ | —C(=O)—OCH$_3$ |
| 1-227 | H, H | H | H | OCH$_3$ | 6-Ethoxypyridin-3-yl | H | H | H | H | CH$_2$CH$_3$ | —C(=O)-cyclopropyl |
| 1-228 | H, H | H | H | OCH$_3$ | 6-Ethoxypyridin-3-yl | H | H | H | H | CH$_2$CH$_3$ | —C(=O)—NHCH$_2$Ph |
| 1-229 | H, H | H | H | OCH$_3$ | 6-Ethoxypyridin-3-yl | H | H | H | H | CH$_2$CH$_3$ | —C(=O)—(cyclopropyl) |
| 1-230 | H, H | H | H | OCH$_3$ | Quinolin-7-yl | H | H | H | H | CH$_2$CH$_3$ | —C(=O)—(cyclopropyl) |
| 1-231 | H, H | H | H | OCH$_3$ | Quinolin-7-yl | H | H | H | H | CH$_2$CH$_3$ | —C(=O)—NHCH$_2$Ph |
| 1-232 | H, H | H | H | OCH$_3$ | Quinolin-7-yl | H | H | H | H | CH$_2$CH$_3$ | —C(=O)—CH$_2$O-(4-chlorophenyl) |
| 1-233 | H, H | H | H | OCH$_3$ | 1-Methyl-1H-pyrazol-4-yl | H | H | H | H | CH$_2$CH$_3$ | —C(=O)—(cyclopropyl) |
| 1-234 | H, H | H | H | OCH$_3$ | 1-Methyl-1H-pyrazol-4-yl | H | H | H | H | CH$_2$CH$_3$ | —C(=O)—NHCH$_2$Ph |
| 1-236 | CH$_3$, CH$_3$ | H | CF$_3$ | H | CF$_3$ | H | H | H | H | CH$_2$CH$_3$ | —C(=O)—(cyclopropyl) |
| 1-237 | (R)—CH$_3$ | H | CF$_3$ | H | CF$_3$ | H | H | H | H | CH$_2$CH$_3$ | —C(=O)—(cyclopropyl) |
| 1-238 | H, H | H | CF$_3$ | H | CF$_3$ | H | H | H | H | CH$_2$CH$_3$ | —C(=O)—NHCH$_2$Ph |
| 1-239 | (S)—CH$_3$ | H | CF$_3$ | H | CF$_3$ | H | H | H | H | CH$_2$CH$_3$ | —C(=O)—(cyclopropyl) |
| 1-240 | (R)—CH$_3$ | H | H | H | CF$_3$ | H | H | H | H | CH$_2$CH$_3$ | —C(=O)—NHCH$_2$Ph |
| 1-241 | (S)—CH$_3$ | H | H | OCH$_3$ | SCH$_3$ | H | H | H | H | CH$_2$CH$_3$ | —C(=O)—(cyclopropyl) |
| 1-242 | H, H | H | Cl | H | SCH$_3$ | H | H | H | H | CH$_2$CH$_3$ | —C(=O)—(cyclopropyl) |
| 1-243 | H, CH$_3$ | H | H | OCH$_3$ | CF$_3$ | H | H | H | H | CH$_2$CH$_3$ | —C(=O)—NH-(cyclopropyl) |

TABLE 1-continued

| | $R^1, R^1$ | $R^2$ | $R^3$ | $R^4$ | $R^5$ | $R^6$ | $R^7$ | $R^8$ | $R^9$ | $R^{11}$ | $R^{10}$ |
|---|---|---|---|---|---|---|---|---|---|---|---|
| 1-244 | H, H | H | H | H | $CF_3$ | H | H | H | H | $-CH_2CH_3$ | $-C(=O)$-(cyclopropyl) |
| 1-245 | H, H | H | H | $OCH_3$ | $CF_3$ | H | H | H | H | $-CH_2CH_3$ | $-C(=O)-C(CH_3)_2$ |
| 1-246 | H, H | H | H | $OCH_3$ | $CF_3$ | H | H | H | H | $-CH_2CH_3$ | $-C(=O)-C(CH_3)_3$ |
| 1-247 | H, H | H | H | $OCH_3$ | Br | H | H | H | H | $-CH_2CH_3$ | $-C(=O)$-(cyclopropyl) |
| 1-249 | H, H | H | H | $OCH_3$ | 5-Fluoropyridin-2-yl | H | H | H | H | $-CH_2CH_3$ | $-C(=O)$-(cyclopropyl) |
| 1-250 | H, H | H | H | $OCH_3$ | 5-Methoxy-pyrimidin-2-yl | H | H | H | H | $-CH_2CH_3$ | $-C(=O)$-(cyclopropyl) |
| 1-252 | H, H | H | H | $OCH_3$ | $CF_3$ | H | H | H | H | $-CH_2CH_3$ | $-C(=O)-NHCH_2$-(4-hydroxyphenyl) |
| 1-253 | H, H | H | H | $OCH_3$ | $CF_3$ | H | H | H | H | $-CH_2CH_3$ | $-C(=O)-NHCH_2$-(2-hydroxyphenyl) |
| 1-254 | H, H | H | H | $OCH_3$ | 6-Ethoxypyridin-3-yl | H | H | H | H | $-CH_2CH_3$ | $-C(=O)$-Ph |
| 1-255 | H, H | H | H | $OCH_3$ | 6-Ethoxypyridin-3-yl | H | H | H | H | $-CH_2CH_3$ | $-C(=O)-CH_2Ph$ |
| 1-256 | H, H | H | H | $OCH_3$ | 6-Ethoxypyridin-3-yl | H | H | H | H | $-CH_2CH_3$ | $-C(=O)-CH_2CH_2Ph$ |
| 1-257 | H, H | H | H | $OCH_3$ | $CF_3$ | H | H | H | H | $-CH_2CH_3$ | $-C(=O)-NHCH_2$-(3-hydroxyphenyl) |

Compounds in Table 1 are named:
{2'-[(Acetyl-methyl-amino)-methyl]-6-methoxy-4'-trifluoromethyl-biphenyl-3-yl}-acetic acid (Compound 1-1); {2'-[(Acetyl-ethyl-amino)-methyl]-6-methoxy-4'-trifluoromethyl-biphenyl-3-yl}-acetic acid (Compound 1-2); (2'-{[Acetyl-(2,2-dimethyl-propyl)-amino]-methyl}-6-methoxy-4'-trifluoromethyl-biphenyl-3-yl)-acetic acid (Compound 1-3); (2'-{[Acetyl-(2,2,2-trifluoro-ethyl)-amino]-methyl}-6-methoxy-4'-trifluoromethyl-biphenyl-3-yl)-acetic acid (Compound 1-4); (2'-{[Acetyl-(2-hydroxy-ethyl)-amino]-methyl}-6-methoxy-4'-trifluoromethyl-biphenyl-3-yl)-acetic acid (Compound 1-5); (2'-{[Acetyl-(2-methoxy-ethyl)-amino]-methyl}-6-methoxy-4'-trifluoromethyl-biphenyl-3-yl)-acetic acid (Compound 1-6); (2'-{[Acetyl-(2-dimethylamino-ethyl)-amino]-methyl}-6-methoxy-4'-trifluoromethyl-biphenyl-3-yl)-acetic acid (Compound 1-7); {2'-[(Acetyl-carboxymethyl-amino)-methyl]-6-methoxy-4'-trifluoromethyl-biphenyl-3-yl}-acetic acid (Compound 1-8); {2'-[(Acetyl-carbamoylmethyl-amino)-methyl]-6-methoxy-4'-trifluoromethyl-biphenyl-3-yl}-acetic acid (Compound 1-9); {2'-[(Acetyl-ethyl-amino)-methyl]-6-fluoro-4'-trifluoromethyl-biphenyl-3-yl}-acetic acid (Compound 1-10); (2'-{[Acetyl-(2,2,2-trifluoro-ethyl)-amino]-methyl}-6-fluoro-4'-trifluoromethyl-biphenyl-3-yl)-acetic acid (Compound 1-11); {2'-[(Acetyl-cyclopropyl-amino)-methyl]-6-methoxy-4'-trifluoromethyl-biphenyl-3-yl}-acetic acid (Compound 1-12); {2'-[((S)-Acetyl-indan-1-yl-amino)-methyl]-6-methoxy-4'-trifluoromethyl-biphenyl-3-yl}-acetic acid (Compound 1-13); {2'-[((R)-Acetyl-indan-1-yl-amino)-methyl]-6-methoxy-4'-trifluoromethyl-biphenyl-3-yl}-acetic acid (Compound 1-14); (2'-{[Acetyl-((1R,2S)-2-hydroxy-indan-1-yl)-amino]-methyl}-6-methoxy-4'-trifluoromethyl-biphenyl-3-yl)-acetic acid (Compound 1-15); (2'-{[Acetyl-((1R,2S)-2-methoxy-indan-1-yl)-amino]-methyl}-6-methoxy-4'-trifluoromethyl-biphenyl-3-yl)-acetic acid (Compound 1-16); {2'-[(Acetyl-indan-2-yl-amino)-methyl]-6-methoxy-4'-trifluoromethyl-biphenyl-3-yl}-acetic acid (Compound 1-17); {2'-[(Acetyl-phenyl-amino)-methyl]-6-methoxy-4'-trifluoromethyl-biphenyl-3-yl}-acetic acid (Compound 1-18); {2'-[(Acetyl-benzyl-amino)-methyl]-6-methoxy-4'-trifluoromethyl-biphenyl-3-yl}-acetic acid (Compound 1-19); {2'-[(Acetyl-phenethyl-amino)-methyl]-6-methoxy-4'-trifluoromethyl-biphenyl-3-yl}-acetic acid (Compound 1-20); 2-{2'-[(Acetyl-ethyl-amino)-methyl]-6-methoxy-4'-trifluoromethyl-biphenyl-3-yl}-propionic acid (Compound 1-21); {2'-[1-(Acetyl-ethyl-amino)-ethyl]-6-methoxy-4'-trifluoromethyl-biphenyl-3-yl}-acetic acid (Compound 1-22); {2'-[(Ethyl-methoxycarbonyl-amino)-methyl]-6-methoxy-4'-trifluoromethyl-biphenyl-3-yl}-acetic acid (Compound 1-23); {2'-[(Benzyl-methoxycarbonyl-amino)-methyl]-6-methoxy-4'-trifluoromethyl-biphenyl-3-yl}-acetic acid (Compound 1-24); {6-Methoxy-2'-[(methoxycarbonyl-phenethyl-amino)-methyl]-4'-trifluoromethyl-biphenyl-3-yl}-acetic acid (Compound 1-25); {2'-[(Indan-2-yl-methoxycarbonyl-amino)-methyl]-6-methoxy-4'-trifluoromethyl-biphenyl-3-yl}-acetic acid (Compound 1-26); {2'-[(Benzyloxycarbonyl-methyl-amino)-methyl]-6-methoxy-4'-trifluoromethyl-biphenyl-3-yl}-acetic acid (Compound 1-27); {2'-[(Benzyloxycarbonyl-ethyl-amino)-methyl]-6-methoxy-4'-trifluoromethyl-biphenyl-3-yl}-acetic acid (Compound 1-28); {2'-[(Benzyloxycarbonyl-methyl-amino)-methyl]-6-fluoro-4'-trifluoromethyl-biphenyl-3-yl}-acetic acid (Compound 1-29); {2'-[(Acetyl-cyclobutyl-amino)-methyl]-6-methoxy-4'-trifluoromethyl-biphenyl-3-yl}-acetic acid (Compound 1-30); {2'-[(Acetyl-cyclopentyl-amino)-methyl]-6-methoxy-4'-trifluoromethyl-biphenyl-3-yl}-acetic acid (Compound 1-31); (2'-{[Ethyl-(2,2,2-trifluoro-acetyl)-amino]-methyl}-6-methoxy-4'-trifluoromethyl-biphenyl-3-yl)-acetic acid (Compound 1-32); {2'-[(Cyclopropanecarbonyl-ethyl-amino)-methyl]-6-methoxy-4'-trifluoromethyl-biphenyl-3-yl}-acetic acid (Compound 1-33); {2'-[(Benzyloxycarbonyl-cyclobutyl-amino)-methyl]-6-methoxy-4'-trifluoromethyl-biphenyl-3-yl}-acetic acid (Compound 1-34); {2'-[(Benzyloxycarbonyl-cyclopentyl-amino)-methyl]-6-methoxy-4'-trifluoromethyl-biphenyl-3-yl}-acetic acid (Compound 1-35); {2'-[(Benzyloxycarbonyl-cyclopropyl-amino)-methyl]-6-methoxy-4'-trifluoromethyl-biphenyl-3-yl}-acetic acid (Compound 1-36); 2-{[Acetyl-(2,2,2-trifluoro-ethyl)-amino]-methyl}-5'-carboxymethyl-2'-methoxy-biphenyl-4-carboxylic acid (Compound 1-37); (2'-{[(3,5-Dichloro-benzyloxycarbonyl)-ethyl-amino]-methyl}-6-methoxy-4'-trifluoromethyl-biphenyl-3-yl)-acetic acid (Compound 1-38); (2'-{[(2-Chloro-benzyloxycarbonyl)-ethyl-amino]-methyl}-6-methoxy-4'-trifluoromethyl-biphenyl-3-yl)-acetic acid (Compound 1-39); (2'-{[(3,5-Difluoro-benzyloxycarbonyl)-ethyl-amino]-methyl}-6-methoxy-4'-trifluoromethyl-biphenyl-3-yl)-acetic acid (Compound 1-40); (2'-{[Ethyl-(4-fluoro-benzyloxycarbonyl)-amino]-methyl}-6-methoxy-4'-trifluoromethyl-biphenyl-3-yl)-acetic acid (Compound 1-41); (2'-{[(4-Chloro-benzyloxycarbonyl)-ethyl-amino]-methyl}-6-methoxy-4'-trifluoromethyl-biphenyl-3-yl)-acetic acid (Compound 1-42); (2'-{[(3-Chloro-benzyloxycarbonyl)-ethyl-amino]-methyl}-6-methoxy-4'-trifluoromethyl-biphenyl-3-yl)-acetic acid (Compound 1-43); [2'-({[1-(4-Chloro-phenyl)-ethoxycarbonyl]-ethyl-amino}-methyl)-6-methoxy-4'-trifluoromethyl-biphenyl-3-yl]-acetic acid (Compound 1-44); (2'-{[Ethyl-(2-phenoxy-propionyl)-amino]-methyl}-6-methoxy-4'-trifluoromethyl-biphenyl-3-yl)-acetic acid (Compound 1-45); (2'-{[Ethyl-(2-methoxy-acetyl)-amino]-methyl}-6-methoxy-4'-trifluoromethyl-biphenyl-3-yl)-acetic acid (Compound 1-46); {2'-[3-(2-Bromo-phenyl)-1-ethyl-ureidomethyl]-6-methoxy-4'-trifluoromethyl-biphenyl-3-yl}-acetic acid (Compound 1-47); (2'-{[Ethyl-(2-phenoxy-acetyl)-amino]-methyl}-6-methoxy-4'-trifluoromethyl-biphenyl-3-yl)-acetic acid (Compound 1-48); (2'-{[Benzyloxycarbonyl-(2,2,2-trifluoro-ethyl)-amino]-methyl}-6-fluoro-4'-trifluoromethyl-biphenyl-3-yl)-acetic acid (Compound 1-49); {2'-[(Acetyl-ethyl-amino)-methyl]-4'-bromo-6-methoxy-biphenyl-3-yl}-acetic acid (Compound 1-50); {4'-Acetylamino-2'-[(acetyl-ethyl-amino)-methyl]-6-methoxy-biphenyl-3-yl}-acetic acid (Compound 1-51); {2'-[(Acetyl-ethyl-amino)-methyl]-6-methoxy-4'-pyrazol-1-yl-biphenyl-3-yl}-acetic acid (Compound 1-52); {2'-[(Acetyl-o-tolyl-amino)-methyl]-6-methoxy-4'-trifluoromethyl-biphenyl-3-yl}-acetic acid (Compound 1-53); {2'-[(Acetyl-thiazol-2-yl-amino)-methyl]-6-methoxy-4'-trifluoromethyl-biphenyl-3-yl}-acetic acid (Compound 1-54); (2'-{[Acetyl-(2-methyl-pyrimidin-4-yl)-amino]-methyl}-6-methoxy-4'-trifluoromethyl-biphenyl-3-yl)-acetic acid (Compound 1-55); {2'-[(Acetyl-ethyl-amino)-methyl]-6-methyl-4'-trifluoromethyl-biphenyl-3-yl}-acetic acid (Compound 1-56); {2'-[(Acetyl-ethyl-amino)-methyl]-4-methoxy-4'-trifluoromethyl-biphenyl-3-yl}-acetic acid (Compound 1-57); {2'-[(Acetyl-methyl-amino)-methyl]-6-fluoro-4'-trifluoromethyl-biphenyl-3-yl}-acetic acid (Compound 1-58); {2'-[(Acetyl-methyl-amino)-methyl]-

6-methyl-4'-trifluoromethyl-biphenyl-3-yl}-acetic acid (Compound 1-59); {2'-[(Acetyl-ethyl-amino)-methyl]-6-cyclopropyl-4'-trifluoromethyl-biphenyl-3-yl}-acetic acid (Compound 1-60); {2'-[(Acetyl-ethyl-amino)-methyl]-6,4'-bis-trifluoromethyl-biphenyl-3-yl}-acetic acid (Compound 1-61); {2'-[(Acetyl-ethyl-amino)-methyl]-4-methyl-4'-trifluoromethyl-biphenyl-3-yl}-acetic acid (Compound 1-62); {2'-[(Acetyl-methyl-amino)-methyl]-4'-bromo-6-methoxy-biphenyl-3-yl}-acetic acid (Compound 1-63); {4'-Acetylamino-2'-[(acetyl-methyl-amino)-methyl]-6-methoxy-biphenyl-3-yl}-acetic acid (Compound 1-64); {2'-[(Acetyl-ethyl-amino)-methyl]-6-methoxy-4'-methoxycarbonylamino-biphenyl-3-yl}-acetic acid (Compound 1-65); {2'-[(Acetyl-ethyl-amino)-methyl]-4'-methanesulfonylamino-6-methoxy-biphenyl-3-yl}-acetic acid (Compound 1-66); {2'-[(Acetyl-ethyl-amino)-methyl]-4'-methanesulfonyl-6-methoxy-biphenyl-3-yl}-acetic acid (Compound 1-67); {2'-[(Acetyl-ethyl-amino)-methyl]-6-methoxy-4'-pyrrolidin-1-yl-biphenyl-3-yl}-acetic acid (Compound 1-68); {2'-[(Acetyl-methyl-amino)-methyl]-6-methoxy-4'-pyrazol-1-yl-biphenyl-3-yl}-acetic acid (Compound 1-69); {2'-[(Acetyl-ethyl-amino)-methyl]-4'-cyclopropyl-6-methoxy-biphenyl-3-yl}-acetic acid (Compound 1-70); {2'-[(Acetyl-ethyl-amino)-methyl]-6-methoxy-[1,1';4'']terphenyl-3-yl}-acetic acid (Compound 1-71); {2'-[(Acetyl-ethyl-amino)-methyl]-6-methoxy-4'-oxazol-2-yl-biphenyl-3-yl}-acetic acid (Compound 1-72); [2'-[(Acetyl-ethyl-amino)-methyl]-6-methoxy-4'-(1H-pyrazol-4-yl)-biphenyl-3-yl]-acetic acid (Compound 1-73); {2'-[(Acetyl-ethyl-amino)-methyl]-6-methoxy-4'-pyridin-2-yl-biphenyl-3-yl}-acetic acid (Compound 1-74); {2'-[(Cyclopropoxycarbonyl-ethyl-amino)-methyl]-6-methoxy-4'-trifluoromethyl-biphenyl-3-yl}-acetic acid (Compound 1-75); [2'-(1-Ethyl-3-methyl-ureidomethyl)-6-methoxy-4'-trifluoromethyl-biphenyl-3-yl]-acetic acid (Compound 1-76); {2'-[(Cyclopropanecarbonyl-methyl-amino)-methyl]-6-methoxy-4'-trifluoromethyl-biphenyl-3-yl}-acetic acid (Compound 1-77); {2'-[(Cyclopentanecarbonyl-ethyl-amino)-methyl]-6-methoxy-4'-trifluoromethyl-biphenyl-3-yl}-acetic acid (Compound 1-78); {2'-[(Acetyl-ethyl-amino)-methyl]-6-chloro-4'-trifluoromethyl-biphenyl-3-yl}-acetic acid (Compound 1-79); {2'-[(Benzoyl-ethyl-amino)-methyl]-6-methoxy-4'-trifluoromethyl-biphenyl-3-yl}-acetic acid (Compound 1-80); (2'-{[Ethyl-(pyridine-2-carbonyl)-amino]-methyl}-6-methoxy-4'-trifluoromethyl-biphenyl-3-yl)-acetic acid (Compound 1-81); (2'-{[Ethyl-(pyrazine-2-carbonyl)-amino]-methyl}-6-methoxy-4'-trifluoromethyl-biphenyl-3-yl)-acetic acid (Compound 1-82); (2'-{[Ethyl-(1-methyl-1H-pyrazole-3-carbonyl)-amino]-methyl}-6-methoxy-4'-trifluoromethyl-biphenyl-3-yl)-acetic acid (Compound 1-83); {2'-[(Acetyl-ethyl-amino)-methyl]-5'-bromo-6-methoxy-biphenyl-3-yl}-acetic acid (Compound 1-84); {5'-Acetylamino-2'-[(acetyl-ethyl-amino)-methyl]-6-methoxy-biphenyl-3-yl}-acetic acid (Compound 1-85); {2'-[(Acetyl-ethyl-amino)-methyl]-6-methoxy-5'-methoxycarbonylamino-biphenyl-3-yl}-acetic acid (Compound 1-86); {2'-[(Acetyl-ethyl-amino)-methyl]-5'-methanesulfonylamino-6-methoxy-biphenyl-3-yl}-acetic acid (Compound 1-87); {2'-[(Acetyl-ethyl-amino)-methyl]-6-methoxy-5'-pyrrolidin-1-yl-biphenyl-3-yl}-acetic acid (Compound 1-88); {2'-[(Acetyl-ethyl-amino)-methyl]-6-methoxy-5'-pyrazol-1-yl-biphenyl-3-yl}-acetic acid (Compound 1-89); {2'-[(Acetyl-ethyl-amino)-methyl]-3'-methanesulfonyl-6-methoxy-biphenyl-3-yl}-acetic acid (Compound 1-90); {2'-[(Acetyl-ethyl-amino)-methyl]-6-methoxy-4'-trifluoromethyl-biphenyl-3-yl}-difluoro-acetic acid (Compound 1-91); (2'-{[(2-Benzyloxy-acetyl)-ethyl-amino]-methyl}-6-methoxy-4'-trifluoromethyl-biphenyl-3-yl)-acetic acid (Compound 1-92); [2'-({[2-(4-Chloro-phenoxy)-acetyl]-ethyl-amino}-methyl)-6-methoxy-4'-trifluoromethyl-biphenyl-3-yl]-acetic acid (Compound 1-93); [2'-(3-Benzyl-1,3-diethyl-ureidomethyl)-6-methoxy-4'-trifluoromethyl-biphenyl-3-yl]-acetic acid (Compound 1-94); [2'-(3-Benzyl-1-ethyl-ureidomethyl)-6-methoxy-4'-trifluoromethyl-biphenyl-3-yl]-acetic acid (Compound 1-96); (2'-{[Ethyl-(pyrrolidine-1-carbonyl)-amino]-methyl}-6-methoxy-4'-trifluoromethyl-biphenyl-3-yl)-acetic acid (Compound 1-97); 2-{2'-[(Benzyloxycarbonyl-ethyl-amino)-methyl]-6-methoxy-4'-trifluoromethyl-biphenyl-3-yl}-propionic acid (Compound 1-98); [2'-(3-Cyano-1-ethyl-ureidomethyl)-6-methoxy-4'-trifluoromethyl-biphenyl-3-yl]-acetic acid (Compound 1-99); (2'-{[(4-Chloro-benzenesulfonyl)-ethyl-amino]-methyl}-6-methoxy-4'-trifluoromethyl-biphenyl-3-yl)-acetic acid (Compound 1-100); {2'-[(Methanesulfonyl-phenethyl-amino)-methyl]-6-methoxy-4'-trifluoromethyl-biphenyl-3-yl}-acetic acid (Compound 1-101); (2'-{[Acetyl-((1S,2R)-2-hydroxy-1-methyl-2-phenyl-ethyl)-amino]-methyl}-6-methoxy-4'-trifluoromethyl-biphenyl-3-yl)-acetic acid (Compound 1-104); {2'-[(Benzyloxycarbonyl-ethyl-amino)-methyl]-4-methoxy-4'-trifluoromethyl-biphenyl-3-yl}-acetic acid (Compound 1-107); {2'-[(Benzyloxycarbonyl-ethyl-amino)-methyl]-5-chloro-4'-trifluoromethyl-biphenyl-3-yl}-acetic acid (Compound 1-108); {2'-[(Benzyloxycarbonyl-ethyl-amino)-methyl]-5,4'-bis-trifluoromethyl-biphenyl-3-yl}-acetic acid (Compound 1-109); {2'-[(Benzyloxycarbonyl-ethyl-amino)-methyl]-6-chloro-4'-trifluoromethyl-biphenyl-3-yl}-acetic acid (Compound 1-110); [2'-(N'-Benzyl-N''-cyano-N-ethyl-guanidinomethyl)-6-methoxy-4'-trifluoromethyl-biphenyl-3-yl]-acetic acid (Compound 1-111); [2'-(N'-Cyano-N''-cyclohexylmethyl-N-ethyl-guanidinomethyl)-6-methoxy-4'-trifluoromethyl-biphenyl-3-yl]-acetic acid (Compound 1-112); {2'-[N'-Cyano-N''-(2,2-dimethyl-propyl)-N-ethyl-guanidinomethyl]-6-methoxy-4'-trifluoromethyl-biphenyl-3-yl}-acetic acid (Compound 1-113); {2'-[N'-Cyano-N-ethyl-N''-(4-methoxy-benzyl)-guanidinomethyl]-6-methoxy-4'-trifluoromethyl-biphenyl-3-yl}-acetic acid (Compound 1-114); 2-{2'-[(Acetyl-ethyl-amino)-methyl]-6-methoxy-4'-trifluoromethyl-biphenyl-3-yl}-2-methyl-propionic acid (Compound 1-115); 2-{2'-[(Benzyloxycarbonyl-ethyl-amino)-methyl]-6-methoxy-4'-trifluoromethyl-biphenyl-3-yl}-2-methyl-propionic acid (Compound 1-116); (2'-{[Ethyl-(2-phenylsulfanyl-acetyl)-amino]-methyl}-6-methoxy-4'-trifluoromethyl-biphenyl-3-yl)-acetic acid (Compound 1-117); [2'-({[2-(4-Chloro-phenoxy)-2-methyl-propionyl]-ethyl-amino}-methyl)-6-methoxy-4'-trifluoromethyl-biphenyl-3-yl]-acetic acid (Compound 1-118); (2'-{[(2-Benzenesulfinyl-acetyl)-ethyl-amino]-methyl}-6-methoxy-4'-trifluoromethyl-biphenyl-3-yl)-acetic acid (Compound 1-119); (2'-{[(2-Benzenesulfonyl-acetyl)-ethyl-amino]-methyl}-6-methoxy-4'-trifluoromethyl-biphenyl-3-yl)-acetic acid (Compound 1-120); [2'-(1-Ethyl-3-phenyl-ureidomethyl)-6-methoxy-4'-trifluoromethyl-biphenyl-3-yl]-acetic acid (Compound 1-121); {2'-[(Benzyloxycarbonyl-ethyl-amino)-methyl]-6'-methoxy-biphenyl-3-yl}-acetic acid (Compound 1-122); (2'-{[(3,5-Difluoro-benzyloxycarbonyl)-ethyl-amino]-methyl}-6'-methoxy-biphenyl-3-yl)-acetic acid (Compound 1-123); {2'-[(Benzyloxycarbonyl-ethyl-amino)-methyl]-4,4'-bis-trifluoromethyl-biphenyl-3-yl}-acetic acid (Compound 1-124); {2'-[(Benzyloxycarbonyl-ethyl-amino)-methyl]-4-chloro-4'-trifluoromethyl-biphenyl-3-yl}-acetic acid (Compound 1-125); {2'-[(Benzyloxycarbonyl-ethyl-amino)-methyl]-5-fluoro-4'-trifluoromethyl-biphenyl-3-yl}-acetic acid (Compound 1-126); {2'-[(Benzyloxycarbonyl-ethyl-amino)-methyl]-4-fluoro-4'-trifluoromethyl-biphenyl-3-yl}-acetic acid (Compound 1-127); {6-Benzyloxy-2'-[(benzyloxycarbonyl-ethyl-amino)-methyl]-4'-trifluoromethyl-biphenyl-3-yl}-acetic acid (Compound 1-128); {2'-[(Benzyloxycarbonyl-ethyl-amino)-methyl]-6-ethoxy-4'-trifluoromethyl-biphenyl-3-yl}-acetic acid (Compound 1-129); {2'-[(Benzyloxycarbonyl-ethyl-amino)-methyl]-6-cyclopropylmethoxy-4'-trifluoromethyl-biphenyl-3-yl}-acetic acid (Compound 1-130); [2'-({[1-(2,4-Dichloro-phenyl)-cyclopropanecarbonyl]-ethyl-amino}-methyl)-6-methoxy-4'-trifluoromethyl-biphenyl-3-yl]-acetic acid (Compound 1-131); {2'-[(Benzyloxycarbonyl-ethyl-amino)-methyl]-6-methoxy-4'-trifluoromethyl-biphenyl-3-yl}-difluoro-acetic acid (Compound 1-132); {5-Chloro-2'-[(cyclopropanecarbonyl-ethyl-amino)-methyl]-4'-trifluoromethyl-biphenyl-3-yl}-acetic acid (Compound 1-135); {2'-[(Cyclopropanecarbonyl-ethyl-amino)-methyl]-5,4'-bis-trifluoromethyl-biphenyl-3-yl}-acetic acid (Compound 1-136); {2'-[(Acetyl-ethyl-amino)-methyl]-5-chloro-4'-trifluoromethyl-biphenyl-3-yl}-acetic acid (Compound 1-137); {2'-[(Acetyl-ethyl-amino)-methyl]-5,4'-bis-trifluoromethyl-biphenyl-3-yl}-acetic acid (Compound 1-138); [2'-(1-Ethyl-3-pyridin-2-ylmethyl-ureidomethyl)-6-methoxy-4'-trifluoromethyl-biphenyl-3-yl]-acetic acid (Compound 1-139); {2'-[3-(4-Chloro-benzyl)-1-ethyl-ureidomethyl]-6-methoxy-4'-trifluoromethyl-biphenyl-3-yl}-acetic acid (Compound 1-140); {2'-[(Benzyloxycarbonyl-ethyl-amino)-methyl]-4'-trifluoromethyl-biphenyl-3-yl}-acetic acid (Compound 1-143); {2"-[(Benzyloxycarbonyl-ethyl-amino)-methyl]-4'''-trifluoromethyl-[1,1';2',1'''] terphenyl-4'-yl}-acetic acid (Compound 1-144); [2'-(N'-Cyano-N-ethyl-N''-propyl-guanidinomethyl)-6-methoxy-4'-trifluoromethyl-biphenyl-3-yl]-acetic acid (Compound 1-145); [2'-(N'-Cyano-N''-cyclopropylmethyl-N-ethyl-guanidinomethyl)-6-methoxy-4'-trifluoromethyl-biphenyl-3-yl]-acetic acid (Compound 1-146); [2'-(N'-Cyano-N-ethyl-N''-pyridin-2-ylmethyl-guanidinomethyl)-6-methoxy-4'-trifluoromethyl-biphenyl-3-yl]acetic acid (Compound 1-147); (2'-{[Ethyl-(2-pyrazol-1-yl-acetyl)-amino]-methyl}-6-methoxy-4'-trifluoromethyl-biphenyl-3-yl)-acetic acid (Compound 1-148); (2'-({Ethyl-[2-(2-methyl-imidazol-1-yl)-acetyl]amino}-methyl)-6-methoxy-4'-trifluoromethyl-biphenyl-3-yl]acetic acid (Compound 1-149); (2'-{[Ethyl-(2-[1,2,4]triazol-1-yl-acetyl)-amino]-methyl}-6-methoxy-4'-trifluoromethyl-biphenyl-3-yl)-acetic acid (Compound 1-150); (2'-{[Ethyl-(2-pyrrolidin-1-yl-acetyl)-amino]-methyl}-6-methoxy-4'-trifluoromethyl-biphenyl-3-yl)-acetic acid (Compound 1-151); {2'-[3-(3,4-Dichloro-benzyl)-1-ethyl-ureidomethyl]-6-methoxy-4'-trifluoromethyl-biphenyl-3-yl}-acetic acid (Compound 1-152); {4'-Acetylamino-2'-[(benzyloxycarbonyl-ethyl-amino)-methyl]-6-methoxy-biphenyl-3-yl}-acetic acid (Compound 1-153); {2'-[(Benzyloxycarbonyl-ethyl-amino)-methyl]-4'-(4-chloro-benzoylamino)-6-methoxy-biphenyl-3-yl]acetic acid (Compound 1-154); {2'-[(Benzyloxycarbonyl-ethyl-amino)-methyl]-4'-methanesulfonylamino-6-methoxy-biphenyl-3-yl}-acetic acid (Compound 1-155); [2'-[(Benzyloxycarbonyl-ethyl-amino)-methyl]-4'-(4-chloro-benzenesulfonylamino)-6-methoxy-biphenyl-3-yl]-acetic acid (Compound 1-156); [2'-(3-Benzyl-1-ethyl-ureidomethyl)-5-chloro-4'-trifluoromethyl-biphenyl-3-yl]-acetic acid (Compound 1-157); [2'-(3-Benzyl-1-ethyl-ureidomethyl)-5,4'-bis-trifluoromethyl-biphenyl-3-yl]-acetic acid (Compound 1-158); [2'-(3-Benzyl-1-ethyl-ureidomethyl)-5-fluoro-4'-trifluoromethyl-biphenyl-3-yl]-acetic acid (Compound 1-159); {2'-[(Ethyl-methoxycarbonyl-amino)-methyl]-5,4'-bis-trifluoromethyl-biphenyl-3-yl}-acetic acid (Compound 1-163); {5-Chloro-2'-[(ethyl-methoxycarbonyl-amino)-methyl]-4'-trifluoromethyl-biphenyl-3-yl}-acetic acid (Compound 1-164); {2'-[3-(3,5-Dichloro-benzyl)-1-ethyl-ureidomethyl]-6-methoxy-4'-trifluoromethyl-biphenyl-3-yl}-acetic acid (Compound 1-165); (2'-{[Ethyl-(4-fluoro-benzyloxycarbonyl)-amino]-methyl}-6-methoxy-5'-trifluoromethyl-biphenyl-3-yl)-acetic acid (Compound 1-168); (2'-{[Ethyl-(4-fluoro-benzyloxycarbonyl)-amino]-methyl}-6-methoxy-5'-methyl-biphenyl-3-yl)-acetic acid (Compound 1-169); {2'-[(Cyclopropanecarbonyl-ethyl-amino)-methyl]-6-methoxy-5'-trifluoromethyl-biphenyl-3-yl}-acetic acid (Compound 1-170); {2'-[(Cyclopropanecarbonyl-ethyl-amino)-methyl]-6-methoxy-5'-methyl-biphenyl-3-yl}-acetic acid (Compound 1-171); [2'-(3-Benzyl-1-ethyl-ureidomethyl)-6-methoxy-5'-trifluoromethyl-biphenyl-3-yl]-acetic acid (Compound 1-172); [2'-(3-Benzyl-1-ethyl-ureidomethyl)-6-methoxy-5'-methyl-biphenyl-3-yl]-acetic acid (Compound 1-173); (2'-{[(4-Chloro-benzyloxycarbonyl)-ethyl-amino]-methyl}-6-methoxy-5'-trifluoromethyl-biphenyl-3-yl)-acetic acid (Compound 1-174); (2'-{[(4-Chloro-benzyloxycarbonyl)-ethyl-amino]-methyl}-6-methoxy-5'-methyl-biphenyl-3-yl)-acetic acid (Compound 1-175); {2'-[1-Ethyl-3-(4-fluoro-benzyl)-ureidomethyl]-6-methoxy-4'-trifluoromethyl-biphenyl-3-yl}-acetic acid (Compound 1-176); {2'-[3-(3-Chloro-benzyl)-1-ethyl-ureidomethyl]-6-methoxy-4'-trifluoromethyl-biphenyl-3-yl}-acetic acid (Compound 1-177); {2'-[3-(3,5-Difluoro-benzyl)-1-ethyl-ureidomethyl]-6-methoxy-4'-trifluoromethyl-biphenyl-3-yl}-acetic acid (Compound 1-178); (2'-{3-[(R)-1-(4-Chloro-phenyl)-ethyl]-1-ethyl-ureidomethyl}-6-methoxy-4'-trifluoromethyl-biphenyl-3-yl)-acetic acid (Compound 1-179); (2'-{3-[(S)-1-(4-Chloro-phenyl)-ethyl]-1-ethyl-ureidomethyl}-6-methoxy-4'-trifluoromethyl-biphenyl-3-yl)-acetic acid (Compound 1-180); [2'-(1,3-Diethyl-ureidomethyl)-6-methoxy-4'-trifluoromethyl-biphenyl-3-yl]-acetic acid (Compound 1-181); [2'-(3-Cyclopropyl-1-ethyl-ureidomethyl)-6-methoxy-4'-trifluoromethyl-biphenyl-3-yl]-acetic acid (Compound 1-182); {2'-[(Benzyloxycarbonyl-ethyl-amino)-methyl]-4'-fluoro-6-methoxy-biphenyl-3-yl}-acetic acid (Compound 1-183); {2'-[(Acetyl-ethyl-amino)-methyl]-4'-fluoro-6-methoxy-biphenyl-3-yl}-acetic acid (Compound 1-184); {2'-[3-(4-Chloro-benzyl)-1-ethyl-ureidomethyl]-4'-fluoro-6-methoxy-biphenyl-3-yl}-acetic acid (Compound 1-185); {2'-[(Cyclopropanecarbonyl-ethyl-amino)-methyl]-4'-fluoro-6-methoxy-biphenyl-3-yl}-acetic acid (Compound 1-186); [2'-(3-Benzyl-1-ethyl-ureidomethyl)-4'-fluoro-6-methoxy-biphenyl-3-yl]-acetic acid (Compound 1-187); (5-Chloro-2'-{[(4-chloro-benzyloxycarbonyl)-ethyl-amino]-methyl}-4'-trifluoromethyl-biphenyl-3-yl)-acetic acid (Compound 1-188); (2'-{[(4-Chloro-benzyloxycarbonyl)-ethyl-amino]-methyl}-5,4'-bis-trifluoromethyl-biphenyl-3-yl)-acetic acid (Compound 1-189); (5-Chloro-2'-{[ethyl-(4-fluoro-benzyloxycarbonyl)-amino]-methyl}-4'-trifluoromethyl-biphenyl-3-yl)-acetic acid (Compound 1-190); (2'-{[Ethyl-(4-fluoro-benzyloxycarbonyl)-amino]-methyl}-5,4'-bis-trifluoromethyl-biphenyl-3-yl)-acetic acid (Compound 1-191); {5-Chloro-2'-[3-(4-chloro-benzyl)-1-ethyl-ureidomethyl]-4'-trifluoromethyl-biphenyl-3-yl}-acetic acid (Compound 1-192); {2'-[3-(4-Chloro-benzyl)-1-ethyl-ureidomethyl]-5,4'-bis-trifluoromethyl-biphenyl-3-yl}-acetic acid (Compound 1-193); (2'-{[Ethyl-(4-fluoro-benzyloxycarbonyl)-amino]-methyl}-6,5'-dimethoxy-biphenyl-3-yl)-acetic acid (Compound 1-194); (2'-{[(4-Chloro-benzyloxycarbonyl)-ethyl-amino]-methyl}-6,5'-dimethoxy-biphenyl-3-yl)-acetic acid (Compound 1-195); {2'-[(Cyclopropanecarbonyl-ethyl-amino)-methyl]-6,5'-dimethoxy-biphenyl-3-yl}-acetic acid (Compound 1-196); [2'-(3-Benzyl-1-ethyl-ureidomethyl)-6,5'-dimethoxy-biphenyl-3-yl]-acetic acid (Compound 1-197); [2'-(1-Ethyl-3-pyridin-3-ylmethyl-ureidomethyl)-6-methoxy-4'-trifluoromethyl-biphenyl-3-yl]-acetic acid (Compound 1-198); [2'-(1-Ethyl-3-pyridin-4-ylmethyl-ureidomethyl)-6-methoxy-4'-trifluoromethyl-biphenyl-3-yl]-acetic acid (Compound 1-199); {2'-[3-(6-Chloro-pyridin-3-ylmethyl)-1-ethyl-ureidomethyl]-6-methoxy-4'-trifluoromethyl-biphenyl-3-yl}-acetic acid (Compound 1-200); [5-Chloro-2'-(1-ethyl-3-methyl-ureidomethyl)-4'-trifluoromethyl-biphenyl-3-yl]-acetic acid (Compound 1-201); [2'-(1-Ethyl-3-methyl-ureidomethyl)-5,4'-bis-trifluoromethyl-biphenyl-3-yl]-acetic acid (Compound 1-202); {2'-[(Benzoyl-ethyl-amino)-methyl]-5-chloro-4'-trifluoromethyl-biphenyl-3-yl}-acetic acid (Compound 1-203); {2'-[(Benzoyl-ethyl-amino)-methyl]-5,4'-bis-trifluoromethyl-biphenyl-3-yl}-acetic acid (Compound 1-204); {2'-[(Cyclobutanecarbonyl-ethyl-amino)-methyl]-6-methoxy-4'-trifluoromethyl-biphenyl-3-yl}-acetic acid (Compound 1-206); {2'-[(Ethyl-phenylacetyl-amino)-methyl]-6-methoxy-4'-trifluoromethyl-biphenyl-3-yl}-acetic acid (Compound 1-207); (2'-{[Ethyl-(3-phenyl-propionyl)-amino]-methyl}-6-methoxy-4'-trifluoromethyl-biphenyl-3-yl)-acetic acid (Compound 1-208); (2'-{[Ethyl-(1-hydroxy-cyclopropanecarbonyl)-amino]-methyl}-6-methoxy-4'-trifluoromethyl-biphenyl-3-yl)-acetic acid (Compound 1-209); {2'-[(1-Ethyl-ureido)-methyl]-6-methoxy-4'-trifluoromethyl-biphenyl-3-yl}-acetic acid (Compound 1-210); 2-{2'-[(Acetyl-ethyl-amino)-methyl]-5-chloro-4'-trifluoromethyl-biphenyl-3-yl}-propionic acid (Compound 1-211); 2-{5-Chloro-2'-[(cyclopropanecarbonyl-ethyl-amino)-methyl]-4'-trifluoromethyl-biphenyl-3-yl}-propionic acid (Compound 1-212); 2-{2'-[(Acetyl-ethyl-amino)-methyl]-5,4'-bis-trifluoromethyl-biphenyl-3-yl}-propionic acid (Compound 1-213); 2-{2'-[(Cyclopropanecarbonyl-ethyl-amino)-methyl]-5,4'-bis-trifluoromethyl-biphenyl-3-yl}-propionic acid (Compound 1-214); {2'-[(Benzyloxycarbonyl-ethyl-amino)-methyl]-4'-methanesulfonyl-6-methoxy-biphenyl-3-yl}-acetic acid (Compound 1-215); [2'-[(Benzyloxycarbonyl-ethyl-amino)-methyl]-4'-(1-hydroxy-1-methyl-ethyl)-6-methoxy-biphenyl-3-yl]-acetic acid (Compound 1-216); 2-{2'-[(Cyclopropanecarbonyl-ethyl-amino)-methyl]-6-methoxy-4'-trifluoromethyl-biphenyl-3-yl}-propionic acid (Compound 1-217); {5-Chloro-2'-[(cyclopropanecarbonyl-ethyl-amino)-methyl]-5'-methoxy-biphenyl-3-yl}-acetic acid (Compound 1-218); [2'-(3-Benzyl-1-ethyl-ureidomethyl)-5-chloro-5'-methoxy-biphenyl-3-yl]-acetic acid (Compound 1-219); [2'-(3-Benzyl-1-ethyl-ureidomethyl)-6-hydroxy-4'-trifluoromethyl-biphenyl-3-yl]-acetic acid (Compound 1-220); [5-Chloro-2'-({[2-(4-chloro-phenoxy)-acetyl]-ethyl-amino}-methyl)-5'-methoxy-biphenyl-3-yl]-acetic acid (Compound 1-221); 2-[2'-(3-Benzyl-1-ethyl-ureidomethyl)-6-methoxy-4'-trifluoromethyl-biphenyl-3-yl]-propionic acid (Compound 1-222); 2-[2'-(3-Benzyl-1-ethyl-ureidomethyl)-5-chloro-4'-trifluoromethyl-biphenyl-3-yl]-propionic acid (Compound 1-223); (R)-2-{2'-[(Cyclopropanecarbonyl-ethyl-amino)-methyl]-6-methoxy-4'-trifluoromethyl-biphenyl-3-yl}-propionic acid (Compound 1-224); (S)-2-{2'-[(Cyclopropanecarbonyl-ethyl-amino)-methyl]-6-methoxy-4'-trifluoromethyl-biphenyl-3-yl}-propionic acid (Compound 1-225); 2-[(Benzyloxycarbonyl-ethyl-amino)-methyl]-5'-carboxymethyl-2'-methoxy-biphenyl-4-carboxylic acid (Compound 1-226); [2'-[(Cyclopropanecarbonyl-ethyl-amino)-methyl]-4'-(6-ethoxy-pyridin-3-yl)-6-methoxy-biphenyl-3-yl]-acetic acid (Compound 1-227); [2'-(3-Benzyl-1-ethyl-ureidomethyl)-4'-(6-ethoxy-pyridin-3-yl)-6-methoxy-biphenyl-3-yl]-acetic acid (Compound 1-228); [2'-({[2-(4-Chloro-phenoxy)-acetyl]-ethyl-amino}-methyl)-4'-(6-ethoxy-pyridin-3-yl)-6-methoxy-biphenyl-3-yl]acetic acid (Compound 1-229); {2'-[(Cyclopropanecarbonyl-ethyl-amino)-methyl]-6-methoxy-4'-quinolin-7-yl-biphenyl-3-yl}-acetic acid (Compound 1-230); [2'-(3-Benzyl-1-ethyl-ureidomethyl)-6-methoxy-4'-quinolin-7-yl-biphenyl-3-yl]-acetic acid (Compound 1-231); [2'-({[2-(4-Chloro-phenoxy)-acetyl]-ethyl-amino}-methyl)-6-methoxy-4'-quinolin-7-yl-biphenyl-3-yl]-acetic acid (Compound 1-232); [2'-[(Cyclopropanecarbonyl-ethyl-amino)-methyl]-6-methoxy-4'-(1-methyl-1H-pyrazol-4-yl)-biphenyl-3-yl]-acetic acid (Compound 1-233); [2'-(3-Benzyl-1-ethyl-ureidomethyl)-6-methoxy-4'-(1-methyl-1H-pyrazol-4-yl)-biphenyl-3-yl]-acetic acid (Compound 1-234); 2-{2'-[(Cyclopropanecarbonyl-ethyl-amino)-methyl]-5,4'-bis-trifluoromethyl-biphenyl-3-yl}-2-methyl-propionic acid (Compound 1-236); (R)-2-{2'-[(Cyclopropanecarbonyl-ethyl-amino)-methyl]-5,4'-bis-trifluoromethyl-biphenyl-3-yl}-propionic acid (Compound 1-237); (S)-2-{2'-[(Cyclopropanecarbonyl-ethyl-amino)-methyl]-5,4'-bis-trifluoromethyl-biphenyl-3-yl}-propionic acid (Compound 1-238); (R)-2-[2'-(3-Benzyl-1-ethyl-ureidomethyl)-5,4'-bis-trifluoromethyl-biphenyl-3-yl]-propionic acid (Compound 1-239); (S)-2-[2'-(3-Benzyl-1-ethyl-ureidomethyl)-5,4'-bis-trifluoromethyl-biphenyl-3-yl]-propionic acid (Compound 1-240); {2'-[(Cyclopropanecarbonyl-ethyl-amino)-methyl]-6-methoxy-4'-methylsulfanyl-biphenyl-3-yl}-acetic acid (Compound 1-241); {5-Chloro-2'-[(cyclopropanecarbonyl-ethyl-amino)-methyl]-4'-methylsulfanyl-biphenyl-3-yl}-acetic acid (Compound 1-242); 2-[2'-(3-Cyclopropyl-1-ethyl-ureidomethyl)-6-methoxy-4'-trifluoromethyl-biphenyl-3-yl]-propionic acid (Compound 1-243); {2'-[(Cyclopropanecarbonyl-ethyl-amino)-methyl]-4'-trifluoromethyl-biphenyl-3-yl}-acetic acid (Compound 1-244); (2'-{[(2,2-Dimethyl-propionyl)-ethyl-amino]-methyl}-6-methoxy-4'-trifluoromethyl-biphenyl-3-yl)-acetic acid (Compound 1-245); {2'-[(Ethyl-isobutyryl-amino)-methyl]-6-methoxy-4'-trifluoromethyl-biphenyl-3-yl}-acetic acid (Compound 1-246); {4'-Bromo-2'-[(cyclopropanecarbonyl-ethyl-amino)-methyl]-6-methoxy-biphenyl-3-yl}-acetic acid (Compound 1-247); [2'-[(Cyclopropanecarbonyl-ethyl-amino)-methyl]-4'-(5-fluoro-pyridin-2-yl)-6-methoxy-biphenyl-3-yl]-acetic acid (Compound 1-249); [2'-[(Cyclopropanecarbonyl-ethyl-amino)-methyl]-6-methoxy-4'-(5-methoxy-pyrimidin-2-yl)-biphenyl-3-yl]-acetic acid (Compound 1-250); {2'-[1-Ethyl-3-(4-hydroxy-benzyl)-ureidomethyl]-6-methoxy-4'-trifluoromethyl-biphenyl-3-yl}-acetic acid (Compound 1-252); {2'-[1-Ethyl-3-(2-hydroxy-benzyl)-ureidomethyl]-6-methoxy-4'-trifluoromethyl-biphenyl-3-yl}-acetic acid (Compound 1-253); [2'-[(Benzoyl-ethyl-amino)-methyl]-4'-(6-ethoxy-pyridin-3-yl)-6-methoxy-biphenyl-3-yl]-acetic acid (Compound 1-254); {4'-(6-Ethoxy-pyridin-3-yl)-2'-[(ethyl-phenylacetyl-amino)-methyl]-6-methoxy-biphenyl-3-yl}-acetic acid (Compound 1-255); (4'-(6-Ethoxy-pyridin-3-yl)-2'-{[ethyl-(3-phenyl-propionyl)-amino]-methyl}-6-methoxy-biphenyl-3-yl)-acetic acid (Compound 1-256); {2'-[1-Ethyl-3-(3-hydroxy-benzyl)-ureidomethyl]-6-methoxy-4'-trifluoromethyl-biphenyl-3-yl}-acetic acid (Compound 1-257).

methoxy-5'-(2H-tetrazol-5-ylmethyl)-4-trifluoromethyl-biphenyl-2-ylmethyl]-amide (Compound 2-7); Cyclopropanecarboxylic acid (5'-carbamoylmethyl-2'-methoxy-4-trifluoromethyl-biphenyl-2-ylmethyl)-ethyl-amide (Compound 2-8); [2'-(3-Benzyl-1-ethyl-ureidomethyl)-6-hydroxy-4'-trifluoromethyl-biphenyl-3-yl]-acetic acid ethyl ester (Compound 2-9); (R)-2-[2'-(3-Benzyl-1-ethyl-ureidomethyl)-5,4'-bis-trifluoromethyl-biphenyl-3-yl]-N—((R)-1-methyl-2-phenyl-ethyl)-propionamide (Compound 2-10); (S)-2-[2'-(3-Benzyl-1-ethyl-ureidomethyl)-5,4'-bis-trifluoromethyl-biphenyl-3-yl]-N—((R)-1-methyl-2-phenyl-ethyl)-propionamide (Compound 2-11);

TABLE 2

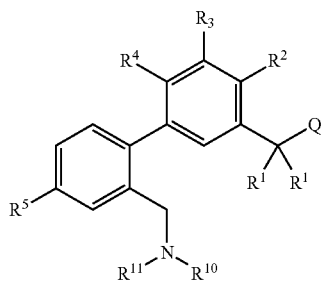

| Cmpd # | $R^1, R^1$ | $R^2$ | $R^3$ | $R^4$ | $R^5$ | $R^{11}$ | $R^{10}$ | Q |
|---|---|---|---|---|---|---|---|---|
| 2-1 | H,H | H | H | OCH₃ | CF₃ | —CH₂CH₃ | —C(=O)—CH₃ | —C(=O)—NH—SO₂CH₃ |
| 2-2 | H,H | H | H | OCH₃ | CF₃ | —CH₂CH₃ | —C(=O)—CH₃ | —C(CH₃)₂(OH) |
| 2-3 | H,H | H | H | OCH₃ | CF₃ | —CH₂CH₃ | —C(=O)-cyclopropyl | —CN |
| 2-4 | H,H | H | H | OCH₃ | CF₃ | —CH₂CH₃ | —C(=O)—OCH₂Ph | —CN |
| 2-5 | H,H | H | H | OCH₃ | CF₃ | —CH₂CH₃ | —C(=O)—OCH₂Ph | Tetrazol-1-yl |
| 2-6 | H,H | H | H | OCH₃ | CF₃ | —CH₂CH₃ | —C(=O)—OCH₂Ph | —C(=O)—NH₂ |
| 2-7 | H,H | H | H | OCH₃ | CF₃ | —CH₂CH₃ | —C(=O)-cyclopropyl | Tetrazol-1-yl |
| 2-8 | H,H | H | H | OCH₃ | CF₃ | —CH₂CH₃ | —C(=O)-cyclopropyl | —C(=O)—NH₂ |
| 2-9 | H,H | H | H | OH | CF₃ | —CH₂CH₃ | —C(=O)—NHCH₂Ph | —C(=O)—OCH₂CH₃ |
| 2-10 | H, (R)—CH₃ | H | CF₃ | H | CF₃ | —CH₂CH₃ | —C(=O)—NHCH₂Ph | (R)—C(=O)—NH—CH(CH₃)(CH₂Ph) |
| 2-11 | H, (S)—CH₃ | H | CF₃ | H | CF₃ | —CH₂CH₃ | —C(=O)—NHCH₂Ph | (R)—C(=O)—NH—CH(CH₃)(CH₂Ph) |
| 2-12 | H, (R)—CH₃ | H | H | OCH₃ | CF₃ | —CH₂CH₃ | —C(=O)—cyclopropyl | —C(=O)—((4R,5S)-4-methyl-2-oxo-5-phenyl-oxazolidin-3-yl) |
| 2-13 | H, (S)—CH₃ | H | H | OCH₃ | CF₃ | CH₂CH₃ | —C(=O)—cyclopropyl | —C(=O)—((4R,5S)-4-methyl-2-oxo-5-phenyl-oxazolidin-3-yl) |
| 2-14 | H,H | H | H | OCH₃ | CO₂H | CH₂CH₃ | —C(=O)—OCH₂Ph | —C(=O)—OCH₂CH₃ |
| 2-15 | H, (R)—CH₃ | H | CF₃ | H | CF₃ | CH₂CH₃ | —C(=O)—cyclopropyl | —C(=O)—((4R,5S)-4-methyl-2-oxo-5-phenyl-oxazolidin-3-yl) |
| 2-16 | H, (S)—CH₃ | H | CF₃ | H | CF₃ | CH₂CH₃ | —C(=O)—cyclopropyl | —C(=O)—((4R,5S)-4-methyl-2-oxo-5-phenyl-oxazolidin-3-yl) |
| 2-17 | H,H | H | H | OCH₃ | CF₃ | CH₂CH₃ | —C(=O)—NHCH₂Ph | —C(=O)—O—((2S,3S,4S,5R,6S)-3,4,5-trihydroxy-tetrahydro-pyran-2-carboxylic acid) |

Compounds in Table 2 are named:
N-Ethyl-N-[5'-(2-methanesulfonylamino-2-oxo-ethyl)-2'-methoxy-4-trifluoromethyl-biphenyl-2-ylmethyl]-acetamide (Compound 2-1); N-Ethyl-N-[5'-(2-hydroxy-2-methyl-propyl)-2'-methoxy-4-trifluoromethyl-biphenyl-2-ylmethyl]-acetamide (Compound 2-2); Cyclopropanecarboxylic acid (5'-cyanomethyl-2'-methoxy-4-trifluoromethyl-biphenyl-2-ylmethyl)-ethyl-amide (Compound 2-3); (5'-Cyanomethyl-2'-methoxy-4-trifluoromethyl-biphenyl-2-ylmethyl)-ethyl-carbamic acid benzyl ester (Compound 2-4); Ethyl-[2'-methoxy-5'-(2H-tetrazol-5-ylmethyl)-4-trifluoromethyl-biphenyl-2-ylmethyl]-carbamic acid benzyl ester (Compound 2-5); (5'-Carbamoylmethyl-2'-methoxy-4-trifluoromethyl-biphenyl-2-ylmethyl)-ethyl-carbamic acid benzyl ester (Compound 2-6); Cyclopropanecarboxylic acid ethyl-[2'-

Cyclopropanecarboxylic acid ethyl-{2'-methoxy-5'-[(R)-1-methyl-2-((4R,5S)-4-methyl-2-oxo-5-phenyl-oxazolidin-3-yl)-2-oxo-ethyl]-4-trifluoromethyl-biphenyl-2-ylmethyl}-amide (Compound 2-12); Cyclopropanecarboxylic acid ethyl-{2'-methoxy-5'-[(S)-1-methyl-2-((4R,5S)-4-methyl-2-oxo-5-phenyl-oxazolidin-3-yl)-2-oxo-ethyl]-4-trifluoromethyl-biphenyl-2-ylmethyl}-amide (Compound 2-13); 2-[(Benzyloxycarbonyl-ethyl-amino)-methyl]-5'-ethoxycarbonylmethyl-2'-methoxy-biphenyl-4-carboxylic acid (Compound 2-14); Cyclopropanecarboxylic acid ethyl-{3'-[(R)-1-methyl-2-((4R,5S)-4-methyl-2-oxo-5-phenyl-oxazolidin-3-yl)-2-oxo-ethyl]-4,5'-bis-trifluoromethyl-biphenyl-2-ylmethyl}-amide (Compound 2-15); Cyclopropanecarboxylic acid ethyl-{3'-[(S)-1-methyl-2-((4R,5S)-4-methyl-2-oxo-5-phenyl-oxazolidin-3-yl)-2- oxo-ethyl]-4,5'-bis-trifluoromethyl-biphenyl-2-ylmethyl}-amide (Compound 2-16); and (2S,3S,4S,5R,6S)-6-{2-[2'-(3-Benzyl-1-ethyl-ureidomethyl)-6-methoxy-4'-trifluoromethyl-biphenyl-3-yl]acetoxy}-3,4,5-trihydroxy-tetrahydro-pyran-2-carboxylic acid (Compound 2-17).

Synthesis of Compounds

Compounds described in the prior section are synthesized using standard synthetic techniques or using methods known in the art in combination with methods described herein. In additions, solvents, temperatures and other reaction conditions presented herein may vary.

The starting material used for the synthesis of the compounds described in the prior section are either synthesized or obtained from commercial sources, such as, but not limited to, Sigma-Aldrich, Fluka, Acros Organics, Alfa Aesar, and the like. The compounds described herein, and other related compounds having different substituents are synthesized using known techniques and materials, including those found in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999). General methods for the preparation of compounds can be modified by the use of appropriate reagents and conditions for the introduction of the various moieties found in the formulae as provided herein.

In certain embodiments, compounds described herein are prepared according to Scheme 1.

Scheme 1:

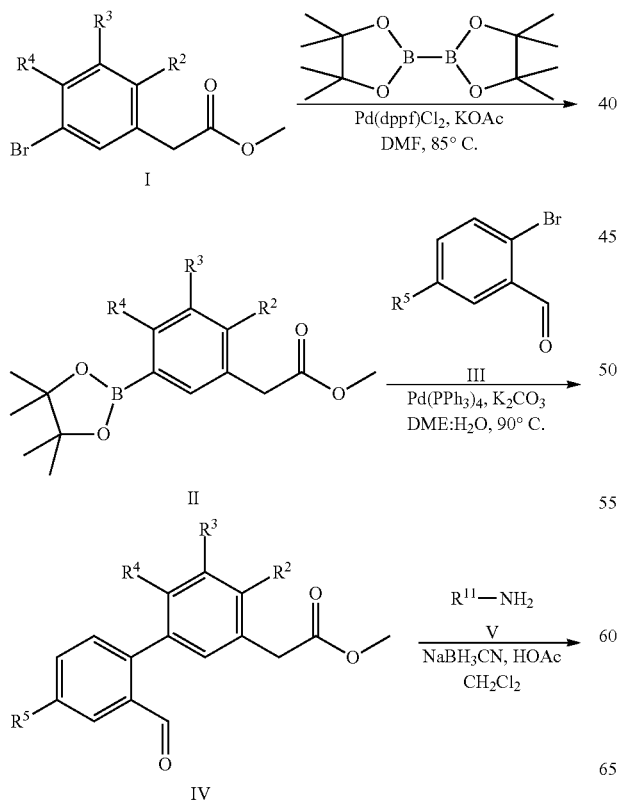

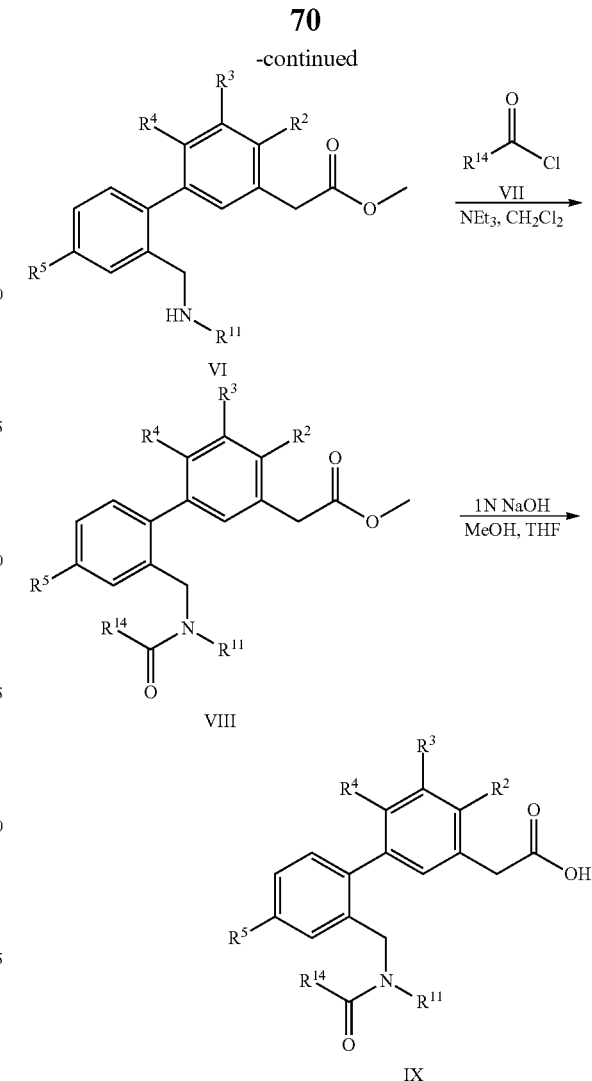

In one aspect, esters of phenyl acetic acids of structure I that have a halide group are reacted with a borylating agent using transition metal mediated reaction conditions to form boronate compounds of structure it. Boronate compounds of structure II are reacted with 2-halobenzaldehydes of structure III under palladium mediated coupling conditions to form biaryl aldehydes of structure IV. Biaryl aldehydes of structure IV are reacted with amines of structure V under reductive amination conditions to form amines of structure VI Amines of structure VI are then reacted with acid chlorides of structure VII to form amides of structure VIII. The ester group of amides of structure VIII is then hydrolyzed to form carboxylic acid compounds of structure IX.

Other metal mediated coupling reactions to form biaryls include, but are not limited to Suzuki reactions, Stille cross couplings, Negishi couplings, Kumada couplings, Ullmann reactions, Hiyama Coupling, and variants thereof (Metal-Catalyzed Cross-Coupling Reactions, Armin de Meijere (Editor), Françcois Diederich (Editor), John Wiley & Sons; 2nd edition, 2004; Özdemir, et al., Tetrahedron, 2005, 61, 9791-9798; Ackermann, et al., Org. Lett., 2006, 8, 3457-3460; Blakey, et al., J. Am. Chem. Soc., 2003, 125, 6046-6047; Dai, et al., Org. Lett., 2004, 6, 221-224; Yoshikai, et al, J. Am. Chem. Soc., 2005, 127, 17978-17979; Tang, et al, J. Org. Chem., 2006, 71, 2167-2169; Murata, et al., Synthesis, 2001, 2231-2233).

In some embodiments, amines of structure VI are reacted with, but not limited to, a carboxylic acid and coupling reagent such as EDC, DCC, BOP, HATU or the like, or a carboxylic acid activated ester or an acid halide, alkylchloroformate, arylchloroformate, benzylchloroformate, alkylisocyanate, benzylisocyanate, arylisocyanate, alkylsulfonyl chloride, arylsulfonyl chloride, heteroarylsulfonyl chloride, or the like in dichloromethane, dichloroethane, tetrahydrofuran, dimethoxyethane or the like in the presence of a hindered base such as triethylamine, diisopropylethylamine, N-methylmorpholine, pyridine or the like, to afford compounds of Formula (I).

Carbamates of structure XI are prepared as outlined in Scheme 2:

Scheme 2:

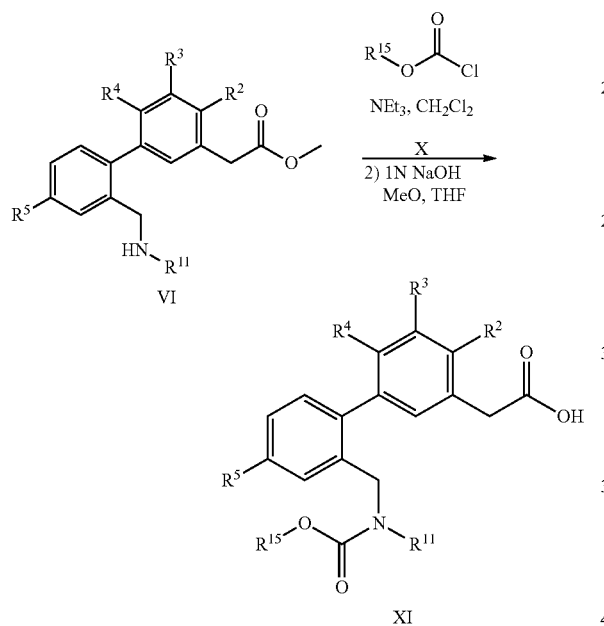

Reaction of amines of structure VI with chloroformates of structure X provide carbamates, which after hydrolysis of the ester moiety, provide carbamates of structure XI. Methods for the preparation of carbamates include those found in, e.g., Greene, T. W. and Wuts, P. G. M "Protective Groups in Organic Synthesis", 3rd Edition, p. 549, New York: Wiley, 1999. In one aspect, alkylamines (compounds of structure VI) are treated with phosgene or a phosgene equivalent, such as, for example, trichloromethyl chloroformate or carbonyldiimidazole, to yield an intermediate, which is then treated with a hydroxy containing compound $R^{15}$—OH to provide carbamates of structure XI.

The synthesis of ureas of structure XIII is depicted in Scheme 3:

Scheme 3:

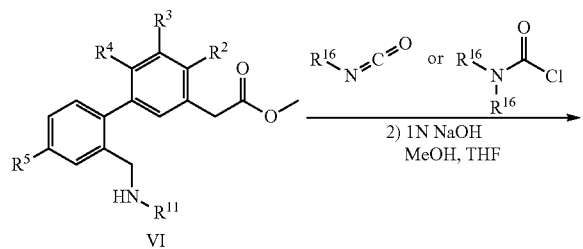

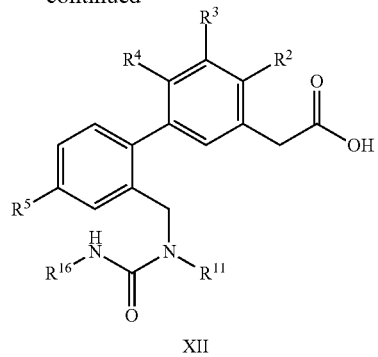

Reaction of benzylamines of structure XII with isocyanates or carbamoyl chlorides provides ureas of structure XII after hydrolysis of the ester group. Common methods for the synthesis of isocyanates include the Curtius rearrangement of acyl azides and the Lossen rearrangement of hydroxamic acids.

The synthesis of sulfonamides of structure XIII is depicted in Scheme 3:

Scheme 3:

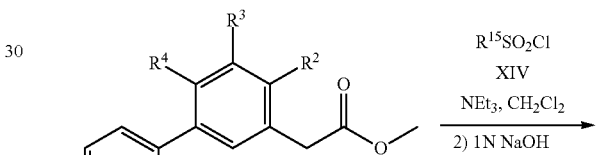

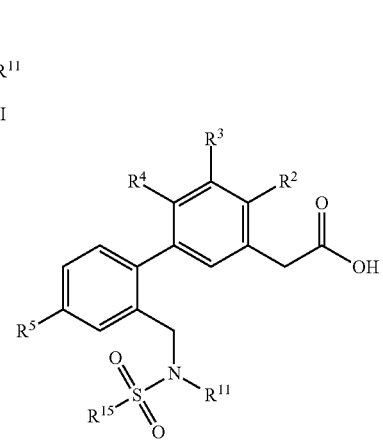

Reaction of amines of structure VI with sulfonyl chlorides of structure XIV provides sulfonamides that are then treated with NaOH to provide sulfonamides of structure XIII.

In the reactions described, it is necessary in certain embodiments to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group is removable by a different means. A detailed description of protecting groups and techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Further Forms of Compounds

In certain embodiments, compounds of any of Formula (I), Formula (II), Formula (III), Formula (IV), Formula (V) Formula (VI), Formula (VII), or Formula (VIII) are prepared as a pharmaceutically acceptable acid addition salt (which is a type of a pharmaceutically acceptable salt) by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

By "pharmaceutically acceptable," as used herein, refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of any of Formula (I), Formula (II), Formula (III), Formula (IV), Formula (V), Formula (VI), Formula (VII), or Formula (VIII) with acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts are also obtained by reacting a compound of any of Formula (I), Formula (II), Formula (III), Formula (IV), Formula (V), Formula (VI), Formula (VII), or Formula (VIII) with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glutamine, tris(hydroxymethyl)methylamine, and salts with amino acids such as arginine, lysine, and the like.

In other embodiments, compounds of any of Formula (I), Formula (II), Formula (III), Formula (IV), Formula (V) Formula (VI), Formula (VII), or Formula (VIII) are prepared as a pharmaceutically acceptable salts by reacting the free acid form of the compound with a pharmaceutically acceptable inorganic or organic base, including, but not limited to organic bases such as ethanolamine, diethanolamine, triethanolamine, tromethamine, N-methylglucamine, and the like, or with an inorganic base such as aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are optionally formed during the process of crystallization with pharmaceutically acceptable solvents such as water, ethanol, and the like. Hydrates are formed when the solvent is water, or alcoholates are formed when the solvent is alcohol. Solvates of compounds of any of Formula (I), Formula (II), Formula (III), Formula (IV), Formula (V) Formula (VI), Formula (VII), or Formula (VIII) are conveniently prepared or formed during the processes described herein. By way of example only, hydrates of compounds of any of Formula (I), Formula (II), Formula (III), Formula (IV), Formula (V) Formula (VI), Formula (VII), or Formula (VIII) are conveniently prepared by recrystallization from an aqueous/organic solvent mixture, using organic solvents including, but not limited to, dioxane, tetrahydrofuran, ethanol, or methanol. In addition, the compounds provided herein can exist in unsolvated as well as solvated forms. In general, the solvated forms are considered equivalent to the unsolvated forms for the purposes of the compounds and methods provided herein.

In yet other embodiments, the compounds of any of Formula (I), Formula (II), Formula (III), Formula (IV), Formula (V) Formula (VI), Formula (VII), or Formula (VIII) are prepared in various forms, including but not limited to, amorphous forms, milled forms and nano-particulate forms. In addition, compounds of any of Formula (I), Formula (II), Formula (III), Formula (IV), Formula (V) Formula (VI), Formula (VII), or Formula (VIII) include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

In some embodiments, compounds of any of Formula (I), Formula (II), Formula (III), Formula (IV), Formula (V) Formula (VI), Formula (VII), or Formula (VIII) are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of any of Formula (I), Formula (II), Formula (III), Formula (IV), Formula (V), Formula (VI), Formula (VII), or Formula (VIII) which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. In certain embodiments, the prodrug of a compound described herein is bioavailable by oral administration whereas the parent is not. Furthermore, in some embodiments, the prodrug of a compound described herein has improved solubility in pharmaceutical compositions over the parent drug.

In other embodiments, prodrugs are designed as reversible drug derivatives, for use as modifiers to enhance drug transport to site-specific tissues. In specific embodiments, the design of prodrugs to date is to increase the effective water solubility of the therapeutic compound for targeting to regions where water is the principal solvent. Fedorak et al., *Am. J. Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Prodrugs as Novel Delivery Systems*, Vol. 14 of the A.C.S. Symposium Series; and Edward B. Roche, *Bioreversible Carriers in Drug Design*, American Pharmaceutical Association and Pergamon Press, 1987.

Additionally, prodrug derivatives of compounds of any of Formula (I), Formula (II), Formula (III), Formula (IV), Formula (V) Formula (VI), Formula (VII), or Formula (VIII) are prepared, if desired (e.g., for further details see Saulnier et al., (1994), *Bioorganic and Medicinal Chemistry Letters*, Vol. 4, p. 1985). By way of example only, in one aspect appropriate prodrugs are prepared by reacting a non-derivatized compound of any of Formula (I), Formula (II), Formula (III), Formula (IV), Formula (V), Formula (VI), Formula (VII), or Formula (VIII) with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds are a prodrug for another derivative or active compound.

In some embodiments, sites on the aromatic ring portion of compounds of any of Formula (I), Formula (II), Formula (III), Formula (IV), Formula (V) Formula (VI), Formula (VII), or Formula (VIII) are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

In yet another embodiment, the compounds of any of Formula (I), Formula (II), Formula (III), Formula (IV), Formula (V) Formula (VI), Formula (VII), or Formula (VIII) possess one or more stereocenters and each center exists independently in either the R or S configuration. The compounds presented herein include all diastereomeric, enantiomeric, and epimeric forms as well as the appropriate mixtures thereof. In certain embodiments, compounds of any of Formula (I), Formula (II), Formula (III), Formula (IV), Formula (V) Formula (VI), Formula (VII), or Formula (VIII) are prepared as their individual stereoisomers by reacting a racemic mixture of the compound with an optically active resolving agent to form a pair of diastereoisomeric compounds, separating the diastereomers and recovering the optically pure enantiomers. In some embodiments, resolution of enantiomers is carried out using covalent diastereomeric derivatives of the compounds described herein. In other embodiments, dissociable complexes are utilized (e.g., crystalline diastereomeric salts). Diastereomers have distinct physical properties (e.g., melting points, boiling points, solubilities, reactivity, etc.) and are, in specific embodiments, separated by taking advantage of these dissimilarities. In these embodiments, the diastereomers are separated by chiral chromatography or by separation/resolution techniques based upon differences in solubility. The optically pure enantiomer is then recovered, along with the resolving agent, by any practical means that does not result in racemization. Jean Jacques, Andre Collet, Samuel H. Wilen, "Enantiomers, Racemates and Resolutions", John Wiley and Sons, Inc., 1981.

Additionally, in certain embodiments, the compounds provided herein exist as geometric isomers. The compounds and methods provided herein include all cis, trans, syn, anti, entgegen (E), and zusammen (Z) isomers as well as the appropriate mixtures thereof. In some embodiments, the compounds described herein exist as tautomers. All tautomers are intended to be within the scope of the molecular formulas described herein. In additional embodiments of the compounds and methods provided herein, mixtures of enantiomers and/or diastereoisomers, resulting from a single preparative step, combination, or interconversion are envisioned.

Certain Chemical Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting.

An "alkoxy" group refers to a (alkyl)O— group, where alkyl is as defined herein.

An "alkyl" group refers to an aliphatic hydrocarbon group. The alkyl moiety may be a saturated alkyl group, which means that it does not contain any units of unsaturation (e.g. carbon-carbon double bonds or carbon-carbon triple bonds). The alkyl moiety may also be an unsaturated alkyl moiety, which means that it contains at least one unit of unsaturation. The alkyl moiety, whether saturated or unsaturated, may be branched, straight chain, or cyclic. The point of attachment of an alkyl is at a sp3 carbon atom that is not part of a ring.

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). In one aspect, alkyl groups are selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, allyl, but-2-enyl, but-3-enyl, cyclopropylmethyl, cyclobutylmethyl, cyclopentylmethyl, cyclohexylmethyl, and the like. In one aspect, an alkyl is a $C_1$-$C_6$ alkyl. In other aspects, an alkyl is a $C_1$-$C_4$ alkyl.

The term "alkylamine" refers to the —N(alkyl)$_x$H$_y$ group, where x and y are selected from the group x=1, y=1 and x=2, y=0. In some embodiments, when x=2 and y=0, the alkyl groups taken together with the nitrogen atom to which they are attached form a cyclic ring system.

An "amide" is a chemical moiety with formula —C(=O)NHR or —NHC(=O)R, where R is selected from the group consisting of alkyl, cycloalkyl, aryl, heteroaryl (bonded through a ring carbon) and heteroalicyclic (bonded through a ring carbon). An amide may be an amino acid or a peptide molecule attached to a compound of Formula (I), Formula (II), Formula (III), Formula (IV), Formula (V), Formula (VI), Formula (VII), or Formula (VIII) thereby forming a prodrug. Any amine, or carboxyl side chain on the compounds described herein is optionally amidified, as desired. See, e.g., Greene and Wuts, Protective Groups in Organic Synthesis, 3$^{rd}$ Ed., John Wiley & Sons, New York, N.Y., 1999, is incorporated herein by reference for such disclosure.

The term "aromatic" refers to a planar ring having a delocalized π-electron system containing 4n+2π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" refers to a ring or ring system where the atoms forming the backbone of the ring are all carbon atoms. The term thus distinguishes carbocyclic from heterocyclic rings in which the ring backbone contains at least one atom which is different from carbon.

As used herein, the term "aryl" refers to an aromatic ring wherein each of the atoms forming the ring is a carbon atom. Aryl rings are formed by five, six, seven, eight, nine, or more than nine carbon atoms. In one aspect, an aryl is a $C_5$-$C_{10}$aryl. Aryl groups are optionally substituted. Examples of aryl groups include, but are not limited to phenyl, and naphthalenyl. In one aspect, an aryl is a phenyl or naphthyl. In another aspect, an aryl is a phenyl. Depending on the structure, an aryl group can be a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. Cycloalkyls may be saturated, or partially unsaturated. Cycloalkyls may be fused with an aromatic ring, and the point of attachment is at a carbon that is not an aromatic ring carbon atom. Cycloalkyl groups include groups having from 3 to 10 ring carbon atoms. In other cases, cycloalkyl groups include groups having from 3 to 6 ring carbon atoms. Illustrative examples of cycloalkyl groups include, but are not limited to, the following moieties:

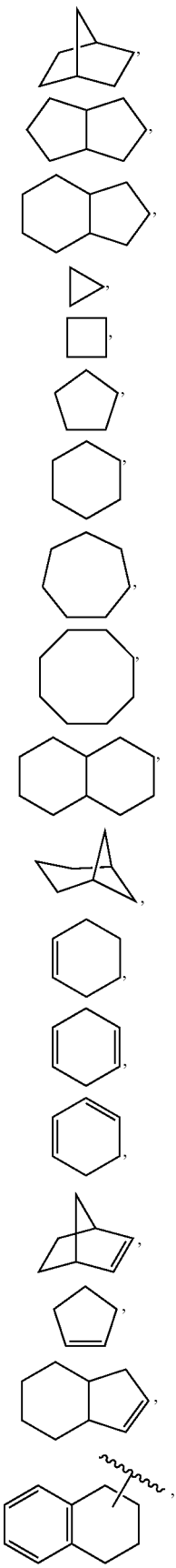

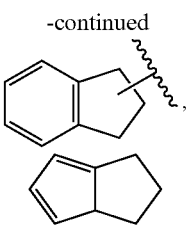

and the like. In some embodiments, cycloalkyl groups are selected from among cyclopropyl, cyclobutyl, cyclopentyl, cyclohexyl, cycloheptyl, and cyclooctyl. In other embodiments, cycloalkyl groups are selected from among cyclopropyl, cyclobutyl, cyclopentyl, and cyclohexyl. In some embodiments, bicyclic cycloalkyl groups are selected from among indanyl, indenyl, and 1,2,3,4-tetrahydronaphthalenyl. Cycloalkyl groups may be substituted or unsubstituted. Depending on the structure, a cycloalkyl group can be a monoradical or a diradical (i.e., an cycloalkylene group, such as, but not limited to, cyclopropan-1,1-diyl, cyclobutan-1,1-diyl, cyclopentan-1,1-diyl, cyclohexan-1,1-diyl, cycloheptan-1,1-diyl, and the like).

The term "ester" refers to a chemical moiety with formula —COOR, where R is selected from the group consisting of alkyl, cycloalkyl, aryl, heteroaryl (bonded through a ring carbon) and heteroalicyclic (bonded through a ring carbon). Any hydroxy, or carboxyl side chain on the compounds described herein is esterified, if desired. Examples of procedures and specific groups to make such esters are found in sources such as Greene and Wuts, Protective Groups in Organic Synthesis, $3^{rd}$ Ed., John Wiley & Sons, New York, N.Y., 1999.

The term "halo" or, alternatively, "halogen" or "halide" means fluoro, chloro, bromo or iodo.

The term "haloalkyl" refers to an alkyl group in which one or more hydrogen atoms are replaced by one or more halide atoms. In one aspect, a haloalkyl is a $C_1$-$C_4$haloalkyl.

The term "fluoroalkyl" refers to an alkyl in which one or more hydrogen atoms are replaced by a fluorine atom. In one aspect, a fluoralkyl is a $C_1$-$C_4$fluoroalkyl. Examples of fluoroalkyls include, —$CF_3$, —$CHF_2$, —$CH_2F$, —$CH_2CF_3$ and —$CF_2CF_3$.

The term "heteroalkyl" refers to an alkyl group in which one or more skeletal atoms of the alkyl are selected from an atom other than carbon, e.g., oxygen, nitrogen, sulfur, phosphorus or combinations thereof. In one aspect, heteroalkyl refers to an alkyl group in which one of the skeletal atoms of the alkyl is oxygen, nitrogen, or sulfur. In another aspect, heteroalkyl refers to an alkyl group in which one of the skeletal atoms of the alkyl is oxygen. In one aspect, a heteroalkyl is a $C_2$-$C_6$ heteroalkyl.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzinaidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may ber substituted with one or two oxo (═O) moieties, such as pyrrolidin-2-one.

The terms "heteroaryl" or, alternatively, "heteroaromatic" refers to an aryl group that includes one or more ring heteroatoms selected from nitrogen, oxygen and sulfur. Illustrative examples of heteroaryl groups include the following moieties:

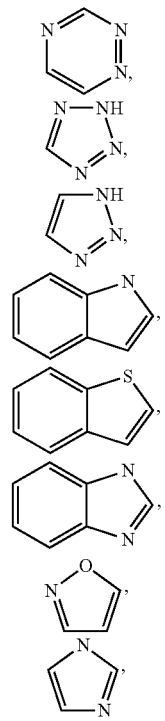

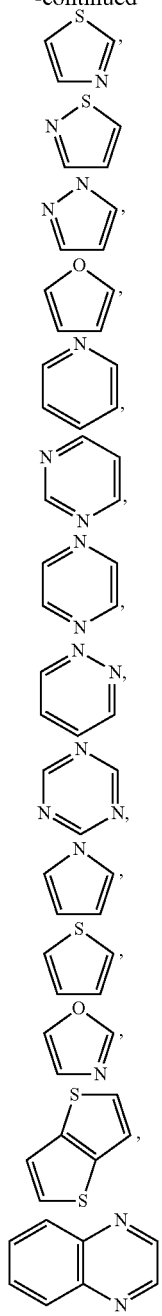

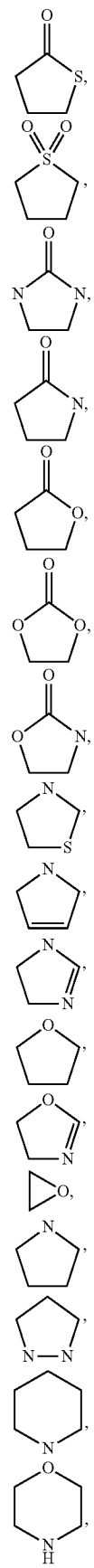

and the like. An N-containing "heteroaromatic" or "heteroaryl" moiety refers to an aromatic group in which at least one of the skeletal atoms of the ring is a nitrogen atom. In one aspect, the heteroaryl is a $C_1$-$C_{10}$heteroaryl. In another aspect, the heteroaryl is a $C_2$-$C_9$heteroaryl. In some cases, the heteroaryl includes at least one N atom in the ring. In one aspect, monocyclic heteroaryl is a $C_1$-$C_5$heteroaryl. In one aspect, bicyclic heteroaryl is a $C_5$-$C_{10}$heteroaryl.

A "heterocycloalkyl" or "heteroalicyclic" group refers to a cycloalkyl group that includes at least one heteroatom selected from nitrogen, oxygen and sulfur. The radicals may be fused with an aryl or heteroaryl. Illustrative examples of heterocycloalkyl groups, also referred to as non-aromatic heterocycles, include:

and the like. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl.

The term "bond" or "single bond" refers to a chemical bond between two atoms, or two moieties when the atoms joined by the bond are considered to be part of larger substructure.

The term "membered ring" includes any cyclic structure. The term "membered" is meant to denote the number of skeletal atoms that constitute the ring. Thus, for example, cyclohexyl, pyridinyl, pyranyl and thiopyranyl are 6-membered rings and cyclopentyl, pyrrolyl, furanyl, and thiophenyl are 5-membered rings.

The term "moiety" refers to a specific segment or functional group of a molecule. Chemical moieties are often recognized chemical entities embedded in or appended to a molecule.

The term "acyclic" refers to a moiety wherein the point of attachment of the moiety to the rest of the molecule is at an atom that is not part of a ring. Non-limiting examples of acyclic groups include alkyl, haloalkyls, heteroalkyl, alkoxy, benzyl, and the like.

The term "cyclic" refers to a moiety wherein the point of attachment to the rest of the molecule is at an atom that is part of a ring. Non-limiting examples of cyclic groups include cycloalkyl, heterocycloalkyl, aryl, heteroaryl, and the like.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, carbonyl, thiocarbonyl, nitro, haloalkyl, fluoroalkyl, and amino, including mono- and di-substituted amino groups, and the protected derivatives thereof. By way of example an optional substituents may may be halide, —CN, —NO$_2$, or $L_sR_s$, wherein each $L_s$ is independently selected from a bond, —O—, —C(=O)—, —C(=O)O—, —S—, —S(=O)—, —S(=O)$_2$—, —NH—, —NHC(=O)—, —C(=O)NH—, S(=O)₂NH—, —NHS(=O)₂, —OC(=O)NH—, —NHC(=O)O—, —(C₁-C₆ alkyl), or —(C₂-C₆ alkenyl); and each R_s is independently selected from H, alkyl, fluoroalkyl, heteroalkyl, cycloalkyl, aryl, heteroaryl, or heterocycloalkyl. In one aspect, substituted groups are substituted with one or more substituents selected from halogen, —OH, —OC₁-C₄alkyl, C₁-C₄alkyl, C₁-C₄heteroalkyl, C₁-C₄fluoroalkyl and —OC₁-C₄fluoroalkyl. In yet another aspect, substituted groups are substituted with one or more substituents selected from F, Cl, Br, —OH, —OCH₃, —CH₃, and —CF₃. In yet other embodiments, substituted groups are substituted with one or more substituents selected from F, Cl, and Br. In one aspect, substituted groups are substituted with one of the preceding groups. The protecting groups that may form the protective derivatives of the above substituents may be found in sources such as Greene and Wuts, above.

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof Stereoisomers are obtained, if desired, by methods such as, the separation of stereoisomers by chiral chromatographic columns.

The methods and formulations described herein include the use of N-oxides (if appropriate), crystalline forms (also known as polymorphs), or pharmaceutically acceptable salts of compounds having the structure of any of Formula (I), Formula (II), Formula (III), Formula (IV), Formula (V) Formula (VI), Formula (VII), or Formula (VIII) as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

Certain Pharmaceutical and Medical Terminology

The term "acceptable" with respect to a formulation, composition or ingredient, as used herein, means having no persistent detrimental effect on the general health of the subject being treated.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist, partial agonist, an inverse agonist and antagonist. In one embodiment, a modulator is an antagonist.

The term "agonist," as used herein, refers to a molecule such as a compound, a drug, an enzyme activator or a hormone modulator that binds to a specific receptor and triggers a response in the cell. An agonist mimics the action of an endogenous ligand (such as prostaglandin, hormone or neurotransmitter) that binds to the same receptor.

The term "antagonist," as used herein, refers to a molecule such as a compound, which diminishes, inhibits, or prevents the action of another molecule or the activity of a receptor site. Antagonists include, but are not limited to, competitive antagonists, non-competitive antagonists, uncompetitive antagonists, partial agonists and inverse agonists.

Competitive antagonists reversibly bind to receptors at the same binding site (active site) as the endogenous ligand or agonist, but without activating the receptor.

Non-competitive antagonists (also known as allosteric antagonists) bind to a distinctly separate binding site from the agonist, exerting their action to that receptor via the other binding site. Non-competitive antagonists do not compete with agonists for binding The bound antagonists may result in a decreased affinity of an agonist for that receptor, or alternatively may prevent conformational changes in the receptor required for receptor activation after the agonist binds.

Uncompetitive antagonists differ from non-competitive antagonists in that they require receptor activation by an agonist before they can bind to a separate allosteric binding site.

Partial agonists are defined as drugs which, at a given receptor, might differ in the amplitude of the functional response that they elicit after maximal receptor occupancy. Although they are agonists, partial agonists can act as a competitive antagonist if co-administered with a full agonist, as it competes with the full agonist for receptor occupancy and producing a net decrease in the receptor activation observed with the full agonist alone.

An inverse agonist can have effects similar to an antagonist, but causes a distinct set of downstream biological responses. Constitutively active receptors which exhibit intrinsic or basal activity can have inverse agonists, which not only block the effects of binding agonists like a classical antagonist, but inhibit the basal activity of the receptor.

The term "PGD₂-dependent", as used herein, refers to conditions or disorders that would not occur, or would not occur to the same extent, in the absence of PGD₂.

The term "PGD₂-mediated", as used herein, refers to refers to conditions or disorders that might occur in the absence of PGD₂ but can occur in the presence of PGD₂.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

The term "rhinitis" as used herein refers to any disorder of the nose in which there is inflammation of the mucous lining of the nose by whatever cause (intrinsic, extrinsic or both; allergic or non-allergic).

The term "bone disease," as used herein, refers to a disease or condition of the bone, including, but not limited to, inappropriate bone remodeling, loss or gain, osteopenia, osteomalacia, osteofibrosis, and Paget's disease.

The term "cardiovascular disease," as used herein refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumaticshock; hypertension, valvular heart disease, heart failure, abnormal blood pressure; shock; vasoconstriction (including that associated with migraines); vascular abnormality, inflammation, insufficiency limited to a single organ or tissue.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to relatively non-toxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, urticaria.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "iatrogenic" means a $PGD_2$-dependent or $PGD_2$-mediated condition, disorder, or disease created or worsened by medical or surgical therapy.

The term "inflammatory disorders" refers to those diseases or conditions that are characterized by one or more of the signs of pain, heat, redness, swelling, and loss of function (temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arteritis); joints (arthritis: crystalline, osteo-, psoriatic, reactive, rheumatoid, Reiter's); gastrointestinal tract (colitis); skin (dermatitis); or multiple organs and tissues (systemic lupus erythematosus).

The term "immunological disorders" refers to those diseases or conditions that are characterized by inappropriate or deleterious response to an endogenous or exogenous antigen that may result in cellular dysfunction or destruction and consequently dysfunction or destruction of an organ or tissue and which may or may not be accompanied by signs or symptoms of inflammation.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The terms "neurogenerative disease" or "nervous system disorder," as used herein, refers to conditions that alter the structure or function of the brain, spinal cord or peripheral nervous system, including but not limited to Alzheimer's Disease, cerebral edema, cerebral ischemia, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica. The acronym "CNS" refers to disorders of the central nervous system, i.e., brain and spinal cord.

The terms "ocular disease" or "ophthalmic disease," as used herein, refer to diseases which affect the eye or eyes and potentially the surrounding tissues as well. Ocular or ophthalmic diseases include, but are not limited to, conjunctivitis, retinitis, scleritis, uveitis, allergic conjuctivitis, vernal conjunctivitis, papillary conjunctivitis.

The term "interstitial cystitis" refers to a disorder characterized by lower abdominal discomfort, frequent and sometimes painful urination that is not caused by anatomical abnormalites, infection, toxins, trauma or tumors.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of any of Formula (I), Formula (II), Formula (III), Formula (IV), Formula (V), Formula (VI), Formula (VII), or Formula (VIII) and a co-agent, are both administered to a patient simultaneously in the form of a single entity or dosage. The term "non-fixed combination" means that the active ingredients, e.g. a compound of any of Formula (I), Formula Up, Formula (III), Formula (IV), Formula (V), Formula (VI), Formula (VII), or Formula (VIII) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound of any of Formula (I), Formula (II), Formula (III), Formula (IV), Formula (V), Formula (VI), Formula (VII), or Formula (VIII) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "respiratory disease," as used herein, refers to diseases affecting the organs that are involved in breathing, such as the nose, throat, larynx, eustachian tubes, trachea, bronchi, lungs, related muscles (e.g., diaphram and intercostals) and nerves. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, neutrophilic asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Composition/Formulation

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

Provided herein are pharmaceutical compositions comprising a compound of any of Formula (I), Formula (II), Formula (III), Formula (IV), Formula (V) Formula (VI), Formula (VII), or Formula (VIII) and a pharmaceutically acceptable diluent(s), excipient(s), or carrier(s). In certain embodiments, the compounds described are administered as pharmaceutical compositions in which compounds of any of Formula (I), Formula (II), Formula (III), Formula (IV), Formula (V) Formula (VI), Formula (VII), or Formula (VIII) are mixed with other active ingredients, as in combination therapy. Encompassed herein are all combinations of actives set forth in the combination therapies section below and throughout this disclosure. In specific embodiments, the pharmaceutical compositions include one or more compounds of any of Formula (I), Formula (II), Formula (III), Formula (IV), Formula (V), Formula (VI) Formula (VII), or Formula (VIII).

A pharmaceutical composition, as used herein, refers to a mixture of a compound of any of Formula Formula (I), Formula (II), Formula (III), Formula (IV), Formula (V) Formula (VI), Formula (VII), or Formula (VIII) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of any of Formula (I), Formula (II), Formula (III), Formula (IV), Formula (V) Formula (VI), Formula (VII), or Formula (VIII) provided herein are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of any of Formula (I), Formula (II), Formula (III), Formula (IV), Formula (V) Formula (VI), Formula (VII), or Formula (VIII) is formulated in an aqueous solution. In specific embodiments, the aqueous solution is selected from, by way of example only, a physiologically compatible buffer, such as Hank's solution, Ringer's solution, or physiological saline buffer. In other embodiments, one or more compound of any of Formula (I), Formula (II), Formula (III), Formula (IV), Formula (V) Formula (VI), Formula (VII), or Formula (VIII) is formulated for transmucosal administration. In specific embodiments, transmucosal formulations include penetrants that are appropriate to the bather to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including compounds of any of Formula (I), Formula (II), Formula (III), Formula (IV), Formula (V) Formula (VI), Formula (VII), or Formula (VIII) are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical composition of any of Formula (I), Formula (II), Formula (HI), Formula (IV), Formula (V), Formula (VI), Formula (VII), or Formula (VIII) are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of any of Formula (I), Formula (U), Formula (III), Formula (IV), Formula (V), Formula (VI), Formula (VII), or Formula (VIII) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of any of Formula (I), Formula (II), Formula (II), Formula (IV), Formula (V) Formula (VI), Formula (VII), or Formula (VIII) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of any of Formula (I), Formula (II), Formula (III), Formula (IV), Formula (V) Formula (VI), Formula (VII), or Formula (VIII) is accomplished by means of iontophoretic patches and the like. In certain embodiments, transdermal patches provide controlled delivery of the compounds of any of Formula (I), Formula (II), Formula (III), Formula (IV), Formula (V), Formula (VI), Formula (VII), or Formula (VIII). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of any of Formula (I), Formula (II), Formula (III), Formula (IV), Formula (V) Formula (VI), Formula (VII), or Formula (VIII) are formulated for administration by inhalation. Various forms suitable for administration by inhalation include, but are not limited to, aerosols, mists or powders. Pharmaceutical compositions of any of Formula (I), Formula (II), Formula (III), Formula (IV), Formula (V) Formula (VI), Formula (VII), or Formula (VIII) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the compounds of any of Formula (I), Formula (II), Formula (III), Formula (IV), Formula (V), Formula (VI), Formula (VII), or Formula (VIII) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients is optionally used as suitable and as understood in the art. Pharmaceutical compositions comprising a compound of any of Formula (I), Formula (II), Formula (III), Formula (IV), Formula (V), Formula (VI), Formula (VII), or Formula (VIII) may be manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of any of Formula (I), Formula (II), Formula (III), Formula (IV), Formula (V), Formula (VI), Formula (VII), or Formula (VIII) described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of any of Formula (I), Formula (II), Formula (III), Formula (IV), Formula (V), Formula (VI), Formula (VII), or Formula (VIII) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspension contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of any of Formula (I), Formula (II), Formula (III), Formula (IV), Formula (V), Formula (VI), Formula (VII), or Formula (VIII). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions may include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization may be employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Methods of Dosing and Treatment Regimens

In one embodiment, the compound of any of Formula (I), Formula (II), Formula (III), Formula (IV), Formula (V), Formula (VI), Formula (VII), or Formula (VIII) are used in the preparation of medicaments for the treatment of $PGD_2$-dependent or $PGD_2$-mediated diseases or conditions. In addition, a method for treating any of the diseases or conditions described herein in a subject in need of such treatment, involves administration of pharmaceutical compositions containing at least one compound of any of Formula (I), Formula (II), Formula (III), Formula (IV), Formula (V), Formula (VI), Formula (VII), or Formula (VIII) or a pharmaceutically acceptable salt, pharmaceutically active metabolite, pharmaceutically acceptable prodrug, or pharmaceutically acceptable solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, administration of the compounds is given continuously; or, alternatively, the dose of drug being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 day, 250 days, 280 days, 300 days, 320 days, 350 days, and 365 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight) of the subject or host in need of treatment, but can nevertheless be determined according to the particular circumstances surrounding the case, including, e.g., the specific agent being administered, the route of administration, the condition being treated, and the subject or host being treated. In general, however, doses employed for adult human treatment are typically in the range of 0.02-5000 mg per day. In one aspect, the dose is in the range of 1-1500 mg per day, 1-500 mg per day, 1-250 mg per day, or 1-100 mg per day. In one embodiment, the desired dose is conveniently presented in a single dose or in divided doses administered simultaneously (or over a short period of time) or at appropriate intervals, for example as two, three, four or more sub-doses per day.

In certain embodiments, the pharmaceutical composition described herein is in unit dosage forms suitable for single administration of precise dosages. In unit dosage form, the formulation is divided into unit doses containing appropriate quantities of one or more compound. In specific embodiments, the unit dosage is in the form of a package containing discrete quantities of the formulation. Non-limiting examples are packaged tablets or capsules, and powders in vials or ampoules. Aqueous suspension compositions are optionally packaged in single-dose non-re-closeable containers. Alternatively, multiple-dose re-closeable containers are used, in which case it is typical to include a preservative in the composition. By way of example only, formulations for parenteral injection are, in some embodiments, presented in unit dosage form, which include, but are not limited to ampoules, or in multi-dose containers, with an added preservative.

In one embodiment, the daily dosages appropriate for the compound of any of Formula (I), Formula (II), Formula (III), Formula (IV), Formula (V), Formula (VI), Formula (VII), or Formula (VIII) described herein are from about 0.01 to about 10 mg/kg per body weight. In specific embodiments, an indicated daily dosage in a large mammal, including, but not limited to, humans, is in the range from about 0.5 mg to about 1000 mg, conveniently administered in divided doses, including, but not limited to, up to four times a day or in extended release form. In certain embodiments, suitable unit dosage forms for oral administration comprise from about 1 to 500 mg active ingredient, from about 1 to 250 mg active ingredient, or from about 1 to 100 mg active ingredient. In other embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

Use of $DP_2$ Antagonists to Prevent and/or Treat $PGD_2$-Dependent or $PGD_2$ Mediated Diseases or Conditions The therapy of $PGD_2$-dependent or $PGD_2$-mediated diseases or conditions is designed to modulate the activity of $DP_2$, $DP_1$ and/or TP. Such modulation includes, in some embodiments, antagonizing $DP_2$ activity. In other embodiments, such modulation includes antagonizing $DP_2$ and $DP_1$. For example, in one embodiment, a $DP_2$ antagonist is administered in order to decrease signal transduction initiated by $PGD_2$ within the individual.

In accordance with one aspect, compositions and methods described herein include compositions and methods for treating, preventing, reversing, halting or slowing the progression of $PGD_2$-dependent or $PGD_2$ mediated diseases or conditions once it becomes clinically evident, or treating the symptoms associated with or related to $PGD_2$-dependent or $PGD_2$ mediated diseases or conditions, by administering to the subject a compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII). In certain embodiments, the subject already has a $PGD_2$-dependent or $PGD_2$ mediated disease or condition at the time of administration, or is at risk of developing a $PGD_2$-dependent or $PGD_2$ mediated disease or condition.

In certain aspects, the activity of $DP_2$ in a mammal is directly or indirectly modulated by the administration of (at least once) an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII) to a mammal. Such modulation includes, but is not limited to, reducing and/or inhibiting the activity of $DP_2$. In additional aspects, the activity of $PGD_2$ in a mammal is directly or indirectly modulated, including reducing and/or inhibiting, by the administration of (at least once) an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII) to a mammal. Such modulation includes, but is not limited to, reducing and/or inhibiting the activity of $DP_2$.

In one embodiment, prevention and/or treatment of $PGD_2$-dependent or $PGD_2$ mediated diseases or conditions comprises administering to a mammal at least once a therapeutically effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII). In specific embodiments, the compound administered to the mammal is a compound of any of Formula (I), Formula (I), Formula (III), Formula (IV), Formula (V), Formula (VI), Formula (VII), or Formula (VII). In some embodiments, there is provided a method of treating $PGD_2$-dependent or $PGD_2$ mediated diseases or conditions that include, but are not limited to, bone diseases and disorders, cardiovascular diseases and disorders, inflammatory diseases and disorders, immunological diseases or disorders, dermatological diseases and disorders, ocular diseases and disorders, cancer and other proliferative diseases and disorders, respiratory diseases and disorder, and non-cancerous disorders.

By way of example only, included in the prevention/treatment methods described herein are methods for treating respiratory diseases comprising administering to the mammal at least once an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII). By way of example, in some embodiments, the respiratory disease is asthma. Other respiratory diseases include, but are not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, neutrophilic asthma, isocapnic hyperventilation, child-onset asthma, adult-onset asthma, cough-variant asthma, occupational asthma, steroid-resistant asthma, seasonal asthma, allergic rhinitis, vascular responses, endotoxin shock, fibrogenesis, pulmonary fibrosis, allergic diseases, chronic inflammation, and adult respiratory distress syndrome.

By way of example only, included in such treatment methods are methods for preventing chronic obstructive pulmonary disease comprising administering to the mammal at least once an effective amount of at least one compound of any of Formula (I), Formula (II), Formula (III), Formula (III), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII). In addition, chronic obstructive pulmonary disease includes, but is not limited to, chronic bronchitis or emphysema, pulmonary hypertension, interstitial lung fibrosis and/or airway inflammation and cystic fibrosis.

By way of example only, included in such treatment methods are methods for preventing increased mucosal secretion and/or edema in a disease or condition comprising administering to the mammal at least once an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII).

By way of example only, included in the prevention/treatment methods described herein are methods for preventing or treating vasoconstriction, atherosclerosis and its sequelae myocardial ischemia, myocardial infarction, aortic aneurysm, vasculitis and stroke comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII).

By way of example only, included in the prevention/treatment methods described herein are methods for reducing cardiac reperfusion injury following myocardial ischemia and/or endotoxic shock comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII).

By way of example only, included in the prevention/treatment methods described herein are methods for reducing the constriction of blood vessels in a mammal comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII).

By way of example only, included in the prevention/treatment methods described herein are methods for lowering or preventing an increase in blood pressure of a mammal comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII).

By way of example only, included in the prevention/treatment methods described herein are methods for preventing or treating eosinophil and/or basophil and/or dendritic cell and/or neutrophil and/or monocyte and/or T-cell recruitment comprising administering at least once to the mammal an effective amount of at least one compound of any of Formula (I), Formula (II), Formula (III), Formula (N), Formula (V), Formula (VI), Formula (VII), or Formula (VIII) or pharmaceutical composition or medicament which includes a compound of any of Formula (I), Formula (II), Formula (Ill), Formula (IV), Formula (V), Formula (VI), Formula (VII), or Formula (VIM.

By way of example only, included in the prevention/treatment methods described herein are methods for the prevention or treatment of abnormal bone remodeling, loss or gain, including diseases or conditions as, by way of example, osteopenia, osteoporosis, Paget's disease, cancer and other diseases comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII).

By way of example only, included in the prevention/treatment methods described herein are methods for preventing ocular inflammation and allergic conjunctivitis, vernal keratoconjunctivitis, and papillary conjunctivitis comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (M), Formula (IV), Formula (V), Formula (VI), Formula (VII), or Formula (VIII).

By way of example only, included in the prevention/treatment methods described herein are methods for preventing otitis, otitis media comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII).

By way of example only, included in the prevention/treatment methods described herein are methods for preventing CNS disorders comprising administering at least once to the mammal an effective amount of at least one compound of any of Formula (I), Formula (II), Formula (III), Formula (W), Formula (V), Formula (VI), Formula (VII), or Formula (VIII) or pharmaceutical composition or medicament which includes a compound of any of Formula (p, Formula (II), Formula (III), Formula (IV), Formula (V), Formula (VI), Formula (VII), or Formula (VIII). CNS disorders include, but are not limited to, multiple sclerosis, Parkinson's disease, Alzheimer's disease, stroke, cerebral ischemia, retinal ischemia, post-surgical cognitive dysfunction, migraine, peripheral neuropathy/neuropathic pain, spinal cord injury, cerebral edema and head injury.

By way of example only, included in the prevention/treatment methods described herein are methods for the treatment of cancer comprising administering at least once to the mammal an effective amount of at least one compound of any of Formula (I), Formula (II), Formula (III), Formula (W), Formula (V), Formula (VI), Formula (VII), or Formula (VIII), or pharmaceutical composition or medicament which includes a compound of any of Formula (I), Formula (II), Formula (III), Formula (IV), Formula (V), Formula (VI), Formula (VII), or Formula (VIII). The type of cancer may include, but is not limited to, pancreatic cancer and other solid or hematological tumors.

By way of example only, included in the prevention/treatment methods described herein are methods for preventing or reducing the chances of endotoxic shock and septic shock comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (Ill), Formula (IV), Formula (V), Formula (VI), Formula (VII), or Formula (VIII).

By way of example only, included in the prevention/treatment methods described herein methods for preventing, treating or alleviating rheumatoid arthritis and osteoarthritis comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII).

By way of example only, included in the prevention/treatment methods described herein are methods for preventing increased, reducing the incidences of or treating gastrointestinal diseases comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII). Such gastrointestinal diseases include, by way of example only, inflammatory bowel disease (IBD), colitis and Crohn's disease.

By way of example only, included in the prevention/treatment methods described herein are methods for the reduction or treatment of inflammation and/or preventing, reducing the incidences of or treating acute or chronic transplant rejection (including any vascular abnormality associated with acute or chronic rejection) or preventing or treating tumors or accelerating the healing of wounds comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII).

By way of example only, included in the prevention/treatment methods described herein are methods for the prevention or treatment of rejection or dysfunction in a transplanted organ or tissue comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII).

By way of example only, included in the prevention/treatment methods described herein are methods for treating pain comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII).

By way of example only, included in the prevention/treatment methods described herein are methods for treating inflammatory responses of the skin comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII). Such inflammatory responses of the skin include, by way of example, psoriasis, dermatitis, contact dermatitis, eczema, urticaria, rosacea, wound healing and scarring. In another aspect are methods for reducing psoriatic lesions in the skin, joints, or other tissues or organs, comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII).

By way of example only, included in the prevention/treatment methods described herein are methods for the treatment of cystitis, including, e.g., interstitial cystitis, comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (In), Formula (IV), Formula (V), Formula (VI), Formula (VII), or Formula (VIII).

By way of example only, included in the prevention/treatment methods described herein are methods for the treatment of Familial Mediterranean Fever comprising administering at least once to the mammal an effective amount of at least one compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII) or Formula (VIII).

In one aspect, compounds of any of Formula (I), Formula (II), Formula (III), Formula (IV), Formula (V), Formula (VI), Formula (VII), or Formula (VIII) are used in the treatment of $PGD_2$-dependent or $PGD_2$-mediated diseases, disorders or conditions as disclosed herein. In one aspect, compounds of any of Formula (I), Formula (II), Formula (III), Formula (IV), Formula (V), Formula (VI), Formula (VII), or Formula (VIII) are $DP_2$ antagonists. In one aspect, the compounds of Formula (I) exhibit negligible modulatory activity on CETP and/or PPAR receptors. CETP assays are known (Epps et al. *Chem. Phys. Lipids.* 77, 51-63, 1995). PPAR assays are known (Example 48 of US 2006/0058301).

Combination Treatments

In certain instances, it is appropriate to administer at least one $DP_2$ antagonist described herein, in combination with another therapeutic agent. By way of example only, if one of the side effects experienced by a patient upon receiving one of the compounds herein is inflammation, then it may be appropriate to administer an anti-inflammatory agent in combination with the initial therapeutic agent. Or, in one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit of experienced by a patient is increased by administering one of the compounds described herein with another therapeutic agent (which also includes a therapeutic regimen) that also has therapeutic benefit. In one specific embodiment, the therapeutic benefit of treating asthma by administering at least one of the compounds described herein is increased by also providing the patient with other therapeutic agents or therapies for asthma. In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a $DP_2$ antagonist described herein is initiated prior to, during, or after treatment with a second agent described above, and continues until any time during treatment with the second agent or after termination of treatment with the second agent. It also includes treatments in which a $DP_2$ antagonist described herein and the second agent being used in combination are administered simultaneously or at different times and/or at decreasing or increasing intervals during the treatment period. Combination treatment further includes periodic treatments that start and stop at various times to assist with the clinical management of the patient. For example, in one embodiment, a $DP_2$ antagonist described herein in the combination treatment is administered weekly at the onset of treatment, decreasing to biweekly, and decreasing further as appropriate.

Compositions and methods for combination therapy are provided herein. In accordance with one aspect, the pharmaceutical compositions disclosed herein are used to treat $PGD_2$-dependent or $PGD_2$ mediated conditions. In accordance with another aspect, the pharmaceutical compositions disclosed herein are used to treat respiratory diseases (e.g., asthma), where treatment with a $DP_2$ antagonist is indicated and to induce bronchodilation in a subject. In one embodiment, the pharmaceutical compositions disclosed herein are used to treat airways or nasal inflammation diseases such as asthma and rhinitis.

In one embodiment, pharmaceutical compositions disclosed herein are used to treat a subject suffering from a vascular inflammation-driven disorder. In one embodiment, the pharmaceutical compositions disclosed herein are used to treat skin inflammation diseases such as atopic dermatitis.

In certain embodiments, combination therapies described herein are used as part of a specific treatment regimen intended to provide a beneficial effect from the co-action of a $DP_2$ described herein and a concurrent treatment. It is understood that the dosage regimen to treat, prevent, or ameliorate the condition(s) for which relief is sought, is modified in accordance with a variety of factors. These factors include the type of respiratory disorder and the type of bronchoconstriction or inflammation from which the subject suffers, as well as the age, weight, sex, diet, and medical condition of the subject. Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more biologically active agents, the compound provided herein is administered either simultaneously with the biologically active agent(s), or sequentially. If administered sequentially, the attending physician decides on the appropriate sequence of administering protein in combination with the biologically active agent(s).

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills). In one embodiment, one of the therapeutic agents is given in multiple doses, and in another, two (or more if present) are given as multiple doses. In some embodiments of non-simultaneous administration, the timing between the multiple doses vary from more than zero weeks to less than four weeks. In addition, the combination methods, compositions and formulations are not to be limited to the use of only two agents; the use of multiple therapeutic combinations is also envisioned.

In additional embodiments, the $DP_2$ antagonist described herein are used in combination with procedures that provide additional or synergistic benefit to the patient. By way of example only, patients are expected to find therapeutic and/or prophylactic benefit in the methods described herein, wherein $DP_2$ antagonists described herein, and/or combinations with other therapeutics are combined with genetic testing to determine whether that individual is a carrier of a mutant gene that is known to be correlated with certain diseases or conditions.

The $DP_2$ antagonist described herein, and combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. The administration of the compounds are initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration is accomplished via any practical route, such as, for example, by intravenous injection, a bolus injection, infusion over 5 minutes to about 5 hours, a pill, a capsule, transdermal patch, buccal delivery, and the like, or combination thereof. In specific embodiments, a compound described herein is administered as soon as is practicable after the onset of a disease or condition is detected or suspected, and for a length of time necessary for the treatment of the disease, such as, for example, from about 1 month to about 3 months. In some embodiments, the length required for effective treatment varies, and the treatment length is adjusted to suit the specific needs of each subject. For example, in specific embodiments, a compound described herein or a formulation containing the compound is administered for at least 2 weeks, about 1 month to about 5 years, or from about 1 month to about 3 years.

By way of example, therapies which combine $DP_2$ antagonists described herein with inhibitors of $PGD_2$ synthesis or $PGD_2$ receptor antagonists, either acting at the same or other points in the $PGD_2$ synthesis pathway, are encompassed herein for treating $PGD_2$-dependent or $PGD_2$ mediated diseases or conditions. In addition, by way of example, encompassed herein are therapies that combine $DP_2$ antagonists described herein with inhibitors of inflammation for treating $PGD_2$-dependent or $PGD_2$ mediated diseases or conditions.

In another embodiment described herein, methods for treatment of $PGD_2$-dependent or $PGD_2$ mediated conditions or diseases include administration to a patient compounds, pharmaceutical compositions, or medicaments described herein in combination with an anti-inflammatory agent including, but not limited to, non-steroidal anti-inflammatory drugs (NSAIDs) and corticosteroids (glucocorticoids). Anti-inflammatory agents include, but are not limited to: arthrotec, mesalamine, auralglan, sulfasalazine, daypro, etodolac, ponstan, and solumedrol; non-steroidal anti-inflammatory agents; corticosteroids; and leukotriene pathway modulators (e.g. montelukast, zilueton).

By way of example only, asthma is a chronic inflammatory disease characterized by pulmonary eosinophilia and airway hyperresponsiveness. In patients with asthma, $PGD_2$ is released from mast cells, eosinophils, and basophils. $PGD_2$ is involved in contraction of airway smooth muscle, an increase in vascular permeability and mucus secretions, and has been reported to attract and activate inflammatory cells in the airways of asthmatics. Thus, in another embodiment described herein, the methods for treatment of respiratory diseases include administration to a patient compounds, pharmaceutical compositions, or medicaments described herein in combination with an anti-inflammatory agent.

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

Corticosteroids, include, but are not limited to: betamethasone (Celestone), prednisone (Deltasone), alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In another embodiment described herein, methods for treatment of $PGD_2$-dependent or $PGD_2$ mediated conditions or diseases include administration to a patient compounds, pharmaceutical compositions, or medicaments described herein in combination in combination with NSAIDs and NO-donors or NSAIDs and proton-pump inhibitors.

In another embodiment described herein, methods for treatment of $PGD_2$-dependent or $PGD_2$ mediated conditions or diseases includes administering to a patient compounds, pharmaceutical compositions, or medicaments described herein in combination with other $PGD_2$ receptor antagonists including, but are not limited to, $DP_1$ receptor antagonists and TP receptor antagonists. In another embodiment described herein, methods for treatment of $PGD_2$-dependent or $PGD_2$ mediated conditions or diseases includes administered to a patient compounds, pharmaceutical compositions, or medicaments described herein in combination with a $DP_1$ receptor antagonist. $DP_1$ receptor antagonists include, but are not limited to, BWA868C (Sharif et at, *Br. J. Pharmacal.*, 2000 November; 131(6): 1025-38), MK-0524 (Sturino et al, *J. Med. Chem.*, 2007, 50, 794-806 and Cheng et al, *PNAS*, 2006 Apr. 25; 103(17):6682-7.) and S-5751 (Arimura et al., *J. Pharmacol. Exp. Ther.*, 2001 August; 298(2):411-9). For some patients, the most appropriate formulation or method of use of such combination treatments depends on the type of $PGD_2$-dependent or $PGD_2$ mediated disorder, the time period in which the $DP_2$ antagonist acts to treat the disorder and/or the time period in which the $DP_1$ receptor antagonist acts to prevent $DP_1$ receptor activity. By way of example only, some embodiments described herein provide for such combination treatments that are used for treating a patient suffering from respiratory disorders such as asthma and rhinitis.

In another embodiment described herein, methods for treatment of $PGD_2$-dependent or $PGD_2$ mediated conditions or diseases includes administering to a patient compounds, pharmaceutical compositions, or medicaments described herein in combination with a TP receptor antagonist. Tp receptor antagonists include, but are not limited to, Ramatroban ("Bayer™"), GR32191 (Beasley et al., *J. Appl. Physiol.*, 1989 April; 66(4):1685-93), IC1192605 (Boersma et al., *Br. J. Pharmacol.*, 1999 December; 128(7):1505-12) and derivatives or analogs thereof. Such combinations may be used to treat $PGD_2$-dependent or $PGD_2$ mediated disorders, including respiratory disorders.

In one embodiment, the co-administration of a $DP_2$ receptor antagonist with a $DP_1$ receptor antagonist or a TP receptor antagonist has therapeutic benefit over and above the benefit derived from the administration of a either a $DP_2$ antagonist, $DP_1$ antagonist or a TP antagonist alone. In the case that substantial inhibition of $PGD_2$ activity has undesired effects, partial inhibition of this pathway through the amelioration of the effects of the proinflammatory agonists combined with the block of the $DP_1$ receptor, TP receptor and/or $DP_2$ receptor may afford substantial therapeutic benefits, particularly for respiratory diseases.

In another embodiment described herein, methods for treatment of $PGD_2$-dependent or $PGD_2$ mediated conditions or diseases, such as proliferative disorders, including cancer, comprises administration to a patient compounds, pharmaceutical compositions, or medicaments described herein in combination with at least one additional agent selected, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclixel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In another embodiment described herein, methods for treatment of $PGD_2$-dependent or $PGD_2$ mediated conditions or diseases, such as the therapy of transplanted organs or tissues or cells, comprises administration to a patient compounds, pharmaceutical compositions, or medicaments described herein in combination with at least one additional agent selected from, by way of example only, azathioprine, a corticosteroid, cyclophosphamide, cyclosporin, dacluzimab, mycophenolate mofetil, OKT3, rapamycin, tacrolimus, thymoglobulin.

In another embodiment described herein, methods for treatment of $PGD_2$-dependent or $PGD_2$ mediated conditions or diseases, such as atherosclerosis, comprises administration to a patient compounds, pharmaceutical compositions, or medicaments described herein in combination with at least one additional agent selected, by way of example only, HMG-CoA reductase inhibitors (e.g., statins in their lactonized or dihydroxy open acid forms and pharmaceutically acceptable salts and esters thereof, including but not limited to lovastatin; simvastatin; dihydroxy open-acid simvastatin, particularly the ammonium or calcium salts thereof; pravastatin, particularly the sodium salt thereof; fluvastatin, particularly the sodium salt thereof; atorvastatin, particularly the calcium salt thereof; nisvastatin, also referred to as NK-104; rosuvastatin); agents that have both lipid-altering effects and other pharmaceutical activities; HMG-CoA synthase inhibitors; cholesterol absorption inhibitors such as ezetimibe; cholesterol ester transfer protein (CETP) inhibitors, for example JTT-705 and CP529, 414; squalene epoxidase inhibitors; squalene synthetase inhibitors (also known as squalene synthase inhibitors); acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists, including the compounds commonly referred to as glitazones, for example troglitazone, pioglitazone and rosiglitazone and including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists such as 5-[(2,4-dioxo-5-thiazolidinyl)methyl]-2-methoxy-N-[[4-(trifluoromethyl)phenyl]methyl]-benzamide, known as KRP-297; vitamin B6 (also known as pyridoxine) and the pharmaceutically acceptable salts thereof such as the HCl salt; vitamin B12 (also known as cyanocobalamin); folic acid or a pharmaceutically acceptable salt or ester thereof such as the sodium salt and the methylglucamine salt; antioxidant vitamins such as vitamin C and E and beta carotene; beta-blockers; angiotensin H antagonists such as losartan; angiotensin converting enzyme inhibitors such as enalapril and captopril; calcium channel blockers such as nifedipine and diltiazam; endothelian antagonists; agents that enhance ABC1 gene expression; FXR and LXR ligands including both inhibitors and agonists; bisphosphonate compounds such as alendronate sodium; and cyclooxygenase-2 inhibitors such as rofecoxib and celecoxib.

In another embodiment described herein, methods for treatment of PGD$_2$-dependent or PGD$_2$ mediated conditions or diseases, such as the therapy of stroke, comprises administration to a patient compounds, pharmaceutical compositions, or medicaments described herein in combination with at least one additional agent selected from, by way of example only, COX-2 inhibitors; nitric oxide synthase inhibitors, such as N-(3-(aminomethyl)benzyl)acetamidine; Rho kinase inhibitors, such as fasudil; angiotension II type-1 receptor antagonists, including candesartan, losartan, irbesartan, eprosartan, telmisartan and valsartan; glycogen synthase kinase 3 inhibitors; sodium or calcium channel blockers, including crobenetine; p38 MAP kinase inhibitors, including SKB 239063; thromboxane AX-synthetase inhibitors, including isbogrel, ozagrel, ridogrel and dazoxiben; statins (HMG CoA reductase inhibitors), including lovastatin, simvastatin, dihydroxy open-acid simvastatin, pravastatin, fluvastatin, atorvastatin, nisvastatin, and rosuvastatin; neuroprotectants, including free radical scavengers, calcium channel blockers, excitatory amino acid antagonists, growth factors, antioxidants, such as edaravone, vitamin C, TROLOX™, citicoline and minicycline, and reactive astrocyte inhibitors, such as (2R)-2-propyloctanoic acid; beta andrenergic blockers, such as propranolol, nadolol, timolol, pindolol, labetalol, metoprolol, atenolol, esmolol and acebutolol; NMDA receptor antagonists, including memantine; NR2B antagonists, such as traxoprodil; 5-HTIA agonists; receptor platelet fibrinogen receptor antagonists, including tirofiban and lamifiban; thrombin inhibitors; antithrombotics, such as argatroban; antihypertensive agents, such as enalapril; vasodilators, such as cyclandelate; nociceptin antagonists; DPIV antagonists; CETP inhibitors; GABA 5 inverse agonists; and selective androgen receptor modulators.

In another embodiment described herein, methods for treatment of PGD$_2$-dependent or PGD$_2$ mediated conditions or diseases, such as the therapy of pulmonary fibrosis, comprises administration to a patient compounds, pharmaceutical compositions, or medicaments described herein in combination with at least one additional agent selected from, by way of example only, anti-inflammatory agents, such as corticosteroids, azathioprine or cyclophosphamide.

In another embodiment described herein, methods for treatment of PGD$_2$-dependent or PGD$_2$ mediated conditions or diseases, such as the therapy of interstitial cystitis, comprises administration to a patient compounds, pharmaceutical compositions, or medicaments described herein in combination with at least one additional agent selected from, by way of example only, dimethylsulfoxide, omalizumab, and pentosan polysulfate.

In another embodiment described herein, methods for treatment of PGD$_2$-dependent or PGD$_2$ mediated conditions or diseases, such as the therapy of disorders of bone, comprises administration to a patient compounds, pharmaceutical compositions, or medicaments described herein in combination with at least one additional agent selected from the, by way of example only, minerals, vitamins, bisphosphonates, anabolic steroids, parathyroid hormone or analogs, and cathepsin K inhibitors.

In yet another embodiment described herein, methods for treating PGD$_2$-dependent or PGD$_2$ mediated conditions or diseases, such as the therapy of respiratory disorders (e.g., asthma, COPD and rhinitis), comprises administration to a patient compounds, pharmaceutical compositions, or medicaments described herein in combination with at least one respiratory agent. Respiratory agents include, but are not limited to, bronchodilators (e.g., sympathomimetic agents and xanthine derivatives), leukotriene receptor antagonists, leukotriene formation inhibitors, leukotriene modulators, nasal decongestants, respiratory enzymes, lung surfactants, antihistamines (e.g., Mepyramine (pyrilamine), Antazoline, Diphenhydramine, Carbinoxamine, Doxylamine, Clemastine, Dimenhydrinate, Pheniramine, Chlorphenamine (chlorpheniramine), Dexchlorpheniramine, Brompheniramine, Triprolidine, cetirizine, Cyclizine, Chlorcyclizine, Hydroxyzine, Meclizine, loratadine, desloratidine, Promethazine, Alimemazine (trimeprazine), Cyproheptadine, Azatadine, Ketotifen, Acrivastine, Astemizole, Cetirizine, Mizolastine, Terfenadine, Azelastine, Levocabastine, Olopatadine, Levocetirizine, Fexofenadine), mucolytics, corticosteroids, glucocorticoids, anticholinergics, antitussives, analgesics, expectorants, albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, zafirlukast, pranlukast, tomelukast, ambrisentan, bosentan, enrasentan, sitaxsentan, tezosentan, iloprost, treprostinil, pirfenidone, FLAP inhibitors, FLAP modulators, 5-LO inhibitors, BLT1 receptor antagonists and BLT2 receptor antagonists.

In a specific embodiment described herein, methods for treating PGD$_2$-dependent or PGD$_2$ mediated conditions or diseases, such as the therapy of asthma and/or COPD, comprises administration to a patient anti-inflammatory agents. In certain embodiments, methods for treating PGD$_2$-dependent or PGD$_2$ mediated conditions or diseases, such as the therapy of asthma and/or COPD, comprise administration to a patient compounds, pharmaceutical compositions, or medicaments described herein in combination with at least one additional agent selected from, but not limited to, epinephrine, isoproterenol, orciprenaline, bronchodilators, glucocorticoids, leukotriene modifiers, mast-cell stabilizers, xanthines, anticholinergics, β-2 agonists, FLAP inhibitors, FLAP modulators or 5-LO inhibitors. β-2 agonists include, but are not limited to, short-acting β-2 agonists (e.g., salbutamol (albuterol), levalbuterol, terbutaline, pirbuterol, procaterol, metaproterenol, fenoterol and bitolterol mesylate) and long-acting β-2 agonists (e.g., salmeterol, formoterol, bambuterol and clenbuterol). FLAP inhibitors and/or FLAP modulators include, but are not limited to, 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid, 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid, MK-886, MK-0591, DG-031 (BAY-x1005) and compounds found in US 2007/0225285, US 2007/0219206, US 2007/0173508, US 2007/0123522 and US 2007/0105866 (each of which are hereby incorporated by reference). Glucocorticoids include, but are not limited to, beclometasone, budesonide, ciclesonide, fluticasone and mometasone. Anticholinergics include, but are not limited to, ipratropium and tiotropium. Mast cell stabilizers include, but are not limited to, cromoglicate and nedocromil. Xanthines include, but are not limited to, amminophylline, theobromine and theophylline. Leukotriene antagonists include, but are not limited to, montelukast, tomelukast, pranlukast and zafirlukast. 5-LO inhibitors include, but are not limited to, zileuton, VIA-2291 (ABT761), MK-0633, CJ-13,610 (PF-4191834), AZ-4407 and ZD-2138 and compounds found in US 2007/0149579, WO2007/016784.

In another specific embodiment described herein, methods for treating PGD$_2$-dependent or PGD$_2$ mediated conditions or diseases, such as the therapy of rhinitis, comprises administration to a patient compounds, pharmaceutical compositions, or medicaments described herein in combination with at least one additional agent selected from, by way of example only, antihistamines, leukotriene antagonists, corticosteroids and decongestants. Leukotriene antagonists include, but are not limited to, montelukast, tomelukast, pranlukast and zafirlukast.

In another aspect, methods for treating $PGD_2$-dependent or $PGD_2$ mediated conditions or diseases, include administering a $DP_2$ antagonist described herein in combination with other agents to treat respiratory diseases or conditions. Therapeutic agents used in the treatment of respiratory conditions and disorders, such as, but not limited to asthma, include: glucocorticoids, such as, ciclesonide, beclomethasone, budesonide, flunisolide, fluticasone, mometasone, and triamcinolone; leukotriene modifiers, such as, montelukast, zafirlukast, pranlukast, and zileuton; mast cell stabilizers, such as, cromoglicate (cromolyn), and nedocromil; antimuscarinics/anticholinergics, such as, ipratropium, oxitropium, and tiotropium; methylxanthines, such as, theophylline and aminophylline; antihistamine, such as, mepyramine (pyrilamine), antazoline, diphenhydramine, carbinoxamine, doxylamine, clemastine, dimenhydrinate, pheniramine, chlorphenamine (chlorpheniramine), dexchlorphenamine, brompheniramine, triprolidine, cyclizine, chlorcyclizine, hydroxyzine, meclizine, promethazine, alimemazine (trimeprazine), cyproheptadine, azatadine, ketotifen, acrivastine, astemizole, cetirizine, loratadine, mizolastine, terfenadine, fexofenadine, levocetirizine, desloratadine, fexofenadine; omalizumab, an IgE blocker; beta2-adrenergic receptor agonists, such as: short acting beta2-adrenergic receptor agonists, such as, salbutamol (albuterol), levalbuterol, terbutaline, pirbuterol, procaterol, metaproterenol, fenoterol, bitolterol mesylate; and long-acting beta2-adrenergic receptor agonists, such as, salmeterol, formoterol, bambuterol.

In one aspect, $DP_2$ anatagonists described herein are admistered in combination with one or more agents used to treat used to treat asthma, including, but not limited to: combination inhalers (fluticasone and salmeterol oral inhalation (e.g. Advair)); inhaled Beta-2 agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled corticosteroids (beclomethasone oral inhalation; budesonide inhalation solution; budesonide inhaler; flunisolide oral inhalation; fluticasone inhalation aerosol; fluticasone powder for oral inhalation; mometasone inhalation powder; triamcinolone oral inhalation); leukotriene modifiers (montelukast; zafirlukast; pranlukast; tomelukast; zileuton); mast cell stabilizers (cromolyn inhaler; nedocromil oral inhalation); monoclonal antibodies (omalizumab); oral Beta-2 agonists (albuterol oral syrup; albuterol oral tablets; metaproterenol; terbutaline); bronchodilator (aminophylline; oxtriphylline; theophylline).

In one aspect, $DP_2$ anatagonists described herein are admistered in combination with one or more agents used to treat allergy, including, but not limited to: antihistamine and decongestant combinations (cetirizine and pseudoephedrine; desloratadine and pseudoephedrine ER; fexofenadine and pseudoephedrine; loratadine and pseudoephedrine); antihistamines (azelastine nasal spray; brompheniramine; brompheniramine oral suspension; carbinoxamine; cetirizine; chlorpheniramine; clemastine; desloratadine; dexchlorpheniramine ER; dexchlorpheniramine oral syrup; diphenhydramine oral; fexofenadine; loratadine; promethazine); decongestants (pseudoephedrine); leukotriene modifiers (montelukast; montelukast granules); nasal anticholinergics (ipratropium); nasal corticosteroids (beclomethasone nasal inhalation; budesonide nasal inhaler; flunisolide nasal inhalation; fluticasone nasal inhalation; mometasone nasal spray; triamcinolone nasal inhalation; triamcinolone nasal spray); nasal decongestants (phenylephrine); nasal mast cell stabilizers (cromolyn nasal spray).

In one aspect, $DP_2$ anatagonists described herein are admistered in combination with one or more agents used to treat chronic obstructive pulmonary disease (COPD), including, but not limited to: anticholinergics—ipratropium bromide oral inhalation); combination Inhalers (albuterol and ipratropium (e.g. Combivent, DuoNeb); fluticasone and salmeterol oral inhalation (e.g. Advair)); corticosteroids (dexamethasone tablets; fludrocortisone acetate; hydrocortisone tablets; methylprednisolone; prednisolone liquid; prednisone oral; triamcinolone oral); inhaled Beta-2 Agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled Corticosteroids (beclomethasone oral inhalation; budesonide inhalation solution; budesonide inhaler; flunisolide oral inhalation; fluticasone inhalation aerosol; fluticasone powder for oral inhalation; triamcinolone oral inhalation); mukolytics (guaifenesin); oral Beta-2 agonists (albuterol oral syrup; albuterol oral tablets; metaproterenol; terbutaline); bronchodilator (aminophylline; oxtriphylline; theophylline).

In one embodiment, $DP_2$ anatagonists described herein are administered to a patient in combination with inhaled corticosteroids.

In one embodiment, $DP_2$ anatagonists described herein are administered to a patient in combination with beta2-adrenergic receptor agonists. In one embodiment, $DP_2$ anatagonists described herein are administered to a patient in combination with short acting beta2-adrenergic receptor agonists. In one embodiment, $DP_2$ anatagonists described herein are administered to a patient in combination with long-acting beta2-adrenergic receptor agonists.

As discussed herein, the administration of compounds of any of Formula (I), Formula (II), Formula (III), Formula (IV), Formula (V), Formula (VI), Formula (VII), or Formula (VIII) is designed to anatagonize the activity of $DP_2$. For example, in specific embodiments, the administration of a $DP_2$ inhibitor decreases signal transduction initiated by $PGD_2$ within the individual Thus, in accordance with one aspect, methods described herein include the diagnosis or determination of whether or not a patient is suffering from a $PGD_2$-dependent or $PGD_2$ mediated disease or condition by administering to the subject a compound of any of Formula (I), Formula (II), Formula (III), Formula (IV), Formula (V), Formula (VI), Formula (VII), or Formula (VIII) or pharmaceutical composition or medicament which includes a compound of any of Formula (I), Formula (II), Formula (III), Formula (IV), Formula (V), Formula (VI), Formula (VII), or Formula (VIII) and determining whether or not the patient responds to the treatment.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are fanned from any acceptable material including, e.g., glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

EXAMPLES

These examples are provided for illustrative purposes only and not to limit the scope of the claims provided herein. In the following examples, M+H (or M+23) refers to mass spectrometric data that was obtained, where M represents the molecular ion peak.

Example 1

Synthesis of {2'-[(Acetyl-methyl-amino)-methyl]-6-methoxy-4'-trifluoromethyl-biphenyl-3-yl}-acetic acid (Compound 1-1)

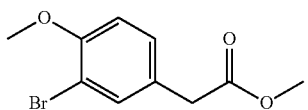

Step 1: (3-Bromo-4-methoxy-phenyl)-acetic acid methyl ester

To (3-bromo-4-methoxy-phenyl)-acetic acid (5.226 g, 21.32 mmol) in MeOH (52 mL) was added thionyl chloride (3.1 mL, 42.65 mmol), and the reaction was stirred at room temperature for 2 hours. Once no starting material was seen by analytical LCMS, the mixture was concentrated and then diluted with CH$_2$Cl$_2$ and aqueous 1N NaOH. The aqueous layer was separated and extracted with CH$_2$Cl$_2$, and the combined organic layers were washed with H$_2$O, dried over MgSO$_4$, filtered, and concentrated to give the title compound.

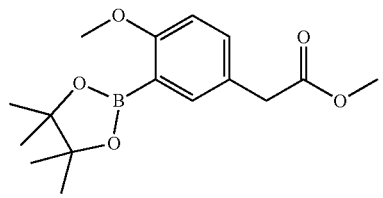

Step 2: [4-Methoxy-3-(4,4,5,5-tetramethyl-[1,3,2] dioxaborolan-2-yl)-phenyl]-acetic acid methyl ester (3-Bromo-4-methoxy-phenyl)-acetic acid methyl ester (5.1 g, 19.68 mmol), bis(pinacolato)diboron (6.54 g, 25.59 mmol), and potassium acetate (5.80 g, 59.05 mmol) were combined in DMF (100 mL) under N$_2$. The solution was purged with N$_2$, and then (1,1 t-bis(diphenylphosphino)ferrocene)-dichloropalladium(II) (0.805 g, 0.98 mmol) was added and the reaction was heated to 85° C. overnight. Starting material was still observed after 16 hours, so additional (1,1'-bis(diphenylphosphino)ferrocene)-dichloropalladium (II) (0.808 g, 0.98 mmol) was added, and the reaction was stirred at 85° C. overnight. Once no starting material was seen by analytical LCMS, the mixture was cooled to room temperature and concentrated. The residue was partitioned between EtOAc and H$_2$O and filtered through Celite. The aqueous layer was separated and extracted with EtOAc, and the combined organic layers were washed with brine, dried over MgSO$_4$, filtered, and concentrated. The residue was purified by silica gel chromatography (0-100% EtOAc in hexanes) to give the title compound.

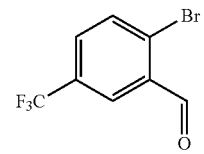 [SMILES: O=Cc1cc(C(F)(F)F)ccc1Br]

Step 3: 2-Bromo-5-trifluoromethyl-benzaldehyde

To (2-bromo-5-trifluoromethyl-phenyl)-methanol (2.216 g, 8.69 mmol) and N-methylmorpholine N-oxide (2.051 g, 17.38 mmol) in CH$_2$Cl$_2$ (44 mL) and MeCN (2.2 mL) was added tetrapropylammonium perruthenate (0.311 g, 0.87 mmol), and the reaction was stirred at room temperature for 20 minutes. Once no starting material was seen by analytical tlc, the mixture was concentrated and purified by silica gel chromatography to give the title compound.

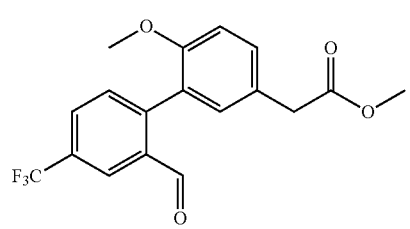 [SMILES: COC(=O)Cc1ccc(OC)c(-c2ccc(C(F)(F)F)cc2C=O)c1]

Step 4: (2'-Formyl-6-methoxy-4'-trifluoromethyl-biphenyl-3-yl)-acetic acid methyl ester 2-Bromo-5-trifluoromethyl-benzaldehyde (4.152 g, 16A1 mmol), [4-methoxy-3-(4,4,5,5-tetramethyl-[1,3,2]dioxaborolan-2-yl)-phenyl]-acetic acid methyl ester (4.988 g, 16.41 mmol), and potassium carbonate (5.67 g, 41.03 mmol) were combined in DME (40 mL) and H$_2$O (20 mL) under N$_2$. The mixture was purged with N$_2$, and then tetrakis(triphenylphosphine)palladium(0) (1.9 g, 1.64 mmol) was added, and the reaction was heated to 90° C. for 10 hours. Once no starting material was seen by analytical LCMS, the mixture was cooled to room temperature and diluted with CH$_2$Cl$_2$ and H$_2$O. The aqueous layer was separated and extracted with CH$_2$Cl$_2$, and the combined organic layers were dried over MgSO$_4$, filtered, and concentrated. The residue was purified by silica gel chromatography (0-100% EtOAc in hexanes) to give the title compound.

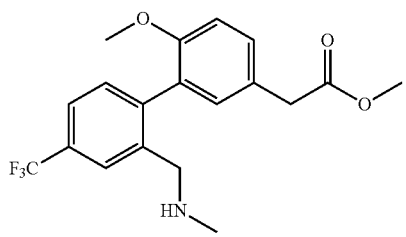 [SMILES: CNCc1cc(C(F)(F)F)ccc1-c1cc(CC(=O)OC)ccc1OC]

Step 5: (6-Methoxy-2'-methylaminomethyl-4'-trifluoromethyl-biphenyl-3-yl)-acetic acid methyl ester To (2-formyl-6-methoxy-4'-trifluoromethyl-biphenyl-3-yl)-acetic acid methyl ester (0.228 g, 0.65 mmol) and methylamine (2M in THF; 0.5 mL, 0.84 mmol) in CH$_2$Cl$_2$ (3.4 mL) was added sodium cyanoborohydride (0.061 g, 0.97 mmol), followed by acetic acid (1 drop). The reaction was stirred at room temperature overnight, until no starting material was seen by analytical LCMS. The solution was neutralized with saturated aqueous NaHCO$_3$ and extracted with CH$_2$Cl$_2$, and the combined organic layers were dried over MgSO$_4$, filtered, and concentrated to give the title compound.

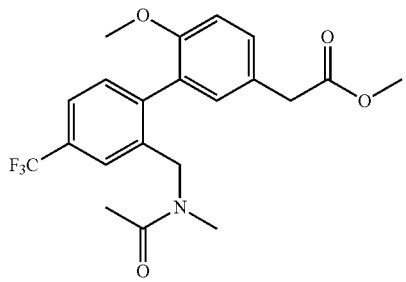 [SMILES: COC(=O)Cc1ccc(OC)c(-c2ccc(C(F)(F)F)cc2CN(C)C(C)=O)c1]

Step 6: {2'-[(Acetyl-methyl-amino)-methyl]-6-methoxy-4'-trifluoromethyl-biphenyl-3-yl}-acetic acid methyl ester To (6-methoxy-2'-methylaminomethyl-4'-trifluoromethyl-biphenyl-3-yl)-acetic acid methyl ester (0.114 g, 0.31 mmol) and triethylamine (0.05 mL, 0.34 mmol) in CH$_2$Cl$_2$ (1.2 mL) was added acetyl chloride (0.02 mL, 0.34 mmol), and the reaction was stirred at room temperature for 1 hour. Once no starting material was seen by analytical LCMS, the mixture was diluted with CH$_2$Cl$_2$ and H$_2$O, and the aqueous layer was extracted with CH$_2$Cl$_2$. The combined organic layers were dried over MgSO$_4$, filtered, and concentrated, and the residue was purified by silica gel chromatography (0-100% EtOAc in hexanes) to give the title compound.

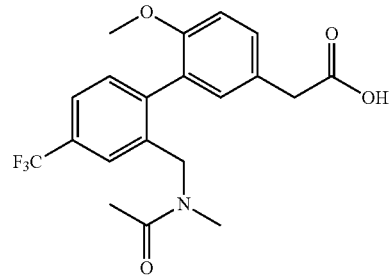 [SMILES: COc1ccc(CC(=O)O)cc1-c1ccc(C(F)(F)F)cc1CN(C)C(C)=O]

Step 7: {2'-[(Acetyl-methyl-amino)-methyl]-6-methoxy-4'-trifluoromethyl-biphenyl-3-yl}-acetic acid {2'-[(Acetyl-methyl-amino)-methyl]-6-methoxy-4'-trifluoromethyl-biphenyl-3-yl}-acetic acid methyl ester (0.038 g, 0.09 mmol) was dissolved in THF (0.38 mL), MeOH (0.3 mL), and aqueous 1N NaOH (0.2 mL), and the mixture was stirred at room temperature for 1 hour. Once no starting material was seen by analytical LCMS, the mixture was diluted with CH$_2$Cl$_2$ and H$_2$O, and the aqueous layer was extracted with CH$_2$Cl$_2$. The combined organic layers were dried over MgSO$_4$, filtered, and concentrated, and the residue was purified by preparative HPLC. The desired fractions were combined, concentrated, and the isolated material was diluted with CH$_2$Cl$_2$ and neutralized with saturated aqueous NaHCO$_3$. The organic layer was separated, dried over MgSO$_4$, filtered, and concentrated to give the title compound. The aqueous layer was acidified and extracted with EtOAc, and the organic layer was concentrated to give additional product. M+H is 396.

Example 2

Synthesis of {2'-[(Acetyl-ethyl-amino)-methyl]-6-methoxy-4'-trifluoromethyl-biphenyl-3-yl}-acetic acid (Compound 1-2)

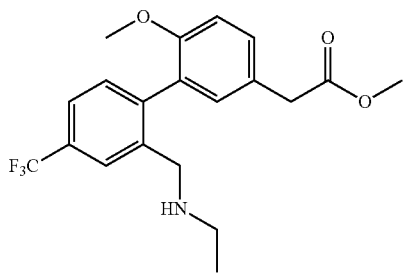 [SMILES: CCNCc1cc(C(F)(F)F)ccc1-c1cc(CC(=O)OC)ccc1OC]

Step 1: (2'-Ethylaminomethyl-6-methoxy-4'-trifluoromethyl-biphenyl-3-yl)-acetic acid methyl ester Prepared according to the procedure described in Example 1, Step 5, using the following starting materials: (2'-formyl- 6-methoxy-4'-trifluoromethyl-biphenyl-3-yl)-acetic acid methyl ester and ethylamine (2M in TI-IF).

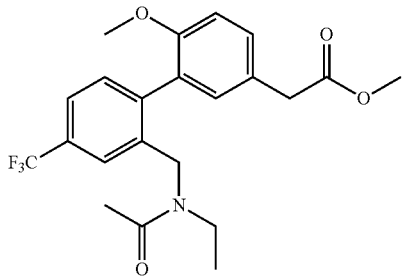 [SMILES: CCN(Cc1cc(C(F)(F)F)ccc1-c1cc(CC(=O)OC)ccc1OC)C(C)=O]

Step 2: {2'-[(Acetyl-ethyl-amino)-methyl]-6-methoxy-4'-trifluoromethyl-biphenyl-3-yl}-acetic acid methyl ester Prepared according to the procedure described in Example 1, Step 6, using the following starting materials: (2'-ethylaminomethyl-6-methoxy-4'-trifluoromethyl-biphenyl-3-yl)-acetic acid methyl ester and acetyl chloride.

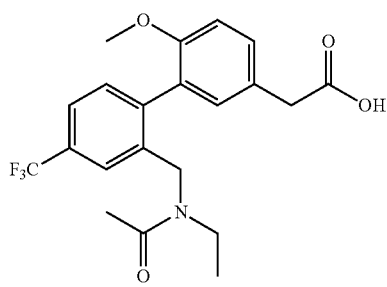 [SMILES: CCN(Cc1cc(C(F)(F)F)ccc1-c1cc(CC(=O)O)ccc1OC)C(C)=O]

Step 3: {2'-[(Acetyl-ethyl-amino)-methyl]-6-methoxy-5'-trifluoromethyl-biphenyl-3-yl}-acetic acid Prepared according to the procedure described in Example 1, Step 7, using the following starting material: {2'-[(acetyl-ethyl-amino)-methyl]-6-methoxy-4'-trifluoromethyl-biphenyl-3-yl}-acetic acid methyl ester. M+H is 410.

Example 3

Synthesis of (2'-{[Acetyl-(2,2-dimethyl-propyl)-amino]-methyl}-6-methoxy-4'-trifluoromethyl-biphenyl-3-yl)-acetic acid (Compound 1-3)

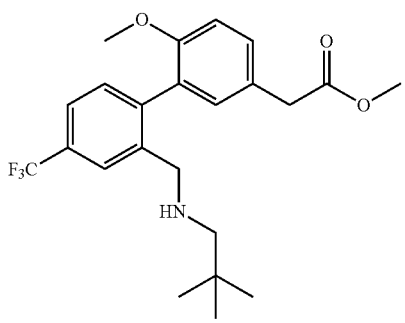 [SMILES: COC(=O)Cc1ccc(OC)c(-c2ccc(C(F)(F)F)cc2CNCC(C)(C)C)c1]

Step 1: {2'-[(2,2-Dimethyl-propylamino)-methyl]-6-methoxy-4'-trifluoromethyl-biphenyl-3-yl}-acetic acid methyl ester Prepared according to the procedure described in Example 1, Step 5, using the following starting materials: (2'-formyl-6-methoxy-4'-trifluoromethyl-biphenyl-3-yl)-acetic acid methyl ester and neopentylamine.

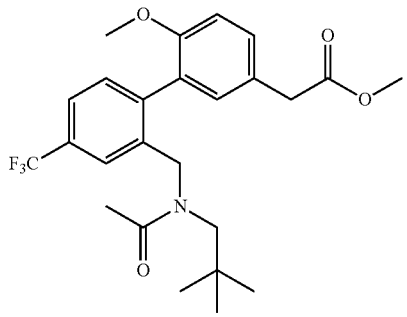 [SMILES: COC(=O)Cc1ccc(OC)c(-c2ccc(C(F)(F)F)cc2CN(CC(C)(C)C)C(C)=O)c1]

Step 2: (2'-{[Acetyl-(2,2-dimethyl-propyl)-amino]-methyl}-6-methoxy-4'-trifluoromethyl-biphenyl-3-yl)-acetic acid methyl ester Prepared according to the procedure described in Example 1, Step 6, using the following starting materials: {T-[(2,2-dimethyl-propylamino)-methyl]-6-methoxy-4'-trifluoromethyl-biphenyl-3-yl}-acetic acid methyl ester and acetyl chloride.

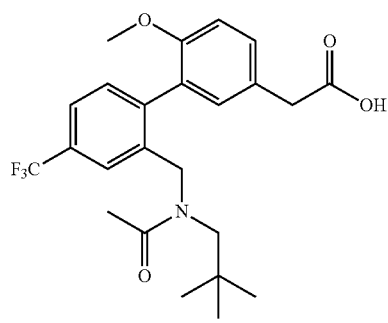 [SMILES: COc1ccc(CC(=O)O)cc1-c1ccc(C(F)(F)F)cc1CN(CC(C)(C)C)C(C)=O]

Step 3: (2'-{[Acetyl-(2,2-dimethyl-propyl)-amino]-methyl}-6-methoxy-4'-trifluoromethyl-biphenyl-3-yl)-acetic acid (2'-{[Acetyl-(2,2-dimethyl-propyl)-amino]-methyl}-6-methoxy-4'-trifluoromethyl-biphenyl-3-yl)-acetic acid methyl ester (0.152 g, 0.33 mmol) was dissolved in THF (1.5 mL), MeOH (1.2 mL), and aqueous 1N NaOH (0.72 mL), and the mixture was stirred at room temperature for 4 hours. Once no starting material was seen by analytical LCMS, the mixture was diluted with $CH_2Cl_2$ and aqueous 1N HCl, and the aqueous layer was extracted with $CH_2Cl_2$. The combined organic layers were dried over $MgSO_4$, filtered, and concentrated to give the title compound. M+H is 452.

Example 4

Synthesis of (2'-{[Acetyl-(2,2,2-trifluoro-ethyl)-amino]-methyl}-6-methoxy-4'-trifluoromethyl-biphenyl-3-yl)-acetic acid (Compound 1-4)

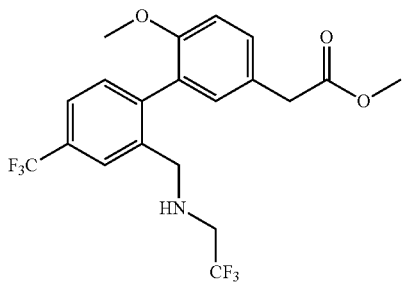 [SMILES: COC(=O)Cc1ccc(OC)c(-c2ccc(C(F)(F)F)cc2CNCC(F)(F)F)c1]

Step 1: {6-Methoxy-2'-[(2,2,2-trifluoro-ethylamino)-methyl]-4'-trifluoromethyl-biphenyl-3-yl}-acetic acid methyl ester 2,2,2-Trifluoroethylamine hydrochloride (0.101 g, 0.71 mmol) was treated with sodium acetate (0.061 g, 0.71 mmol) in MeOH (1 mL) with heating and sonication. (2'-Formyl-6-methoxy-4'-trifluoromethyl-biphenyl-3-yl)-acetic acid methyl ester (0.207 g, 0.59 mmol) in MeOH (2 mL) was added, followed by sodium cyanoborohydride (0.069 g, 1.06 mmol), and the reaction was stirred at room temperature for 1 hour. Once no starting material was seen by analytical LCMS, the mixture was quenched with $H_2O$ and extracted twice with $CH_2Cl_2$. The combined organic layers were dried over $MgSO_4$, filtered, and concentrated to give the title compound.

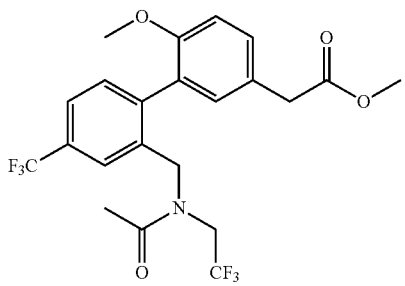 [SMILES: COC(=O)Cc1ccc(OC)c(-c2ccc(C(F)(F)F)cc2CN(CC(F)(F)F)C(C)=O)c1]

Step 2: (2'-{[Acetyl-(2,2,2-trifluoro-ethyl)-amino]-methyl}-6-methoxy-4'-trifluoromethyl-biphenyl-3-yl)-acetic acid methyl ester Prepared according to the procedure described in Example 1, Step 6, using the following starting materials: {6-methoxy-2'-[(2,2,2-trifluoro-ethylamino)-methyl]-4'-trifluoromethyl-biphenyl-3-yl}-acetic acid methyl ester and acetyl chloride.

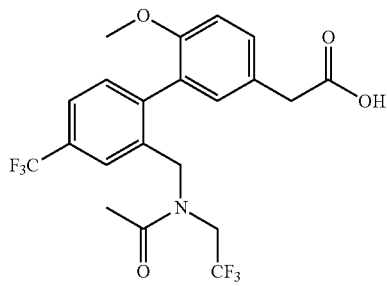 [SMILES: COc1ccc(CC(=O)O)cc1-c1ccc(C(F)(F)F)cc1CN(CC(F)(F)F)C(C)=O]

Step 3: (2'-{[Acetyl-(2,2,2-trifluoro-ethyl)-amino]-methyl}-6-methoxy-4'-trifluoromethyl-biphenyl-3-yl)-acetic acid Prepared according to the procedure described in Example 1, Step 7, using the following starting material: (2'-{[acetyl-(2,2,2-trifluoro-ethyl)-amino]-methyl}-6-methoxy-4'-trifluoromethyl-biphenyl-3-yl)-acetic acid methyl ester. M+H is 464.

Example 5

Synthesis of (2'-{[Acetyl-(2-hydroxy-ethyl)-amino]-methyl}-6-methoxy-4'-trifluoromethyl-biphenyl-3-yl)-acetic acid (Compound 1-5)

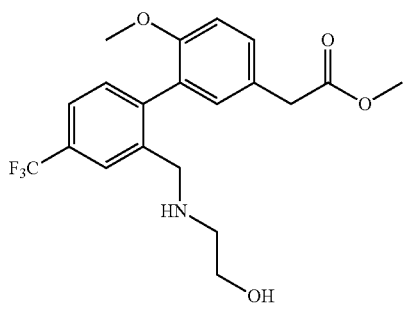 [SMILES: COC(=O)Cc1ccc(OC)c(-c2ccc(C(F)(F)F)cc2CNCCO)c1]

Step 1: {2'-[(2-Hydroxy-ethylamino)-methyl]-6-methoxy-4'-trifluoromethyl-biphenyl-3-yl}-acetic acid methyl ester Prepared according to the procedure described in Example 1, Step 5, using the following starting materials: (2'-formyl-6-methoxy-4'-trifluoromethyl-biphenyl-3-yl)-acetic acid methyl ester and ethanolamine.

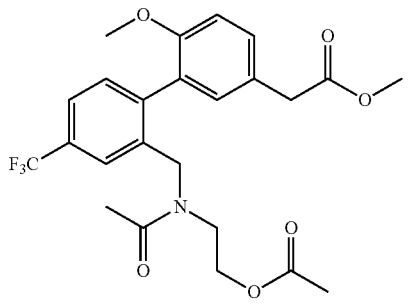 [SMILES: COC(=O)Cc1ccc(OC)c(-c2ccc(C(F)(F)F)cc2CN(CCOC(C)=O)C(C)=O)c1]

Step 2: (2'-{[(2-Acetoxy-ethyl)-acetyl-amino]-methyl}-6-methoxy-4'-trifluoromethyl-biphenyl-3-yl)-acetic acid methyl ester Prepared according to the procedure described in Example 1, Step 6, using the following starting materials: {2'-[(2-hydroxy-ethylamino)-methyl]-6-methoxy-4'-trifluoromethyl-biphenyl-3-yl}-acetic acid methyl ester and acetyl chloride.

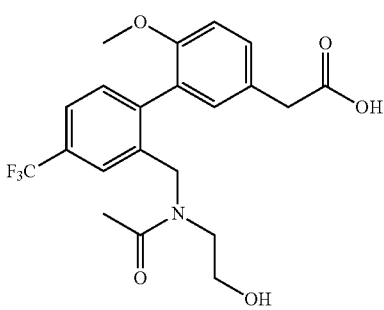 [SMILES: COc1ccc(CC(=O)O)cc1-c1ccc(C(F)(F)F)cc1CN(CCO)C(C)=O]

Step 3: (2'-{[Acetyl-(2-hydroxy-ethyl)-amino]-methyl}-6-methoxy-4'-trifluoromethyl-biphenyl-3-yl)-acetic acid Prepared according to the procedure described in Example 3, Step 3, using the following starting materials: (2'-{[(2-acetoxy-ethyl)-acetyl-amino]-methyl}-6-methoxy-4'-trifluoromethyl-biphenyl-3-yl)-acetic acid methyl ester. M+H is 426.

Example 6

Synthesis of (2'-{[Acetyl-(2-methoxy-ethyl)-amino]-methyl}-6-methoxy-4'-trifluoromethyl-biphenyl-3-yl)-acetic acid (Compound 1-6)

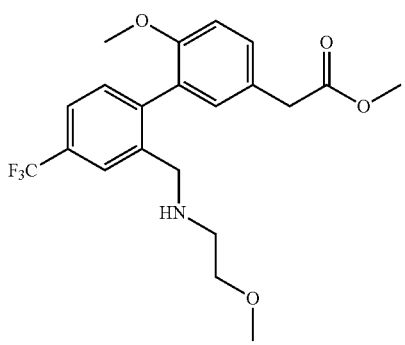 [SMILES: COCCNCc1cc(C(F)(F)F)ccc1-c1cc(CC(=O)OC)ccc1OC]

Step 1: {6-Methoxy-2'-[(2-methoxy-ethylamino)-methyl]-4'-trifluoromethyl-biphenyl-3-yl}-acetic acid methyl ester Prepared according to the procedure described in Example 1, Step 5, using the following starting materials: (2'-formyl-6-methoxy-4'-trifluoromethyl-biphenyl-3-yl)-acetic acid methyl ester and 2-methoxyethylamine.

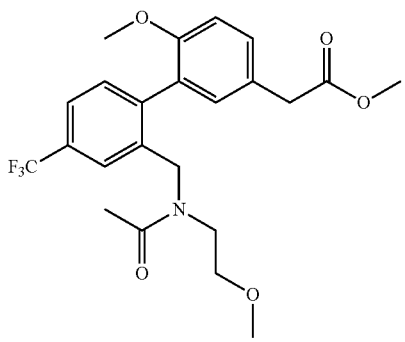 [SMILES: COCCN(Cc1cc(C(F)(F)F)ccc1-c1cc(CC(=O)OC)ccc1OC)C(C)=O]

Step 2: (2'-{[Acetyl-(2-methoxy-ethyl)-amino]-methyl}-6-methoxy-4'-trifluoromethyl-biphenyl-3-yl)-acetic acid methyl ester Prepared according to the procedure described in Example 1, Step 6, using the following starting materials: {6-methoxy-2'-[(2-methoxy-ethylamino)-methyl]-4'-trifluoromethyl-biphenyl-3-yl}-acetic acid methyl ester and acetyl chloride.

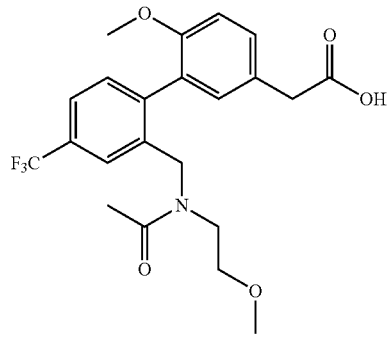 [SMILES: COCCN(Cc1cc(C(F)(F)F)ccc1-c1cc(CC(=O)O)ccc1OC)C(C)=O]

Step 3: (2'-{[Acetyl-(2-methoxy-ethyl)-amino]-methyl}-6-methoxy-4'-trifluoromethyl-biphenyl-3-yl)-acetic acid methyl ester Prepared according to the procedure described in Example 3, Step 3, using the following starting material: (2'-{[acetyl-(2-methoxy-ethyl)-amino]-methyl}-6-methoxy-4'-trifluoromethyl-biphenyl-3-yl)-acetic acid methyl ester. M+H is 440.

Example 7

Synthesis of (2'-{[Acetyl-(2-dimethylamino-ethyl)-amino]-methyl}-6-methoxy-4'-trifluoromethyl-biphenyl-3-yl)-acetic acid (Compound 1-7)

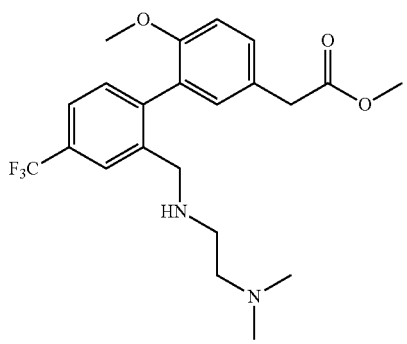 [SMILES: COC(=O)Cc1ccc(OC)c(-c2ccc(C(F)(F)F)cc2CNCCN(C)C)c1]

Step 1: {2'-[(2-Dimethylamino-ethylamino)-methyl]-6-methoxy-4'-trifluoromethyl-biphenyl-3-yl}-acetic acid methyl ester Prepared according to the procedure described in Example 1, Step 5, using the following starting materials: (2'-formyl-6-methoxy-4'-trifluoromethyl-biphenyl-3-yl)-acetic acid methyl ester and N,N-dimethylethylenediamine.

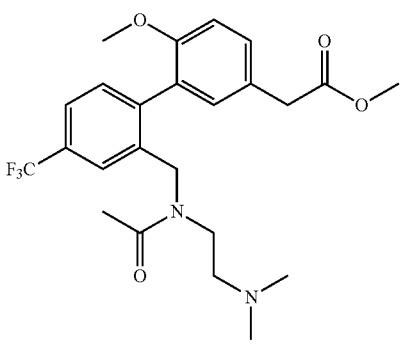 [SMILES: COC(=O)Cc1ccc(OC)c(-c2ccc(C(F)(F)F)cc2CN(CCN(C)C)C(C)=O)c1]

Step 2: (2'-{[Acetyl-(2-dimethylamino-ethyl)-amino]-methyl}-6-methoxy-4'-trifluoromethyl-biphenyl-3-yl)-acetic acid methyl ester Prepared according to the procedure described in Example 1, Step 6, using the following starting materials: {2'-[(2-dimethylamino-ethyl)-amino]-methyl}-6-methoxy-4'-trifluoromethyl-biphenyl-3-yl)-acetic acid methyl ester and acetyl chloride.

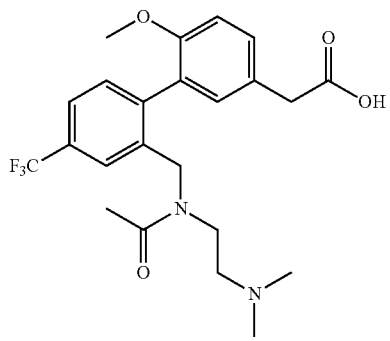 [SMILES: COc1ccc(CC(=O)O)cc1-c1ccc(C(F)(F)F)cc1CN(CCN(C)C)C(C)=O]

Step 3: (2'-{[Acetyl-(2-dimethylamino-ethyl)-amino]-methyl}-6-methoxy-4'-trifluoromethyl-biphenyl-3-yl)-acetic acid Prepared according to the procedure described in Example 3, Step 3, using the following starting material: (2'-(2'-{[acetyl-(2-dimethylamino-ethyl)-amino]-methyl}-6-methoxy-4'-trifluoromethyl-biphenyl-3-yl)-acetic acid methyl ester. M+H is 453.

Example 8

Synthesis of {2'-[(Acetyl-carboxymethyl-amino)-methyl]-6-methoxy-4'-trifluoromethyl-biphenyl-3-yl}-acetic acid (Compound 1-8)

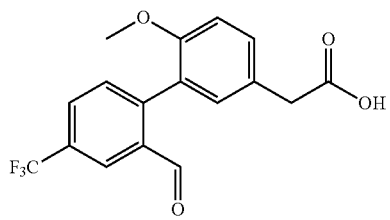 [SMILES: COc1ccc(CC(=O)O)cc1-c1ccc(C(F)(F)F)cc1C=O]

Step 1: (2'-Formyl-6-methoxy-4'-trifluoromethyl-biphenyl-3-yl)-acetic acid

To (2'-formyl-6-methoxy-4'-trifluoromethyl-biphenyl-3-yl)-acetic acid methyl ester (0.301 g, 0.85 mmol) in MeOH (2.4 mL) and THF (3 mL) was added aqueous 1N NaOH (1.9 mL), and the solution was stirred overnight at room temperature. Once no starting material was seen by analytical LCMS, the reaction was neutralized with aqueous 1N HCl and extracted with $CH_2Cl_2$. The combined organic layers were dried over $MgSO_4$, filtered, and concentrated, and the residue was purified by silica gel chromatography (50-100% EtOAc in hexanes, followed by 5% MeOH in $CH_2Cl_2$) to give the title compound.

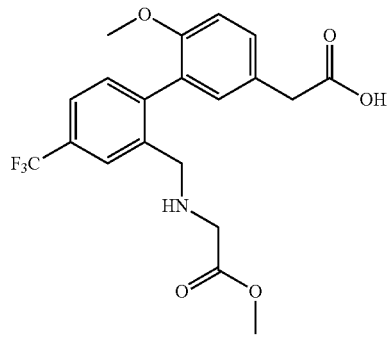 [SMILES: COC(=O)CNCc1cc(C(F)(F)F)ccc1-c1cc(CC(=O)O)ccc1OC]

Step 2: {6-Methoxy-2'-[(methoxycarbonylmethyl-amino)-methyl]-4'-trifluoromethyl-biphenyl-3-yl}-acetic acid Glycine methyl ester hydrochloride (0.057 g, 0.44 mmol) and sodium acetate (0.038 g, 0.44 mmol) were combined in a flask. (2'-Formyl-6-methoxy-4'-trifluoromethyl-biphenyl-3-yl)-acetic acid (0.099 g, 0.29 mmol) in MeOH (3 mL) was added, followed by sodium cyanoborohydride (0.029 g, 0.44 mmol), and the reaction was stirred at room temperature for 3.5 hours. Once no starting material was seen by analytical LCMS, the mixture was diluted with $CH_2Cl_2$ and $H_2O$. The organic layer was separated, dried over $MgSO_4$, filtered, and concentrated to give the title compound.

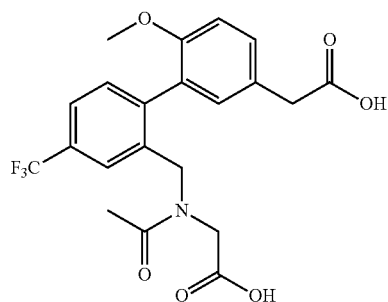 [SMILES: COc1ccc(CC(=O)O)cc1-c1ccc(C(F)(F)F)cc1CN(CC(=O)O)C(C)=O]

Step 3: {2'-[(Acetyl-carboxymethyl-amino)-methyl]-6-methoxy-4'-trifluoromethyl-biphenyl-3-yl}-acetic acid {6-Methoxy-2'-[(methoxycarbonylmethyl-amino)-methyl]-4'-trifluoromethyl-biphenyl-3-yl}-acetic acid (0.094 g, 0.23 mmol), acetyl chloride (0.03 mL, 0.46 mmol), and triethylamine (0.08 mL, 0.57 mmol) were combined in CH$_2$Cl$_2$ (1 mL) and stirred at room temperature for 1 hour. Once no starting material was seen by analytical LCMS, aqueous 1N NaOH was added. After stirring at room temperature for 45 minutes, analytical LCMS indicated that both acids had been hydrolyzed to the free acid, and so the mixture was neutralized with aqueous 1N HCl and extracted with CH$_2$Cl$_2$. The combined organic layers were dried over MgSO$_4$, filtered, and concentrated to give the title compound. M+H is 440.

Example 9

Synthesis of {2'-[(Acetyl-carbamoylmethyl-amino)-methyl]-6-methoxy-4'-trifluoromethyl-biphenyl-3-yl}-acetic acid (Compound 1-9)

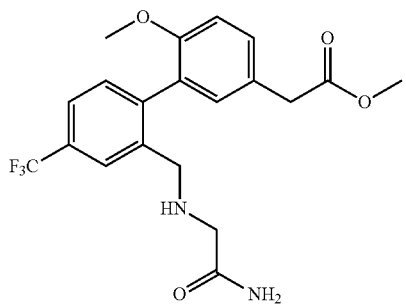 [SMILES: COC(=O)Cc1ccc(OC)c(-c2ccc(C(F)(F)F)cc2CNCC(N)=O)c1]

Step 1: {2'-[(Carbanoylmethyl-amino)-methyl]-6-methoxy-4'-trifluoromethyl-biphenyl-3-yl}-acetic acid methyl ester Prepared according to the procedure described in Example 4, Step 1, using the following starting materials: (2'-formyl-6-methoxy-4'-trifluoromethyl-biphenyl-3-yl)-acetic acid methyl ester and glycinamide hydrochloride.

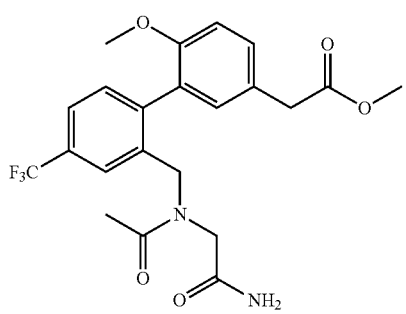 [SMILES: COC(=O)Cc1ccc(OC)c(-c2ccc(C(F)(F)F)cc2CN(CC(N)=O)C(C)=O)c1]

Step 2: {2'-[(Acetyl-carbamoylmethyl-amino)-methyl]-6-methoxy-4'-trifluoromethyl-biphenyl-3-yl}-acetic acid methyl ester Prepared according to the procedure described in Example 1, Step 6, using the following starting materials: {2%[(carbamoylmethyl-amino)-methyl]-6-methoxy-4'-trifluoromethyl-biphenyl-3-yl}-acetic acid methyl ester and acetyl chloride.

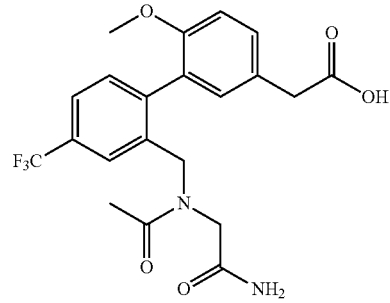

Step 3: {2'-[(Acetyl-carbamoylmethyl-amino)-methyl]-6-methoxy-4'-trifluoromethyl-biphenyl-3-yl}-acetic acid Prepared according to the procedure described in Example 3, Step 3, using the following starting material: {2'-[(acetyl-carbamoylmethyl-amino)-methyl]-6-methoxy-4'-trifluoromethyl-biphenyl-3-yl}-acetic acid methyl ester. M+H is 439.

Example 10

Synthesis of {2'-[(Acetyl-ethyl-amino)-methyl]-6-fluoro-4'-trifluoromethyl-biphenyl-3-yl}-acetic acid (Compound 1-10)

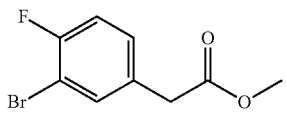

Step 1: (3-Bromo-4-fluoro-phenyl)-acetic acid methyl ester

Prepared according to the procedure described in Example 1, Step 1, using the following starting material: (3-bromo-4-fluoro-phenyl)-acetic acid.

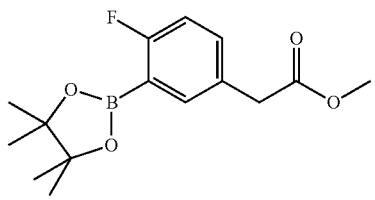

Step 2: [4-Fluoro-3-(4,4,5,5-tetramethyl-[1,3,2]dioxaborolan-2-yl)-phenyl]-acetic acid methyl ester Prepared according to the procedure described in Example 1, Step 2, using the following starting materials: (3-bromo-4-fluoro-phenyl)-acetic acid methyl ester and bis(pinacolato)diboron.

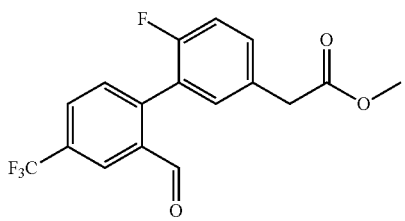 [SMILES: COC(=O)Cc1ccc(F)c(-c2ccc(C(F)(F)F)cc2C=O)c1]

Step 3: (6-Fluoro-2'-formyl-4'-trifluoromethyl-biphenyl-3-yl)-acetic acid methyl ester Prepared according to the procedure described in Example 1, Step 4, using the following starting materials: 2-bromo-5-trifluoromethyl-benzaldehyde and [4-fluoro-3-(4,4,5,5-tetramethyl-[1,3,2]dioxaborolan-2-yl)-phenyl]-acetic acid methyl ester; the isolated product was further purified by preparative HPLC.

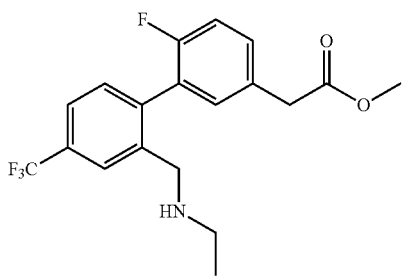

Step 4: (2'-Ethylaminomethyl-6-fluoro-4'-trifluoromethyl-biphenyl-3-yl)-acetic acid methyl ester Prepared according to the procedure described in Example 1, Step 5, using the following starting materials: (6-fluoro-2'-formyl-4'-trifluoromethyl-biphenyl-3-yl)-acetic acid methyl ester and ethylamine (2M in THF).

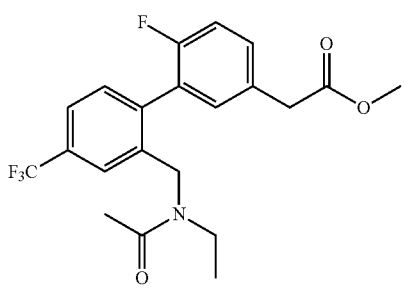

Step 5: {2'-[(Acetyl-ethyl-amino)-methyl]-6-fluoro-4'-trifluoromethyl-biphenyl-3-yl}-acetic acid methyl ester Prepared according to the procedure described in Example 1, Step 6, using the following starting materials: (2'-ethylaminomethyl-6-fluoro-4'-trifluoromethyl-biphenyl-3-yl)-acetic acid methyl ester and acetyl chloride.

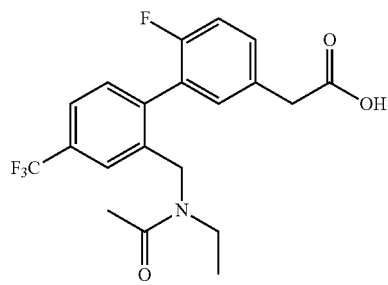 [SMILES: CCN(Cc1cc(C(F)(F)F)ccc1-c1cc(CC(=O)O)ccc1F)C(C)=O]

Step 6: {2'-[(Acetyl-ethyl-amino)-methyl]-6-fluoro-4'-trifluoromethyl-biphenyl-3-yl}-acetic acid Prepared according to the procedure described in Example 3, Step 3, using the following starting material: {2'-[(acetyl-ethyl-amino)-methyl]-6-fluoro-4'-trifluoromethyl-biphenyl-3-yl}-acetic acid methyl ester. M+H is 398.

Example 11

Synthesis of (2'-{[Acetyl-(2,2,2-trifluoro-ethyl)-amino]-methyl}-6-fluoro-4'-trifluoromethyl-biphenyl-3-yl)-acetic acid (Compound 1-11)

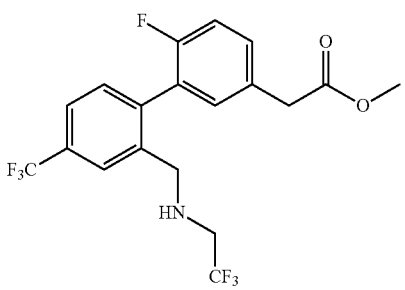 [SMILES: COC(=O)Cc1ccc(F)c(-c2ccc(C(F)(F)F)cc2CNCC(F)(F)F)c1]

Step 1: {6-Fluoro-2'[(2,2,2-trifluoro-ethylamino)-methyl]-4'-trifluoromethyl-biphenyl-3-yl}-acetic acid methyl ester Prepared according to the procedure described in Example 4, Step 1, using the following starting materials: (6-fluoro-4'-formyl-4'-trifluoromethyl-biphenyl-3-yl)-acetic acid methyl ester and 2,2,2-trifluoroethylamine hydrochloride.

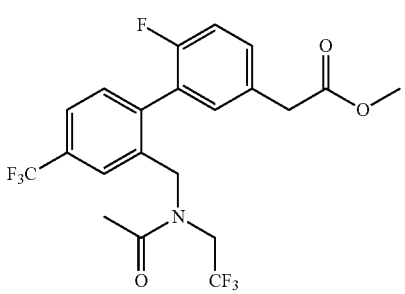 [SMILES: COC(=O)Cc1ccc(F)c(-c2ccc(C(F)(F)F)cc2CN(CC(F)(F)F)C(C)=O)c1]

Step 2: (2'-{[Acetyl-(2,2,2-trifluoro-ethyl)-amino]-methyl}-6-fluoro-4'-trifluoromethyl-biphenyl-3-yl)-acetic acid methyl ester Prepared according to the procedure described in Example 1, Step 6, using the following starting materials: {6-fluoro-2'-[(2,2,2-trifluoro-ethylamino)-methyl]-4'-trifluoromethyl-biphenyl-3-yl}-acetic acid methyl ester and acetyl chloride.

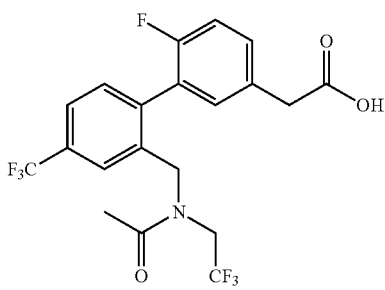 [SMILES: CC(=O)N(Cc1cc(C(F)(F)F)ccc1-c1cc(CC(=O)O)ccc1F)CC(F)(F)F]

Step 3: (2'-{[Acetyl-(2,2,2-trifluoro-ethyl)-amino]-methyl}-6-fluoro-4'-trifluormethyl-biphenyl-3-yl)-acetic acid Prepared according to the procedure described in Example 1, Step 7, using the following starting materials: (2'-{[acetyl-(2,2,2-trifluoro-ethyl)-amino]-methyl}-6-fluoro-4'-trifluoromethyl-biphenyl-3-yl)-acetic acid methyl ester. M+H is 452.

Example 12

Synthesis of {2'-[(Acetyl-cyclopropyl-amino)-methyl]-6-methoxy-4'-trifluoromethyl-biphenyl-3-yl}-acetic acid (Compound 1-12)

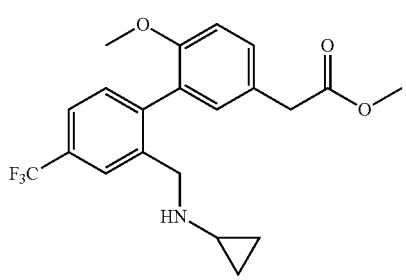 [SMILES: COC(=O)Cc1ccc(OC)c(-c2ccc(C(F)(F)F)cc2CNC2CC2)c1]

Step 1: (2'-Cyclopropylaminomethyl-6-methoxy-4'-trifluoromethyl-biphenyl-3-yl)-acetic acid methyl ester Prepared according to the procedure described in Example 1, Step 5, using the following starting materials: (2'-formyl-6-methoxy-4'-trifluoromethyl-biphenyl-3-yl)-acetic acid methyl ester and cyclopropylamine.

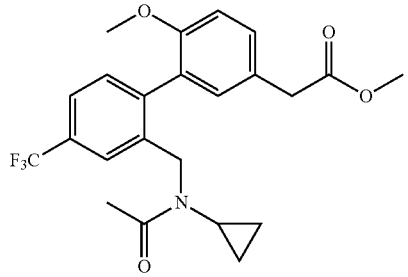 [SMILES: COC(=O)Cc1ccc(OC)c(-c2ccc(C(F)(F)F)cc2CN(C(C)=O)C2CC2)c1]

Step 2: {2'-[(Acetyl-cyclopropyl-amino)-methyl]-6-methoxy-4'-trifluoromethyl-biphenyl-3-yl}-acetic acid methyl ester Prepared according to the procedure described in Example 1, Step 6, using the following starting materials: (T-cyclopropylaminomethyl-6-methoxy-4'-trifluoromethyl-biphenyl-3-yl)-acetic acid methyl ester and acetyl chloride.

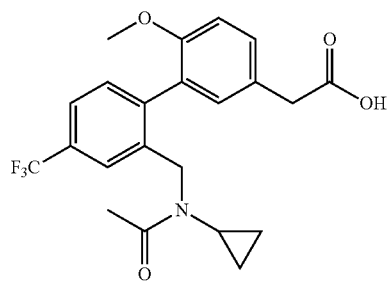 [SMILES: COc1ccc(CC(=O)O)cc1-c1ccc(C(F)(F)F)cc1CN(C(C)=O)C1CC1]

Step 3: {2'-[(Acetyl-cyclopropyl-amino)-methyl]-6-methoxy-4'-trifluoromethyl-biphenyl-3-yl}-acetic acid Prepared according to the procedure described in Example 3, Step 3, using the following starting material: {2'-[(acetyl-cyclopropyl-amino)-methyl]-6-methoxy-4'-trifluoromethyl-biphenyl-3-yl}-acetic acid methyl ester. M+H is 422.

Example 13

Synthesis of {2'-[((R)-Acetyl-indan-1-yl-amino)-methyl]-6-methoxy-4'-trifluoromethyl-biphenyl-3-yl}-acetic acid (Compound 1-13)

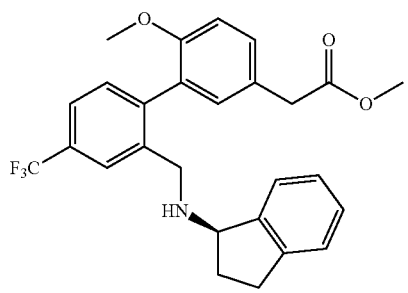 [SMILES: COC(=O)Cc1ccc(OC)c(-c2ccc(C(F)(F)F)cc2CN[C@@H]2CCc3ccccc32)c1]

Step 1: [2'-((R)-Indan-1-ylaminomethyl)-6-methoxy-4'-trifluoromethyl-biphenyl-3-yl]-acetic acid methyl ester Prepared according to the procedure described in Example 4, Step 1, using the following starting materials: (2'-formyl-6-methoxy-4'-trifluoromethyl-biphenyl-3-yl)-acetic acid methyl ester and (R)-(−)-1-aminoindan.

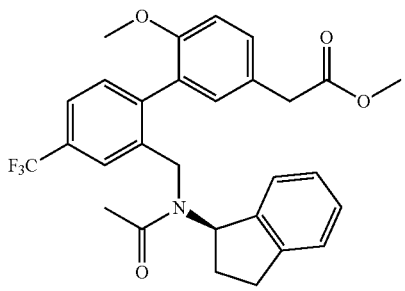 [SMILES: COC(=O)Cc1ccc(OC)c(-c2ccc(C(F)(F)F)cc2CN(C(C)=O)[C@@H]2CCc3ccccc32)c1]

Step 2: {2'-[((R)-Acetyl-indan-1-yl-amino)-methyl]-6-methoxy-4'-trifluoromethyl-biphenyl-3-yl}-acetic acid methyl ester Prepared according to the procedure described in Example 1, Step 6, using the following starting materials: [2'-((R)-indan-1-ylaminomethyl)-6-methoxy-4'-trifluoromethyl-biphenyl-3-yl]-acetic acid methyl ester and acetyl chloride.

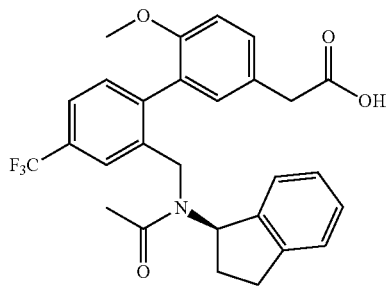 [SMILES: COc1ccc(CC(=O)O)cc1-c1ccc(C(F)(F)F)cc1CN(C(C)=O)[C@@H]1CCc2ccccc21]

Step 3: {2'-[((R)-Acetyl-indan-1-yl-amino)-methyl]-6-methoxy-4'-trifluoromethyl-biphenyl-3-yl}-acetic acid Prepared according to the procedure described in Example 3, Step 3, using the following starting material: {2'-[(((R)-acetyl-indan-1-yl-amino)-methyl]-6-methoxy-4'-trifluoromethyl-biphenyl-3-yl}-acetic acid methyl ester. M+H is 498.

Example 14

Synthesis of {2'-[((S)-Acetyl-indan-1-yl-amino)-methyl]-6-methoxy-4'-trifluoromethyl-biphenyl-3-yl}-acetic acid (Compound 1-14)

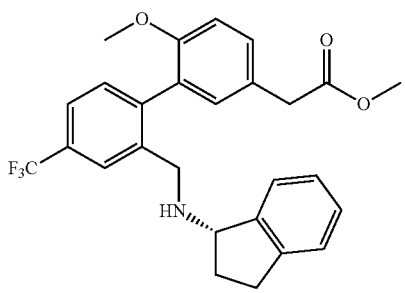 [SMILES: COC(=O)Cc1ccc(OC)c(-c2ccc(C(F)(F)F)cc2CN[C@H]2CCc3ccccc32)c1]

Step 1: [2'-((S)-Indan-1-ylaminomethyl)-6-methoxy-4'-trifluoromethyl-biphenyl-3-yl]-acetic acid methyl ester Prepared according to the procedure described in Example 4, Step 1, using the following starting materials: (2'-formyl-6-methoxy-4'-trifluoromethyl-biphenyl-3-yl)-acetic acid methyl ester and (S)-(+)-1-aminoindan.

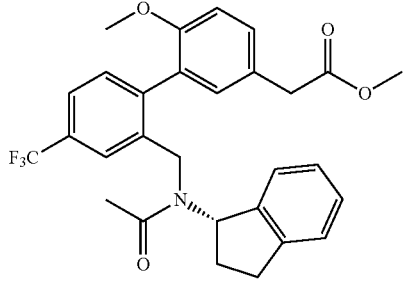 [SMILES: COC(=O)Cc1ccc(OC)c(-c2ccc(C(F)(F)F)cc2CN(C(C)=O)[C@H]2CCc3ccccc32)c1]

Step 2: {2'-[((S)-Acetyl-indan-1-yl-amino)-methyl]-6-methoxy-4'-trifluoromethyl-biphenyl-3-yl}-acetic acid methyl ester Prepared according to the procedure described in Example 1, Step 6, using the following starting materials: [2'-((S)-Indan-1-ylaminomethyl)-6-methoxy-4'-trifluoromethyl-biphenyl-3-yl]-acetic acid methyl ester and acetyl chloride.

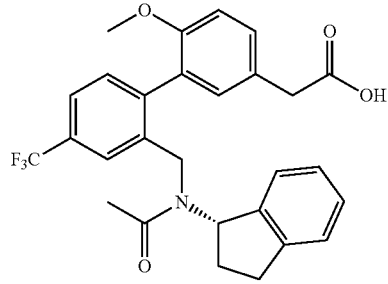 [SMILES: COc1ccc(CC(=O)O)cc1-c1ccc(C(F)(F)F)cc1CN(C(C)=O)[C@H]1CCc2ccccc21]

Step 3: {2'-[((S)-Acetyl-indan-1-yl-amino)-methyl]-6-methoxy-4'-trifluoromethyl-biphenyl-3-yl}-acetic acid Prepared according to the procedure described in Example 3, Step 3, using the following starting material: [2'-((S)-acetyl-indan-1-yl-amino)-methyl]-6-methoxy-4'-trifluoromethyl-biphenyl-3-yl)-acetic acid methyl ester. M+H is 498.

Example 15

Synthesis of (2'-{[Acetyl-((1R,2S)-2-hydroxy-indan-1-yl)-amino]-methyl}-6-methoxy-4'-trifluoromethyl-biphenyl-3-yl)-acetic acid (Compound 1-15)

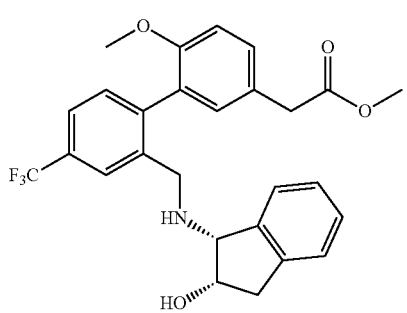 [SMILES: COC(=O)Cc1ccc(OC)c(-c2ccc(C(F)(F)F)cc2CN[C@@H]2c3ccccc3C[C@@H]2O)c1]

Step 1: {2'-[((1R,2S)-2-Hydroxy-indan-1-ylamino)-methyl]-6-methoxy-4'-trifluoromethyl-biphenyl-3-yl}-acetic acid methyl ester Prepared according to the procedure described in Example 1, Step 5, using the following starting materials: (2'-formyl-6-methoxy-4'-trifluoromethyl-biphenyl-3-yl)-acetic acid methyl ester and (1S,2R)-(−)-cis-1-amino-2-indanol.

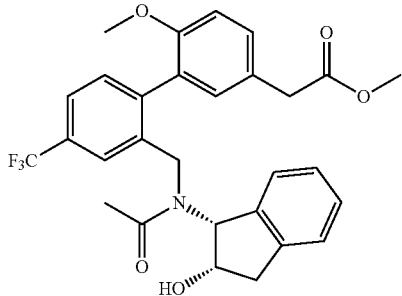 [SMILES: COC(=O)Cc1ccc(OC)c(-c2ccc(C(F)(F)F)cc2CN(C(C)=O)[C@@H]2c3ccccc3C[C@@H]2O)c1]

Step 2: (2'-{[Acetyl-((1R,2S)-2-hydroxy-indan-1-yl)-amino]-methyl}-6-methoxy-4'-trifluoromethyl-biphenyl-3-yl)-acetic acid methyl ester Prepared according to the procedure described in Example 1, Step 6, using the following starting materials: {2'-[((1R,2S)-2-hydroxy-indan-1-ylamino)-methyl]-6-methoxy-4'-trifluoromethyl-biphenyl-3-yl}-acetic acid methyl ester and acetyl chloride.

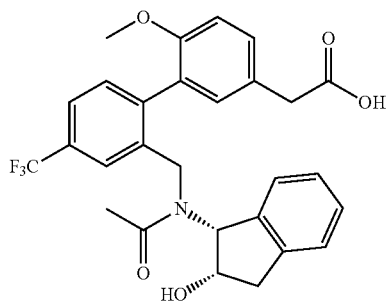 [SMILES: COc1ccc(CC(=O)O)cc1-c1ccc(C(F)(F)F)cc1CN(C(C)=O)[C@@H]1c2ccccc2C[C@@H]1O]

Step 3: (2'-{[Acetyl-((1R,2S)-2-hydroxy-indan-1-yl)-amino]-methyl}-6-methoxy-4'-trifluoromethyl-biphenyl-3-yl)-acetic acid Prepared according to the procedure described in Example 1, Step 7, using the following starting material: (2'-{[acetyl-((1R,2S)-2-hydroxy-indan-1-yl)-amino]-methyl}-6-methoxy-4'-trifluoromethyl-biphenyl-3-yl)-acetic acid methyl ester. M+H is 514.

Example 16

Synthesis of (2'-{[Acetyl-((1R,2S)-2-methoxy-indan-1-yl)-amino]-methyl}-6-methoxy-4'-trifluoromethyl-biphenyl-3-yl)-acetic acid (Compound 1-16)

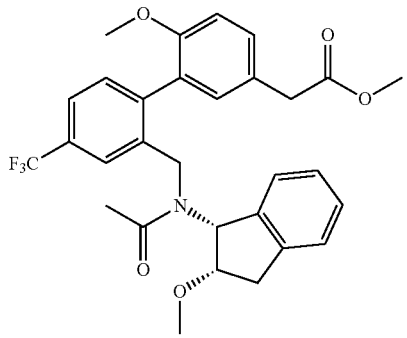 [SMILES: COC(=O)Cc1ccc(OC)c(-c2ccc(C(F)(F)F)cc2CN(C(C)=O)[C@@H]2c3ccccc3C[C@@H]2OC)c1]

Step 1: (2'-{[Acetyl-((1R,2S)-2-methoxy-indan-1-yl)-amino]-methyl}-6-methoxy-4'-trifluoromethyl-biphenyl-3-yl)-acetic acid methyl ester To (2'-{[acetyl-((1R,2S)-2-hydroxy-indan-1-yl)-amino]-methyl}-6-methoxy-4'-trifluoromethyl-biphenyl-3-yl)-acetic acid methyl ester (0.163 g, 0.31 mmol) and iodomethane (0.02 mL, 0.34 mmol) in DMF (1.6 mL) was added sodium hydride (60% in mineral oil; 0.015 g, 0.37 mmol), and the mixture was stirred at room temperature for 1 hour. Once minimal starting material was seen by analytical LCMS, the solution was diluted with aqueous 1N HCl and $CH_2Cl_2$. The organic layer was separated, dried over $MgSO_4$, filtered, and concentrated to give the title compound.

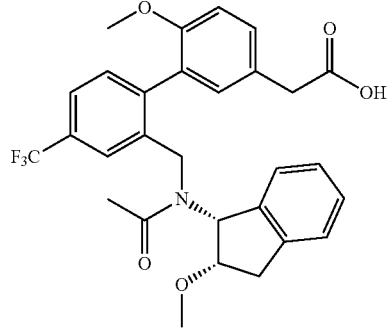 [SMILES: COc1ccc(CC(=O)O)cc1-c1ccc(C(F)(F)F)cc1CN(C(C)=O)[C@@H]1c2ccccc2C[C@@H]1OC]

Step 2: (2'-{[Acetyl-((1R,2S)-2-methoxy-indan-1-yl)-amino]-methyl}-6-methoxy-4'-trifluoromethyl-biphenyl-3-A-acetic acid Prepared according to the procedure described in Example 1, Step 7, using the following starting material: (2'-{[acetyl-((1R,2S)-2-methoxy-indan-1-yl)-amino]-methyl}-6-methoxy-4'-trifluoromethyl-biphenyl-3-yl)-acetic acid methyl ester. M-1-H is 528.

Example 17

Synthesis of {2'-[(Acetyl-indan-2-yl-amino)-methyl]-6-methoxy-4'-trifluoromethyl-biphenyl-3-yl}-acetic acid (Compound 1-17)

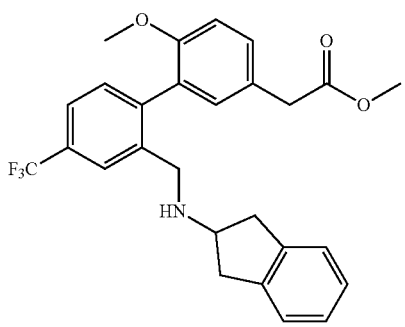 [SMILES: COC(=O)Cc1ccc(OC)c(-c2ccc(C(F)(F)F)cc2CNC2Cc3ccccc3C2)c1]

Step 1: [2'-(Indan-2-ylaminomethyl)-6-methoxy-4'-trifluoromethyl-biphenyl-3-yl]-acetic acid methyl ester Prepared according to the procedure described in Example 4, Step 1, using the following starting materials: (2'-formyl-6-methoxy-4'-trifluoromethyl-biphenyl-3-yl)-acetic acid methyl ester and 2-aminoindan hydrochloride.

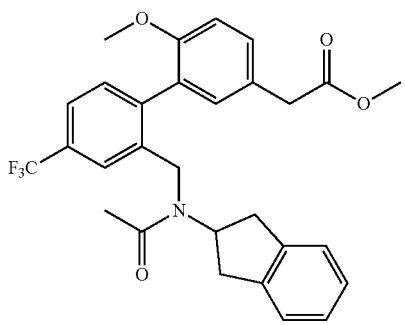 [SMILES: COC(=O)Cc1ccc(OC)c(-c2ccc(C(F)(F)F)cc2CN(C(C)=O)C2Cc3ccccc3C2)c1]

Step 2: {2'-[(Acetyl-indan-2-yl-amino)-methyl]-6-methoxy-4'-trifluoromethyl-biphenyl-3-yl}-acetic acid methyl ester Prepared according to the procedure described in Example 1, Step 6, using the following starting materials: [2'-(indan-2-ylaminomethyl)-6-methoxy-4'-trifluoromethyl-biphenyl-3-yl]-acetic acid methyl ester and acetyl chloride.

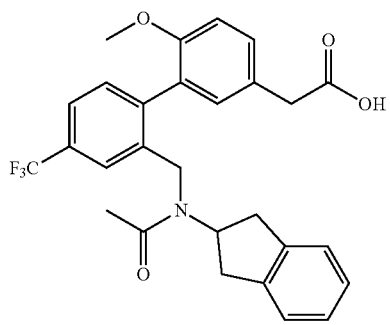 [SMILES: COc1ccc(CC(=O)O)cc1-c1ccc(C(F)(F)F)cc1CN(C(C)=O)C1Cc2ccccc2C1]

Step 3: {2'-[(Acetyl-indan-2-yl-amino)-methyl]-6-methoxy-4'-trifluoromethyl-biphenyl-3-yl}-acetic acid Prepared according to the procedure described in Example 3, Step 3, using the following starting materials: {2'-[(acetyl-indan-2-yl-amino)-methyl]-6-methoxy-4'-trifluoromethyl-biphenyl-3-yl}-acetic acid methyl ester. M+H is 498.

Example 18

Synthesis of {2'-[(Acetyl-phenyl-amino)-methyl]-6-methoxy-4'-trifluoromethyl-biphenyl-3-yl}-acetic acid (Compound 1-18)

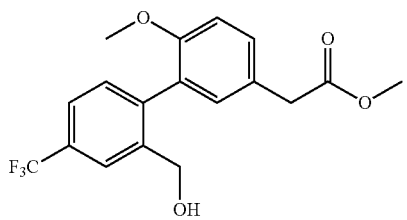 [SMILES: COC(=O)Cc1ccc(OC)c(-c2ccc(C(F)(F)F)cc2CO)c1]

Step 1: (2'-Hydroxymethyl-6-methoxy-4'-trifluoromethyl-biphenyl-3-yl)-acetic acid methyl ester Prepared according to the procedure described in Example 1, Step 4, using the following starting materials: (2-bromo-5-trifluoromethyl-phenyl)-methanol and [4-methoxy-3-(4,4,5,5-tetramethyl-[1,3,2]dioxaborolan-2-yl)-phenyl]-acetic acid methyl ester.

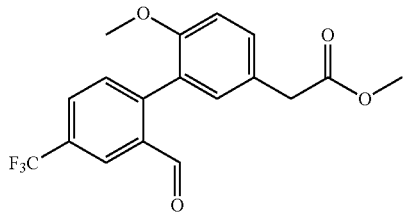 [SMILES: COC(=O)Cc1ccc(OC)c(-c2ccc(C(F)(F)F)cc2C=O)c1]

Step 2: (2'-Formyl-6-methoxy-4'-trifluoromethyl-biphenyl-3-yl)-acetic acid methyl ester Prepared according to the procedure described in Example 1, Step 3, using the following starting material: (2'-hydroxymethyl-6-methoxy-4'-trifluoromethyl-biphenyl-3-yl)-acetic acid methyl ester.

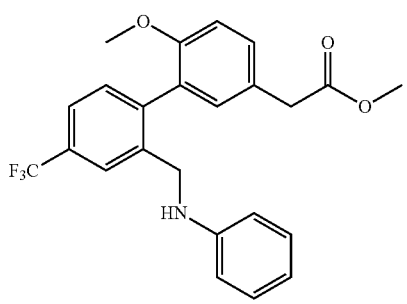 [SMILES: COC(=O)Cc1ccc(OC)c(-c2ccc(C(F)(F)F)cc2CNc2ccccc2)c1]

Step 3: (6-Methoxy-2'-phenylaminomethyl-4'-trifluoromethyl-biphenyl-3-yl)-acetic acid methyl ester Prepared according to the procedure described in Example 1, Step 5, using the following starting materials: (2'-formyl-6-methoxy-4'-trifluoromethyl-biphenyl-3-yl)-acetic acid methyl ester and aniline.

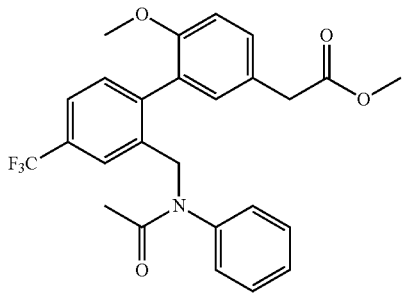 [SMILES: COC(=O)Cc1ccc(OC)c(-c2ccc(C(F)(F)F)cc2CN(C(C)=O)c2ccccc2)c1]

Step 4: {2'-[(Acetyl-phenyl-amino)-methyl]-6-methoxy-4'-trifluoromethyl-biphenyl-3-yl}-acetic acid methyl ester Prepared according to the procedure described in Example 1, Step 6, using the following starting materials: (6-methoxy-2'-phenylaminomethyl-4'-trifluoromethyl-biphenyl-3-yl)-acetic acid methyl ester and acetyl chloride.

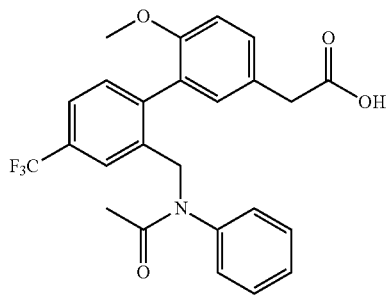 [SMILES: COc1ccc(CC(=O)O)cc1-c1ccc(C(F)(F)F)cc1CN(C(C)=O)c1ccccc1]

Step 5: {2'-[(Acetyl-phenyl-amino)-methyl]-6-methoxy-4'-trifluoromethyl-biphenyl-3-yl}-acetic acid Prepared according to the procedure described in Example 3, Step 3, using the following starting material: {2'-[(acetyl-phenyl-amino)-methyl]-6-methoxy-4'-trifluoromethyl-biphenyl-3-yl}-acetic acid methyl ester. M+H is 458.

Example 19

Synthesis of {2'-[(Acetyl-benzyl-amino)-methyl]-6-methoxy-4'-trifluoromethyl-biphenyl-3-yl}-acetic acid (Compound 1-19)

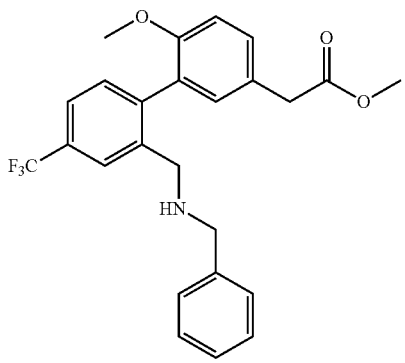 [SMILES: COC(=O)Cc1ccc(OC)c(-c2ccc(C(F)(F)F)cc2CNCc2ccccc2)c1]

Step 1: [2'-(Benzylamino-methyl)-6-methoxy-4'-trifluoromethyl-biphenyl-3-yl]-acetic acid methyl ester Prepared according to the procedure described in Example 1, Step 5, using the following starting materials: (2'-formyl-6-methoxy-4'-trifluoromethyl-biphenyl-3-yl)-acetic acid methyl ester and benzylamine.

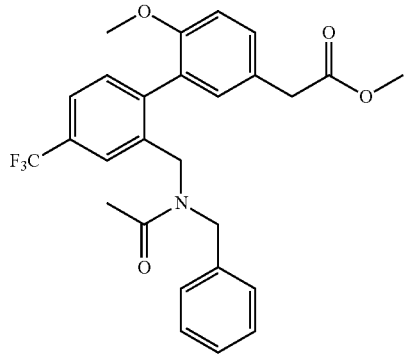 [SMILES: COC(=O)Cc1ccc(OC)c(-c2ccc(C(F)(F)F)cc2CN(Cc2ccccc2)C(C)=O)c1]

Step 2: {2'-[(Acetyl-benzyl-amino)-methyl]-6-methoxy-4'-trifluoromethyl-biphenyl-3-yl}-acetic acid methyl ester Prepared according to the procedure described in Example 1, Step 6, using the following starting materials: [2'-(benzylamino-methyl)-6-methoxy-4'-trifluoromethyl-biphenyl-3-yl]-acetic methyl ester and acetyl chloride.

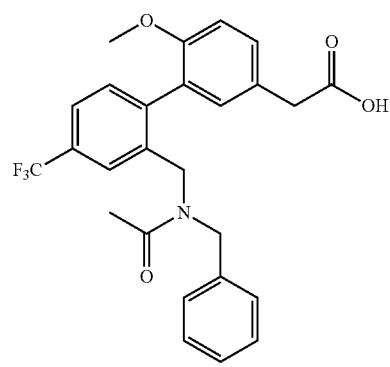 [SMILES: COc1ccc(CC(=O)O)cc1-c1ccc(C(F)(F)F)cc1CN(Cc1ccccc1)C(C)=O]

Step 3: {2'-[(Acetyl-benzyl-amino)-methyl]-6-methoxy-4'-trifluoromethyl-biphenyl-3-yl}-acetic acid Prepared according to the procedure described in Example 3, Step 3, using the following starting material: {2'-[(acetyl-benzyl-amino)-methyl]-6-methoxy-4'-trifluoromethyl-biphenyl-3-yl}-acetic acid methyl ester. M+H is 472.

Example 20

Synthesis of {2'-[(Acetyl-phenethyl-amino)-methyl]-6-methoxy-4'-trifluoromethyl-biphenyl-3-yl}-acetic acid (Compound 1-20)

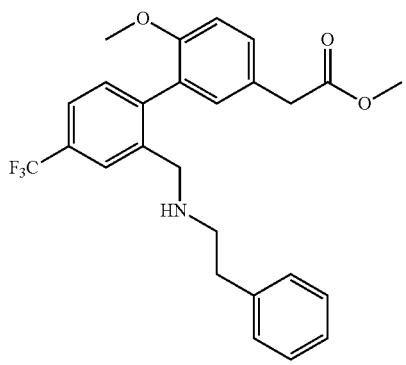 [SMILES: COC(=O)Cc1ccc(OC)c(-c2ccc(C(F)(F)F)cc2CNCCc2ccccc2)c1]

Step 1: [6-Methoxy-2'-(phenethylamino-methyl)-4'-trifluoromethyl-biphenyl-3-yl]-acetic acid methyl ester Prepared according to the procedure described in Example 1, Step 5, using the following starting materials: (2'-formyl-6-methoxy-4'-trifluoromethyl-biphenyl-3-yl)-acetic acid methyl ester and 2-phenylethylamine.

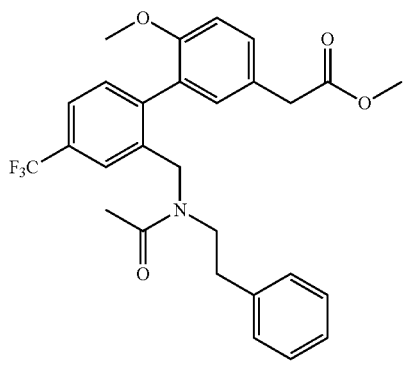 [SMILES: COC(=O)Cc1ccc(OC)c(-c2ccc(C(F)(F)F)cc2CN(CCc2ccccc2)C(C)=O)c1]

Step 2: {2'-[(Acetyl-phenethyl-amino)-methyl]-6-methoxy-4'-trifluoromethyl-biphenyl-3-yl}-acetic acid methyl ester Prepared according to the procedure described in Example 1, Step 6, using the following starting materials: [6-methoxy-2'-(phenethylamino-methyl)-4'-trifluoromethyl-biphenyl-3-yl]-acetic acid methyl ester and acetyl chloride.

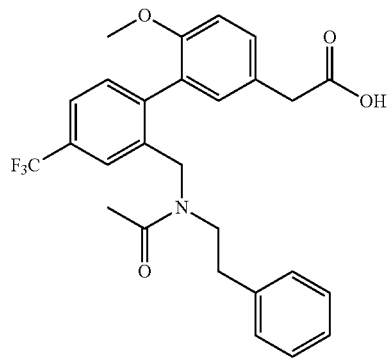 [SMILES: COc1ccc(CC(=O)O)cc1-c1ccc(C(F)(F)F)cc1CN(CCc1ccccc1)C(C)=O]

Step 3: {2'-[(Acetyl-phenethyl-amino)-methyl]-6-methoxy-4'-trifluoromethyl-biphenyl-3-yl}-acetic acid Prepared according to the procedure described in Example 3, Step 3, using the following starting material: {2'-[(Acetyl-phenethyl-amino)-methyl]-6-methoxy-4'-trifluoromethyl-biphenyl-3-yl}-acetic acid methyl ester. M+H is 486.

Example 21

Synthesis of 2-{2'-[(Acetyl-ethyl-amino)-methyl]-6-methoxy-4'-trifluoromethyl-biphenyl-3-yl}-propionic acid (Compound 1-21)

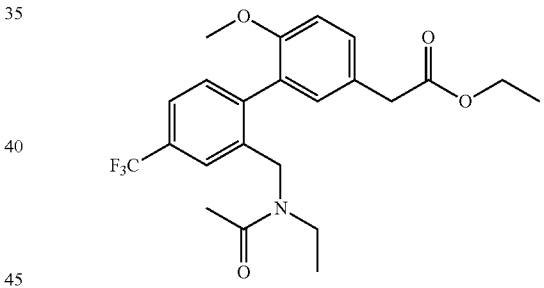

Step 1: {4'-[(Acetyl-ethyl-amino)-methyl]-6-methoxy-4'-trifluoromethyl-biphenyl-3-yl}-acetic acid ethyl ester To {2'-[(acetyl-ethyl-amino)-methyl]-6-methoxy-4'-trifluoromethyl-biphenyl-3-yl}-acetic acid methyl ester (0.292 g, 0.69 mmol) in MeOH (2.3 mL) and THF (2.9 mL) was added aqueous 1N NaOH (1.7 mL), and the solution was stirred at room temperature for 2 hours. The mixture was neutralized with aqueous 114 HCl, and the aqueous layer was separated and extracted with $CH_2Cl_2$. The combined organic layers were dried over $MgSO_4$, filtered, and concentrated. The residue was dissolved in EtOH, and thionyl chloride (0.11 mL, 1.5 mmol) was added. The reaction was stirred for 30 minutes, until no starting material was seen by analytical LCMS. The solution was neutralized with saturated aqueous $NaHCO_3$, and the aqueous layer was separated and extracted with $CH_2Cl_2$. The combined organic layers were washed with $H_2O$, dried over $MgSO_4$, filtered, and concentrated to give the title compound.

141

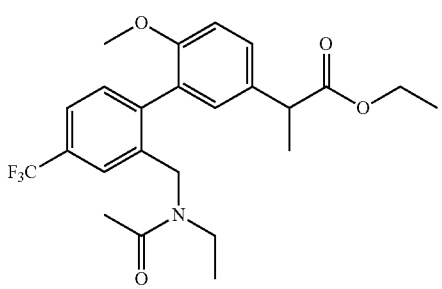 [SMILES: CCOC(=O)C(C)c1ccc(OC)c(-c2ccc(C(F)(F)F)cc2CN(CC)C(C)=O)c1]

Step 2: 2-{2'-[(Acetyl-ethyl-amino)-methyl]-6-methoxy-4'-trifluoromethyl-biphenyl-3-yl}-propionic acid ethyl ester {2'-[(Acetyl-ethyl-amino)-methyl]-6-methoxy-4'-trifluoromethyl-biphenyl-3-yl}-acetic acid ethyl ester (0.143 g, 0.33 mmol) and iodomethane (0.02 mL, 0.36 mmol) were combined in THF (1.5 mL) and cooled to −78° C. Sodium hexamethyldisilazide (1M in THF; 0.36 mL, 0.36 mmol) was added, and the mixture was stirred for 1 hour at −78° C. Once no starting material was seen by analytical LCMS, the mixture was quenched with aqueous 1N HCl and diluted with $CH_2Cl_2$. The aqueous layer was separated and extracted with $CH_2Cl_2$, and the combined organic layers were washed with $H_2O$, dried over $MgSO_4$, filtered, and concentrated. The residue was purified by silica gel chromatography (0-100% EtOAc in hexanes) to give the title compound.

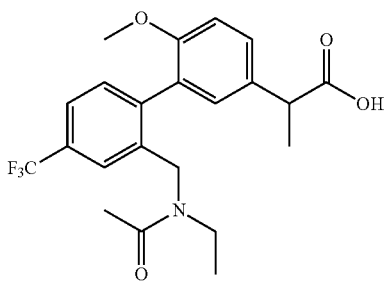

Step 3: 2-{2'-[(Acetyl-ethyl-amino)-methyl]-6-methoxy-4'-trifluoromethyl-biphenyl-3-yl}-propionic acid Prepared according to the procedure described in Example 3, Step 3, using the following starting material: 2-{2'-[(acetyl-ethyl-amino)-methyl]-6-methoxy-4'-trifluoromethyl-biphenyl-3-yl}-propionic acid ethyl ester. M±H is 424.

Example 22

Synthesis of {2'-[1-(Acetyl-ethyl-amino)-ethyl]-6-methoxy-4'-trifluoromethyl-biphenyl-3-yl}-acetic acid (Compound 1-22)

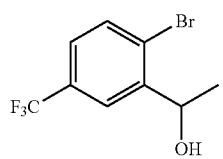

142

Step 1:
1-(2-Bromo-5-trifluoromethyl-phenyl)-ethanol

To 2-bromo-5-trifluoromethyl-benzaldehyde (1.0 g, 3.95 mmol) in THF (10 mL) at 0° C. under $N_2$ was added methylmagnesium iodide (3M in diethyl ether; 2.6 mL, 7.91 mmol). The reaction was stirred for 2 hours, and then quenched with saturated aqueous $NH_4Cl$ and diluted with $CH_2Cl_2$. The aqueous layer was separated and extracted with $CH_2Cl_2$, and the combined organic layers were dried over $MgSO_4$, filtered, and concentrated to give the title compound.

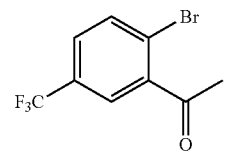

Step 2:
1-(2-Bromo-5-trifluoromethyl-phenyl)-ethanone 1-(2-Bromo-5-trifluoromethyl-phenyl)-ethanol (0.914 g, 3.40 mmol), N-methylmorpholine N-oxide (0331 g, 6.24 mmol), and tetrapropylammonium perruthenate (0.109 g, 0.31 mmol) were combined in $CH_2Cl_2$ (18 mL) and MeCN (0.9 mL) and stirred at room temperature for 30 minutes. Once no starting material was seen by analytical LCMS, the mixture was filtered through Celite and purified by silica gel chromatography (0-100% EtOAc in hexanes) to give the title compound.

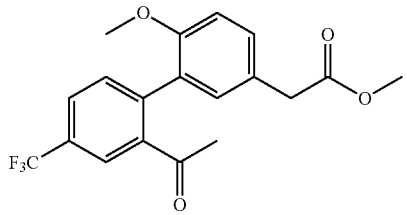 [SMILES: COC(=O)Cc1ccc(OC)c(-c2ccc(C(F)(F)F)cc2C(C)=O)c1]

Step 3: (2'-Acetyl-6-methoxy-4'-trifluoromethyl-biphenyl-3-yl)acetic acid methyl ester Prepared according to the procedure described in Example 1, Step 4, using the following starting materials: 1-(2-bromo-5-trifluoromethyl-phenyl)-ethanone and [4-methoxy-3-(4,4,5,5-tetramethyl-[1,3,2]dioxaborolan-2-yl)-phenyl]-acetic acid methyl ester.

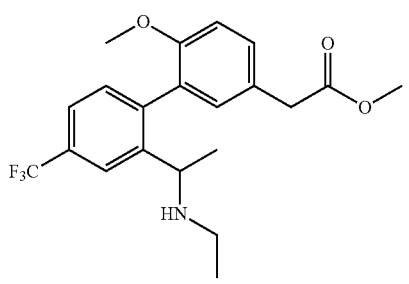 [SMILES: CCNC(C)c1cc(C(F)(F)F)ccc1-c1cc(CC(=O)OC)ccc1OC]

Step 4: [2'-(1-Ethylamino-ethyl)-6-methoxy-4'-trifluoromethyl-biphenyl-3-yl]-acetic acid methyl ester (2'-Acetyl-6-methoxy-4'-trifluoromethyl-biphenyl-3-yl)-acetic acid methyl ester (0.222 g, 0.61 mmol), ethylamine (2M in THF; 0.46 mL, 0.91 mmol), sodium cyanoborohydride (0.058 g, 0.91 mmol), and acetic acid (0.05 mL, 0.91 mmol) were combined in MeOH (2.2 mL) and heated to 60° C. overnight. Analytical LCMS showed starting material remained, so the reaction was stirred at 60° C. over the weekend. Once minimal starting material was seen by analytical LCMS, the mixture was cooled to room temperature and neutralized with saturated aqueous NaHCO$_3$. The solution was extracted with CH$_2$Cl$_2$, and the combined organic layers were dried over MgSO$_4$, filtered, and concentrated to give the title compound.

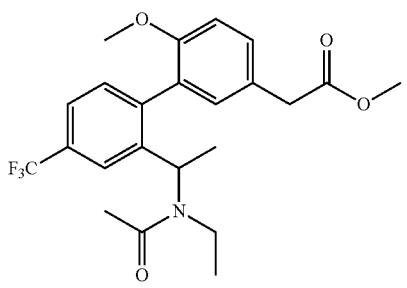 [SMILES: CCN(C(C)=O)C(C)c1cc(C(F)(F)F)ccc1-c1cc(CC(=O)OC)ccc1OC]

Step 5: {2'-[1-(Acetyl-ethyl-amino)-ethyl]-6-methoxy-4'-trifluoromethyl-biphenyl-3-yl}-acetic acid methyl ester Prepared according to the procedure described in Example 1, Step 6, using the following starting materials: [2'-(1-ethylamino-ethyl)-6-methoxy-4'-trifluoromethyl-biphenyl-3-yl]-acetic acid methyl ester and acetyl chloride.

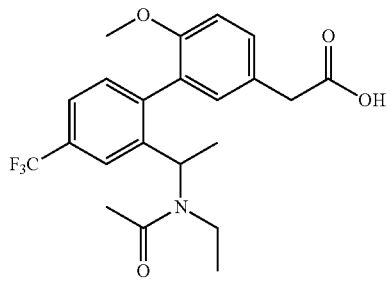 [SMILES: CCN(C(C)=O)C(C)c1cc(C(F)(F)F)ccc1-c1cc(CC(=O)O)ccc1OC]

Step 6: {2'-[1-(Acetyl-ethyl-amino)-ethyl]-6-methoxy-4'-trifluoromethyl-biphenyl-3-yl}-acetic acid Prepared according to the procedure described in Example 1, Step 7, using the following starting material: {2'-[1-(acetyl-ethyl-amino)-ethyl]-6-methoxy-4'-trifluoromethyl-biphenyl-3-yl}-acetic acid methyl ester. M+H is 424.

Example 23

Synthesis of {2'-[(Ethyl-methoxycarbonyl-amino)-methyl]-6-methoxy-4'-trifluoromethyl-biphenyl-3-yl}-acetic acid (Compound 1-23)

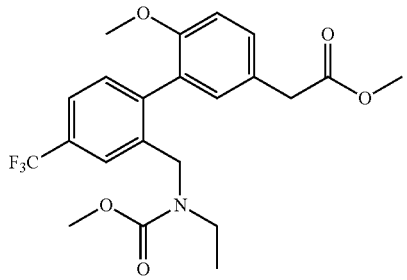 [SMILES: CCN(Cc1cc(C(F)(F)F)ccc1-c1cc(CC(=O)OC)ccc1OC)C(=O)OC]

Step 1: {2'-[(Ethyl-methoxycarbonyl-amino)-methyl]-6-methoxy-4'-trifluoromethyl-biphenyl-3-yl}-acetic acid methyl ester To (2'-ethylaminomethyl-6-methoxy-4'-trifluoromethyl-biphenyl-3-yl)-acetic acid methyl ester (0.091 g, 0.24 mmol) and triethylamine (0.05 mL, 0.36 mmol) in CH$_2$Cl$_2$ (1 mL) was added methyl chloroformate (0.03 mL, 0.36 mmol), and the mixture was stirred at room temperature for 20 minutes. Once no starting material was seen by analytical LCMS, the reaction was quenched with H$_2$O and diluted with CH$_2$Cl$_2$ and saturated aqueous NaHCO$_3$. The aqueous layer was separated and extracted with CH$_2$Cl$_2$, and the combined organic layers were dried over MgSO$_4$, filtered, and concentrated, and the residue was purified by silica gel chromatography (0-100% EtOAc in hexanes) to give the title compound.

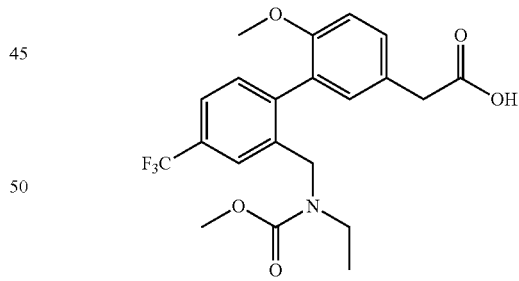

Step 2: {2'-[(Ethyl-methoxycarbonyl-amino)-methyl]-6-methoxy-4'-trifluoromethyl-biphenyl-3-yl}-acetic acid Prepared according to the procedure described in Example 3, Step 3, using the following starting material: {2'-[(ethyl-methoxycarbonyl-amino)-methyl]-6-methoxy-4'-trifluoromethyl-biphenyl-3-yl}-acetic acid methyl ester. M+H is 426.

Example 24

Synthesis of {2'-[(Benzyl-methoxycarbonyl-amino)-methyl]-6-methoxy-4'-trifluoromethyl-biphenyl-3-yl}-acetic acid (Compound 1-24)

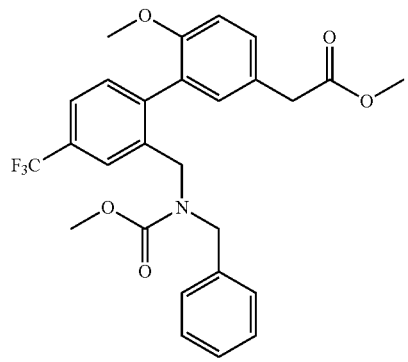 [SMILES: COC(=O)Cc1ccc(OC)c(-c2ccc(C(F)(F)F)cc2CN(Cc2ccccc2)C(=O)OC)c1]

Step 1: {2'-[(Benzyl-methoxycarbonyl-amino)-methyl]-6-methoxy-4'-trifluoromethyl-biphenyl-3-yl}-acetic acid methyl ester Prepared according to the procedure described in Example 23, Step 1, using the following starting materials: [2'-(benzylamino-methyl)-6-methoxy-4'-trifluoromethyl-biphenyl-3-yl]-acetic acid methyl ester and methyl chloroformate.

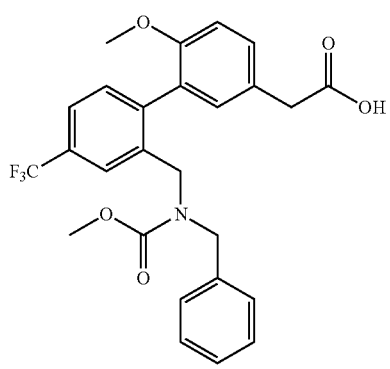 [SMILES: COC(=O)N(Cc1ccccc1)Cc1cc(C(F)(F)F)ccc1-c1cc(CC(=O)O)ccc1OC]

Step 2: {2'-[(Benzyl-methoxycarbonyl-amino)-methyl]-6-methoxy-4'-trifluoromethyl-biphenyl-3-yl}-acetic acid Prepared according to the procedure described in Example 3, Step 3, using the following starting material: (2'-[(benzyl-methoxycarbonyl-amino)-methyl]-6-methoxy-4'-trifluoromethyl-biphenyl-3-yl)-acetic acid methyl ester. M+H is 488.

Example 25

Synthesis of {6-Methoxy-2'-[(methoxycarbonyl-phenethyl-amino)-methyl]-4'-trifluoromethyl-biphenyl-3-yl}-acetic acid (Compound 1-25)

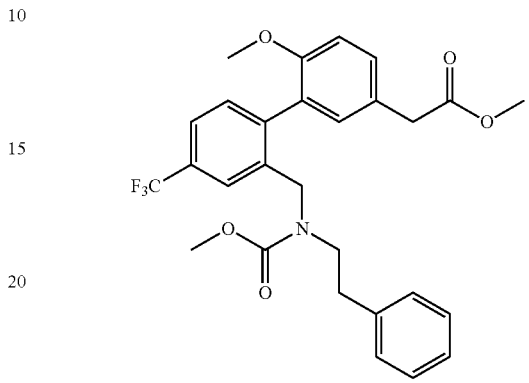

Step 1: {6-Methoxy-2'-[(methoxycarbonyl-phenethyl-amino)-methyl]-4'-trifluoromethyl-biphenyl-3-yl}-acetic acid methyl ester Prepared according to the procedure described in Example 23, Step 1, using the following starting materials: [6-methoxy-2'-(phenethylamino-methyl)-4-'-trifluoromethyl-biphenyl-3-yl]-acetic acid methyl ester and methyl chloroformate.

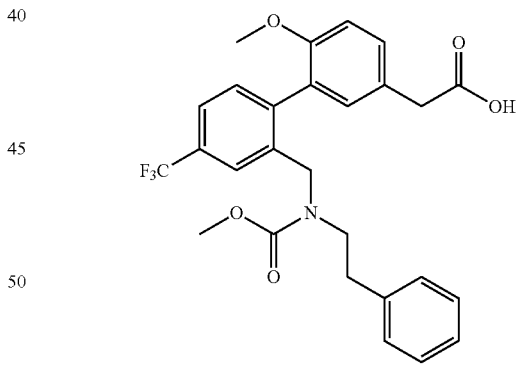

Step 2: {6-Methoxy-2'-[(methoxycarbonyl-phenethyl-amino)-methyl]-4'-trifluoromethyl-biphenyl-3-yl}-acetic acid Prepared according to the procedure described in Example 3, Step 3, using the following starting material:
{6-methoxy-2'-[(methoxycarbonyl-phenethyl-amino)-methyl]-4'-trifluoromethyl-biphenyl-3-yl}-acetic acid methyl ester. M+H is 502.

Example 26

Synthesis of {2'-[(Indan-2-yl-methoxycarbonyl-amino)-methyl]-6-methoxy-4'-trifluoromethyl-biphenyl-3-yl}-acetic acid (Compound 1-26)

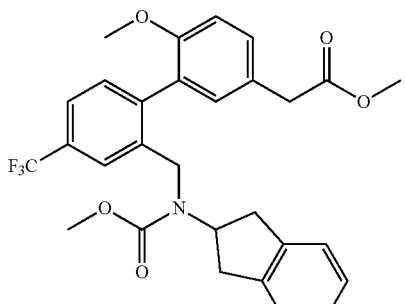

Step 1: {2'-[(Indan-2-yl-methoxycarbonyl-amino)-methyl]-6-methoxy-4'-trifluoromethyl-biphenyl-3-yl}-acetic acid methyl ester Prepared according to the procedure described in Example 23, Step 1, using the following starting materials: [2'-(indan-2-ylaminomethyl)-6-methoxy-4'-trifluoromethyl-biphenyl-3-yl]-acetic acid methyl ester and methyl chloroformate.

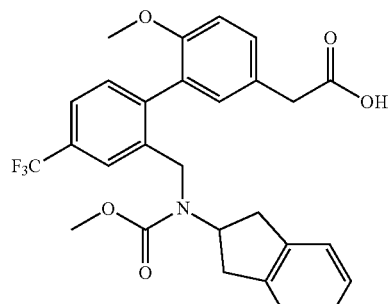

Step 2: {2'-[(Indan-2-yl-methoxycarbonyl-amino)-methyl]-6-methoxy-4'-trifluoromethyl-biphenyl-3-yl}-acetic acid Prepared according to the procedure described in Example 3, Step 3, using the following starting material:

{2'-[(indan-2-yl-methoxycarbonyl-amino)-methyl]-6-methoxy-4'-trifluoromethyl-biphenyl-3-yl}-acetic acid methyl ester. M+H is 514.

Example 27

Synthesis of {2'-[(Benzyloxycarbonyl-methyl-amino)-methyl]-6-methoxy-4'-trifluoromethyl-biphenyl-3-yl}-acetic acid (Compound 1-27)

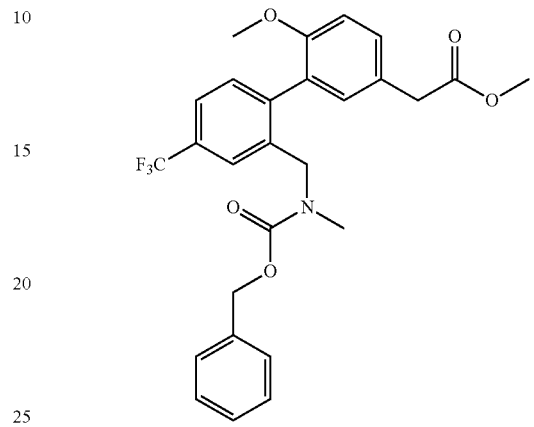

Step 1: {2'-[(Benzyloxycarbonyl-methyl-amino)-methyl]-6-methoxy-4'-trifluoromethyl-biphenyl-3-yl}-acetic acid methyl ester Prepared according to the procedure described in Example 23, Step 1, using the following starting materials: (6-methoxy-2'-methylaminomethyl-4'-trifluoromethyl-biphenyl-3-yl)-acetic acid methyl ester and benzyl chloroformate.

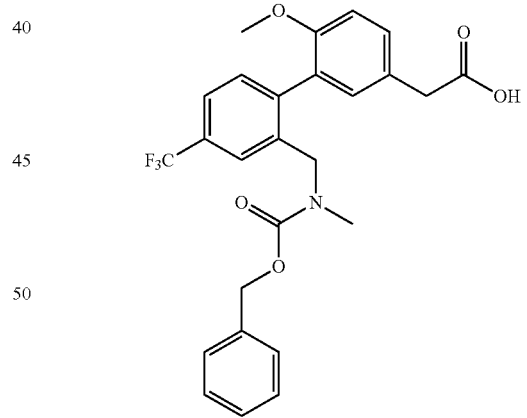

Step 2: {2'-[(Benzyloxycarbonyl-methyl-amino)-methyl]-6-methoxy-4'-trifluoromethyl-biphenyl-3-yl}-acetic acid Prepared according to the procedure described in Example 3, Step 3, using the following starting material: {2'-[(benzyloxycarbonyl-methyl-amino)-methyl]-6-methoxy-4'-trifluoromethyl-biphenyl-3-yl}-acetic acid methyl ester. M±H is 488.

Example 28

Synthesis of {2'-[(Benzyloxycarbonyl-ethyl-amino)-methyl]-6-methoxy-4'-trifluoromethyl-biphenyl-3-yl}-acetic acid (Compound 1-28)

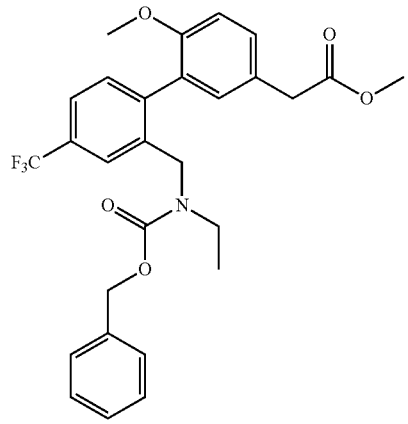 [SMILES: CCN(Cc1cc(C(F)(F)F)ccc1-c1cc(CC(=O)OC)ccc1OC)C(=O)OCc1ccccc1]

Step 1: {2'-[(Benzyloxycarbonyl-ethyl-amino)-methyl]-6-methoxy-4'-trifluoromethyl-biphenyl-3-yl}-acetic acid methyl ester Prepared according to the procedure described in Example 23, Step 1, using the following starting materials: (2'-ethylaminomethyl-6-methoxy-4'-trifluoromethyl-biphenyl-3-yl)-acetic acid methyl ester and benzyl chloroformate.

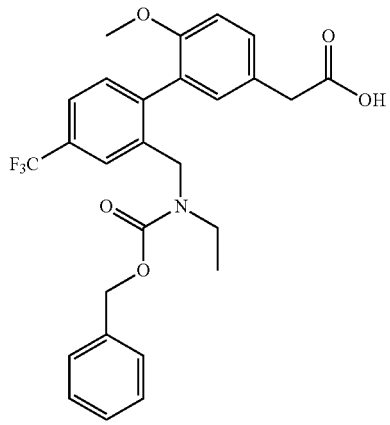 [SMILES: CCN(Cc1cc(C(F)(F)F)ccc1-c1cc(CC(=O)O)ccc1OC)C(=O)OCc1ccccc1]

Step 2: {2'-[(Benzyloxycarbonyl-ethyl-amino)-methyl]-6-methoxy-4'-trifluoromethyl-biphenyl-3-yl}-acetic acid Prepared according to the procedure described in Example 3, Step 3, using the following starting material: {2'-[(benzyloxycarbonyl-ethyl-amino)-methyl]-6-methoxy-4'-trifluoromethyl-biphenyl-3-yl}-acetic acid methyl ester. M+H is 502.

Example 29

Synthesis of {2'-[(Benzyloxycarbonyl-methyl-amino)-methyl]-6-fluoro-4'-trifluoromethyl-biphenyl-3-yl}-acetic acid (Compound 1-29)

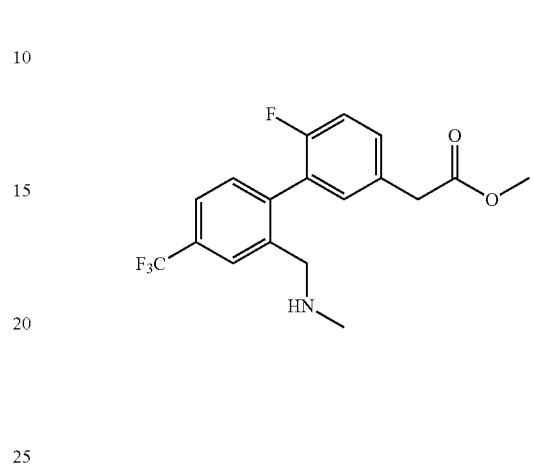

Step 1: (6-Fluoro-2'-methylaminomethyl-4'-trifluoromethyl-biphenyl-3-yl)-acetic acid methyl ester Prepared according to the procedure described in Example 1, Step 5, using the following starting materials: (6-fluoro-2'-formyl-4'-trifluoromethyl-biphenyl-3-yl)-acetic acid methyl ester and methylamine (2M in THF).

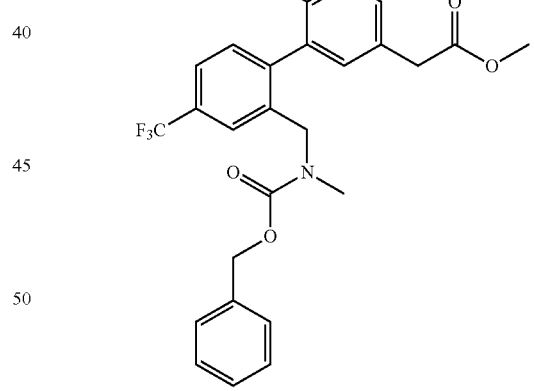

Step 2: {2'-[(Benzyloxycarbonyl-methyl-amino)-methyl]-6-fluoro-4'-trifluoromethyl-biphenyl-3-yl}-acetic acid methyl ester Prepared according to the procedure described in Example 23, Step 1, using the following starting materials: (6-fluoro-2'-methylaminomethyl-4'-trifluoromethyl-biphenyl-3-yl)-acetic acid methyl ester and benzyl chloroformate.

151

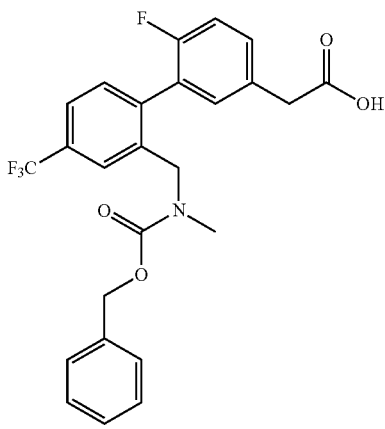 [SMILES: CN(Cc1cc(C(F)(F)F)ccc1-c1cc(CC(=O)O)ccc1F)C(=O)OCc1ccccc1]

Step 3: {2'-[(Benzyloxycarbonyl-methyl-amino)-methyl]-6-fluoro-4'-trifluoromethyl-biphenyl-3-yl}-acetic acid Prepared according to the procedure described in Example 1 Step 7, using the following starting material: (2'-[(benzyloxycarbonyl-methyl-amino)-methyl]-6-fluoro-4'-trifluoromethyl-biphenyl-3-yl)-acetic acid methyl ester. M+H is 476.

Example 30

Synthesis of {2'-[(Cyclopropanecarbonyl-ethyl-amino)-methyl]-6-methoxy-4'-trifluoromethyl-biphenyl-3-yl}-acetic acid (Compound 1-33)

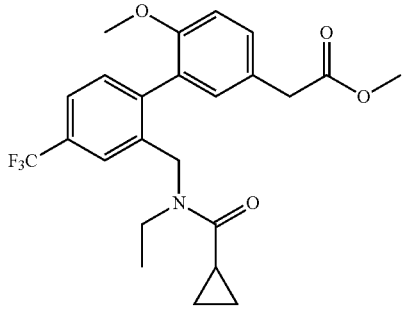 [SMILES: CCN(Cc1cc(C(F)(F)F)ccc1-c1cc(CC(=O)OC)ccc1OC)C(=O)C1CC1]

Step 1: {2'-[(Cyclopropanecarbonyl-ethyl-amino)-methyl]-6-methoxy-4'-trifluoromethyl-biphenyl-3-yl}-acetic acid methyl ester Prepared according to the procedure described in Example 1, Step 6, using the following starting materials: (2'-ethylaminomethyl-6-methoxy-4'-trifluoromethyl-biphenyl-3-yl)-acetic acid methyl ester and cyclopropanecarbonyl chloride.

152

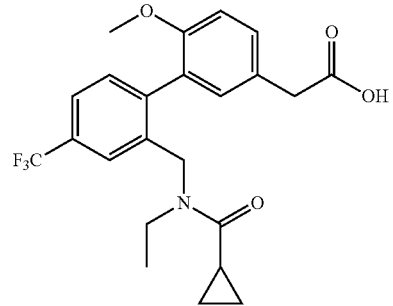 [SMILES: CCN(Cc1cc(C(F)(F)F)ccc1-c1cc(CC(=O)O)ccc1OC)C(=O)C1CC1]

Step 2: {2'-[(Cyclopropanecarbonyl-ethyl-amino)-methyl]-6-methoxy-4'-trifluoromethyl-biphenyl-3-yl}-acetic acid Prepared according to the procedure described in Example 3, Step 3, using the following starting material: {2'-[(cyclopropanecarbonyl-ethyl-amino)-methyl]-6-methoxy-4'-trifluoromethyl-biphenyl-3-yl}-acetic acid methyl ester. M+H is 436.

Example 31

Synthesis of (2'-{[Ethyl-(2-methoxy-acetyl)-amino]-methyl}-6-methoxy-4'-trifluoromethyl-biphenyl-3-yl)-acetic acid (Compound 1-46)

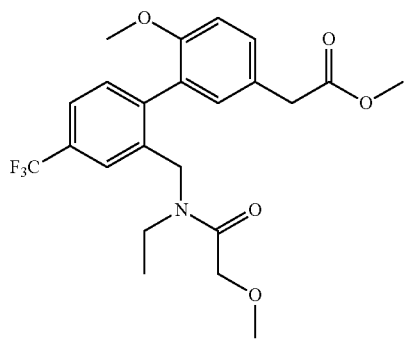 [SMILES: CCN(Cc1cc(C(F)(F)F)ccc1-c1cc(CC(=O)OC)ccc1OC)C(=O)COC]

Step 1: (2'-{[Ethyl-(2-methoxy-acetyl)-amino]-methyl}-6-methoxy-4'-trifluoromethyl-biphenyl-3-yl)-acetic acid methyl ester Prepared according to the procedure described in Example 1, Step 6, using the following starting materials: (2'-ethylaminomethyl-6-methoxy-4'-trifluoromethyl-biphenyl-3-yl)-acetic acid methyl ester and methoxyacetyl chloride.

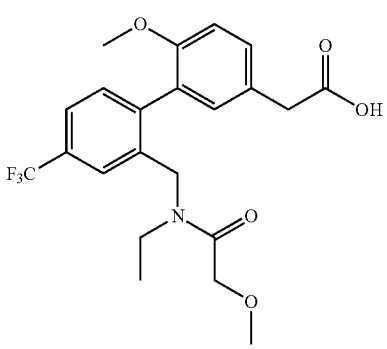 [SMILES: CCN(Cc1cc(C(F)(F)F)ccc1-c1cc(CC(=O)O)ccc1OC)C(=O)COC]

Step 2: (2'-{[Ethyl-(2-methoxy-acetyl)-amino]-methyl}-6-methoxy-4'-trifluoromethyl-biphenyl-3-yl)-acetic acid (2'-{[Ethyl-(2-methoxy-acetyl)-amino]-methyl}-6-methoxy-4'-trifluoromethyl-biphenyl-3-yl)-acetic acid methyl ester (0.135 g, 0.31 mmol) in THF (2 mL) was treated with 1N aqueous LiOH (2 mL) for 2 hours at room temperature. The mixture was acidified with 1N aqueous HCl and extracted three times with EtOAc. The combined organic layers were dried and concentrated, and the residue was purified by preparative HPLC to give the title compound. M+H is 440.

Example 32

Synthesis of [2'-(3-Benzyl-1-ethyl-ureidomethyl)-6-methoxy-4'-trifluoromethyl-biphenyl-3-yl]-acetic acid (Compound 1-96)

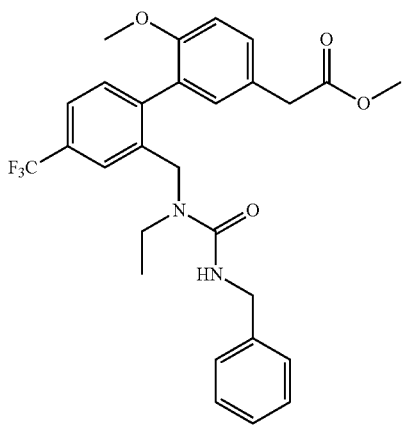 [SMILES: CCN(Cc1cc(C(F)(F)F)ccc1-c1cc(CC(=O)OC)ccc1OC)C(=O)NCc1ccccc1]

Step 1: [2'-(3-Benzyl-1-ethyl-ureidomethyl)-6-methoxy-4'-trifluoromethyl-biphenyl-3-yl]-acetic acid methyl ester To (2'-ethylaminomethyl-6-methoxy-4'-trifluoromethyl-biphenyl-3-yl)-acetic acid methyl ester (0.207 g, 0.54 mmol) in CH$_2$Cl$_2$ (2 mL) at 0° C. was added diisopropylethylamine (0.21 mL, 1.19 mmol), followed by phosgene (20% in toluene; 0.34 mL, 0.65 mmol), and the reaction was stirred for 2 hours at 0° C. Benzylamine (0.09 mL, 0.81 mmol) was then added, and the reaction was stirred for 15 minutes. Triethylamine (0.1 mL, 0.72 mmol) was added, and the reaction was stirred for 1 hour. Additional benzylamine (0.09 mL, 0.81 mmol) and diisopropylethylamine (0.21 mL, 1.19 mmol) were added, and the reaction was stirred for 3 hours, until no starting material was seen by analytical LCMS. The mixture was partitioned between H$_2$O and CH$_2$Cl$_2$, and the aqueous layer was separated and extracted twice with CH$_2$Cl$_2$. The combined organic layers were dried and concentrated, and the residue was purified by silica gel chromatography (20-40% EtOAc in hexanes) to give the title compound.

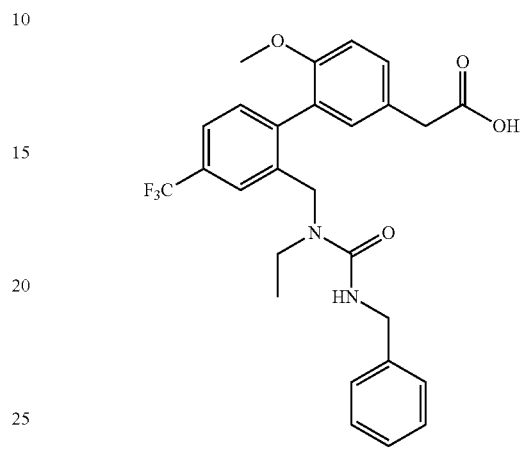

Step 2: [2'-(3-Benzyl-1-ethyl-ureidomethyl)-6-methoxy-4'-trifluoromethyl-biphenyl-3-yl]-acetic acid Prepared according to the procedure described in Example 31, Step 2, using the following starting material: [2'-(3-benzyl-1-ethyl-ureidomethyl)-6-methoxy-4'-trifluoromethyl-biphenyl-3-yl]-acetic acid methyl ester. M+H is 501.

Alternative synthesis: To (2'-ethylaminomethyl-6-methoxy-4'-trifluoromethyl-biphenyl-3-yl)-acetic acid ethyl ester (prepared as described in Example 1, Step 1 but using EtOH in place of MeOH; 44.9 g, 0.114 mol) in CH$_2$Cl$_2$ (450 mL) at room temperature was added triethylamine (24 mL, 0.17mol), followed by benzylisocyanate (16.7 mL, 0.136 mol), and the reaction was stirred for 2 hours until no starting material was seen by analytical LCMS. The mixture was partitioned between H$_2$O and CH$_2$Cl$_2$, and the aqueous layer was separated and extracted with CH$_2$Cl$_2$. The combined organic layers were dried (MgSO$_4$) and concentrated, and the residue was purified by silica gel chromatography (0-60% EtOAc in hexanes) to give the [2'-(3-benzyl-1-ethyl-ureidomethyl)-6-methoxy-4'-trifluoromethyl-biphenyl-3-yl]-acetic acid ethyl ester. Hydrolysis of the ethyl ester according to the procedure described in Example 1, Step 7 provided [2'-(3-benzyl-1-ethyl-ureidomethyl)-6-methoxy-4'-trifluoromethyl-biphenyl-3-yl]-acetic acid.

Example 33

Synthesis of [2'-(N'-Benzyl-N"-cyano-N-ethyl-guanidinomethyl)-6-methoxy-4'-trifluoromethyl-biphenyl-3-yl]acetic acid (Compound 1-111)

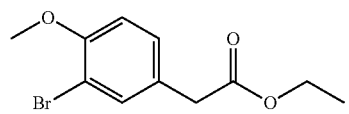

Step 1: (3-Bromo-4-methoxy-phenyl)-acetic acid ethyl ester

Prepared according to the procedure described in Example 1, Step 1, using the following starting materials: 3-bromo-4-methoxyphenylacetic acid and ethanol.

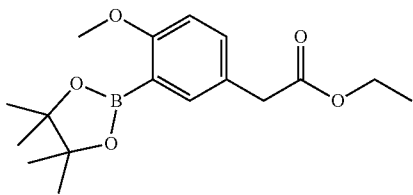 [SMILES: CCOC(=O)Cc1ccc(OC)c(B2OC(C)(C)C(C)(C)O2)c1]

Step 2: [4-Methoxy-3-(4,4,5,5-tetramethyl-[1,3,2] dioxaborolan-2-yl)-phenyl]-acetic acid ethyl ester (3-Bromo-4-methoxy-phenyl)-acetic acid ethyl ester (27.4 g, 100.3 mmol), bis(pinacolato)diboron (25.47 g, 100.3 mmol), and potassium acetate (24.6 g, 250.8 mmol) were combined in 1,4-dioxane (250 mL) under $N_2$. The solution was purged with $N_2$, and then (1,1'-bis(diphenylphosphino) ferrocene)-dichloropalladium(II) (4.10 g, 5.02 mmol) was added and the reaction was heated to 110° C. overnight. The mixture was filtered through Celite and partitioned between EtOAc and brine. The aqueous layer was separated and extracted twice with EtOAc, and the combined organic layers were dried and concentrated. The residue was purified by silica gel chromatography (20-60% EtOAc in hexanes) to give the title compound.

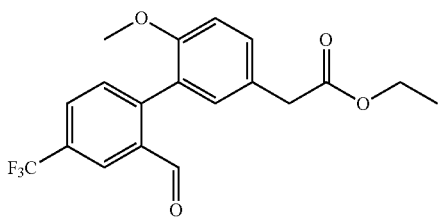

Step 3: (2'-Formyl-6-methoxy-4'-trifluoromethyl-biphenyl-3-yl)-acetic acid ethyl ester Prepared according to the procedure described in Example 1, Step 4, using the following starting materials: 2-bromo-5-(trifluoromethyl)benzaldehyde and [4-methoxy-3-(4,4,5,5-tetramethyl-[1,3,2]dioxaborolan-2-yl)-phenyl]-acetic acid ethyl ester.

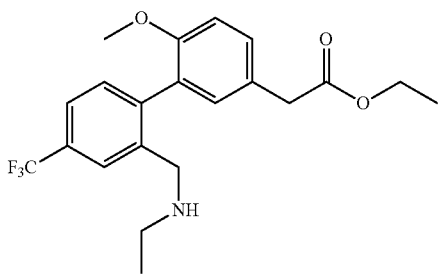 [SMILES: CCNCc1cc(C(F)(F)F)ccc1-c1cc(CC(=O)OCC)ccc1OC]

Step 4: (2'-Ethylaminomethyl-6-methoxy-4'-trifluoromethyl-biphenyl-3-yl)-acetic acid ethyl ester To (2'-formyl-6-methoxy-4'-trifluoromethyl-biphenyl-3-yl)-acetic acid ethyl ester (1.0 g, 2.73 mmol) in MeOH (8 mL) was added ethylamine (2M in THF; 5 mL, 10 mmol), followed by acetic acid (0.23 mL, 4.09 mmol). Sodium cyanoborohydride (0.260 g, 4.14 mmol) was then added, and the reaction was stirred at room temperature and monitored by analytical LCMS. The reaction never reached completion, so the mixture was concentrated and partitioned between EtOAc and saturated aqueous $NaHCO_3$. The aqueous layer was extracted with EtOAc, and the combined organic layers were dried over $MgSO_4$, filtered, and concentrated. The residue was purified by silica gel chromatography (0-6% MeOH in $CH_2Cl_2$) to give the title compound.

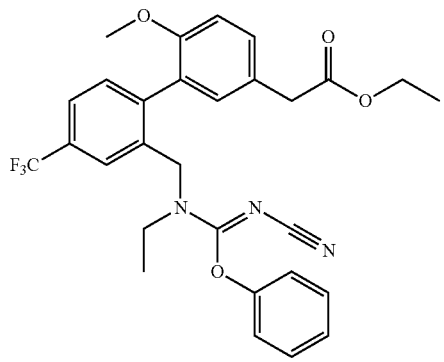 [SMILES: CCOC(=O)Cc1ccc(OC)c(-c2ccc(C(F)(F)F)cc2CN(CC)/C(=N/C#N)Oc2ccccc2)c1]

Step 5: [2'-(3-Cyano-1-ethyl-2-phenyl-isoureidomethyl)-6-methoxy-4'-trifluoromethyl-biphenyl-3-yl]-acetic acid ethyl ester (2'-Ethylaminomethyl-6-methoxy-4'-trifluoromethyl-biphenyl-3-yl)-acetic acid ethyl ester (0.50 g, 1.26mmol) and diphenyl cyanocarbonimidate (0.60 g, 2.51 mmol) were combined in MeCN (5 mL) and stirred at 40° C. until no starting material was seen by analytical LCMS. The mixture was concentrated and purified by silica gel chromatography (10-40% EtOAc in hexanes) to give the title compound.

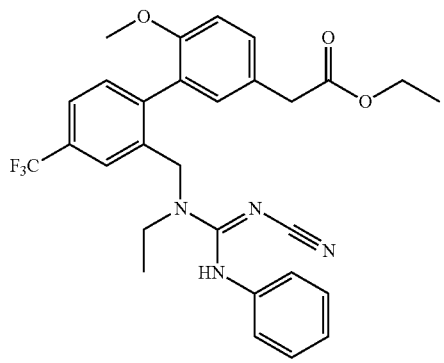 [SMILES: CCOC(=O)Cc1ccc(OC)c(-c2ccc(C(F)(F)F)cc2CN(CC)/C(=N/C#N)Nc2ccccc2)c1]

Step 6: [2'-(N'-Benzyl-N''-cyano-N-ethyl-guanidinomethyl)-6-methoxy-4'-trifluoromethyl-biphenyl-3-yl]-acetic acid ethyl ester

[2'-(3-Cyano-1-ethyl-2-phenyl-isoureidomethyl)-6-methoxy-4'-trifluoromethyl-biphenyl-3-yl]-acetic acid ethyl ester (0.10 g, 0.17 mmol) and benzylamine (0.04 mL, 0.34 mmol) were combined in EtOH (1 mL) and heated to 60° C. The reaction was monitored by analytical LCMS, and additional benzylamine (0.04 mL, 0.34 mmol) was added to push the reaction to completion. Further benzylamine (0.10 mL, 0.92 mmol) was added, and the reaction was heated for a total of 48 hours. The mixture was partitioned between EtOAc and H₂O, and the aqueous layer was extracted with EtOAc. The combined organic layers were concentrated and purified by silica gel chromatography (0-50% EtOAc in hexanes) to give the title compound.

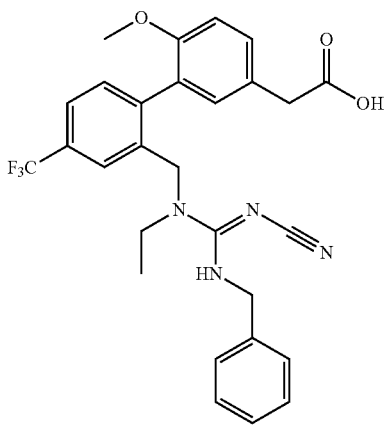 [SMILES: CCN(Cc1cc(C(F)(F)F)ccc1-c1cc(CC(=O)O)ccc1OC)/C(=N/C#N)NCc1ccccc1]

Step 7: [2'-(N'-Benzyl-N"-cyano-N-ethyl-guanidinomethyl)-6-methoxy-4'-trifluoromethyl-biphenyl-3-yl]-acetic acid

[2'-(N'-Benzyl-N"-cyano-N-ethyl-guanidinomethyl)-6-methoxy-4'-trifluoromethyl-biphenyl-3-yl]-acetic acid ethyl ester (0.055 g, 0.1 mmol) in TIFF (2 mL) and H₂O (0.5 mL) was treated with lithium hydroxide (0.02 g, 0.5 mmol), and the reaction was monitored by analytical LCMS. Once no starting material was seen, the mixture was diluted with EtOAc and H₂O. Citric acid was added to neutralize the solution to pH 3, and the mixture was extracted with EtOAc. The combined organic layers were washed with H₂O, dried over MgSO₄, filtered, and concentrated twice from CH₂Cl₂ to give the title compound. M+H is 525.

Example 34

Synthesis of (2'-{[Ethyl-(2-phenylsulfanyl-acetyl)-amino]-methyl}-6-methoxy-4'-trifluoromethyl-biphenyl-3-yl)-acetic acid (Compound 1-117)

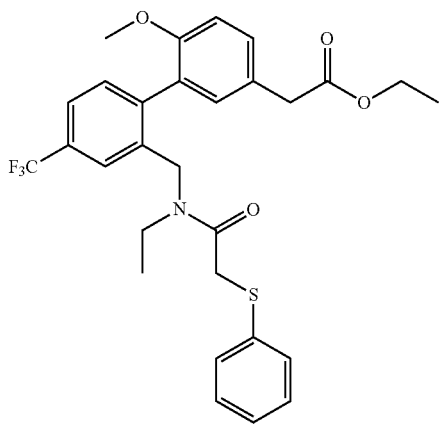 [SMILES: CCOC(=O)Cc1ccc(OC)c(-c2ccc(C(F)(F)F)cc2CN(CC)C(=O)CSc2ccccc2)c1]

Step 1: (2'-{[Ethyl-(2-phenylsulfanyl-acetyl)-amino]-methyl}-6-methoxy-4'-trifluoromethyl-biphenyl-3-yl)-acetic acid ethyl ester Prepared according to the procedure described in Example 1, Step 6, using the following starting materials: (T-ethylaminomethyl-6-methoxy-4'-trifluoromethyl-biphenyl-3-yl)-acetic acid ethyl ester and (phenylthio)acetyl chloride.

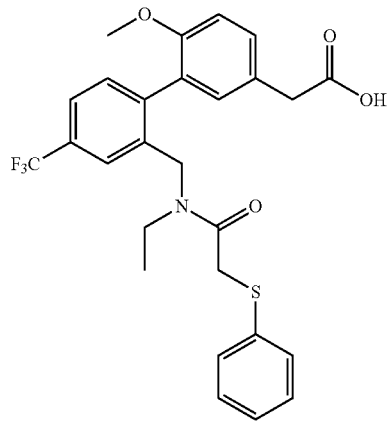 [SMILES: CCN(Cc1cc(C(F)(F)F)ccc1-c1cc(CC(=O)O)ccc1OC)C(=O)CSc1ccccc1]

Step 2: (2'-{[Ethyl-(2-phenylsulfanyl-acetyl)-amino]-methyl}-6-methoxy-4'-trifluoromethyl-biphenyl-3-yl)-acetic acid (2'-{[Ethyl-(2-phenylsulfanyl-acetyl)-amino]-methyl}-6-methoxy-4'-trifluoromethyl-biphenyl-3-yl)-acetic acid ethyl ester (0.291 g, 0.53 mmol) in THF (3 mL) was treated with 1N aqueous LiOH (3 mL) at room temperature overnight. The mixture was acidified with 1N aqueous HCl and extracted three times with EtOAc. The combined organic layers were dried and concentrated, and the residue was purified by silica gel chromatography (30-70% EtOAc in hexanes) to give the title compound. M+H is 518.

Example 35

Synthesis of (2'-{[(2-Benzenesulfonyl-acetyl)-ethyl-amino]-methyl}-6-methoxy-4'-trifluoromethyl-biphenyl-3-yl)-acetic acid (Compound 1-120)

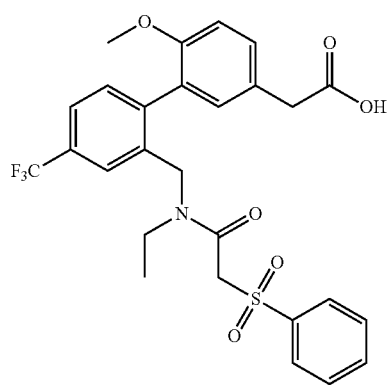 [SMILES: CCN(Cc1cc(C(F)(F)F)ccc1-c1cc(CC(=O)O)ccc1OC)C(=O)CS(=O)(=O)c1ccccc1]

Step 1: (2'-{[(2-Benzenesulfonyl-acetyl)-ethyl-amino]-methyl}-6-methoxy-4'-trifluoromethyl-biphenyl-3-yl)-acetic acid To (2'-{[ethyl-(2-phenylsulfanyl-acetyl)-amino]-methyl}-6-methoxy-4'-trifluoromethyl-biphenyl-3-yl)-acetic acid (0.096 g, 0.19 mmol) in CH$_2$Cl$_2$ (2 mL) was added 3-chloroperoxybenzoic acid (0.083 g, 0.37 mmol), and the reaction was stirred at room temperature for 1 hour. The mixture was concentrated and purified by preparative HPLC to give the title compound. M+H is 550.

Example 36

Synthesis of {2''-[(Benzyloxycarbonyl-ethyl-amino)-methyl]-4''-trifluoromethyl-[1,1';2',1'']terphenyl-4'-yl}-acetic acid (Compound 1-144)

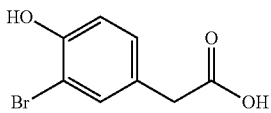 [SMILES: O=C(O)Cc1ccc(O)c(Br)c1]

Step 1: (3-Bromo-4-hydroxy-phenyl)-acetic acid

3-Bromo-4-methoxyphenylacetic acid (1.3 g, 5.6 mmol) was heated in a solution of hydrogen bromide (3 mL) and acetic acid (3 mL) at 100° C. overnight. The mixture was then partitioned between EtOAc and H$_2$O, and the aqueous layer was separated and extracted with EtOAc. The combined organic layers were washed with brine, dried over MgSO$_4$, filtered, and concentrated to give the title compound.

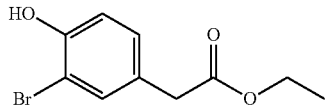

Step 2: (3-Bromo-4-hydroxy-phenyl)-acetic acid ethyl ester (3-Bromo-4-hydroxy-phenyl)-acetic acid (5.6 mmol) in EtOH (20 mL) was treated with sulfuric acid (1 mL) and stirred at room temperature over the weekend. The mixture was concentrated to give the title compound.

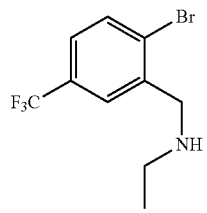

Step 3: (2-Bromo-5-trifluoromethyl-benzyl)-ethyl-amine

Prepared according to the procedure described in Example 33, Step 4, using the following starting materials: 2-bromo-5-(trifluoromethyl)benzaldehyde and ethylamine (2M in THF).

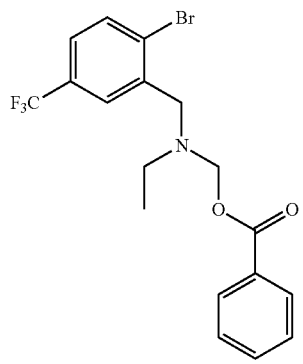 [SMILES: CCN(COC(=O)c1ccccc1)Cc1cc(C(F)(F)F)ccc1Br]

Step 4: (2-Broom-5-trifluoromethyl-benzyl)-ethyl-carbamic acid benzyl ester

Prepared according to the procedure described in Example 1, Step 6, using the following starting materials: (2-bromo-5-trifluoromethyl-benzyl)-ethyl-amine and benzyl chloroformate.

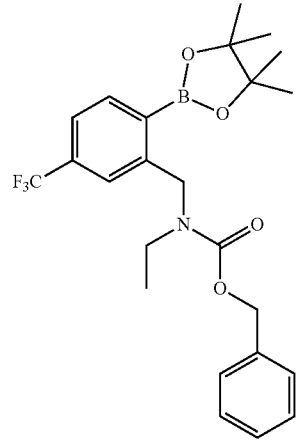 [SMILES: CCN(Cc1cc(C(F)(F)F)ccc1B1OC(C)(C)C(C)(C)O1)C(=O)OCc1ccccc1]

Step 5: Ethyl-[2-(4,4,5,5-tetramethyl-[1,3,2]dioxaborolan-2-yl)-5-trifluoromethyl-benzyl]-carbamic acid benzyl ester Prepared according to the procedure described in Example 33, Step 2, using the following starting materials: (2-bromo-5-trifluoromethyl-benzyl)-ethyl-carbamic acid benzyl ester and bis(pinacolato)diboron.

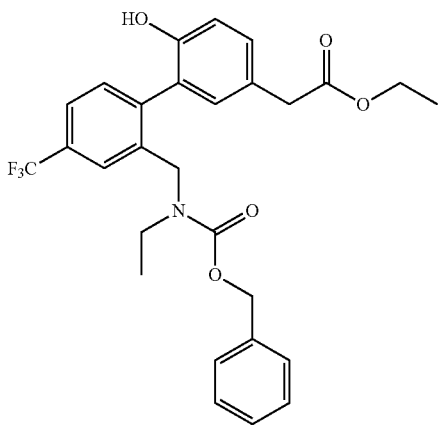 [SMILES: CCOC(=O)Cc1ccc(O)c(-c2ccc(C(F)(F)F)cc2CN(CC)C(=O)OCc2ccccc2)c1]

Step 6: {2'-[(Benzyloxycarbonyl-ethyl-amino)-methyl]-6-hydroxy-4'-trifluoromethyl-biphenyl-3-yl}-acetic acid ethyl ester Prepared according to the procedure described in Example 1, Step 4, using the following starting materials: (3-bromo-4-hydroxy-phenyl)-acetic acid ethyl ester and ethyl-[2-(4,4,5,5-tetramethyl-[1,3,2]dioxaborolan-2-yl)-5-trifluoromethyl-benzyl]-carbamic acid benzyl ester.

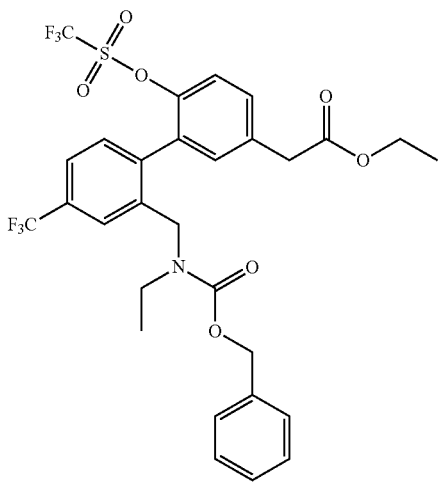 [SMILES: CCOC(=O)Cc1ccc(OS(=O)(=O)C(F)(F)F)c(-c2ccc(C(F)(F)F)cc2CN(CC)C(=O)OCc2ccccc2)c1]

Step 7: {2'-[(Benzyloxycarbonyl-ethyl-amino)-methyl]-6-trifluoromethanesulfonyloxy-4'-trifluoromethyl-biphenyl-3-yl}-acetic acid ethyl ester To a slurry of {2'-[(benzyloxycarbonyl-ethyl-amino)-methyl]-6-hydroxy-4'-trifluoromethyl-biphenyl-3-yl}-acetic acid ethyl ester (0.120 g, 0.23 mmol) and cesium carbonate (0.090 g, 0.28 mmol) in $CH_2Cl_2$ was added N-phenyl-bis(trifluoromethanesulfonimide) (0.092 g, 0.26 mmol), and the reaction was stirred at room temperature overnight. The mixture was partitioned between $CH_2Cl_2$ and $H_2O$, and the aqueous layer was separated and extracted with $CH_2Cl_2$. The combined organic layers were dried over $MgSO_4$, filtered, and concentrated, and the residue was purified by silica gel chromatography to give the title compound.

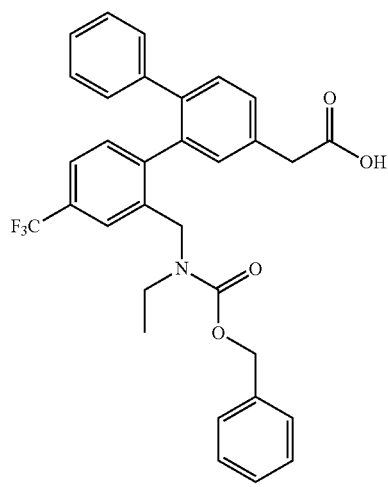 [SMILES: CCN(Cc1cc(C(F)(F)F)ccc1-c1cc(CC(=O)O)ccc1-c1ccccc1)C(=O)OCc1ccccc1]

Step 8: {2''-[(Benzyloxycarbonyl-ethyl-amino)-methyl]-4''-trifluoromethyl-[1,1';2',1'']terphenyl-4'-yl}-acetic acid A solution of {2'-[(benzyloxycarbonyl-ethyl-amino)-methyl]-6-trifluoromethanesulfonyloxy-4'-trifluoromethyl-biphenyl-3-yl}-acetic acid ethyl ester (0.11 g, 0.17 mmol), phenylboronic acid (0.023 g, 0.19 mmol), and potassium carbonate (0.070 g, 0.51 mmol) in 2:1 $DME:H_2O$ (5 mL) was purged with $N_2$ for 15 minutes. Tetrakis(triphenylphosphine)palladium(0) (0.020 g, 0.02 mmol) was added, and the reaction was purged with $N_2$ for another 10 minutes, and then stirred at 90° C. overnight. The mixture was partitioned between EtOAc and $H_2O$, and the aqueous layer was separated and extracted with EtOAc. The combined organic layers were dried over $MgSO_4$, filtered, and concentrated, and the residue was purified by preparative HPLC to give the title compound. M+H is 548.

Example 37

Synthesis of [2'-({Ethyl-[2-(2-methyl-imidazol-1-yl)-acetyl]-amino}-methyl)-6-methoxy-4'-trifluoromethyl-biphenyl-3-yl]-acetic acid (Compound 1-149)

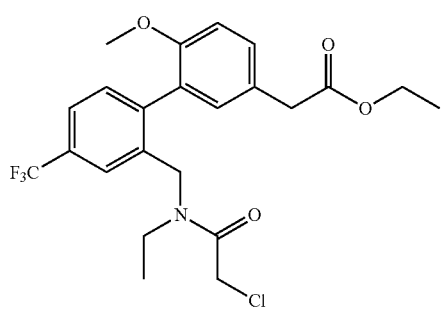 [SMILES: CCOC(=O)Cc1ccc(OC)c(-c2ccc(C(F)(F)F)cc2CN(CC)C(=O)CCl)c1]

Step 1: (2'-{[(2-Chloro-acetyl)-ethyl-amino]-methyl}-6-methoxy-4'-trifluoromethyl-biphenyl-3-yl)-acetic acid ethyl ester Prepared according to the procedure described in Example 1, Step 6, using the following starting materials: (2'-ethylaminomethyl-6-methoxy-4'-trifluoromethyl-biphenyl-3-yl)-acetic acid ethyl ester and chloroacetyl chloride.

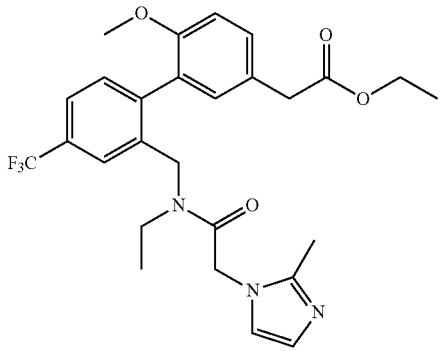 [SMILES: CCOC(=O)Cc1ccc(OC)c(-c2ccc(C(F)(F)F)cc2CN(CC)C(=O)Cn2ccnc2C)c1]

Step 2: [2'-({Ethyl-[2-(2-methyl-imidazol-1-yl)-acetyl]-amino}-methyl)-6-methoxy-4'-trifluoromethyl-biphenyl-3-yl]-acetic acid ethyl ester To 2-methylimidazole (0.047 g, 0.57 mmol) in DMF (2 mL) at 0° C. was added sodium hydride (60% in mineral oil; 0.031 g, 0.78 mmol), and the reaction was stirred for 15 minutes. (2'-{[2-Chloro-acetyl)-ethyl-amino]-methyl}-6-methoxy-4'-trifluoromethyl-biphenyl-3-yl)-acetic acid ethyl ester (0.52 mmol) was added in DMF, and the reaction was stirred at room temperature for 1.5 hours. Analytical LCMS showed that a lot of starting material remained, so tetrabutylammonium iodide (0.005 g, 0.01 mmol) was added, and the reaction was stirred for 3 hours. Analytical LCMS showed that no change had occurred, so additional sodium hydride (60% in mineral oil; 0.031 g, 0.78 mmol) was added, and the reaction was stirred overnight at room temperature. The mixture was partitioned between EtOAc and H₂O, and the aqueous layer was separated and extracted twice with EtOAc. The combined organic layers were washed three times with H₂O, and then dried and concentrated to give the title compound.

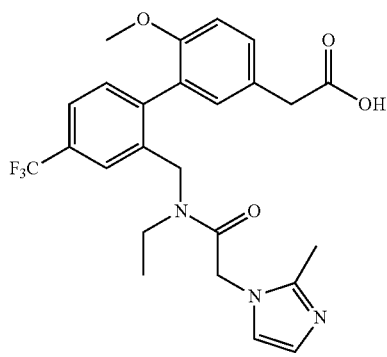 [SMILES: CCN(Cc1cc(C(F)(F)F)ccc1-c1cc(CC(=O)O)ccc1OC)C(=O)Cn1ccnc1C]

Step 3: [2'-({Ethyl-[2-(2-methyl-imidazol-1-yl)-acetyl]-amino}-methyl)-6-methoxy-4'-trifluoromethyl-biphenyl-3-yl]-acetic acid Prepared according to the procedure described in Example 31, Step 2, using the following starting material: [2'-({ethyl-[2-(2-methyl-imidazol-1-yl)-acetyl]-amino}-methyl)-6-methoxy-4'-trifluoromethyl-biphenyl-3-yl]-acetic acid ethyl ester. M+H is 490.

Example 38

Synthesis of [2'-[(Benzyloxycarbonyl-ethyl-amino)-methyl]-4'-(4-chloro-benzoylamino)-6-methoxy-biphenyl-3-yl]-acetic acid (Compound 1-154)

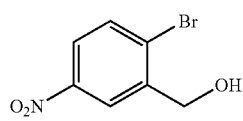 [SMILES: O=[N+]([O-])c1ccc(Br)c(CO)c1]

Step 1: (2-Bromo-5-nitro-phenyl)-methanol

To 2-bromo-5-nitrobenzoic acid (5 g, 20 mmol) at 0° C. was added borane tetrahydrofuran complex (1M in THF; 200 mL, 200 mmol), and the reaction was stirred at room temperature overnight. The mixture was quenched with 1N aqueous HCl to give the title compound.

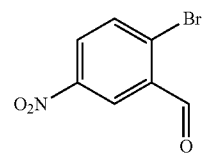 [SMILES: O=Cc1cc([N+](=O)[O-])ccc1Br]

Step 2: 2-Bromo-5-nitro-benzaldehyde

Prepared according to the procedure described in Example 1, Step 3, using the following starting material: (2-bromo-5-nitro-phenyl)-methanol.

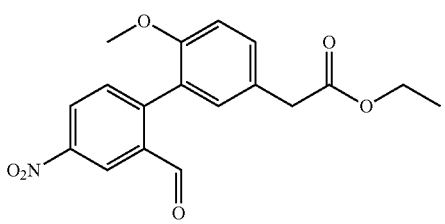 [SMILES: CCOC(=O)Cc1ccc(OC)c(-c2ccc([N+](=O)[O-])cc2C=O)c1]

Step 3: (2'-Formyl-6-methoxy-4'-nitro-biphenyl-3-yl)-acetic acid ethyl ester

Prepared according to the procedure described in Example 1, Step 4, using the following starting materials: 2-bromo-5-nitro-benzaldehyde and [4-methoxy-3-(4,4,5,5-tetramethyl-[1,3,2]dioxaborolan-2-yl)-phenyl]-acetic acid ethyl ester.

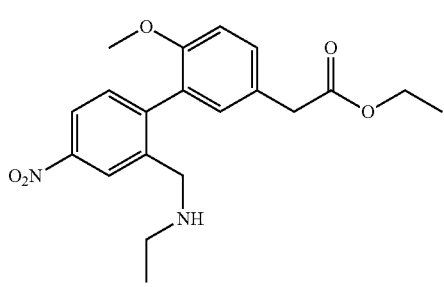 [SMILES: CCNCc1cc([N+](=O)[O-])ccc1-c1cc(CC(=O)OCC)ccc1OC]

Step 4: (2'-Ethylaminomethyl-6-methoxy-4'-nitro-biphenyl-3-yl)-acetic acid ethyl ester Prepared according to the procedure described in Example 33, Step 4, using the following starting materials: (2'-formyl-6-methoxy-4'-nitro-biphenyl-3-yl)-acetic acid ethyl ester and ethylamine (2M in THF).

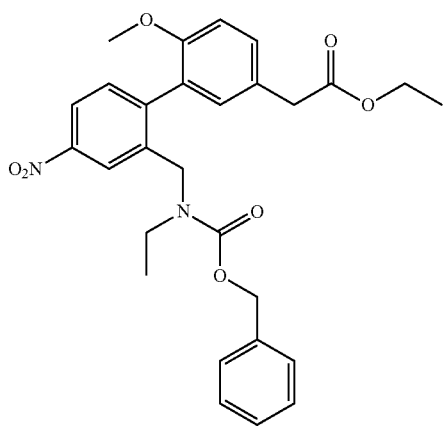 [SMILES: CCOC(=O)Cc1ccc(OC)c(-c2ccc([N+](=O)[O-])cc2CN(CC)C(=O)OCc2ccccc2)c1]

Step 5: {2'-[(Benzyloxycarbonyl-ethyl-amino)-methyl]-6-methoxy-4'-nitro-biphenyl-3-yl}-acetic acid ethyl ester Prepared according to the procedure described in Example 1, Step 6, using the following starting materials: (2'-ethylaminomethyl-6-methoxy-4'-nitro-biphenyl-3-yl)-acetic acid ethyl ester and benzyl chloroformate.

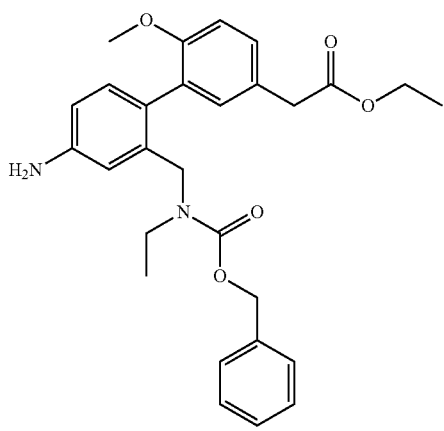

Step 6: {4'-Amino-2'-[(benzyloxycarbonyl-ethyl-amino)-methyl]-6-methoxy-biphenyl-3-yl}-acetic acid ethyl ester To a solution of {2'-[(benzyloxycarbonyl-ethyl-amino)-methyl]-6-methoxy-4'-nitro-biphenyl-3-yl}-acetic acid ethyl ester (0.70 g, 1.75 mmol) in EtOH (70 mL) was added tin (II) chloride (1.97 g, 8.75 mmol). The reaction was heated to reflux for 5 h, and then the mixture was acidified to pH 1 with concentrated HCl and diluted with EtOAc. The resulting biphasic mixture was filtered through Celite, and the organic layer was separated. The aqueous layer was neutralized to pH 7 with solid NaOH and extracted with EtOAc. The combined organic extracts were dried and filtered, and the residue was purified by silica gel chromatography to give the title compound.

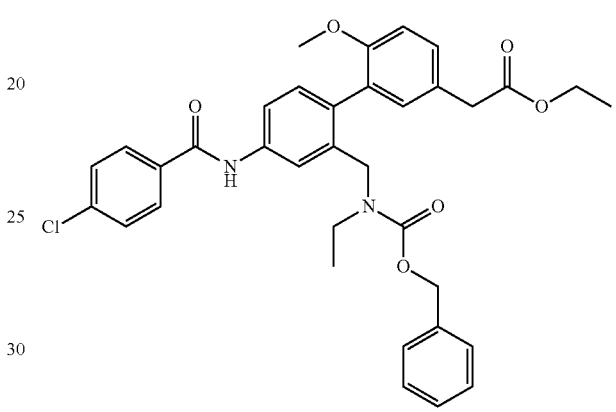

Step 7: [2'-[(Benzyloxycarbonyl-ethyl-amino)-methyl]-4'-(4-chloro-benzoylamino)-6-methoxy-biphenyl-3-yl]-acetic acid ethyl ester {4'-Amino-2'-[(benzyloxycarbonyl-ethyl-amino)-methyl]-6-methoxy-biphenyl-3-yl}-acetic acid ethyl ester (0.08 g, 0.2 mmol), 4-chlorobenzoyl chloride (0.04 mL, 0.3 mmol), and triethylamine were reacted in CH$_2$Cl$_2$ to give the title compound.

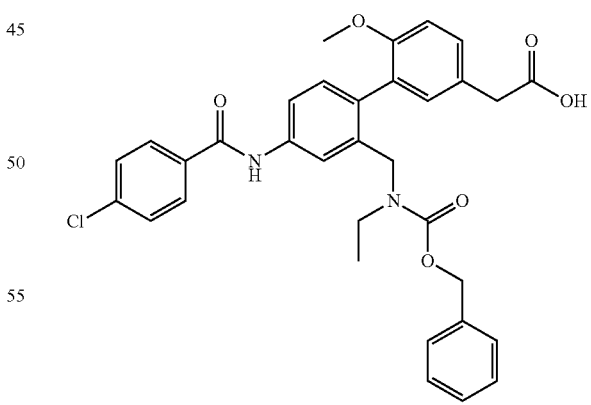

Step 8: [2'-[(Benzyloxycarbonyl-ethyl-amino)-methyl]-4'-(4-chloro-benzoylamino)-6-methoxy-biphenyl-3-yl]-acetic acid

[2'-[(Benzyloxycarbonyl-ethyl-amino)-methyl]-4'-(4-chloro-benzoylamino)-6-methoxy-biphenyl-3-yl]-acetic acid ethyl ester (0.2 mmol) was hydrolyzed with lithium hydroxide to give the title compound.

Example 39

Synthesis of {2'-[(Benzyloxycarbonyl-ethyl-amino)-methyl]-4'-methanesulfonylamino-6-methoxy-biphenyl-3-yl}-acetic acid (Compound 1-155)

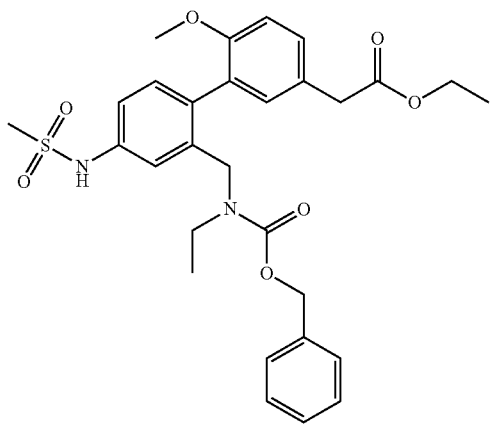 [SMILES: CCOC(=O)Cc1ccc(OC)c(-c2ccc(NS(C)(=O)=O)cc2CN(CC)C(=O)OCc2ccccc2)c1]

Step 1: {2'-[(Benzyloxycarbonyl-ethyl-amino)-methyl]-4'-methanesulfonylamino-6-methoxy-biphenyl-3-yl}-acetic acid ethyl ester {4'-Amino-2'-[(benzyloxycarbonyl-ethyl-amino)-methyl]-6-methoxy-biphenyl-3-yl}-acetic acid ethyl ester (0.080 g, 0.2 mmol), methanesulfonyl chloride (0.04 mL, 0.3 mmol), and triethylamine were reacted in CH$_2$Cl$_2$ to give the title compound.

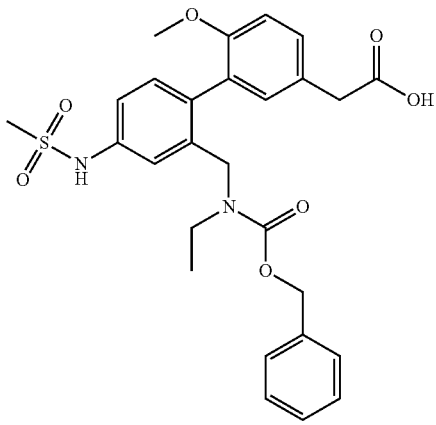 [SMILES: CCN(Cc1cc(NS(C)(=O)=O)ccc1-c1cc(CC(=O)O)ccc1OC)C(=O)OCc1ccccc1]

Step 2: {2'-[(Benzyloxycarbonyl-ethyl-amino)-methyl]-4'-methanesulfonylamino-6-methoxy-biphenyl-3-yl}-acetic acid {2'-[(Benzyloxycarbonyl-ethyl-amino)-methyl]-4'-methanesulfonylamino-6-methoxy-biphenyl-3-yl}-acetic acid ethyl ester (0.2 mmol) was hydrolyzed with lithium hydroxide to give the title compound.

Example 40

Synthesis of {2'-[(Cyclopropanecarbonyl-ethyl-amino)-methyl]-6,5'-dimethoxy-biphenyl-3-yl}-acetic acid (Compound 1-196)

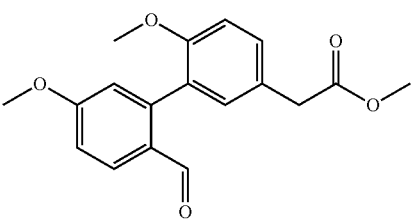

Step 1: (2'-Formyl-6,5'-dimethoxy-biphenyl-3-yl)-acetic acid methyl ester

Prepared according to the procedure described in Example 1, Step 4, using the following starting materials: (3-bromo-4-methoxy-phenyl)-acetic acid methyl ester and 2-formyl-5-methoxyphenylboronic acid.

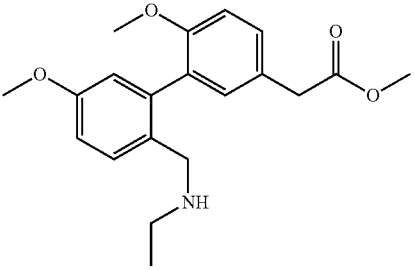

Step 2: (2'-Ethylaminomethyl-6,5'-dimethoxy-biphenyl-3-yl)-acetic acid methyl ester Prepared according to the procedure described in Example 33, Step 4, using the following starting materials: (2'-formyl-6,5'-dimethoxy-biphenyl-3-yl)-acetic acid methyl ester and ethylamine (2M in THF).

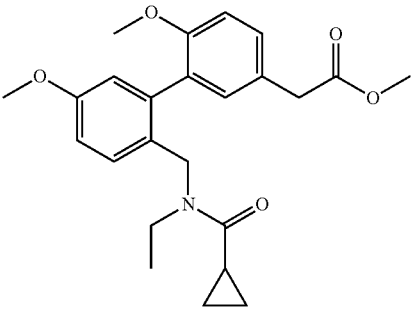

Step 3: {2'-[(Cyclopropanecarbonyl-ethyl-amino)-methyl]-6,5'-dimethoxy-biphenyl-3-yl}-acetic acid methyl ester Prepared according to the procedure described in Example 1, Step 6, using the following starting materials: (2'-ethylaminomethyl-6,5'-dimethoxy-biphenyl-3-yl)-acetic acid methyl ester and cyclopropanecarbonyl chloride.

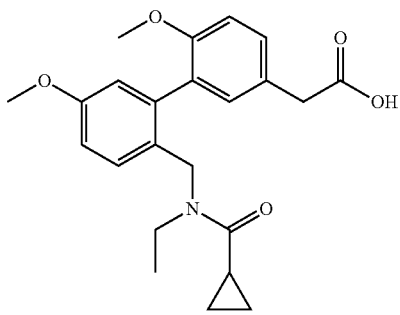 [SMILES: CCN(Cc1ccc(OC)cc1-c1cc(CC(=O)O)ccc1OC)C(=O)C1CC1]

Step 4: {2'-[(Cyclopropanecarbonyl-ethyl-amino)-methyl]-6,5'-dimethoxy-biphenyl-3-yl}-acetic acid Prepared according to the procedure described in Example 31, Step 2, using the following starting material: {2'-[(cyclopropanecarbonyl-ethyl-amino)-methyl]-6,5'-dimethoxy-biphenyl-3-yl}-acetic acid methyl ester.

Example 41

Synthesis of [2'(1-Ethyl-3-methyl-ureidomethyl)-5,4'-bis-trifluoromethyl-biphenyl-3-yl]-acetic acid (Compound 1-202)

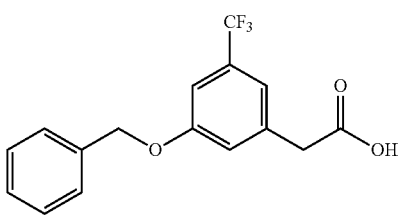 [SMILES: O=C(O)Cc1cc(OCc2ccccc2)cc(C(F)(F)F)c1]

Step 1: (3-Benzyloxy-5-trifluoromethyl-phenyl)-acetic acid

To 3-fluoro-5-(trifluoromethyl)phenylacetic acid (2.0 g, 9.0 mmol) and benzyl alcohol (1.9 mL, 18.0 mmol) in NMP (10 mL) was added sodium hydride (60% in mineral oil; 0.8 g, 19.8 mmol), and the reaction was stirred at 120° C. for 3 hours. The mixture was acidified and extracted with EtOAc, and the crude material was purified by silica gel chromatography to give the title compound.

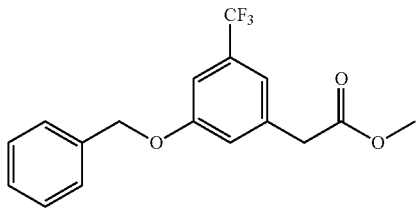 [SMILES: COC(=O)Cc1cc(OCc2ccccc2)cc(C(F)(F)F)c1]

Step 2: (3-Benzyloxy-5-trifluoromethyl-phenyl)-acetic acid methyl ester

To a solution of (3-benzyloxy-5-trifluoromethyl-phenyl)-acetic acid (1.5 g, 4.8 mmol) in MeOH (10 mL) was added 4N HCl in 1,4-dioxane (2 mL), and the reaction was stirred at 80° C. for 1 hour. The mixture was concentrated and purified by silica gel chromatography to give the title compound.

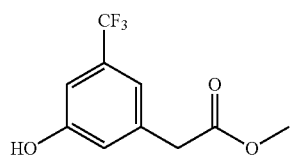 [SMILES: COC(=O)Cc1cc(O)cc(C(F)(F)F)c1]

Step 3: (3-Hydroxy-5-trifluoromethyl-phenyl)-acetic acid methyl ester (3-Benzyloxy-5-trifluoromethyl-phenyl)-acetic acid methyl ester (4.8 mmol) in EtOH was treated with 10% palladium on carbon (10% by weight), and stirred under a balloon of $H_2$ at 60° C. overnight. The mixture was filtered to remove the palladium, and then concentrated to give the title compound.

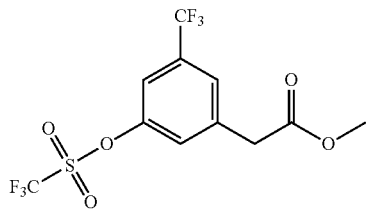 [SMILES: COC(=O)Cc1cc(OS(=O)(=O)C(F)(F)F)cc(C(F)(F)F)c1]

Step 4: (3-Trifluoromethanesulfonyloxy-5-trifluoromethyl-phenyl)-acetic acid methyl ester To a solution of (3-hydroxy-5-trifluoromethyl-phenyl)-acetic acid methyl ester (0.5 g, 2.1 mmol) in DMF (10 mL) was added cesium carbonate (1.4 g, 4.3 mmol), followed by N-phenyl-bis(trifluoromethanesulfonimide) (0.83 g, 2.3 mmol), and the reaction was stirred at room temperature for 1 hour. Once no starting material was seen by analytical LCMS, the mixture was worked up with EtOAc and $H_2O$, and the residue was purified by silica gel chromatography to give the title compound.

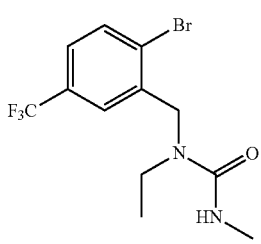 [SMILES: CCN(Cc1cc(C(F)(F)F)ccc1Br)C(=O)NC]

Step 5: 1-(2-Bromo-5-trifluoromethyl-benzyl)-1-ethyl-3-methyl-urea

To (2-bromo-5-trifluoromethyl-benzyl)-ethyl-amine (0.5 g, 1.8 mmol) in $CH_2Cl_2$ (5 mL) was added triethylamine (0.5 mL, 3.5 mmol), followed by methyl isocyanate (0.121 g, 2.2 mmol), and the reaction was stirred at room temperature under $N_2$ for 30 minutes. The mixture was worked-up with $CH_2Cl_2$ and $H_2O$, and the residue was purified by silica gel chromatography to give the title compound.

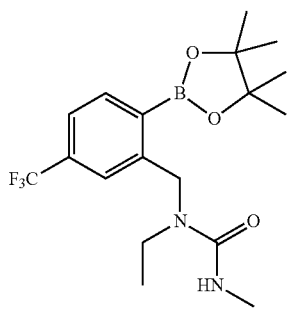 [SMILES: CCN(Cc1cc(C(F)(F)F)ccc1B1OC(C)(C)C(C)(C)O1)C(=O)NC]

Step 6: 1-Ethyl-3-methyl-1-[2-(4,4,5,5-tetramethyl-[1,3,2]dioxaborolan-2-yl)-5-trifluoromethyl-benzyl]-urea Prepared according to the procedure described in Example 33, Step 2, using the following starting materials: 1-(2-bromo-5-trifluoromethyl-benzyl)-1-ethyl-3-methyl-urea and bis(pinacolato)diboron.

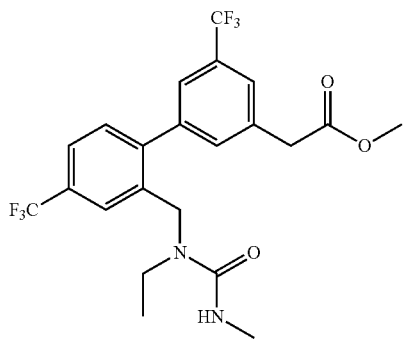 [SMILES: CCN(Cc1cc(C(F)(F)F)ccc1-c1cc(CC(=O)OC)cc(C(F)(F)F)c1)C(=O)NC]

Step 7: [2'-(1-Ethyl-3-methyl-ureidomethyl)-5,4'-bis-trifluoromethyl-biphenyl-3-yl]-acetic acid methyl ester (3-Trifluoromethanesulfonyloxy-5-trifluoromethyl-phenyl)-acetic acid methyl ester (0.063 g, 0.18 mmol), 1-ethyl-3-methyl-1-[2-(4,4,5,5-tetramethyl-[1,3,2]dioxaborolan-2-yl)-5-trifluoromethyl-benzyl]-urea (0.070 g, 0.18 mmol, potassium carbonate (0.062 g, 0.45 mmol), and tetrakis(triphenylphosphine)palladium(0) (0.021 g, 0.02 mmol) were combined in 2:1 $DME:H_2O$ (3 mL) and degassed with $N_2$ for 10 minutes. The reaction was then stirred at 90° C. for 2 hours, until no starting material was seen by analytical LCMS. The mixture was cooled to room temperature and used directly in the hydrolysis step.

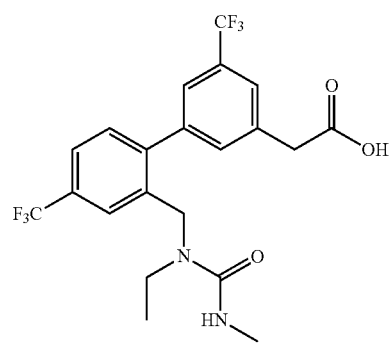 [SMILES: CCN(Cc1cc(C(F)(F)F)ccc1-c1cc(CC(=O)O)cc(C(F)(F)F)c1)C(=O)NC]

Step 8: [2'-(1-Ethyl-3-methyl-ureidomethyl)-5,4'-bis-trifluoromethyl-biphenyl-3-yl]-acetic acid To [2'-(1-ethyl-3-methyl-ureidomethyl)-5,4'-bis-trifluoromethyl-biphenyl-3-yl]-acetic acid methyl ester (0.18 mmol) was added 1:1 1N aqueous LiOH:1,4-dioxane (2 mL), and the reaction was stirred at room temperature for 30 minutes. 10% Aqueous HCl was added to acidify the solution to pH 3, and the mixture was extracted with EtOAc. The crude material was purified by silica gel chromatography to give the title compound. M+H is 463.

Example 42

Synthesis of (R)-2-[2'-(3-Benzyl-1-ethyl-ureidomethyl)-5,4'-bis-trifluoromethyl-biphenyl-3-yl]-propionic acid (Compound 2-10)

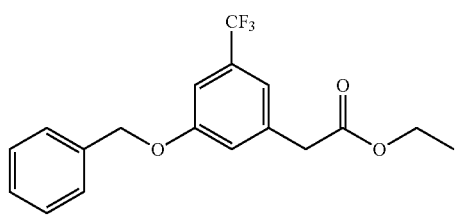 [SMILES: CCOC(=O)Cc1cc(OCc2ccccc2)cc(C(F)(F)F)c1]

Step 1: (3-Benzyloxy-5-trifluoromethyl-phenyl)-acetic acid ethyl ester

Prepared according to the procedure described in Example 41, Step 2, using the following starting materials: (3-benzyloxy-5-trifluoromethyl-phenyl)-acetic acid and ethanol.

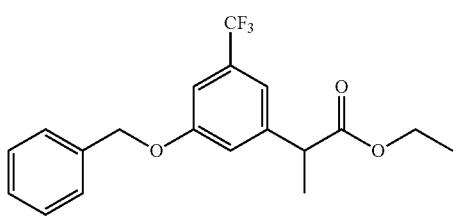 [SMILES: CCOC(=O)C(C)c1cc(OCc2ccccc2)cc(C(F)(F)F)c1]

Step 2: 2-(3-Benzyloxy-5-trifluoromethyl-phenyl)-propionic acid ethyl ester

To a solution of (3-benzyloxy-5-trifluoromethyl-phenyl)-acetic acid ethyl ester (5.0 g, 14.8 mmol) in DMF (50 mL) at 0° C. under N₂ was added sodium hydride (60% in mineral oil; 0.65 g, 16.3 mmol), and the mixture was stirred at room temperature for 15 minutes. Iodomethane (1 mL, 16.3 mmol) was added, and the reaction was monitored by analytical LCMS and tlc. After work-up with EtOAc and H₂O, the crude material was purified by silica gel chromatography to give the title compound.

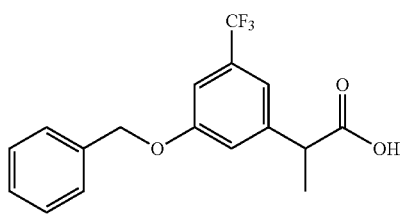 [SMILES: CC(C(=O)O)c1cc(OCc2ccccc2)cc(C(F)(F)F)c1]

Step 3: 2-(3-Benzyloxy-5-trifluoromethyl-phenyl)-propionic acid 2-(3-Benzyloxy-5-trifluoromethyl-phenyl)-propionic acid ethyl ester (1.4 g, 4.0 mmol) in 2:2:1 MeOH:THF:H₂O was treated with 1N aqueous LiOH (3 mL) at room temperature overnight. The mixture was acidified with 10% aqueous HCl and extracted three times with EtOAc. The combined organic layers were concentrated and purified by silica gel chromatography to give the title compound.

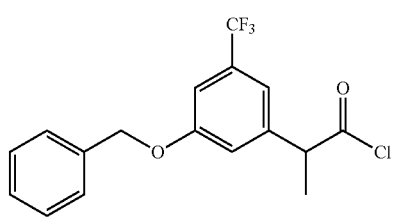 [SMILES: CC(C(=O)Cl)c1cc(OCc2ccccc2)cc(C(F)(F)F)c1]

Step 4: 2-(3-Benzyloxy-5-trifluoromethyl-phenyl)-propionyl chloride

To a solution of 2-(3-benzyloxy-5-trifluoromethyl-phenyl)-propionic acid (1.4 g, 4.0 mmol) in CH₂Cl₂ was added oxalyl chloride (0.76 mL, 8.0 mmol), followed by 3 drops of DMF. After stirring for 15 minutes at room temperature, the mixture was concentrated to give the title compound.

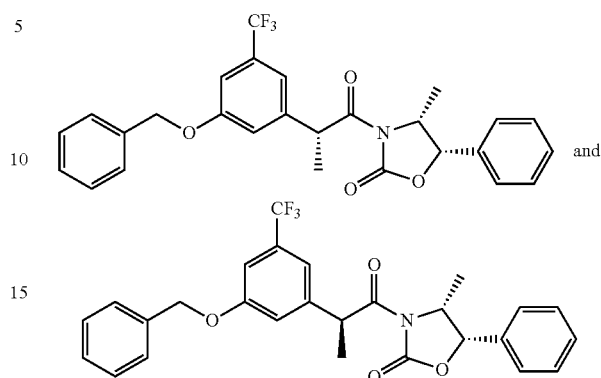

Step 5: (4R,5S)-3-[(R)-2-(3-Benzyloxy-5-trifluoromethyl-phenyl)-propionyl]-4-methyl-5-phenyl-oxazolidin-2-one and (4R,5S)-3-[(S)-2-(3-Benzyloxy-5-trifluoromethyl-phenyl)-propionyl]-4-methyl-5-phenyl-oxazolidin-2-one To a solution of (4R,5S)-4-methyl-5-phenyl-2-oxazolidinone (0.644 g, 3.6 mmol) in THF (20 mL) at −78° C. was slowly added n-butyllithium (2.5M in THF; 1.8 mL, 4.0 mmol). After stirring for 1 hour at −78° C., 2-(3-benzyloxy-5-trifluoromethyl-phenyl)-propionyl chloride (4.0 mmol) in TIN (10 mL) was slowly added, and the reaction was stirred for 1.5 hours. The mixture was worked up with EtOAc and H₂O, and the residue was purified by silica gel chromatography to give the title compounds as separated products.

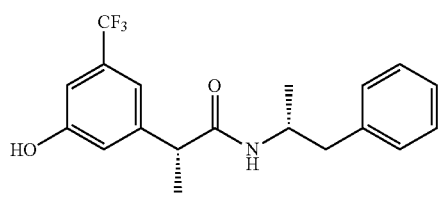 [SMILES: C[C@H](Cc1ccccc1)NC(=O)[C@H](C)c1cc(O)cc(C(F)(F)F)c1]

Step 6: (R)-2-(3-Hydroxy-5-trifluoromethyl-phenyl)-N—((R)-1-methyl-2-phenyl-ethyl)-propionamide Prepared according to the procedure described in Example 41, Step 3, using the following starting material: (4R,5S)-3-[(R)-2-(3-benzyloxy-5-trifluoromethyl-phenyl)-propionyl]-4-methyl-5-phenyl-oxazolidin-2-one.

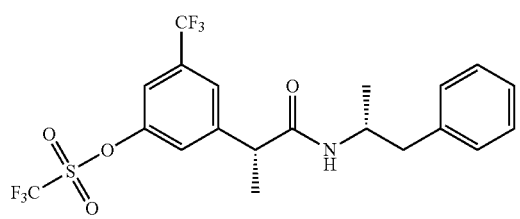 [SMILES: C[C@H](Cc1ccccc1)NC(=O)[C@H](C)c1cc(OS(=O)(=O)C(F)(F)F)cc(C(F)(F)F)c1]

Step 7: Trifluoro-methanesulfonic acid 3-[(R)-1((R)-1-methyl-2-phenyl-ethylcarbamoyl)-ethyl]-5-trifluoromethyl-phenyl ester Prepared according to the procedure described in Example 41, Step 4, using the following starting materials: (R)-2-(3-Hydroxy-5-trifluoromethyl-phenyl)-N—((R)-1-methyl-2-phenyl-ethyl)-propionamide and N-phenyl-bis(trifluoromethanesulfonimide).

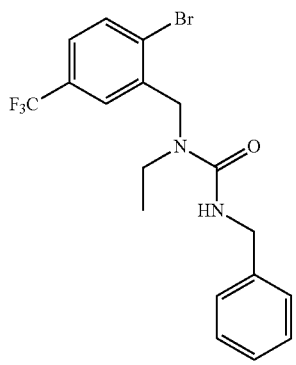 [SMILES: CCN(Cc1cc(C(F)(F)F)ccc1Br)C(=O)NCc1ccccc1]

Step 8: 3-Benzyl-1-(2-bromo-5-trifluoromethyl-benzyl)-1-ethyl-urea

To a solution of (2-bromo-5-trifluoromethyl-benzyl)-ethyl-amine (1.5 g, 5.3 mmol) in CH$_2$Cl$_2$ (20 mL) at 0° C. was added diisopropylethylamine (1.7 mL, 13.3 mmol). Phosgene (1.9M in toluene; 4.2 mL, 8.0 mmol) was then added dropwise, and the reaction was stirred for 2 hours. Triethylamine (1.48 mL, 10.6 mmol) was added, followed by benzylamine (0.87 mL, 8.0 mmol), and the reaction was stirred at room temperature for 2.5 hours. After work-up with CH$_2$Cl$_2$ and H$_2$O, the crude material was purified by silica gel chromatography to give the title compound.

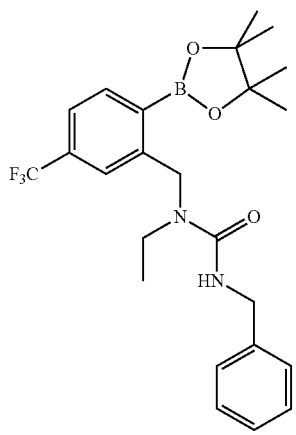 [SMILES: CCN(Cc1cc(C(F)(F)F)ccc1B1OC(C)(C)C(C)(C)O1)C(=O)NCc1ccccc1]

Step 9: 3-Benzyl-1-ethyl-1-[2-(4,4,5,5-tetramethyl-[1,3,2]dioxaborolan-2-yl)-5-trifluoromethyl-benzyl]-urea 3-Benzyl-1-(2-bromo-5-trifluoromethyl-benzyl)-1-ethyl-urea (2.0 g, 4.8 mmol), bis(pinacolato)diboron (1.7 g, 7.2 mmol), (1,1'-bis(diphenylphosphino)ferrocene)-dichloropalladium(II) (0.40 g, 0.48 mmol), and potassium acetate (1.4 g, 1.4 mmol) were combined in 1,4-dioxane (20 mL) under N$_2$. The solution was purged with N$_2$ for 10 minutes, and the reaction was heated to 80° C. for 3 hours Once no starting material was seen by analytical LCMS, the mixture was worked up with EtOAc and brine, and the crude material was purified by silica gel chromatography to give the title compound.

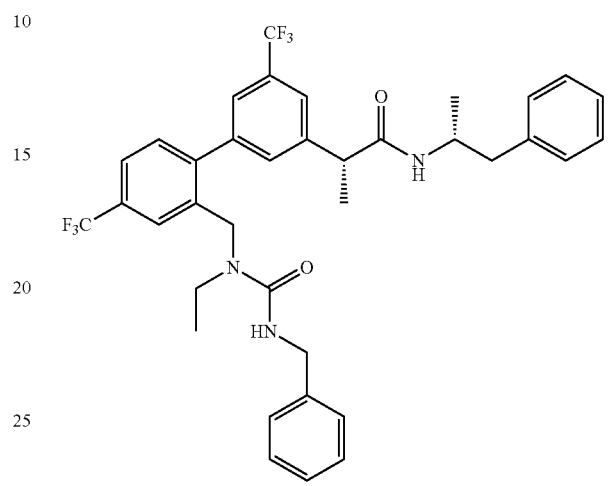

Step 10: (R)-2-[2'-(3-Benzyl-1-ethyl-ureidomethyl)-5,4'-bis-trifluoromethyl-biphenyl-3-yl]-N—((R)-1-methyl-2-phenyl-ethyl)-propionamide Prepared according to the procedure described in Example 1, Step 4, using the following starting materials: trifluoromethanesulfonic acid 3-[(R)-1-(R)-1-methyl-2-phenyl-ethylcarbamoyl)-ethyl]-5-trifluoromethyl-phenyl ester and 3-benzyl-1-ethyl-1-[2-(4,4,5,5-tetramethyl-[1,3,2]dioxaborolan-2-yl)-5-trifluoromethyl-benzyl]-urea. M+H is 670.

Example 43

Synthesis of (R)-2-[2'-(3-Benzyl-1-ethyl-ureidomethyl)-5,4'-bis-trifluoromethyl-biphenyl-3-yl]-propionic acid (Compound 1-239)

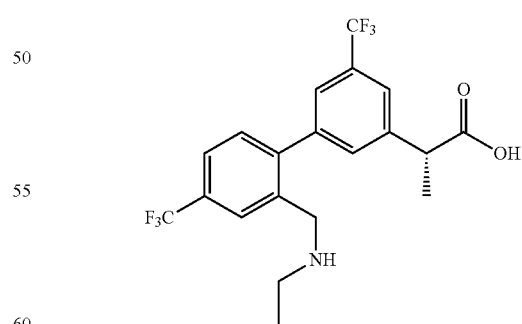

Step 1: (R)-2-(2'-Ethylaminomethyl-5,4'-bis-trifluoromethyl-biphenyl-3-yl)-propionic acid (R)-2-[2'-(3-Benzyl-1-ethyl-ureidomethyl)-5,4'-bis-trifluoromethyl-biphenyl-3-yl]-N—((R)-1-methyl-2-phenylethyl)-propionamide (0.08 g, 0.12 mmol) was treated with 5N aqueous H₂SO₄ in 1,4-dioxane at 100° C. for 24 hours. The mixture was purified by preparative HPLC to give the title compound.

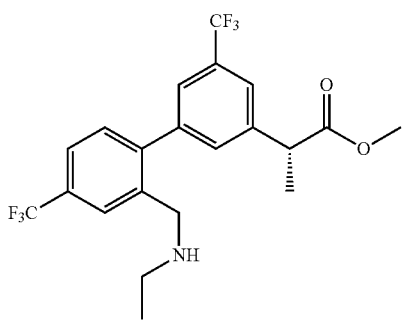 [SMILES: CCNCc1cc(C(F)(F)F)ccc1-c1cc([C@@H](C)C(=O)OC)cc(C(F)(F)F)c1]

Step 2: (R)-2-(2'-Ethylaminomethyl-5,4'-bis-trifluoromethyl-biphenyl-3-yl)-propionic acid methyl ester (R)-2-(2'-Ethylaminomethyl-5,4'-bis-trifluoromethyl-biphenyl-3-yl)-propionic acid (0.04 g, 0.10 mmol) in MeOH (2 mL) was treated with 2 drops of sulfuric acid at room temperature overnight. The mixture was concentrated, and the crude material was used directly in the next step.

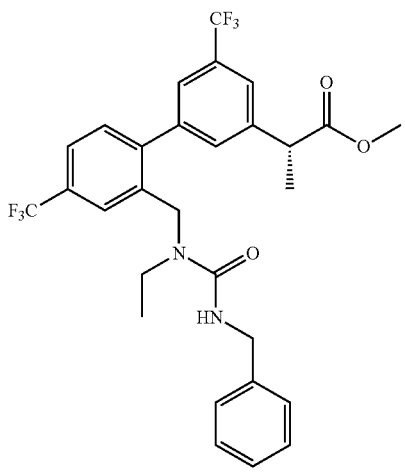 [SMILES: CCN(Cc1cc(C(F)(F)F)ccc1-c1cc([C@@H](C)C(=O)OC)cc(C(F)(F)F)c1)C(=O)NCc1ccccc1]

Step 3: (R)-2-[2'-(3-Benzyl-1-ethyl-ureidomethyl)-5,4'-bis-trifluoromethyl-biphenyl-3-yl]-propionic acid methyl ester (R)-2-(2'-Ethylaminomethyl-5,4'-bis-trifluoromethyl-biphenyl-3-yl)-propionic acid methyl ester (0.10 mmol) in CH₂Cl₂ was treated with triethylamine (0.03 mL, 0.20 mmol) and benzyl isocyanate (0.02 mL, 0.20 mmol) at room temperature for 2 hours. The mixture was worked up with CH₂Cl₂ and H₂O to give the title compound.

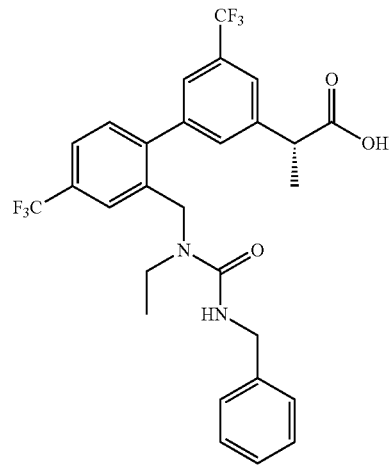 [SMILES: CCN(Cc1cc(C(F)(F)F)ccc1-c1cc([C@@H](C)C(=O)O)cc(C(F)(F)F)c1)C(=O)NCc1ccccc1]

Step 4: (R)-2-[2'-(3-Benzyl-1-ethyl-ureidomethyl)-5, 4'-bis-trifluoromethyl-biphenyl-3-yl]-propionic acid To a solution of (R)-2-[2'-(3-benzyl-1-ethyl-ureidomethyl)-5,4'-bis-trifluoromethyl-biphenyl-3-yl]-propionic acid methyl ester (0.036 g, 0.06mmol) in 1:1 THF:H₂O was added lithium hydroxide (0.005 g, 0.12 mmol) and hydrogen peroxide (29% in water; 0.01 mL, 0.12 mmol). The reaction was stirred at room temperature overnight, and then the mixture was acidified to pH 5 with 10% aqueous HCl. The solution was extracted with EtOAc, and the crude material was purified by preparative HPLC to give the title compound. M+H is 553.

Example 44

Synthesis of (S)-2-[2'-(3-Benzyl-1-ethyl-ureidomethyl)-5,4'-bis-trifluoromethyl-biphenyl-3-yl]-N—((R)-1-methyl-2-phenyl-ethyl)-propionamide (Compound 2-11)

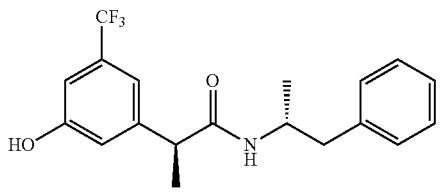 [SMILES: C[C@H](Cc1ccccc1)NC(=O)[C@@H](C)c1cc(O)cc(C(F)(F)F)c1]

Step 1: (S)-2-(3-Hydroxy-5-trifluoromethyl-phenyl)-N—((R)-1-methyl-2-phenyl-ethyl)-propionamide Prepared according to the procedure described in Example 41, Step 3, using the following starting material: (4R,5S)-3-[(S)-2-(3-benzyloxy-5-trifluoromethyl-phenyl)-propionyl]-4-methyl-5-phenyl-oxazolidin-2-one.

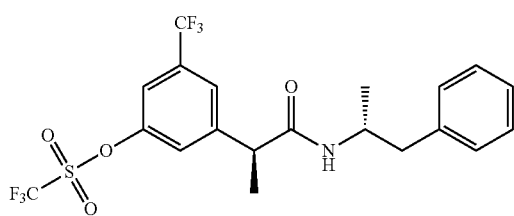 [SMILES: C[C@H](Cc1ccccc1)NC(=O)[C@@H](C)c1cc(OS(=O)(=O)C(F)(F)F)cc(C(F)(F)F)c1]

Step 2: Trifluoro-methanesulfonic acid 3-[(S)-1-((R)-1-methyl-2-phenyl-ethylcarbamoyl)-ethyl]-5-trifluoromethyl-phenyl ester Prepared according to the procedure described in Example 41, Step 4, using the following starting materials: (S)-2-(3-Hydroxy-5-trifluoromethyl-phenyl)-N—((R)-1-methyl-2-phenyl-ethyl)-propionamide and N-phenyl-bis(trifluoromethanesulfonimide).

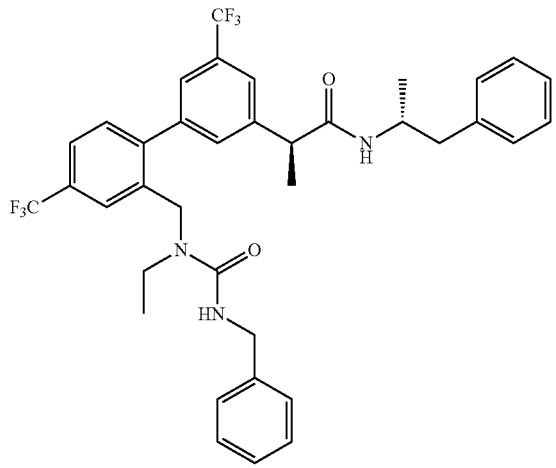 [SMILES: CCN(Cc1cc(C(F)(F)F)ccc1-c1cc([C@H](C)C(=O)N[C@H](C)Cc2ccccc2)cc(C(F)(F)F)c1)C(=O)NCc1ccccc1]

Step 3: (S)-2-[2'-(3-Benzyl-1-ethyl-ureidomethyl)-5,4'-bis-trifluoromethyl-biphenyl-3-yl]-N—((R)-1-methyl-2-phenyl-ethyl)-propionamide Prepared according to the procedure described in Example 1, Step 4, using the following starting materials: trifluoromethanesulfonic acid 3-[(S)-1-((R)-1-methyl-2-phenyl-ethylcarbamoyl)-ethyl]-5-trifluoromethyl-phenyl ester and 3-benzyl-1-ethyl-1-[2-(4,4,5,5-tetramethyl-[1,3,2]dioxaborolan-2-yl)-5-trifluoromethyl-benzyl]-urea. M+H is 670.

Example 45

Synthesis of (S)-2-[2'-(3-Benzyl-1-ethyl-ureidomethyl)-5,4'-bis-trifluoromethyl-biphenyl-3-yl]-propionic acid (Compound 1-240)

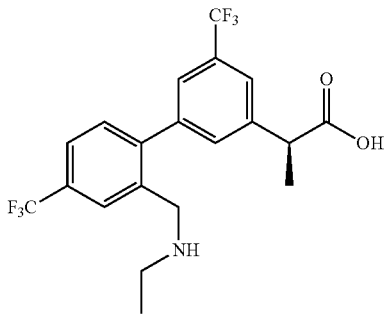 [SMILES: CCNCc1cc(C(F)(F)F)ccc1-c1cc([C@H](C)C(=O)O)cc(C(F)(F)F)c1]

Step 1: (S)-2-(2'-Ethylaminomethyl-5,4'-bis-trifluoromethyl-biphenyl-3-yl)-propionic acid Prepared according to the procedure described in Example 43, Step 1, using the following starting material: (S)-2-[2'-(3-benzyl-1-ethyl-ureidomethyl)-5,4'-bis-trifluoromethyl-biphenyl-3-yl]-N—((R)-1-methyl-2-phenyl-ethyl)-propionamide.

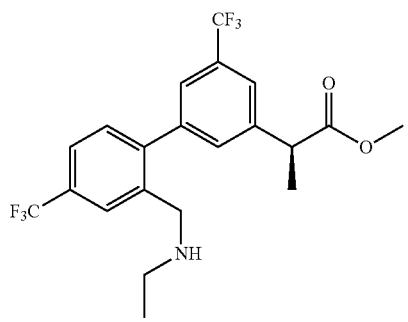 [SMILES: CCNCc1cc(C(F)(F)F)ccc1-c1cc([C@H](C)C(=O)OC)cc(C(F)(F)F)c1]

Step 2: (S)-2-(2'-Ethylaminomethyl-5,4'-bis-trifluoromethyl-biphenyl-3-yl)-propionic acid methyl ester Prepared according to the procedure described in Example 43, Step 2, using the following starting material: (S)-2-(2'-ethylaminomethyl-5,4'-bis-trifluoromethyl-biphenyl-3-yl)-propionic acid.

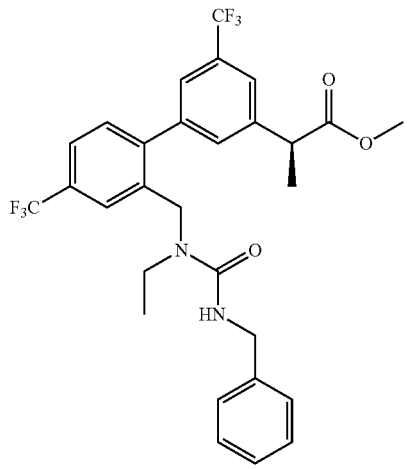 [SMILES: CCN(Cc1cc(C(F)(F)F)ccc1-c1cc([C@H](C)C(=O)OC)cc(C(F)(F)F)c1)C(=O)NCc1ccccc1]

Step 3: (S)-2-[2'-(3-Benzyl-1-ethyl-ureidomethyl)-5,4'-bis-trifluoromethyl-biphenyl-3-yl]-propionic acid methyl ester Prepared according to the procedure described in Example 43, Step 3, using the following starting materials: (S)-2-(2'-ethylaminomethyl-5,4'-bis-trifluoromethyl-biphenyl-3-yl)-propionic acid methyl ester and benzyl isocyanate.

181

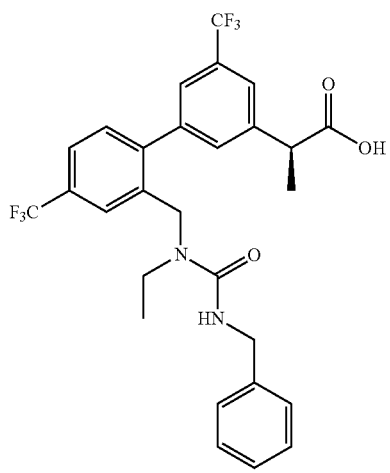 [SMILES: CCN(Cc1cc(C(F)(F)F)ccc1-c1cc([C@H](C)C(=O)O)cc(C(F)(F)F)c1)C(=O)NCc1ccccc1]

Step 4: (S)-2-[2'-(3-Benzyl-1-ethyl-ureidomethyl)-5,4'-bis-trifluoromethyl-biphenyl-3-yl]-propionic acid Prepared according to the procedure described in Example 43, Step 4, using the following starting material: (S)-2-[2'-(3-benzyl-1-ethyl-ureidomethyl)-5,4'-bis-trifluoromethyl-biphenyl-3-yl]-propionic acid methyl ester. M+H is 553.

Example 46

Synthesis of (4'-(6-Ethoxy-pyridin-3-yl)-2'-{[ethyl-(3-phenyl-propionyl)-amino]-methyl}-6-methoxy-biphenyl-3-yl)-acetic acid (Compound 1-256)

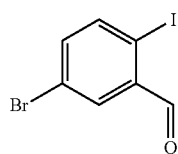

Step 1: 5-Bromo-2-iodo-benzaldehyde

To 5-bromo-2-iodobenzonitrile (7.4 g, 24.2 mmol) in THF (40 mL) at −78° C. was added diisobutylaluminium hydride (1M in hexanes; 24.2 mL, 24.2 mmol) over 5 minutes, and the reaction was allowed to warm to room temperature and monitored by analytical tlc. After stirring overnight at room temperature, starting material was still present, so the mixture was cooled to 0° C. and additional diisobutylaluminium hydride (1M in hexanes; 10.0 mL, 10.0 mmol) was added. After stirring for 2 hours at room temperature, no starting material was seen by analytical tlc, so the mixture was carefully quenched with freshly saturated aqueous Na$_2$SO$_4$ and diluted with EtOAc. The mixture was stirred vigorously for 1 hour and then filtered through Celite. The filtrate was concentrated, and the resulting oil solidified on standing. The solid was stirred vigorously in CH$_2$Cl$_2$ and 1N aqueous HCl, and the aqueous layer was separated and extracted with CH$_2$Cl$_2$. The combined organic layers were dried over MgSO$_4$, filtered, and concentrated to give the title compound.

182

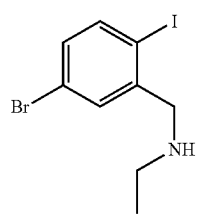

Step 2: (5-Bromo-2-iodo-benzyl)-ethyl-amine

To 5-bromo-2-iodo-benzaldehyde (5.0 g, 16.1 mmol) in MeOH (20 mL) was added ethylamine (2M in MeOH; 16 mL, 24.0 mmol), followed by acetic acid (1.0 mL, 17.8 mmol), and the mixture was stirred at room temperature for 30 minutes. Sodium cyanoborohydride (2.0 g, 31.8 mmol) was then added over 5 minutes, and the reaction was stirred at room temperature over the weekend. The mixture was concentrated and partitioned between EtOAc and saturated aqueous NaHCO$_3$. The aqueous layer was extracted with EtOAc, and the combined organic layers were dried over MgSO$_4$, filtered, and concentrated. The residue was purified by silica gel chromatography (0-5% MeOH in CH$_2$Cl$_2$) to give the title compound.

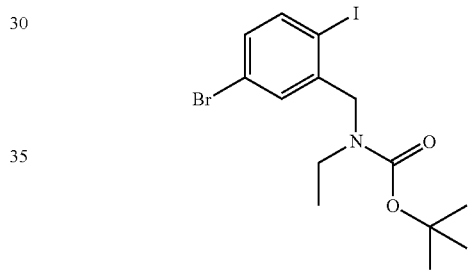

Step 3: (5-Bromo-2-iodo-benzyl)-ethyl-carbamic acid tert-butyl ester (5-Bromo-2-iodo-benzyl)-ethyl-amine (4.05 g, 11.9 mmol) in CH$_2$Cl$_2$ (30 mL) was treated with di-tert-butyl dicarbonate (3.12 g, 14.3 mmol) at room temperature overnight. The mixture was diluted with CH$_2$Cl$_2$ and washed with H$_2$O, dried over MgSO$_4$, filtered, and concentrated to give the title compound.

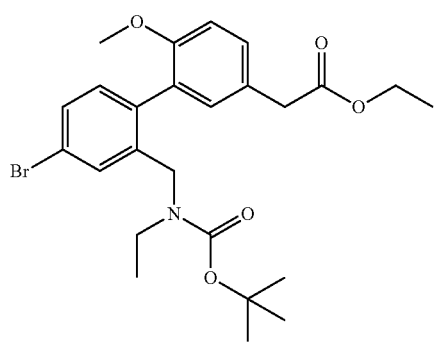 [SMILES: CCOC(=O)Cc1ccc(OC)c(-c2ccc(Br)cc2CN(CC)C(=O)OC(C)(C)C)c1]

Step 4: {4'-Bromo-2'-[(tert-butoxycarbonyl-ethyl-amino)-methyl]-6-methoxy-biphenyl-3-yl}-acetic acid ethyl ester Prepared according to the procedure described in Example 1, Step 4, using the following starting materials: (5-bromo-2-iodo-benzyl)-ethyl-carbamic acid tert-butyl ester and [4-methoxy-3-(4,4,5,5-tetramethyl-[1,3,2]dioxaborolan-2-yl)-phenyl]-acetic acid ethyl ester.

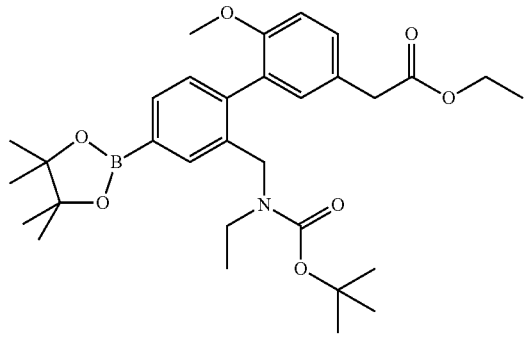 [SMILES: CCOC(=O)Cc1ccc(OC)c(-c2ccc(B3OC(C)(C)C(C)(C)O3)cc2CN(CC)C(=O)OC(C)(C)C)c1]

Step 5: [2'-[(tert-Butoxycarbonyl-ethyl-amino)-methyl]-6-methoxy-4'-(4,4,5,5-tetramethyl-[1,3,2]dioxaborolan-2-yl)-biphenyl-3-yl]-acetic acid ethyl ester Prepared according to the procedure described in Example 33, Step 2, using the following starting materials: {4'-bromo-2'-[tert-butoxycarbonyl-ethyl-amino)-methyl]-6-methoxy-biphenyl-3-yl}-acetic acid ethyl ester and bis(pinacolato)diboron.

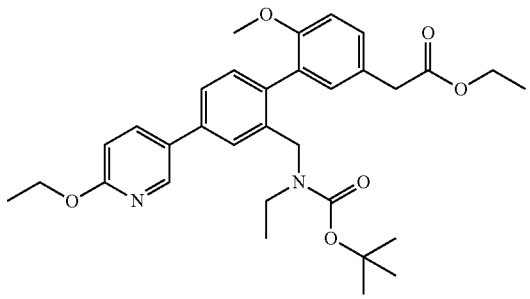 [SMILES: CCOC(=O)Cc1ccc(OC)c(-c2ccc(-c3ccc(OCC)nc3)cc2CN(CC)C(=O)OC(C)(C)C)c1]

Step 6: [2'-[(tert-Butoxycarbonyl-ethyl-amino)-methyl]-4'-(6-ethoxy-pyridin-3-yl)-6-methoxy-biphenyl-3-yl]-acetic acid ethyl ester Prepared according to the procedure described in Example 1, Step 4, using the following starting materials: [2'-[(tert-butoxycarbonyl-ethyl-amino)-methyl]-6-methoxy-4'-(4,4,5,5-tetramethyl-[1,3,2]dioxaborolan-2-yl)-biphenyl-3-yl]-acetic acid ethyl ester and 5-bromo-2-ethoxypyridine.

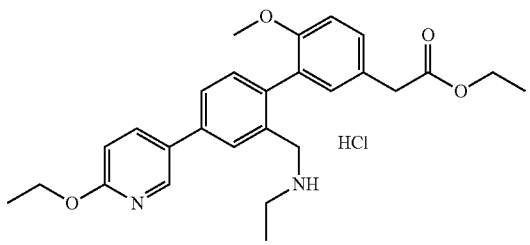 [SMILES: CCNCc1cc(-c2ccc(OCC)nc2)ccc1-c1cc(CC(=O)OCC)ccc1OC ; Cl]

Step 7: [4'-(6-Ethoxy-pyridin-3-yl)-2'-ethylaminomethyl-6-methoxy-biphenyl-3-yl]-acetic acid ethyl ester, hydrochloride

[2'-[(tert-Butoxycarbonyl-ethyl-amino)-methyl]-4'-(6-ethoxy-pyridin-3-yl)-6-methoxy-biphenyl-3-yl]-acetic acid ethyl ester (1.09 g, 2.0 mmol) in CH$_2$Cl$_2$ (10 mL) was treated with 4N HCl in 1,4-dioxane (6 mL, 24.0 mmol) at room temperature, until complete conversion was seen by analytical LCMS. The mixture was concentrated to give the title compound.

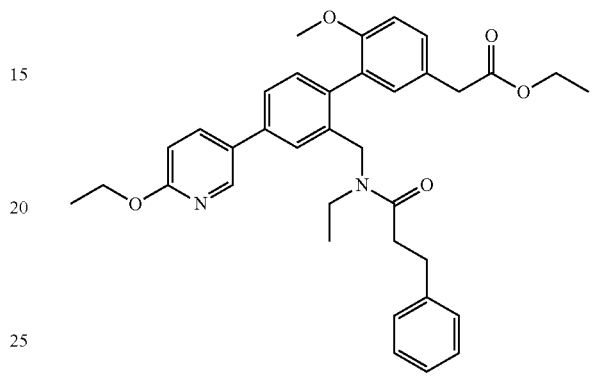

Step 8: (4'-(6-Ethoxy-pyridin-3-yl)-2'-{[ethyl-(3-phenyl-propionyl)-amino]-methyl}-6-methoxy-biphenyl-3-yl)-acetic acid ethyl ester Prepared according to the procedure described in Example 1, Step 6, using the following starting materials: [4'-(6-ethoxy-pyridin-3-yl)-2'-ethylaminomethyl-6-methoxy-biphenyl-3-yl]-acetic acid ethyl ester, hydrochloride and hydrocinnamoyl chloride.

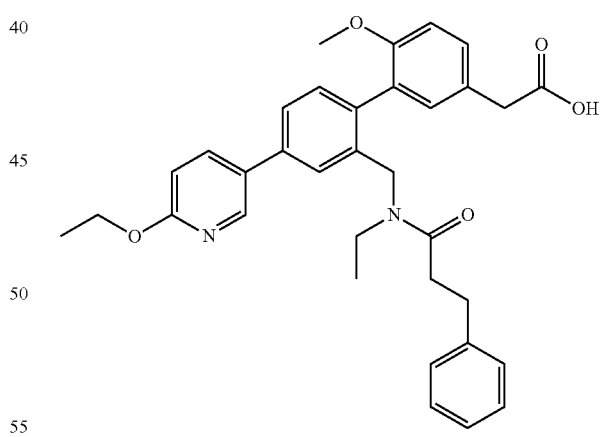

Step 9: (4'-(6-Ethoxy-pyridin-3-yl)-2'-{[ethyl-(3-phenyl-propionyl)-amino]-methyl}-6-methoxy-biphenyl-3-yl)-acetic acid Prepared according to the procedure described in Example 31, Step 2, using the following starting material: (4'-(6-ethoxy-pyridin-3-yl)-2'-{[ethyl-(3-phenyl-propionyl)-amino]-methyl}-6-methoxy-biphenyl-3-yl)-acetic acid ethyl ester. M+H is 553.

Example 47

Synthesis of (2'-{[(4-Chloro-benzenesulfonyl)-ethyl-amino]-methyl}-6-methoxy-4'-trifluoromethyl-biphenyl-3-yl)-acetic acid (Compound 1-100)

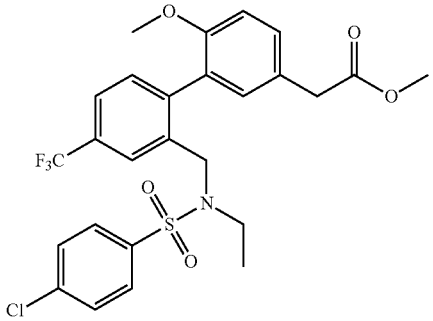 [SMILES: CCN(Cc1cc(C(F)(F)F)ccc1-c1cc(CC(=O)OC)ccc1OC)S(=O)(=O)c1ccc(Cl)cc1]

Step 1: (2'-{[(4-Chloro-benzenesulfonyl)-ethyl-amino]-methyl}-6-methoxy-4'-trifluoromethyl-biphenyl-3-yl)-acetic acid methyl ester To (2'-ethylaminomethyl-6-methoxy-4'-trifluoromethyl-biphenyl-3-yl)-acetic acid methyl ester (0.096 g, 0.25 mmol) and 4-chlorobenzenesulfonyl chloride (0.070 g, 0.33 mmol) in $CH_2Cl_2$ (1 mL) was added triethylamine (0.06 mL, 0.45 mmol), and the mixture was stirred for 15 minutes at room temperature. Once no starting material was seen by analytical LCMS, the solution was concentrated and purified by silica gel chromatography (0-100% EtOAc in hexanes) to give the title compound.

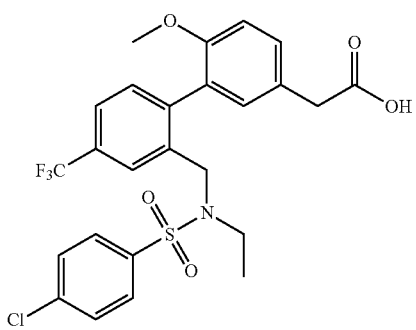 [SMILES: CCN(Cc1cc(C(F)(F)F)ccc1-c1cc(CC(=O)O)ccc1OC)S(=O)(=O)c1ccc(Cl)cc1]

Step 2: (2'-{[(4-Chloro-benzenesulfonyl)-ethyl-amino]-methyl}-6-methoxy-4'-trifluoromethyl-biphenyl-3-yl)-acetic acid Prepared according to the procedure described in Example 3, Step 3, using the following starting material: (2'-{[(4-chloro-benzenesulfonyl)-ethyl-amino]-methyl}-6-methoxy-4'-trifluoromethyl-biphenyl-3-yl)-acetic acid methyl ester. M+H is 542.

Example 48

Synthesis of {2-[(Methanesulfonyl-phenethyl-amino)-methyl]-6-methoxy-4'-trifluoromethyl-biphenyl-3-yl}-acetic acid (Compound 1-101)

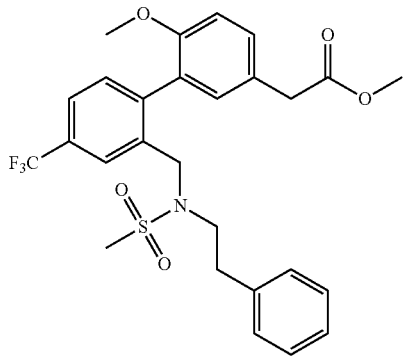 [SMILES: COC(=O)Cc1ccc(OC)c(-c2ccc(C(F)(F)F)cc2CN(CCc2ccccc2)S(C)(=O)=O)c1]

Step 1: {2'-[(Methanesulfonyl-phenethyl-amino)-methyl]-6-methoxy-4'-trifluoromethyl-biphenyl-3-yl}-acetic acid methyl ester To [6-methoxy-2'-(phenethylamino-methyl)-4'-trifluoromethyl-biphenyl-3-yl]-acetic acid methyl ester (0.068 g, 0.15 mmol) and triethylamine (0.02 mL, 0.16 mmol) in $CH_2Cl_2$ (1 mL) was added methanesulfonyl chloride (0.01 mL, 0.16 mmol), and the mixture was stirred for 1 hour. Starting material was still present by analytical LCMS, so additional methanesulfonyl chloride was added, and the reaction was stirred overnight at room temperature. Additional methanesulfonyl chloride and triethylamine was added after 20 hours to push the reaction to completion. The solution was then diluted with $CH_2Cl_2$ and $H_2O$, and the aqueous layer was separated and extracted with $CH_2Cl_2$. The combined organic layers were dried over $MgSO_4$, filtered, and concentrated, and the residue was purified by silica gel chromatography to give the title compound.

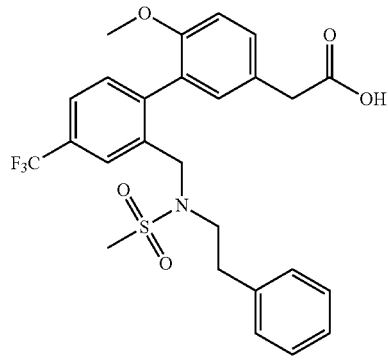 [SMILES: COc1ccc(CC(=O)O)cc1-c1ccc(C(F)(F)F)cc1CN(CCc1ccccc1)S(C)(=O)=O]

Step 2: {2'-[(Methanesulfonyl-phenethyl-amino)-methyl]-6-methoxy-4'-trifluoromethyl-biphenyl-3-yl}-acetic acid Prepared according to the procedure described in Example 3, Step 3, using the following starting material: {2'-[(methanesulfonyl-phenethyl-amino)-methyl]-6-methoxy-4'-trifluoromethyl-biphenyl-3-yl}-acetic acid methyl ester. M+23 is 544.

Example 49

Synthesis of {2'-[(Acetyl-cyclobutyl-amino)-methyl]-6-methoxy-4'-trifluoromethyl-biphenyl-3-yl}-acetic acid (Compound 1-30)

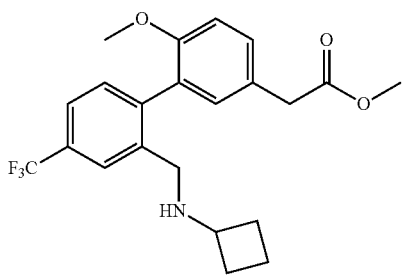 [SMILES: COC(=O)Cc1ccc(OC)c(-c2ccc(C(F)(F)F)cc2CNC2CCC2)c1]

Step 1: (2'-Cyclobutylaminomethyl-6-methoxy-4'-trifluoromethyl-biphenyl-3-yl)-acetic acid methyl ester Prepared according to the procedure described in Example 1, Step 5, using the following starting materials: (2'-formyl-6-methoxy-4'-trifluoromethyl-biphenyl-3-yl)-acetic acid methyl ester and cyclobutylamine.

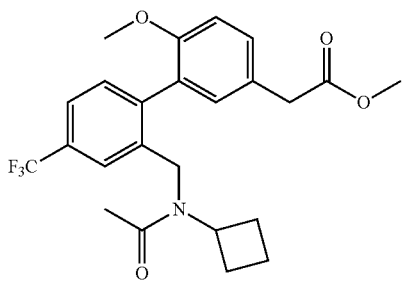 [SMILES: COC(=O)Cc1ccc(OC)c(-c2ccc(C(F)(F)F)cc2CN(C(C)=O)C2CCC2)c1]

Step 2: {2'-[(Acetyl-cyclobutyl-amino)-methyl]-6-methoxy-4'-trifluoromethyl-biphenyl-3-yl}-acetic acid methyl ester Prepared according to the procedure described in Example 1, Step 6, using the following starting materials: (2'-cyclobutylaminomethyl-6-methoxy-4'-trifluoromethyl-biphenyl-3-yl)-acetic acid methyl ester and acetyl chloride.

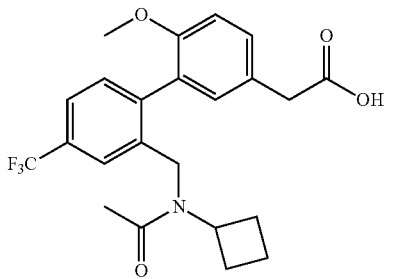 [SMILES: COc1ccc(CC(=O)O)cc1-c1ccc(C(F)(F)F)cc1CN(C(C)=O)C1CCC1]

Step 3: {2'-[(Acetyl-cyclobutyl-amino)-methyl]-6-methoxy-4'-trifluoromethyl-biphenyl-3-yl}-acetic acid Prepared according to the procedure described in Example 3, Step 3, using the following starting material: {2'-[(acetyl-cyclobutyl-amino)-methyl]-6-methoxy-4'-trifluoromethyl-biphenyl-3-yl}-acetic acid methyl ester. M+H is 436.

Example 50

Synthesis of {2'-[(Acetyl-cyclopentyl-amino)-methyl]-6-methoxy-4'-trifluoromethyl-biphenyl-3-yl}-acetic acid (Compound 1-31)

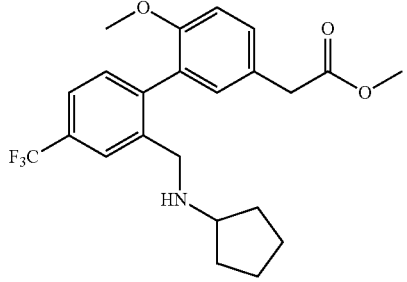 [SMILES: COC(=O)Cc1ccc(OC)c(-c2ccc(C(F)(F)F)cc2CNC2CCCC2)c1]

Step 1: (2'-Cyclopentylaminomethyl-6-methoxy-4'-trifluoromethyl-biphenyl-3-yl)-acetic acid methyl ester Prepared according to the procedure described in Example 1, Step 5, using the following starting materials: (2'-formyl-6-methoxy-4'-trifluoromethyl-biphenyl-3-yl)-acetic acid methyl ester and cyclopentylamine.

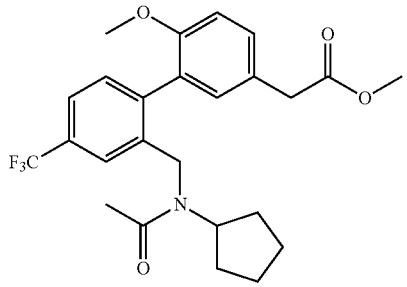 [SMILES: COC(=O)Cc1ccc(OC)c(-c2ccc(C(F)(F)F)cc2CN(C(C)=O)C2CCCC2)c1]

Step 2: {2'-[(Acetyl-cyclopentyl-amino)-methyl]-6-methoxy-4'-trifluoromethyl-biphenyl-3-yl}-acetic acid methyl ester Prepared according to the procedure described in Example 1, Step 6, using the following starting materials: (2'-cyclopentylaminomethyl-6-methoxy-4'-trifluoromethyl-biphenyl-3-yl)-acetic acid methyl ester and acetyl chloride.

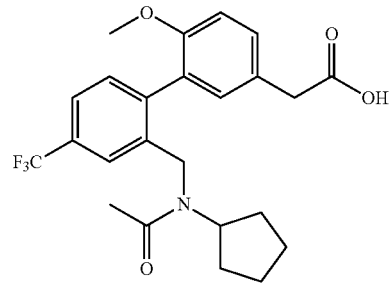 [SMILES: COc1ccc(CC(=O)O)cc1-c1ccc(C(F)(F)F)cc1CN(C(C)=O)C1CCCC1]

Step 3: {2'-[(Acetyl-cyclopentyl-amino)-methyl]-6-methoxy-4'-trifluoromethyl-biphenyl-3-yl}-acetic acid Prepared according to the procedure described in Example 3, Step 3, using the following starting material: {2'-[(acetyl-cyclopentyl-amino)-methyl]-6-methoxy-4'-trifluoromethyl-biphenyl-3-yl}-acetic acid methyl ester. M+H is 450.

Example 51

Synthesis of (2'-{[Ethyl-(2,2,2-trifluoro-acetyl)-amino]-methyl}-6-methoxy-4'-trifluoromethyl-biphenyl-3-yl)-acetic acid (Compound 1-32)

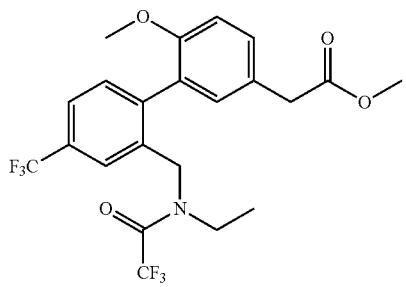 [SMILES: CCN(Cc1cc(C(F)(F)F)ccc1-c1cc(CC(=O)OC)ccc1OC)C(=O)C(F)(F)F]

Step 1: (2'-{[Ethyl-(2,2,2-trifluoro-acetyl)-amino]-methyl}-6-methoxy-4'-trifluoromethyl-biphenyl-3-yl)-acetic acid methyl ester A solution of (2'-ethylaminomethyl-6-methoxy-4'-trifluoromethyl-biphenyl-3-yl)-acetic acid methyl ester (0.106 g, 0.28 mmol) and triethylamine (0.06 mL, 0.42 mmol) in $CH_2Cl_2$ (1 mL) was cooled to −78° C. Trifluoroacetic anhydride (0.06 mL, 0.42 mmol) was added, and the reaction was stirred at room temperature for 1 hour. Analytical LCMS indicated that starting material was still present, so additional triethylamine and trifluoroacetic anhydride were added. After 2 hours, the mixture was diluted with $CH_2Cl_2$ and $H_2O$, and the aqueous layer was extracted with $CH_2Cl_2$. The combined organic layers were dried over $Na_2SO_4$, filtered, and concentrated, and the residue was purified by silica gel chromatography (0-100% EtOAc in hexanes) to give the title compound.

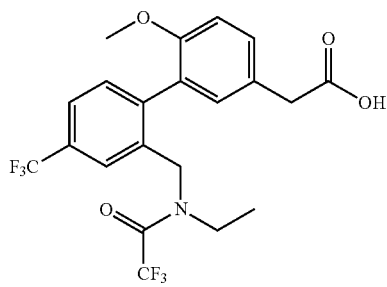 [SMILES: CCN(Cc1cc(C(F)(F)F)ccc1-c1cc(CC(=O)O)ccc1OC)C(=O)C(F)(F)F]

Step 2: (2'-{[Ethyl-(2,2,2-trifluoro-acetyl)-amino]-methyl}-6-methoxy-4'-trifluoromethyl-biphenyl-3-yl)-acetic acid Prepared according to the procedure described in Example 3, Step 3, using the following starting material: (2'-{[ethyl-(2,2,2-trifluoro-acetyl)-amino]-methyl}-6-methoxy-4'-trifluoromethyl-biphenyl-3-yl)-acetic acid methyl ester. M+H is 464.

Example 52

Synthesis of {2'-[(Benzyloxycarbonyl-cyclobutyl-amino)-methyl]-6-methoxy-4'-trifluoromethyl-biphenyl-3-yl}-acetic acid (Compound 1-34))

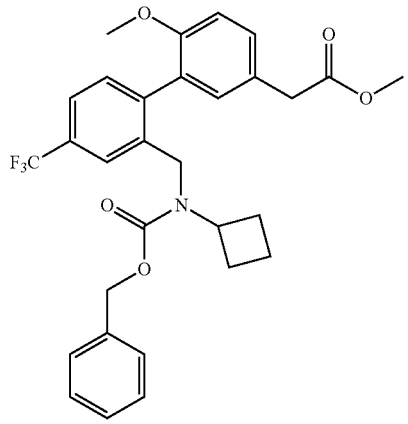 [SMILES: COC(=O)Cc1ccc(OC)c(-c2ccc(C(F)(F)F)cc2CN(C(=O)OCc2ccccc2)C2CCC2)c1]

Step 1: {2'-[(Benzyloxycarbonyl-cyclobutyl-amino)-methyl]-6-methoxy-4'-trifluoromethyl-biphenyl-3-yl}-acetic acid methyl ester Prepared according to the procedure described in Example 1, Step 6, using the following starting materials: (2'-cyclobutylaminomethyl-6-methoxy-4'-trifluoromethyl-biphenyl-3-yl)-acetic acid methyl ester and benzyl chloroformate.

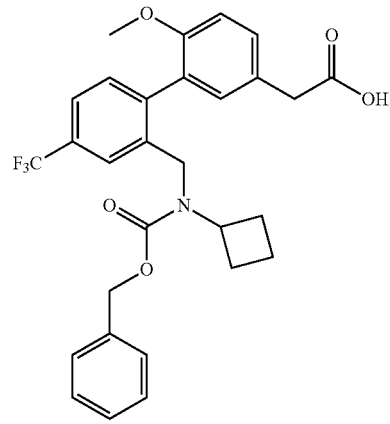 [SMILES: COc1ccc(CC(=O)O)cc1-c1ccc(C(F)(F)F)cc1CN(C(=O)OCc1ccccc1)C1CCC1]

Step 2: {2'-[(Benzyloxycarbonyl-cyclobutyl-amino)-methyl]-6-methoxy-4'-trifluoromethyl-biphenyl-3-yl}-acetic acid Prepared according to the procedure described in Example 3, Step 3, using the following starting material: {2'-[(benzyloxycarbonyl-cyclobutyl-amino)-methyl]-6-methoxy-4'-trifluoromethyl-biphenyl-3-yl}-acetic acid methyl ester. M+H is 528.

Example 53

Synthesis of {2'-[(Benzyloxycarbonyl-cyclopentyl-amino)-methyl]-6-methoxy-4'-trifluoromethyl-biphenyl-3-yl}-acetic acid (Compound 1-35)

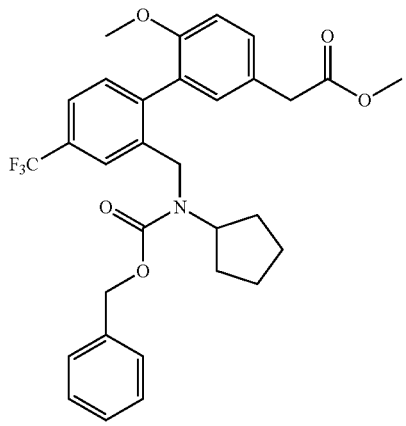 [SMILES: COC(=O)Cc1ccc(OC)c(-c2ccc(C(F)(F)F)cc2CN(C(=O)OCc2ccccc2)C2CCCC2)c1]

Step 1: {2'-[(Benzyloxycarbonyl-cyclopentyl-amino)-methyl]-6-methoxy-4'-trifluoromethyl-biphenyl-3-yl}-acetic acid methyl ester Prepared according to the procedure described in Example 1, Step 6, using the following starting materials: (2'-cyclopentylaminomethyl-6-methoxy-4'-trifluoromethyl-biphenyl-3-yl)-acetic acid methyl ester and benzyl chloroformate.

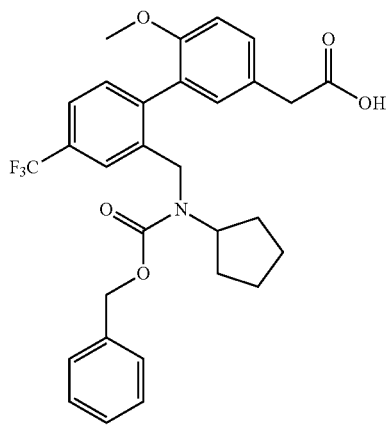 [SMILES: COc1ccc(CC(=O)O)cc1-c1ccc(C(F)(F)F)cc1CN(C(=O)OCc1ccccc1)C1CCCC1]

Step 2: {2'-[(Benzyloxycarbonyl-cyclopentyl-amino)-methyl]-6-methoxy-4'-trifluoromethyl-biphenyl-3-yl}-acetic acid Prepared according to the procedure described in Example 3, Step 3, using the following starting material: {2'-[(benzyloxycarbonyl-cyclopentyl-amino)-methyl]-6-methoxy-4'-trifluoromethyl-biphenyl-3-yl}-acetic acid methyl ester. M+H is 542.

Example 54

Synthesis of {2'-[(Benzyloxycarbonyl-cyclopropyl-amino)-methyl]-6-methoxy-4'-trifluoromethyl-biphenyl-3-yl}-acetic acid (Compound 1-36)

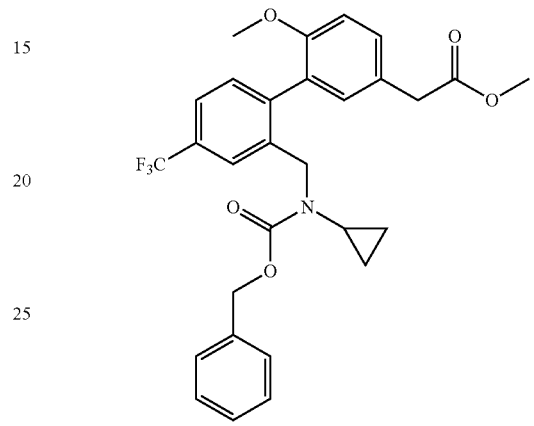

Step 1: {2'-[(Benzyloxycarbonyl-cyclopropyl-amino)-methyl]-6-methoxy-4'-trifluoromethyl-biphenyl-3-yl}-acetic acid methyl ester Prepared according to the procedure described in Example 1, Step 6, using the following starting materials: (2'-cyclopropylaminomethyl-6-methoxy-4'-trifluoromethyl-biphenyl-3-yl)-acetic acid methyl ester and benzyl chloroformate.

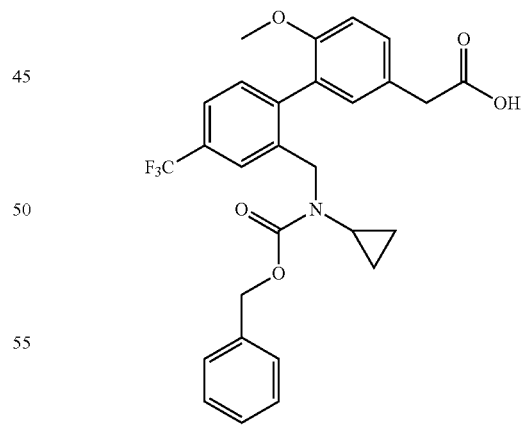

Step 2: {2'-[(Benzyloxycarbonyl-cyclopropyl-amino)-methyl]-6-methoxy-4'-trifluoromethyl-biphenyl-3-yl}-acetic acid Prepared according to the procedure described in Example 3, Step 3, using the following starting material: {2'-[(benzy-

Example 55

Synthesis of 2-{[Acetyl-(2,2,2-trifluoro-ethyl)-amino]-methyl}-5'-carboxymethyl-2'-methoxy-biphenyl-4-carboxylic acid (Compound 1-37)

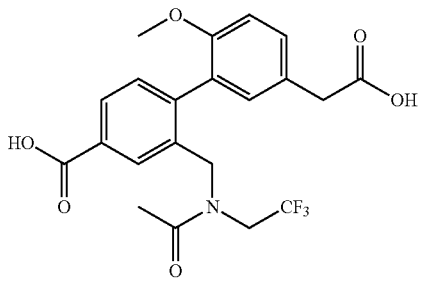 [SMILES: COc1ccc(CC(=O)O)cc1-c1ccc(C(=O)O)cc1CN(CC(F)(F)F)C(C)=O]

(2'-{[Acetyl-(2,2,2-trifluoro-ethyl)-amino]-methyl}-6-methoxy-4'-trifluoromethyl-biphenyl-3-yl)-acetic acid (0.709 g, 1.46 mmol) was dissolved in 1N aqueous NaOH (4 mL, 4 mmol) with heating, and stirred at 100° C. for 1 hour. Ethylene glycol (10 mL) was added, and the reaction was stirred at 150° C. for 3 hours. Sodium hydroxide pellets (0.727 g, 18.2 mmol) was added, and the reaction was stirred at 150° C. overnight. After cooling to room temperature, the mixture was neutralized with 1N aqueous HCl and extracted twice with $CH_2Cl_2$. The combined organic layers were dried over $MgSO_4$, filtered, and concentrated, and the residue was purified by preparative HPLC. The isolated material was repurified by preparative HPLC to give the title compound. M+H is 440.

Example 56

Synthesis of (2'-{[(3,5-Dichloro-benzyloxycarbonyl)-ethyl-amino]-methyl}-6-methoxy-4'-trifluoromethyl-biphenyl-3-yl)-acetic acid (Compound 1-38)

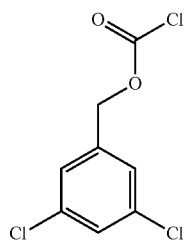 [SMILES: O=C(Cl)OCc1cc(Cl)cc(Cl)c1]

Step 1: 3,5-Dichlorobenzyl Chloroformate

To 3,5-dichlorobenzyl alcohol (0.201 g, 1.06 mmol) in $CH_2Cl_2$ (0.5 mL) was added phosgene (20% in toluene; 0.42 mL, 0.79 mmol), and the mixture was stirred at room temperature for 30 minutes to give the title compound, which was used directly in the next step.

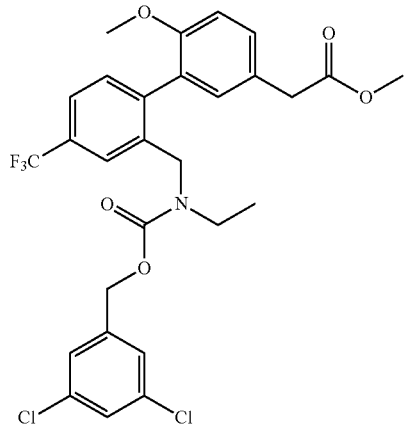 [SMILES: CCN(Cc1cc(C(F)(F)F)ccc1-c1cc(CC(=O)OC)ccc1OC)C(=O)OCc1cc(Cl)cc(Cl)c1]

Step 2: (2'-{[(3,5-Dichloro-benzyloxycarbonyl)-ethyl-amino]-methyl}-6-methoxy-4'-trifluoromethyl-biphenyl-3-yl)-acetic acid methyl ester To (2'-ethylaminomethyl-6-methoxy-4'-trifluoromethyl-biphenyl-3-yl)-acetic acid methyl ester (0.101 g, 0.26 mmol) and diisopropylethylamine (0.23 mL, 1.32 mmol) in $CH_2Cl_2$ (1 mL) was added 3,5-dichlorobenzyl chloroformate (1.06 mmol) in $CH_2Cl_2$, and the reaction was stirred at room temperature for 5 minutes. The mixture was diluted with $H_2O$ and extracted with $CH_2Cl_2$. The combined organic layers were dried over $Na_2SO_4$, decanted, and concentrated, and the residue was purified by silica gel chromatography to give the title compound,

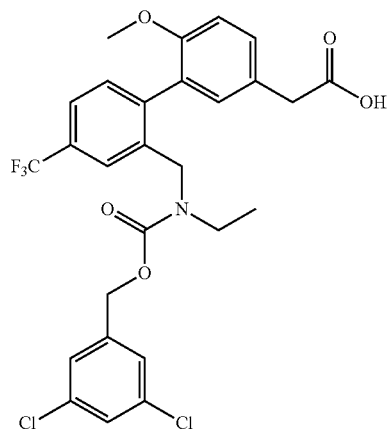 [SMILES: CCN(Cc1cc(C(F)(F)F)ccc1-c1cc(CC(=O)O)ccc1OC)C(=O)OCc1cc(Cl)cc(Cl)c1]

Step 3: (2'-{[(3,5-Dichloro-benzyloxycarbonyl)-ethyl-amino]-methyl}-6-methoxy-4'-trifluoromethyl-biphenyl-3-yl)-acetic acid (2'-{[(3,5-Dichloro-benzyloxycarbonyl)-ethyl-amino]-methyl}-6-methoxy-4'-trifluoromethyl-biphenyl-3-yl)-acetic acid methyl ester (0.088 g, 0.15 mmol) in THF (1 mL) and MeOH (0.8 mL) was hydrolyzed with 1N aqueous NaOH (0.5 mL) for 2.5 hours. The mixture was acidified with 1N aqueous HCl and extracted with $CH_2Cl_2$. The combined organic layers were dried over Na₂SO₄, decanted, and concentrated, and the residue was purified by preparative HPLC to give the title compound. M+H is 571.

Example 57

Synthesis of (2'-{[(2-Chloro-benzyloxycarbonyl)-ethyl-amino]-methyl}-6-methoxy-4'-trifluoromethyl-biphenyl-3-yl)-acetic acid (Compound 1-39)

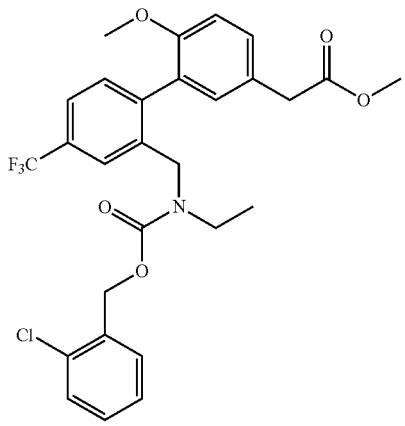 [SMILES: CCN(Cc1cc(C(F)(F)F)ccc1-c1cc(CC(=O)OC)ccc1OC)C(=O)OCc1ccccc1Cl]

Step 1: (2'-{[(2-Chloro-benzyloxycarbonyl)-ethyl-amino]-methyl}-6-methoxy-4'-trifluoromethyl-biphenyl-3-yl)-acetic acid methyl ester To (2'-ethylaminomethyl-6-methoxy-4'-trifluoromethyl-biphenyl-3-yl)-acetic acid methyl ester (0.103 g, 0.27 mmol) and triethylamine (0.06 mL, 0.40 mmol) in CH₂Cl₂ (1 mL) was added 2-chlorobenzyl chloroformate (0.06 mL, 0.40 mmol), and the reaction was stirred at room temperature for 1 hour. The mixture was diluted with CH₂Cl₂ and H₂O, and the aqueous layer was extracted with CH₂Cl₂. The combined organic layers were dried over Na₂SO₄, decanted, and concentrated, and the residue was purified by silica gel chromatography (0-100% EtOAc in hexanes) to give the title compound.

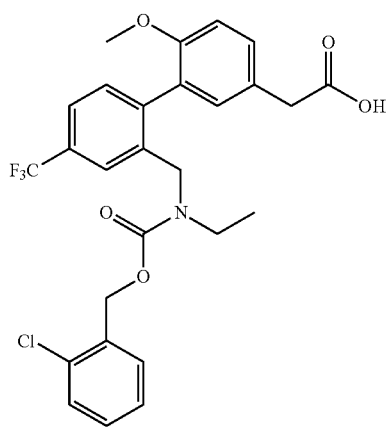 [SMILES: CCN(Cc1cc(C(F)(F)F)ccc1-c1cc(CC(=O)O)ccc1OC)C(=O)OCc1ccccc1Cl]

Step 2: (2'-{[(2-Chloro-benzyloxycarbonyl)-ethyl-amino]-methyl}-6-methoxy-4'-trifluoromethyl-biphenyl-3-yl)-acetic acid (2'-{[(2-Chloro-benzyloxycarbonyl)-ethyl-amino]-methyl}-6-methoxy-4'-trifluoromethyl-biphenyl-3-yl)-acetic acid methyl ester (0.27 mmol) in THF (1 mL) and MeOH (0.8 mL) was hydrolyzed with 1N aqueous NaOH (0.7 mL) for 1 hour. The mixture was acidified with 1N aqueous HCl and extracted with CH₂Cl₂. The combined organic layers were dried over MgSO₄, filtered, and concentrated to give the title compound. M+H is 536.

Example 58

Synthesis of (2'-{[(3,5-Difluoro-benzyloxycarbonyl)-ethyl-amino]-methyl}-6-methoxy-4'-trifluoromethyl-biphenyl-3-yl)-acetic acid (Compound 1-40)

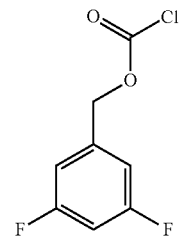

Step 1: 3,5-Difluorobenzyl Chloroformate

Prepared according to the procedure described in Example 56, Step 1, using the following starting materials: 3,5-difluorobenzyl alcohol and phosgene (20% in toluene).

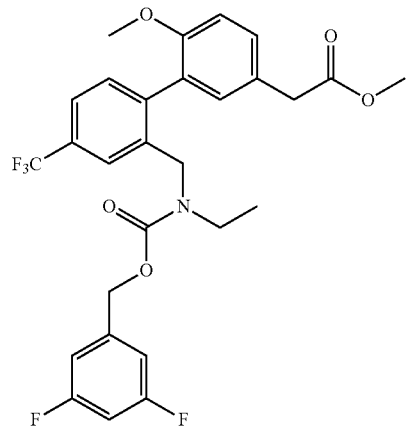 [SMILES: CCN(Cc1cc(C(F)(F)F)ccc1-c1cc(CC(=O)OC)ccc1OC)C(=O)OCc1cc(F)cc(F)c1]

Step 2: (2'-{[(3,5-Difluoro-benzyloxycarbonyl)-ethyl-amino]-methyl}-6-methoxy-4'-trifluoromethyl-biphenyl-3-yl)-acetic acid methyl ester Prepared according to the procedure described in Example 56, Step 2, using the following starting materials: (2'-ethy laminomethyl-6-methoxy-4'-trifluoromethyl-biphenyl-3-yl)-acetic acid methyl ester and 3,5-difluorobenzyl chloroformate.

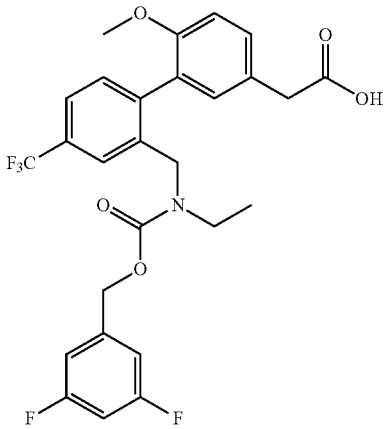

Step 3: (2'-{[(3,5-Difluoro-benzyloxycarbonyl)-ethyl-amino]-methyl}-6-methoxy-4'-trifluoromethyl-biphenyl-3-yl)-acetic acid Prepared according to the procedure described in Example 56, Step 3, using the following starting material: (2'-{[(3,5-difluoro-benzyloxycarbonyl)-ethyl-amino]-methyl}-6-methoxy-4'-trifluoromethyl-biphenyl-3-yl)-acetic acid methyl ester. M+H is 538.

Example 59

Synthesis of (2'-{[Ethyl-(4-fluoro-benzyloxycarbonyl)-amino]-methyl}-6-methoxy-4'-trifluoromethyl-biphenyl-3-yl)-acetic acid (Compound 1-41)

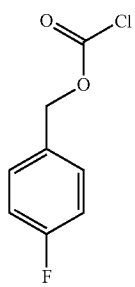

Step 1: 4-Fluorobenzyl Chloroformate

Prepared according to the procedure described in Example 56, Step 1, using the following starting materials: 4-fluorobenzyl alcohol and phosgene (20% in toluene).

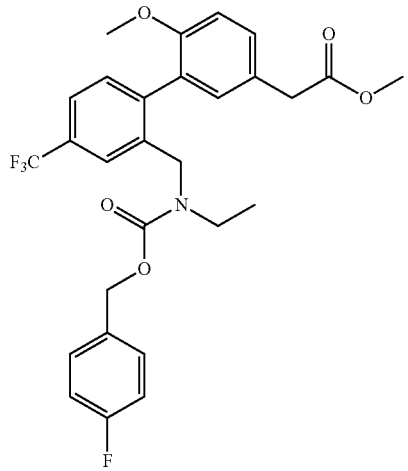 [SMILES: CCN(Cc1cc(C(F)(F)F)ccc1-c1cc(CC(=O)OC)ccc1OC)C(=O)OCc1ccc(F)cc1]

Step 2: (2'-{[Ethyl-(4-fluoro-benzyloxycarbonyl)-amino]-methyl}-6-methoxy-4'-trifluoromethyl-biphenyl-3-yl)-acetic acid methyl ester Prepared according to the procedure described in Example 56, Step 2, using the following starting materials: (2'-ethylaminomethyl-6-methoxy-4'-trifluoromethyl-biphenyl-3-yl)-acetic acid methyl ester and 4-fluorobenzyl chloroformate.

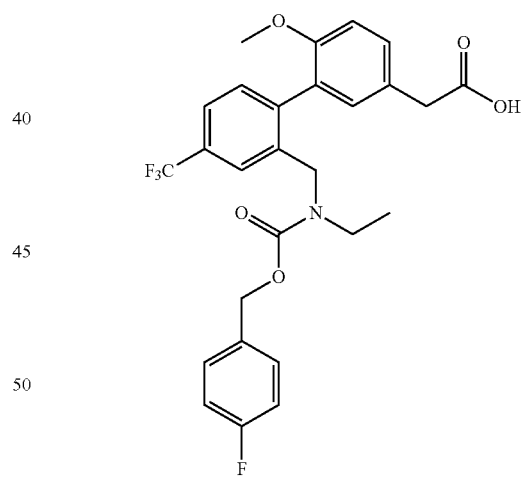

Step 3: (2'-{[Ethyl-(4-fluoro-benzyloxycarbonyl)-amino]-methyl}-6-methoxy-4'-trifluoromethyl-biphenyl-3-yl)-acetic acid Prepared according to the procedure described in Example 56, Step 3, using the following starting material: (2'-{[ethyl-(4-fluoro-benzyloxycarbonyl)-amino]-methyl}-6-methoxy-4'-trifluoromethyl-biphenyl-3-yl)-acetic acid methyl ester. M+H is 520.

Example 60

Synthesis of (2'-{[(4-Chloro-benzyloxycarbonyl)-ethyl-amino]-methyl}-6-methoxy-4'-trifluoromethyl-biphenyl-3-yl)-acetic acid (Compound 1-42)

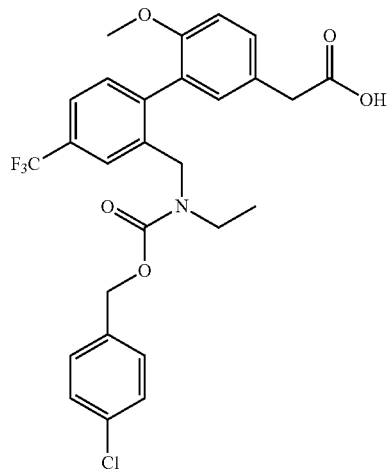

Step 1: 4-Chlorobenzyl Chloroformate

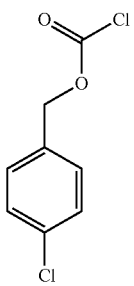

Prepared according to the procedure described in Example 56, Step 1, using the following starting materials: 4-chlorobenzyl alcohol and phosgene (20% in toluene).

Step 2: (2'-{[(4-Chloro-benzyloxycarbonyl)-ethyl-amino]-methyl}-6-methoxy-4'-trifluoromethyl-biphenyl-3-yl)-acetic acid methyl ester

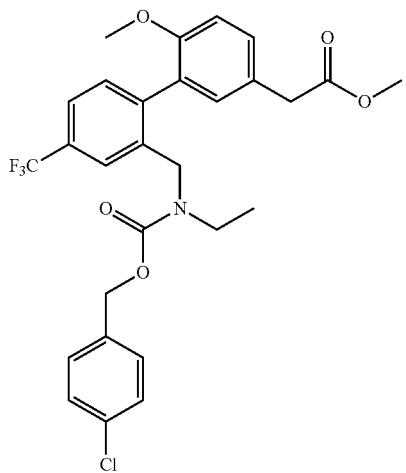 [SMILES: CCN(Cc1cc(C(F)(F)F)ccc1-c1cc(CC(=O)OC)ccc1OC)C(=O)OCc1ccc(Cl)cc1]

Prepared according to the procedure described in Example 56, Step 2, using the following starting materials: (2'-ethylaminomethyl-6-methoxy-4'-trifluoromethyl-biphenyl-3-yl)-acetic acid methyl ester and 4-chlorobenzyl chloroformate.

Step 3: (2'-{[(4-Chloro-benzyloxycarbonyl)-ethyl-amino]-methyl}-6-methoxy-4'-trifluoromethyl-biphenyl-3-yl)-acetic acid Prepared according to the procedure described in Example 56, Step 3, using the following starting material: (2'-{[(4-chloro-benzyloxycarbonyl)-ethyl-amino]-methyl}-6-methoxy-4'-trifluoromethyl-biphenyl-3-yl)-acetic acid methyl ester. M+H is 536.

Example 61

Synthesis of (2'-{[(3-Chloro-benzyloxycarbonyl)-ethyl-amino]-methyl}-6-methoxy-4'-trifluoromethyl-biphenyl-3-yl)-acetic acid (Compound 1-43)

Step 1: 3-Chlorobenzyl Chloroformate

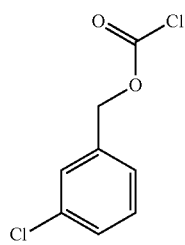

Prepared according to the procedure described in Example 56, Step 1, using the following starting materials: 3-chlorobenzyl alcohol and phosgene (20% in toluene).

202

Example 62

Synthesis of [2'-({[1-(4-Chloro-phenyl)-ethoxycarbonyl]-ethyl-amino}-methyl)-6-methoxy-4'-trifluoromethyl-biphenyl-3-yl]-acetic acid (Compound 1-44)

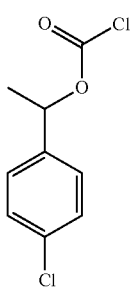

Step 1: 1-(4-Chlorophenyl)ethyl Chloroformate

Prepared according to the procedure described in Example 56, Step 1, using the following starting materials: 1-(4-chlorophenyl)ethanol and phosgene (20% in toluene).

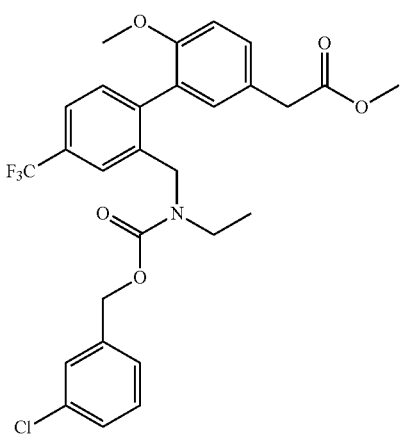 [SMILES: CCN(Cc1cc(C(F)(F)F)ccc1-c1cc(CC(=O)OC)ccc1OC)C(=O)OCc1cccc(Cl)c1]

Step 2: (2'-{[(3-Chloro-benzyloxycarbonyl)-ethyl-amino]-methyl}-6-methoxy-4'-trifluoromethyl-biphenyl-3-yl)-acetic acid methyl ester Prepared according to the procedure described in Example 56, Step 2, using the following starting materials: (2'-ethylaminomethyl-6-methoxy-4'-trifluoromethyl-biphenyl-3-yl)-acetic acid methyl ester and 3-chlorobenzyl chloroformate.

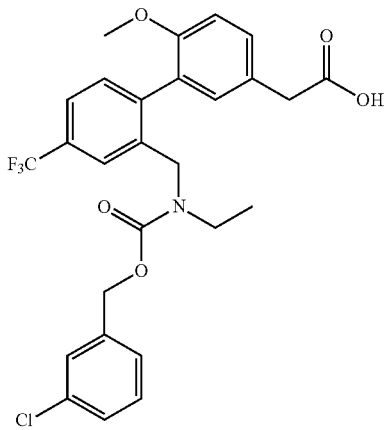 [SMILES: CCN(Cc1cc(C(F)(F)F)ccc1-c1cc(CC(=O)O)ccc1OC)C(=O)OCc1cccc(Cl)c1]

Step 3: (2'-{[(3-Chloro-benzyloxycarbonyl)-ethyl-amino]-methyl}-6-methoxy-4'-trifluoromethyl-biphenyl-3-yl)-acetic acid Prepared according to the procedure described in Example 56, Step 3, using the following starting material: (2'-{[(3-chloro-benzyloxycarbonyl)-ethyl-amino]-methyl}-6-methoxy-4'-trifluoromethyl-biphenyl-3-yl)-acetic acid methyl ester. M+H is 536.

Step 2: [2'-({[1-(4-Chloro-phenyl)-ethoxycarbonyl]-ethyl-amino}-methyl)-6-methoxy-4'-trifluoromethyl-biphenyl-3-yl]-acetic acid methyl ester Prepared according to the procedure described in Example 56, Step 2, using the following starting materials: (2'-ethylaminomethyl-6-methoxy-4'-trifluoromethyl-biphenyl-3-yl)-acetic acid methyl ester and 1-(4-chlorophenyl)ethyl chloroformate.

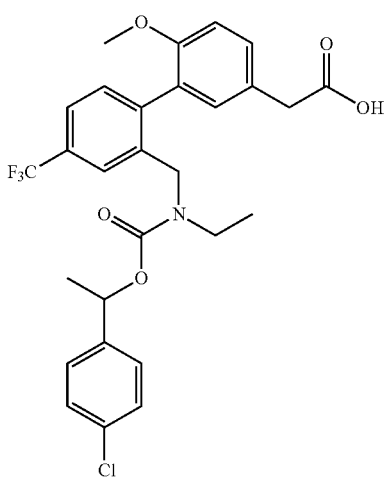 [SMILES: CCN(Cc1cc(C(F)(F)F)ccc1-c1cc(CC(=O)O)ccc1OC)C(=O)OC(C)c1ccc(Cl)cc1]

Step 3: [2'-({[1-(4-Chloro-phenyl)-ethoxycarbonyl]-ethyl-amino}-methyl)-6-methoxy-4'-trifluoromethyl-biphenyl-3-yl]-acetic acid Prepared according to the procedure described in Example 56, Step 3, using the following starting material: [2'-({[1-(4-chloro-phenyl)-ethoxycarbonyl]-ethyl-amino}-methyl)-6-methoxy-4'-trifluoromethyl-biphenyl-3-yl]-acetic acid methyl ester. M+H is 550.

Example 63

Synthesis of (2'-{[Benzyloxycarbonyl-(2,2,2-trifluoro-ethyl)-amino]-methyl}-6-fluoro-4'-trifluoromethyl-biphenyl-3-yl)-acetic acid (Compound 1-49)

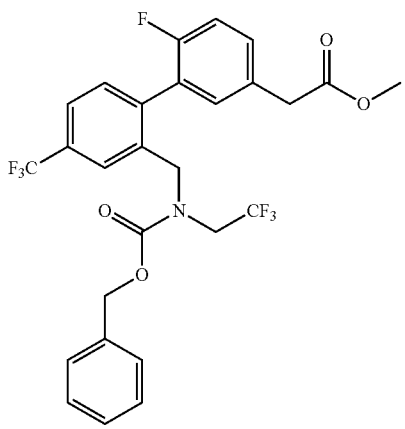 [SMILES: COC(=O)Cc1ccc(F)c(-c2ccc(C(F)(F)F)cc2CN(CC(F)(F)F)C(=O)OCc2ccccc2)c1]

Step 1: (2'-{[Benzyloxycarbonyl-(2,2,2-trifluoro-ethyl)-amino]-methyl}-6-fluoro-4'-trifluoromethyl-biphenyl-3-yl)-acetic acid methyl ester {6-Fluoro-2'-[(2,2,2-trifluoro-ethylamino)-methyl]-4'-trifluoromethyl-biphenyl-3-yl}-acetic acid methyl ester (0.26 g, 0.62 mmol), benzyl chloroformate (0.13 mL, 0.93 mmol), and triethylamine (0.13 mL, 0.93 mmol) were combined in CH₂Cl₂ (2.1 mL), and the reaction was stirred at room temperature for 2 hours. Analytical LCMS indicated that starting material was still present, so additional benzyl chloroformate (0.13 mL, 0.93 mmol), and triethylamine (0.13 mL, 0.93 mmol) were added, and the reaction was stirred for 1 hour. Starting material was still present, so an aqueous work-up was performed, and the residue was dissolved in DMF and cooled to 0° C. Sodium hydride (60% in mineral oil; 0.030 g, 0.75 mmol) was added, followed by benzyl chloroformate (0.13 mL, 0.93 mmol), and the reaction was stirred for 20 minutes. The mixture was worked up with CH₂Cl₂ and H₂O, and the organic layer was dried over MgSO₄, filtered, and concentrated. The residue was purified by silica gel chromatography to give the title compound.

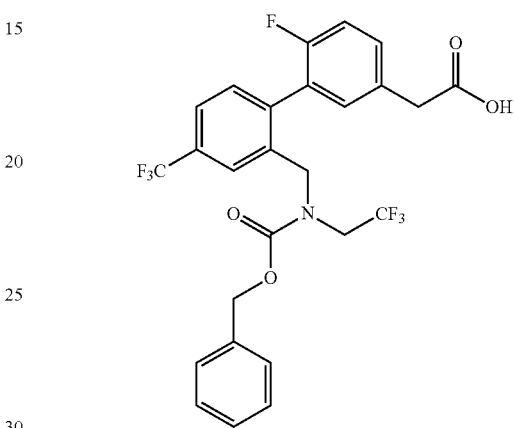

Step 2: (2'-{[Benzyloxycarbonyl-(2,2,2-trifluoro-ethyl)-amino]-methyl}-6-fluoro-4'-trifluoromethyl-biphenyl-3-yl)-acetic acid Prepared according to the procedure described in Example 56, Step 3, using the following starting material: (2'-{[benzyloxycarbonyl-(2,2,2-trifluoro-ethyl)-amino]-methyl}-6-fluoro-4'-trifluoromethyl-biphenyl-3-yl)-acetic acid methyl ester. M+H is 544.

Example 64

Synthesis of 2-{2'-[(Benzyloxycarbonyl-ethyl-amino)-methyl]-6-methoxy-4'-trifluoromethyl-biphenyl-3-yl}-propionic acid (Compound 1-98)

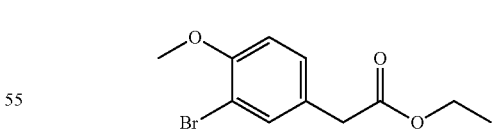

Step 1: (3-Bromo-4-methoxy-phenyl)-acetic acid ethyl ester

A solution of 3-bromo-4-methoxyphenylacetic acid (3.0 g, 12.2 mmol) in EtOH and sulfuric acid was stirred at 100° C. for 2 hours. The mixture was concentrated and partitioned between EtOAc and H₂O, and the organic layer was separated to give the title compound.

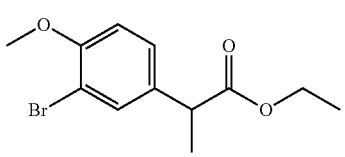 [SMILES: CCOC(=O)C(C)c1ccc(OC)c(Br)c1]

Step 2: 2-(3-Bromo-4-methoxy-phenyl)-propionic acid ethyl ester

To (3-bromo-4-methoxy-phenyl)-acetic acid ethyl ester (12.2 mmol) in THF was added iodomethane (0.75 mL, 12.2 mmol), and the mixture was cooled to −78° C. Sodium bis(trimethylsilyl)amide (1M in THF; 12.2 mL, 12.2 mmol) was added, and subsequent work-up gave the title compound.

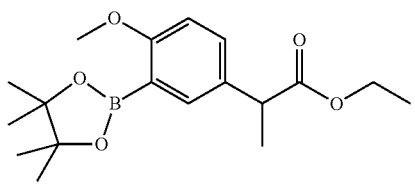 [SMILES: CCOC(=O)C(C)c1ccc(OC)c(B2OC(C)(C)C(C)(C)O2)c1]

Step 3: 2-[4-Methoxy-3-(4,4,5,5-tetramethyl-[1,3,2]dioxaborolan-2-yl)-phenyl]-propionic acid ethyl ester Prepared according to the procedure described in Example 1, Step 2, using the following starting materials: 2-(3-Bromo-4-methoxy-phenyl)-propionic acid ethyl ester and bis(pinacolato)diboron.

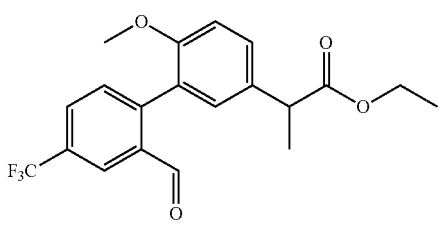 [SMILES: CCOC(=O)C(C)c1ccc(OC)c(-c2ccc(C(F)(F)F)cc2C=O)c1]

Step 4: 2-(2'-Formyl-6-methoxy-4'-trifluoromethyl-biphenyl-3-yl)-propionic acid ethyl ester Prepared according to the procedure described in Example 1, Step 4, using the following starting materials: 2-[4-methoxy-3-(4,4,5,5-tetramethyl-[1,3,2]dioxaborolan-2-yl)-phenyl]-propionic acid ethyl ester and 2-bromo-5-(trifluoromethyl)benzaldehyde.

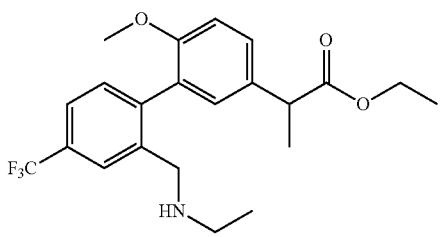 [SMILES: CCNCc1cc(C(F)(F)F)ccc1-c1cc(C(C)C(=O)OCC)ccc1OC]

Step 5: 2-(2'-Ethylaminomethyl-6-methoxy-4'-trifluoromethyl-biphenyl-3-yl)-propionic acid ethyl ester Prepared according to the procedure described in Example 1, Step 5, using the following starting materials: 2-(2'-formyl-6-methoxy-4'-trifluoromethyl-biphenyl-3-yl)-propionic acid ethyl ester and ethylamine (2M in THF).

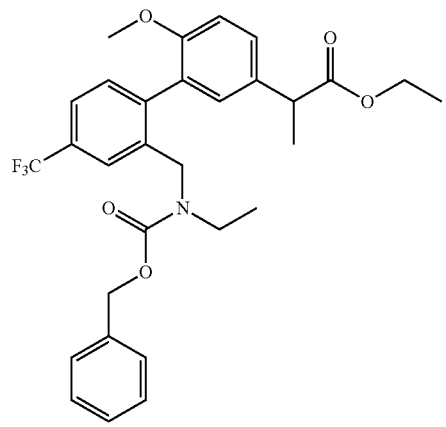 [SMILES: CCOC(=O)C(C)c1ccc(OC)c(-c2ccc(C(F)(F)F)cc2CN(CC)C(=O)OCc2ccccc2)c1]

Step 6: 2-{2'-[(Benzyloxycarbonyl-ethyl-amino)-methyl]-6-methoxy-4'-trifluoromethyl-biphenyl-3-yl}-propionic acid ethyl ester Prepared according to the procedure described in Example 1, Step 6, using the following starting materials: 2-(2'-ethylaminomethyl-6-methoxy-4'-trifluoromethyl-biphenyl-3-yl)-propionic acid ethyl ester and benzyl chloroformate.

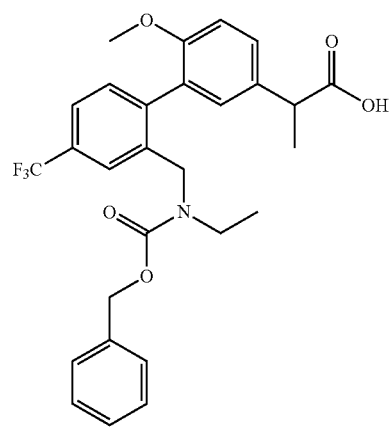 [SMILES: CCN(Cc1cc(C(F)(F)F)ccc1-c1cc(C(C)C(=O)O)ccc1OC)C(=O)OCc1ccccc1]

Step 7: 2-{2'-[(Benzyloxycarbonyl-ethyl-amino)-methyl]-6-methoxy-4'-trifluoromethyl-biphenyl-3-yl}-propionic acid Prepared according to the procedure described in Example 1, Step 7, using the following starting material: 2-{2'-[(benzyloxycarbonyl-ethyl-amino)-methyl]-6-methoxy-4-trifluoromethyl-biphenyl-3-yl}-propionic acid ethyl ester.

Example 65

Synthesis of {2'-[((1S,2R)-2-Hydroxy-1-methyl-2-phenyl-ethylamino)-methyl]-6-methoxy-4'-trifluoromethyl-biphenyl-3-yl}-acetic acid (Compound 1-102)

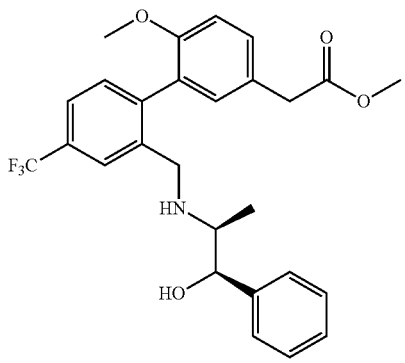 [SMILES: COC(=O)Cc1ccc(OC)c(-c2ccc(C(F)(F)F)cc2CN[C@@H](C)[C@H](O)c2ccccc2)c1]

Step 1: {2'-[((1S,2R)-2-Hydroxy-1-methyl-2-phenyl-ethylamino)-methyl]-6-methoxy-4'-trifluoromethyl-biphenyl-3-yl}-acetic acid methyl ester (2'-Formyl-6-methoxy-4'-trifluoromethyl-biphenyl-3-yl)-acetic acid methyl ester (0.094 g, 0.27 mmol), (1R,2S)-(−)-norephedrine (0.054 g, 0.35 mmol), and sodium triacetoxyborohydride (0.113 g, 0.53 mmol) were combined in dichloroethane (1 mL). Acetic acid (1 drop) was added, and the reaction was stirred at room temperature for 40 minutes. Analytical tlc showed that only starting material was present, so the reaction was heated to 50° C. and stirred overnight. Analytical LCMS showed that some starting material was still present, so additional (1R,2S)-(−)-norephedrine (0.057 g, 0.38 mmol), and sodium triacetoxyborohydride (0.115 g, 0.53 mmol) were added, and the reaction was stirred for 3.5 hours at 50° C. After cooling to room temperature, the mixture was diluted with $CH_2Cl_2$ and saturated aqueous $NaHCO_3$, and the aqueous layer was extracted twice with $CH_2Cl_2$. The combined organic layers were dried over $MgSO_4$, filtered, and concentrated, and the residue was purified by silica gel chromatography (0-100% EtOAc in hexanes) to give the title compound.

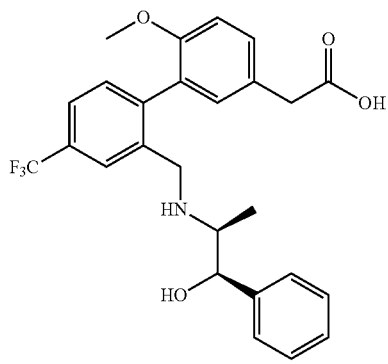 [SMILES: COc1ccc(CC(=O)O)cc1-c1ccc(C(F)(F)F)cc1CN[C@@H](C)[C@H](O)c1ccccc1]

Step 2: {2'-[((1S,2R)-2-Hydroxy-1-methyl-2-phenyl-ethylamino)-methyl]-6-methoxy-4'-trifluoromethyl-biphenyl-3-yl}-acetic acid {2'-[((1S,2R)-2-Hydroxy-1-methyl-2-phenyl-ethylamino)-methyl]-6-methoxy-4'-trifluoromethyl-biphenyl-3-yl}-acetic acid methyl ester (0.021 g, 0.04 mmol) in MeOH (0.33 mL) and THY (0.4 mL) was treated with 1N aqueous NaOH (0.1 mL) and stirred at room temperature for 4 hours. Analytical LCMS showed that some starting material was still present, so additional 1N aqueous NaOH (0.05 mL) was added, and the reaction was stirred at room temperature overnight. Analytical LCMS showed that starting material still remained, so additional 1N aqueous NaOH (0.1 mL) was added, and the reaction was stirred for 4 hours. After work-up with $CH_2Cl_2$ and 1N aqueous HCl, the combined organic layers were dried over $MgSO_4$, filtered, and concentrated to give the title compound.

Example 66

Synthesis of [6-Methoxy-2'-(phenethylamino-methyl)-4'-trifluoromethyl-biphenyl-3-yl]-acetic acid (Compound 1-103)

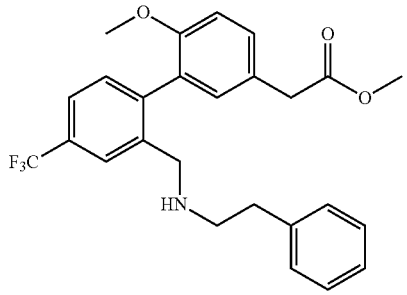 [SMILES: COC(=O)Cc1ccc(OC)c(-c2ccc(C(F)(F)F)cc2CNCCc2ccccc2)c1]

Step 1: [6-Methoxy-2'-(phenethylamino-methyl)-4'-trifluoromethyl-biphenyl-3-yl]-acetic acid methyl ester To a solution of (2'-formyl-6-methoxy-4'-trifluoromethyl-biphenyl-3-yl)-acetic acid methyl ester (0.277 g, 0.79 mmol) and 2-phenylethylamine (0.15 mL, 1.18 mmol) in $CH_2Cl_2$ (4 mL) was added sodium triacetoxyborohydride (0.251 g, 1.18 mmol), and the reaction was stirred at room temperature for 2 hours. Analytical LCMS indicated that some starting material was still present, so additional 2-phenylethylamine (0.15 mL, 1.18 mmol) was added, along with acetic acid (1 drop), and the reaction was stirred overnight at room temperature. Analytical LCMS showed that starting material still remained, so additional sodium triacetoxyborohydride (0.260 g, 1.23 mmol) was added, and the reaction was stirred for 2.5 hours. Additional sodium triacetoxyborohydride (0.500 g, 2.36 mmol) was added, and the reaction was stirred for 1.5 hours, until no starting material was seen by analytical LCMS. The mixture was worked-up, and the residue was purified by silica gel chromatography (0-100% EtOAc in hexanes) to give the title compound.

209

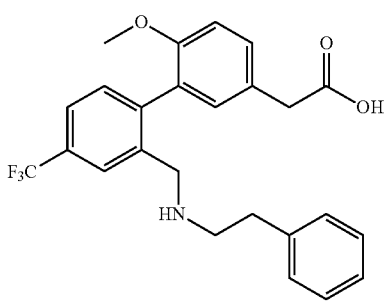 [SMILES: COc1ccc(CC(=O)O)cc1-c1ccc(C(F)(F)F)cc1CNCCc1ccccc1]

Step 2: [6-Methoxy-2'-(phenethylamino-methyl)-4'-trifluoromethyl-biphenyl-3-yl]-acetic acid Prepared according to the procedure described in Example 65, Step 2, using the following starting material: [6-methoxy-2'-(phenethylamino-methyl)-4'-trifluoromethyl-biphenyl-3-yl]-acetic acid methyl ester.

Example 67

Synthesis of (2'-{[Acetyl-((1S,2R)-2-hydroxy-1-methyl-2-phenyl-ethyl)-amino]-methyl}-6-methoxy-4'-trifluoromethyl-biphenyl-3-yl)-acetic acid (Compound 1-104)

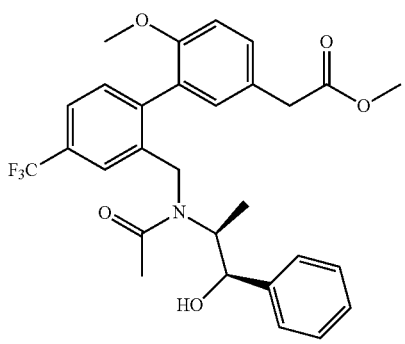 [SMILES: COC(=O)Cc1ccc(OC)c(-c2ccc(C(F)(F)F)cc2CN(C(C)=O)[C@@H](C)[C@H](O)c2ccccc2)c1]

Step 1: (2'-{[Acetyl-((1S,2R)-2-hydroxy-1-methyl-2-phenyl-ethyl)-amino]-methyl}-6-methoxy-4'-trifluoromethyl-biphenyl-3-yl)-acetic acid methyl ester Prepared according to the procedure described in Example 1, Step 6, using the following starting materials: {2'-[((1S,2R)-2-hydroxy-1-methyl-2-phenyl-ethylamino)-methyl]-6-methoxy-4'-trifluoromethyl-biphenyl-3-yl}-acetic acid methyl ester and acetyl chloride.

210

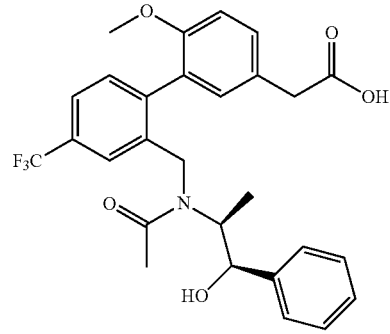 [SMILES: COc1ccc(CC(=O)O)cc1-c1ccc(C(F)(F)F)cc1CN(C(C)=O)[C@@H](C)[C@H](O)c1ccccc1]

Step 2: (2'-{[Acetyl-((1S,2R)-2-hydroxy-1-methyl-2-phenyl-ethyl)-amino]-methyl}-6-methoxy-4'-trifluoromethyl-biphenyl-3-yl)-acetic acid Prepared according to the procedure described in Example 3, Step 3, using the following starting material: (2'-{[acetyl-((1S,2R)-2-hydroxy-1-methyl-2-phenyl-ethyl)-amino]-methyl}-6-methoxy-4'-trifluoromethyl-biphenyl-3-yl)-acetic acid methyl ester. M+H is 516.

Example 68

Synthesis of (2'-Ethylaminomethyl-6-methoxy-4'-trifluoromethyl-biphenyl-3-yl)-acetic acid (Compound 1-105)

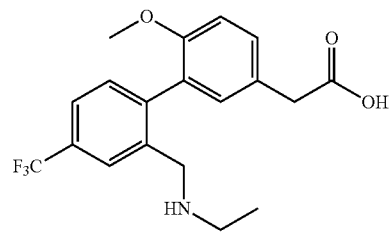 [SMILES: CCNCc1cc(C(F)(F)F)ccc1-c1cc(CC(=O)O)ccc1OC]

Step 1: (2'-Ethylaminomethyl-6-methoxy-4'-trifluoromethyl-biphenyl-3-yl)-acetic acid Prepared according to the procedure described in Example 1, Step 7, using the following starting material: (2'-ethylaminomethyl-6-methoxy-4'-trifluoromethyl-biphenyl-3-yl)-acetic acid methyl ester.

Example 69

Synthesis of 2-{2'-[(Acetyl-ethyl-amino)-methyl]-6-methoxy-4'-trifluoromethyl-biphenyl-3-yl}-2-methyl-propionic acid (Compound 1-115)

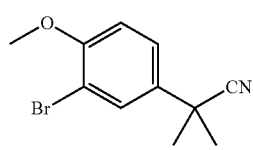

Step 1: 2-(3-Bromo-4-methoxy-phenyl)-2-methyl-propionitrile

To 3-bromo-4-methoxyphenylacetonitrile (1.013 g, 4.48 mmol) and iodomethane (0.62 mL, 9.85 mmol) in THF (10 mL) at −78° C. was added sodium bis(trimethylsilyl)amide (1M in THF; 9.9 mL, 9.9 mmol), and the reaction was stirred at −78° C. for 20 minutes. The mixture was partitioned between EtOAc and 1N aqueous HCl, and the aqueous layer was extracted with EtOAc. The combined organic layers were dried over Na$_2$SO$_4$, filtered, and concentrated to give the title compound.

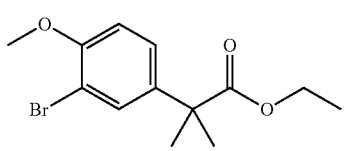 [SMILES: CCOC(=O)C(C)(C)c1ccc(OC)c(Br)c1]

Step 2: 2-(3-Bromo-4-methoxy-phenyl)-2-methyl-propionic acid ethyl ester 2-(3-Bromo-4-methoxy-phenyl)-2-methyl-propionitrile (1.166 g, 4.48 mmol) was treated with potassium hydroxide (2.1 g, 35.8 mmol) in t-BuOH (10 mL), and the reaction was stirred at 85° C. overnight. Analytical LCMS indicated that no starting material remained, so the mixture was worked-up with EtOAc and 1N aqueous HCl, dried over MgSO$_4$, filtered, and concentrated. The residue was dissolved in EtOH with heating, and then thionyl chloride (0.65 mL, 8.96 mmol) was added, and the reaction was stirred for 1 hour. Analytical LCMS indicated that no reaction has occurred, so additional thionyl chloride was added, and the reaction was stirred for another 4 hours. Sulfuric acid (5 drops) was added, and the reaction was stirred at reflux, but analytical LCMS indicated that no reaction had occurred. The mixture was neutralized with 1N aqueous NaOH and extracted with CH$_2$Cl$_2$, and the organic layers were combined and concentrated. The residue was dissolved in ethylene glycol (10 mL) and treated with potassium hydroxide (2.26 g, 40.2 mmol) and H$_2$O (1 mL) to ensure complete hydrolysis to the acid. The reaction was stirred overnight at 150° C., and then cooled to room temperature and worked up with EtOAc and 1N aqueous HCl. The organic layer was dried over Na$_2$SO$_4$, decanted, and concentrated, and the residue was dissolved in EtOH (10 mL) and treated with thionyl chloride (0.65 mL, 8.96 mmol). Analytical LCMS indicated that no reaction had occurred after 20 minutes, so sulfuric acid was added, and the reaction was stirred at 80° C. for 4 days. The mixture was partitioned between CH$_2$Cl$_2$ and saturated aqueous NaHCO$_3$, and the aqueous layer was extracted with CH$_2$Cl$_2$. The combined organic layers were dried over Na$_2$SO$_4$, decanted, and concentrated, and the residue was purified by silica gel chromatography (0-100% EtOAc in hexanes) to give the title compound.

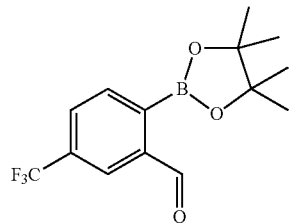 [SMILES: CC1(C)OB(c2ccc(C(F)(F)F)cc2C=O)OC1(C)C]

Step 3: 2-(4,4,5,5-Tetramethyl-[1,3,2]dioxaborolan-2-yl)-5-trifluoromethyl-benzaldehyde Prepared according to the procedure described in Example 1, Step 2, using the following starting materials: 2-bromo-5-trifluoromethyl-benzaldehyde and bis(pinacolato)diboron.

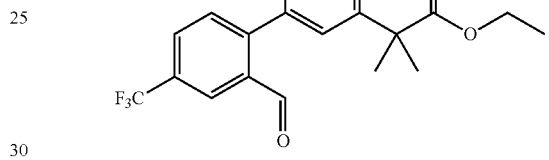

Step 4: 2-(2'-Formyl-6-methoxy-4'-trifluoromethyl-biphenyl-3-yl)-2-methyl-propionic acid ethyl ester Prepared according to the procedure described in Example 1, Step 4, using the following starting materials: 2-(3-bromo-4-methoxy-phenyl)-2-methyl-propionic acid ethyl ester and 2-(4,4,5,5-tetramethyl-[1,3,2]dioxaborolan-2-yl)-5-trifluoromethyl-benzaldehyde.

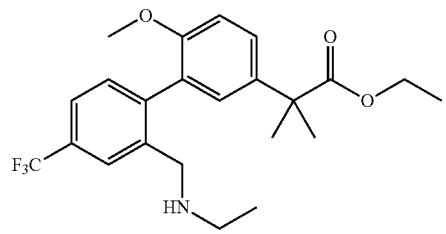 [SMILES: CCNCc1cc(C(F)(F)F)ccc1-c1cc(C(C)(C)C(=O)OCC)ccc1OC]

Step 5: 2-(2'-Ethylaminomethyl-6-methoxy-4'-trifluoromethyl-biphenyl-3-yl)-2-methyl-propionic acid ethyl ester Prepared according to the procedure described in Example 1, Step 5, using the following starting materials: 2-(2'-formyl-6-methoxy-4'-trifluoromethyl-biphenyl-3-yl)-2-methyl-propionic acid ethyl ester and ethylamine (2M in THF).

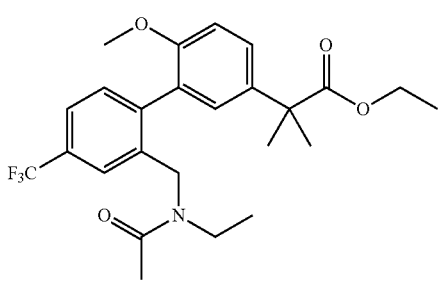 [SMILES: CCOC(=O)C(C)(C)c1ccc(OC)c(-c2ccc(C(F)(F)F)cc2CN(CC)C(C)=O)c1]

Step 6: 2-{2'-[(Acetyl-ethyl-amino)-methyl]-6-methoxy-4'-trifluoromethyl-biphenyl-3-yl}-2-methyl-propionic acid ethyl ester Prepared according to the procedure described in Example 1, Step 6, using the following starting materials: 2-(2'-ethylaminomethyl-6-methoxy-4'-trifluoromethyl-biphenyl-3-yl)-2-methyl-propionic acid ethyl ester and acetyl chloride.

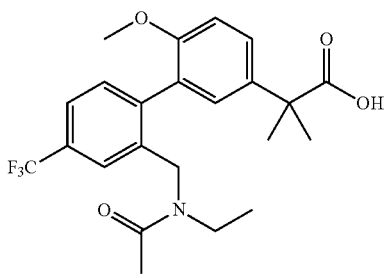 [SMILES: CCN(Cc1cc(C(F)(F)F)ccc1-c1cc(C(C)(C)C(=O)O)ccc1OC)C(C)=O]

Step 7: 2-{2'-[(Acetyl-ethyl-amino)-methyl]-6-methoxy-4'-trifluoromethyl-biphenyl-3-yl}-2-methyl-propionic acid To 2-{2'-[(acetyl-ethyl-amino)-methyl]-6-methoxy-4'-trifluoromethyl-biphenyl-3-yl}-2-methyl-propionic acid ethyl ester (0290 g, 0.63 mmol) in THF (2.6 mL) and EtOH (2 mL) was added 1N aqueous NaOH (1.9 mL), and the reaction was stirred at 50° C. overnight. Analytical LCMS indicated that starting material was still present, so additional 1N aqueous NaOH (1 mL) was added, and the reaction was stirred at 70° C. for 2 hours. Additional 1N aqueous NaOH (1 mL) was added, and the reaction was stirred for another 6 hours. The mixture was worked-up with $CH_2Cl_2$ and 1N aqueous HCl, and the organic layer was dried over $Na_2SO_4$, decanted, and concentrated. The residue was purified by preparative HPLC to give the title compound. M+H is 438.

Example 70

Synthesis of 2-{2'-[(Benzyloxycarbonyl-ethyl-amino)-methyl]-6-methoxy-4'-trifluoromethyl-biphenyl-3-yl}-2-methyl-propionic acid (Compound 1-116)

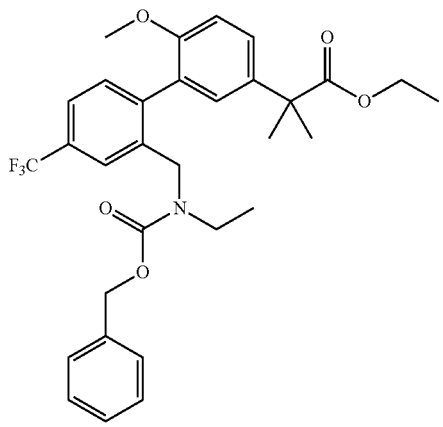 [SMILES: CCOC(=O)C(C)(C)c1ccc(OC)c(-c2ccc(C(F)(F)F)cc2CN(CC)C(=O)OCc2ccccc2)c1]

Step 1: 2-{2'-[(Benzyloxycarbonyl-ethyl-amino)-methyl]-6-methoxy-4'-trifluoromethyl-biphenyl-3-yl}-2-methyl-propionic acid ethyl ester Prepared according to the procedure described in Example 1, Step 6, using the following starting materials: 2-(2'-ethylaminomethyl-6-methoxy-4'-trifluoromethyl-biphenyl-3-yl)-2-methyl-propionic acid ethyl ester and benzyl chloroformate.

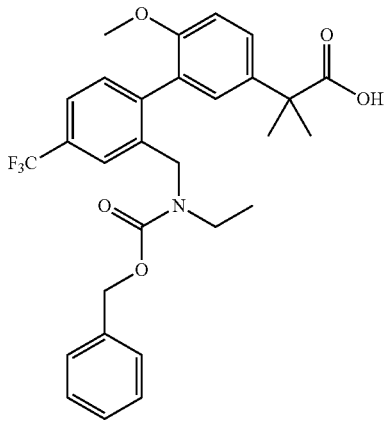 [SMILES: CCN(Cc1cc(C(F)(F)F)ccc1-c1cc(C(C)(C)C(=O)O)ccc1OC)C(=O)OCc1ccccc1]

Step 2: 2-{2'-[(Benzyloxycarbonyl-ethyl-amino)-methyl]-6-methoxy-4'-trifluoromethyl-biphenyl-3-yl}-2-methyl-propionic acid Prepared according to the procedure described in Example 69, Step 7, using the following starting material: 2-{2'-[(benzyloxycarbonyl-ethyl-amino)-methyl]-6-methoxy-4'-trifluoromethyl-biphenyl-3-yl}-2-methyl-propionic acid ethyl ester. M+H is 530.

Example 71

Synthesis of {6-Methoxy-2'-[(2,2,2-trifluoro-ethylamino)-methyl]-4'-trifluoromethyl-biphenyl-3-yl}-acetic acid (Compound 1-133)

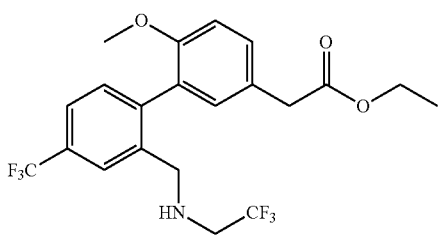 [SMILES: CCOC(=O)Cc1ccc(OC)c(-c2ccc(C(F)(F)F)cc2CNCC(F)(F)F)c1]

Step 1: {6-Methoxy-2'-[(2,2,2-trifluoro-ethylamino)-methyl]-4'-trifluoromethyl-biphenyl-3-yl}-acetic acid ethyl ester Prepared according to the procedure described in Example 4, Step 1, using the following starting materials: (2'-formyl-6-methoxy-4'-trifluoromethyl-biphenyl-3-yl)-acetic acid ethyl ester and 2,2,2-trifluoroethylamine hydrochloride.

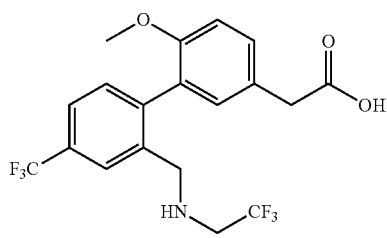 [SMILES: COc1ccc(CC(=O)O)cc1-c1ccc(C(F)(F)F)cc1CNCC(F)(F)F]

Step 2: {6-Methoxy-2'-[(2,2,2-trifluoro-ethylamino)-methyl]-4'-trifluoromethyl-biphenyl-3-yl}-acetic acid Prepared according to the procedure described in Example 3, Step 3, using the following starting material: {6-methoxy-2'-[(2,2,2-trifluoro-ethylamino)-methyl]-4'-trifluoromethyl-biphenyl-3-yl}-acetic acid ethyl ester.

Example 72

Synthesis of (2'-Cyclopropylaminomethyl-6-methoxy-4'-trifluoromethyl-biphenyl-3-yl)-acetic acid (Compound 1-134)

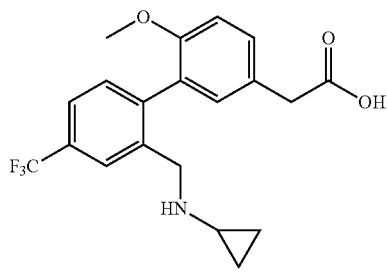 [SMILES: COc1ccc(CC(=O)O)cc1-c1ccc(C(F)(F)F)cc1CNC1CC1]

{2'-[(Benzyloxycarbonyl-cyclopropyl-amino)-methyl]-6-methoxy-4'-trifluoromethyl-biphenyl-3-yl}-acetic acid (0.054 g, 0.10 mmol) and 10% palladium on carbon (17.5 g) were combined in MeOH (2 mL) and stirred under a balloon of H$_2$ at room temperature for 1 hour. The mixture was filtered and concentrated to give the title compound.

Example 73

Synthesis of (2'-Aminomethyl-6-methoxy-4'-trifluoromethyl-biphenyl-3-yl)-acetic acid (Compound 1-141)

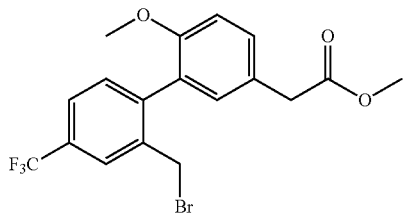 [SMILES: COC(=O)Cc1ccc(OC)c(-c2ccc(C(F)(F)F)cc2CBr)c1]

Step 1: (2'-Bromomethyl-6-methoxy-4'-trifluoromethyl-biphenyl-3-yl)-acetic acid methyl ester To (2'-hydroxymethyl-6-methoxy-4'-trifluoromethyl-biphenyl-3-yl)-acetic acid methyl ester (1.855 g, 5.23 mmol) in DME (19 mL) was added phosphorus tribromide (0.74 mL, 7.85 mmol), and the reaction was stirred at room temperature for 1.5 hours. The mixture was cooled to 0° C., and saturated aqueous NaHCO$_3$ and EtOAc were added. The aqueous layer was extracted with EtOAc, and the combined organic layers were dried over MgSO$_4$, filtered, and concentrated. The residue was purified by silica gel chromatography (0-100% EtOAc in hexanes) to give the title compound.

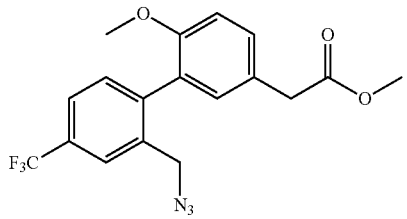 [SMILES: COC(=O)Cc1ccc(OC)c(-c2ccc(C(F)(F)F)cc2CN=[N+]=[N-])c1]

Step 2: (2'-Azidomethyl-6-methoxy-4'-trifluoromethyl-biphenyl-3-yl)-acetic acid methyl ester To (2'-bromomethyl-6-methoxy-4'-trifluoromethyl-biphenyl-3-yl)-acetic acid methyl ester (0.867 g, 2.08 mmol) in DMSO (9 mL) was added sodium azide (0.175 g, 2.49 mmol), and the reaction was stirred at 60° C. for 4 hours. The mixture was cooled to room temperature and diluted with EtOAc and H$_2$O. The aqueous layer was extracted with EtOAc, and the combined organic layers were washed with H$_2$O, then brine, and dried over MgSO$_4$, filtered, and concentrated to give the title compound.

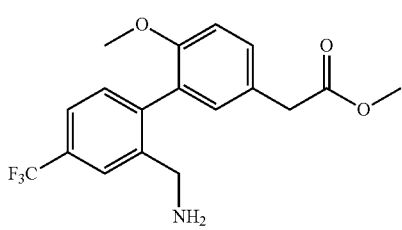 [SMILES: COC(=O)Cc1ccc(OC)c(-c2ccc(C(F)(F)F)cc2CN)c1]

Step 3: (2'-Aminomethyl-6-methoxy-4'-trifluoromethyl-biphenyl-3-yl)-acetic acid methyl ester (2'-Azidomethyl-6-methoxy-4'-trifluoromethyl-biphenyl-3-yl)-acetic acid methyl ester (0.784 g, 2.07 mmol) and 10% palladium on carbon (440 g) were combined in MeOH (8 mL) and stirred under a balloon of $H_2$ at room temperature for 1 hour. The mixture was filtered and concentrated, and the residue was purified by preparative HPLC. The desired fractions were combined, concentrated, and the isolated material was diluted with EtOAc and neutralized with saturated aqueous $NaHCO_3$. The organic layer was washed with brine, dried over $Na_2SO_4$, decanted, and concentrated to give the title compound.

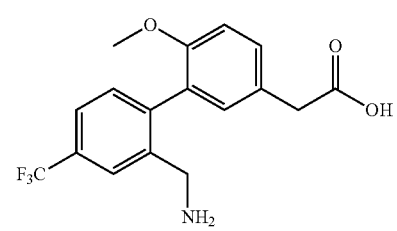 [SMILES: COc1ccc(CC(=O)O)cc1-c1ccc(C(F)(F)F)cc1CN]

Step 4: (2'-Aminomethyl-6-methoxy-4'-trifluoromethyl-biphenyl-3-yl)-acetic acid (2'-Aminomethyl-6-methoxy-4'-trifluoromethyl-biphenyl-3-yl)-acetic acid methyl ester (0.058 g, 0.17 mmol) in THF (0.59 mL) and MeOH (0.47 mL) was treated with 1N aqueous NaOH (0.17 mL, 0.17 mmol) and stirred overnight at room temperature. Analytical LCMS indicated that starting material was still present, so the reaction was stirred at 50° C. for 4.5 hours. Analytical LCMS showed that no change had occurred, so additional 1N aqueous NaOH (0.20 mL, 0.20 mmol) was added, and the reaction was stirred at 50° C. overnight. The mixture was cooled to room temperature and acidified with 1N aqueous HCl. The aqueous layer was extracted with $CH_2Cl_2$, and then diluted with brine and extracted twice with EtOAc. The combined organic layers were dried over $MgSO_4$, filtered, and concentrated to give the title compound.

Example 74

Synthesis of [2'-(Benzyloxycarbonylamino-methyl)-6-methoxy-4'-trifluoromethyl-biphenyl-3-yl]-acetic acid (Compound 1-142)

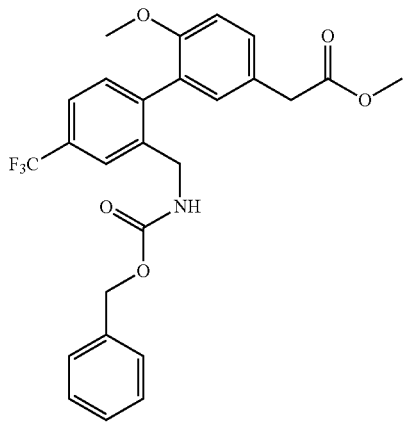

Step 1: [2'-(Benzyloxycarbonylamino-methyl)-6-methoxy-4'-trifluoromethyl-biphenyl-3-yl]-acetic acid methyl ester Prepared according to the procedure described in Example 1, Step 6, using the following starting materials: (2'-aminomethyl-6-methoxy-4'-trifluoromethyl-biphenyl-3-yl)-acetic acid methyl ester and benzyl chloroformate.

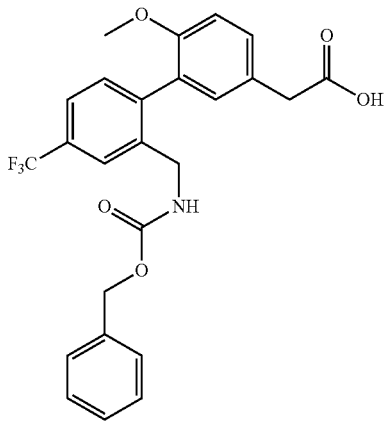 [SMILES: COc1ccc(CC(=O)O)cc1-c1ccc(C(F)(F)F)cc1CNC(=O)OCc1ccccc1]

Step 2: [2'-(Benzyloxycarbonylamino-methyl)-6-methoxy-4'-trifluoromethyl-biphenyl-3-yl]-acetic acid Prepared according to the procedure described in Example 3, Step 3, using the following starting material: [2'-(benzyloxycarbonylamino-methyl)-6-methoxy-4'-trifluoromethyl-biphenyl-3-yl]-acetic acid methyl ester.

Example 75

Synthesis of {2'-[(Benzyloxycarbonyl-ethyl-amino)-methyl]-4'-trifluoromethyl-biphenyl-3-yl}-acetic acid (Compound 1-143)

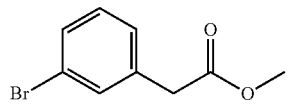

Step 1: (3-Bromo-phenyl)-acetic acid methyl ester

To 3-bromophenylacetic acid (5.03 g, 23.4 mmol) in MeOH (50 mL) was added thionyl chloride (3.4 mL, 46.8 mmol), and the reaction was stirred at 65° C. for 5 hours. The mixture was concentrated, and the residue was partitioned between CH$_2$Cl$_2$ and saturated aqueous NaHCO$_3$. The mixture was basified with 1N aqueous NaOH, and the aqueous layer was extracted with CH$_2$Cl$_2$. The combined organic layers were washed with H$_2$O, dried over MgSO$_4$, filtered, and concentrated to give the title compound.

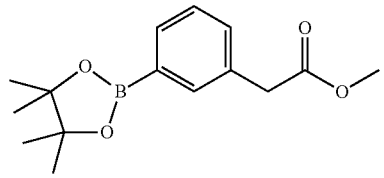

Step 2: [3-(4,4,5,5-Tetramethyl-[1,3,2]dioxaborolan-2-yl)-phenyl]-acetic acid methyl ester Prepared according to the procedure described in Example 1, Step 2, using the following starting materials: (3-bromo-phenyl)-acetic acid methyl ester and bis(pinacolato)diboron.

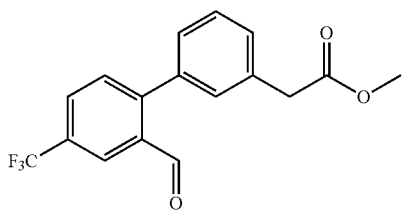 [SMILES: COC(=O)Cc1cccc(-c2ccc(C(F)(F)F)cc2C=O)c1]

Step 3: (2'-Formyl-4'-trifluoromethyl-biphenyl-3-yl)-acetic acid methyl ester Prepared according to the procedure described in Example 1, Step 4, using the following starting materials: [3-(4,4,5,5-tetramethyl-[1,3,2]dioxaborolan-2-yl)-phenyl]-acetic acid methyl ester and 2-bromo-5-(trifluoromethyl)benzaldehyde.

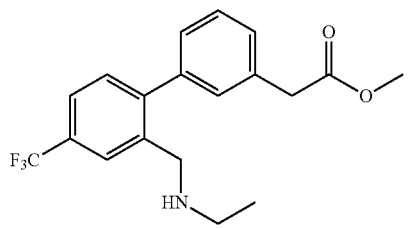 [SMILES: CCNCc1cc(C(F)(F)F)ccc1-c1cccc(CC(=O)OC)c1]

Step 4: (2'-Ethylaminomethyl-4'-trifluoromethyl-biphenyl-3-yl)-acetic acid methyl ester Prepared according to the procedure described in Example 1, Step 5, using the following starting materials: (2'-formyl-4'-trifluoromethyl-biphenyl-3-yl)-acetic acid methyl ester and ethylamine (2M in THF).

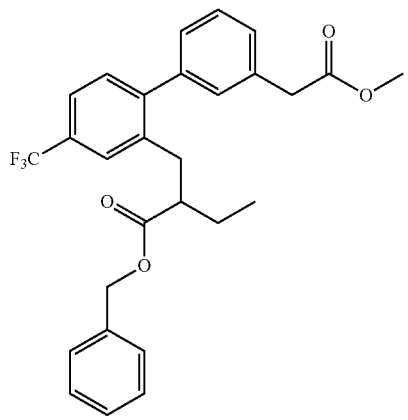 [SMILES: CCC(Cc1cc(C(F)(F)F)ccc1-c1cccc(CC(=O)OC)c1)C(=O)OCc1ccccc1]

Step 5: {2'-[(Benzyloxycarbonyl-ethyl-amino)-methyl]-4'-trifluoromethyl-biphenyl-3-yl}-acetic acid methyl ester Prepared according to the procedure described in Example 1, Step 6, using the following starting materials: (2'-ethylaminomethyl-4'-trifluoromethyl-biphenyl-3-yl)-acetic acid methyl ester and benzyl chloroformate.

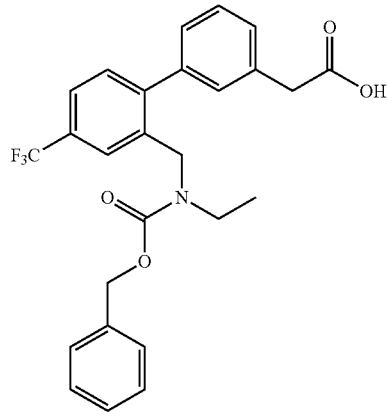 [SMILES: CCN(Cc1cc(C(F)(F)F)ccc1-c1cccc(CC(=O)O)c1)C(=O)OCc1ccccc1]

Step 6: {2'-[(Benzyloxycarbonyl-ethyl-amino)-methyl]-4'-trifluoromethyl-biphenyl-3-yl}-acetic acid Prepared according to the procedure described in Example 3, Step 3, using the following starting material: {2'-[(benzyloxycarbonyl-ethyl-amino)-methyl]-4'-trifluoromethyl-biphenyl-3-yl}-acetic acid methyl ester. M+H is 472.

Example 76

Synthesis of {2'-[1-Ethyl-3-(4-hydroxy-benzyl)-ureidomethyl]-6-methoxy-4'-trifluoromethyl-biphenyl-3-yl}-acetic acid (Compound 1-252)

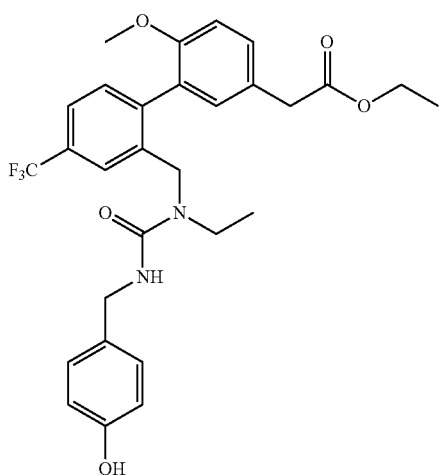 [SMILES: CCOC(=O)Cc1ccc(OC)c(-c2ccc(C(F)(F)F)cc2CN(CC)C(=O)NCc2ccc(O)cc2)c1]

Step 1: {2'-[1-Ethyl-3-(4-hydroxy-benzyl)-ureidomethyl]-6-methoxy-4'-trifluoromethyl-biphenyl-3-yl}-acetic acid ethyl ester To (2'-ethylaminomethyl-6-methoxy-4'-trifluoromethyl-biphenyl-3-yl)-acetic acid ethyl ester (0.59 g, 1.49 mmol) and diisopropylethylamine (0.65 mL, 3.73 mmol) in CH$_2$Cl$_2$ (6 mL) at 0° C. was added phosgene (20% in toluene; 1.2 mL, 2.24 mmol), and the reaction was stirred for 1 hour. 4-Hydroxybenzylamine (0.278 g, 2.24 mmol) and triethylamine (1 mL, 7.47 mmol) were then added, and the reaction was stirred for 2 hours. Analytical LCMS indicated the starting material was still present, so additional 4-hydroxybenzylamine (0.184 g, 1.49 mmol) was added, and the reaction was stirred for another 30 minutes. The mixture was partitioned between CH$_2$Cl$_2$ and H$_2$O, and the organic layer was dried over MgSO$_4$, filtered, and concentrated. The residue was purified by silica gel chromatography (0-100% EtOAc in hexanes) to give the title compound.

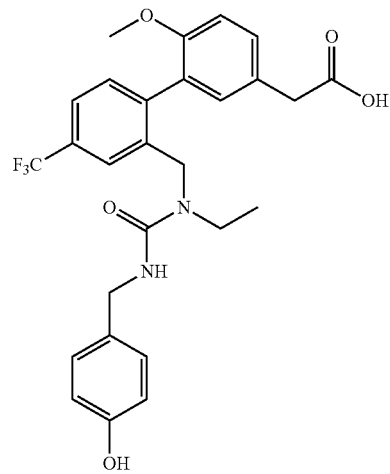

Step 2: {2'-[1-Ethyl-3-(4-hydroxy-benzyl)-ureidomethyl]-6-methoxy-4'-trifluoromethyl-biphenyl-3-yl}-acetic acid {2'-[1-Ethyl-3-(4-hydroxy-benzyl)-ureidomethyl]-6-methoxy-4'-trifluoromethyl-biphenyl-3-yl}-acetic acid ethyl ester (0.535 g, 0.98 mmol) in THF (5 mL) and EtOH (4 mL) was treated with 1N aqueous NaOH (3 mL), and the reaction was stirred for 2.5 hours. Analytical LCMS indicated that starting material was still present, so additional 1N aqueous NaOH was added, and the reaction was heated with a heat gun. Once no starting material was seen by analytical LCMS, the mixture was worked-up with CH$_2$Cl$_2$ and 1N aqueous HCl, and the organic layer was dried over MgSO$_4$, filtered, and concentrated to give the title compound. M+H is 517.

Example 77

Synthesis of {2'-[1-Ethyl-3-(2-hydroxy-benzyl)-ureidomethyl]-6-methoxy-4'-trifluoromethyl-biphenyl-3-yl}-acetic acid (Compound 1-253)

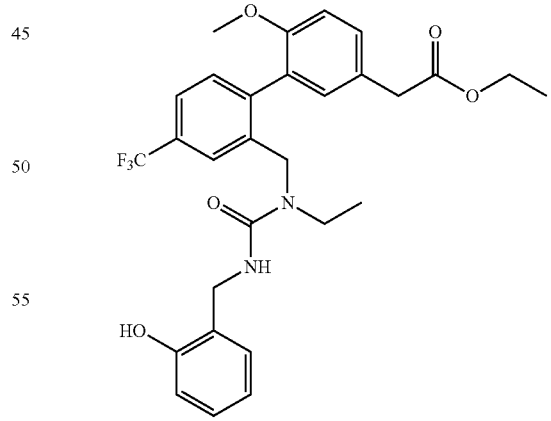

Step 1: {2'-[1-Ethyl-3-(2-hydroxy-benzyl)-ureidomethyl]-6-methoxy-4'-trifluoromethyl-biphenyl-3-yl}-acetic acid ethyl ester Prepared according to the procedure described in Example 76, Step 1, using the following starting materials: (2'-ethylaminomethyl-6-methoxy-4'-trifluoromethyl-biphenyl-3-yl)-acetic acid ethyl ester and 2-hydroxybenzylamine.

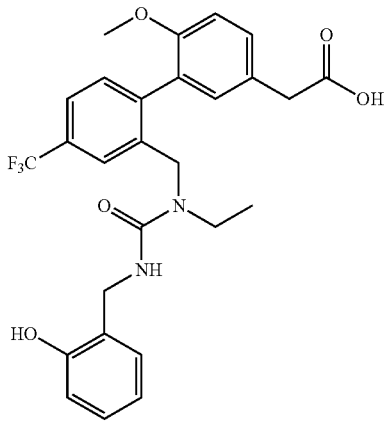 [SMILES: CCN(Cc1cc(C(F)(F)F)ccc1-c1cc(CC(=O)O)ccc1OC)C(=O)NCc1ccccc1O]

Step 2: {2'-[1-Ethyl-3-(2-hydroxy-benzyl)-ureidomethyl]-6-methoxy-4'-trifluoromethyl-biphenyl-3-yl}-acetic acid Prepared according to the procedure described in Example 76, Step 2, using the following starting material: {2'-[1-ethyl-3-(2-hydroxy-benzyl)-ureidomethyl]-6-methoxy-4)-trifluoromethyl-biphenyl-3-yl}-acetic acid ethyl ester. M+H is 517.

Example 78

Synthesis of {2'-[1-Ethyl-3-(3-hydroxy-benzyl)-ureidomethyl]-6-methoxy-4'-trifluoromethyl-biphenyl-3-yl}-acetic acid (Compound 1-257)

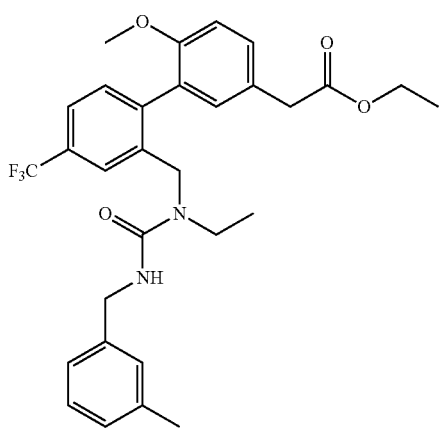 [SMILES: CCOC(=O)Cc1ccc(OC)c(-c2ccc(C(F)(F)F)cc2CN(CC)C(=O)NCc2cccc(C)c2)c1]

Step 1: {2'-[1-Ethyl-3-(3-hydroxy-benzyl)-ureidomethyl]-6-methoxy-4'-trifluoromethyl-biphenyl-3-yl}-acetic acid ethyl ester Prepared according to the procedure described in Example 76, Step 1, using the following starting materials: (2'-ethylaminomethyl-6-methoxy-4'-trifluoromethyl-biphenyl-3-yl)-acetic acid ethyl ester and 3-(aminomethyl)phenol.

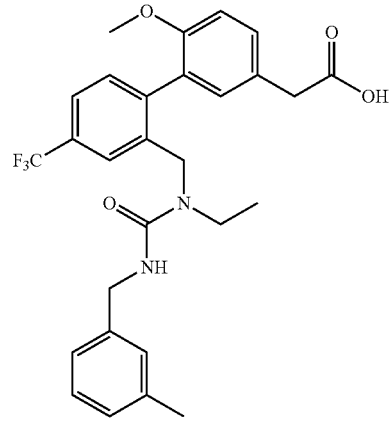 [SMILES: CCN(Cc1cc(C(F)(F)F)ccc1-c1cc(CC(=O)O)ccc1OC)C(=O)NCc1cccc(C)c1]

Step 2: {2'-[1-Ethyl-3-(3-hydroxy-benzyl)-ureidomethyl]-6-methoxy-4'-trifluoromethyl-biphenyl-3-yl}-acetic acid Prepared according to the procedure described in Example 76, Step 2, using the following starting material: {2'-[1-ethyl-3-(3-hydroxy-benzyl)-ureidomethyl]-6-methoxy-4'-trifluoromethyl-biphenyl-3-yl}-acetic acid ethyl ester. M+H is 517.

Example 79

Synthesis of (2'-{[Ethyl-(2-phenoxy-propionyl)-amino]-methyl}-6-methoxy-4'-trifluoromethyl-biphenyl-3-yl)-acetic acid (Compound 1-45)

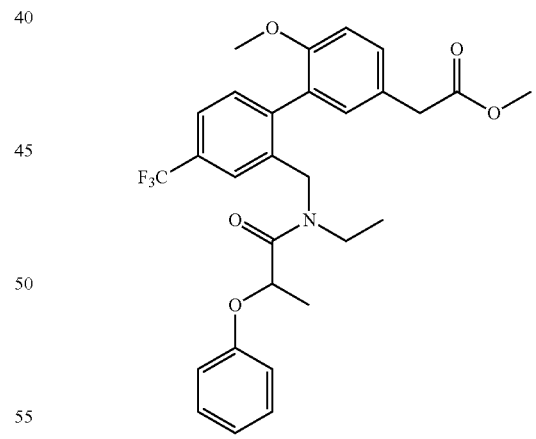

Step 1: (2'-{[Ethyl-(2-phenoxy-propionyl)-amino]-methyl}-6-methoxy-4'-trifluoromethyl-biphenyl-3-yl)-acetic acid methyl ester Prepared according to the procedure described in Example 1, Step 6, using the following starting materials: (2'-ethylaminomethyl-6-methoxy-4'-trifluoromethyl-biphenyl-3-yl)-acetic acid methyl ester and 2-phenoxypropionyl chloride.

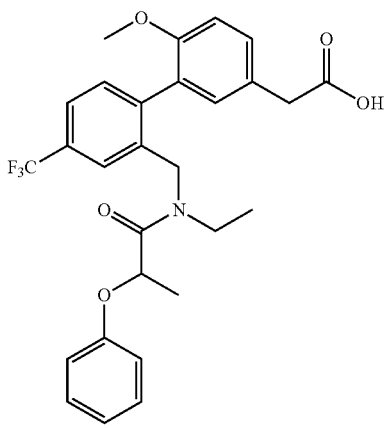 [SMILES: CCN(Cc1cc(C(F)(F)F)ccc1-c1cc(CC(=O)O)ccc1OC)C(=O)C(C)Oc1ccccc1]

Step 2: (2'-{[Ethyl-(2-phenoxy-propionyl)-amino]-methyl}-6-methoxy-4'-trifluoromethyl-biphenyl-3-yl)-acetic acid Prepared according to the procedure described in Example 31, Step 2, using the following starting material: (2'-{[ethyl-(2-phenoxy-propionyl)-amino]-methyl}-6-methoxy-4'-trifluoromethyl-biphenyl-3-yl)-acetic acid methyl ester. M+H is 516.

Example 80

Synthesis of {2'-[3-(2-Bromo-phenyl)-1-ethyl-ureidomethyl]-6-methoxy-4'-trifluoromethyl-biphenyl-3-yl}-acetic acid (Compound 1-47)

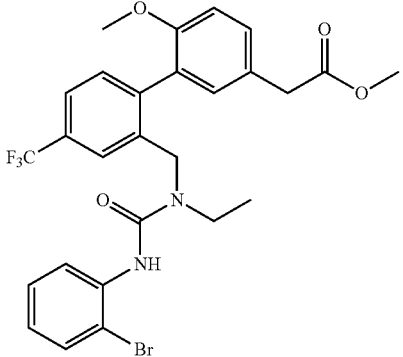 [SMILES: CCN(Cc1cc(C(F)(F)F)ccc1-c1cc(CC(=O)OC)ccc1OC)C(=O)Nc1ccccc1Br]

Step 1: {2'-[3-(2-Bromo-phenyl)-1-ethyl-ureidomethyl]-6-methoxy-4'-trifluoromethyl-biphenyl-3-yl}-acetic acid methyl ester Prepared according to the procedure described in Example 41, Step 5, using the following starting materials: (2'-ethylaminomethyl-6-methoxy-4'-trifluoromethyl-biphenyl-3-yl)-acetic acid methyl ester and 2-bromophenyl isocyanate.

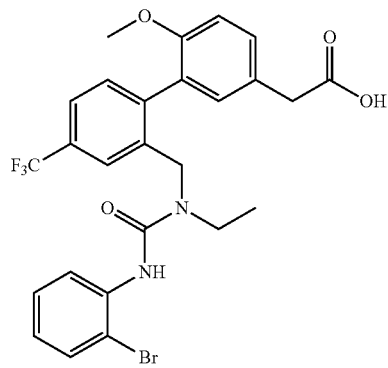 [SMILES: CCN(Cc1cc(C(F)(F)F)ccc1-c1cc(CC(=O)O)ccc1OC)C(=O)Nc1ccccc1Br]

Step 2: {2'-[3-(2-Bromo-phenyl)-1-ethyl-ureidomethyl]-6-methoxy-4'-trifluoromethyl-biphenyl-3-yl}-acetic acid Prepared according to the procedure described in Example 31, Step 2, using the following starting material: {2'-[3-(2-bromo-phenyl)-1-ethyl-ureidomethyl]-6-methoxy-4'-trifluoromethyl-biphenyl-3-yl}-acetic acid methyl ester. M+H is 566.

Example 81

Synthesis of (2'-{[Ethyl-(2-phenoxy-acetyl)-amino]-methyl}-6-methoxy-4'-trifluoromethyl-biphenyl-3-yl)-acetic acid (Compound 1-48)

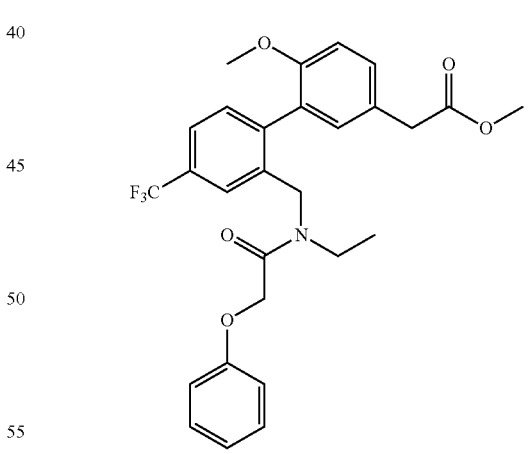

Step 1: (2'-{[Ethyl-(2-phenoxy-acetyl)-amino]-methyl}-6-methoxy-4'-trifluoromethyl-biphenyl-3-yl)-acetic acid methyl ester Prepared according to the procedure described in Example 1, Step 6, using the following starting materials: (2'-ethylaminomethyl-6-methoxy-4'-trifluoromethyl-biphenyl-3-yl)-acetic acid methyl ester and phenoxyacetyl chloride.

227

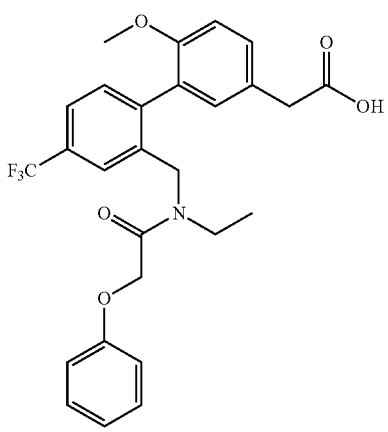

Step 2: (2'-{[Ethyl-(2-phenoxy-acetyl)-amino]-methyl}-6-methoxy-4'-trifluoromethyl-biphenyl-3-yl)-acetic acid Prepared according to the procedure described in Example 31, Step 2, using the following starting material: (2'-{[ethyl-(2-phenoxy-acetyl)-amino]-methyl}-6-methoxy-4'-trifluoromethyl-biphenyl-3-yl)-acetic acid methyl ester. M+H is 502.

Example 82

Synthesis of {2'-[(Benzoyl-ethyl-amino)-methyl]-6-methoxy-4'-trifluoromethyl-biphenyl-3-yl}-acetic acid (Compound 1-80)

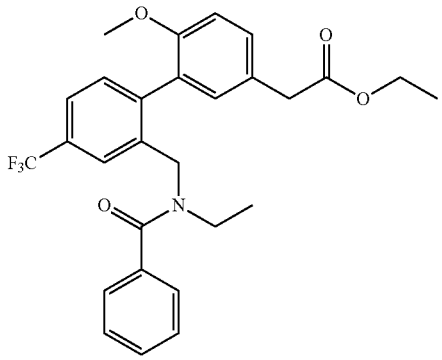 [SMILES: CCOC(=O)Cc1ccc(OC)c(-c2ccc(C(F)(F)F)cc2CN(CC)C(=O)c2ccccc2)c1]

Step 1: {2'-[(Benzoyl-ethyl-amino)-methyl]-6-methoxy-4'-trifluoromethyl-biphenyl-3-yl}-acetic acid ethyl ester Prepared according to the procedure described in Example 1, Step 6, using the following starting materials: (2'-ethylaminomethyl-6-methoxy-4'-trifluoromethyl-biphenyl-3-yl)-acetic acid ethyl ester and benzoyl chloride.

228

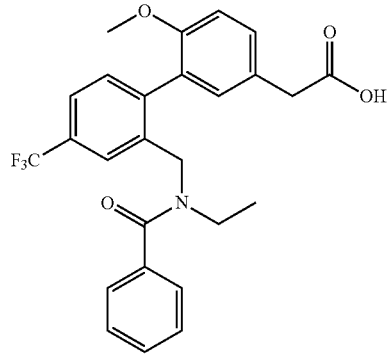 [SMILES: CCN(Cc1cc(C(F)(F)F)ccc1-c1cc(CC(=O)O)ccc1OC)C(=O)c1ccccc1]

Step 2: {2'-[(Benzoyl-ethyl-amino)-methyl]-6-methoxy-4'-trifluoromethyl-biphenyl-3-yl}-acetic acid Prepared according to the procedure described in Example 31, Step 2, using the following starting material: {2'-[(benzoyl-ethyl-amino)-methyl]-6-methoxy-4'-trifluoromethyl-biphenyl-3-yl}-acetic acid ethyl ester.

Example 83

Synthesis of (2'-{[(2-Benzyloxy-acetyl)-ethyl-amino]-methyl}-6-methoxy-4'-trifluoromethyl-biphenyl-3-yl)-acetic acid (Compound 1-92)

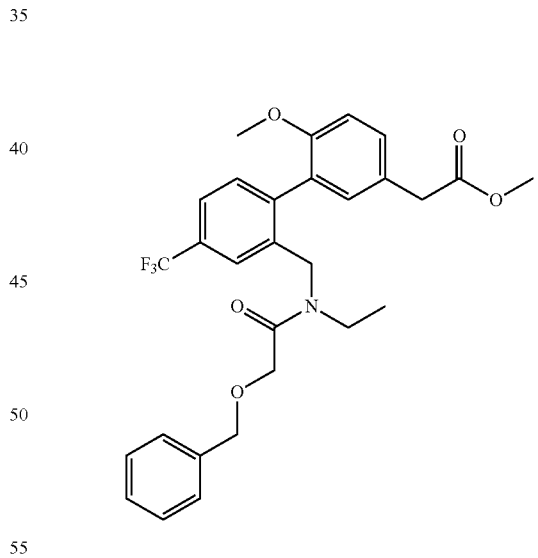

Step 1: (2'-{[(2-Benzyloxy-acetyl)-ethyl-amino]-methyl}-6-methoxy-4'-trifluoromethyl-biphenyl-3-yl)-acetic acid methyl ester Prepared according to the procedure described in Example 1, Step 6, using the following starting materials: (2'-ethylaminomethyl-6-methoxy-4'-trifluoromethyl-biphenyl-3-yl)-acetic acid methyl ester and benzyloxyacetyl chloride.

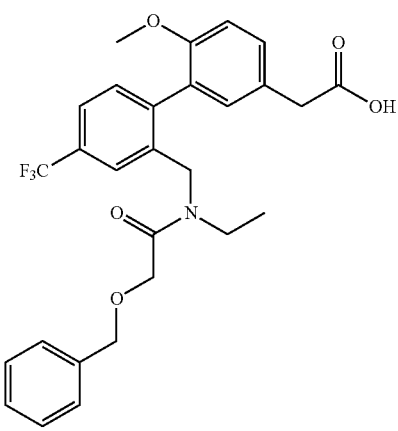 [SMILES: CCN(Cc1cc(C(F)(F)F)ccc1-c1cc(CC(=O)O)ccc1OC)C(=O)COCc1ccccc1]

Step 2: (2'-{[(2-Benzyloxy-acetyl)-ethyl-amino]-methyl}-6-methoxy-4'-trifluoromethyl-biphenyl-3-yl)-acetic acid Prepared according to the procedure described in Example 31, Step 2, using the following starting material: (2'-{[(2-benzyloxy-acetyl)-ethyl-amino]methyl}-6-methoxy-4'-trifluoromethyl-biphenyl-3-yl)-acetic acid methyl ester.

Example 84

Synthesis of [2'-({[2-(4-Chloro-phenoxy)-acetyl]-ethyl-amino}-methyl)-6-methoxy-4'-trifluoromethyl-biphenyl-3-yl]-acetic acid (Compound 1-93)

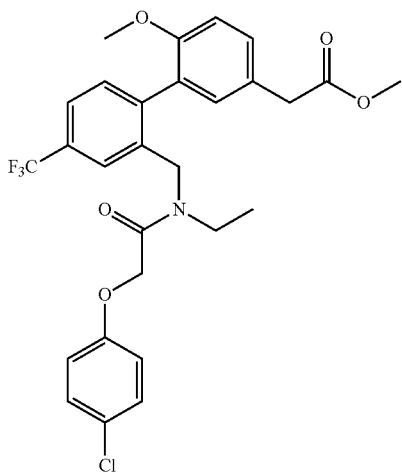 [SMILES: CCN(Cc1cc(C(F)(F)F)ccc1-c1cc(CC(=O)OC)ccc1OC)C(=O)COc1ccc(Cl)cc1]

Step 1: [2'-({[2-(4-Chloro-phenoxy)-acetyl]-ethyl-amino}-methyl)-6-methoxy-4'-trifluoromethyl-biphenyl-3-yl]-acetic acid methyl ester Prepared according to the procedure described in Example 1, Step 6, using the following starting materials: (2'-ethylaminomethyl-6-methoxy-4'-trifluoromethyl-biphenyl-3-yl)-acetic acid methyl ester and 4-chlorophenoxyacetyl chloride.

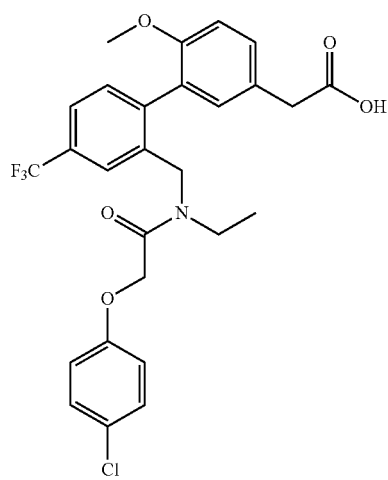 [SMILES: CCN(Cc1cc(C(F)(F)F)ccc1-c1cc(CC(=O)O)ccc1OC)C(=O)COc1ccc(Cl)cc1]

Step 2: [2'-({[2-(4-Chloro-phenoxy)-acetyl]-ethyl-amino}-methyl)-6-methoxy-4'-trifluoromethyl-biphenyl-3-yl]-acetic acid Prepared according to the procedure described in Example 31, Step 2, using the following starting material: [2'-({[2-(4-chloro-phenoxy)-acetyl]-ethyl-amino}-methyl)-6-methoxy-4'-trifluoromethyl-biphenyl-3-yl]-acetic acid methyl ester.

Example 85

Synthesis of (2'-{[Ethyl-(pyrrolidine-1-carbonyl)-amino]-methyl}-6-methoxy-4'-trifluoromethyl-biphenyl-3-yl)-acetic acid (Compound 1-97)

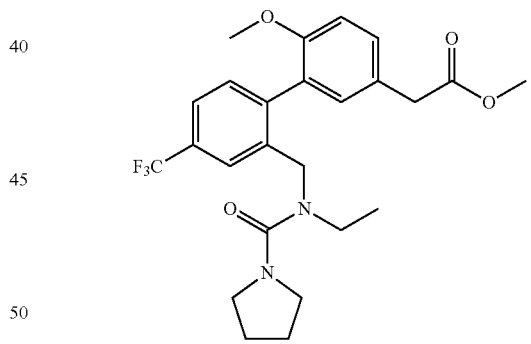

Step 1: (2'-{[Ethyl-(pyrrolidine-1-carbonyl)-amino]-methyl}-6-methoxy-4'-trifluoromethyl-biphenyl-3-yl)-acetic acid methyl ester To a solution of (2'-ethylaminomethyl-6-methoxy-4'-trifluoromethyl-biphenyl-3-yl)-acetic acid methyl ester (0.207 g, 0.54 mmol) and diisopropylethylamine (0.38 mL, 2.16 mmol) in CH$_2$Cl$_2$ (2 mL) at 0° C. was added phosgene (20% in toluene; 0.43 mL, 0.81 mmol), and the reaction was stirred for 2 hours. Pyrrolidine (0.13 mL, 1.62 mmol) was added, and the reaction was stirred at 0° C. for 30 minutes. The mixture was concentrated, and the residue was purified by silica gel chromatography (20-40% EtOAc in hexanes) to give the title compound.

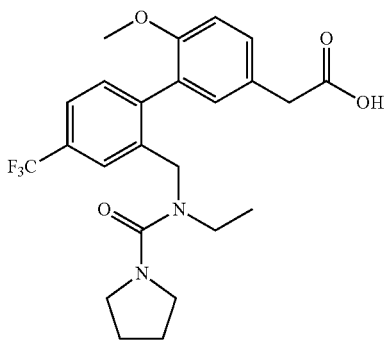 [SMILES: CCN(Cc1cc(C(F)(F)F)ccc1-c1cc(CC(=O)O)ccc1OC)C(=O)N1CCCC1]

Step 2: (2'-{[Ethyl-(pyrrolidine-1-carbonyl)-amino]-methyl}-6-methoxy-4'-trifluoromethyl-biphenyl-3-yl)-acetic acid Prepared according to the procedure described in Example 31, Step 2, using the following starting material: (2'-{[ethyl-(pyrrolidine-1-carbonyl)-amino]-methyl}-6-methoxy-4'-trifluoromethyl-biphenyl-3-yl)-acetic acid methyl ester.

Example 86

Synthesis of [2'-({[2-(4-Chloro-phenoxy)-2-methyl-propionyl]-ethyl-amino}-methyl)-6-methoxy-4'-trifluoromethyl-biphenyl-3-yl]-acetic acid (Compound 1-118)

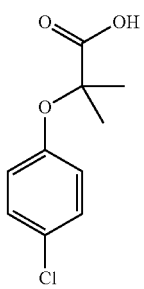

Step 1: 2-(4-Chloro-phenoxy)-2-methyl-propionic acid

A solution of 2-(4-chlorophenoxy)isobutyric acid ethyl ester (1.0 g, 4.12 mmol) in THF (10 mL) was treated with 1N aqueous LiOH (10 mL) and stirred overnight at room temperature. The mixture was acidified with 1N aqueous HCl to pH 3-4 and extracted three times with EtOAc. The combined organic layers were dried and concentrated to give the title compound.

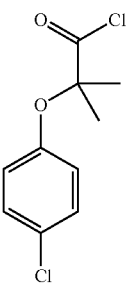

Step 2: 2-(4-Chloro-phenoxy)-2-methyl-propionyl chloride 2-(4-Chloro-phenoxy)-2-methyl-propionic acid (0.124 g, 0.58 mmol) and triethylamine (0.09 mL, 0.62 mmol) were combined in CH$_2$Cl$_2$ (2 mL) and cooled to 0° C. Oxalyl chloride (0.05 mL, 0.62 mmol) was added, followed by DMF (3 drops), and the mixture was slowly warmed to room temperature and stirred for 2 hours to give the title compound, which was used directly in the next step.

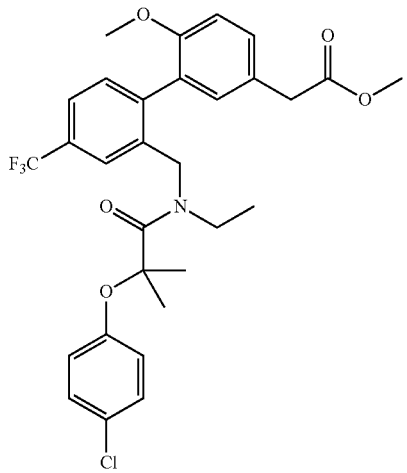 [SMILES: CCN(Cc1cc(C(F)(F)F)ccc1-c1cc(CC(=O)OC)ccc1OC)C(=O)C(C)(C)Oc1ccc(Cl)cc1]

Step 3: [2'-({[2-(4-Chloro-phenoxy)-2-methyl-propionyl]-ethyl-amino}-methyl)-6-methoxy-4'-trifluoromethyl-biphenyl-3-yl]-acetic acid methyl ester To a solution of 2-(4-chloro-phenoxy)-2-methyl-propionyl chloride (0.58 mmol) in CH$_2$Cl$_2$ was added (2'-ethylaminomethyl-6-methoxy-4'-trifluoromethyl-biphenyl-3-yl)-acetic acid methyl ester (0.200 g, 0.52 mmol) in triethylamine (0.17 mL, 1.23 mmol), and the reaction was stirred at room temperature for 30 minutes. The mixture was concentrated and purified by silica gel chromatography (10-30% EtOAc in hexanes) to give the title compound.

233

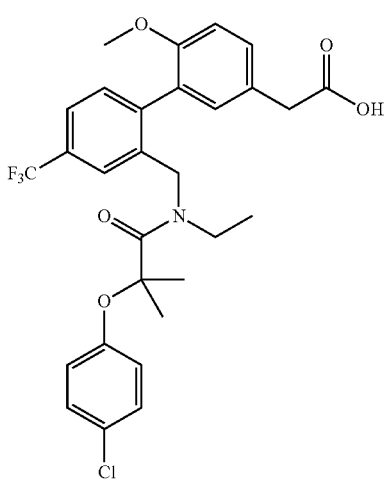 [SMILES: CCN(Cc1cc(C(F)(F)F)ccc1-c1cc(CC(=O)O)ccc1OC)C(=O)C(C)(C)Oc1ccc(Cl)cc1]

Step 4: [2'-({[2-(4-Chloro-phenoxy)-2-methyl-propionyl]-ethyl-amino}-methyl)-6-methoxy-4'-trifluoromethyl-biphenyl-3-yl]-acetic acid Prepared according to the procedure described in Example 31, Step 2, using the following starting material: [2'-({[2-(4-chloro-phenoxy)-2-methyl-propionyl]-ethyl-amino}-methyl)-6-methoxy-4'-trifluoromethyl-biphenyl-3-yl]-acetic acid methyl ester. M+H is 565.

Example 87

Synthesis of (2'-{[(2-Benzenesulfinyl-acetyl)-ethyl-amino]-methyl}-6-methoxy-4'-trifluoromethyl-biphenyl-3-yl)-acetic acid (Compound 1-119)

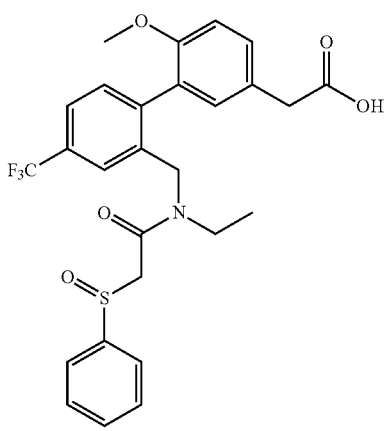 [SMILES: CCN(Cc1cc(C(F)(F)F)ccc1-c1cc(CC(=O)O)ccc1OC)C(=O)CS(=O)c1ccccc1]

Step 1: (2'-{[(2-Benzenesulfinyl-acetyl)-ethyl-amino]-methyl}-6-methoxy-4'-trifluoromethyl-biphenyl-3-yl)-acetic acid Prepared according to the procedure described in Example 35, Step 1, using the following starting material: (2'-{[ethyl-

234

(2-phenylsulfanyl-acetyl)-amino]-methyl}-6-methoxy-4'-trifluoromethyl-biphenyl-3-yl)-acetic acid. M+H is 534.

Example 88

Synthesis of [2'-(1-Ethyl-3-phenyl-ureidomethyl)-6-methoxy-4'-trifluoromethyl-biphenyl-3-yl]-acetic acid (Compound 1-121)

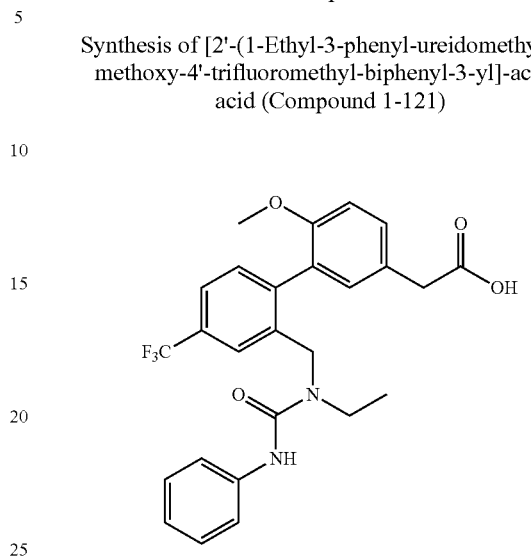

To a solution of {2'-[3-(2-bromo-phenyl)-1-ethyl-ureidomethyl]-6-methoxy-4'-trifluoromethyl-biphenyl-3-yl}-acetic acid (0.072 g, 0.13 mmol) in EtOH was added 10% palladium on carbon (0.020 g), and the reaction was stirred under H$_2$ using a Parr apparatus overnight. The mixture was filtered through a pad of Celite and concentrated, and the residue was acidified with 1N aqueous HCl and extracted with CH$_2$Cl$_2$. The combined organic layers were dried and concentrated, and the crude material was purified by silica gel chromatography (20-60% EtOAc in hexanes) to give the title compound. M+H is 487.

Example 89

Synthesis of [2'-({[1-(2,4-Dichloro-phenyl)-cyclopropanecarbonyl]-ethyl-amino}-methyl)-6-methoxy-4'-trifluoromethyl-biphenyl-3-yl]-acetic acid (Compound 1-131)

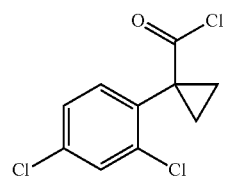 [SMILES: O=C(Cl)C1(c2ccc(Cl)cc2Cl)CC1]

Step 1: 1-(2,4-Dichloro-phenyl)-cyclopropanecarbonyl chloride 1-(2,4-Dichlorophenyl)-cyclopropanecarboxylic acid (0.086 g, 0.37 mmol) and triethylamine (0.08 mL, 0.56 mmol) were combined in CH$_2$Cl$_2$ (2 mL) and cooled to 0° C. Oxalyl chloride (0.05 mL, 0.56 mmol) was added, followed by DMF (3 drops), and the reaction was stirred for 20 minutes at 0° C. and then warmed to room temperature to give the title compound, which was used directly in the next step.

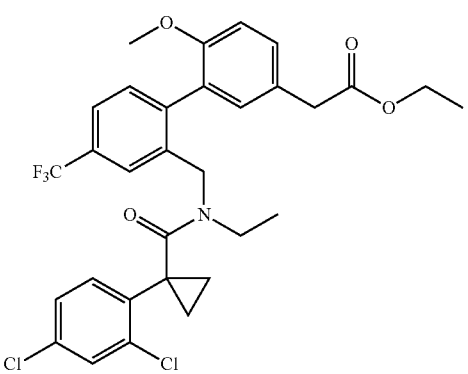 [SMILES: CCOC(=O)Cc1ccc(OC)c(-c2ccc(C(F)(F)F)cc2CN(CC)C(=O)C2(c3ccc(Cl)cc3Cl)CC2)c1]

Step 2: [2'-({[1-(2,4-Dichloro-phenyl)-cyclopropan-ecarbonyl]-ethyl-amino}-methyl)-6-methoxy-4'-trifluoromethyl-biphenyl-3-yl]-acetic acid ethyl ester To a solution of 1-(2,4-dichloro-phenyl)-cyclopropanecarbonyl chloride (0.37 mmol) in $CH_2Cl_2$ was added triethylamine (0.16 mL, 1.12 mmol), and the mixture was stirred for 10 minutes. (2'-Ethylaminomethyl-6-methoxy-4'-trifluoromethyl-biphenyl-3-yl)-acetic acid ethyl ester (0.146 g, 0.37 mmol) in $CH_2Cl_2$ was then added, and the reaction was stirred for 30 minutes at room temperature. Additional triethylamine (0.1 mL, 0.72 mmol) was added, and the reaction was stirred for another 30 minutes. Analytical LCMS indicated that starting material was still present, so another portion of triethylamine (0.1 mL, 0.72 mmol) was added, and the reaction was stirred for 1 hour and then worked-up with $CH_2Cl_2$ and $H_2O$. The combined organic layers were dried and concentrated, and the residue was purified by silica gel chromatography (10-40% EtOAc in hexanes) to give the title compound.

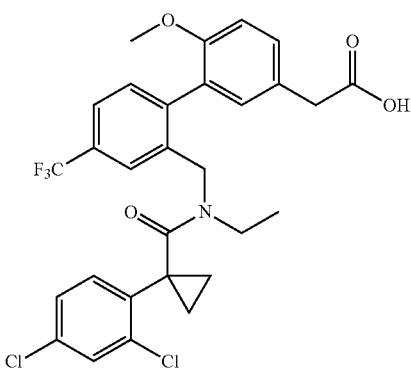 [SMILES: CCN(Cc1cc(C(F)(F)F)ccc1-c1cc(CC(=O)O)ccc1OC)C(=O)C1(c2ccc(Cl)cc2Cl)CC1]

Step 3: [2'-({[1-(2,4-Dichloro-phenyl)-cyclopropan-ecarbonyl]-ethyl-amino}-methyl)-6-methoxy-4'-trifluoromethyl-biphenyl-3-yl]-acetic acid Prepared according to the procedure described in Example 31, Step 2, using the following starting material: [2'-({[1-(2,4-dichloro-phenyl)-cyclopropanecarbonyl]-ethyl-amino}-methyl)-6-methoxy-4'-trifluoromethyl-biphenyl-3-yl]-acetic acid ethyl ester. M+H is 580.

Example 90

Synthesis of [2'-(1-Ethyl-3-pyridin-2-ylmethyl-ureidomethyl)-6-methoxy-4'-trifluoromethyl-biphenyl-3-yl]-acetic acid (Compound 1-139)

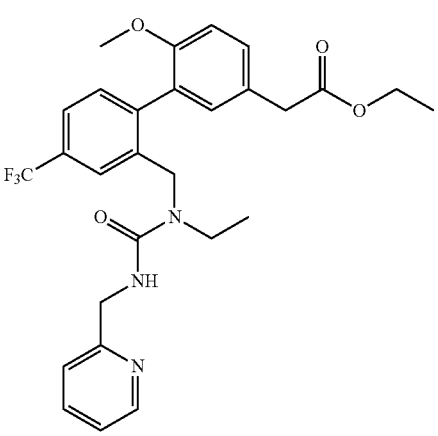 [SMILES: CCOC(=O)Cc1ccc(OC)c(-c2ccc(C(F)(F)F)cc2CN(CC)C(=O)NCc2ccccn2)c1]

Step 1: [2'-(1-Ethyl-3-pyridin-2-ylmethyl-ureidomethyl)-6-methoxy-4'-trifluoromethyl-biphenyl-3-yl]-acetic acid ethyl ester (2'-Ethylaminomethyl-6-methoxy-4'-trifluoromethyl-biphenyl-3-yl)-acetic acid ethyl ester (0.203 g, 0.51 mmol) and diisopropylethylamine (0.22 mL, 1.28 mmol) were combined in $CH_2Cl_2$ (2 mL) and cooled to 0° C. Phosgene (20% in toluene; 0.41 mL, 0.77 mmol) was added, and the reaction was stirred for 2.5 hours. After warming to room temperature, 2-(aminomethyl)pyridine (0.08 mL, 0.77 mol) was added, followed by triethylamine (0.14 mL, 1.02 mmol), and the reaction was stirred for 30 minutes. Analytical LCMS indicated that some starting material was still present, so additional triethylamine (0.07 mL, 0.51 mmol) was added, and the reaction was stirred for 45 minutes. The mixture was diluted with $CH_2Cl_2$ and $H_2O$, and the aqueous layer was extracted twice with $CH_2Cl_2$. The combined organic layers were dried and concentrated, and the residue was purified by silica gel chromatography (40-100% EtOAc in hexanes) to give the title compound.

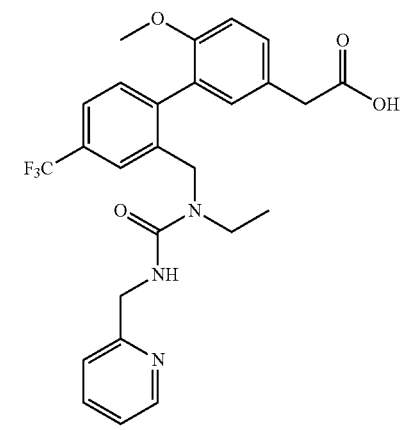 [SMILES: CCN(Cc1cc(C(F)(F)F)ccc1-c1cc(CC(=O)O)ccc1OC)C(=O)NCc1ccccn1]

Step 2: [2'-(1-Ethyl-3-pyridin-2-ylmethyl-ureidomethyl)-6-methoxy-4'-trifluoromethyl-biphenyl-3-yl]-acetic acid Prepared according to the procedure described in Example 31, Step 2, using the following starting material: [2'-(1-ethyl-3-pyridin-2-ylmethyl-ureidomethyl)-6-methoxy-4'-trifluoromethyl-biphenyl-3-yl]-acetic acid ethyl ester. M+H is 524.

Example 91

Synthesis of {2'-[3-(4-Chloro-benzyl)-1-ethyl-ureidomethyl]-6-methoxy-4'-trifluoromethyl-biphenyl-3-yl}-acetic acid (Compound 1-140)

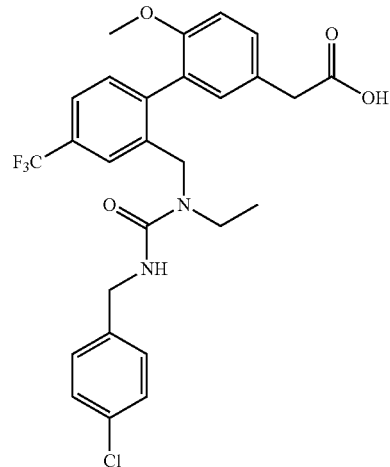

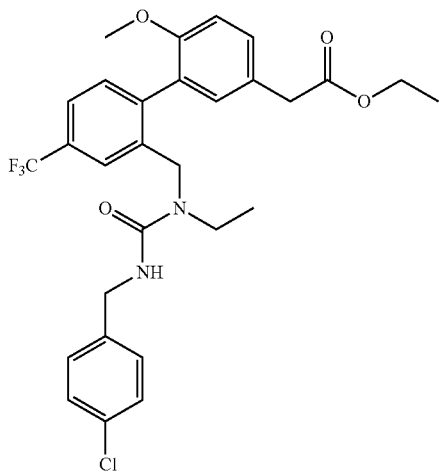 [SMILES: CCOC(=O)Cc1ccc(OC)c(-c2ccc(C(F)(F)F)cc2CN(CC)C(=O)NCc2ccc(Cl)cc2)c1]

Step 1: {2'-[3-(4-Chloro-benzyl)-1-ethyl-ureidomethyl]-6-methoxy-4'-trifluoromethyl-biphenyl-3-yl}-acetic acid ethyl ester To (2'-ethylaminomethyl-6-methoxy-4'-trifluoromethyl-biphenyl-3-yl)-acetic acid ethyl ester (0.196 g, 0.50 mmol) in $CH_2Cl_2$ (2 mL) at 0° C. was added diisopropylethylamine (0.21 mL, 1.24 mmol), followed by phosgene (20% in toluene, 0.39 mL, 0.75 mmol), and the mixture was stirred for 3 hours. 4-Chlorobenzylamine (0.09 mL, 0.75 mmol) was added, followed by triethylamine (0.14 mL, 1.0 mmol), and the reaction was stirred at room temperature for 20 minutes. Additional triethylamine (0.07 mL, 0.5 mmol) was added, and the reaction was stirred for 1 hour and then worked-up with $CH_2Cl_2$ and $H_2O$. The organic layer was dried and concentrated, and the residue was purified by silica gel chromatography (0-50% EtOAc in hexanes) to give the title compound.

Step 2: {2'-[3-(4-Chloro-benzyl)-1-ethyl-ureidomethyl]-6-methoxy-4'-trifluoromethyl-biphenyl-3-yl}-acetic acid To {2'-[3-(4-chloro-benzyl)-1-ethyl-ureidomethyl]-6-methoxy-4'-trifluoromethyl-biphenyl-3-yl}-acetic acid ethyl ester (0.196 g, 0.35 mmol) in THF (2 mL) and MeOH (2 mL) was added 1N aqueous LiOH (2 mL), and the reaction was stirred at room temperature for 2 hours. The mixture was acidified with 1N aqueous HCl and extracted three times with EtOAc, and the combined organic layers were dried and concentrated. The residue was purified by preparative HPLC to give the title compound. M+H is 535.

Example 92

Synthesis of (2'-{[Ethyl-(2-pyrazol-1-yl-acetyl)-amino]-methyl}-6-methoxy-4'-trifluoromethyl-biphenyl-3-yl)-acetic acid (Compound 1-148)

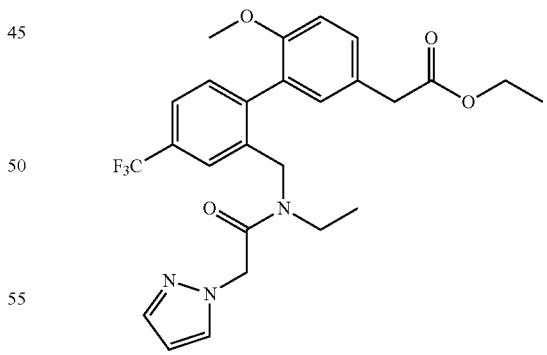

Step 1: (2'-{[Ethyl-(2-pyrazol-1-yl-acetyl)-amino]-methyl}-6-methoxy-4'-trifluoromethyl-biphenyl-3-yl)-acetic acid ethyl ester Prepared according to the procedure described in Example 37, Step 2, using the following starting materials: (2'-{[(2-chloro-acetyl)-ethyl-amino]-methyl}-6-methoxy-4'-trifluoromethyl-biphenyl-3-yl)-acetic acid ethyl ester and pyrazole.

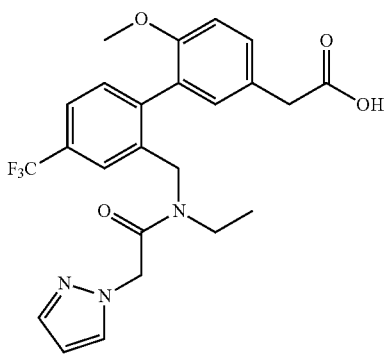 [SMILES: CCN(Cc1cc(C(F)(F)F)ccc1-c1cc(CC(=O)O)ccc1OC)C(=O)Cn1cccn1]

Step 2: (2'-{[Ethyl-(2-pyrazol-1-yl-acetyl)-amino]-methyl}-6-methoxy-4'-trifluoromethyl-biphenyl-3-yl)-acetic acid Prepared according to the procedure described in Example 31, Step 2, using the following starting material: (2'-{[ethyl-(2-pyrazol-1-yl-acetyl)-amino]-methyl}-6-methoxy-4'-trifluoromethyl-biphenyl-3-yl)-acetic acid ethyl ester. M+H is 476.

Example 93

Synthesis of (2'-{[Ethyl-(2-[1,2,4]triazol-1-yl-acetyl)-amino]-methyl}-6-methoxy-4'-trifluoromethyl-biphenyl-3-yl)-acetic acid (Compound 1-150)

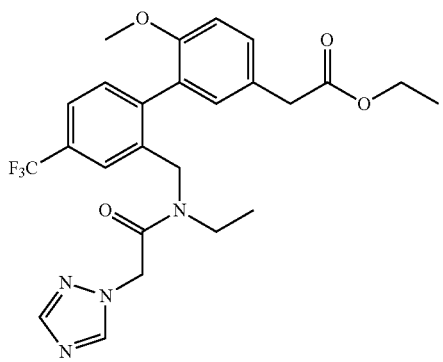 [SMILES: CCOC(=O)Cc1ccc(OC)c(-c2ccc(C(F)(F)F)cc2CN(CC)C(=O)Cn2cncn2)c1]

Step 1: (2'-{[Ethyl-(2-[1,2,4]triazol-1-yl-acetyl)-amino]-methyl}-6-methoxy-4'-trifluoromethyl-biphenyl-3-yl)-acetic acid ethyl ester To a solution of 1,2,4-triazole (0.042 g, 0.61 mmol) in DMF at 0° C. was added sodium hydride (60% in mineral oil; 0.044 g, 1.1 mmol), and the mixture was stirred for 30 minutes. (2'-{[(2-Chloro-acetyl)-ethyl-amino]-methyl}-6-methoxy-4'-trifluoromethyl-biphenyl-3-yl)-acetic acid ethyl ester (0.55 mmol) in DMF was added, followed by tetrabutylammonium iodide (0.1022 g, 0.06 mmol), and the reaction was warmed to room temperature and stirred for 1.5 hours. The mixture was diluted with EtOAc and H$_2$O, and the aqueous layer was extracted twice with EtOAc. The combined organic layers were washed three times with H$_2$O, and then dried and concentrated, and the residue was purified by silica gel chromatography (40-90% EtOAc in hexanes) to give the title compound.

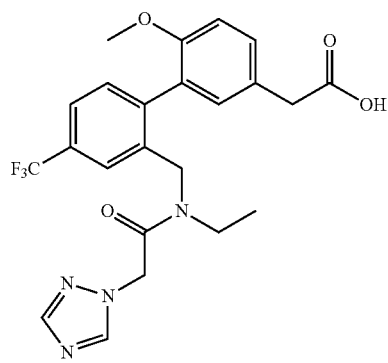 [SMILES: CCN(Cc1cc(C(F)(F)F)ccc1-c1cc(CC(=O)O)ccc1OC)C(=O)Cn1cncn1]

Step 2: (2'-{[Ethyl-(2-[1,2,4]triazol-1-yl-acetyl)-amino]-methyl}-6-methoxy-4'-trifluoromethyl-biphenyl-3-yl)-acetic acid Prepared according to the procedure described in Example 31, Step 2, using the following starting material: (2'-{[ethyl-(2-[1,2,4]triazol-1-yl-acetyl)-amino]-methyl}-6-methoxy-4'-trifluoromethyl-biphenyl-3-yl)-acetic acid ethyl ester. M+H is 477.

Example 94

Synthesis of (2'-{[Ethyl-(2-pyrrolidin-1-yl-acetyl)-amino]-methyl}-6-methoxy-4'-trifluoromethyl-biphenyl-3-yl)-acetic acid (Compound 1-151)

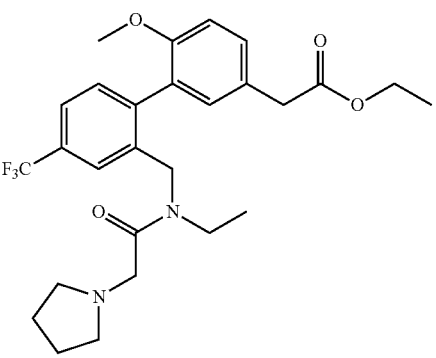 [SMILES: CCOC(=O)Cc1ccc(OC)c(-c2ccc(C(F)(F)F)cc2CN(CC)C(=O)CN2CCCC2)c1]

Step 1: (2'-{[Ethyl-(2-pyrrolidin-1-yl-acetyl)-amino]-methyl}-6-methoxy-4'-trifluoromethyl-biphenyl-3-yl)-acetic acid ethyl ester (2'-{[(2-Chloro-acetyl)-ethyl-amino]-methyl}-6-methoxy-4'-trifluoromethyl-biphenyl-3-yl)-acetic acid ethyl ester (0.55 mmol), pyrrolidine (0.05 mL, 0.61 mmol), potassium carbonate (0.152 g, 1.1 mmol), and sodium iodide (0.082 g, 0.55 mmol) were combined in MeCN (3 mL), and the reaction was stirred for 3 hours at room temperature. Analytical LCMS indicated that some starting material was still present, so additional potassium carbonate (0.053 g, 0.39 mmol) was added, and the reaction was stirred for 45 minutes. The mixture was diluted with EtOAc and H$_2$O, and the aqueous layer was extracted twice with EtOAc. The combined organic layers were dried and concentrated to give the title compound.

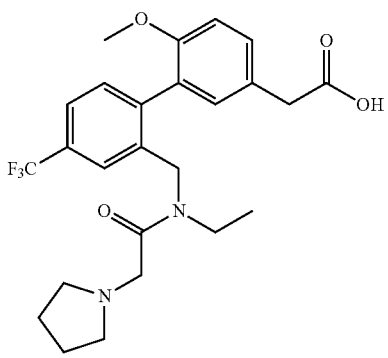 [SMILES: CCN(Cc1cc(C(F)(F)F)ccc1-c1cc(CC(=O)O)ccc1OC)C(=O)CN1CCCC1]

Step 2: (2'-{[Ethyl-(2-pyrrolidin-1-yl-acetyl)-amino]-methyl}-6-methoxy-4'-trifluoromethyl-biphenyl-3-yl)-acetic acid Prepared according to the procedure described in Example 31, Step 2, using the following starting material: (2'-{[ethyl-(2-pyrrolidin-1-yl-acetyl)-amino]-methyl}-6-methoxy-4'-trifluoromethyl-biphenyl-3-yl)-acetic acid ethyl ester. M+H is 479.

Example 95

Synthesis of {2'-[3-(3,4-Dichloro-benzyl)-1-ethyl-ureidomethyl]-6-methoxy-4'-trifluoromethyl-biphenyl-3-yl}-acetic acid (Compound 1-152)

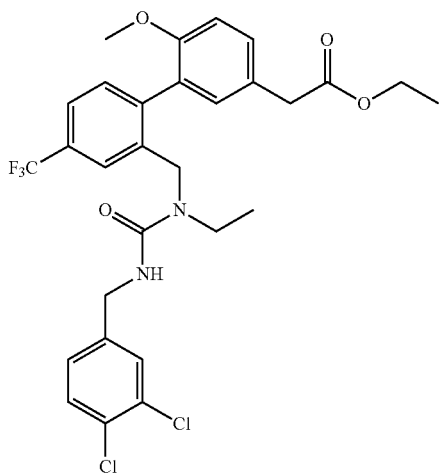 [SMILES: CCOC(=O)Cc1ccc(OC)c(-c2ccc(C(F)(F)F)cc2CN(CC)C(=O)NCc2ccc(Cl)c(Cl)c2)c1]

Step 1: {2'-[3-(3,4-Dichloro-benzyl)-1-ethyl-ureidomethyl]-6-methoxy-4'-trifluoromethyl-biphenyl-3-yl}-acetic acid ethyl ester (2'-Ethylaminomethyl-6-methoxy-4'-trifluoromethyl-biphenyl-3-yl)-acetic acid ethyl ester (0.170 g, 0.42 mmol) and triethylamine (0.12 mL, 0.86 mmol) were combined in CH$_2$Cl$_2$ (2 mL). 3,4-Dichlorobenzyl isocyanate (0.08 mL, 0.52 mmol) was added, and the reaction was stirred at room temperature for 15 minutes. After concentrating, the crude material was purified by silica gel chromatography (20-50% EtOAc in hexanes) to give the title compound.

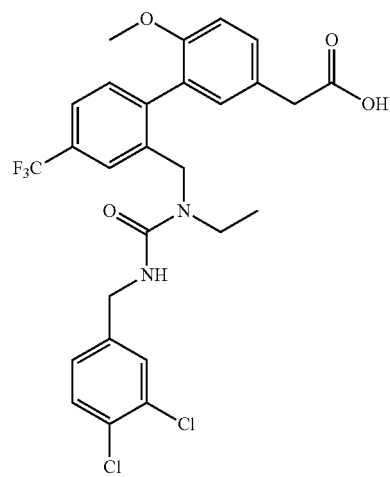 [SMILES: CCN(Cc1cc(C(F)(F)F)ccc1-c1cc(CC(=O)O)ccc1OC)C(=O)NCc1ccc(Cl)c(Cl)c1]

Step 2: {2'-[3-(3,4-Dichloro-benzyl)-1-ethyl-ureidomethyl]-6-methoxy-4'-trifluoromethyl-biphenyl-3-yl}-acetic acid Prepared according to the procedure described in Example 91, Step 2, using the following starting material: {2'-[3-(3,4-dichloro-benzyl)-1-ethyl-ureidomethyl]-6-methoxy-4'-trifluoromethyl-biphenyl-3-yl}-acetic acid ethyl ester. M+H is 569.

Example 96

Synthesis of {2'-[3-(3,5-Dichloro-benzyl)-1-ethyl-ureidomethyl]-6-methoxy-4'-trifluoromethyl-biphenyl-3-yl}-acetic acid (Compound 1-165)

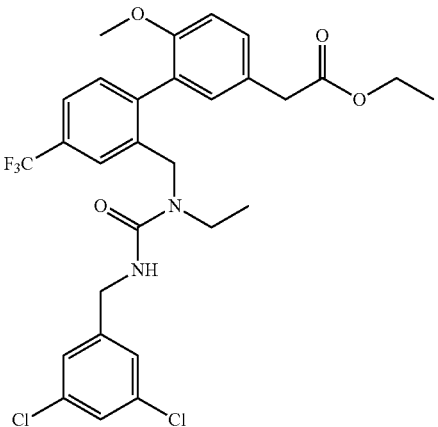 [SMILES: CCOC(=O)Cc1ccc(OC)c(-c2ccc(C(F)(F)F)cc2CN(CC)C(=O)NCc2cc(Cl)cc(Cl)c2)c1]

Step 1: {2'-[3-(3,5-Dichloro-benzyl)-1-ethyl-ureidomethyl]-6-methoxy-4'-trifluoromethyl-biphenyl-3-yl}-acetic acid ethyl ester To a solution of (2'-ethylaminomethyl-6-methoxy-4'-trifluoromethyl-biphenyl-3-yl)-acetic acid ethyl ester (0.170 g, 0.43 mmol) in CH$_2$Cl$_2$ (2 mL) at 0° C. was added diisopropylethylamine (0.19 mL, 1.08 mmol), followed by phosgene (20% in toluene; 0.34 mL, 0.64 mmol), and the mixture was stirred for 1.5 hours. 3,5-Dichlorobenzylamine (0.091 g, 0.52 mmol) was added, followed by triethylamine (0.12 mL, 0.86 mmol), and the reaction was warmed to room temperature and stirred for 45 minutes. Analytical LCMS indicated that some starting material was still present, so additional triethylamine (0.12 mL, 0.86 mmol) was added, and the reaction was stirred for 1.5 hours. Analytical LCMS showed that starting material still remained, so another portion of triethylamine (0.25 mL, 17.9 mmol) was added, and the reaction was stirred overnight at room temperature. The mixture was worked up with CH$_2$Cl$_2$ and H$_2$O, and the aqueous layer was extracted twice with CH$_2$Cl$_2$. The combined organic layers were dried and concentrated, and the residue was purified by silica gel chromatography (0-50% EtOAc in hexanes) to give the title compound.

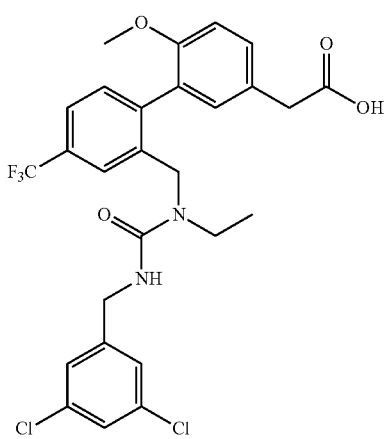

Step 2: {2'-[3-(3,5-Dichloro-benzyl)-1-ethyl-ureidomethyl]-6-methoxy-4'-trifluoromethyl-biphenyl-3-yl}-acetic acid Prepared according to the procedure described in Example 91, Step 2, using the following starting material: {2'-[3-(3,5-dichloro-benzyl)-1-ethyl-ureidomethyl]-6-methoxy-4'-trifluoromethyl-biphenyl-3-yl}-acetic acid ethyl ester. M+H is 570.

Example 97

Synthesis of {2'-[1-Ethyl-3-(4-fluoro-benzyl)-ureidomethyl]-6-methoxy-4'-trifluoromethyl-biphenyl-3-yl}-acetic acid (Compound 1-176)

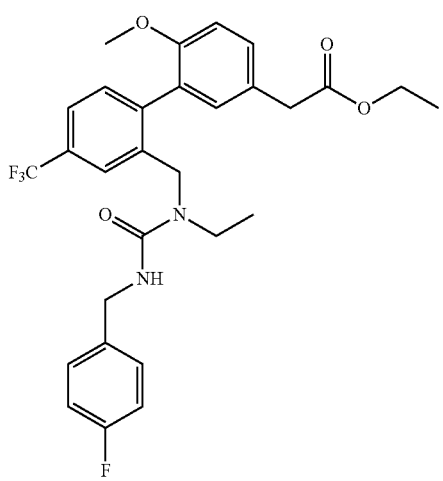 [SMILES: CCOC(=O)Cc1ccc(OC)c(-c2ccc(C(F)(F)F)cc2CN(CC)C(=O)NCc2ccc(F)cc2)c1]

Step 1: {2'-[1-Ethyl-3-(4-fluoro-benzyl)-ureidomethyl]-6-methoxy-4'-trifluoromethyl-biphenyl-3-yl}-acetic acid ethyl ester Prepared according to the procedure described in Example 96, Step 1, using the following starting materials: (2'-ethylaminomethyl-6-methoxy-4'-trifluoromethyl-biphenyl-3-yl)-acetic acid ethyl ester and 4-fluorobenzylamine.

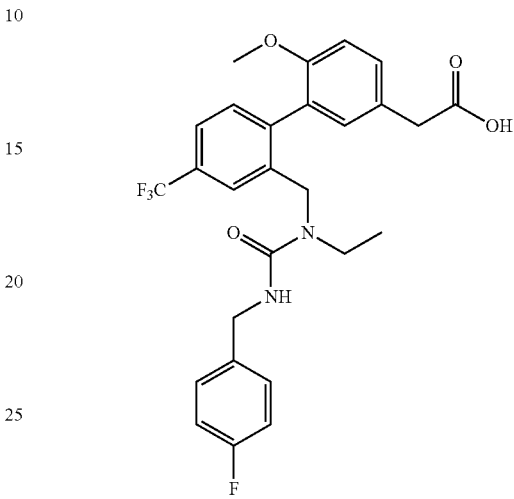

Step 2: {2'-[1-Ethyl-3-(4-fluoro-benzyl)-ureidomethyl]-6-methoxy-4'-trifluoromethyl-biphenyl-3-yl}-acetic acid Prepared according to the procedure described in Example 91, Step 2, using the following starting material: {2'-[1-ethyl-3-(4-fluoro-benzyl)-ureidomethyl]-6-methoxy-4'-trifluoromethyl-biphenyl-3-yl}-acetic acid ethyl ester. M+H is 519.

Example 98

Synthesis of {2'-[3-(3-Chloro-benzyl)-1-ethyl-ureidomethyl]-6-methoxy-4'-trifluoromethyl-biphenyl-3-yl}-acetic acid (Compound 1-177)

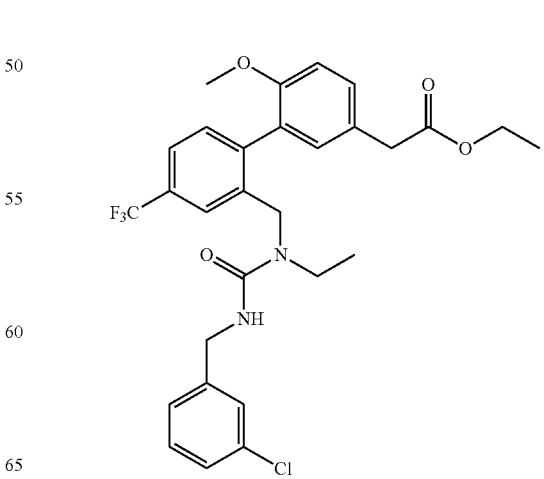

Step 1: {2'-[3-(3-Chloro-benzyl)-1-ethyl-ureidomethyl]-6-methoxy-4'-trifluoromethyl-biphenyl-3-yl}-acetic acid ethyl ester Prepared according to the procedure described in Example 96, Step 1, using the following starting materials: (2'-ethylaminomethyl-6-methoxy-4'-trifluoromethyl-biphenyl-3-yl)-acetic acid ethyl ester and 3-chlorobenzylamine.

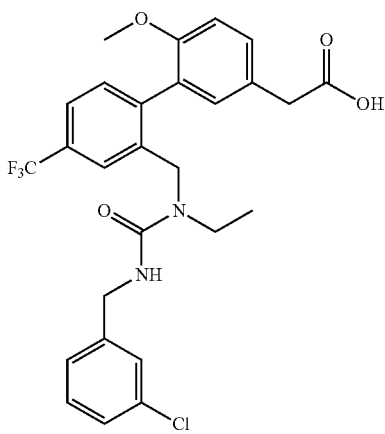 [SMILES: CCN(Cc1cc(C(F)(F)F)ccc1-c1cc(CC(=O)O)ccc1OC)C(=O)NCc1cccc(Cl)c1]

Step 2: {2'-[3-(3-Chloro-benzyl)-1-ethyl-ureidomethyl]-6-methoxy-4'-trifluoromethyl-biphenyl-3-yl}-acetic acid Prepared according to the procedure described in Example 91, Step 2, using the following starting material: {2'-[3-(3-chloro-benzyl)-1-ethyl-ureidomethyl]-6-methoxy-4'-trifluoromethyl-biphenyl-3-yl}-acetic acid ethyl ester. M+H is 535.

Example 99

Synthesis of {2'-[3-(3,5-Difluoro-benzyl)-1-ethyl-ureidomethyl]-6-methoxy-4'-trifluoromethyl-biphenyl-3-yl}-acetic acid (Compound 1-178)

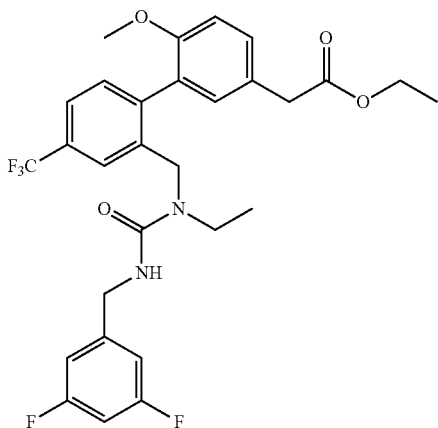 [SMILES: CCOC(=O)Cc1ccc(OC)c(-c2ccc(C(F)(F)F)cc2CN(CC)C(=O)NCc2cc(F)cc(F)c2)c1]

Step 1: {2'-[3-(3,5-Difluoro-benzyl)-1-ethyl-ureidomethyl]-6-methoxy-4'-trifluoromethyl-biphenyl-3-yl}-acetic acid ethyl ester Prepared according to the procedure described in Example 96, Step 1, using the following starting materials: (2'-ethylaminomethyl-6-methoxy-4'-trifluoromethyl-biphenyl-3-yl)-acetic acid ethyl ester and 3,5-difluorobenzylamine.

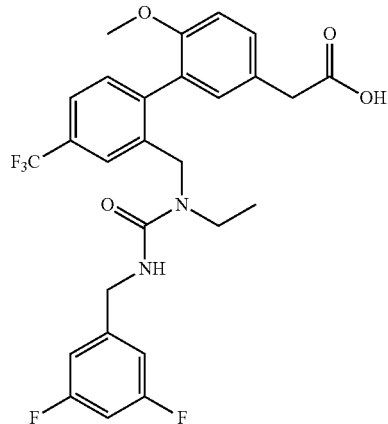 [SMILES: CCN(Cc1cc(C(F)(F)F)ccc1-c1cc(CC(=O)O)ccc1OC)C(=O)NCc1cc(F)cc(F)c1]

Step 2: {2'-[3-(3,5-Difluoro-benzyl)-1-ethyl-ureidomethyl]-6-methoxy-4'-trifluoromethyl-biphenyl-3-yl}-acetic acid Prepared according to the procedure described in Example 91, Step 2, using the following starting material: {2'-[3-(3,5-difluoro-benzyl)-1-ethyl-ureidomethyl]-6-methoxy-4'-trifluoromethyl-biphenyl-3-yl}-acetic acid ethyl ester. M+H is 537.

Example 100

Synthesis of (2'-{3-[(R)-1-(4-Chloro-phenyl)-ethyl]-1-ethyl-ureidomethyl}-6-methoxy-4'-trifluoromethyl-biphenyl-3-yl)-acetic acid (Compound 1-179)

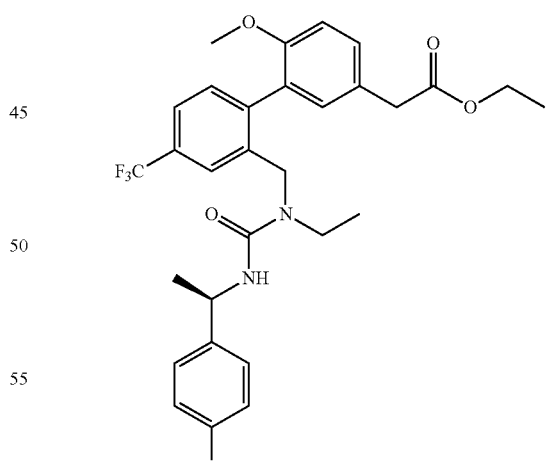

Step 1: (2'-{3-[(R)-1-(4-Chloro-phenyl)-ethyl]-1-ethyl-ureidomethyl}-6-methoxy-4'-trifluoromethyl-biphenyl-3-yl)-acetic acid ethyl ester Prepared according to the procedure described in Example 96, Step 1, using the following starting materials: (2'-ethylaminomethyl-6-methoxy-4'-trifluoromethyl-biphenyl-3-yl)-acetic acid ethyl ester and (R)-(+)-1-(4-chlorophenyl)ethylamine.

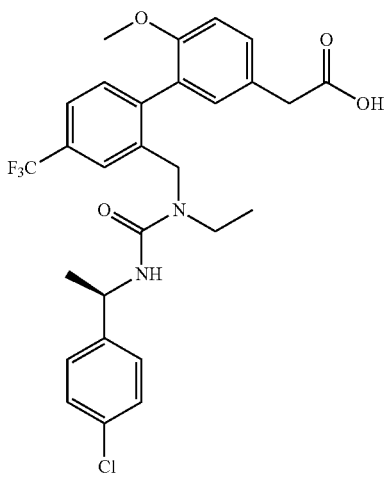 [SMILES: CCN(Cc1cc(C(F)(F)F)ccc1-c1cc(CC(=O)O)ccc1OC)C(=O)N[C@H](C)c1ccc(Cl)cc1]

Step 2: (2'-{3-[(R)-1-(4-Chloro-phenyl)-ethyl]-1-ethyl-ureidomethyl}-6-methoxy-4'-trifluoromethyl-biphenyl-3-yl)-acetic acid Prepared according to the procedure described in Example 91, Step 2, using the following starting material: (2'-{3-[(R)-1-(4-chloro-phenyl)-ethyl]-1-ethyl-ureidomethyl}-6-methoxy-4'-trifluoromethyl-biphenyl-3-yl)-acetic acid ethyl ester. M+H is 549.

Example 101

Synthesis of (2'-{3-[(S)-1-(4-Chloro-phenyl)-ethyl]-1-ethyl-ureidomethyl}-6-methoxy-4'-trifluoromethyl-biphenyl-3-yl)-acetic acid (Compound 1-180)

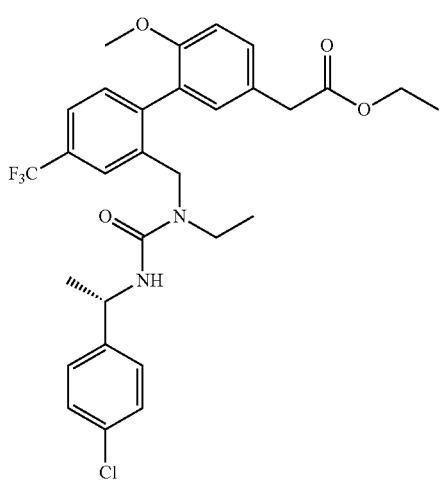 [SMILES: CCOC(=O)Cc1ccc(OC)c(-c2ccc(C(F)(F)F)cc2CN(CC)C(=O)N[C@@H](C)c2ccc(Cl)cc2)c1]

Step 1: (2'-{3-[(S)-1-(4-Chloro-phenyl)-ethyl]-1-ethyl-ureidomethyl}-6-methoxy-4'-trifluoromethyl-biphenyl-3-yl)-acetic acid ethyl ester Prepared according to the procedure described in Example 96, Step 1, using the following starting materials: (2'-ethylaminomethyl-6-methoxy-4'-trifluoromethyl-biphenyl-3-yl)-acetic acid ethyl ester and (S)-4-chloro-alpha-methylbenzylamine.

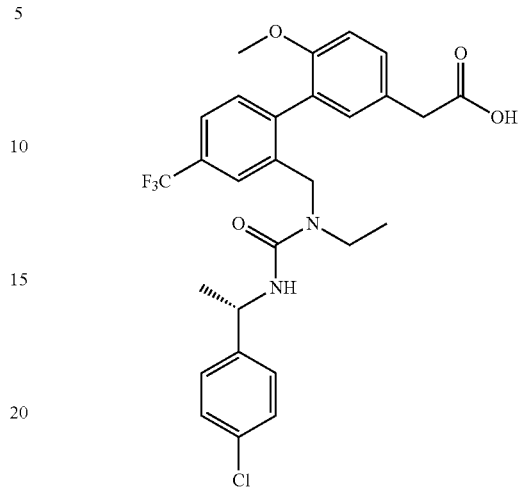

Step 2: (2'-{3-[(S)-1-(4-Chloro-phenyl)-ethyl]-1-ethyl-ureidomethyl}-6-methoxy-4'-trifluoromethyl-biphenyl-3-yl)-acetic acid Prepared according to the procedure described in Example 91, Step 2, using the following starting material: (2'-{3-[(S)-1-(4-chloro-phenyl)-ethyl]-1-ethyl-ureidomethyl}-6-methoxy-4'-trifluoromethyl-biphenyl-3-yl)-acetic acid ethyl ester. M+H is 549.

Example 102

Synthesis of [2'-(1,3-Diethyl-ureidomethyl)-6-methoxy-4'-trifluoromethyl-biphenyl-3-yl]-acetic acid (Compound 1-181)

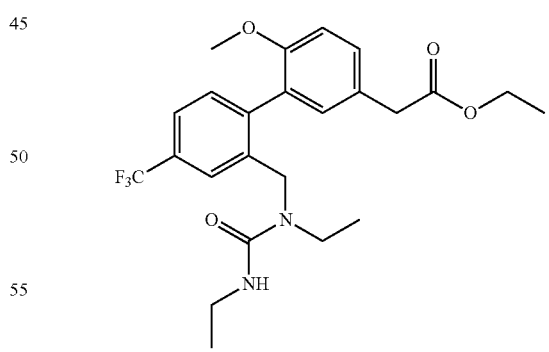

Step 1: [2'-(1,3-Diethyl-ureidomethyl)-6-methoxy-4'-trifluoromethyl-biphenyl-3-yl]-acetic acid ethyl ester Prepared according to the procedure described in Example 96, Step 1, using the following starting materials: (2'-ethylaminomethyl-6-methoxy-4'-trifluoromethyl-biphenyl-3-yl)-acetic acid ethyl ester and ethylamine (2M in THF).

249

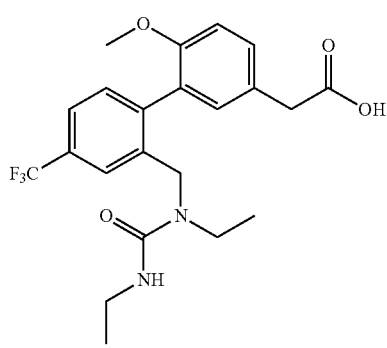 [SMILES: CCNC(=O)N(CC)Cc1cc(C(F)(F)F)ccc1-c1cc(CC(=O)O)ccc1OC]

Step 2: [2'-(1,3-Diethyl-ureidomethyl)-6-methoxy-4'-trifluoromethyl-biphenyl-3-yl]-acetic acid Prepared according to the procedure described in Example 91, Step 2, using the following starting material: [2'-(1,3-diethyl-ureidomethyl)-6-methoxy-4'-trifluoromethyl-biphenyl-3-yl]-acetic acid ethyl ester. M+H is 439.

Example 103

Synthesis of [2'-(3-Cyclopropyl-1-ethyl-ureidomethyl)-6-methoxy-4'-trifluoromethyl-biphenyl-3-yl]-acetic acid (Compound 1-182)

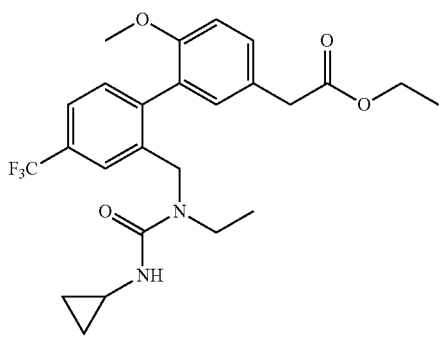 [SMILES: CCOC(=O)Cc1ccc(OC)c(-c2ccc(C(F)(F)F)cc2CN(CC)C(=O)NC2CC2)c1]

Step 1: [2'-(3-Cyclopropyl-1-ethyl-ureidomethyl)-6-methoxy-4'-trifluoromethyl-biphenyl-3-yl]-acetic acid ethyl ester Prepared according to the procedure described in Example 96, Step 1, using the following starting materials: (2'-ethylaminomethyl-6-methoxy-4'-trifluoromethyl-biphenyl-3-yl)-acetic acid ethyl ester and cyclopropylamine.

250

Step 2: [2'-(3-Cyclopropyl-1-ethyl-ureidomethyl)-6-methoxy-4'-trifluoromethyl-biphenyl-3-yl]-acetic acid Prepared according to the procedure described in Example 91, Step 2, using the following starting material: [2'-(3-cyclopropyl-1-ethyl-ureidomethyl)-6-methoxy-4'-trifluoromethyl-biphenyl-3-yl]-acetic acid ethyl ester. M+H is 451.

Example 104

Synthesis of [2'-(1-Ethyl-3-pyridin-3-ylmethyl-ureidomethyl)-6-methoxy-4'-trifluoromethyl-biphenyl-3-yl]-acetic acid (Compound 1-198)

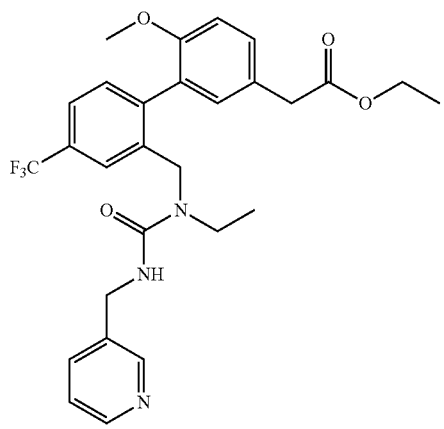 [SMILES: CCOC(=O)Cc1ccc(OC)c(-c2ccc(C(F)(F)F)cc2CN(CC)C(=O)NCc2cccnc2)c1]

Step 1: [2'-(1-Ethyl-3-pyridin-3-ylmethyl-ureidomethyl-6-methoxy-4'-trifluoromethyl-biphenyl-3-yl]-acetic acid ethyl ester Prepared according to the procedure described in Example 96, Step 1, using the following starting materials: (2'-ethylaminomethyl-6-methoxy-4'-trifluoromethyl-biphenyl-3-yl)-acetic acid ethyl ester and 3-(aminomethyl)pyridine.

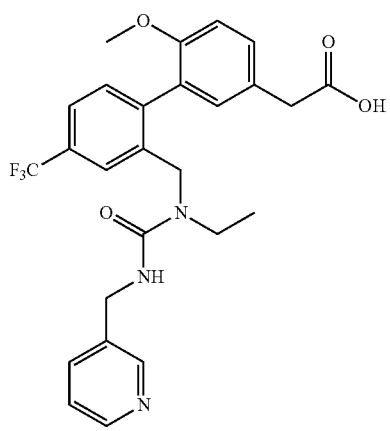 [SMILES: CCN(Cc1cc(C(F)(F)F)ccc1-c1cc(CC(=O)O)ccc1OC)C(=O)NCc1cccnc1]

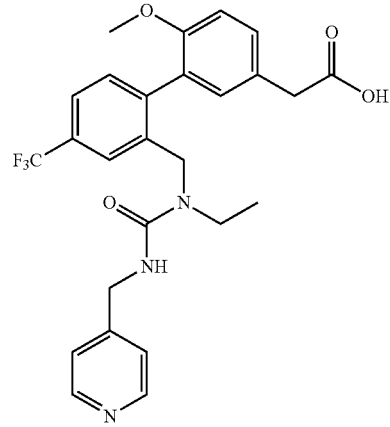

Step 2: [2'-(1-Ethyl-3-pyridin-3-ylmethyl-ureidomethyl)-6-methoxy-4'-trifluoromethyl-biphenyl-3-yl]-acetic acid Prepared according to the procedure described in Example 91, Step 2, using the following starting material: [2'-(1-ethyl-3-pyridin-3-ylmethyl-ureidomethyl)-6-methoxy-4'-trifluoromethyl-biphenyl-3-yl]-acetic acid ethyl ester. M+H is 502.

Step 2: [2'-(1-Ethyl-3-pyridin-4-ylmethyl-ureidomethyl)-6-methoxy-4'-trifluoromethyl-biphenyl-3-yl]-acetic acid Prepared according to the procedure described in Example 91, Step 2, using the following starting material: [2'-(1-ethyl-3-pyridin-4-ylmethyl-ureidomethyl)-6-methoxy-4'-trifluoromethyl-biphenyl-3-yl]-acetic acid ethyl ester. M+H is 502.

Example 105

Synthesis of [2'-(1-Ethyl-3-pyridin-4-ylmethyl-ureidomethyl)-6-methoxy-4'-trifluoromethyl-biphenyl-3-yl]-acetic acid (Compound 1-199)

Example 106

Synthesis of {2'-[3-(6-Chloro-pyridin-3-ylmethyl)-1-ethyl-ureidomethyl]-6-methoxy-4'-trifluoromethyl-biphenyl-3-yl}-acetic acid (Compound 1-200)

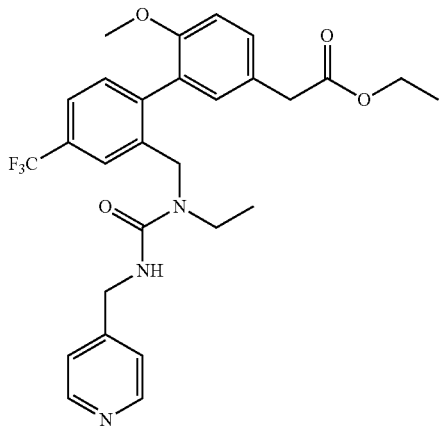 [SMILES: CCOC(=O)Cc1ccc(OC)c(-c2ccc(C(F)(F)F)cc2CN(CC)C(=O)NCc2ccncc2)c1]

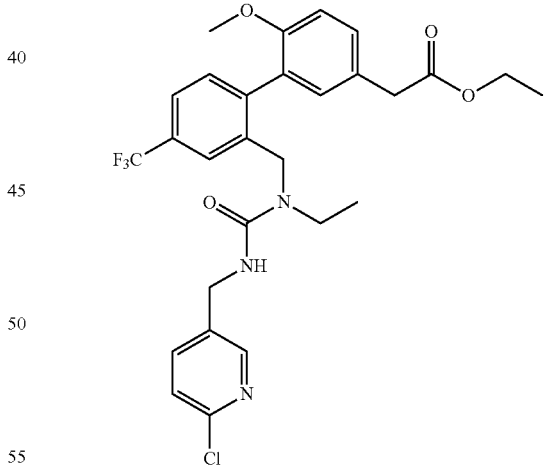

Step 1: [2'-(1-Ethyl-3-pyridin-4-ylmethyl-ureidomethyl)-6-methoxy-4'-trifluoromethyl-biphenyl-3-yl]-acetic acid ethyl ester Prepared according to the procedure described in Example 96, Step 1, using the following starting materials: (2'-ethylaminomethyl-6-methoxy-4'-trifluoromethyl-biphenyl-3-yl)-acetic acid ethyl ester and 4-(aminomethyl)pyridine.

Step 1: {2'-[3-(6-Chloro-pyridin-3-ylmethyl)-1-ethyl-ureidomethyl]-6-methoxy-4'-trifluoromethyl-biphenyl-3-yl}-acetic acid ethyl ester Prepared according to the procedure described in Example 96, Step 1, using the following starting materials: (2'-ethylaminomethyl-6-methoxy-4'-trifluoromethyl-biphenyl-3-yl)-acetic acid ethyl ester and 5-aminomethyl-2-chloropyridine.

253

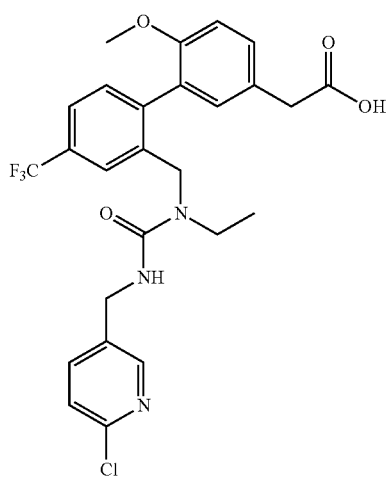 [SMILES: CCN(Cc1cc(C(F)(F)F)ccc1-c1cc(CC(=O)O)ccc1OC)C(=O)NCc1ccc(Cl)nc1]

Step 2: {2'-[3-(6-Chloro-pyridin-3-ylmethyl)-1-ethyl-ureidomethyl]-6-methoxy-4'-trifluoromethyl-biphenyl-3-yl}-acetic acid Prepared according to the procedure described in Example 91, Step 2, using the following starting material: {2'-[3-(6-chloro-pyridin-3-ylmethyl)-1-ethyl-ureidomethyl]-6-methoxy-4'-trifluoromethyl-biphenyl-3-yl}-acetic acid ethyl ester. M+H is 536.

Example 107

Synthesis of {2'-[(Cyclobutanecarbonyl-ethyl-amino)-methyl]-6-methoxy-4'-trifluoromethyl-biphenyl-3-yl}-acetic acid (Compound 1-206)

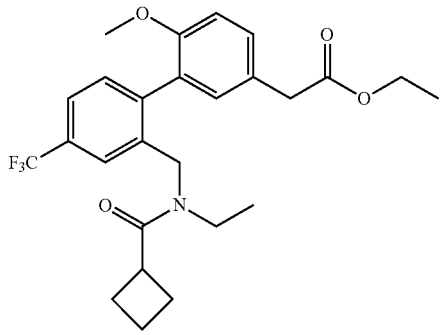 [SMILES: CCOC(=O)Cc1ccc(OC)c(-c2ccc(C(F)(F)F)cc2CN(CC)C(=O)C2CCC2)c1]

Step 1: {2'-[(Cyclobutanecarbonyl-ethyl-amino)-methyl]-6-methoxy-4'-trifluoromethyl-biphenyl-3-yl}-acetic acid ethyl ester Prepared according to the procedure described in Example 1, Step 6, using the following starting materials: (2'-ethylaminomethyl-6-methoxy-4'-trifluoromethyl-biphenyl-3-yl)-acetic acid ethyl ester and cyclobutanecarbonyl chloride.

254

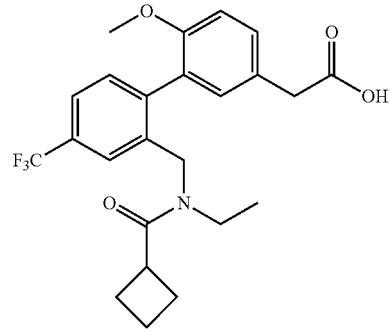 [SMILES: CCN(Cc1cc(C(F)(F)F)ccc1-c1cc(CC(=O)O)ccc1OC)C(=O)C1CCC1]

Step 2: {2'-[(Cyclobutanecarbonyl-ethyl-amino)-methyl]-6-methoxy-4'-trifluoromethyl-biphenyl-3-yl}-acetic acid Prepared according to the procedure described in Example 91, Step 2, using the following starting material: {2'-[(cyclobutanecarbonyl-ethyl-amino)-methyl]-6-methoxy-4'-trifluoromethyl-biphenyl-3-yl}-acetic acid ethyl ester. M+H is 450.

Example 108

Synthesis of {2'-[(Ethyl-phenylacetyl-amino)-methyl]-6-methoxy-4'-trifluoromethyl-biphenyl-3-yl}-acetic acid (Compound 1-207)

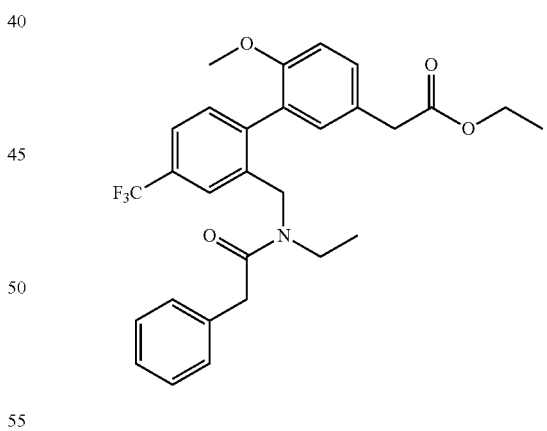

Step 1: {2'-[(Ethyl-phenylacetyl-amino)-methyl]-6-methoxy-4'-trifluoromethyl-biphenyl-3-yl}-acetic acid ethyl ester Prepared according to the procedure described in Example 1, Step 6, using the following starting materials: (2'-ethylaminomethyl-6-methoxy-4'-trifluoromethyl-biphenyl-3-yl)-acetic acid ethyl ester and phenylacetyl chloride.

255

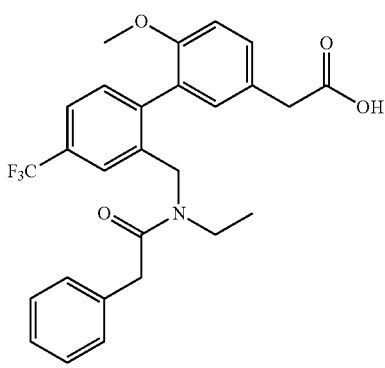 [SMILES: CCN(Cc1cc(C(F)(F)F)ccc1-c1cc(CC(=O)O)ccc1OC)C(=O)Cc1ccccc1]

Step 2: {2'-[(Ethyl-phenylacetyl-amino)-methyl]-6-methoxy-4'-trifluoromethyl-biphenyl-3-yl}-acetic acid Prepared according to the procedure described in Example 91, Step 2, using the following starting material: {2'-[(ethyl-phenylacetyl-amino)-methyl]-6-methoxy-4'-trifluoromethyl-biphenyl-3-yl}-acetic acid ethyl ester. M+H is 486.

Example 109

Synthesis of (2'-{[Ethyl-(3-phenyl-propionyl)-amino]-methyl}-6-methoxy-4'-trifluoromethyl-biphenyl-3-yl)-acetic acid (Compound 1-208)

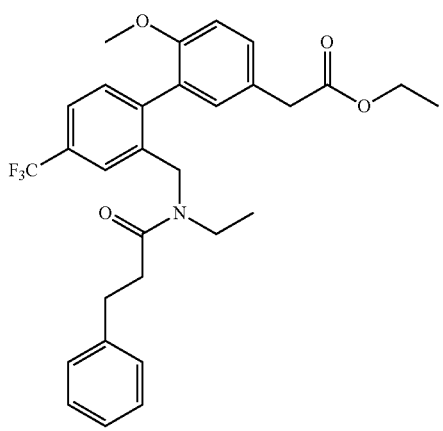 [SMILES: CCOC(=O)Cc1ccc(OC)c(-c2ccc(C(F)(F)F)cc2CN(CC)C(=O)CCc2ccccc2)c1]

Step 1: (2'-{[Ethyl-(3-phenyl-propionyl)-amino]-methyl}-6-methoxy-4'-trifluoromethyl-biphenyl-3-yl)-acetic acid ethyl ester Prepared according to the procedure described in Example 1, Step 6, using the following starting materials: (2'-ethylaminomethyl-6-methoxy-4'-trifluoromethyl-biphenyl-3-yl)-acetic acid ethyl ester and hydrocinnamoyl chloride.

256

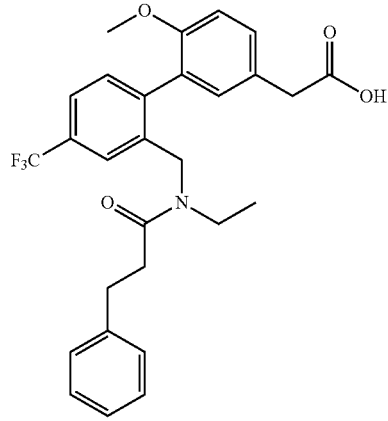 [SMILES: CCN(Cc1cc(C(F)(F)F)ccc1-c1cc(CC(=O)O)ccc1OC)C(=O)CCc1ccccc1]

Step 2: (2'-{[Ethyl-(3-phenyl-propionyl)-amino]-methyl}-6-methoxy-4'-trifluoromethyl-biphenyl-3-yl)-acetic acid Prepared according to the procedure described in Example 91, Step 2, using the following starting material: (2'-{[ethyl-(3-phenyl-propionyl)-amino]-methyl}-6-methoxy-4'-trifluoromethyl-biphenyl-3-yl)-acetic acid ethyl ester. M+H is 500.

Example 110

Synthesis of (2'-{[Ethyl-(1-hydroxy-cyclopropanecarbonyl)-amino]-methyl}-6-methoxy-4'-trifluoromethyl-biphenyl-3-yl)-acetic acid (Compound 1-209)

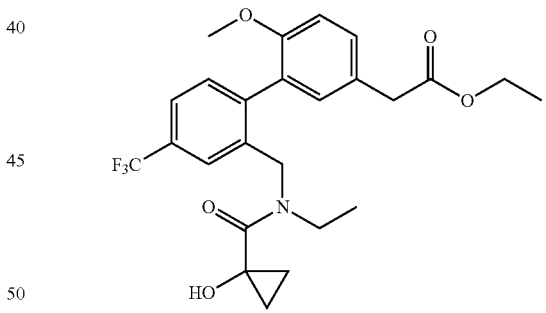

Step 1: (2'-{[Ethyl-(1-hydroxy-cyclopropanecarbonyl)-amino]-methyl}-6-methoxy-4'-trifluoromethyl-biphenyl-3-yl)-acetic acid ethyl ester (2'-Ethylaminomethyl-6-methoxy-4'-trifluoromethyl-biphenyl-3-yl)-acetic acid ethyl ester (0.240 g, 0.61 mmol), 1-hydroxy-1-cyclopropanecarboxylic acid (0.074 g, 0.73 mmol), 1-ethyl-3-(3-dimethylaminopropyl)carbodiimide hydrochloride (0.175 g, 0.92 mmol), 1-hydroxybenzotriazole (0.124 g, 0.92 mmol), and triethylamine (0.21 mL, 1.53 mmol) were combined in $CH_2Cl_2$ (2 mL) and stirred at room temperature for 2 hours. The mixture was concentrated, and the residue was purified by silica gel chromatography (20-90% EtOAc in hexanes) to give the title compound.

257

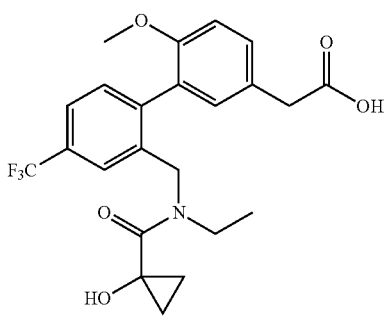 [SMILES: CCN(Cc1cc(C(F)(F)F)ccc1-c1cc(CC(=O)O)ccc1OC)C(=O)C1(O)CC1]

Step 2: (2'-{[Ethyl-(1-hydroxy-cyclopropanecarbonyl)-amino]-methyl}-6-methoxy-4'-trifluoromethyl-biphenyl-3-yl)-acetic acid Prepared according to the procedure described in Example 91, Step 2, using the following starting material: (2'-{[ethyl-(1-hydroxy-cyclopropanecarbonyl)-amino]-methyl}-6-methoxy-4'-trifluoromethyl-biphenyl-3-yl)-acetic acid ethyl ester. M+H is 452.

Example 111

Synthesis of {2'-[(1-Ethyl-ureido)-methyl]-6-methoxy-4'-trifluoromethyl-biphenyl-3-yl}-acetic acid (Compound 1-210)

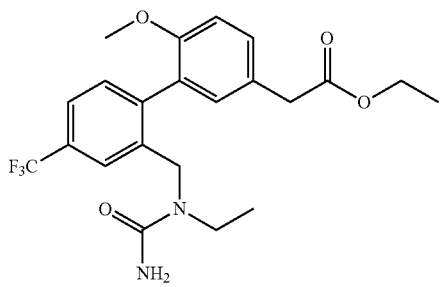 [SMILES: CCOC(=O)Cc1ccc(OC)c(-c2ccc(C(F)(F)F)cc2CN(CC)C(N)=O)c1]

Step 1: {2'-[(1-Ethyl-ureido)-methyl]-6-methoxy-4'-trifluoromethyl-biphenyl-3-yl}-acetic acid ethyl ester (2'-Ethylaminomethyl-6-methoxy-4'-trifluoromethyl-biphenyl-3-yl)-acetic acid ethyl ester (0.202 g, 0.51 mmol) and sodium cyanate (0.052 g, 0.77 mmol) were combined in $H_2O$ (2 mL). Acetic acid (0.04 mL, 0.77 mmol) was added, and the reaction was stirred for 1 hour. DMF (1 mL) was added to facilitate stirring, and the reaction was stirred for 1.5 hours. The solution was extracted with EtOAc, and the combined organic layers were dried and concentrated to give the title compound.

258

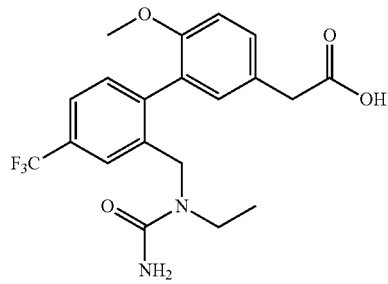 [SMILES: CCN(Cc1cc(C(F)(F)F)ccc1-c1cc(CC(=O)O)ccc1OC)C(N)=O]

Step 2: {2'-[(1-Ethyl-ureido)-methyl]-6-methoxy-4'-trifluoromethyl-biphenyl-3-yl}-acetic acid Prepared according to the procedure described in Example 91, Step 2, using the following starting material: {2'-[(1-ethyl-ureido)-methyl]-6-methoxy-4'-trifluoromethyl-biphenyl-3-yl}-acetic acid ethyl ester. M+H is 411.

Example 112

Synthesis of 2-{2'-[(Cyclopropanecarbonyl-ethyl-amino)-methyl]-6-methoxy-4'-trifluoromethyl-biphenyl-3-yl}-propionic acid (Compound 1-217)

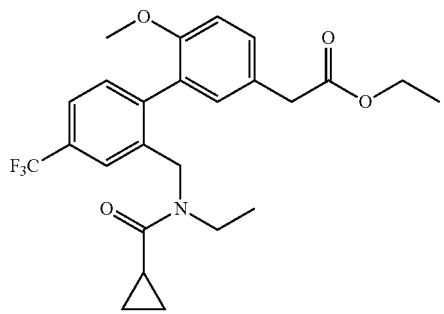 [SMILES: CCOC(=O)Cc1ccc(OC)c(-c2ccc(C(F)(F)F)cc2CN(CC)C(=O)C2CC2)c1]

Step 1: {2'-[(Cyclopropanecarbonyl-ethyl-amino)-methyl]-6-methoxy-4'-trifluoromethyl-biphenyl-3-yl}-acetic acid ethyl ester Prepared according to the procedure described in Example 1, Step 6, using the following starting materials: (2'-ethylaminomethyl-6-methoxy-4'-trifluoromethyl-biphenyl-3-yl)-acetic acid ethyl ester and cyclopropanecarbonyl chloride.

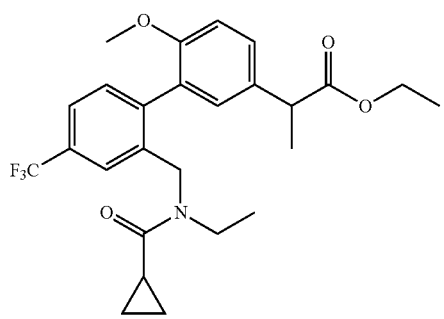

Step 2: 2-{2'-[(Cyclopropanecarbonyl-ethyl-amino)-methyl]-6-methoxy-4'-trifluoromethyl-biphenyl-3-yl}-propionic acid ethyl ester {2'-[(Cyclopropanecarbonyl-ethyl-amino)-methyl]-6-methoxy-4'-trifluoromethyl-biphenyl-3-yl}-acetic acid ethyl ester (0.408 g, 0.88 mmol) was dissolved in THF (4 mL) and cooled to −78° C. Sodium bis(trimethylsilyl)amide (1M in THF; 1.06 mL, 1.06 mmol) was added, followed by iodomethane (0.06 mL, 0.97 mmol), and the reaction was stirred at −78° C. for 30 minutes. The mixture was quenched with saturated aqueous NH₄Cl and warmed to room temperature. The mixture was extracted three times with EtOAc, and the combined organic layers were dried, concentrated, and purified by silica gel chromatography (10-40% EtOAc in hexanes) to give the title compound.

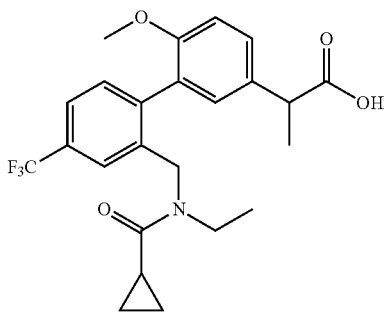

Step 3: 2-{2'-[(Cyclopropanecarbonyl-ethyl-amino)-methyl]-6-methoxy-4'-trifluoromethyl-biphenyl-3-yl}-propionic acid Prepared according to the procedure described in Example 91, Step 2, using the following starting material: 2-{2'-[(cyclopropanecarbonyl-ethyl-amino)-methyl]-6-methoxy-4'-trifluoromethyl-biphenyl-3-yl}-propionic acid ethyl ester. M+H is 450.

Example 113

Synthesis of 2-[2'-(3-Benzyl-1-ethyl-ureidomethyl)-6-methoxy-4'-trifluoromethyl-biphenyl-3-yl]-propionic acid (Compound 1-222)

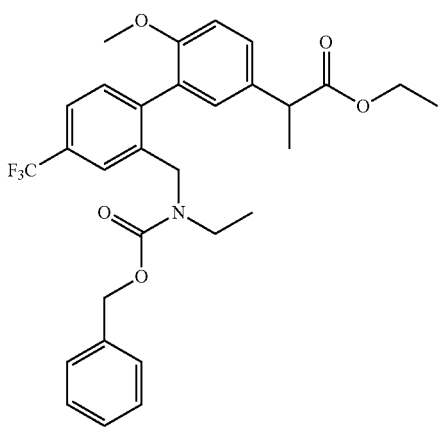 [SMILES: CCOC(=O)C(C)c1ccc(OC)c(-c2ccc(C(F)(F)F)cc2CN(CC)C(=O)OCc2ccccc2)c1]

Step 1: 2-{2'-[(Benzyloxycarbonyl-ethyl-amino)-methyl]-6-methoxy-4'-trifluoromethyl-biphenyl-3-yl}-propionic acid ethyl ester 2-{2'-[(Benzyloxycarbonyl-ethyl-amino)-methyl]-6-methoxy-4'-trifluoromethyl-biphenyl-3-yl}-propionic acid (0.058 g, 0.11 mmol) in EtOH (3 mL) was treated with sulfuric acid (2 drops) at 70° C. for 1.5 hours to give the title compound.

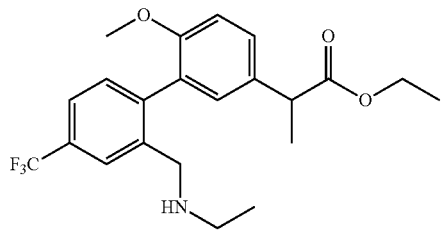 [SMILES: CCNCc1cc(C(F)(F)F)ccc1-c1cc(C(C)C(=O)OCC)ccc1OC]

Step 2: 2-(2'-Ethylaminomethyl-6-methoxy-4'-trifluoromethyl-biphenyl-3-yl)-propionic acid ethyl ester To a solution of 2-{2'-[(benzyloxycarbonyl-ethyl-amino)-methyl]-6-methoxy-4'-trifluoromethyl-biphenyl-3-yl}-propionic acid ethyl ester (0.11 mmol) in EtOH (12 mL) was added 10% palladium on carbon (0.050 g), and the reaction was stirred under a balloon of H₂ at room temperature for 1 hour. The mixture was filtered through a pad of Celite and rinsed with EtOH. The filtrate was concentrated to give the title compound.

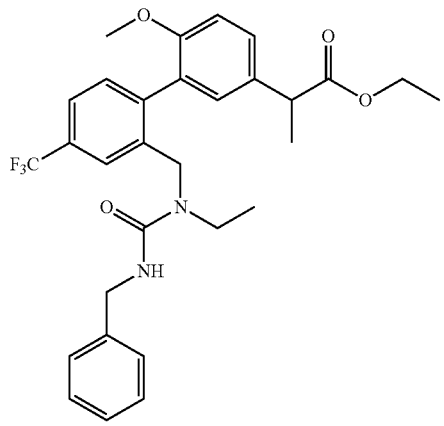

Step 3: 2-[2'-(3-Benzyl-1-ethyl-ureidomethyl)-6-methoxy-4'-trifluoromethyl-biphenyl-3-yl]-propionic acid ethyl ester Prepared according to the procedure described in Example 95, Step 1, using the following starting materials: 2-(2'-ethylaminomethyl-6-methoxy-4'-trifluoromethyl-biphenyl-3-yl)-propionic acid ethyl ester and benzyl isocyanate.

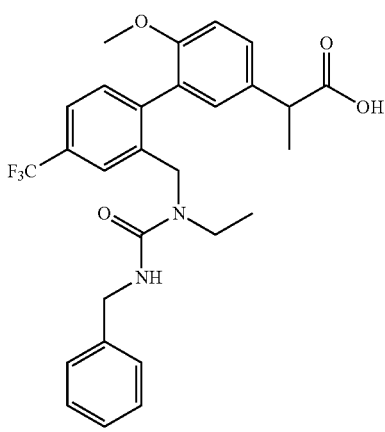 [SMILES: CCN(Cc1cc(C(F)(F)F)ccc1-c1cc(C(C)C(=O)O)ccc1OC)C(=O)NCc1ccccc1]

Step 4: 2-[2'-(3-Benzyl-1-ethyl-ureidomethyl)-6-methoxy-4'-trifluoromethyl-biphenyl-3-yl]-propionic acid Prepared according to the procedure described in Example 91, Step 2, using the following starting material: 2-[2'-(3-benzyl-1-ethyl-ureidomethyl)-6-methoxy-4'-trifluoromethyl-biphenyl-3-yl]-propionic acid ethyl ester. M+H is 515.

Example 114

Synthesis of Cyclopropanecarboxylic acid ethyl-{2'-methoxy-5'-[(R)-1-methyl-2-((4R,5S)-4-methyl-2-oxo-5-phenyl-oxazolidin-3-yl)-2-oxo-ethyl]-4-trifluoromethyl-biphenyl-2-ylmethyl}-amide (Compound 2-12) and Cyclopropanecarboxylic acid ethyl-{2'-methoxy-5'-[(S)-1-methyl-2-((4R,5S)-4-methyl-2-oxo-5-phenyl-oxazolidin-3-yl)-2-oxo-ethyl]-4-trifluoromethyl-biphenyl-2-ylmethyl}-amide (Compound 2-13)

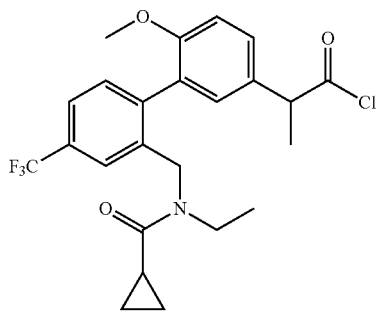 [SMILES: CCN(Cc1cc(C(F)(F)F)ccc1-c1cc(C(C)C(=O)Cl)ccc1OC)C(=O)C1CC1]

Step 1: 2-{2'-[(Cyclopropanecarbonyl-ethyl-amino)-methyl]-6-methoxy-4'-trifluoromethyl-biphenyl-3-yl}-propionyl chloride To 2-{2'-[(cyclopropanecarbonyl-ethyl-amino)-methyl]-6-methoxy-4'-trifluoromethyl-biphenyl-3-yl}-propionic acid (0.096 g, 0.21 mmol) and triethylamine (0.04 mL, 0.26 mmol) in CH$_2$Cl$_2$ (2 mL) at 0° C. was added oxalyl chloride (0.02 mL, 0.26 mmol), followed by DMF (2 drop and the reaction was stirred at 0° C. for 1.5 hours. The mixture was concentrated to give the title compound.

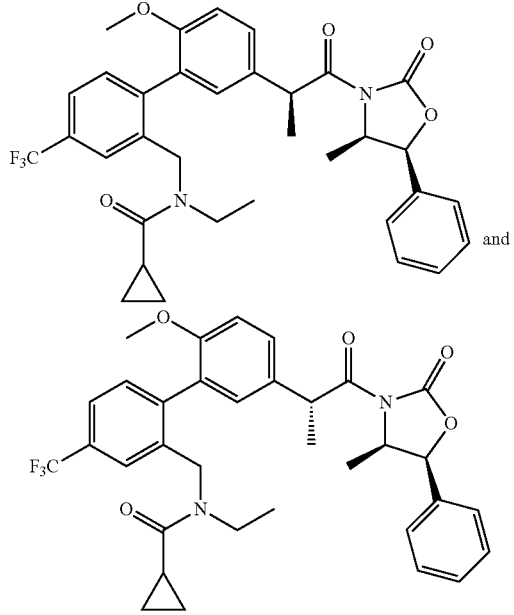

and

Step 2: Cyclopropanecarboxylic acid ethyl-{2'-methoxy-5'-[(S)-1-methyl-2-((4R,5S)-4-methyl-2-oxo-5-phenyl-oxazolidin-3-yl)-2-oxo-ethyl]-4-trifluoromethyl-biphenyl-2-ylmethyl}-amide and Cyclopropanecarboxylic acid ethyl-{2'-methoxy-5'-[(R)-1-methyl-2-((4R,5S)-4-methyl-2-oxo-5-phenyl-oxazolidin-3-yl)-2-oxo-ethyl]-4-trifluoromethyl-biphenyl-2-ylmethyl}-amide To (4R,5S)-4-methyl-5-phenyl-2-oxazolidinone (0.037 g, 0.21 mmol) in THF (2 mL) at −78° C. was added n-butyllithium (1.6M in hexanes; 0.20 mL, 0.32 mmol), and the mixture was stirred for 1 hour. A solution of 2-{2'-[(cyclopropanecarbonyl-ethyl-amino)-methyl]-6-methoxy-4'-trifluoromethyl-biphenyl-3-yl}-propionyl chloride (0.21 mmol) in THF (2 mL) was added dropwise, and the reaction was stirred for 1 hour at −78° C. The mixture was worked-up with EtOAc and H$_2$O, and the organic layer was dried and concentrated. The residue was purified by preparative HPLC to give the title compounds as separate products. M+H is 609 (Compound 2-12); M+H is 609 (Compound 2-13).

Example 115

Synthesis of (R)-2-{2'-[(Cyclopropanecarbonyl-ethyl-amino)-methyl]-6-methoxy-4'-trifluoromethyl-biphenyl-3-yl}-propionic acid (Compound 1-224)

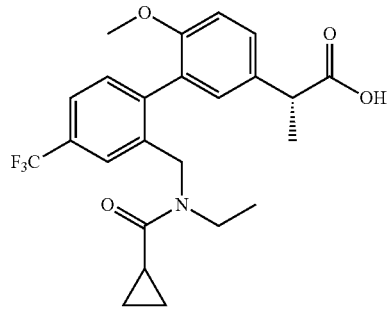 [SMILES: CCN(Cc1cc(C(F)(F)F)ccc1-c1cc([C@@H](C)C(=O)O)ccc1OC)C(=O)C1CC1]

Cyclopropanecarboxylic acid ethyl-{2'-methoxy-5'-[(R)-1-methyl-2-((4R,5S)-4-methyl-2-oxo-5-phenyl-oxazolidin- 3-yl)-2-oxo-ethyl]-4-trifluoromethyl-biphenyl-2-ylmethyl}-amide (0.011 g, 0.02 mmol) in THF (1 mL) and H₂O (1 mL) was treated with hydrogen peroxide (30%; 0.004 mL, 0.04 mmol) and lithium hydroxide (0.002 g, 0.04 mmol), and the reaction was stirred overnight at room temperature. The mixture was acidified to pH 3-4 with 1N aqueous HCl and extracted three times with EtOAc. The combined organic layers were dried and concentrated to give the title compound. M+H is 450.

Example 116

Synthesis of (S)-2-{2'-[(Cyclopropanecarbonyl-ethyl-amino)-methyl]-6-methoxy-4'-trifluoromethyl-biphenyl-3-yl}-propionic acid (Compound 1-225)

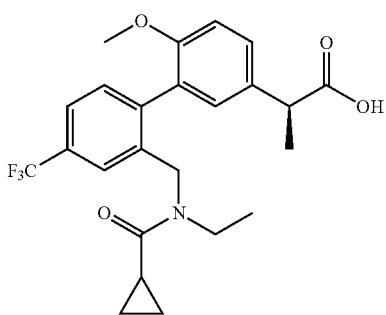 [SMILES: CCN(Cc1cc(C(F)(F)F)ccc1-c1cc([C@H](C)C(=O)O)ccc1OC)C(=O)C1CC1]

Prepared according to the procedure described in Example 115, Step 1, using the following starting material: Cyclopropanecarboxylic acid ethyl-{2'-methoxy-5'-[(S)-1-methyl-2-((4R,5S)-4-methyl-2-oxo-5-phenyl-oxazolidin-3-yl)-2-oxo-ethyl]-4-trifluoromethyl-biphenyl-2-ylmethyl}-amide. M+H is 450.

Example 117

Synthesis of 2-[2'-(3-Cyclopropyl-1-ethyl-ureidomethyl)-6-methoxy-4'-trifluoromethyl-biphenyl-3-yl]-propionic acid (Compound 1-243)

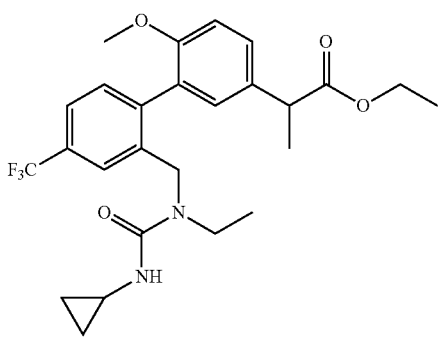 [SMILES: CCOC(=O)C(C)c1ccc(OC)c(-c2ccc(C(F)(F)F)cc2CN(CC)C(=O)NC2CC2)c1]

Step 1: 2-[2'-(3-Cyclopropyl-1-ethyl-ureidomethyl)-6-methoxy-4'-trifluoromethyl-biphenyl-3-yl]-propionic acid ethyl ester Prepared according to the procedure described in Example 96, Step 1, using the following starting material: 2-(2'-ethylaminomethyl-6-methoxy-4'-trifluoromethyl-biphenyl-3-yl)-propionic acid ethyl ester and cyclopropylamine.

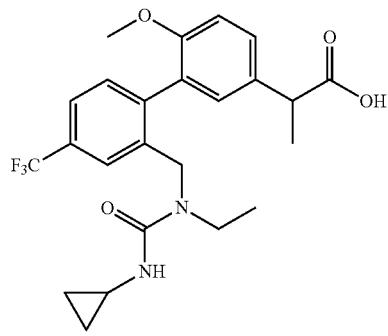 [SMILES: CCN(Cc1cc(C(F)(F)F)ccc1-c1cc(C(C)C(=O)O)ccc1OC)C(=O)NC1CC1]

Step 2: 2-[2'-(3-Cyclopropyl-1-ethyl-ureidomethyl)-6-methoxy-4'-trifluoromethyl-biphenyl-3-yl]-propionic acid Prepared according to the procedure described in Example 91, Step 2, using the following starting material: 2-[2'-(3-cyclopropyl-1-ethyl-ureidomethyl)-6-methoxy-4'-trifluoromethyl-biphenyl-3-yl]-propionic acid ethyl ester. M+H is 465.

Example 118

Synthesis of {2'-[(Cyclopropanecarbonyl-ethyl-amino)-methyl]-4'-trifluoromethyl-biphenyl-3-yl}-acetic acid (Compound 1-244)

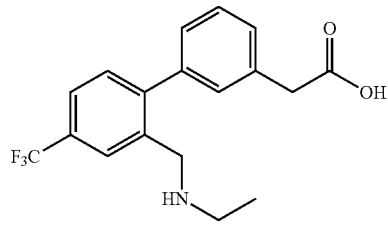 [SMILES: CCNCc1cc(C(F)(F)F)ccc1-c1cccc(CC(=O)O)c1]

Step 1: (2'-Ethylaminomethyl-4'-trifluoromethyl-biphenyl-3-yl)-acetic acid

{2'-[(Benzyloxycarbonyl-ethyl-amino)-methyl]-4'-trifluoromethyl-biphenyl-3-yl}-acetic acid (0.16 g, 0.34 mmol) in EtOH (7 mL) was treated with 10% palladium on carbon (0.072 g), and the reaction was stirred under a balloon of H₂ for 3 hours to give the title compound.

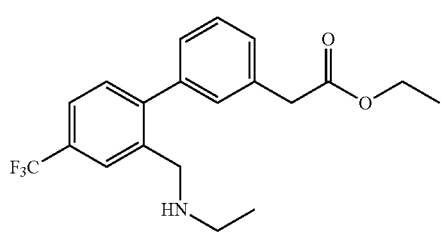 [SMILES: CCNCc1cc(C(F)(F)F)ccc1-c1cccc(CC(=O)OCC)c1]

Step 2: (2'-Ethylaminomethyl-4'-trifluoromethyl-biphenyl-3-yl)-acetic acid ethyl ester To a solution of (2'-ethylaminomethyl-4'-trifluoromethyl-biphenyl-3-yl)-acetic acid (0.34 mmol) in EtOH (7 mL) was added sulfuric acid (34 drops), and the reaction was stirred at 50° C. overnight. Once no starting material was seen by analytical LCMS, the mixture was filtered over a pad of Celite and rinsed with EtOH. The filtrate was concentrated to give the title compound.

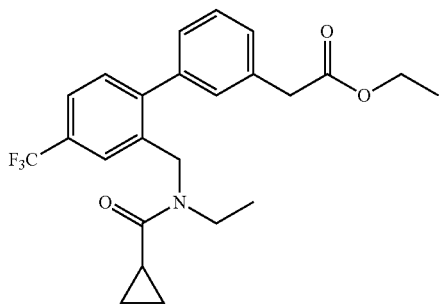 [SMILES: CCOC(=O)Cc1cccc(-c2ccc(C(F)(F)F)cc2CN(CC)C(=O)C2CC2)c1]

Step 3: {2'-[(Cyclopropanecarbonyl-ethyl-amino)-methyl]-4'-trifluoromethyl-biphenyl-3-yl}-acetic acid ethyl ester Prepared according to the procedure described in Example 1, Step 6, using the following starting materials: (2'-ethylaminomethyl-4'-trifluoromethyl-biphenyl-3-yl)-acetic acid ethyl ester and cyclopropanecarbonyl chloride.

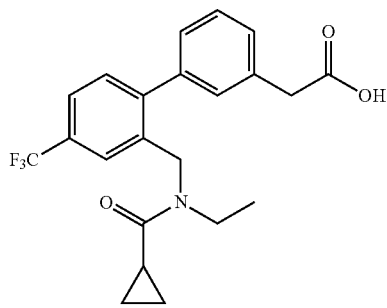 [SMILES: CCN(Cc1cc(C(F)(F)F)ccc1-c1cccc(CC(=O)O)c1)C(=O)C1CC1]

Step 4: {2'-[(Cyclopropanecarbonyl-ethyl-amino)-methyl]-4'-trifluoromethyl-biphenyl-3-yl}-acetic acid Prepared according to the procedure described in Example 91, Step 2, using the following starting material: {2'-[(cyclopropanecarbonyl-ethyl-amino)-methyl]-4'-trifluoromethyl-biphenyl-3-yl}-acetic acid ethyl ester. M+H is 406.

Example 119

Synthesis of (2'-{[(2,2-Dimethyl-propionyl)-ethyl-amino]-methyl}-6-methoxy-4'-trifluoromethyl-biphenyl-3-yl)-acetic acid (Compound 1-245)

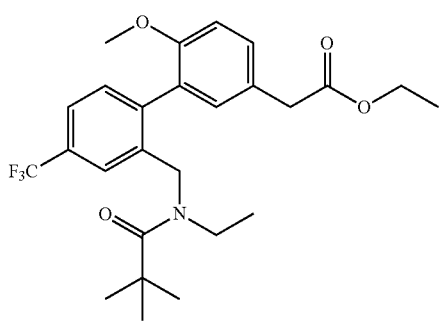 [SMILES: CCOC(=O)Cc1ccc(OC)c(-c2ccc(C(F)(F)F)cc2CN(CC)C(=O)C(C)(C)C)c1]

Step 1: (2'-{[(2,2-Dimethyl-propionyl)-ethyl-amino]-methyl}-6-methoxy-4'-trifluoromethyl-biphenyl-3-yl)-acetic acid ethyl ester Prepared according to the procedure described in Example 1, Step 6, using the following starting materials: (2'-ethylaminomethyl-6-methoxy-4'-trifluoromethyl-biphenyl-3-yl)-acetic acid ethyl ester and trimethylacetyl chloride.

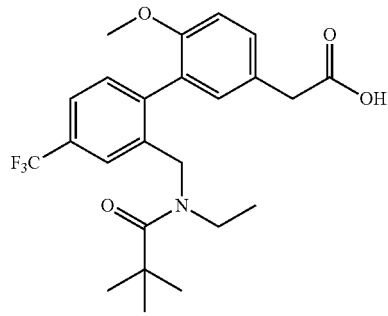 [SMILES: CCN(Cc1cc(C(F)(F)F)ccc1-c1cc(CC(=O)O)ccc1OC)C(=O)C(C)(C)C]

Step 2: (2'-{[(2,2-Dimethyl-propionyl)-ethyl-amino]-methyl}-6-methoxy-4'-trifluoromethyl-biphenyl-3-yl)-acetic acid Prepared according to the procedure described in Example 91, Step 2, using the following starting material: (2'-{[(2,2-dimethyl-propionyl)-ethyl-amino]-methyl}-6-methoxy-4'-trifluoromethyl-biphenyl-3-yl)-acetic acid ethyl ester. M+H is 452.

Example 120

Synthesis of {2'-[(Ethyl-isobutyryl-amino)-methyl]-6-methoxy-4'-trifluoromethyl-biphenyl-3-yl}-acetic acid (Compound 1-246)

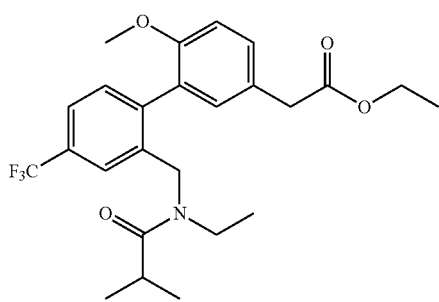 [SMILES: CCOC(=O)Cc1ccc(OC)c(-c2ccc(C(F)(F)F)cc2CN(CC)C(=O)C(C)C)c1]

Step 1: {2'-[(Ethyl-isobutyryl-amino)-methyl]-6-methoxy-4'-trifluoromethyl-biphenyl-3-yl}-acetic acid ethyl ester Prepared according to the procedure described in Example 1, Step 6, using the following starting materials: (2'-ethylaminomethyl-6-methoxy-4'-trifluoromethyl-biphenyl-3-yl)-acetic acid ethyl ester and isobutyryl chloride.

267

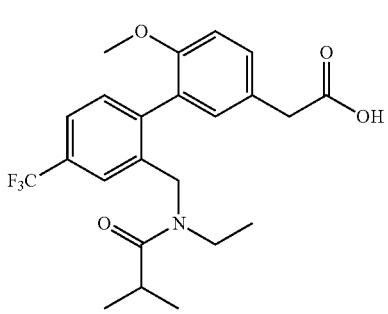 [SMILES: CCN(Cc1cc(C(F)(F)F)ccc1-c1cc(CC(=O)O)ccc1OC)C(=O)C(C)C]

Step 2: {2'-[(Ethyl-isobutyryl-amino)-methyl]-6-methoxy-4'-trifluoromethyl-biphenyl-3-yl}-acetic acid Prepared according to the procedure described in Example 91, Step 2, using the following starting material: {2'-[(ethyl-isobutyryl-amino)-methyl]-6-methoxy-4'-trifluoromethyl-biphenyl-3-yl}-acetic acid ethyl ester. M+H is 438.

Example 121

Synthesis of {4'-Bromo-2'-[(cyclopropanecarbonyl-ethyl-amino)-methyl]-6-methoxy-biphenyl-3-yl}-acetic acid (Compound 1-247)

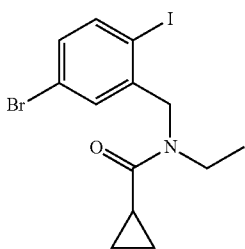 [SMILES: CCN(Cc1cc(Br)ccc1I)C(=O)C1CC1]

Step 1: Cyclopropanecarboxylic acid(5-bromo-2-iodo-benzyl)-ethyl-amide

Prepared according to the procedure described in Example 1, Step 6, using the following starting materials: (5-bromo-2-iodo-benzyl)-ethyl-amine and cyclopropanecarbonyl chloride.

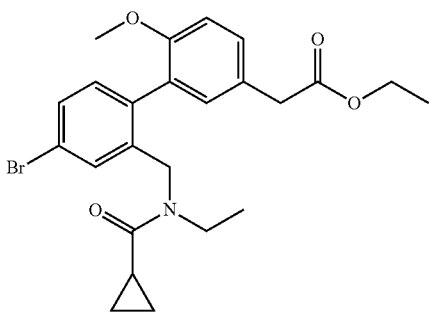 [SMILES: CCOC(=O)Cc1ccc(OC)c(-c2ccc(Br)cc2CN(CC)C(=O)C2CC2)c1]

268

Step 2: {4'-Bromo-2'-[(cyclopropanecarbonyl-ethyl-amino)-methyl]-6-methoxy-biphenyl-3-yl}-acetic acid ethyl ester Prepared according to the procedure described in Example 1, Step 4, using the following starting materials: cyclopropanecarboxylic acid(5-bromo-2-iodo-benzyl)-ethyl-amide and [4-methoxy-3-(4,4,5,5-tetramethyl-[1,3,2]dioxaborolan-2-yl)-phenyl]-acetic acid ethyl ester.

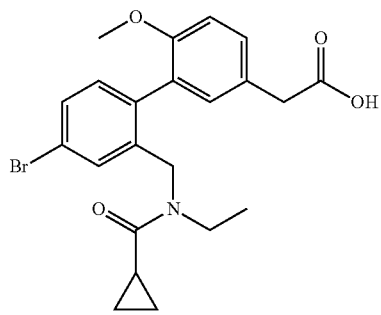 [SMILES: CCN(Cc1cc(Br)ccc1-c1cc(CC(=O)O)ccc1OC)C(=O)C1CC1]

Step 3: {4'-Bromo-2'-[(cyclopropanecarbonyl-ethyl-amino)-methyl]-6-methoxy-biphenyl-3-yl}-acetic acid Prepared according to the procedure described in Example 31, Step 2, using the following starting material: {4'-bromo-2'-[(cyclopropanecarbonyl-ethyl-amino)-methyl]-6-methoxy-biphenyl-3-yl}-acetic acid ethyl ester. M+H is 446.

Example 122

Synthesis of [2'-(3-Benzyl-ureidomethyl)-6-methoxy-4'-trifluoromethyl-biphenyl-3-yl]-acetic acid (Compound 1-251)

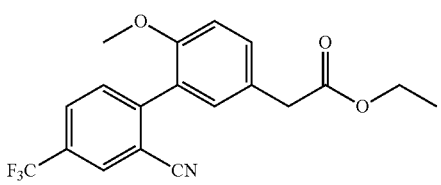 [SMILES: CCOC(=O)Cc1ccc(OC)c(-c2ccc(C(F)(F)F)cc2C#N)c1]

Step 1: (2'-Cyano-6-methoxy-4'-trifluoromethyl-biphenyl-3-yl)-acetic acid ethyl ester 2-Bromo-5-(trifluoromethyl)benzonitrile (5.5 g, 22 mmol), [4-methoxy-3-(4,4,5,5-tetramethyl-[1,3,2]dioxaborolan-2-yl)-phenyl]-acetic acid ethyl ester (7.04 g, 22 mmol), potassium carbonate (7.6 g, 55 mmol), and tetrakis(triphenylphosphine)palladium(0) (0.300 g, 0.25 mmol) were combined in DME (40 mL) and $H_2O$ (20 mL). The mixture was purged with $N_2$, and then stirred at 85° C. for 36 hours. After standard work-up, the residue was purified by silica gel chromatography to give the title compound.

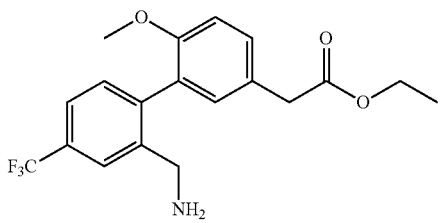 [SMILES: CCOC(=O)Cc1ccc(OC)c(-c2ccc(C(F)(F)F)cc2CN)c1]

Step 2: (2'-Aminomethyl-6-methoxy-4'-trifluoromethyl-biphenyl-3-yl)-acetic acid ethyl ester To a solution of (2'-cyano-6-methoxy-4'-trifluoromethyl-biphenyl-3-yl)-acetic acid ethyl ester (0.545 g, 1.5 mmol) and cobalt(II) chloride hexahydrate (0.71 g, 3.0 mmol) in MeOH (60 mL) and THF (24 mL) was added sodium borohydride (0.58 g, 15.3 mmol), and the reaction was stirred at room temperature for 2 hours. 2N Aqueous HCl (67 mL) was added, and the mixture was concentrated. 2N Aqueous $NH_4OH$ was added until the solution was basic, and the mixture was extracted twice with $CH_2Cl_2$. The combined organic layers were washed three times with $H_2O$, dried over $Na_2SO_4$, filtered, and concentrated to give the title compound.

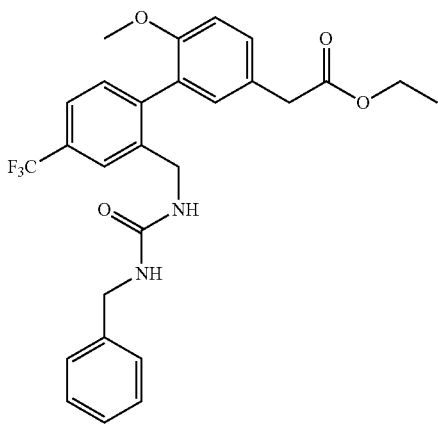 [SMILES: CCOC(=O)Cc1ccc(OC)c(-c2ccc(C(F)(F)F)cc2CNC(=O)NCc2ccccc2)c1]

Step 3: [2'-(3-Benzyl-ureidomethyl)-6-methoxy-4'-trifluoromethyl-biphenyl-3-yl]-acetic acid ethyl ester Prepared according to the procedure described in Example 95, Step 1, using the following starting materials: (2'-aminomethyl-6-methoxy-4'-trifluoromethyl-biphenyl-3-yl)-acetic acid ethyl ester and benzyl isocyanate.

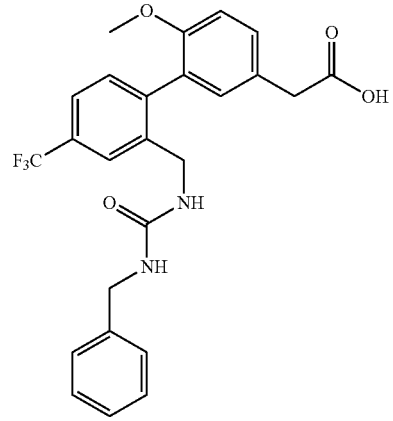 [SMILES: COc1ccc(CC(=O)O)cc1-c1ccc(C(F)(F)F)cc1CNC(=O)NCc1ccccc1]

Step 4: [2'-(3-Benzyl-ureidomethyl)-6-methoxy-4'-trifluoromethyl-biphenyl-3-yl]-acetic add Prepared according to the procedure described in Example 31, Step 2, using the following starting material: [2'-(3-benzyl-ureidomethyl)-6-methoxy-4'-trifluoromethyl-biphenyl-3-yl]-acetic acid ethyl ester.

Example 123

Synthesis of {6-Benzyloxy-2'-[(benzyloxycarbonyl-ethyl-amino)-methyl]-4'-trifluoromethyl-biphenyl-3-yl}-acetic acid (Compound 1-128)

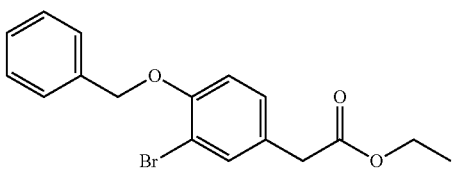 [SMILES: CCOC(=O)Cc1ccc(OCc2ccccc2)c(Br)c1]

Step 1: (4-Benzyloxy-3-bromo-phenyl)-acetic acid ethyl ester

To a suspension of (3-bromo-4-hydroxy-phenyl)-acetic acid ethyl ester (0.100 g, 0.39 mmol) and cesium carbonate (0.376 g, 1.16 mmol) in MeCN was added benzyl bromide (0.06 mL, 0.46 mmol), and the reaction was stirred at room temperature until no starting material was seen by analytical tlc. The mixture was partitioned between EtOAc and H2O, and the aqueous layer was extracted with EtOAc. The combined organic layers were dried over MgSO4, filtered, and concentrated to give the title compound.

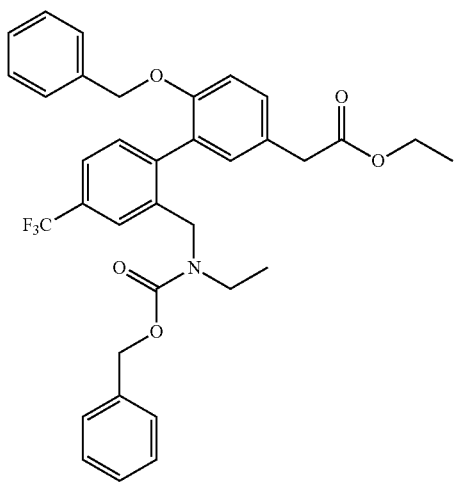 [SMILES: CCOC(=O)Cc1ccc(OCc2ccccc2)c(-c2ccc(C(F)(F)F)cc2CN(CC)C(=O)OCc2ccccc2)c1]

Step 2: {6-Benzyloxy-2'-[(benzyloxycarbonyl-ethyl-amino)-methyl]-4'-trifluoromethyl-biphenyl-3-yl}-acetic acid ethyl ester Prepared according to the procedure described in Example 1, Step 4, using the following starting materials: ethyl-[2-(4,4,5,5-tetramethyl-[1,3,2]dioxaborolan-2-yl)-5-trifluoromethyl-benzyl]-carbamic acid benzyl ester and (4-benzyloxy-3-bromo-phenyl)-acetic acid ethyl ester.

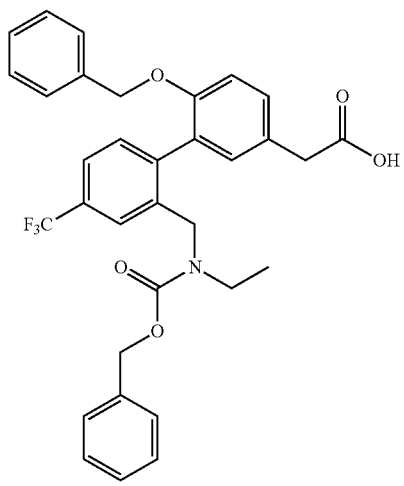 [SMILES: CCN(Cc1cc(C(F)(F)F)ccc1-c1cc(CC(=O)O)ccc1OCc1ccccc1)C(=O)OCc1ccccc1]

Step 3: {6-Benzyloxy-2'-[(benzyloxycarbonyl-ethyl-amino)-methyl]-4'-trifluoromethyl-biphenyl-3-yl}-acetic acid To a solution of {6-benzyloxy-2'-[(benzyloxycarbonyl-ethyl-amino)-methyl]-4'-trifluoromethyl-biphenyl-3-yl}-acetic acid ethyl ester (0.050 g, 0.08 mmol) in MeOH (3 mL) was added 1N aqueous LiOH (1 mL), and the reaction was stirred at 65° C. overnight. The mixture was acidified with 1N aqueous HCl and extracted with EtOAc. The combined organic layers were dried over MgSO$_4$, filtered, and concentrated, and the residue was purified by preparative HPLC to give the title compound. M+H is 578.

Example 124

Synthesis of {2'-[(Benzyloxycarbonyl-ethyl-amino)-methyl]-6-ethoxy-4'-trifluoromethyl-biphenyl-3-yl}-acetic acid (Compound 1-129)

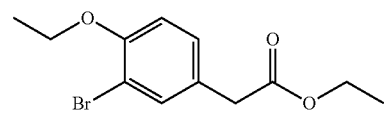 [SMILES: CCOC(=O)Cc1ccc(OCC)c(Br)c1]

Step 1: (3-Bromo-4-ethoxy-phenyl)-acetic acid ethyl ester

Prepared according to the procedure described in Example 123, Step 1, using the following starting materials: (3-bromo-4-hydroxy-phenyl)-acetic acid ethyl ester and iodoethane.

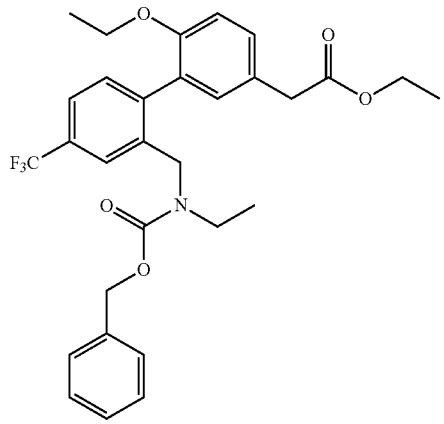 [SMILES: CCOC(=O)Cc1ccc(OCC)c(-c2ccc(C(F)(F)F)cc2CN(CC)C(=O)OCc2ccccc2)c1]

Step 2: {2'-[(Benzyloxycarbonyl-ethyl-amino)-methyl]-6-ethoxy-4'-trifluoromethyl-biphenyl-3-yl}-acetic acid ethyl ester Prepared according to the procedure described in Example 1, Step 4, using the following starting materials: ethyl-[2-(4,4,5,5-tetramethyl-[1,3,2]dioxaborolan-2-yl)-5-trifluoromethyl-benzyl]-carbamic acid benzyl ester and (3-bromo-4-ethoxy-phenyl)-acetic acid ethyl ester.

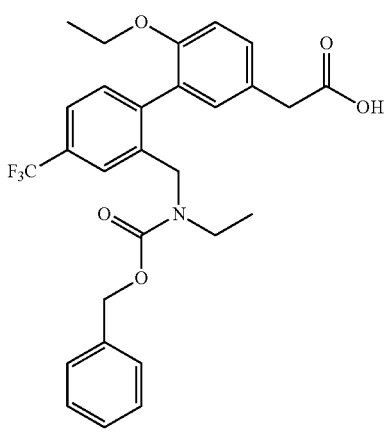 [SMILES: CCOc1ccc(CC(=O)O)cc1-c1ccc(C(F)(F)F)cc1CN(CC)C(=O)OCc1ccccc1]

Step 3: {2'-[(Benzyloxycarbonyl-ethyl-amino)-methyl]-6-ethoxy-4'-trifluoromethyl-biphenyl-3-yl}-acetic acid Prepared according to the procedure described in Example 123, Step 3, using the following starting material: {2'-[(benzyloxycarbonyl-ethyl-amino)-methyl]-6-ethoxy-4'-trifluoromethyl-biphenyl-3-yl}-acetic acid ethyl ester. M+H is 516.

Example 125

Synthesis of {2'-[(Benzyloxycarbonyl-ethyl-amino)-methyl]-6-cyclopropylmethoxy-4'-trifluoromethyl-biphenyl-3-yl}-acetic acid (Compound 1-130)

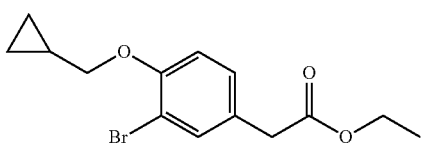 [SMILES: CCOC(=O)Cc1ccc(OCC2CC2)c(Br)c1]

Step 1: (3-Bromo-4-cyclopropylmethoxy-phenyl)-acetic acid ethyl ester

Prepared according to the procedure described in Example 123, Step 1, using the following starting materials: (3-bromo-4-hydroxy-phenyl)-acetic acid ethyl ester and (bromomethyl)cyclopropane.

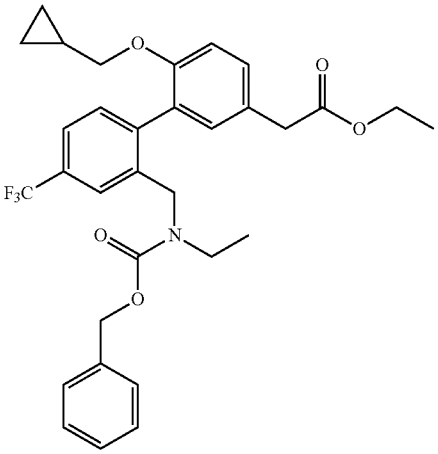 [SMILES: CCOC(=O)Cc1ccc(OCC2CC2)c(-c2ccc(C(F)(F)F)cc2CN(CC)C(=O)OCc2ccccc2)c1]

Step 2: {2'-[(Benzyloxycarbonyl-ethyl-amino)-methyl]-6-cyclopropylmethoxy-4'-trifluoromethyl-biphenyl-3-yl}-acetic acid ethyl ester Prepared according to the procedure described in Example 1, Step 4, using the following starting materials: ethyl-[2-(4,4,5,5-tetramethyl-[1,3,2]dioxaborolan-2-yl)-5-trifluoromethyl-benzyl]-carbamic acid benzyl ester and (3-bromo-4-cyclopropylmethoxy-phenyl)-acetic acid ethyl ester.

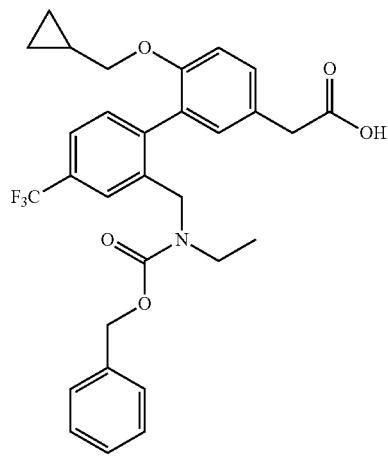 [SMILES: CCN(Cc1cc(C(F)(F)F)ccc1-c1cc(CC(=O)O)ccc1OCC1CC1)C(=O)OCc1ccccc1]

Step 3: {2'-[(Benzyloxycarbonyl-ethyl-amino)-methyl]-6-cyclopropylmethoxy-4'-trifluoromethyl-biphenyl-3-yl}-acetic acid Prepared according to the procedure described in Example 123, Step 3, using the following starting material: {2'-[(benzyloxycarbonyl-ethyl-amino)-methyl]-6-cyclopropylmethoxy-4'-trifluoromethyl-biphenyl-3-yl}-acetic acid ethyl ester. M+H is 542.

Example 126

Synthesis of [2'-(3-Benzyl-1-ethyl-ureidomethyl)-6-hydroxy-4'-trifluoromethyl-biphenyl-3-yl]-acetic acid ethyl ester (Compound 2-9)

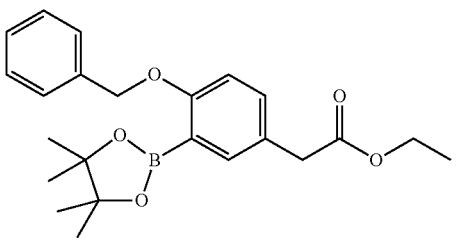 [SMILES: CCOC(=O)Cc1ccc(OCc2ccccc2)c(B2OC(C)(C)C(C)(C)O2)c1]

Step 1: [4-Benzyloxy-3-(4,4,5,5-tetramethyl-[1,3,2]dioxaborolan-2-yl)-phenyl]-acetic acid ethyl ester Prepared according to the procedure described in Example 1, Step 2, using the following starting materials: (4-benzyloxy-3-bromo-phenyl)-acetic acid ethyl ester and bis(pinacolato)diboron.

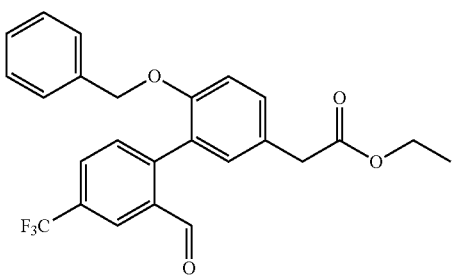 [SMILES: CCOC(=O)Cc1ccc(OCc2ccccc2)c(-c2ccc(C(F)(F)F)cc2C=O)c1]

Step 2: (6-Benzyloxy-2'-formyl-4'-trifluoromethyl-biphenyl-3-yl)-acetic acid ethyl ester Prepared according to the procedure described in Example 1, Step 4, using the following starting materials: [4-benzyloxy-3-(4,4,5,5-tetramethyl-[1,3,2]dioxaborolan-2-yl)-phenyl]-acetic acid ethyl ester and 2-bromo-5-(trifluoromethyl)benzaldehyde.

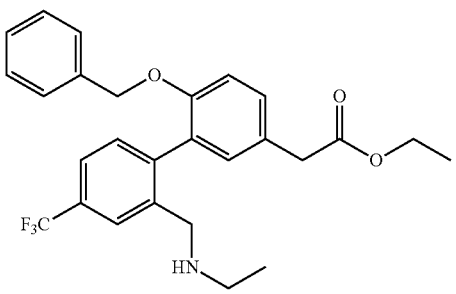 [SMILES: CCNCc1cc(C(F)(F)F)ccc1-c1cc(CC(=O)OCC)ccc1OCc1ccccc1]

Step 3: (6-Benzyloxy-2'-ethylaminomethyl-4'-trifluoromethyl-biphenyl-3-yl)-acetic acid ethyl ester Prepared according to the procedure described in Example 1, Step 5, using the following starting materials: (6-benzyloxy-2'-formyl-4'-trifluoromethyl-biphenyl-3-yl)-acetic acid ethyl ester and ethylamine (2M in THF).

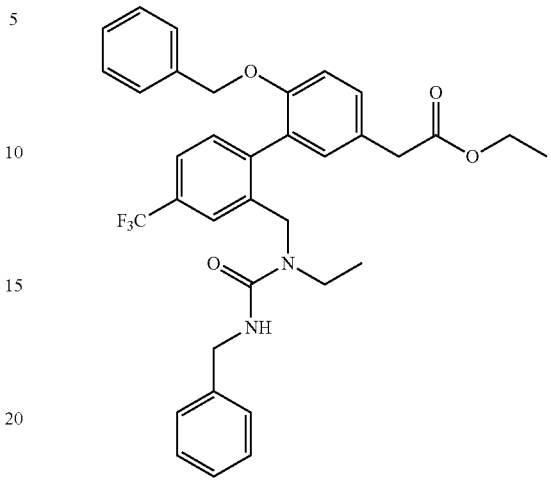

Step 4: [2'-(3-Benzyl-1-ethyl-ureidomethyl)-6-benzyloxy-4'-trifluoromethyl-biphenyl-3-yl]-acetic acid ethyl ester Prepared according to the procedure described in Example 95, Step 1, using the following starting materials: (6-benzyloxy-2'-ethylaminomethyl-4'-trifluoromethyl-biphenyl-3-yl)-acetic acid ethyl ester and benzyl isocyanate.

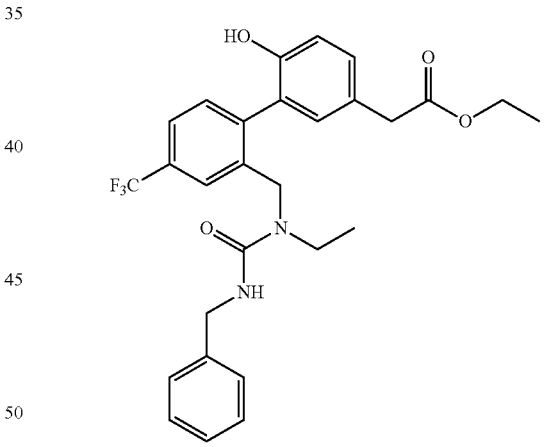

Step 5: [2'-(3-Benzyl-1-ethyl-ureidomethyl)-6-hydroxy-4'-trifluoromethyl-biphenyl-3-yl]-acetic acid ethyl ester

[2'-(3-Benzyl-1-ethyl-ureidomethyl)-6-benzyloxy-4'-trifluoromethyl-biphenyl-3-yl]-acetic acid ethyl ester (0.580 g, 0.96 mmol) in EtOAc was treated with 10% palladium on carbon (catalytic) and stirred under a balloon of $H_2$ overnight Analytical tlc indicated that some starting material was still present, so fresh palladium on carbon was added, and the reaction was stirred under a balloon of $H_2$ for an additional 24 hours. Once no starting material was seen by analytical tlc, the mixture was filtered over Celite, and the filtrate was concentrated and purified by silica gel chromatography to give the title compound. M+H is 515.

Example 127

Synthesis of [2'-(3-Benzyl-1-ethyl-ureidomethyl)-6-hydroxy-4'-trifluoromethyl-biphenyl-3-yl]-acetic acid (Compound 1-220)

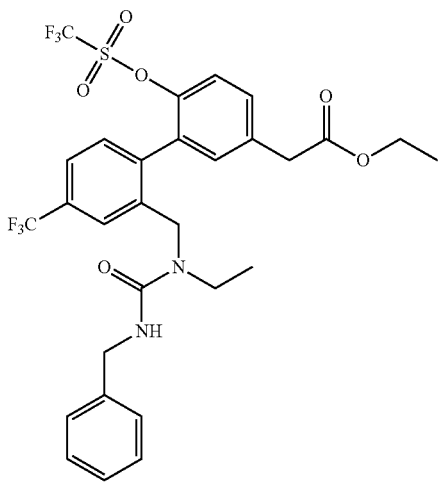 [SMILES: CCOC(=O)Cc1ccc(OS(=O)(=O)C(F)(F)F)c(-c2ccc(C(F)(F)F)cc2CN(CC)C(=O)NCc2ccccc2)c1]

Step 1: [2'-(3-Benzyl-1-ethyl-ureidomethyl)-6-trifluoromethanesulfonyloxy-4'-trifluoromethyl-biphenyl-3-yl]-acetic acid ethyl ester Prepared according to the procedure described in Example 36, Step 7, using the following starting materials: [2'-(3-benzyl-1-ethyl-ureidomethyl)-6-hydroxy-4'-trifluoromethyl-biphenyl-3-yl]-acetic acid ethyl ester and N-phenyl-bis(trifluoromethanesulfonimide).

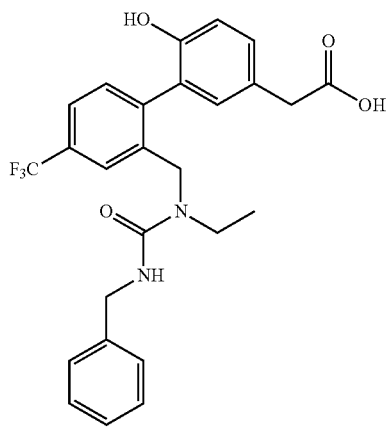 [SMILES: CCN(Cc1cc(C(F)(F)F)ccc1-c1cc(CC(=O)O)ccc1O)C(=O)NCc1ccccc1]

Step 2: [2'-(3-Benzyl-1-ethyl-ureidomethyl)-6-hydroxy-4'-trifluoromethyl-biphenyl-3-yl]-acetic acid Prepared according to the procedure described in Example 123, Step 3, using the following starting material: [2'-(3-benzyl-1-ethyl-ureidomethyl)-6-trifluoromethanesulfonyloxy-4'-trifluoromethyl-biphenyl-3-yl]-acetic acid ethyl ester. M+H is 487.

Example 128

Synthesis of 2-[(Benzyloxycarbonyl-ethyl-amino)-methyl]-5'-ethoxycarbonylmethyl-2'-methoxy-biphenyl-4-carboxylic acid (Compound 2-14)

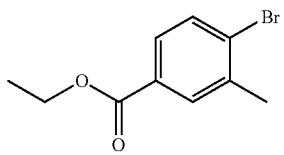

Step 1: 4-Bromo-3-methyl-benzoic acid ethyl ester

To 4-bromo-3-methylbenzoic acid (16.27 g, 75.7 mmol) in EtOH (500 mL) was added concentrated sulfuric acid (0.5 mL), and the reaction was stirred at 95° C. overnight. Additional sulfuric acid (2 mL) was added to push the reaction to completion, and then the mixture was quenched with the slow addition of sodium carbonate. The mixture was filtered and concentrated, and the residue was diluted and washed with $H_2O$ twice, saturated aqueous $NaHCO_3$, brine, and $H_2O$ to give the title compound.

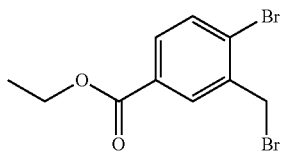

Step 2: 4-Bromo-3-bromomethyl-benzoic acid ethyl ester

4-Bromo-3-methyl-benzoic acid ethyl ester (18.24 g, 75.4 mmol), N-bromosuccinimide (14.1 g, 79.2 mmol), and benzoyl peroxide (0.9 g, 3.77 mmol) were combined in $CCl_4$, and the reaction was heated to 80° C. and stirred with a halogen desk lamp shining on it for 6 hours. The mixture was concentrated and partitioned between $CH_2Cl_2$ and $H_2O$. The organic layer was separated and washed with $H_2O$ and brine, and then dried and concentrated. The residue was triturated with hexane (3×50 mL) and dried to give the title compound.

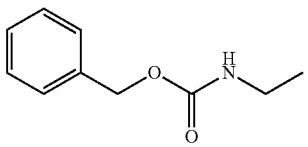

Step 3: Ethyl-carbamic acid benzyl ester

Ethylamine (1.3 mL, 20.0 mmol) and diisopropylethylamine (7 mL, 40.0 mmol) were combined in $CH_2Cl_2$ (200 mL) and cooled to 0° C. Benzyl chloroformate (2.86 mL, 20.0 mmol) was added dropwise, and the reaction was stirred at 0° C. for 30 minutes. Once no starting material was seen by analytical tlc, the mixture was warmed to room temperature and washed with H₂O, 0.1N aqueous HCl, and H₂O, and then dried and concentrated to give the title compound.

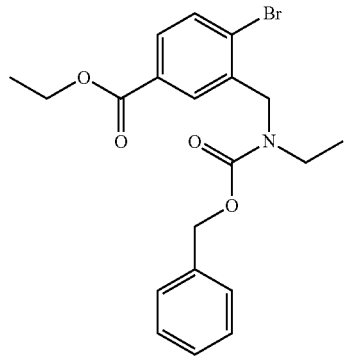 [SMILES: CCOC(=O)c1ccc(Br)c(CN(CC)C(=O)OCc2ccccc2)c1]

Step 4: 3-[(Benzyloxycarbonyl-ethyl-amino)-methyl]-4-bromo-benzoic acid ethyl ester 4-Bromo-3-bromomethyl-benzoic acid ethyl ester (2.95 g, 9.2 mmol) and ethyl-carbamic acid benzyl ester (3.30 g, 18.4 mmol) were combined in DMF (100 mL) and cooled to 0° C. Sodium hydride (60% in mineral oil; 0.772 g, 19.3 mmol) was added slowly, and the reaction was stirred at room temperature for 10 minutes. The mixture was quenched with H₂O and 1N aqueous HCl (20 mL), and then extracted with 1:1 EtOAc: hexanes three times. The organic layer was washed with brine, and then dried and concentrated. The residue was purified by silica gel chromatography (0-100% EtOAc in hexanes) to give the title compound, as well as the hydrolyzed product, which was combined with the product from the next step.

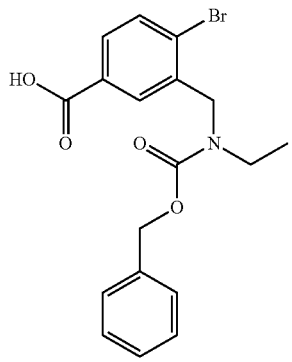 [SMILES: CCN(Cc1cc(C(=O)O)ccc1Br)C(=O)OCc1ccccc1]

Step 5: 3-[(Benzyloxycarbonyl-ethyl-amino)-methyl]-4-bromo-benzoic acid

3-[(Benzyloxycarbonyl-ethyl-amino)-methyl]-4-bromo-benzoic acid ethyl ester (3.62 g, 7.2 mmol) was dissolved in MeOH (40 mL) and cooled to 0° C. 1N Aqueous LiOH (22 mL, 22 mmol) was added, and the reaction was stirred at room temperature for 3 hours. The mixture was quenched with 1N aqueous HCl (22 mL) and extracted three times with EtOAc.

The combined organic layers were washed with brine, dried, and concentrated to give the title compound, which was combined with the hydrolyzed product isolated in step 5.

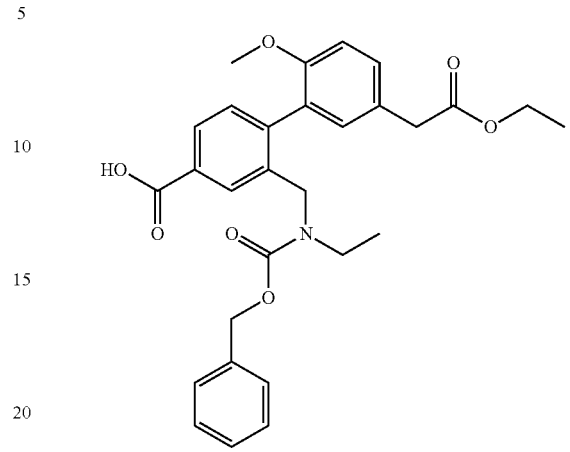

Step 6: 2-[(Benzyloxycarbonyl-ethyl-amino)-methyl]-5'-ethoxycarbonylmethyl-2'-methoxy-biphenyl-4-carboxylic acid Prepared according to the procedure described in Example 1, Step 4, using the following starting materials: 3-[(benzyloxycarbonyl-ethyl-amino)-methyl]-4-bromo-benzoic acid and [4-methoxy-3-(4,4,5,5-tetramethyl-[1,3,2]dioxaborolan-2-yl)-phenyl]-acetic acid ethyl ester. M+H is 506.

Example 129

Synthesis of 2-[(Benzyloxycarbonyl-ethyl-amino)-methyl]-5'-carboxymethyl-2'-methoxy-biphenyl-4-carboxylic acid (Compound 1-226)

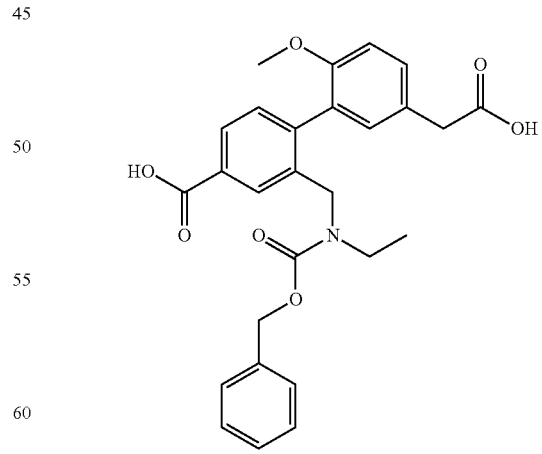

Prepared according to the procedure described in Example 31, Step 2, using the following starting material: 2-[(benzyloxycarbonyl-ethyl-amino)-methyl]-5'-ethoxycarbonylmethyl-2'-methoxy-biphenyl-4-carboxylic acid. M+H is 478.

Example 130

Synthesis of {5-Chloro-2'-[(cyclopropanecarbonyl-ethyl-amino)-methyl]-4'-methylsulfanyl-biphenyl-3-yl}-acetic acid (Compound 1-242)

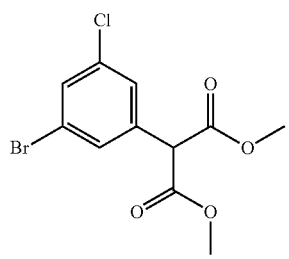 [SMILES: COC(=O)C(C(=O)OC)c1cc(Cl)cc(Br)c1]

Step 1: 2-(3-Bromo-5-chloro-phenyl)-malonic acid dimethyl ester 1,3-Dibromo-5-chlorobenzene (25 g, 93 mmol), dimethyl malonate (23.4 mL, 204 mmol), and copper(I) bromide (29.2 g, 204 mmol) were combined in 1,4-dioxane (300 mL) and cooled to 0° C. Sodium hydride (60% in mineral oil; 8.2 g, 204 mmol) was added slowly, and the reaction was stirred at room temperature for 20 minutes, and then stirred at 105° C. for 4 hours. After cooling to room temperature, the mixture was worked-up with CH$_2$Cl$_2$ and aqueous Na$_4$OH. The organic layer was concentrated, and the residue was purified by silica gel chromatography (0-20% EtOAc in hexanes) to give the title compound.

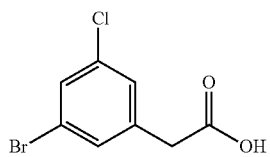 [SMILES: O=C(O)Cc1cc(Cl)cc(Br)c1]

Step 2: (3-Bromo-5-chloro-phenyl)-acetic acid 2-(3-Bromo-5-chloro-phenyl)-malonic acid dimethyl ester (19 g, 59 mmol) in MeOH (500 mL) was treated with 1N aqueous NaOH (237 mL, 237 mmol) at 50° C. for 1.5 hours. The mixture was concentrated, and the residue was acidified and extracted twice with EtOAc. The combined organic layers were dried, filtered, and concentrated to give the title compound.

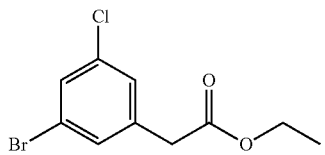

Step 3: (3-Bromo-5-chloro-phenyl)-acetic acid ethyl ester (3-Bromo-5-chloro-phenyl)-acetic acid (14 g, 56 mmol) in EtOH (150 mL) was treated with sulfuric acid (2 mL) at 50° C. for 2 hours. The mixture was worked-up with CH$_2$Cl$_2$ and H$_2$O, and the organic layer was concentrated to give the title compound.

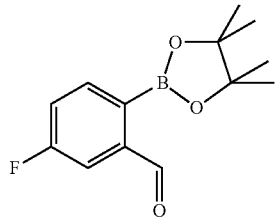 [SMILES: CC1(C)OB(c2ccc(F)cc2C=O)OC1(C)C]

Step 4: 5-Fluoro-2-(4,4,5,5-tetramethyl-[1,3,2]dioxaborolan-2-yl)-benzaldehyde Prepared according to the procedure described in Example 1, Step 2, using the following starting materials: 2-bromo-5-fluorobenzaldehyde and bis(pinacolato)diboron.

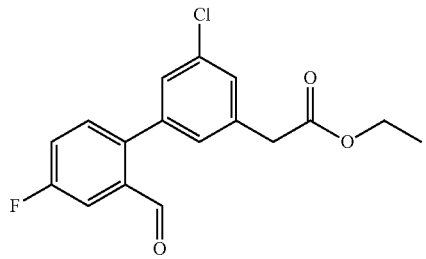 [SMILES: CCOC(=O)Cc1cc(Cl)cc(-c2ccc(F)cc2C=O)c1]

Step 5: (5-Chloro-4'-fluoro-2'-formyl-biphenyl-3-yl)-acetic acid ethyl ester Prepared according to the procedure described in Example 1, Step 4, using the following starting materials: (3-bromo-5-chloro-phenyl)-acetic acid ethyl ester and 5-fluoro-2-(4,4,5,5-tetramethyl-[1,3,2]dioxaborolan-2-yl)-benzaldehyde.

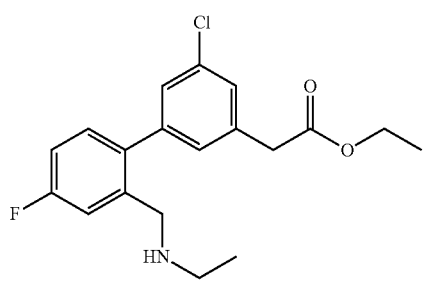 [SMILES: CCNCc1cc(F)ccc1-c1cc(Cl)cc(CC(=O)OCC)c1]

Step 6: (5-Chloro-2'-ethylaminomethyl-4'-fluoro-biphenyl-3-yl)-acetic acid ethyl ester Prepared according to the procedure described in Example 1, Step 5, using the following starting materials: (5-chloro-4'-fluoro-2'-formyl-biphenyl-3-yl)-acetic acid ethyl ester and ethylamine (2M in THF).

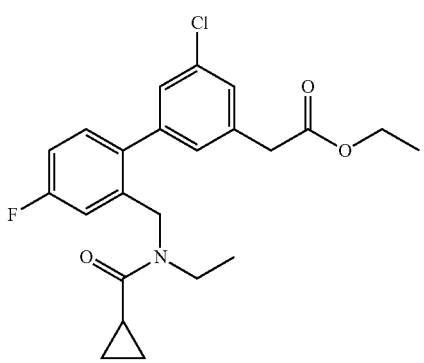 [SMILES: CCOC(=O)Cc1cc(Cl)cc(-c2ccc(F)cc2CN(CC)C(=O)C2CC2)c1]

Step 7: {5-Chloro-2'-[(cyclopropanecarbonyl-ethyl-amino)-methyl]-4'-fluoro-biphenyl-3-yl}-acetic acid ethyl ester Prepared according to the procedure described in Example 1, Step 6, using the following starting materials: (5-chloro-2'-ethylaminomethyl-4'-fluoro-biphenyl-3-yl)-acetic acid ethyl ester and cyclopropanecarbonyl chloride.

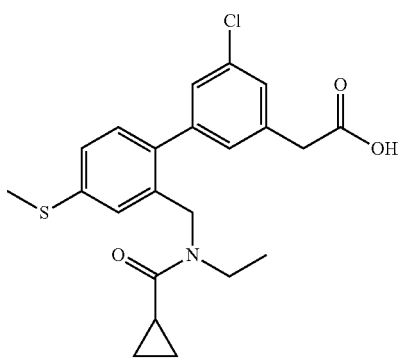 [SMILES: CCN(Cc1cc(SC)ccc1-c1cc(Cl)cc(CC(=O)O)c1)C(=O)C1CC1]

Step 8: {5-Chloro-2'-[(cyclopropanecarbonyl-ethyl-amino)-methyl]-4'-methylsulfanyl-biphenyl-3-yl}-acetic acid {5-Chloro-2'-[(cyclopropanecarbonyl-ethyl-amino)-methyl]-4'-fluoro-biphenyl-3-yl}-acetic acid ethyl ester (0.118 g, 0.28 mmol) and sodium thiomethoxide (0.043 g, 0.62 mmol) were combined in DMF (2 mL) and stirred at 100° C. overnight. Analytical LCMS indicated that the fluoride hadn't been displaced, but the ethyl ester had hydrolyzed. Additional sodium thiomethoxide (0.040 g, 0.57 mmol) was added, and the reaction was stirred overnight at 100° C. Analytical LCMS indicated that the reaction was complete, so the mixture was acidified with 1N aqueous HCl (4 mL) and worked-up with EtOAc and H$_2$O. The combined organic layers were dried, filtered, and concentrated, and the residue was purified by preparative HPLC to give the title compound. M+H is 418.

Example 131

Synthesis of [2'-(3-Benzyl-1,3-diethyl-ureidom-ethyl)-6-methoxy-4'-trifluoromethyl-biphenyl-3-yl]-acetic acid (Compound 1-94)

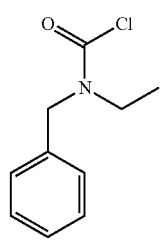

Step 1: N-Ethyl-N-benzylcarbamoyl Chloride

N-Ethylbenzylamine (0.56 mL, 3.8 mmol) and diisopropylethylamine (1 mL, 5.7 mmol) were combined in CH$_2$Cl$_2$ (12 mL) and cooled to 0° C. Phosgene (20% in toluene; 2.4 mL, 4.6 mmol) was added, and the reaction was stirred overnight at room temperature. The mixture was concentrated, and the residue was dissolved in Et$_2$O and washed twice with H$_2$O. The organic layer was dried, filtered, and concentrated to give the title compound.

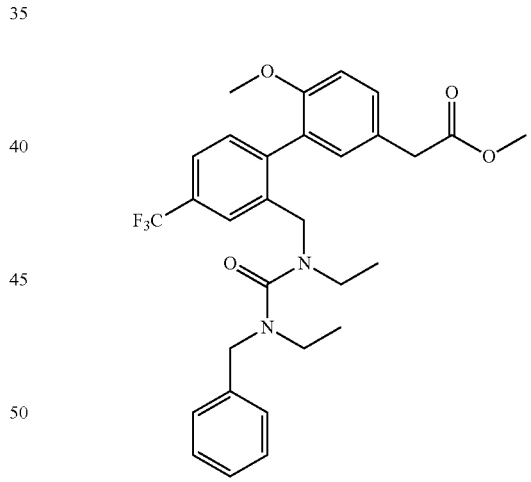

Step 1: [2'-(3-Benzyl-1,3-diethyl-ureidomethyl)-6-methoxy-4'-trifluoromethyl-biphenyl-3-yl]-acetic acid methyl ester (2'-Ethylaminomethyl-6-methoxy-4'-trifluoromethyl-biphenyl-3-yl)-acetic acid methyl ester (0.130 g, 0.34 mmol), N-ethyl-N-benzylcarbamoyl chloride (0.081 g, 0.41 mmol), 4-dimethylaminopyridine (0.010 g, 0.08 mmol), and triethylamine (0.12 mL, 0.85 mmol) were combined in CH$_2$Cl$_2$ (5 mL) and stirred at reflux overnight. The mixture was purified by silica gel chromatography (0-100% EtOAc in hexanes) to give the title compound.

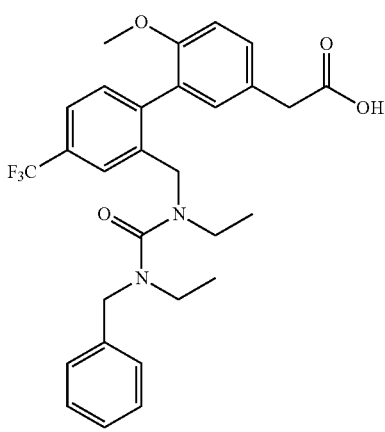 [SMILES: CCN(Cc1ccccc1)C(=O)N(CC)Cc1cc(C(F)(F)F)ccc1-c1cc(CC(=O)O)ccc1OC]

Step 2: [2'-(3-Benzyl-1,3-diethyl-ureidomethyl)-6-methoxy-4'-trifluoromethyl-biphenyl-3-yl]-acetic acid Prepared according to the procedure described in Example 31, Step 2, using the following starting material: [2'-(3-benzyl-1,3-diethyl-ureidomethyl)-6-methoxy-4'-trifluoromethyl-biphenyl-3-yl]-acetic acid methyl ester.

Example 132

Synthesis of [2'-(3-Benzyl-3-ethyl-ureidomethyl)-6-methoxy-4'-trifluoromethyl-biphenyl-3-yl]-acetic acid (Compound 1-106)

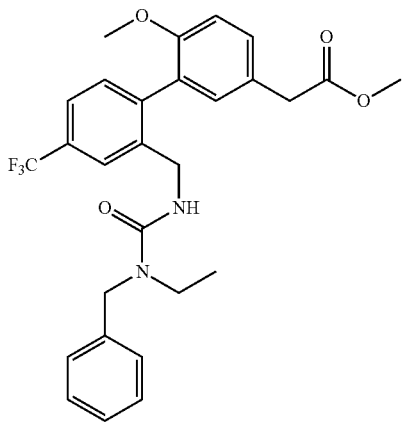 [SMILES: CCN(Cc1ccccc1)C(=O)NCc1cc(C(F)(F)F)ccc1-c1cc(CC(=O)OC)ccc1OC]

Step 1: [2'-(3-Benzyl-3-ethyl-ureidomethyl)-6-methoxy-4'-trifluoromethyl-biphenyl-3-yl]-acetic acid methyl ester Prepared according to the procedure described in Example 131, Step 2, using the following starting materials: (2'-aminomethyl-6-methoxy-4'-trifluoromethyl-biphenyl-3-yl)-acetic acid methyl ester, N-ethyl-N-benzylcarbamoyl chloride.

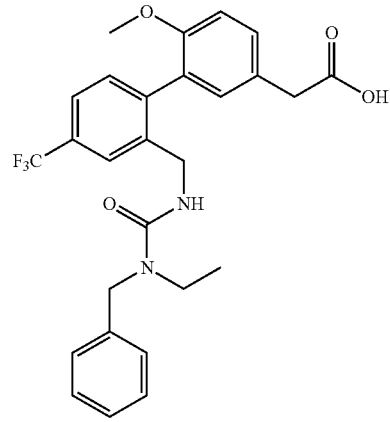 [SMILES: CCN(Cc1ccccc1)C(=O)NCc1cc(C(F)(F)F)ccc1-c1cc(CC(=O)O)ccc1OC]

Step 2: [2'-(3-Benzyl-3-ethyl-ureidomethyl)-6-methoxy-4'-trifluoromethyl-biphenyl-3-yl]-acetic acid Prepared according to the procedure described in Example 31, Step 2, using the following starting material: [2'-(3-benzyl-3-ethyl-ureidomethyl)-6-methoxy-4'-trifluoromethyl-biphenyl-3-yl]-acetic acid methyl ester.

Example 133

Synthesis of {2'-[(Benzyloxycarbonyl-ethyl-amino)-methyl]-4'-fluoro-6-methoxy-biphenyl-3-yl}-acetic acid (Compound 1-183)

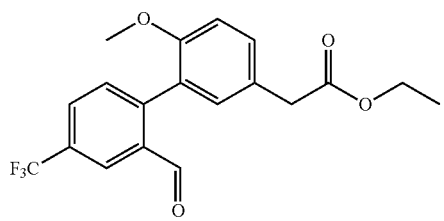 [SMILES: CCOC(=O)Cc1ccc(OC)c(-c2ccc(C(F)(F)F)cc2C=O)c1]

Step 1: (4'-Fluoro-2'-formyl-6-methoxy-biphenyl-3-yl)-acetic acid ethyl ester

Prepared according to the procedure described in Example 1, Step 4, using the following starting materials: 2-bromo-5-fluorobenzaldehyde and [4-methoxy-3-(4,4,5,5-tetramethyl-[1,3,2]dioxaborolan-2-yl)-phenyl]-acetic acid ethyl ester.

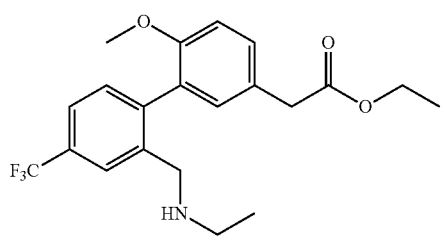 [SMILES: CCNCc1cc(C(F)(F)F)ccc1-c1cc(CC(=O)OCC)ccc1OC]

Step 2: (2'-Ethylaminomethyl-4'-fluoro-6-methoxy-biphenyl-3-yl)-acetic acid ethyl ester Prepared according to the procedure described in Example 1, Step 5, using the following starting materials: (4'-Fluoro-2'-formyl-6-methoxy-biphenyl-3-yl)-acetic acid ethyl ester and ethylamine (2M in THF).

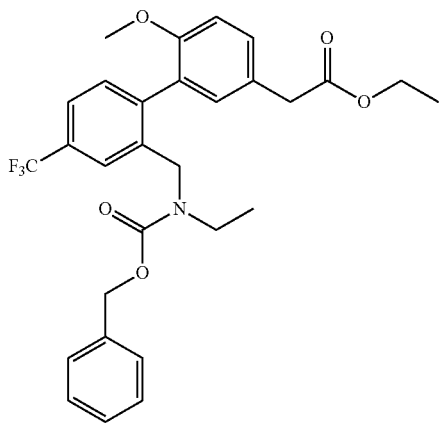

Step 3: {2'-[(Benzyloxycarbonyl-ethyl-amino)-methyl]-4'-fluoro-6-methoxy-biphenyl-3-yl}-acetic acid ethyl ester (2'-Ethylaminomethyl-4'-fluoro-6-methoxy-biphenyl-3-yl)-acetic acid ethyl ester (0.172 g, 0.5 mmol) and diisopropylethylamine (0.18 mL, 1.0 mmol) were combined in CH$_2$Cl$_2$ (2.5 mL) and cooled to 0° C. Benzyl chloroformate (0.1 mL, 0.7 mmol) was added, and the reaction was stirred for 1 hour. The mixture was purified by silica gel chromatography, and then further purified by preparative HPLC to give the title compound.

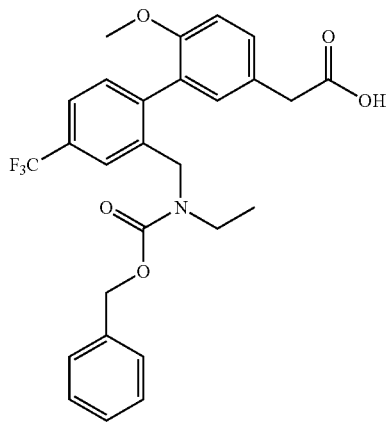

Step 4: {2'-[(Benzyloxycarbonyl-ethyl-amino)-methyl]-4'-fluoro-6-methoxy-biphenyl-3-yl}-acetic acid Prepared according to the procedure described in Example 31, Step 2, using the following starting material: {2'-[(benzyloxycarbonyl-ethyl-amino)-methyl]-4'-fluoro-6-methoxy-biphenyl-3-yl}-acetic acid ethyl ester. M+H is 452.

Example 134

Synthesis of {2'-[(Acetyl-ethyl-amino)-methyl]-4'-fluoro-6-methoxy-biphenyl-3-yl}-acetic acid (Compound 1-184)

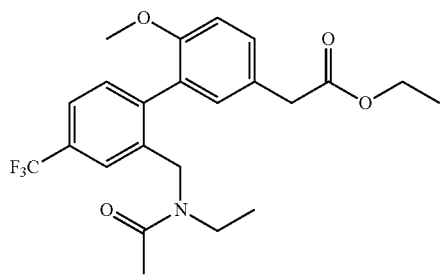 [SMILES: CCOC(=O)Cc1ccc(OC)c(-c2ccc(C(F)(F)F)cc2CN(CC)C(C)=O)c1]

Step 1: {2'-[(Acetyl-ethyl-amino)-methyl]-4'-fluoro-6-methoxy-biphenyl-3-yl}-acetic acid ethyl ester Prepared according to the procedure described in Example 1, Step 6, using the following starting materials: (2'-ethylaminomethyl-4'-fluoro-6-methoxy-biphenyl-3-yl)-acetic acid ethyl ester and acetyl chloride.

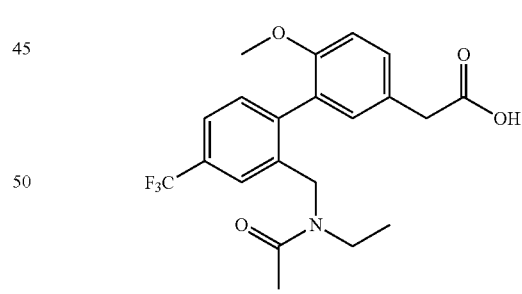

Step 2: {2'-[(Acetyl-ethyl-amino)-methyl]-4'-fluoro-6-methoxy-biphenyl-3-yl}-acetic acid Prepared according to the procedure described in Example 31, Step 2, using the following starting material: {2'-[(acetyl-ethyl-amino)-methyl]-4'-fluoro-6-methoxy-biphenyl-3-yl}-acetic acid ethyl ester. M+H is 360.

Example 135

Synthesis of {2'-[3-(4-Chloro-benzyl)-1-ethyl-ureidomethyl]-4'-fluoro-6-methoxy-biphenyl-3-yl}-acetic acid (Compound 1-185)

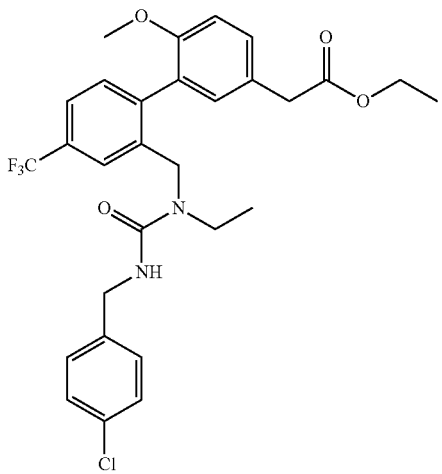

Step 1: {2'-[3-(4-Chloro-benzyl)-1-ethyl-ureidomethyl]-4'-fluoro-6-methoxy-biphenyl-3-yl}-acetic acid ethyl ester (2'-Ethylaminomethyl-4'-fluoro-6-methoxy-biphenyl-3-yl)-acetic acid ethyl ester (0.172 g, 0.5 mmol) and diisopropylethylamine (0.43 mL, 2.5 mmol) were combined in CH$_2$Cl$_2$ (2.5 mL) and cooled to 0° C. Phosgene (20% in toluene; 0.40 mL, 0.75 mmol) was added, and the mixture was stirred for 1 hour. 4-Chlorobenzylamine (0.012 mL, 1.0 mmol) was added, and the reaction was stirred for 1 hour. The mixture was diluted with CH$_2$Cl$_2$ and washed with H$_2$O. The organic layer was dried, filtered, and concentrated, and the residue was purified by preparative HPLC to give the title compound.

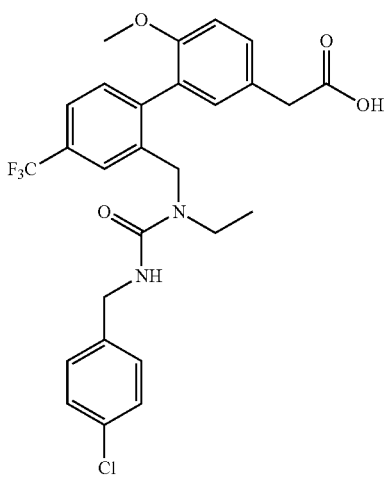 [SMILES: CCN(Cc1cc(C(F)(F)F)ccc1-c1cc(CC(=O)O)ccc1OC)C(=O)NCc1ccc(Cl)cc1]

Step 2: {2'-[3-(4-Chloro-benzyl)-1-ethyl-ureidomethyl]-4'-fluoro-6-methoxy-biphenyl-3-yl}-acetic acid Prepared according to the procedure described in Example 31, Step 2, using the following starting material: {2'-[3-(4-chloro-benzyl)-1-ethyl-ureidomethyl]-4'-fluoro-6-methoxy-biphenyl-3-yl}-acetic acid ethyl ester. M+H is 486.

Example 136

Synthesis of {2'-[(Cyclopropanecarbonyl-ethyl-amino)-methyl]-4'-fluoro-6-methoxy-biphenyl-3-yl}-acetic acid (Compound 1-186)

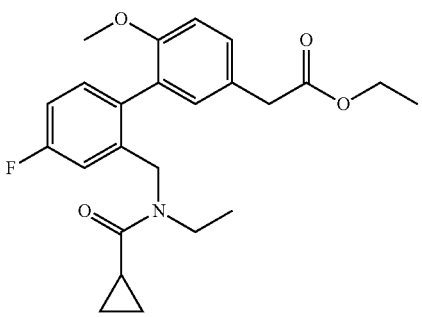 [SMILES: CCOC(=O)Cc1ccc(OC)c(-c2ccc(F)cc2CN(CC)C(=O)C2CC2)c1]

Step 1: {2'-[(Cyclopropanecarbonyl-ethyl-amino)-methyl]-4'-fluoro-6-methoxy-biphenyl-3-yl}-acetic acid ethyl ester Prepared according to the procedure described in Example 1, Step 6, using the following starting materials: (2'-ethylaminomethyl-4'-fluoro-6-methoxy-biphenyl-3-yl)-acetic acid ethyl ester and cyclopropanecarbonyl chloride.

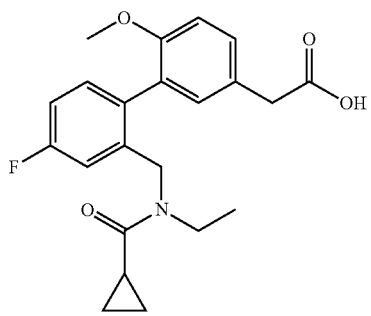 [SMILES: CCN(Cc1cc(F)ccc1-c1cc(CC(=O)O)ccc1OC)C(=O)C1CC1]

Step 2: {2'-[(Cyclopropanecarbonyl-ethyl-amino)-methyl]-4'-fluoro-6-methoxy-biphenyl-3-yl}-acetic acid Prepared according to the procedure described in Example 31, Step 2, using the following starting material: {2'-[(cyclopropanecarbonyl-ethyl-amino)-methyl]-4'-fluoro-6-methoxy-biphenyl-3-yl}-acetic acid ethyl ester. M+H is 386.

Example 137

Synthesis of [2'-(3-Benzyl-1-ethyl-ureidomethyl)-4'-fluoro-6-methoxy-biphenyl-3-yl]-acetic acid (Compound 1-187)

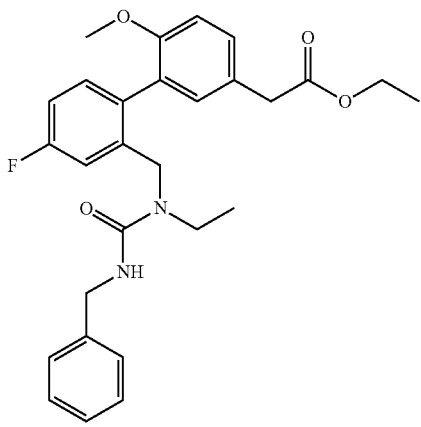 [SMILES: CCOC(=O)Cc1ccc(OC)c(-c2ccc(F)cc2CN(CC)C(=O)NCc2ccccc2)c1]

Step 1: [2'-(3-Benzyl-1-ethyl-ureidomethyl)-4'-fluoro-6-methoxy-biphenyl-3-yl]-acetic acid ethyl ester Prepared according to the procedure described in Example 95, Step 1, using the following starting materials: (2'-ethylaminomethyl-4'-fluoro-6-methoxy-biphenyl-3-yl)-acetic acid ethyl ester and benzyl isocyanate.

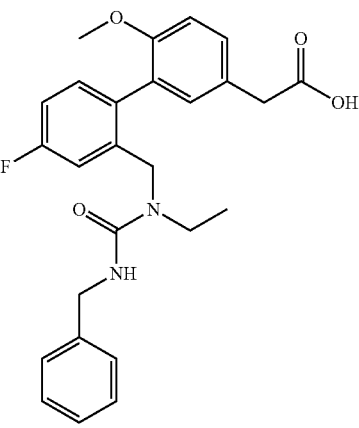 [SMILES: CCN(Cc1cc(F)ccc1-c1cc(CC(=O)O)ccc1OC)C(=O)NCc1ccccc1]

Step 2: [2'-(3-Benzyl-1-ethyl-ureidomethyl)-4'-fluoro-6-methoxy-biphenyl-3-yl]-acetic acid Prepared according to the procedure described in Example 31, Step 2, using the following starting material: [2'-(3-Benzyl-1-ethyl-ureidomethyl)-4'-fluoro-6-methoxy-biphenyl-3-yl]-acetic acid ethyl ester. M+H is 451.

Example 138

Synthesis of {2'-[(Benzyloxycarbonyl-ethyl-amino)-methyl]-4'-methanesulfonyl-6-methoxy-biphenyl-3-yl}-acetic acid (Compound 1-215)

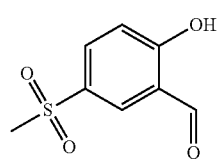

Step 1: 2-Hydroxy-5-methanesulfonyl-benzaldehyde

5-Bromosalicylaldehyde (0.402 g, 2.0 mmol), sodium methanesulfinate (0.918 g, 9.0 mmol), and copper(I) iodide (1.71 g, 9.0 mmol) were combined in NMP (16 mL) and stirred under $N_2$ at 140° C. overnight. The mixture was diluted with 1:1 EtOAc:hexanes (150 mL) and filtered through a pad of Celite. The filtrate was washed three times with $H_2O$, and then dried, filtered, and concentrated. The residue was purified by silica gel chromatography (0-100% EtOAc in hexanes) to give the title compound.

Step 2: 2-Ethylaminomethyl-4-methanesulfonyl-phenol

2-Hydroxy-5-methanesulfonyl-benzaldehyde (0.200 g, 1.0 mmol), ethylamine (2M in THF; 0.75 mL, 1.5 mmol), and sodium cyanoborohydride (0.095 g, 1.5 mmol) were combined in MeOH (10 mL). 4 Å Molecular sieves were added, followed by acetic acid (0.09 mL, 1.5 mmol), and the reaction was stirred for 1 hour. The mixture was filtered, and $H_2O$ (0.5 mL) was added and the solution was concentrated. The residue was partitioned between EtOAc (100 mL) and brine (20 mL), and the mixture was neutralized with 1N aqueous HCl (lint) and extracted six times with EtOAc, until minimal product was seen in the aqueous layer by analytical tlc. The combined organic layers were dried, filtered, and concentrated to give the title compound.

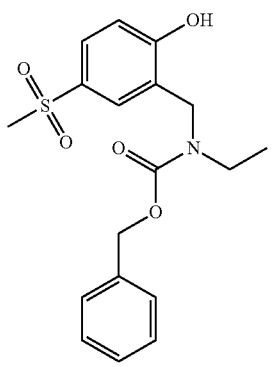 [SMILES: CCN(Cc1cc(S(C)(=O)=O)ccc1O)C(=O)OCc1ccccc1]

Step 3: Ethyl-(2-hydroxy-5-methanesulfonyl-benzyl)-carbamic acid benzyl ester To 2-ethylaminomethyl-4-methanesulfonyl-phenol (0.229 g, 1.0 mmol) and diisopropylamine (0.94 mL, 2.5 mmol) in CH$_2$Cl$_2$ (10 mL) was added benzyl chloroformate (0.16 mL, 1.1 mmol). Some over-acylation product was observed, so additional benzyl chloroformate (0.21 mL) was added to convert all of the product to the diacylated product. After aqueous work-up, the organic layer was concentrated, and the residue was dissolved in MeOH (10 mL) and treated with 1N aqueous LiOH (4 mL). Once the hydrolysis was complete, the mixture was worked-up, and the residue was purified to give the title compound.

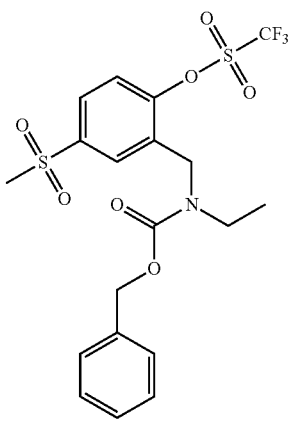 [SMILES: CCN(Cc1cc(S(C)(=O)=O)ccc1OS(=O)(=O)C(F)(F)F)C(=O)OCc1ccccc1]

Step 4: Trifluoro-methanesulfonic acid 2-[(benzyloxycarbonyl-ethyl-amino)-methyl]-4-methanesulfonyl-phenyl ester Ethyl-(2-hydroxy-5-methanesulfonyl-benzyl)-carbamic acid benzyl ester (0.200 g, 0.55 mmol) and diisopropylethylamine (0.24 mL, 1.38 mmol) were combined in CH$_2$Cl$_2$ (10 mL). Trifluoromethanesulfonic anhydride (0.11 mL, 0.65 mmol) was added, and the reaction was stirred for 5 minutes at room temperature. The mixture was quenched with H$_2$O and diluted with CH$_2$Cl$_2$. The organic layer was dried, filtered, and concentrated, and the residue was purified by silica gel chromatography (0-50% EtOAc in hexanes) to give the title compound.

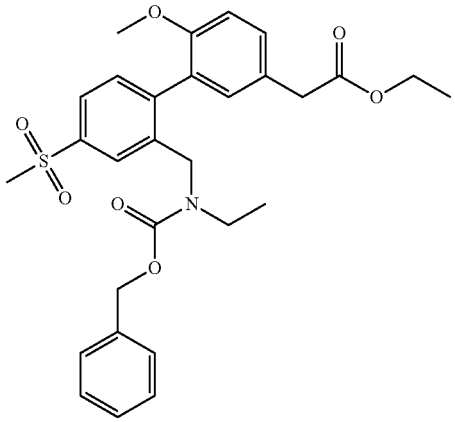 [SMILES: CCOC(=O)Cc1ccc(OC)c(-c2ccc(S(C)(=O)=O)cc2CN(CC)C(=O)OCc2ccccc2)c1]

Step 5: {2'-[(Benzyloxycarbonyl-ethyl-amino)-methyl]-4'-methanesulfonyl-6-methoxy-biphenyl-3-yl}-acetic acid ethyl ester Trifluoro-methanesulfonic acid 2-[(benzyloxycarbonyl-ethyl-amino)-methyl]-4-methanesulfonyl-phenyl ester (1.3 g, 2.62 mmol), [4-methoxy-3-(4,4,5,5-tetramethyl-[1,3,2]dioxaborolan-2-yl)-phenyl]-acetic acid ethyl ester (1.26 g, 3.93 mmol), and cesium carbonate (2.55 g, 7.85 mmol) were combined in DMF. (1,1'-Bis(diphenylphosphino)ferrocene)-dichloropalladium(II) (0.213 g, 0.26 mmol) was added, and the reaction was immediately immersed in an oil bath preheated to 45° C. The reaction was stirred at 65° C. for 20 minutes, and then worked-up and purified to give the title compound, contaminated with a phenol by-product. The mixture was dissolved in CH$_2$Cl$_2$ (100 mL) and washed with 0.5N aqueous NaOH, and then concentrated to give the title compound.

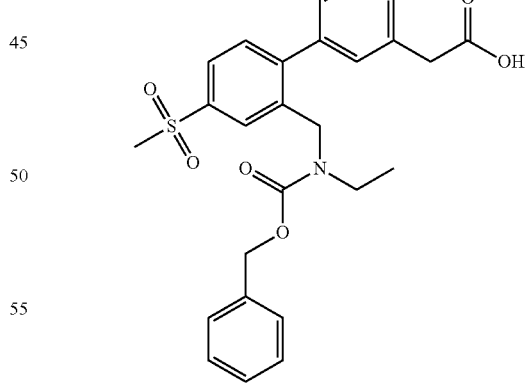

Step 6: {2'-[(Benzyloxycarbonyl-ethyl-amino)-methyl]-4'-methanesulfonyl-6-methoxy-biphenyl-3-yl}-acetic acid Prepared according to the procedure described in Example 31, Step 2, using the following starting material: {2'-[(benzyloxycarbonyl-ethyl-amino)-methyl]-4'-methanesulfonyl-6-methoxy-biphenyl-3-yl}-acetic acid ethyl ester. M+H is 512.

Example 139

Synthesis of [2'-[(Benzyloxycarbonyl-ethyl-amino)-methyl]-4'-(1-hydroxy-1-methyl-ethyl)-6-methoxy-biphenyl-3-yl]-acetic acid (Compound 1-216)

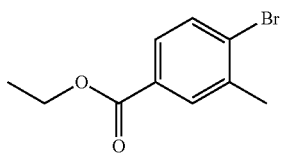

Step 1: 4-Bromo-3-methyl-benzoic acid ethyl ester

To 4-bromo-3-methylbenzoic acid (3 g, 14 mmol) in EtOH (200 mL) was added thionyl chloride (2 mL, 28 mmol), and the reaction was stirred for 10 minutes. Additional thionyl chloride (3 mL, 35 mmol) was added, and the reaction was stirred overnight at 50° C. After cooling to room temperature, the mixture was quenched with the slow addition of powdered Na₂CO₃, and then filtered and concentrated. The residue was partitioned between EtOAc and H₂O, and the organic layer was dried, filtered, and concentrated to give the title compound.

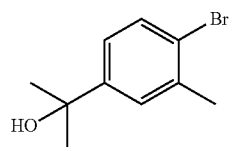

Step 2: 2-(4-Bromo-3-methyl-phenyl)-propan-2-ol

To 4-bromo-3-methyl-benzoic acid ethyl ester (0.968 g, 4.0 mmol) in THF (50 mL) at 0° C. was added methylmagnesium bromide (3M in Et₂O; 4 mL, 12 mmol), and the reaction was stirred at 1 hour at 0° C. and then warmed to room temperature. Only starting material was present, so additional methylmagnesium bromide (3M in Et₂O; 4 mL, 12 mmol) was added, and the reaction was stirred for 30 minutes. The mixture was quenched with saturated aqueous NH₄Cl and partitioned between EtOAc and H₂O. The organic layer was dried, filtered, and concentrated to give the title compound.

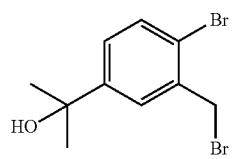

Step 3: 2-(4-Bromo-3-bromomethyl-phenyl)-propan-2-ol 2-(4-Bromo-3-methyl-phenyl)-propan-2-ol (0.916 g, 4.0 mmol) in CCl₄ (30 mL) was treated with N-bromosuccinimide (0.750 g, 4.2 mmol) and benzoyl peroxide (0.050 g, 0.2 mmol), and the reaction was refluxed under a halogen lamp for 2 hours. After cooling to room temperature, the mixture was partitioned between CH₂Cl₂ and H₂O, and the organic layer was dried, filtered, and concentrated. The residue was purified by silica gel chromatography to give the title compound.

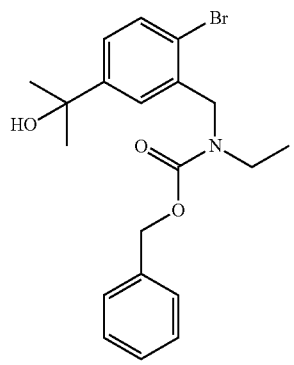 [SMILES: CCN(Cc1cc(C(C)(C)O)ccc1Br)C(=O)OCc1ccccc1]

Step 4: [2-Bromo-5-(1-hydroxy-1-methyl-ethyl)-benzyl]-ethyl-carbamic acid benzyl ester To 2-(4-bromo-3-bromomethyl-phenyl)-propan-2-ol (0.255 g, 0.83 mmol) and ethyl-carbamic acid benzyl ester (0.446 g, 2.49 mmol) in DMF (15 mL) was added sodium hydride (60% in mineral oil; 0.103 g, 2.57 mmol), and the reaction was stirred for 30 minutes. The mixture was quenched with H₂O and worked-up. The residue was purified by silica gel chromatography (0-40% EtOAc in hexanes) to give the title compound.

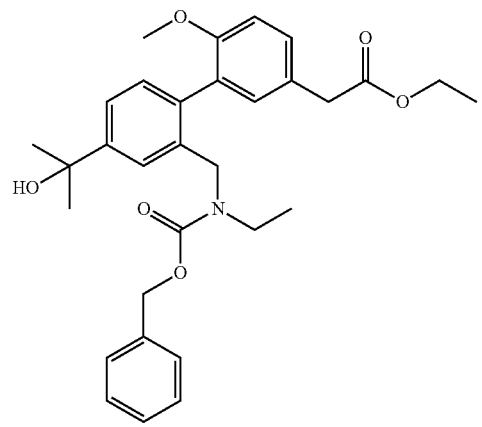 [SMILES: CCOC(=O)Cc1ccc(OC)c(-c2ccc(C(C)(C)O)cc2CN(CC)C(=O)OCc2ccccc2)c1]

Step 5: [2'-[(Benzyloxycarbonyl-ethyl-amino)-methyl]-4'-(1-hydroxy-1-methyl-ethyl)-6-methoxy-biphenyl-3-yl]-acetic acid ethyl ester Prepared according to the procedure described in Example 1, Step 4, using the following starting materials: [2-bromo-5-(1-hydroxy-1-methyl-ethyl)-benzyl]ethyl-carbamic acid benzyl ester and [4-methoxy-3-(4,4,5,5-tetramethyl-[1,3,2]dioxaborolan-2-yl)-phenyl]-acetic acid ethyl ester.

297

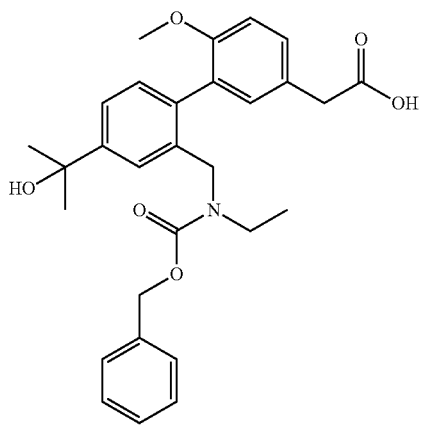 [SMILES: CCN(Cc1cc(C(C)(C)O)ccc1-c1cc(CC(=O)O)ccc1OC)C(=O)OCc1ccccc1]

Step 6: [2'-[(Benzyloxycarbonyl-ethyl-amino)-methyl]-4'-(1-hydroxy-1-methyl-ethyl)-6-methoxy-biphenyl-3-yl]-acetic acid Prepared according to the procedure described in Example 31, Step 2, using the following starting material: [2'-[(benzyloxycarbonyl-ethyl-amino)-methyl]-4'-(1-hydroxy-1-methyl-ethyl)-6-methoxy-biphenyl-3-yl]-acetic acid ethyl ester. M+H is 492.

Example 140

Synthesis of {2'-[(Cyclopropanecarbonyl-ethyl-amino)-methyl]-6-methoxy-4'-methylsulfanyl-biphenyl-3-yl}-acetic acid (Compound 1-241)

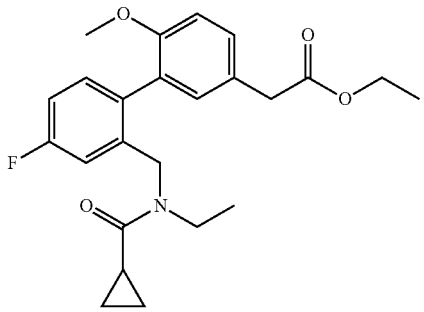 [SMILES: CCOC(=O)Cc1ccc(OC)c(-c2ccc(F)cc2CN(CC)C(=O)C2CC2)c1]

Step 1: {2'-[(Cyclopropanecarbonyl-ethyl-amino)-methyl]-4'-fluoro-6-methoxy-biphenyl-3-yl}-acetic acid ethyl ester Prepared according to the procedure described in Example 1, Step 6, using the following starting materials: (2'-ethylaminomethyl-4'-fluoro-6-methoxy-biphenyl-3-yl)-acetic acid ethyl ester and cyclopropanecarbonyl chloride.

298

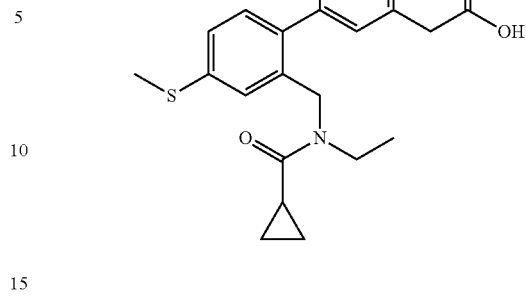

Step 2: {2'-[(Cyclopropanecarbonyl-ethyl-amino)-methyl]-6-methoxy-4'-methylsulfanyl-biphenyl-3-yl}-acetic acid To {2'-[(cyclopropanecarbonyl-ethyl-amino)-methyl]-4'-fluoro-6-methoxy-biphenyl-3-yl}-acetic acid ethyl ester 0.186 g, 0.45 mmol) in DMF (0.5 mL) was added sodium thiomethoxide (0.035 g, 0.50 mmol), and the reaction was stirred at 85° C. for 2 hours. Analytical LCMS indicated that starting material was still present, so additional sodium thiomethoxide (0.070 g, 1.0 mmol) was added, and the reaction was stirred at 85° C. for another 2 hours. Analytical LCMS showed that no starting material remained, and that the ethyl ester had been hydrolyzed, so an aqueous work-up was performed, and the residue was purified by preparative HPLC to give the title compound. M+H is 414.

Example 141

Synthesis of {2-[(Acetyl-ethyl-amino)-methyl]-6-methoxy-4'-trifluoromethyl-biphenyl-3-yl}-difluoroacetic acid (Compound 1-91)

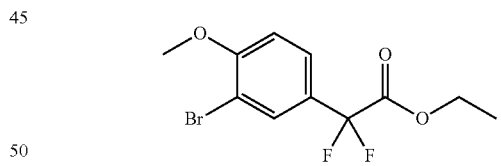

Step 1: (3-Bromo-4-methoxy-phenyl)-difluoro-acetic acid ethyl ester (3-Bromo-4-methoxy-phenyl)-acetic acid ethyl ester (1.2 g, 4 mmol) was dissolved in THF and cooled to −78° C. Sodium hexamethyldisilazide (1M in THF; 10 mL, 10 mmol) was added, and the mixture was stirred for 20 minutes. N-Fluorobenzenesulfonimide (3.15 g, 10 mmol) in THF was added, and the reaction was stirred at −78° C. overnight. The reaction was warmed to 0° C. and stirred for 15 minutes, and then quenched with 1N aqueous HCl. The mixture was worked-up and purified by silica gel chromatography to give the title compound.

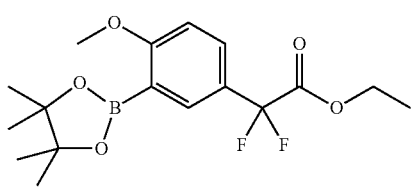 [SMILES: CCOC(=O)C(F)(F)c1ccc(OC)c(B2OC(C)(C)C(C)(C)O2)c1]

Step 2: Difluoro-[4-methoxy-3-(4,4,5,5-tetramethyl-[1,3,2]dioxaborolan-2-yl)-phenyl]-acetic acid ethyl ester Prepared according to the procedure described in Example 1, Step 2, using the following starting materials: (3-bromo-4-methoxy-phenyl)-difluoro-acetic acid ethyl ester and bis(pinacolato)diboron.

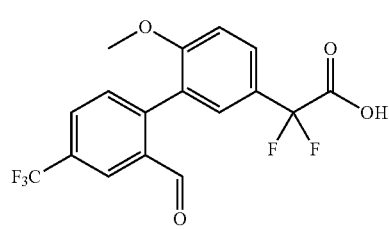 [SMILES: COc1ccc(C(F)(F)C(=O)O)cc1-c1ccc(C(F)(F)F)cc1C=O]

Step 3: Difluoro-(2'-formyl-6-methoxy-4'-trifluoromethyl-biphenyl-3-yl)-acetic acid Prepared according to the procedure described in Example 1, Step 4, using the following starting materials: difluoro-[4-methoxy-3-(4,4,5,5-tetramethyl-[1,3,2]dioxaborolan-2-yl)-phenyl]-acetic acid ethyl ester and 2-bromo-5-(trifluoromethyl)benzaldehyde; the ester was hydrolyzed under the reaction conditions.

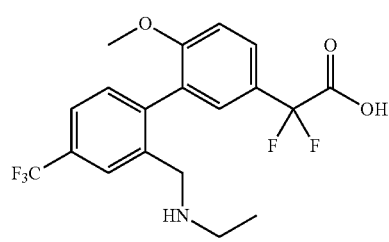 [SMILES: CCNCc1cc(C(F)(F)F)ccc1-c1cc(C(F)(F)C(=O)O)ccc1OC]

Step 4: (2'-Ethylaminomethyl-6-methoxy-4'-trifluoromethyl-biphenyl-3-yl)-difluoro-acetic acid Prepared according to the procedure described in Example 1, Step 5, using the following starting materials: difluoro-(2'-formyl-6-methoxy-4'-trifluoromethyl-biphenyl-3-yl)-acetic acid and ethylamine (2M in THF).

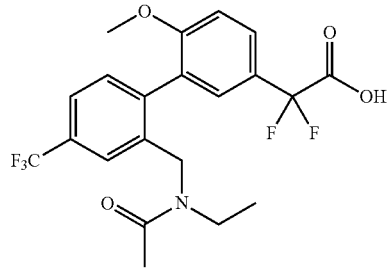 [SMILES: CCN(Cc1cc(C(F)(F)F)ccc1-c1cc(C(F)(F)C(=O)O)ccc1OC)C(C)=O]

Step 5: {2'-[(Acetyl-ethyl-amino)-methyl]-6-methoxy-4'-trifluoromethyl-biphenyl-3-yl}-difluoro-acetic acid Prepared according to the procedure described in Example 1, Step 6, using the following starting materials: (2'-ethylaminomethyl-6-methoxy-4'-trifluoromethyl-biphenyl-3-yl)-difluoro-acetic acid and acetyl chloride.

Example 142

Synthesis of {2-[(Benzyloxycarbonyl-ethyl-amino)-methyl]-6-methoxy-4'-trifluoromethyl-biphenyl-3-yl}-difluoro-acetic acid (Compound 1-132)

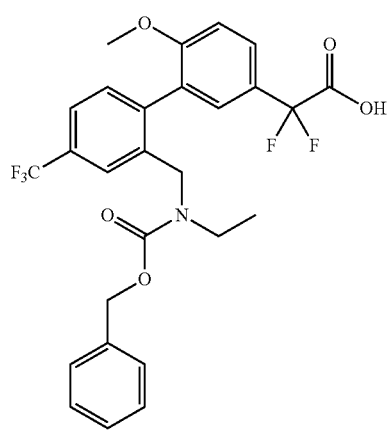 [SMILES: CCN(Cc1cc(C(F)(F)F)ccc1-c1cc(C(F)(F)C(=O)O)ccc1OC)C(=O)OCc1ccccc1]

Prepared according to the procedure described in Example 1, Step 6, using the following starting materials: (2'-ethylaminomethyl-6-methoxy-4'-trifluoromethyl-biphenyl-3-yl)-difluoro-acetic acid and benzyl chloroformate.

Example 143

Synthesis of {4'-Acetylamino-2'-[(benzyloxycarbonyl-ethyl-amino)-methyl]-6-methoxy-biphenyl-3-yl}-acetic acid (Compound 1-153)

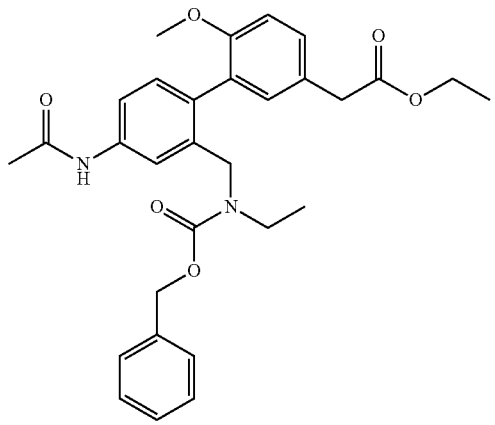 [SMILES: CCOC(=O)Cc1ccc(OC)c(-c2ccc(NC(C)=O)cc2CN(CC)C(=O)OCc2ccccc2)c1]

Step 1: {4'-Acetylamino-2'-[(benzyloxycarbonyl-ethyl-amino)-methyl]-6-methoxy-biphenyl-3-yl}-acetic acid ethyl ester Prepared according to the procedure described in Example 39, Step 1, using the following starting materials: {4'-amino-2'-[(benzyloxycarbonyl-ethyl-amino)-methyl]-6-methoxy-biphenyl-3-yl}-acetic acid ethyl ester and acetyl chloride.

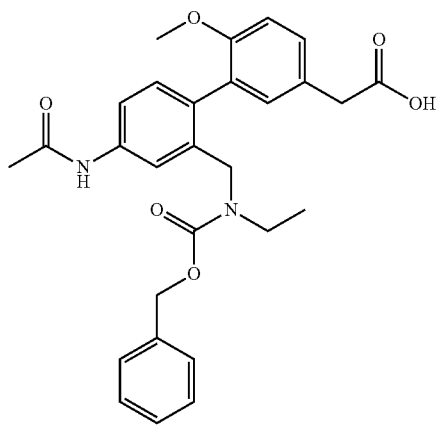 [SMILES: CCN(Cc1cc(NC(C)=O)ccc1-c1cc(CC(=O)O)ccc1OC)C(=O)OCc1ccccc1]

Step 2: {4'-Acetylamino-2'-[(benzyloxycarbonyl-ethyl-amino)-methyl]-6-methoxy-biphenyl-3-yl}-acetic acid Prepared according to the procedure described in Example 39, Step 2, using the following starting material: {4'-acetylamino-2'-[(benzyloxycarbonyl-ethyl-amino)-methyl]-6-methoxy-biphenyl-3-yl}-acetic acid ethyl ester.

Example 144

Synthesis of [2'-[(Benzyloxycarbonyl-ethyl-amino)-methyl]-4'-(4-chloro-benzenesulfonylamino)-6-methoxy-biphenyl-3-yl]-acetic acid (Compound 1-156)

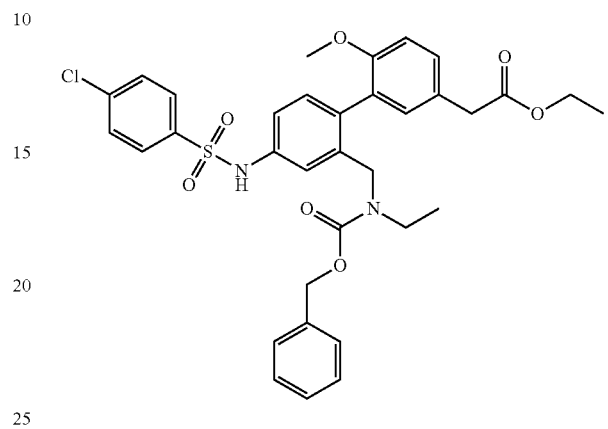

Step 1: [2'-[(Benzyloxycarbonyl-ethyl-amino)-methyl]-4'-(4-chloro-benzenesulfonylamino)-6-methoxy-biphenyl-3-yl]-acetic acid ethyl ester Prepared according to the procedure described in Example 39, Step 1, using the following starting materials: {4'-amino-2'-[benzyloxycarbonyl-ethyl-amino)-methyl]-6-methoxy-biphenyl-3-yl}-acetic acid ethyl ester and 4-chlorobenzenesulfonyl chloride.

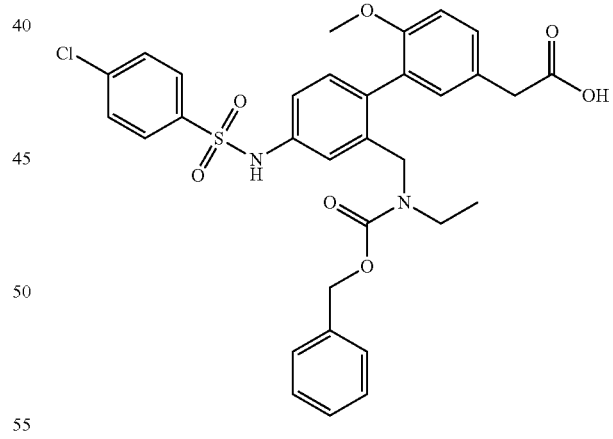

Step 2: [2'-[(Benzyloxycarbonyl-ethyl-amino)-methyl]-4'-(4-chloro-benzenesulfonylamino)-6-methoxy-biphenyl-3-yl]-acetic acid Prepared according to the procedure described in Example 39, Step 2, using the following starting material: [2'-[(benzyloxycarbonyl-ethyl-amino)-methyl]-4'-(4-chloro-benzenesulfonylamino)-6-methoxy-biphenyl-3-yl]-acetic acid ethyl ester.

Example 145

Synthesis of [2'-(3-Cyano-1-ethyl-ureidomethyl)-6-methoxy-4'-trifluoromethyl-biphenyl-3-yl]-acetic acid (Compound 1-99)

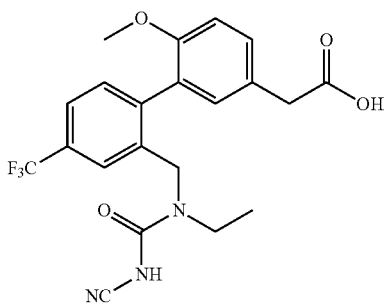 [SMILES: CCN(Cc1cc(C(F)(F)F)ccc1-c1cc(CC(=O)O)ccc1OC)C(=O)NC#N]

[2'-(3-Cyano-1-ethyl-2-phenyl-isoureidomethyl)-6-methoxy-4'-trifluoromethyl-biphenyl-3-yl]-acetic acid ethyl ester (0.100 g, 0.19 mmol) in THF (2 mL), MeOH (0.5 mL), and H$_2$O (0.5 mL) was treated with lithium hydroxide (0.030 g, 0.71 mmol), and the reaction was stirred at room temperature until no starting material was seen by analytical LCMS. The crude material was purified by preparative HPLC to give the title compound.

Example 146

Synthesis of [2'-(N'-Cyano-N''-cyclohexylmethyl-N-ethyl-guanidinomethyl)-6-methoxy-4'-trifluoromethyl-biphenyl-3-yl]-acetic acid (Compound 1-112)

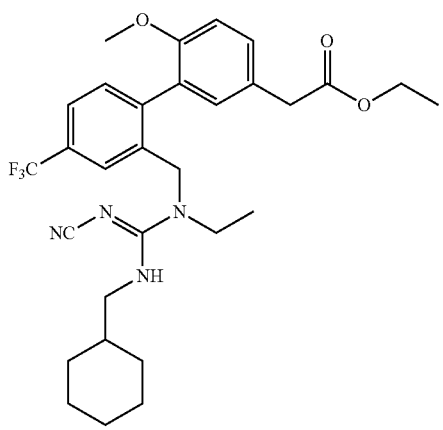 [SMILES: CCOC(=O)Cc1ccc(OC)c(-c2ccc(C(F)(F)F)cc2CN(CC)/C(=N/C#N)NCC2CCCCC2)c1]

Step 1: [2'-(N''-Cyano-N'-cyclohexylmethyl-N-ethyl-guanidinomethyl)-6-methoxy-4'-trifluoromethyl-biphenyl-3-yl]-acetic acid ethyl ester Prepared according to the procedure described in Example 33, Step 6, using the following starting materials: [2'-(3-cyano-1-ethyl-2-phenyl-isoureidomethyl)-6-methoxy-4'-trifluoromethyl-biphenyl-3-yl]-acetic acid ethyl ester and cyclohexanemethylamine.

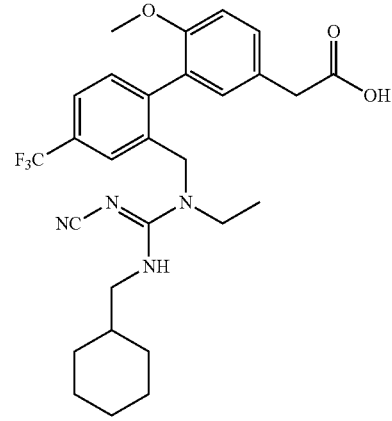 [SMILES: CCN(Cc1cc(C(F)(F)F)ccc1-c1cc(CC(=O)O)ccc1OC)/C(=N/C#N)NCC1CCCCC1]

Step 2: [2'-(N''-Cyano-N'-cyclohexylmethyl-N-ethyl-guanidinomethyl)-6-methoxy-4'-trifluoromethyl-biphenyl-3-yl]-acetic acid Prepared according to the procedure described in Example 33, Step 7, using the following starting material: [2'-(N''-cyano-N'-cyclohexylmethyl-N-ethyl-guanidinomethyl)-6-methoxy-4'-trifluoromethyl-biphenyl-3-yl]-acetic acid ethyl ester. M+H is 531.

Example 147

Synthesis of {2'-[N'-Cyano-N''-(2,2-dimethyl-propyl)-N-ethyl-guanidinomethyl]-6-methoxy-4'-trifluoromethyl-biphenyl-3-yl}-acetic acid (Compound 1-113)

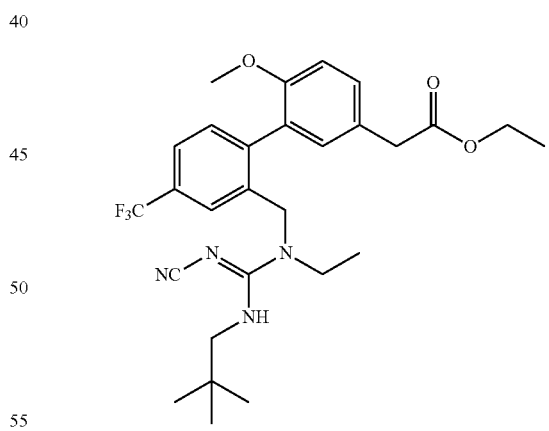

Step 1: {2'-[N''-Cyano-N'-(2,2-dimethyl-propyl)-N-ethyl-guanidinomethyl]-6-methoxy-4'-trifluoromethyl-biphenyl-3-yl}-acetic acid ethyl ester Prepared according to the procedure described in Example 33, Step 6, using the following starting materials: [2'-(3-cyano-1-ethyl-2-phenyl-isoureidomethyl)-6-methoxy-4'-trifluoromethyl-biphenyl-3-yl]-acetic acid ethyl ester and neopentylamine.

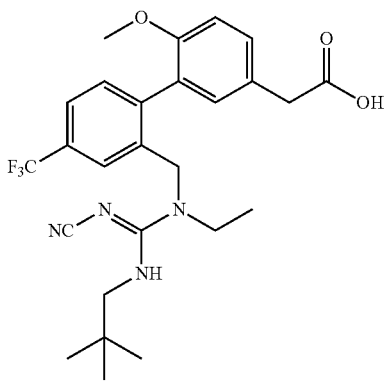 [SMILES: CCN(Cc1cc(C(F)(F)F)ccc1-c1cc(CC(=O)O)ccc1OC)/C(=N/C#N)NCC(C)(C)C]

Step 2: {2'-[N''-Cyano-N'-(2,2-dimethyl-propyl)-N-ethyl-guanidinomethyl]-6-methoxy-4'-trifluoromethyl-biphenyl-3-yl}-acetic acid Prepared according to the procedure described in Example 33, Step 7, using the following starting material: {2'-[N''-cyano-N'-(2,2-dimethyl-propyl)-N-ethyl-guanidinomethyl]-6-methoxy-4'-trifluoromethyl-biphenyl-3-yl}-acetic acid ethyl ester. M+H is 505.

Example 148

Synthesis of {2'-[N'-Cyano-N-ethyl-N''-(4-methoxy-benzyl)-guanidinomethyl]-6-methoxy-4'-trifluoromethyl-biphenyl-3-yl}-acetic acid (Compound 1-114)

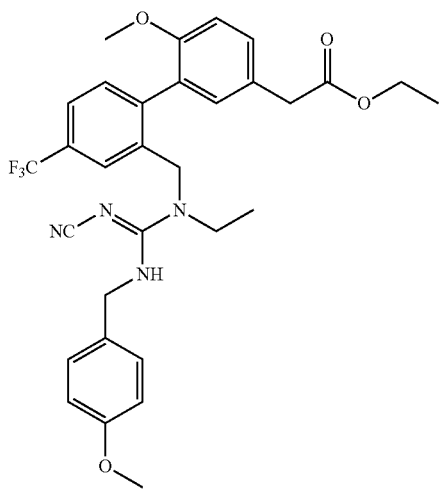 [SMILES: CCOC(=O)Cc1ccc(OC)c(-c2ccc(C(F)(F)F)cc2CN(CC)/C(=N/C#N)NCc2ccc(OC)cc2)c1]

Step 1: {2'-[N''-Cyano-N-ethyl-N'-(4-methoxy-benzyl)-guanidinomethyl]-6-methoxy-4'-trifluoromethyl-biphenyl-3-yl}-acetic acid ethyl ester Prepared according to the procedure described in Example 33, Step 6, using the following starting materials: [2'-(3-cyano-1-ethyl-2-phenyl-isoureidomethyl)-6-methoxy-4'-trifluoromethyl-biphenyl-3-yl]-acetic acid ethyl ester and 4-methoxybenzylamine.

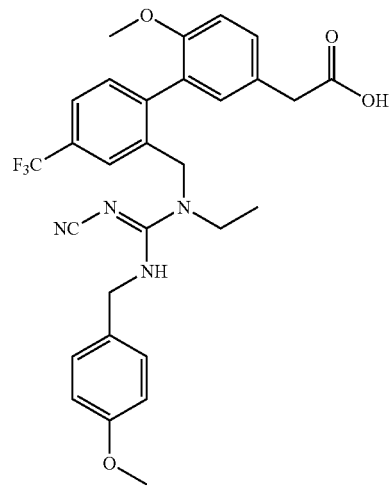 [SMILES: CCN(Cc1cc(C(F)(F)F)ccc1-c1cc(CC(=O)O)ccc1OC)/C(=N/C#N)NCc1ccc(OC)cc1]

Step 2: {2'-[N''-Cyano-N-ethyl-N'-(4-methoxy-benzyl)-guanidinomethyl]-6-methoxy-4'-trifluoromethyl-biphenyl-3-yl}-acetic acid Prepared according to the procedure described in Example 33, Step 7, using the following starting material: {2'-[N''-cyano-N-ethyl-N'-(4-methoxy-benzyl)-guanidinomethyl]-6-methoxy-4'-trifluoromethyl-biphenyl-3-yl}-acetic acid ethyl ester. M+H is 555.

Example 149

Synthesis of [2'-(N'-Cyano-N-ethyl-N''-propyl-guanidinomethyl)-6-methoxy-4'-trifluoromethyl-biphenyl-3-yl]-acetic acid (Compound 1-145)

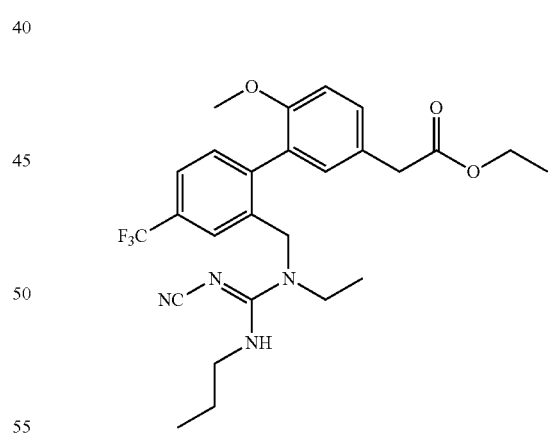

Step 1: [2'-(N'-Cyano-N-ethyl-N''-propyl-guanidinomethyl)-6-methoxy-4'-trifluoromethyl-biphenyl-3-yl]-acetic acid ethyl ester Prepared according to the procedure described in Example 33, Step 6, using the following starting materials: [2'-(3-cyano-1-ethyl-2-phenyl-isoureidomethyl)-6-methoxy-4'-trifluoromethyl-biphenyl-3-yl]-acetic acid ethyl ester and propylamine.

307

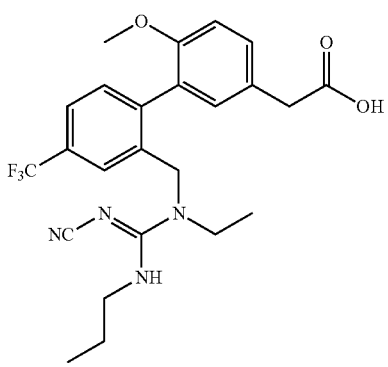 [SMILES: CCCN/C(=N\C#N)N(CC)Cc1cc(C(F)(F)F)ccc1-c1cc(CC(=O)O)ccc1OC]

Step 2: [2'-(N'-Cyano-N-ethyl-N"-propyl-guanidinomethyl)-6-methoxy-4'-trifluoromethyl-biphenyl-3-yl]-acetic acid Prepared according to the procedure described in Example 33, Step 7, using the following starting material: [2'-(N'-cyano-N-ethyl-N"-propyl-guanidinomethyl)-6-methoxy-4'-trifluoromethyl-biphenyl-3-yl]-acetic acid ethyl ester. M+H is 477.

Example 150

Synthesis of [2'-(N'-Cyano-N"-cyclopropylmethyl-N-ethyl-guanidinomethyl)-6-methoxy-4'-trifluoromethyl-biphenyl-3-yl]-acetic acid (Compound 1-146)

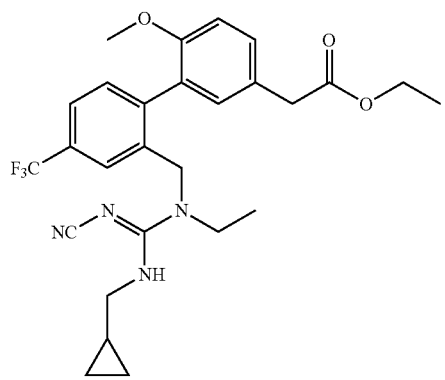 [SMILES: CCOC(=O)Cc1ccc(OC)c(-c2ccc(C(F)(F)F)cc2CN(CC)/C(=N/C#N)NCC2CC2)c1]

Step 1: [2'-(N"-Cyano-N'-cyclopropylmethyl-N-ethyl-guanidinomethyl)-6-methoxy-4'-trifluoromethyl-biphenyl-3-yl]-acetic acid ethyl ester Prepared according to the procedure described in Example 33, Step 6, using the following starting materials: [2'-(3-cyano-1-ethyl-2-phenyl-isoureidomethyl)-6-methoxy-4'-trifluoromethyl-biphenyl-3-yl]-acetic acid ethyl ester and (aminomethyl)cyclopropane.

308

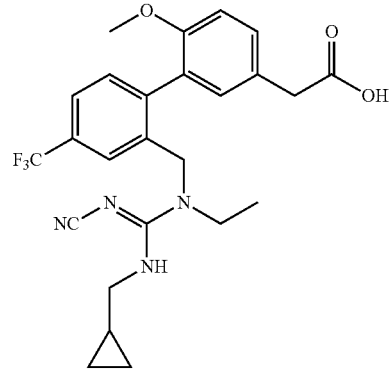 [SMILES: CCN(Cc1cc(C(F)(F)F)ccc1-c1cc(CC(=O)O)ccc1OC)/C(=N/C#N)NCC1CC1]

Step 2: [2'-(N"-Cyano-N'-cyclopropylmethyl-N-ethyl-guanidinomethyl)-6-methoxy-4'-trifluoromethyl-biphenyl-3-yl]-acetic acid Prepared according to the procedure described in Example 33, Step 7, using the following starting material: [2'-(N"-cyano-N'-cyclopropylmethyl-N-ethyl-guanidinomethyl)-6-methoxy-4'-trifluoromethyl-biphenyl-3-yl]-acetic acid ethyl ester. M+H is 489.

Example 151

Synthesis of [2'-(N'Cyano-N-ethyl-N"-pyridin-2-ylmethyl-guanidinomethyl)-6-methoxy-4'-trifluoromethyl-biphenyl-3-yl]-acetic acid (Compound 1-147)

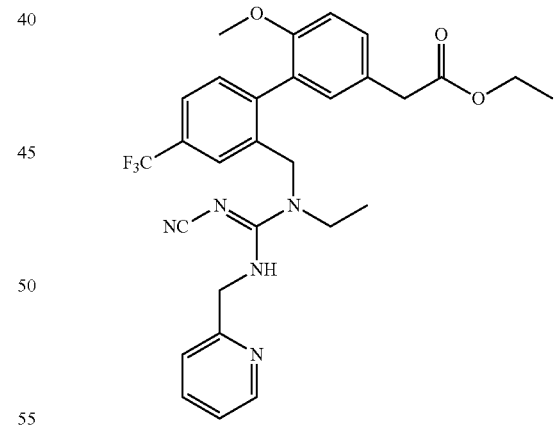

Step 1: [2'-(N'-Cyano-N-ethyl-N"-pyridin-2-ylmethyl-guanidinomethyl)-6-methoxy-4'-trifluoromethyl-biphenyl-3-yl]-acetic acid ethyl ester Prepared according to the procedure described in Example 33, Step 6, using the following starting materials: [2'-(3-cyano-1-ethyl-2-phenyl-isoureidomethyl)-6-methoxy-4'-trifluoromethyl-biphenyl-3-yl]-acetic acid ethyl ester and 2-(aminomethyl)pyridine.

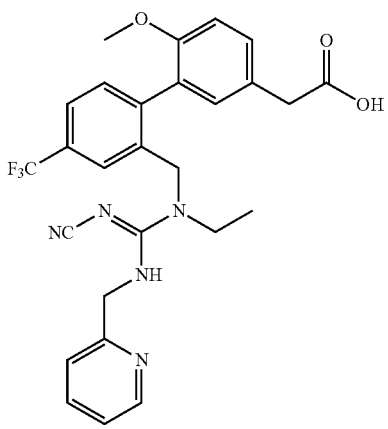 [SMILES: CCN(Cc1cc(C(F)(F)F)ccc1-c1cc(CC(=O)O)ccc1OC)/C(=N/C#N)NCc1ccccn1]

Step 2: [2'-(N'-Cyano-N-ethyl-N''-pyridin-2-ylmethyl-guanidinomethyl)-6-methoxy-4'-trifluoromethyl-biphenyl-3-yl]-acetic acid Prepared according to the procedure described in Example 33, Step 7, using the following starting material: [2'-(N'-cyano-N-ethyl-N''-pyridin-2-ylmethyl-guanidinomethyl)-6-methoxy-4'-trifluoromethyl-biphenyl-3-yl]-acetic acid ethyl ester. M+H is 526.

Example 152

Synthesis of [2'-[(Cyclopropanecarbonyl-ethyl-amino)-methyl]-4'-(6-ethoxy-pyridin-3-yl)-6-methoxy-biphenyl-3-yl]-acetic acid (Compound 1-227)

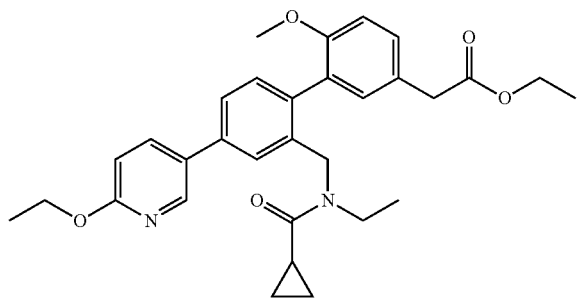 [SMILES: CCOC(=O)Cc1ccc(OC)c(-c2ccc(-c3ccc(OCC)nc3)cc2CN(CC)C(=O)C2CC2)c1]

Step 1: [2'-[(Cyclopropanecarbonyl-ethyl-amino)-methyl]-4'-(6-ethoxy-pyridin-3-yl)-6-methoxy-biphenyl-3-yl]-acetic acid ethyl ester Prepared according to the procedure described in Example 1, Step 6, using the following starting materials: [4'-(6-ethoxy-pyridin-3-yl)-2'-ethylaminomethyl-6-methoxy-biphenyl-3-yl]-acetic acid ethyl ester, hydrochloride and cyclopropanecarbonyl chloride.

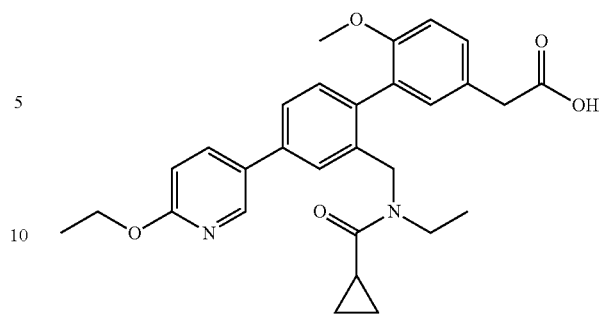

Step 2: [2'-[(Cyclopropanecarbonyl-ethyl-amino)-methyl]-4'-(6-ethoxy-pyridin-3-yl)-6-methoxy-biphenyl-3-yl]-acetic acid Prepared according to the procedure described in Example 31, Step 2, using the following starting material: [2'-[(cyclopropanecarbonyl-ethyl-amino)-methyl]-4'-(6-ethoxy-pyridin-3-yl)-6-methoxy-biphenyl-3-yl]-acetic acid ethyl ester. M+H is 489.

Example 153

Synthesis of (2'-{[Ethyl-(5-methyl-benzooxazol-2-yl)-amino]-methyl}-6-methoxy-4'-trifluoromethyl-biphenyl-3-yl)-acetic acid (Compound 1-248)

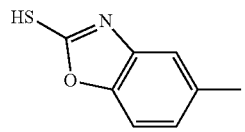

Step 1: 5-Methyl-benzooxazole-2-thiol

To a solution of 3,4-diaminotoluene (20.0 g, 162.6 mmol) and potassium hydroxide (11.36 g, 203.0 mmol) in $H_2O$ (40 mL) and MeOH (150 mL) was added carbon disulfide (13.3 mL, 220.8 mmol) slowly via syringe, and the reaction was heated to 78° C. for 2.5 hours. The mixture was poured over a mixture of ice (200 mL) and acetic acid (30 mL), and thick yellow precipitate formed. The mixture was stirred at 45° C. for 30 minutes, and then filtered to collect the solid precipitate, which was washed twice with $H_2O$ (40 mL total). The filter cake was triturated in a minimum of EtOAc, and then filtered and dried to give the title compound.

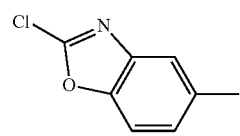

Step 2: 2-Chloro-5-methyl-benzooxazole

5-Methyl-benzooxazole-2-thiol (5.0 g, 30.2 mmol), phosphorus oxychloride (25.0 mL, 269.4 mmol), and phosphorus pentachloride (7.56 g, 36.3 mmol) were combined in $CH_2Cl_2$ (30 mL), and the reaction was stirred at room temperature overnight. The mixture was concentrated several times from fresh CH$_2$Cl$_2$ to remove traces of phosphorus oxychloride, and the residue was treated with saturated aqueous Na$_2$CO$_3$ to adjust to pH 8. The aqueous layer was extracted twice with CH$_2$Cl$_2$, and the combined organic layers were washed with H$_2$O and brine, and then dried over Na$_2$SO$_4$, decanted, and concentrated. The crude material was purified by silica gel chromatography (0-100% EtOAc in hexanes) to give the title compound.

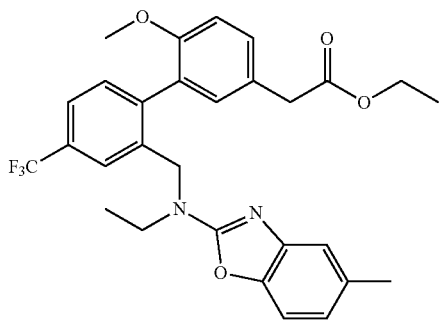 [SMILES: CCOC(=O)Cc1ccc(OC)c(-c2ccc(C(F)(F)F)cc2CN(CC)c2nc3cc(C)ccc3o2)c1]

Step 3: (2'-{[Ethyl-(5-methyl-benzooxazol-2-yl)-amino]-methyl}-6-methoxy-4'-trifluoromethyl-biphenyl-3-yl)-acetic acid ethyl ester (2'-Ethylaminomethyl-6-methoxy-4'-trifluoromethyl-biphenyl-3-yl)-acetic acid ethyl ester (0.300 g, 0.76 mmol), chloro-5-methyl-benzooxazole (0.135 g, 0.81 mmol), and diisopropylethylamine (0.5 mL, 2.87 mmol) were combined in EtOH (2 mL) in a sealed tube, and the reaction was stirred at 80° C. for 8 hours. The mixture was concentrated, and the residue was purified by silica gel chromatography to give the title compound.

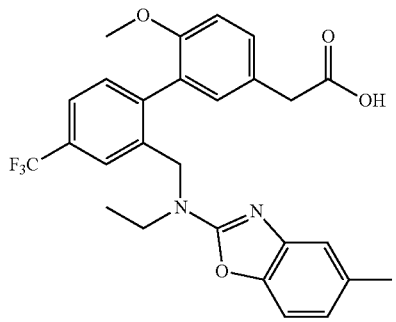 [SMILES: CCN(Cc1cc(C(F)(F)F)ccc1-c1cc(CC(=O)O)ccc1OC)c1nc2cc(C)ccc2o1]

Step 4: (2'-{[Ethyl-(5-methyl-benzooxazol-2-yl)-amino]-methyl}-6-methoxy-4'-trifluoromethyl-biphenyl-3-yl)-acetic acid Prepared according to the procedure described in Example 31, Step 2, using the following starting material: (2'-{[ethyl-(5-methyl-benzooxazol-2-yl)-amino]-methyl}-6-methoxy-4'-trifluoromethyl-biphenyl-3-yl)-acetic acid ethyl ester. M+H is 499.

Example 154

Synthesis of [2'-[(Cyclopropanecarbonyl-ethyl-amino)-methyl]-4'-(5-fluoro-pyridin-2-yl)-6-methoxy-biphenyl-3-yl]-acetic acid (Compound 1-249)

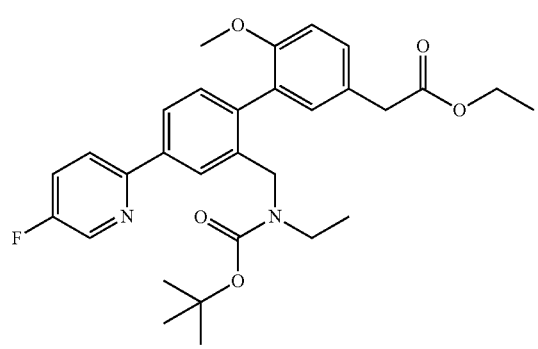 [SMILES: CCOC(=O)Cc1ccc(OC)c(-c2ccc(-c3ccc(F)cn3)cc2CN(CC)C(=O)OC(C)(C)C)c1]

Step 1: [2'-[(tert-Butoxycarbonyl-ethyl-amino)-methyl]-4'-(5-fluoro-pyridin-2-yl)-6-methoxy-biphenyl-3-yl]-acetic acid ethyl ester Prepared according to the procedure described in Example 1, Step 4, using the following starting materials: [2'-[(tert-butoxycarbonyl-ethyl-amino)-methyl]-6-methoxy-4'-(4,4,5,5-tetramethyl-[1,3,2]dioxaborolan-2-yl)-biphenyl-3-yl]-acetic acid ethyl ester and 2-bromo-5-fluoropyridine.

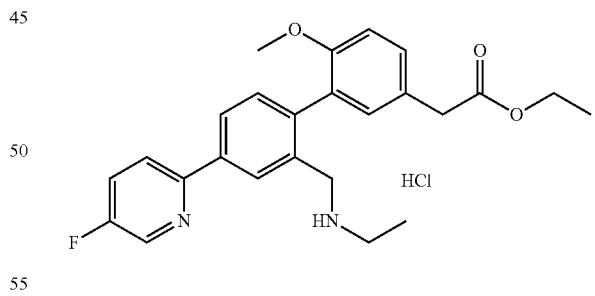

Step 2: [2'-Ethylaminomethyl-4'-(5-fluoro-pyridin-2-yl)-6-methoxy-biphenyl-3-yl]-acetic acid ethyl ester, hydrochloride Prepared according to the procedure described in Example 46, Step 7, using the following starting material: [2'-[(tert-butoxycarbonyl-ethyl-amino)-methyl]-4'-(5-fluoro-pyridin-2-yl)-6-methoxy-biphenyl-3-yl]-acetic acid ethyl ester.

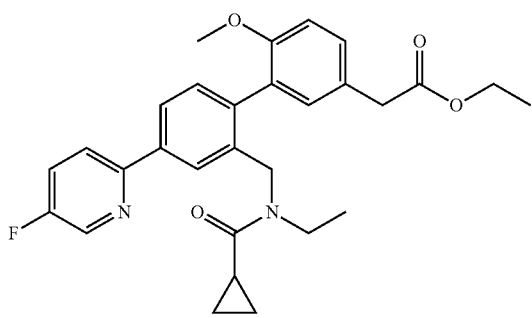 [SMILES: CCOC(=O)Cc1ccc(OC)c(-c2ccc(-c3ccc(F)cn3)cc2CN(CC)C(=O)C2CC2)c1]

Step 3: [2'-[(Cyclopropanecarbonyl-ethyl-amino)-methyl]-4'-(5-fluoro-pyridin-2-yl)-6-methoxy-biphenyl-3-yl]-acetic acid ethyl ester Prepared according to the procedure described in Example 1, Step 6, using the following starting materials: [2'-ethylaminomethyl-4'-(5-fluoro-pyridin-2-yl)-6-methoxy-biphenyl-3-yl]-acetic acid ethyl ester, hydrochloride and cyclopropanecarbonyl chloride.

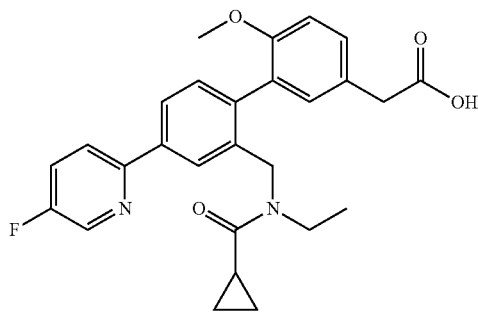 [SMILES: CCN(Cc1cc(-c2ccc(F)cn2)ccc1-c1cc(CC(=O)O)ccc1OC)C(=O)C1CC1]

Step 4: [2'-[(Cyclopropanecarbonyl-ethyl-amino)-methyl]-4'-(5-fluoro-pyridin-2-yl)-6-methoxy-biphenyl-3-yl]-acetic acid Prepared according to the procedure described in Example 31, Step 2, using the following starting material: [2'-[(cyclopropanecarbonyl-ethyl-amino)-methyl]-4'-(5-fluoro-pyridin-2-yl)-6-methoxy-biphenyl-3-yl]-acetic acid ethyl ester. M+H is 463.

Example 155

Synthesis of [2'-[(Cyclopropanecarbonyl-ethyl-amino)-methyl]-6-methoxy-4'-(5-methoxy-pyrimidin-2-yl)-biphenyl-3-yl]-acetic acid (Compound 1-250)

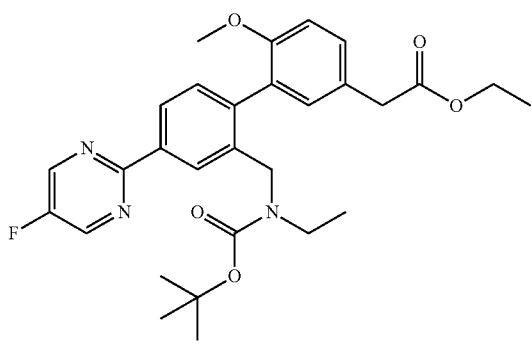 [SMILES: CCOC(=O)Cc1ccc(OC)c(-c2ccc(-c3ncc(F)cn3)cc2CN(CC)C(=O)OC(C)(C)C)c1]

Step 1: [2-[(tert-Butoxycarbonyl-ethyl-amino)-methyl]-4'-(5-fluoro-pyrimidin-2-yl)-6-methoxy-biphenyl-3-yl]-acetic acid ethyl ester Prepared according to the procedure described in Example 1, Step 4, using the following starting materials: [2'-[(tert-butoxycarbonyl-ethyl-amino)-methyl]-6-methoxy-4'-(4,4,5,5-tetramethyl-[1,3,2]dioxaborolan-2-yl)-biphenyl-3-yl]-acetic acid ethyl ester and 2-chloro-5-fluoropyrimidine.

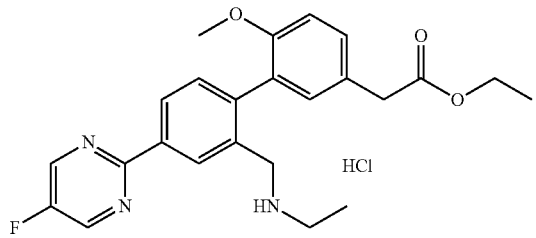 [SMILES: CCNCc1cc(-c2ncc(F)cn2)ccc1-c1cc(CC(=O)OCC)ccc1OC ; Cl]

Step 2: [2'-Ethylaminomethyl-4'-(5-fluoro-pyrimidin-2-yl)-6-methoxy-biphenyl-3-yl]-acetic acid ethyl ester Prepared according to the procedure described in Example 46, Step 7, using the following starting material: [2'-[(tert-butoxycarbonyl-ethyl-amino)-methyl]-4'-(5-fluoro-pyrimidin-2-yl)-6-methoxy-biphenyl-3-yl]-acetic acid ethyl ester.

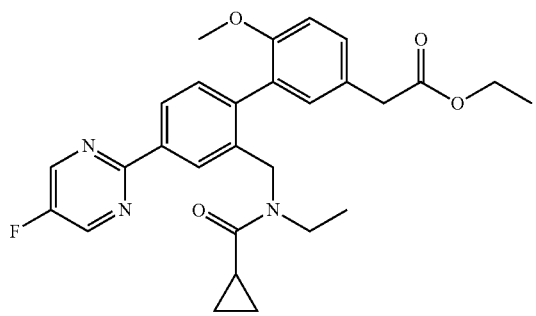 [SMILES: CCOC(=O)Cc1ccc(OC)c(-c2ccc(-c3ncc(F)cn3)cc2CN(CC)C(=O)C2CC2)c1]

Step 3: [2'-[(Cyclopropanecarbonyl-ethyl-amino)-methyl]-4'-(5-fluoro-pyrimidin-2-yl)-6-methoxy-biphenyl-3-yl]-acetic acid ethyl ester Prepared according to the procedure described in Example 1, Step 6, using the following starting materials: [2'-ethylaminomethyl-4'-(5-fluoro-pyrimidin-2-yl)-6-methoxy-biphenyl-3-yl]-acetic acid ethyl ester and cyclopropanecarbonyl chloride.

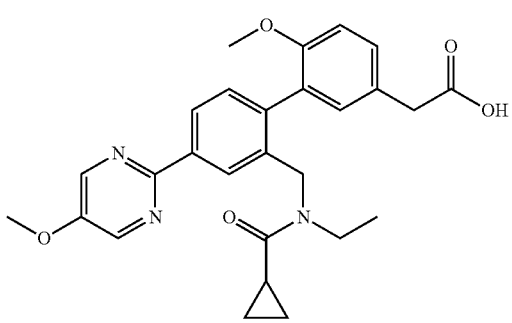 [SMILES: CCN(Cc1cc(-c2ncc(OC)cn2)ccc1-c1cc(CC(=O)O)ccc1OC)C(=O)C1CC1]

Step 4: [2'-[(Cyclopropanecarbonyl-ethyl-amino)-methyl]-6-methoxy-4'-(5-methoxy-pyrimidin-2-yl)-biphenyl-3-yl]-acetic acid Prepared according to the procedure described in Example 31, Step 2, using the following starting material: [2'-[(cyclopropanecarbonyl-ethyl-amino)-methyl]-4'-(5-fluoro-pyrimidin-2-yl)-6-methoxy-biphenyl-3-yl]-acetic acid ethyl ester. M+H is 476.

Example 156

Synthesis of [2'-[(Benzoyl-ethyl-amino)-methyl]-4'-(6-ethoxy-pyridin-3-yl)-6-methoxy-biphenyl-3-yl]-acetic acid (Compound 1-254)

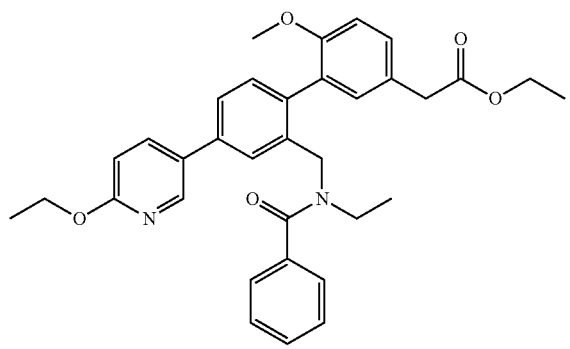 [SMILES: CCOC(=O)Cc1ccc(OC)c(-c2ccc(-c3ccc(OCC)nc3)cc2CN(CC)C(=O)c2ccccc2)c1]

Step 1: [2'-[(Benzoyl-ethyl-amino)-methyl]-4'-(6-ethoxy-pyridin-3-yl)-6-methoxy-biphenyl-3-yl]-acetic acid ethyl ester Prepared according to the procedure described in Example 1, Step 6, using the following starting materials: [4'-(6-ethoxy-pyridin-3-yl)-2'-ethylaminomethyl-6-methoxy-biphenyl-3-yl]-acetic acid ethyl ester, hydrochloride and benzoyl chloride.

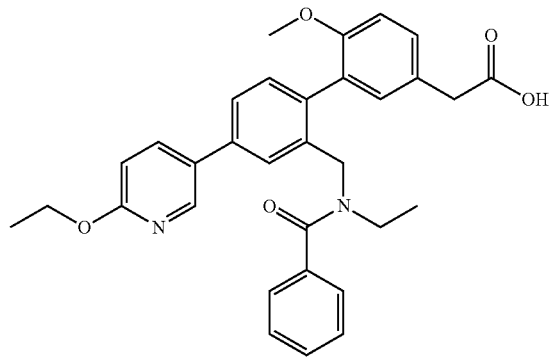 [SMILES: CCOc1ccc(-c2ccc(-c3cc(CC(=O)O)ccc3OC)c(CN(CC)C(=O)c3ccccc3)c2)cn1]

Step 2: [2'-[(Benzoyl-ethyl-amino)-methyl]-4'-(6-ethoxy-pyridin-3-yl)-6-methoxy-biphenyl-3-yl]-acetic acid Prepared according to the procedure described in Example 31, Step 2, using the following starting material: [2'-[(benzoyl-ethyl-amino)-methyl]-4'-(6-ethoxy-pyridin-3-yl)-6-methoxy-biphenyl-3-yl]-acetic acid ethyl ester. M+H is 525.

Example 157

Synthesis of {4'-(6-Ethoxy-pyridin-3-yl)-2'-[(ethyl-phenylacetyl-amino)-methyl]-6-methoxy-biphenyl-3-yl}-acetic acid (Compound 1-255)

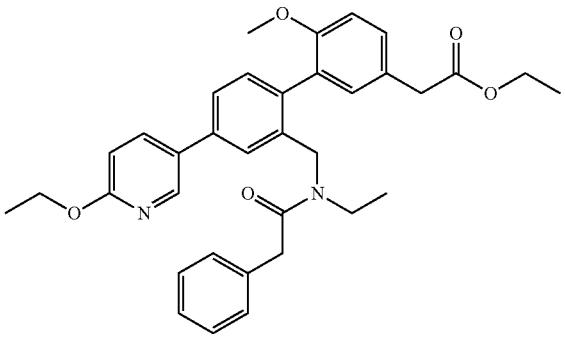 [SMILES: CCOC(=O)Cc1ccc(OC)c(-c2ccc(-c3ccc(OCC)nc3)cc2CN(CC)C(=O)Cc2ccccc2)c1]

Step 1: {4'-(6-Ethoxy-pyridin-3-yl)-2'-[(ethyl-phenylacetyl-amino)-methyl]-6-methoxy-biphenyl-3-yl}-acetic acid ethyl ester Prepared according to the procedure described in Example 1, Step 6, using the following starting materials: [4'-(6-ethoxy-pyridin-3-yl)-2'-ethylaminomethyl-6-methoxy-biphenyl-3-yl]-acetic acid ethyl ester, hydrochloride and phenylacetyl chloride.

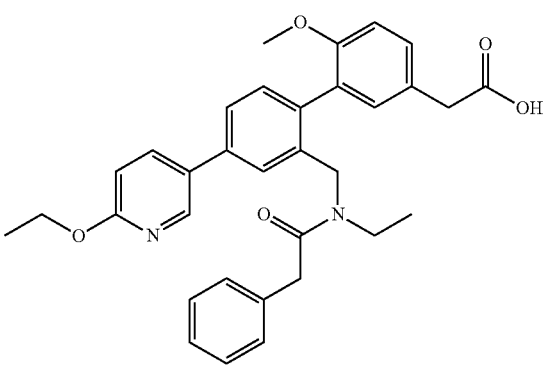 [SMILES: CCOc1ccc(-c2ccc(-c3cc(CC(=O)O)ccc3OC)c(CN(CC)C(=O)Cc3ccccc3)c2)cn1]

Step 2: {4'-(6-Ethoxy-pyridin-3-yl)-2'-[(ethyl-phenylacetyl-amino)-methyl]-6-methoxy-biphenyl-3-yl}-acetic acid Prepared according to the procedure described in Example 31, Step 2, using the following starting material: {4'-(6-ethoxy-pyridin-3-yl)-2'-[(ethyl-phenylacetyl-amino)-methyl]-6-methoxy-biphenyl-3-yl}-acetic acid ethyl ester. M+H is 539.

Example 158

Synthesis of {2'-[(Benzyloxycarbonyl-ethyl-amino)-methyl]-6'-methoxy-biphenyl-3-yl}-acetic acid (Compound 1-122)

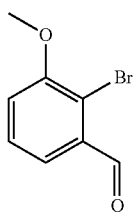

Step 1: 2-Bromo-3-methoxy-benzaldehyde

To a solution of 2-bromo-3-hydroxybenzaldehyde (0.5 g, 2.4 mmol) was added potassium carbonate (0.77 g, 5.6 mmol), and the mixture was stirred for 5 minutes. Iodomethane (0.17 mL, 2.7 mmol) was added, and the reaction was stirred at room temperature for 2 hours. The mixture was diluted with $H_2O$ (30 mL) and EtOAc (30 mL), and the organic layer was washed with 1N aqueous NaOH, then brine, dried over $Na_2SO_4$, decanted, and concentrated. The residue was purified by silica gel chromatography (0-60% EtOAc in hexanes) to give the title compound.

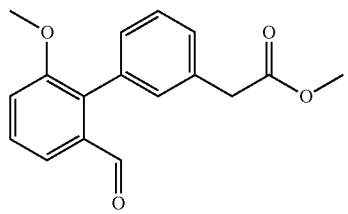 [SMILES: COC(=O)Cc1cccc(-c2c(C=O)cccc2OC)c1]

Step 2: (2'-Formyl-6'-methoxy-biphenyl-3-yl)-acetic acid methyl ester

Prepared according to the procedure described in Example 1, Step 4, using the following starting materials: 2-bromo-3-methoxy-benzaldehyde and [3-(4,4,5,5-tetramethyl-[1,3,2]dioxaborolan-2-yl)-phenyl]-acetic acid methyl ester.

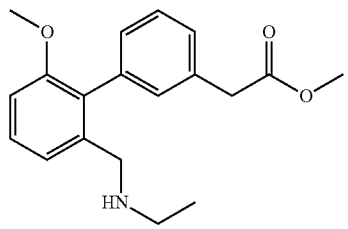 [SMILES: CCNCc1cccc(OC)c1-c1cccc(CC(=O)OC)c1]

Step 3: (2'-Ethylaminomethyl-6'-methoxy-biphenyl-3-yl)-acetic acid methyl ester Prepared according to the procedure described in Example 33, Step 4, using the following starting materials: (2'-formyl-6'-methoxy-biphenyl-3-yl)-acetic acid methyl ester and ethylamine (2M in THF).

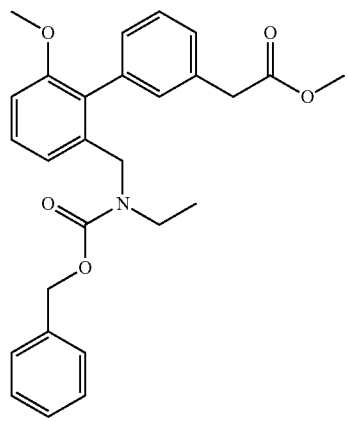 [SMILES: CCN(Cc1cccc(OC)c1-c1cccc(CC(=O)OC)c1)C(=O)OCc1ccccc1]

Step 4: {2'-[(Benzyloxycarbonyl-ethyl-amino)-methyl]-6'-methoxy-biphenyl-3-yl}-acetic acid methyl ester Prepared according to the procedure described in Example 1, Step 6, using the following starting materials: (2'-ethylaminomethyl-6'-methoxy-biphenyl-3-yl)-acetic acid methyl ester and benzyl chloroformate.

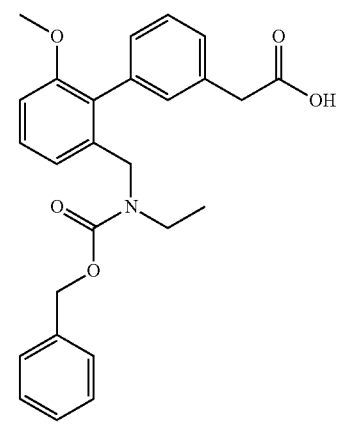 [SMILES: CCN(Cc1cccc(OC)c1-c1cccc(CC(=O)O)c1)C(=O)OCc1ccccc1]

Step 5: {2'-[(Benzyloxycarbonyl-ethyl-amino)-methyl]-6'-methoxy-biphenyl-3-yl}-acetic acid Prepared according to the procedure described in Example 31, Step 2, using the following starting material: {2'-[(benzyloxycarbonyl-ethyl-amino)-methyl]-6'-methoxy-biphenyl-3-yl}-acetic acid methyl ester. M+H is 434.

Example 159

Synthesis of (2'-{[(3,5-Difluoro-benzyloxycarbonyl)-ethyl-amino]-methyl}-6'-methoxy-biphenyl-3-yl)-acetic acid (Compound 1-123)

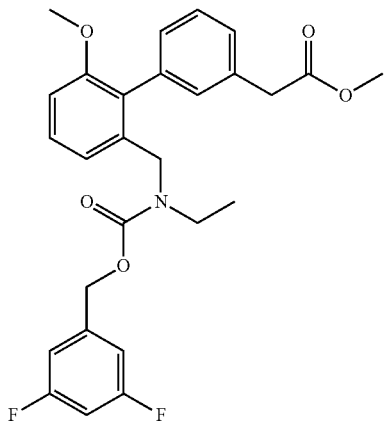 [SMILES: CCN(Cc1cccc(OC)c1-c1cccc(CC(=O)OC)c1)C(=O)OCc1cc(F)cc(F)c1]

Step 1: (2'-{[(3,5-Difluoro-benzyloxycarbonyl)-ethyl-amino]-methyl}-6'-methoxy-biphenyl-3-yl)-acetic acid methyl ester Prepared according to the procedure described in Example 1, Step 6, using the following starting materials: (2'-ethylaminomethyl-6'-methoxy-biphenyl-3-yl)-acetic acid methyl ester and 3,5-difluorobenzyl chloroformate.

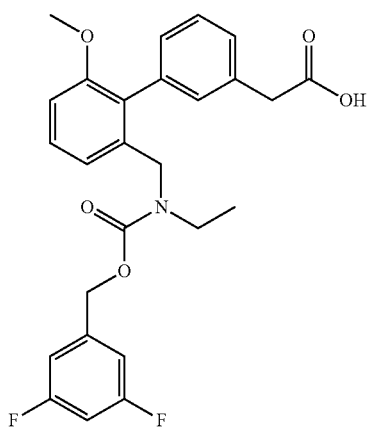 [SMILES: CCN(Cc1cccc(OC)c1-c1cccc(CC(=O)O)c1)C(=O)OCc1cc(F)cc(F)c1]

Step 2: (2'-{[(3,5-Difluoro-benzyloxycarbonyl)-ethyl-amino]-methyl}-6'-methoxy-biphenyl-3-yl)-acetic acid Prepared according to the procedure described in Example 31, Step 2, using the following starting material: (2'-{[(3,5-difluoro-benzyloxycarbonyl)-ethyl-amino]-methyl}-6'-methoxy-biphenyl-3-yl)-acetic acid methyl ester. M+H is 470.

Example 160

Synthesis of (2'-{[Ethyl-(2-morpholin-4-yl-ethyl)-amino]-methyl}-6'-methoxy-biphenyl-3-yl)-acetic acid (Compound 1-166)

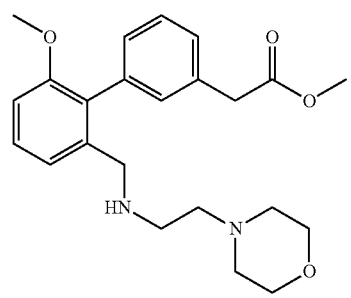 [SMILES: COC(=O)Cc1cccc(-c2c(CNCCN3CCOCC3)cccc2OC)c1]

Step 1: {6'-Methoxy-2'-[(2-morpholin-4-yl-ethylamino)-methyl]-biphenyl-3-yl}-acetic acid methyl ester Prepared according to the procedure described in Example 33, Step 4, using the following starting materials: (2'-formyl-6'-methoxy-biphenyl-3-yl)-acetic acid methyl ester and 4-(2-aminoethyl)morpholine.

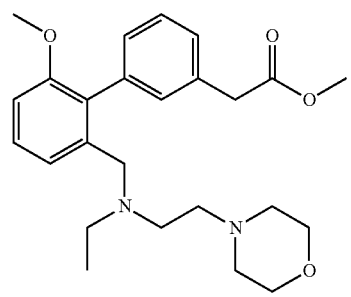 [SMILES: CCN(CCN1CCOCC1)Cc1cccc(OC)c1-c1cccc(CC(=O)OC)c1]

Step 2: (2'-{[Ethyl-(2-morpholin-4-yl-ethyl)-amino]-methyl}-6'-methoxy-biphenyl-3-yl)-acetic acid methyl ester Prepared according to the procedure described in Example 33, Step 4, using the following starting materials: {6-methoxy-2'-[(2-morpholin-4-yl-ethylamino)-methyl]-biphenyl-3-yl}-acetic acid methyl ester and acetaldehyde.

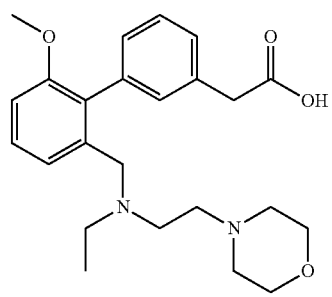 [SMILES: CCN(CCN1CCOCC1)Cc1cccc(OC)c1-c1cccc(CC(=O)O)c1]

Step 3: (2'-{[Ethyl-(2-morpholin-4-yl-ethyl)-amino]-methyl}-6'-methoxy-biphenyl-3-yl)-acetic acid Prepared according to the procedure described in Example 31, Step 2, using the following starting material: (2'-{[ethyl-(2-morpholin-4-yl-ethyl)-amino]-methyl}-6'-methoxy-biphenyl-3-yl)-acetic acid methyl ester. M+H is 414.

Example 161

Synthesis of [2'-({Ethyl-[3-(2-oxo-pyrrolidin-1-yl)-propyl]-amino}-methyl)-6'-methoxy-biphenyl-3-yl]-acetic acid (Compound 1-167)

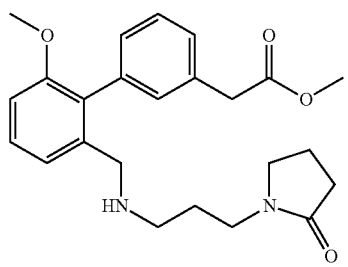 [SMILES: COC(=O)Cc1cccc(-c2c(CNCCCN3CCCC3=O)cccc2OC)c1]

Step 1: (6'-Methoxy-2'-{[3-(2-oxo-pyrrolidin-1-yl)-propyl]amino}-methyl)-biphenyl-3-yl)-acetic acid methyl ester Prepared according to the procedure described in Example 33, Step 4, using the following starting materials: (2'-formyl-6'-methoxy-biphenyl-3-yl)-acetic acid methyl ester and 1-(3-aminopropyl)-2-pyrrolidinone.

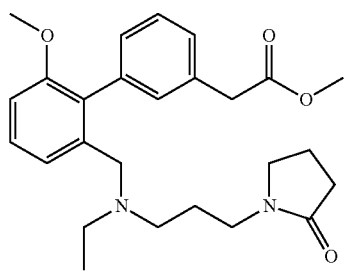 [SMILES: CCN(CCCN1CCCC1=O)Cc1cccc(OC)c1-c1cccc(CC(=O)OC)c1]

Step 2: [2'-({Ethyl-[3-(2-oxo-pyrrolidin-1-yl)-propyl]-amino}-methyl)-6'-methoxy-biphenyl-3-yl]-acetic acid methyl ester Prepared according to the procedure described in Example 33, Step 4, using the following starting materials: (6'-methoxy-2'-{[3-(2-oxo-pyrrolidin-1-yl)-propylamino]-methyl}-biphenyl-3-yl)-acetic acid methyl ester and acetaldehyde.

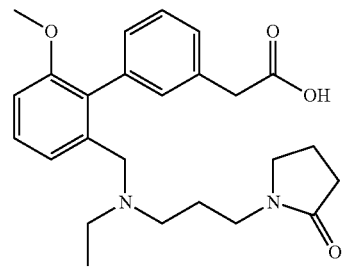 [SMILES: CCN(CCCN1CCCC1=O)Cc1cccc(OC)c1-c1cccc(CC(=O)O)c1]

Step 3: [2'-({Ethyl-[3-(2-oxo-pyrrolidin-1-yl)-propyl]-amino}-methyl)-6'-methoxy-biphenyl-3-yl]-acetic acid Prepared according to the procedure described in Example 31, Step 2, using the following starting material: [2'-({ethyl-[3-(2-oxo-pyrrolidin-1-yl)-propyl]-amino)}-methyl)-6'-methoxy-biphenyl-3-yl]-acetic acid methyl ester. M+H is 426.

Example 162

Synthesis of (2'-{[Ethyl-(4-fluoro-benzyloxycarbonyl)-amino]-methyl}-6-methoxy-5'-trifluoromethyl-biphenyl-3-yl)-acetic acid (Compound 1-168)

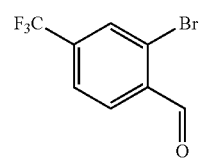

Step 1: 2-Bromo-4-trifluoromethyl-benzaldehyde

2-Bromo-4-(trifluoromethyl)benzyl alcohol (4.0 g, 15.88 mmol) and Dess-Martin periodinane (7.14 g, 16.67 mmol) were combined in $CH_2Cl_2$ and stirred for 1.5 hours at room temperature. Saturated aqueous $Na_2CO_3$ was added, and a white precipitate was formed. The mixture was diluted with $CH_2Cl_2$ and saturated aqueous $Na_2CO_3$ and stirred for 1 hour. 1N Aqueous NaOH was added, and the organic layer was separated and concentrated. The residue was purified by silica gel chromatography (0-80% EtOAc in hexanes) to give the title compound.

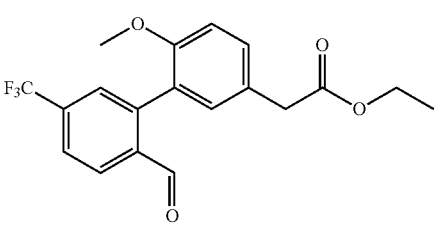 [SMILES: CCOC(=O)Cc1ccc(OC)c(-c2cc(C(F)(F)F)ccc2C=O)c1]

Step 2: (2'-Formyl-6-methoxy-5'-trifluoromethyl-biphenyl-3-yl)-acetic acid ethyl ester Prepared according to the procedure described in Example 1, Step 4, using the following starting materials: 2-bromo-4- trifluoromethyl-benzaldehyde and [4-methoxy-3-(4,4,5,5-tetramethyl-[1,3,2]dioxaborolan-2-yl)-phenyl]-acetic acid ethyl ester.

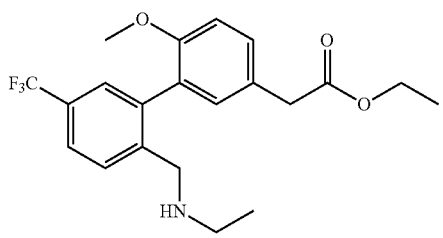 [SMILES: CCNCc1ccc(C(F)(F)F)cc1-c1cc(CC(=O)OCC)ccc1OC]

Step 3: (2'-Ethylaminomethyl-6-methoxy-5'-trifluoromethyl-biphenyl-3-yl)-acetic acid ethyl ester Prepared according to the procedure described in Example 33, Step 4, using the following starting materials: (2'-formyl-6-methoxy-5'-trifluoromethyl-biphenyl-3-yl)-acetic acid ethyl ester and ethylamine (2M in THF).

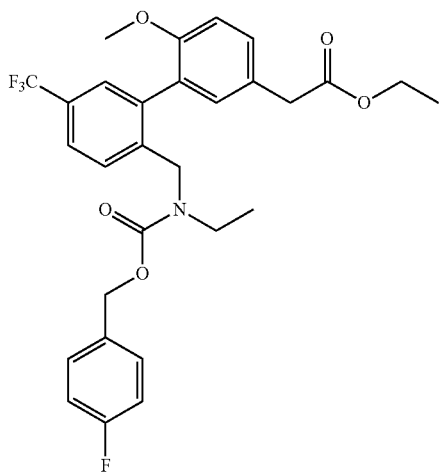

Step 4: (2'-{[Ethyl-(4-fluoro-benzyloxycarbonyl)-amino]-methyl}-6-methoxy-5'-trifluoromethyl-biphenyl-3-yl)-acetic acid ethyl ester Prepared according to the procedure described in Example 1, Step 6, using the following starting materials: (2'-ethylaminomethyl-6-methoxy-5'-trifluoromethyl-biphenyl-3-yl)-acetic acid ethyl ester and 4-fluorobenzyl chloroformate.

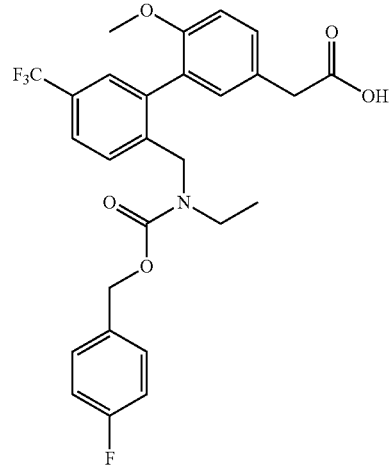 [SMILES: CCN(Cc1ccc(C(F)(F)F)cc1-c1cc(CC(=O)O)ccc1OC)C(=O)OCc1ccc(F)cc1]

Step 5: (2'-{[Ethyl-(4-fluoro-benzyloxycarbonyl)-amino]-methyl}-6-methoxy-5'-trifluoromethyl-biphenyl-3-yl)-acetic acid Prepared according to the procedure described in Example 31, Step 2, using the following starting material: (2'-{[ethyl-(4-fluoro-benzyloxycarbonyl)-amino]-methyl}-6-methoxy-5'-trifluoromethyl-biphenyl-3-yl)-acetic acid ethyl ester. M+H is 519.

Example 163

Synthesis of (2'-{[Ethyl-(4-fluoro-benzyloxycarbonyl)-amino]-methyl}-6-methoxy-5'-methyl-biphenyl-3-yl)-acetic acid (Compound 1-169)

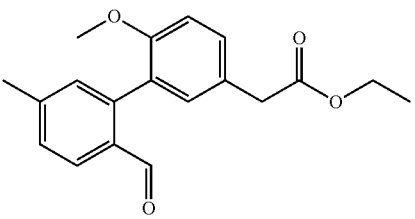 [SMILES: CCOC(=O)Cc1ccc(OC)c(-c2cc(C)ccc2C=O)c1]

Step 1: (2'-Formyl-6-methoxy-5'-methyl-biphenyl-3-yl)-acetic acid ethyl ester Prepared according to the procedure described in Example 1, Step 4, using the following starting materials: [4-methoxy-3-(4,4,5,5-tetramethyl-[1,3,2]dioxaborolan-2-yl)-phenyl]-acetic acid ethyl ester and 2-bromo-4-methylbenzaldehyde.

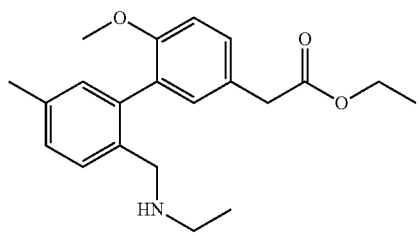 [SMILES: CCNCc1ccc(C)cc1-c1cc(CC(=O)OCC)ccc1OC]

Step 2: (2'-Ethylaminomethyl-6-methoxy-5'-methyl-biphenyl-3-yl)-acetic acid ethyl ester Prepared according to the procedure described in Example 33, Step 4, using the following starting materials: (2'-formyl-6-methoxy-5'-methyl-biphenyl-3-yl)-acetic acid ethyl ester and ethylamine (2M in THF).

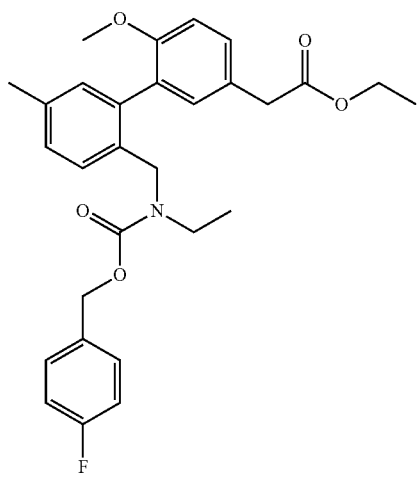

Step 3: (2'-{[Ethyl-(4-fluoro-benzyloxycarbonyl)-amino]-methyl}-6-methoxy-5'-methyl-biphenyl-3-yl)-acetic acid ethyl ester Prepared according to the procedure described in Example 1, Step 6, using the following starting materials: (2'-ethylaminomethyl-6-methoxy-5'-methyl-biphenyl-3-yl)-acetic acid ethyl ester and 4-fluorobenzyl chloroformate.

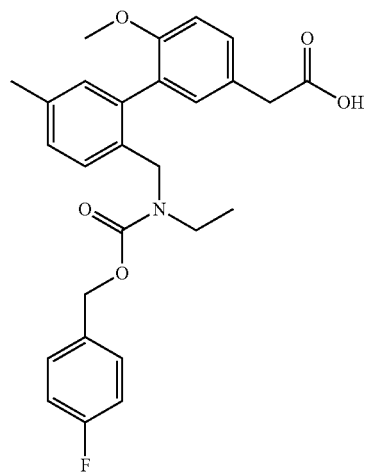 [SMILES: CCN(Cc1ccc(C)cc1-c1cc(CC(=O)O)ccc1OC)C(=O)OCc1ccc(F)cc1]

Step 4: (2'-{[Ethyl-(4-fluoro-benzyloxycarbonyl)-amino]-methyl}-6-methoxy-5'-methyl-biphenyl-3-yl)-acetic acid Prepared according to the procedure described in Example 31, Step 2, using the following starting material: (2'-{[ethyl-(4-fluoro-benzyloxycarbonyl)-amino]-methyl}-6-methoxy-5'-methyl-biphenyl-3-yl)-acetic acid ethyl ester. M+H is 466.

Example 164

Synthesis of {2'-[(Cyclopropanecarbonyl-ethyl-amino)-methyl]-6-methoxy-5'-trifluoromethyl-biphenyl-3-yl}-acetic acid (Compound 1-170)

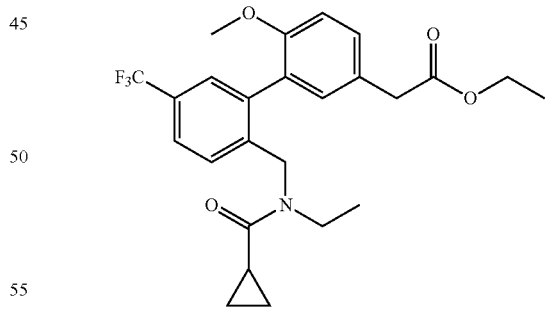

Step 1: {2'-[(Cyclopropanecarbonyl-ethyl-amino)-methyl]-6-methoxy-5'-trifluoromethyl-biphenyl-3-yl}-acetic acid ethyl ester Prepared according to the procedure described in Example 1, Step 6, using the following starting materials: (2'-ethylaminomethyl-6-methoxy-5'-trifluoromethyl-biphenyl-3-yl)-acetic acid ethyl ester and cyclopropanecarbonyl chloride.

327

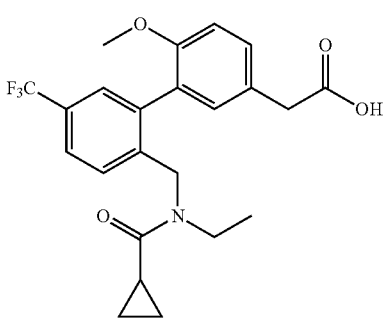 [SMILES: CCN(Cc1ccc(C(F)(F)F)cc1-c1cc(CC(=O)O)ccc1OC)C(=O)C1CC1]

Step 2: {2'-[(Cyclopropanecarbonyl-ethyl-amino)-methyl]-6-methoxy-5'-trifluoromethyl-biphenyl-3-yl}-acetic acid Prepared according to the procedure described in Example 31, Step 2, using the following starting material: {2'-[(cyclopropanecarbonyl-ethyl-amino)-methyl]-6-methoxy-5'-trifluoromethyl-biphenyl-3-yl}-acetic acid ethyl ester. M+H is 436.

Example 165

Synthesis of {2'-[(Cyclopropanecarbonyl-ethyl-amino)-methyl]-6-methoxy-5'-methyl-biphenyl-3-yl}-acetic acid (Compound 1-171)

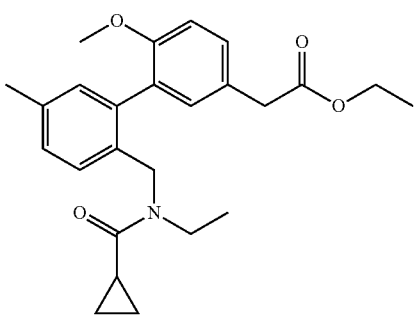 [SMILES: CCOC(=O)Cc1ccc(OC)c(-c2cc(C)ccc2CN(CC)C(=O)C2CC2)c1]

Step 1: {2'-[(Cyclopropanecarbonyl-ethyl-amino)-methyl]-6-methoxy-5'-methyl-biphenyl-3-yl}-acetic acid ethyl ester Prepared according to the procedure described in Example 1, Step 6, using the following starting materials: (2'-ethylaminomethyl-6-methoxy-5'-methyl-biphenyl-3-yl)-acetic acid ethyl ester and cyclopropanecarbonyl chloride.

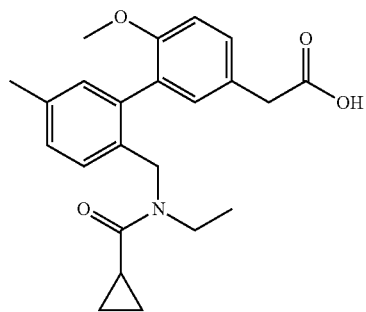 [SMILES: CCN(Cc1ccc(C)cc1-c1cc(CC(=O)O)ccc1OC)C(=O)C1CC1]

328

Step 2: {2'-[(Cyclopropanecarbonyl-ethyl-amino)-methyl]-6-methoxy-5'-methyl-biphenyl-3-yl}-acetic acid Prepared according to the procedure described in Example 31, Step 2, using the following starting material: {2'-[(cyclopropanecarbonyl-ethyl-amino)-methyl]-6-methoxy-5'-methyl-biphenyl-3-yl}-acetic acid ethyl ester. M+H is 382.

Example 166

Synthesis of [2'-(3-Benzyl-1-ethyl-ureidomethyl)-6-methoxy-5'-trifluoromethyl-biphenyl-3-yl]-acetic acid (Compound 1-172)

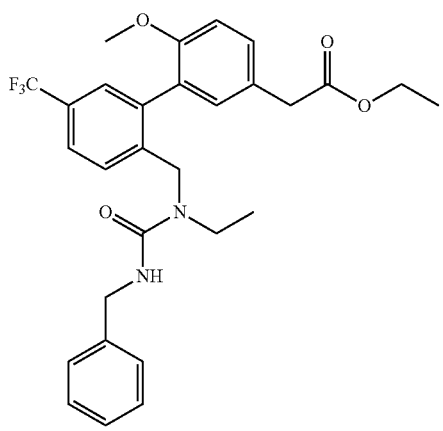 [SMILES: CCOC(=O)Cc1ccc(OC)c(-c2cc(C(F)(F)F)ccc2CN(CC)C(=O)NCc2ccccc2)c1]

Step 1: [2'-(3-Benzyl-1-ethyl-ureidomethyl)-6-methoxy-5'-trifluoromethyl-biphenyl-3-yl]-acetic acid ethyl ester Prepared according to the procedure described in Example 1, Step 6, using the following starting materials: (2'-ethylaminomethyl-6-methoxy-5'-trifluoromethyl-biphenyl-3-yl)-acetic acid ethyl ester and benzyl isocyanate.

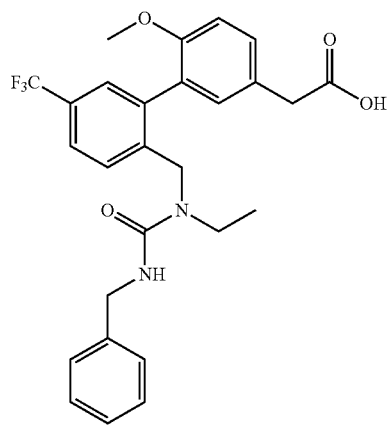 [SMILES: CCN(Cc1ccc(C(F)(F)F)cc1-c1cc(CC(=O)O)ccc1OC)C(=O)NCc1ccccc1]

Step 2: [2'-(3-Benzyl-1-ethyl-ureidomethyl)-6-methoxy-5'-trifluoromethyl-biphenyl-3-yl]-acetic acid Prepared according to the procedure described in Example 31, Step 2, using the following starting material: [2'-(3-benzyl-1-ethyl-ureidomethyl)-6-methoxy-5'-trifluoromethyl-biphenyl-3-yl]-acetic acid ethyl ester. M+H is 501.

Example 167

Synthesis of [2'-(3-Benzyl-1-ethyl-ureidomethyl)-6-methoxy-5'-methyl-biphenyl-3-yl]-acetic acid (Compound 1-173)

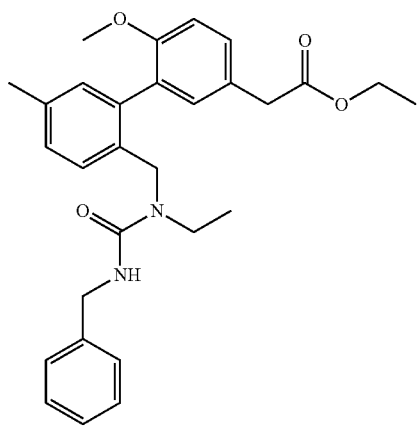 [SMILES: CCOC(=O)Cc1ccc(OC)c(-c2cc(C)ccc2CN(CC)C(=O)NCc2ccccc2)c1]

Step 1: [2'-(3-Benzyl-1-ethyl-ureidomethyl)-6-methoxy-5'-methyl-biphenyl-3-yl]-acetic acid ethyl ester Prepared according to the procedure described in Example 1, Step 6, using the following starting materials: (2'-ethylaminomethyl-6-methoxy-5'-methyl-biphenyl-3-yl)-acetic acid ethyl ester and benzyl isocyanate.

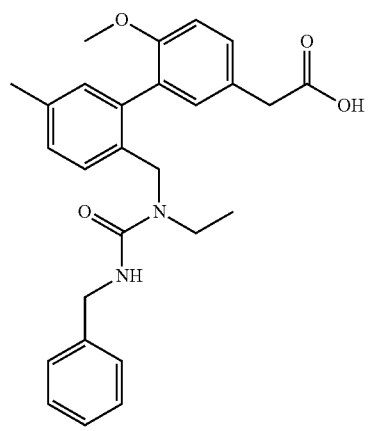 [SMILES: CCN(Cc1ccc(C)cc1-c1cc(CC(=O)O)ccc1OC)C(=O)NCc1ccccc1]

Step 2: [2'-(3-Benzyl-1-ethyl-ureidomethyl)-6-methoxy-5'-methyl-biphenyl-3-yl]-acetic acid Prepared according to the procedure described in Example 31, Step 2, using the following starting material: [2'-(3-benzyl-1-ethyl-ureidomethyl)-6-methoxy-5'-methyl-biphenyl-3-yl]-acetic acid ethyl ester. M+H is 447.

Example 168

Synthesis of (2'-{[(4-Chloro-benzyloxycarbonyl)-ethyl-amino]-methyl}-6-methoxy-5'-trifluoromethyl-biphenyl-3-yl)-acetic acid (Compound 1-174)

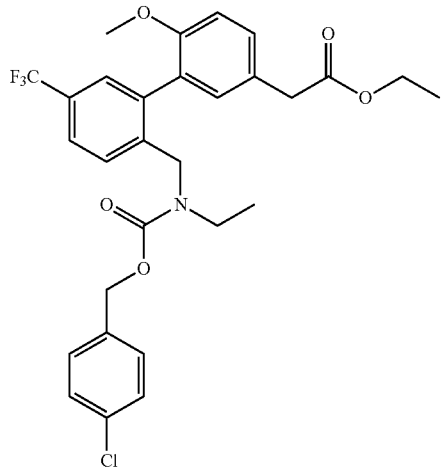 [SMILES: CCOC(=O)Cc1ccc(OC)c(-c2cc(C(F)(F)F)ccc2CN(CC)C(=O)OCc2ccc(Cl)cc2)c1]

Step 1: (2'-{[(4-Chloro-benzyloxycarbonyl)-ethyl-amino]-methyl}-6-methoxy-5'-trifluoromethyl-biphenyl-3-yl)-acetic acid ethyl ester Prepared according to the procedure described in Example 1, Step 6, using the following starting materials: (2'-ethylaminomethyl-6-methoxy-5'-trifluoromethyl-biphenyl-3-yl)-acetic acid ethyl ester and 4-chlorobenzyl chloroformate.

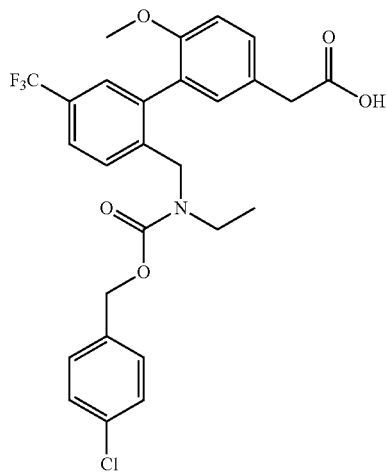

Step 2: (2'-{[(4-Chloro-benzyloxycarbonyl)-ethyl-amino]-methyl}-6-methoxy-5'-trifluoromethyl-biphenyl-3-yl)-acetic acid Prepared according to the procedure described in Example 31, Step 1, using the following starting material: (2'-{[(4- chloro-benzyloxycarbonyl)-ethyl-amino]-methyl}-6-methoxy-5'-trifluoromethyl-biphenyl-3-yl)-acetic acid ethyl ester. M+H is 559.

Example 169

Synthesis of (2'-{[(4-Chloro-benzyloxycarbonyl)-ethyl-amino]-methyl}-6-methoxy-5'-methyl-biphenyl-3-yl)-acetic acid (Compound 1-175)

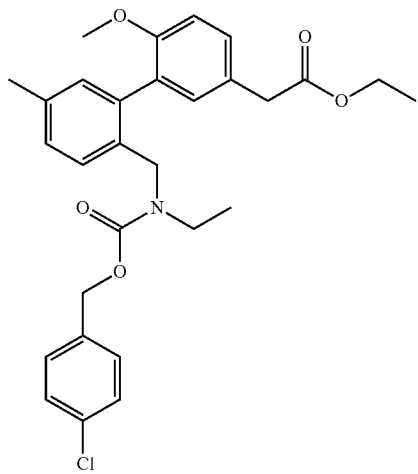 [SMILES: CCOC(=O)Cc1ccc(OC)c(-c2cc(C)ccc2CN(CC)C(=O)OCc2ccc(Cl)cc2)c1]

Step 1: (2'-{[(4-Chloro-benzyloxycarbonyl)-ethyl-amino]-methyl}-6-methoxy-5'-methyl-biphenyl-3-yl)-acetic acid ethyl ester Prepared according to the procedure described in Example 1, Step 6, using the following starting materials: (2'-ethylaminomethyl-6-methoxy-5'-methyl-biphenyl-3-yl)-acetic acid ethyl ester and 4-chlorobenzyl chloroformate.

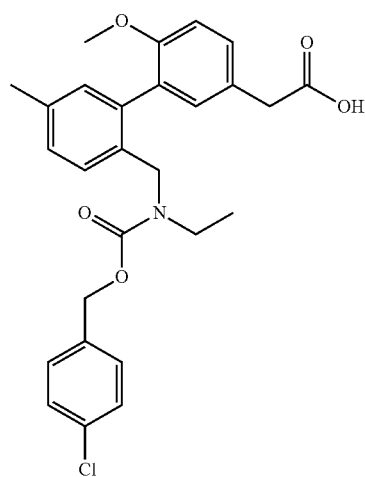 [SMILES: CCN(Cc1ccc(C)cc1-c1cc(CC(=O)O)ccc1OC)C(=O)OCc1ccc(Cl)cc1]

Step 2: (2'-{[(4-Chloro-benzyloxycarbonyl)-ethyl-amino]-methyl}-6-methoxy-5'-methyl-biphenyl-3-yl)-acetic acid Prepared according to the procedure described in Example 31, Step 2, using the following starting material: (2'-{[(4- chloro-benzyloxycarbonyl)-ethyl-amino]-methyl}-6-methoxy-5'-methyl-biphenyl-3-yl)-acetic acid ethyl ester. M+H is 482.

Example 170

Synthesis of (2'-{[Ethyl-(4-fluoro-benzyloxycarbonyl)-amino]-methyl}-6,5'-dimethoxy-biphenyl-3-yl)-acetic acid (Compound 1-194)

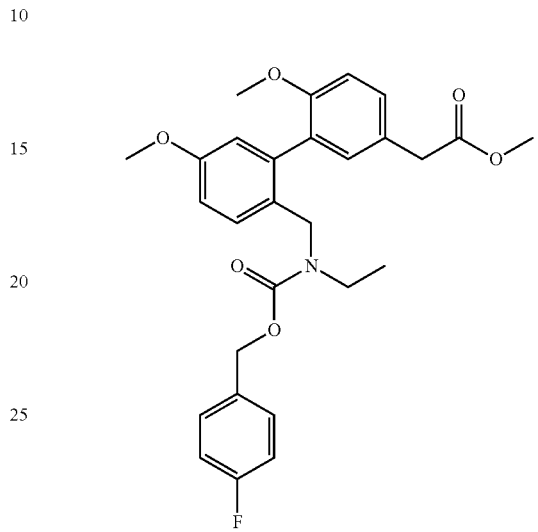

Step 1: (2'-{[Ethyl-(4-fluoro-benzyloxycarbonyl)-amino]-methyl}-6,5'-dimethoxy-biphenyl-3-yl)-acetic acid methyl ester Prepared according to the procedure described in Example 1, Step 6, using the following starting materials: (2'-ethylaminomethyl-6,5'-dimethoxy-biphenyl-3-yl)-acetic acid methyl ester and 4-fluorobenzyl chloroformate.

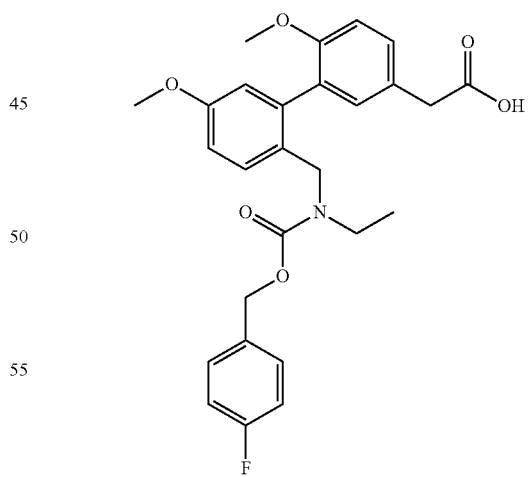

Step 2: (2'-{[Ethyl-(4-fluoro-benzyloxycarbonyl)-amino]-methyl}-6,5'-dimethoxy-biphenyl-3-yl)-acetic acid Prepared according to the procedure described in Example 31, Step 2, using the following starting material: (2'-{[ethyl- (4-fluoro-benzyloxycarbonyl)-amino]-methyl}-6,5'-dimethoxy-biphenyl-3-yl)-acetic acid methyl ester. M+H is 482.

Example 171

Synthesis of (2'-{[(4-Chloro-benzyloxycarbonyl)-ethyl-amino]-methyl}-6,5'-dimethoxy-biphenyl-3-yl)-acetic acid (Compound 1-195)

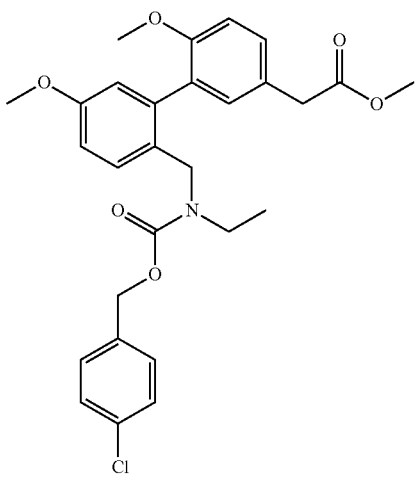

Step 1: (2'-{[(4-Chloro-benzyloxycarbonyl)-ethyl-amino]-methyl}-6,5'-dimethoxy-biphenyl-3-yl)-acetic acid methyl ester Prepared according to the procedure described in Example 1, Step 6, using the following starting materials: (2'-ethylaminomethyl-6,5'-dimethoxy-biphenyl-3-yl)-acetic acid methyl ester and 4-chlorobenzyl chloroformate.

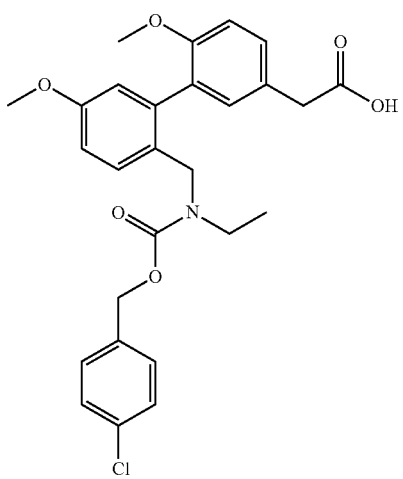 [SMILES: CCN(Cc1ccc(OC)cc1-c1cc(CC(=O)O)ccc1OC)C(=O)OCc1ccc(Cl)cc1]

Step 2: (2'-{[(4-Chloro-benzyloxycarbonyl)-ethyl-amino]-methyl}-6,5'-dimethoxy-biphenyl-3-yl)-acetic acid Prepared according to the procedure described in Example 31, Step 2, using the following starting material: (2'-{[(4-chloro-benzyloxycarbonyl)-ethyl-amino]-methyl}-6,5'-dimethoxy-biphenyl-3-yl)-acetic acid methyl ester. M+H is 498.

Example 172

Synthesis of [2'-(3-Benzyl-1-ethyl-ureidomethyl)-6,5'-dimethoxy-biphenyl-3-yl]-acetic acid (Compound 1-197)

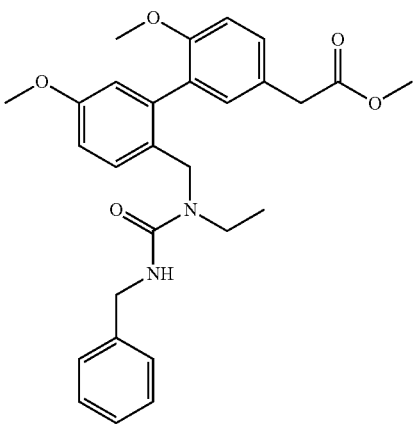

Step 1: [2'-(3-Benzyl-1-ethyl-ureidomethyl)-6,5'-dimethoxy-biphenyl-3-yl]-acetic acid methyl ester Prepared according to the procedure described in Example 95, Step 1, using the following starting materials: (2'-ethylaminomethyl-6,5'-dimethoxy-biphenyl-3-yl)-acetic acid methyl ester and benzyl isocyanate.

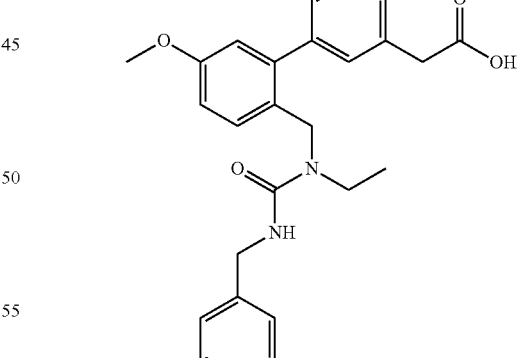

Step 2: [2'-(3-Benzyl-1-ethyl-ureidomethyl)-6,5'-dimethoxy-biphenyl-3-yl]-acetic acid Prepared according to the procedure described in Example 31, Step 2, using the following starting material: [2'-(3-benzyl-1-ethyl-ureidomethyl)-6,5'-dimethoxy-biphenyl-3-yl]-acetic acid methyl ester. M+H is 463.

Example 173

Synthesis of {5-Chloro-2'-[(cyclopropanecarbonyl-ethyl-amino)-methyl]-5'-methoxy-biphenyl-3-yl}-acetic acid (Compound 1-218)

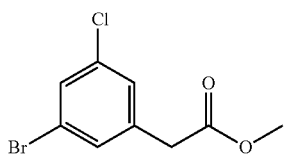

Step 1: (3-Bromo-5-chloro-phenyl)-acetic acid methyl ester

To a solution of (3-bromo-5-chloro-phenyl)-acetic acid (0.400 g, 1.60 mmol) in MeOH (15 mL) was added 4N aqueous HCl (2 mL), and the reaction was stirred at 90° C. for 2 hours. The mixture was concentrated and purified by silica gel chromatography (0-5% EtOAc in hexanes) to give the title compound.

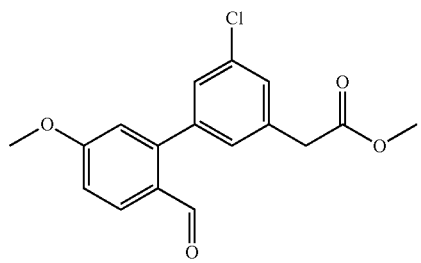

Step 2: (5-Chloro-2'-formyl-5'-methoxy-biphenyl-3-yl)-acetic acid methyl ester

Prepared according to the procedure described in Example 1, Step 4, using the following starting materials: (3-bromo-5-chloro-phenyl)-acetic acid methyl ester and 2-formyl-5-methoxyphenylboronic acid.

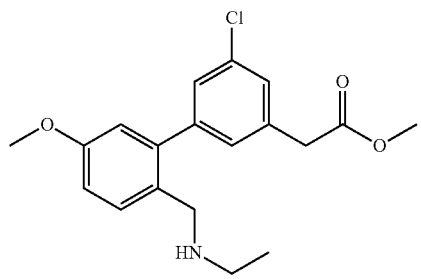

Step 3: (5-Chloro-2'-ethylaminomethyl-5'-methoxy-biphenyl-3-yl)-acetic acid methyl ester Prepared according to the procedure described in Example 33, Step 4, using the following starting materials: (5-chloro-2'-formyl-5'-methoxy biphenyl-3-yl)-acetic acid methyl ester and ethylamine (2M in THF).

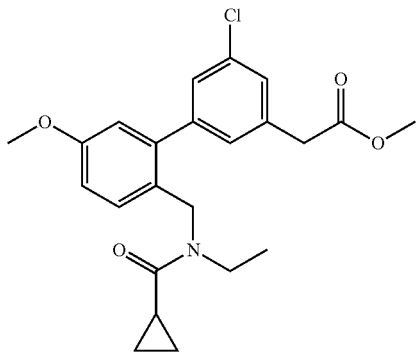

Step 4: {5-Chloro-2'-[(cyclopropanecarbonyl-ethyl-amino)-methyl]-5'-methoxy-biphenyl-3-yl}-acetic acid methyl ester Prepared according to the procedure described in Example 1, Step 6, using the following starting materials: (5-chloro-2'-ethylaminomethyl-5'-methoxy-biphenyl-3-yl)-acetic acid methyl ester and cyclopropanecarbonyl chloride.

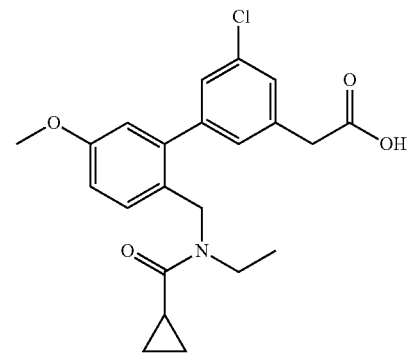 [SMILES: CCN(Cc1ccc(OC)cc1-c1cc(Cl)cc(CC(=O)O)c1)C(=O)C1CC1]

Step 5: {5-Chloro-2'-[(cyclopropanecarbonyl-ethyl-amino)-methyl]-5'-methoxy-biphenyl-3-yl}-acetic acid Prepared according to the procedure described in Example 31, Step 2, using the following starting material: {5-chloro-2'-[(cyclopropanecarbonyl-ethyl-amino)-methyl]-5'-methoxy-biphenyl-3-yl}-acetic acid methyl ester. M+H is 402.

Example 174

Synthesis of [2'-(3-Benzyl-1-ethyl-ureidomethyl)-5-chloro-5'-methoxy-biphenyl-3-yl]-acetic acid (Compound 1-219)

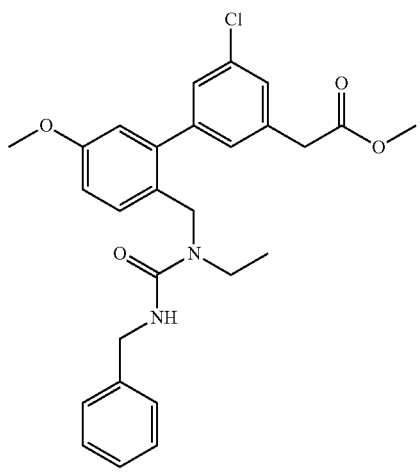

Step 1: [2'-(3-Benzyl-1-ethyl-ureidomethyl)-5-chloro-5'-methoxy-biphenyl-3-yl]-acetic acid methyl ester Prepared according to the procedure described in Example 95, Step 1, using the following starting materials: (5-chloro-2'-ethylaminomethyl-5'-methoxy-biphenyl-3-yl)-acetic acid methyl ester and benzyl isocyanate.

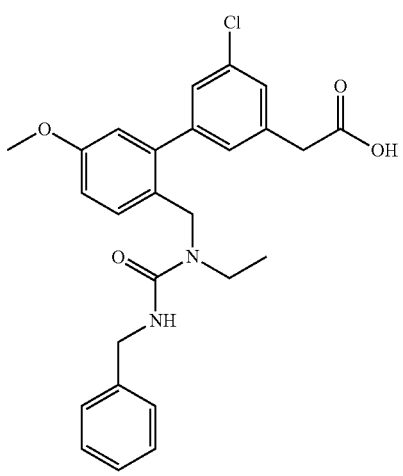 [SMILES: CCN(Cc1ccc(OC)cc1-c1cc(Cl)cc(CC(=O)O)c1)C(=O)NCc1ccccc1]

Step 2: [2'-(3-Benzyl-1-ethyl-ureidomethyl)-5-chloro-5'-methoxy-biphenyl-3-yl]-acetic acid Prepared according to the procedure described in Example 31, Step 2, using the following starting material: [2'-(3-benzyl-1-ethyl-ureidomethyl)-5-chloro-5'-methoxy-biphenyl-3-yl]-acetic acid methyl ester. M+H is 468.

Example 175

Synthesis of [5-Chloro-2'-({[2-(4-chloro-phenoxy)-acetyl]-ethyl-amino}-methyl)-5'-methoxy-biphenyl-3-yl]-acetic acid (Compound 1-221)

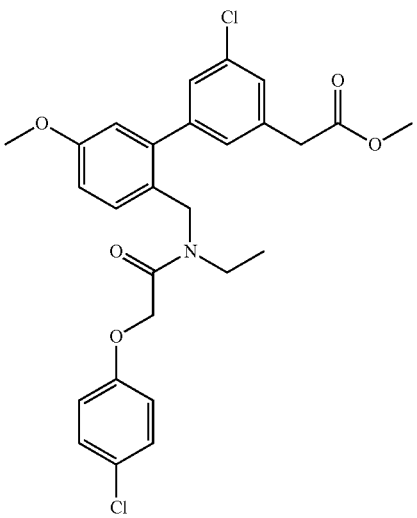

Step 1: [5-Chloro-2'-({[2-(4-chloro-phenoxy)-acetyl]-ethyl-amino}-methyl)-5'-methoxy-biphenyl-3-yl]-acetic acid methyl ester Prepared according to the procedure described in Example 1, Step 6, using the following starting materials: (5-chloro-2'-ethylaminomethyl-5'-methoxy-biphenyl-3-yl)-acetic acid methyl ester and 4-chlorophenoxyacetyl chloride.

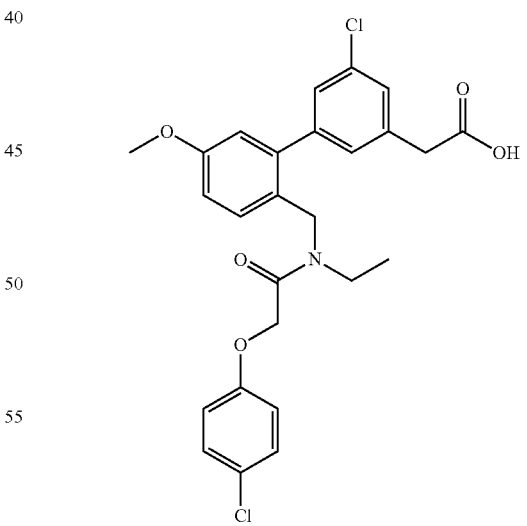

Step 2: [5-Chloro-2'-({[2-(4-chloro-phenoxy)-acetyl]-ethyl-amino}-methyl)-5'-methoxy-biphenyl-3-yl]-acetic acid Prepared according to the procedure described in Example 31, Step 2, using the following starting material: [5-chloro- 2'-({[2-(4-chloro-phenoxy)-acetyl]-ethyl-amino}-methyl)-5'-methoxy-biphenyl-3-yl]-acetic acid methyl ester. M+H is 503.

Example 176

Synthesis of [2'-(3-Benzyl-1-ethyl-ureidomethyl)-4'-(6-ethoxy-pyridin-3-yl)-6-methoxy-biphenyl-3-yl]-acetic acid (Compound 1-228)

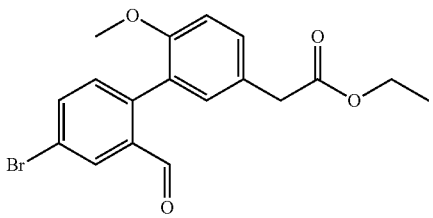 [SMILES: CCOC(=O)Cc1ccc(OC)c(-c2ccc(Br)cc2C=O)c1]

Step 1: (4'-Bromo-2'-formyl-6-methoxy-biphenyl-3-yl)-acetic acid ethyl ester

Prepared according to the procedure described in Example 1, Step 4, using the following starting materials: 5-bromo-2-iodo-benzaldehyde and [4-methoxy-3-(4,4,5,5-tetramethyl-[1,3,2]dioxaborolan-2-yl)-phenyl]-acetic acid ethyl ester.

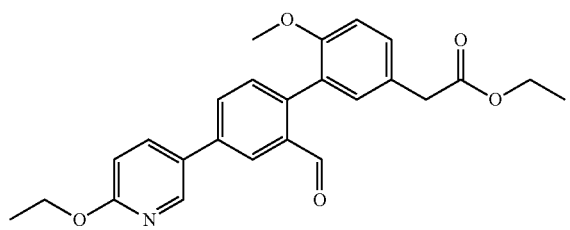 [SMILES: CCOC(=O)Cc1ccc(OC)c(-c2ccc(-c3ccc(OCC)nc3)cc2C=O)c1]

Step 2: [4'-(6-Ethoxy-pyridin-3-yl)-2'-formyl-6-methoxy-biphenyl-3-yl]-acetic acid ethyl ester Prepared according to the procedure described in Example 1, Step 4, using the following starting materials: (4'-bromo-2'-formyl-6-methoxy-biphenyl-3-yl)-acetic acid ethyl ester and 2-ethoxy-5-(4,4,5,5-tetramethyl-1,3,2-dioxaborolan-2-yl)pyridine.

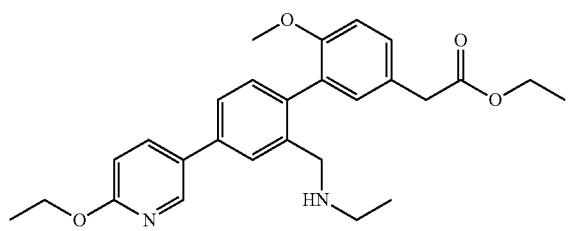 [SMILES: CCNCc1cc(-c2ccc(OCC)nc2)ccc1-c1cc(CC(=O)OCC)ccc1OC]

Step 3: [4'-(6-Ethoxy-pyridin-3-yl)-2'-ethylaminomethyl-6-methoxy-biphenyl-3-yl]-acetic acid ethyl ester Prepared according to the procedure described in Example 33, Step 4, using the following starting materials: [4'-(6-ethoxy-pyridin-3-yl)-2'-formyl-6-methoxy-biphenyl-3-yl]-acetic acid ethyl ester and ethylamine (2M in THF).

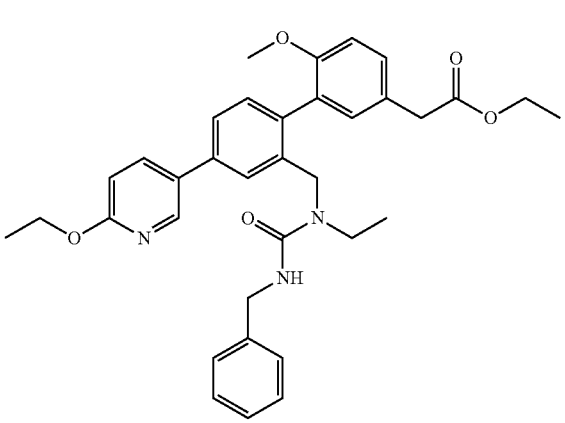 [SMILES: CCOC(=O)Cc1ccc(OC)c(-c2ccc(-c3ccc(OCC)nc3)cc2CN(CC)C(=O)NCc2ccccc2)c1]

Step 4: [2'-(3-Benzyl-1-ethyl-ureidomethyl)-4'-(6-ethoxy-pyridin-3-yl)-6-methoxy-biphenyl-3-yl]-acetic acid ethyl ester Prepared according to the procedure described in Example 95, Step 1, using the following starting materials: [4'-(6-ethoxy-pyridin-3-yl)-2'-ethylaminomethyl-6-methoxy-biphenyl-3-yl]-acetic acid ethyl ester and benzyl isocyanate.

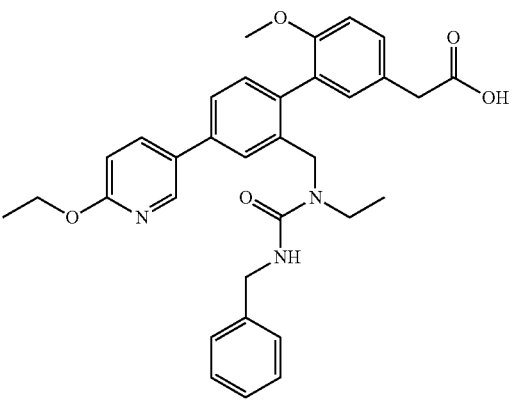 [SMILES: CCOc1ccc(-c2ccc(-c3cc(CC(=O)O)ccc3OC)c(CN(CC)C(=O)NCc3ccccc3)c2)cn1]

Step 5: [2'-(3-Benzyl-1-ethyl-ureidomethyl)-4'-(6-ethoxy-pyridin-3-yl)-6-methoxy-biphenyl-3-yl]-acetic acid Prepared according to the procedure described in Example 31, Step 2, using the following starting material: [2'-(3-benzyl-1-ethyl-ureidomethyl)-4'-(6-ethoxy-pyridin-3-yl)-6-methoxy-biphenyl-3-yl]-acetic acid ethyl ester. M+H is 555.

Example 177

Synthesis of [2'-({[2-(4-Chloro-phenoxy)-acetyl]-ethyl-amino}-methyl)-4'-(6-ethoxy-pyridin-3-yl)-6-methoxy-biphenyl-3-yl]-acetic acid (Compound 1-229)

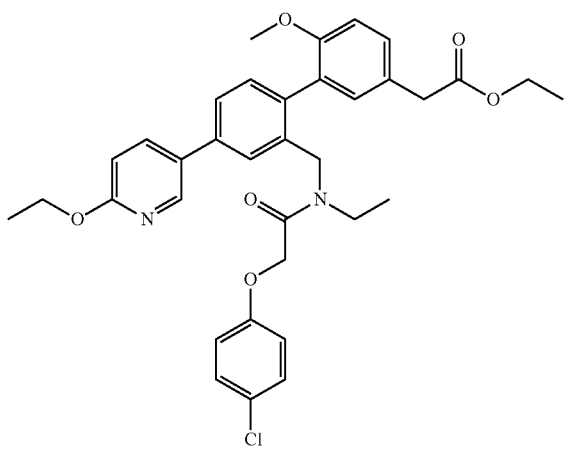 [SMILES: CCOC(=O)Cc1ccc(OC)c(-c2ccc(-c3ccc(OCC)nc3)cc2CN(CC)C(=O)COc2ccc(Cl)cc2)c1]

Step 1: [2'-({[2-Chloro-phenoxy)-acetyl]-ethyl-amino}-methyl)-4'-(6-ethoxy-pyridin-3-yl)-6-methoxy-biphenyl-3-yl]-acetic acid ethyl ester Prepared according to the procedure described in Example 1, Step 6, using the following starting materials: [4'-(6-ethoxy-pyridin-3-yl)-2'-ethylaminomethyl-6-methoxy-biphenyl-3-yl]-acetic acid ethyl ester and 4-chlorophenoxy-acetyl chloride.

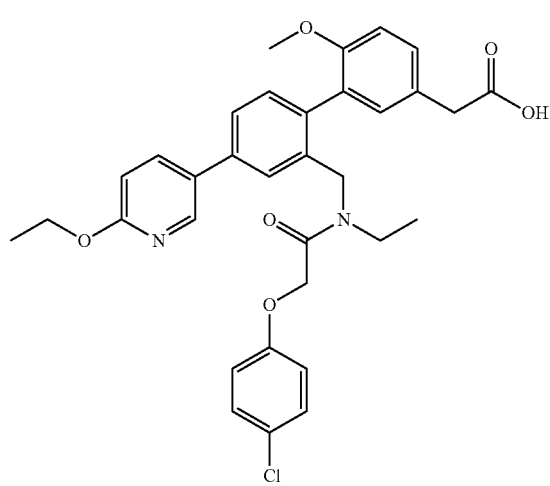 [SMILES: CCOc1ccc(-c2ccc(-c3cc(CC(=O)O)ccc3OC)c(CN(CC)C(=O)COc3ccc(Cl)cc3)c2)cn1]

Step 2: [2'-({[2-(4-Chloro-phenoxy)-acetyl]-ethyl-amino}-methyl)-4'-(6-ethoxy-pyridin-3-yl)-6-methoxy-biphenyl-3-yl]-acetic acid Prepared according to the procedure described in Example 31, Step 2, using the following starting material: [2'-({[2-(4-chloro-phenoxy)-acetyl]-ethyl-amino}-methyl)-4'-(6-ethoxy-pyridin-3-yl)-6-methoxy-biphenyl-3-yl]-acetic acid ethyl ester. M+H is 590.

Example 178

Synthesis of {2'-[(Cyclopropanecarbonyl-ethyl-amino)-methyl]-6-methoxy-4'-quinolin-6-yl-biphenyl-3-yl}-acetic acid (Compound 1-230)

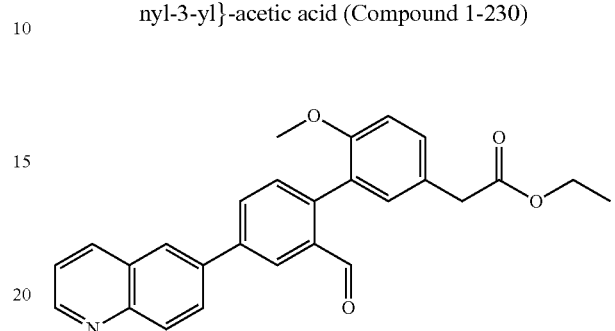

Step 1: (2'-Formyl-6-methoxy-4'-quinolin-6-yl-biphenyl-3-yl)-acetic acid ethyl ester Prepared according to the procedure described in Example 1, Step 4, using the following starting materials: (4'-bromo-2'-formyl-6-methoxy-biphenyl-3-yl)-acetic acid ethyl ester and 6-quinolineboronic acid pinacol ester.

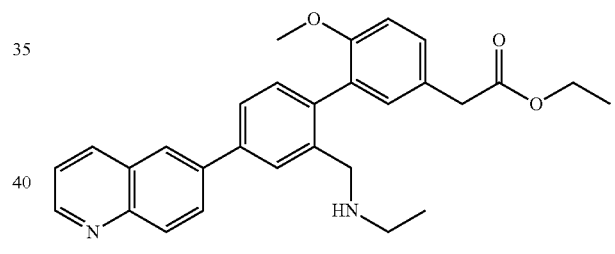

Step 2: (2'-Ethylaminomethyl-6-methoxy-4'-quinolin-6-yl-biphenyl-3-yl)-acetic acid ethyl ester Prepared according to the procedure described in Example 33, Step 4, using the following starting materials: (2'-formyl-6-methoxy-4'-quinolin-6-yl-biphenyl-3-yl)-acetic acid ethyl ester and ethylamine (2M in THF).

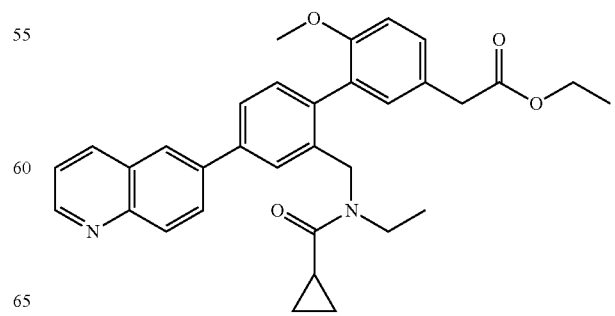

Step 3: {2'-[(Cyclopropanecarbonyl-ethyl-amino)-methyl]-6-methoxy-4'-quinolin-6-yl-biphenyl-3-yl}-acetic acid ethyl ester Prepared according to the procedure described in Example 1, Step 6, using the following starting materials: (2'-ethylaminomethyl-6-methoxy-4'-quinolin-6-yl-biphenyl-3-yl)-acetic acid ethyl ester and cyclopropanecarbonyl chloride.

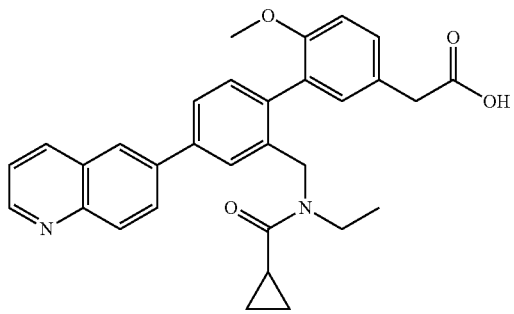 [SMILES: CCN(Cc1cc(-c2ccc3ncccc3c2)ccc1-c1cc(CC(=O)O)ccc1OC)C(=O)C1CC1]

Step 4: {2'-[(Cyclopropanecarbonyl-ethyl-amino)-methyl]-6-methoxy-4'-quinolin-6-yl-biphenyl-3-yl}-acetic acid Prepared according to the procedure described in Example 31, Step 2, using the following starting material: {2'-[(cyclopropanecarbonyl-ethyl-amino)-methyl]-6-methoxy-4'-quinolin-6-yl-biphenyl-3-yl}-acetic acid ethyl ester. M+H is 496.

Example 179

Synthesis of [2'-(3-Benzyl-1-ethyl-ureidomethyl)-6-methoxy-4'-quinolin-6-yl-biphenyl-3-yl]-acetic acid (Compound 1-231)

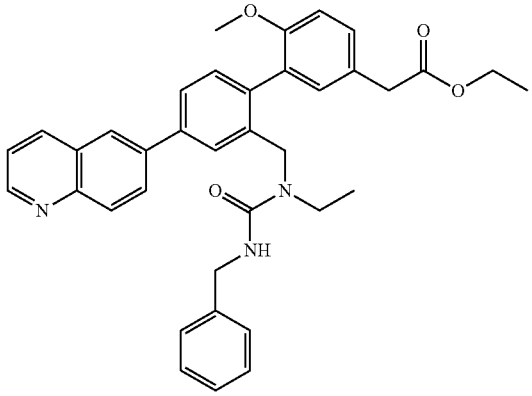 [SMILES: CCOC(=O)Cc1ccc(OC)c(-c2ccc(-c3ccc4ncccc4c3)cc2CN(CC)C(=O)NCc2ccccc2)c1]

Step 1: [2'-(3-Benzyl-1-ethyl-ureidomethyl)-6-methoxy-4'-quinolin-6-yl-biphenyl-3-yl]-acetic acid ethyl ester Prepared according to the procedure described in Example 95, Step 1, using the following starting materials: (2'-ethylaminomethyl-6-methoxy-4'-quinolin-6-yl-biphenyl-3-yl)-acetic acid ethyl ester and benzyl isocyanate.

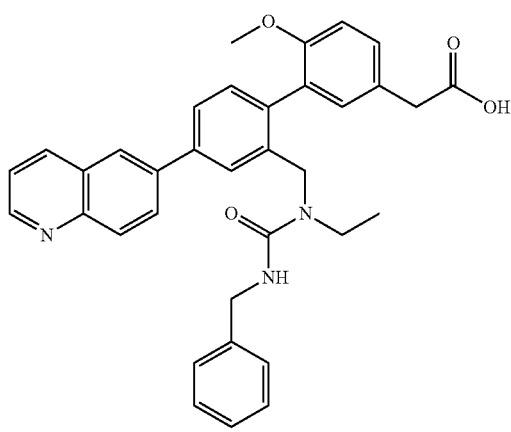 [SMILES: CCN(Cc1cc(-c2ccc3ncccc3c2)ccc1-c1cc(CC(=O)O)ccc1OC)C(=O)NCc1ccccc1]

Step 2: [2'-(3-Benzyl-1-ethyl-ureidomethyl)-6-methoxy-4'-quinolin-6-yl-biphenyl-3-yl]-acetic acid Prepared according to the procedure described in Example 31, Step 2, using the following starting material: [2'-(3-benzyl-1-ethyl-ureidomethyl)-6-methoxy-4'-quinolin-6-yl-biphenyl-3-yl]-acetic acid ethyl ester. M+H is 561.

Example 180

Synthesis of [2'-({[2-(4-Chloro-phenoxy)-acetyl]-ethyl-amino}-methyl)-6-methoxy-4'-quinolin-6-yl-biphenyl-3-yl]-acetic acid (Compound 1-232)

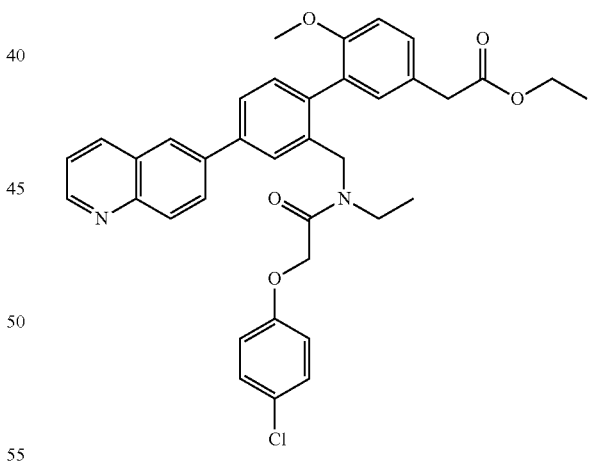

Step 1: [2'-({[2-(4-Chloro-phenoxy)-acetyl]-ethyl-amino}-methyl)-6-methoxy-4'-quinolin-6-yl-biphenyl-3-yl]-acetic acid ethyl ester Prepared according to the procedure described in Example 1, Step 6, using the following starting materials: (2'-ethylaminomethyl-6-methoxy-4'-quinolin-6-yl-biphenyl-3-yl)-acetic acid ethyl ester and 4-chlorophenoxyacetyl chloride.

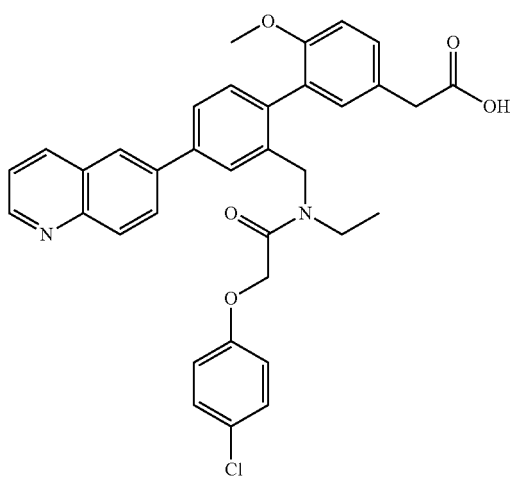 [SMILES: CCN(Cc1cc(-c2ccc3ncccc3c2)ccc1-c1cc(CC(=O)O)ccc1OC)C(=O)COc1ccc(Cl)cc1]

Step 2: [2'-({[2-(4-Chloro-phenoxy)-acetyl]-ethyl-amino}-methyl)-6-methoxy-4'-quinolin-6-yl-biphenyl-3-yl]-acetic acid Prepared according to the procedure described in Example 31, Step 2, using the following starting material: [2'-({[2-(4-chloro-phenoxy)-acetyl]-ethyl-amino}-methyl)-6-methoxy-4'-quinolin-6-yl-biphenyl-3-yl]-acetic acid ethyl ester. M+H is 596.

Example 181

Synthesis of [2'-[(Cyclopropanecarbonyl-ethyl-amino)-methyl]-6-methoxy-4'-(1-methyl-1H-pyrazol-4-yl)-biphenyl-3-yl]-acetic acid (Compound 1-233)

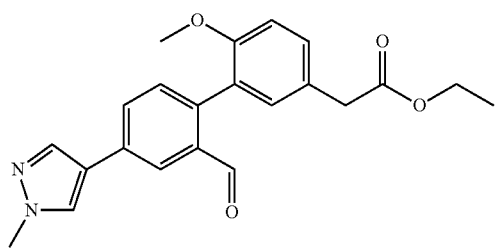 [SMILES: CCOC(=O)Cc1ccc(OC)c(-c2ccc(-c3cnn(C)c3)cc2C=O)c1]

Step 1: [2'-Formyl-6-methoxy-4'-(1-methyl-1H-pyrazol-4-yl)-biphenyl-3-yl]-acetic acid ethyl ester Prepared according to the procedure described in Example 1, Step 4, using the following starting materials: (4'-bromo-2'-formyl-6-methoxy-biphenyl-3-yl)-acetic acid ethyl ester and 1-methylpyrazole-4-boronic acid pinacol ester.

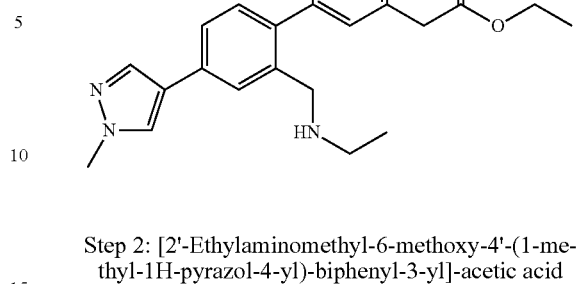

Step 2: [2'-Ethylaminomethyl-6-methoxy-4'-(1-methyl-1H-pyrazol-4-yl)-biphenyl-3-yl]-acetic acid ethyl ester Prepared according to the procedure described in Example 33, Step 4, using the following starting materials: [2'-formyl-6-methoxy-4'-(1-methyl-1H-pyrazol-4-yl)-biphenyl-3-yl]-acetic acid ethyl ester and ethylamine (2M in THF).

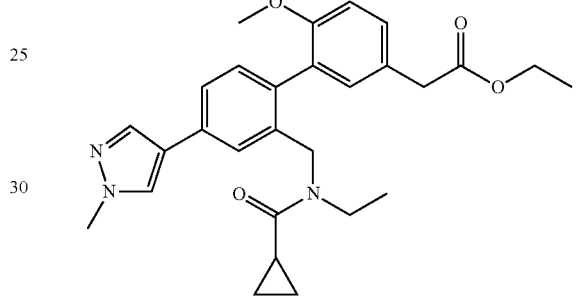

Step 3: [2'-[(Cyclopropanecarbonyl-ethyl-amino)-methyl]-6-methoxy-4'-(1-methyl-1H-pyrazol-4-yl)-biphenyl-3-yl]-acetic acid ethyl ester Prepared according to the procedure described in Example 1, Step 6, using the following starting materials: [2'-ethylaminomethyl-6-methoxy-4'-(1-methyl-1H-pyrazol-4-yl)-biphenyl-3-yl]-acetic acid ethyl ester and cyclopropanecarbonyl chloride.

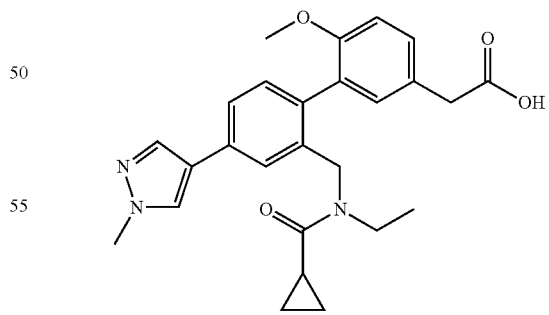

Step 4: [2'-[(Cyclopropanecarbonyl-ethyl-amino)-methyl]-6-methoxy-4'-(1-methyl-1H-pyrazol-4-yl)-biphenyl-3-yl]-acetic acid Prepared according to the procedure described in Example 31, Step 2, using the following starting material: [2'-[(cyclopropanecarbonyl-ethyl-amino)-methyl]-6-methoxy-4'-(1-methyl-1H-pyrazol-4-yl)-biphenyl-3-yl]-acetic acid ethyl ester. M+H is 449.

Example 182

Synthesis of [2'-(3-Benzyl-1-ethyl-ureidomethyl)-6-methoxy-4'-(1-methyl-1H-pyrazol-4-yl)-biphenyl-3-yl]-acetic acid (Compound 1-234)

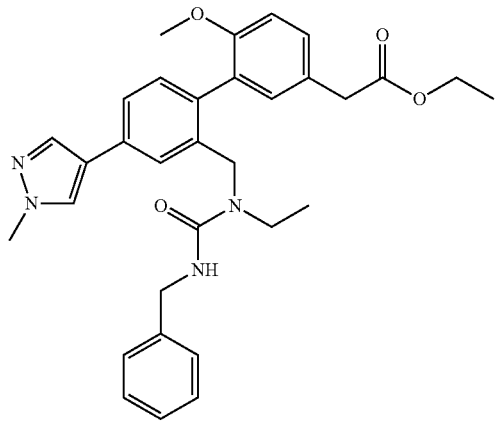 [SMILES: CCOC(=O)Cc1ccc(OC)c(-c2ccc(-c3cnn(C)c3)cc2CN(CC)C(=O)NCc2ccccc2)c1]

Step 1: [2'-(3-Benzyl-1-ethyl-ureidomethyl)-6-methoxy-4'-(1-methyl-1H-pyrazol-4-yl)-biphenyl-3-yl]-acetic acid ethyl ester Prepared according to the procedure described in Example 95, Step 2, using the following starting materials: [2'-ethylaminomethyl-6-methoxy-4'-(1-methyl-1H-pyrazol-4-yl)-biphenyl-3-yl]-acetic acid ethyl ester and benzyl isocyanate.

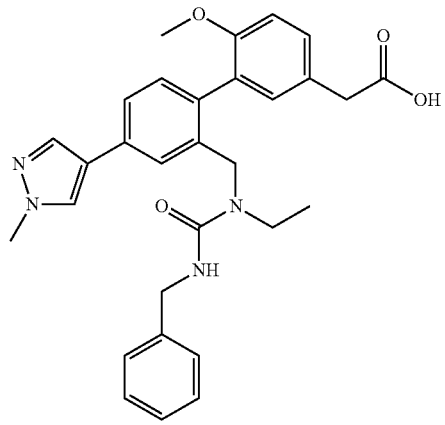 [SMILES: CCN(Cc1cc(-c2cnn(C)c2)ccc1-c1cc(CC(=O)O)ccc1OC)C(=O)NCc1ccccc1]

Step 2: [2'-(3-Benzyl-1-ethyl-ureidomethyl)-6-methoxy-4'-(1-methyl-1H-pyrazol-4-yl)-biphenyl-3-yl]-acetic acid Prepared according to the procedure described in Example 31, Step 2, using the following starting material: [2'-(3-benzyl-1-ethyl-ureidomethyl)-6-methoxy-4'-(1-methyl-1H-pyrazol-4-yl)-biphenyl-3-yl]-acetic acid ethyl ester. M+H is 514.

Example 183

Synthesis of {6-Methoxy-2'-[(5-methyl-benzooxazol-2-ylamino)-methyl]-4'-trifluoromethyl-biphenyl-3-yl}-acetic acid (Compound 1-235)

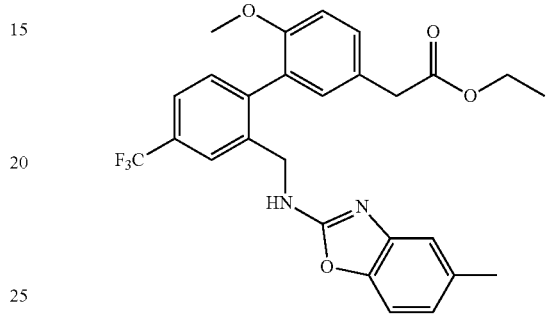

Step 1: {6-Methoxy-2'-[(5-methyl-benzooxazol-2-ylamino)-methyl]-4'-trifluoromethyl-biphenyl-3-yl}-acetic acid ethyl ester Prepared according to the procedure described in Example 1, Step 6, using the following starting materials: (2'-aminomethyl-6-methoxy-4'-trifluoromethyl-biphenyl-3-yl)-acetic acid ethyl ester and 2-chloro-5-methyl-benzooxazole.

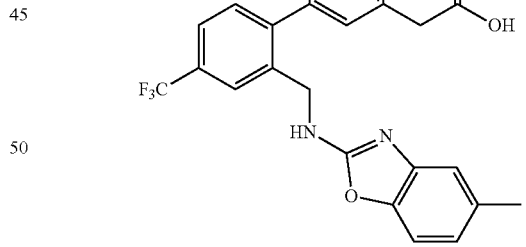

Step 2: {6-Methoxy-2'-[(5-methyl-benzooxazol-2-ylamino)-methyl]-4'-trifluoromethyl-biphenyl-3-yl}-acetic acid Prepared according to the procedure described in Example 31, Step 2, using the following starting material: {6-methoxy-2'-[(5-methyl-benzooxazol-2-ylamino)-methyl]-4'-trifluoromethyl-biphenyl-3-yl}-acetic acid ethyl ester.

Example 184

Synthesis of {2'-[(Benzyloxycarbonyl-ethyl-amino)-methyl]-4-methoxy-4'-trifluoromethyl-biphenyl-3-yl}-acetic acid (Compound 1-107)

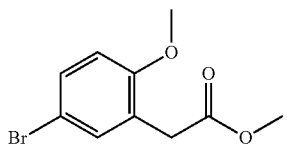

Step 1: (5-Bromo-2-methoxy-phenyl)-acetic acid methyl ester

5-Bromo-2-methoxyphenylacetic acid (0.900 g, 3.67 mmol) in MeOH (20 mL) was treated with 4N HCl in 1,4-dioxane (4 mL) and stirred at 80° C. for 6 hours. The mixture was concentrated to give the title compound.

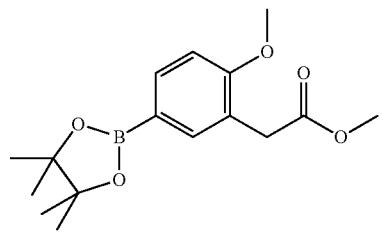

Step 2: [2-Methoxy-5-(4,4,5,5-tetramethyl-[1,3,2]dioxaborolan-2-yl)-phenyl]-acetic acid methyl ester Prepared according to the procedure described in Example 33, Step 2, using the following starting materials: (5-bromo-2-methoxy-phenyl)-acetic acid methyl ester and bis(pinacolato)diboron.

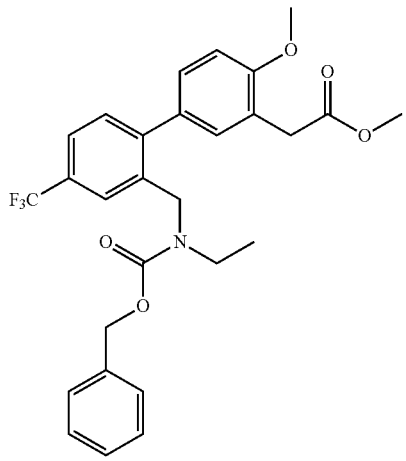 [SMILES: CCN(Cc1cc(C(F)(F)F)ccc1-c1ccc(OC)c(CC(=O)OC)c1)C(=O)OCc1ccccc1]

Step 3: {2'-[(Benzyloxycarbonyl-ethyl-amino)-methyl]-4-methoxy-4'-trifluoromethyl-biphenyl-3-yl}-acetic acid methyl ester Prepared according to the procedure described in Example 1, Step 4, using the following starting materials: [2-methoxy-5-(4,4,5,5-tetramethyl-[1,3,2]dioxaborolan-2-yl)-phenyl]-acetic acid methyl ester and (2-bromo-5-trifluoromethyl-benzyl)-ethyl-carbamic acid benzyl ester.

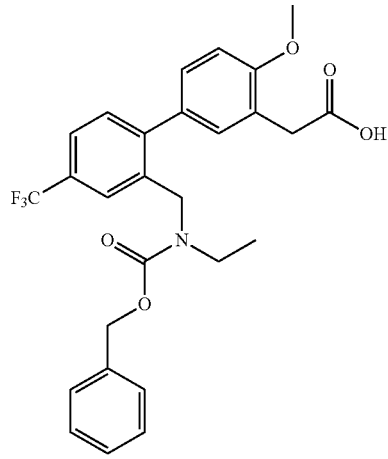 [SMILES: CCN(Cc1cc(C(F)(F)F)ccc1-c1ccc(OC)c(CC(=O)O)c1)C(=O)OCc1ccccc1]

Step 4: {2'-[(Benzyloxycarbonyl-ethyl-amino)-methyl]-4-methoxy-4'-trifluoromethyl-biphenyl-3-yl}-acetic acid Prepared according to the procedure described in Example 41, Step 8, using the following starting material: {2'-[(benzyloxycarbonyl-ethyl-amino)-methyl]-4-methoxy-4'-trifluoromethyl-biphenyl-3-yl}-acetic acid methyl ester. M+H is 502.

Example 185

Synthesis of {2'-[(Benzyloxycarbonyl-ethyl-amino)-methyl]-4-chloro-4'-trifluoromethyl-biphenyl-3-yl}-acetic acid (Compound 1-125)

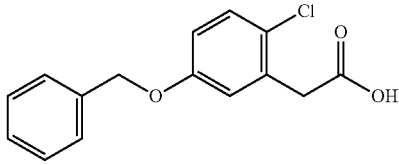 [SMILES: O=C(O)Cc1cc(OCc2ccccc2)ccc1Cl]

Step 1: (5-Benzyloxy-2-chloro-phenyl)-acetic acid

To benzyl alcohol (1.1 g, 10 mmol) in NMP (20 mL) was added sodium hydride (60% in mineral oil; 0.44 g, 11 mmol), and the mixture was stirred for 30 minutes at room temperature. The mixture was then added to a vial containing 2-chloro-5-fluorophenylacetic acid (1 g, 4.5 mmol), and the reaction was stirred at 120° C. for 3 hours. Acidic work-up gave the title compound.

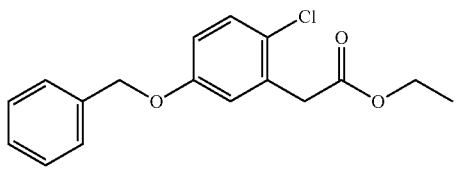 [SMILES: CCOC(=O)Cc1cc(OCc2ccccc2)ccc1Cl]

Step 2: (5-Benzyloxy-2-chloro-phenyl)-acetic acid ethyl ester

To (5-benzyloxy-2-chloro-phenyl)-acetic acid (1.5 g, 5.4 mmol) in EtOH (30 mL) was added sulfuric acid (1 mL), and the mixture was stirred overnight at room temperature. Once no starting material was seen by analytical LCMS, the reaction was worked up to give the title compound.

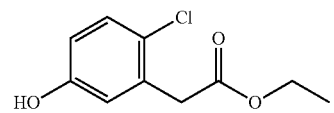

Step 3: (2-Chloro-5-hydroxy-phenyl)-acetic acid ethyl ester (5-Benzyloxy-2-chloro-phenyl)-acetic acid ethyl ester (1.7 g, 5.6 mmol) was dissolved in EtOH (30 mL) and degassed with $N_2$. 5% Palladium on carbon (1 g) was added, and the reaction was purged with $H_2$ and then stirred under an $H_2$ balloon at 50° C. overnight. The mixture was filtered and concentrated to give the title compound.

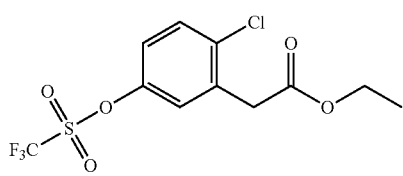

Step 4: (2-Chloro-5-trifluoromethanesulfonyloxy-phenyl)-acetic acid ethyl ester To a solution of (2-chloro-5-hydroxy-phenyl)-acetic acid ethyl ester (0.177 g, 0.87 mmol) in DMF (5 mL) was added cesium carbonate (0.567 g, 1.74 mmol) and N-phenyl-bis(trifluoromethanesulfonimide) (0.621 g, 1.74 mmol), and the reaction was stirred for 1 hour. After aqueous work-up, the residue was purified by silica gel chromatography to give the title compound.

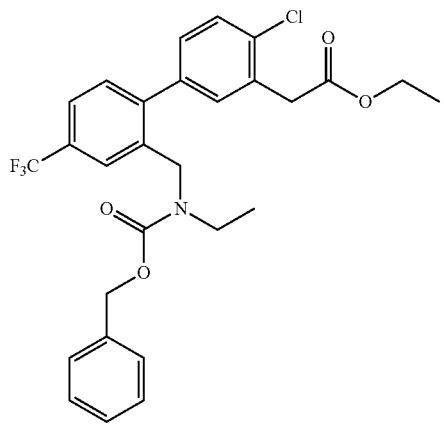 [SMILES: CCOC(=O)Cc1cc(-c2ccc(C(F)(F)F)cc2CN(CC)C(=O)OCc2ccccc2)ccc1Cl]

Step 5: {2'-[(Benzyloxycarbonyl-ethyl-amino)-methyl]-4-chloro-V-trifluoromethyl-biphenyl-3-yl}-acetic acid ethyl ester Prepared according to the procedure described in Example 1, Step 4, using the following starting materials: ethyl-[2-(4,4,5,5-tetramethyl-[1,3,2]dioxaborolan-2-yl)-5-trifluoromethyl-benzyl]-carbamic acid benzyl ester and (2-chloro-5-trifluoromethanesulfonyloxy-phenyl)-acetic acid ethyl ester.

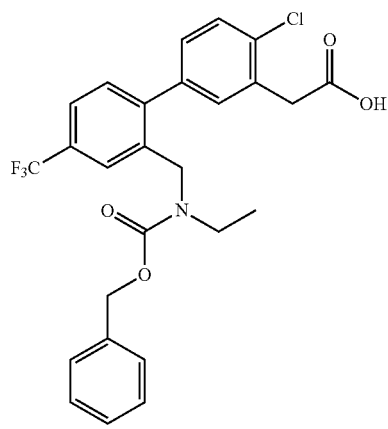

Step 6: {2'-[(Benzyloxycarbonyl-ethyl-amino)-methyl]-4-chloro-4'-trifluoromethyl-biphenyl-3-yl}-acetic acid To a solution of 2'-[(benzyloxycarbonyl-ethyl-amino)-methyl]-4-chloro-4'-trifluoromethyl-biphenyl-3-yl}-acetic acid ethyl ester (0.17 mmol) in 1,4-dioxane (2 mL) and H2O (1 mL) was added 1N aqueous LiOH (1.7 mL, 1.7 mmol), and the reaction was stirred overnight at room temperature. The mixture was adjusted to pH 6 with 1N aqueous HCl, and then extracted with EtOAc. The combined organic layers were dried, filtered, and concentrated, and the residue was purified by silica gel chromatography to give the title compound. M+H is 506.

Example 186

Synthesis of {2'-[(Benzyloxycarbonyl-ethyl-amino)-methyl]-5-chloro-4'-trifluoromethyl-biphenyl-3-yl}-acetic acid (Compound 1-108)

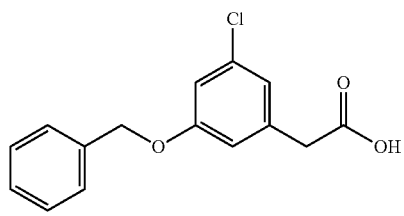

Step 1: (3-Benzyloxy-5-chloro-phenyl)-acetic acid

Prepared according to the procedure described in Example 185, Step 1, using the following starting materials: 3-chloro-5-fluorophenylacetic acid and benzyl alcohol.

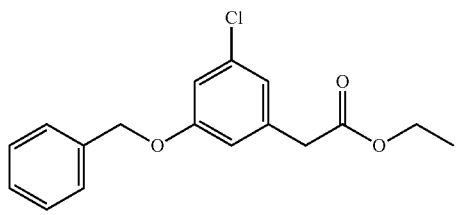

Step 2: (3-Benzyloxy-5-chloro-phenyl)-acetic acid ethyl ester

Prepared according to the procedure described in Example 185, Step 2, using the following starting material: (3-benzyloxy-5-chloro-phenyl)-acetic acid.

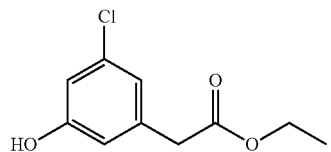

Step 3: (3-Chloro-5-hydroxy-phenyl)-acetic acid ethyl ester

Prepared according to the procedure described in Example 185, Step 3, using the following starting material: (3-benzyloxy-5-chloro-phenyl)-acetic acid ethyl ester.

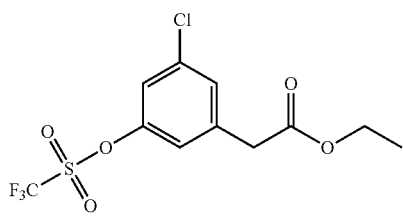 [SMILES: CCOC(=O)Cc1cc(Cl)cc(OS(=O)(=O)C(F)(F)F)c1]

Step 4: (3-Chloro-5-trifluoromethanesulfonyloxy-phenyl)-acetic acid ethyl ester Prepared according to the procedure described in Example 185, Step 4, using the following starting materials: (3-chloro-5-hydroxy-phenyl)-acetic acid ethyl ester and N-phenyl-bis(trifluoromethanesulfonimide).

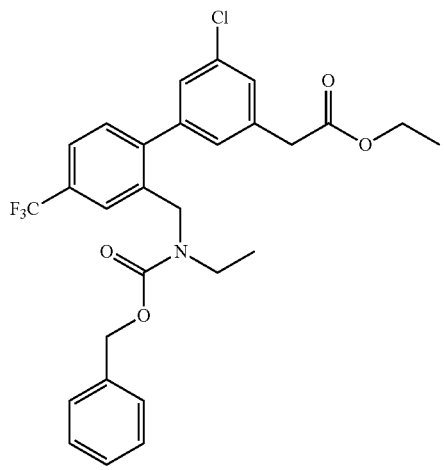 [SMILES: CCOC(=O)Cc1cc(Cl)cc(-c2ccc(C(F)(F)F)cc2CN(CC)C(=O)OCc2ccccc2)c1]

Step 5: {2'-[(Benzyloxycarbonyl-ethyl-amino)-methyl]-5-chloro-4'-trifluoromethyl-biphenyl-3-yl}-acetic acid ethyl ester Prepared according to the procedure described in Example 1, Step 4, using the following starting materials: ethyl-[2-(4,4,5,5-tetramethyl-[1,3,2]dioxaborolan-2-yl)-5-trifluoromethyl-benzyl]-carbamic acid benzyl ester and (3-chloro-5-trifluoromethanesulfonyloxy-phenyl)-acetic acid ethyl ester.

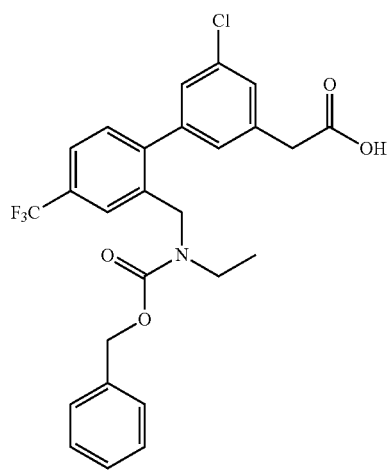 [SMILES: CCN(Cc1cc(C(F)(F)F)ccc1-c1cc(Cl)cc(CC(=O)O)c1)C(=O)OCc1ccccc1]

Step 6: {2'-[(Benzyloxycarbonyl-ethyl-amino)-methyl]-5-chloro-4'-trifluoromethyl-biphenyl-3-yl}-acetic acid Prepared according to the procedure described in Example 185, Step 6, using the following starting material: {2'-[(benzyloxycarbonyl-ethyl-amino)-methyl]-5-chloro-4'-trifluoromethyl-biphenyl-3-yl}-acetic acid ethyl ester. M+H is 506.

Example 187

Synthesis of {2'-[(Benzyloxycarbonyl-ethyl-amino)-methyl]-5,4'-bis-trifluoromethyl-biphenyl-3-yl}-acetic acid (Compound 1-109)

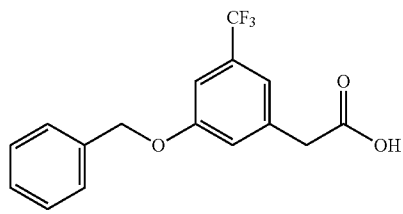 [SMILES: O=C(O)Cc1cc(OCc2ccccc2)cc(C(F)(F)F)c1]

Step 1:
(3-Benzyloxy-5-trifluoromethyl-phenyl)-acetic acid

Prepared according to the procedure described in Example 185, Step 1, using the following starting materials: 3-fluoro-5-(trifluoromethyl)phenylacetic acid and benzyl alcohol.

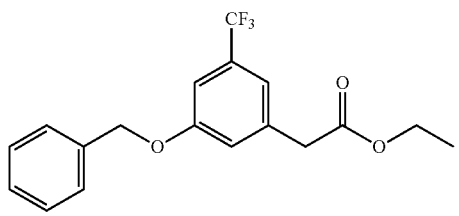

Step 2:
(3-Benzyloxy-5-trifluoromethyl-phenyl)-acetic acid ethyl ester

Prepared according to the procedure described in Example 185, Step 2, using the following starting material: (3-benzyloxy-5-trifluoromethyl-phenyl)-acetic acid.

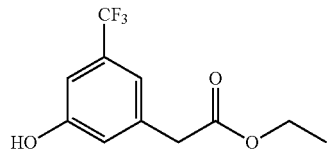 [SMILES: CCOC(=O)Cc1cc(O)cc(C(F)(F)F)c1]

Step 3: (3-Hydroxy-5-trifluoromethyl-phenyl)-acetic acid ethyl ester

Prepared according to the procedure described in Example 185, Step 3, using the following starting material: (3-benzyloxy-5-trifluoromethyl-phenyl)-acetic acid ethyl ester.

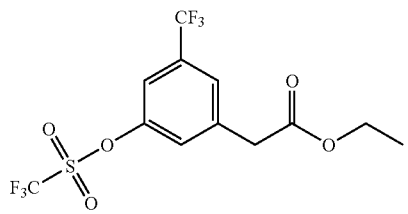 [SMILES: CCOC(=O)Cc1cc(OS(=O)(=O)C(F)(F)F)cc(C(F)(F)F)c1]

Step 4: (3-Trifluoromethanesulfonyloxy-5-trifluoromethyl-phenyl)-acetic acid ethyl ester Prepared according to the procedure described in Example 185, Step 4, using the following starting materials: (3-hydroxy-5-trifluoromethyl-phenyl)-acetic acid ethyl ester and N-phenyl-bis(trifluoromethanesulfonimide).

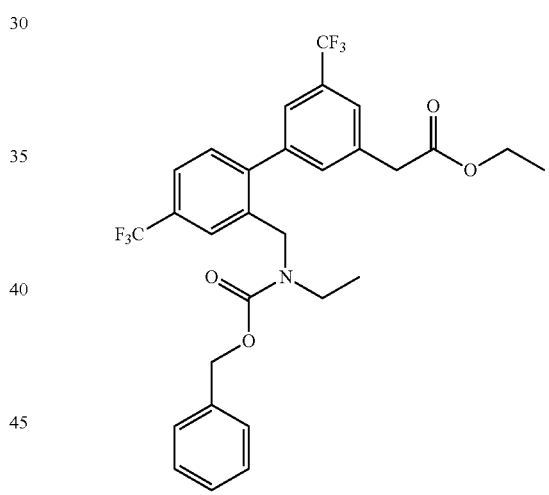

Step 5: {2'-[(Benzyloxycarbonyl-ethyl-amino)-methyl]-5,4'-bis-trifluoromethyl-biphenyl-3-yl}-acetic acid ethyl ester Prepared according to the procedure described in Example 1, Step 4, using the following starting materials: ethyl-[2-(4,4,5,5-tetramethyl-[1,3,2]dioxaborolan-2-yl)-5-trifluoromethyl-benzyl]-carbamic acid benzyl ester and (3-trifluoromethanesulfonyloxy-5-trifluoromethyl-phenyl)-acetic acid ethyl ester.

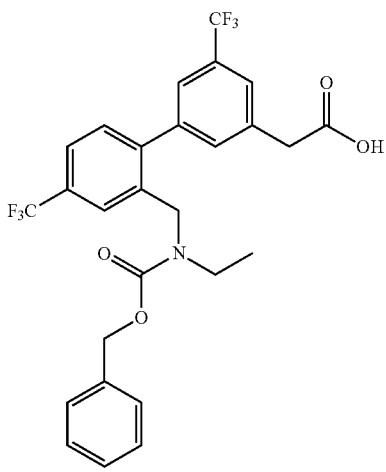 [SMILES: CCN(Cc1cc(C(F)(F)F)ccc1-c1cc(CC(=O)O)cc(C(F)(F)F)c1)C(=O)OCc1ccccc1]

Step 6: {2'-[(Benzyloxycarbonyl-ethyl-amino)-methyl]-5,4'-bis-trifluoromethyl-biphenyl-3-yl}-acetic acid Prepared according to the procedure described in Example 185, Step 6, using the following starting material: {2'-[(benzyloxycarbonyl-ethyl-amino)-methyl]-5,4'-bis-trifluoromethyl-biphenyl-3-yl}-acetic acid ethyl ester. M+H is 540.

Example 188

Synthesis of {2-[(Benzyloxycarbonyl-ethyl-amino)-methyl]-6-chloro-4'-trifluoromethyl-biphenyl-3-yl}-acetic acid (Compound 1-110)

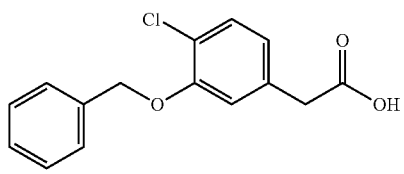 [SMILES: O=C(O)Cc1ccc(Cl)c(OCc2ccccc2)c1]

Step 1: (3-Benzyloxy-4-chloro-phenyl)-acetic acid

Prepared according to the procedure described in Example 185, Step 1, using the following starting materials: 4-chloro-3-fluorophenylacetic acid and benzyl alcohol.

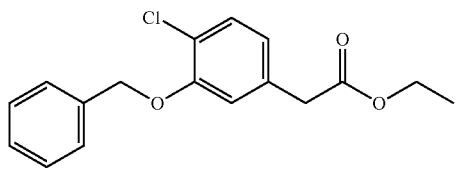 [SMILES: CCOC(=O)Cc1ccc(Cl)c(OCc2ccccc2)c1]

Step 2: (3-Benzyloxy-4-chloro-phenyl)-acetic acid ethyl ester

Prepared according to the procedure described in Example 185, Step 2, using the following starting material: (3-benzyloxy-4-chloro-phenyl)-acetic acid.

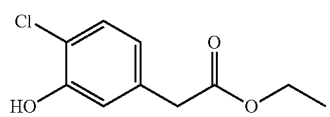

Step 3: (4-Chloro-3-hydroxy-phenyl)-acetic acid ethyl ester

Prepared according to the procedure described in Example 185, Step 3, using the following starting material: (3-benzyloxy-4-chloro-phenyl)-acetic acid ethyl ester.

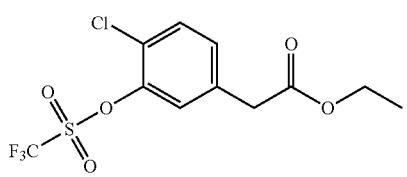 [SMILES: CCOC(=O)Cc1ccc(Cl)c(OS(=O)(=O)C(F)(F)F)c1]

Step 4: (4-Chloro-3-trifluoromethanesulfonyloxy-phenyl)-acetic acid ethyl ester

Prepared according to the procedure described in Example 185, Step 4, using the following starting materials: (4-chloro-3-hydroxy-phenyl)-acetic acid ethyl ester and N-phenyl-bis(trifluoromethanesulfonimide).

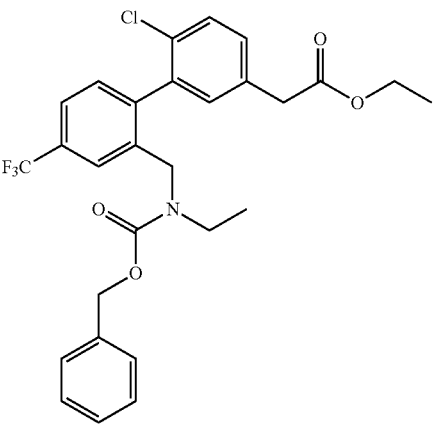

Step 5: {2'-[(Benzyloxycarbonyl-ethyl-amino)-methyl]-6-chloro-4'-trifluoromethyl-biphenyl-3-yl}-acetic acid ethyl ester Prepared according to the procedure described in Example 1, Step 4, using the following starting materials: ethyl-[2-(4,4,5,5-tetramethyl-[1,3,2]dioxaborolan-2-yl)-5-trifluoromethyl-benzyl]-carbamic acid benzyl ester and (4-chloro-3-trifluoromethanesulfonyloxy-phenyl)-acetic acid ethyl ester.

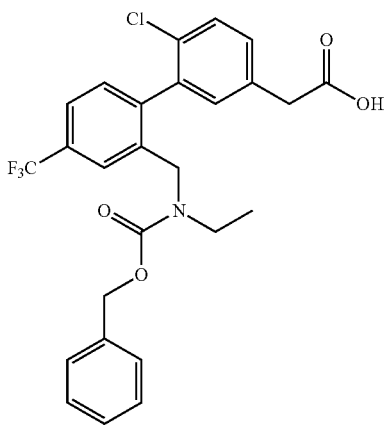 [SMILES: CCN(Cc1cc(C(F)(F)F)ccc1-c1cc(CC(=O)O)ccc1Cl)C(=O)OCc1ccccc1]

Step 6: {2'-[(Benzyloxycarbonyl-ethyl-amino)-methyl]-6-chloro-4'-trifluoromethyl-biphenyl-3-yl}-acetic acid Prepared according to the procedure described in Example 185, Step 6, using the following starting material: {2'-[(benzyloxycarbonyl-ethyl-amino)-methyl]-6-chloro-4'-trifluoromethyl-biphenyl-3-yl}-acetic acid ethyl ester. M+H is 506.

Example 189

Synthesis of {2'-[(Benzyloxycarbonyl-ethyl-amino)-methyl]-4,4'-bis-trifluoromethyl-biphenyl-3-yl}-acetic acid (Compound 1-124)

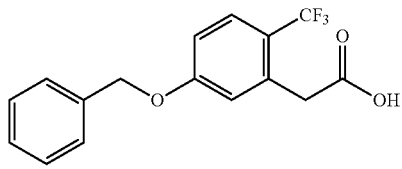 [SMILES: O=C(O)Cc1cc(OCc2ccccc2)ccc1C(F)(F)F]

Step 1:
(5-Benzyloxy-2-trifluoromethyl-phenyl)-acetic acid

Prepared according to the procedure described in Example 185, Step 1, using the following starting materials: 5-fluoro-2-(trifluoromethyl)phenylacetic acid and benzyl alcohol.

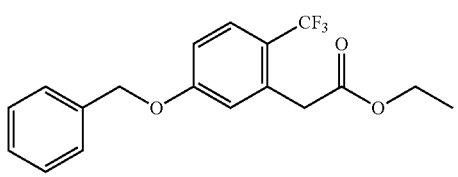 [SMILES: CCOC(=O)Cc1cc(OCc2ccccc2)ccc1C(F)(F)F]

Step 2:
(5-Benzyloxy-2-trifluoromethyl-phenyl)acetic acid ethyl ester

Prepared according to the procedure described in Example 185, Step 2, using the following starting material: (5-benzyloxy-2-trifluoromethyl-phenyl)-acetic acid.

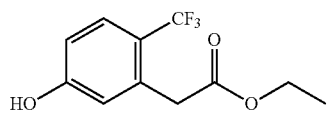

Step 3: (5-Hydroxy-2-trifluoromethyl-phenyl)-acetic acid ethyl ester

Prepared according to the procedure described in Example 185, Step 3, using the following starting material: (5-benzyloxy-2-trifluoromethyl-phenyl)-acetic acid ethyl ester.

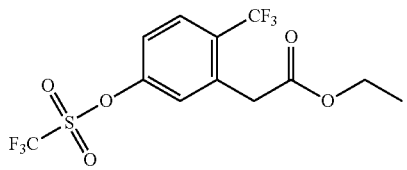

Step 4: (5-Trifluoromethanesulfonyloxy-2-trifluoromethyl-phenyl)-acetic acid ethyl ester Prepared according to the procedure described in Example 185, Step 4, using the following starting materials: (5-hydroxy-2-trifluoromethyl-phenyl)-acetic acid ethyl ester and N-phenyl-bis(trifluoromethanesulfonimide).

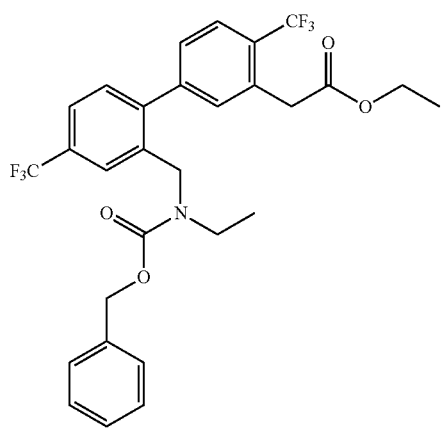

Step 5: {2'-[(Benzyloxycarbonyl-ethyl-amino)-methyl]-4,4'-bis-trifluoromethyl-biphenyl-3-yl}-acetic acid ethyl ester Prepared according to the procedure described in Example 1, Step 4, using the following starting materials: ethyl-[2-(4,4,5,5-tetramethyl-[1,3,2]dioxaborolan-2-yl)-5-trifluoromethyl-benzyl]-carbamic acid benzyl ester and (5-trifluoromethanesulfonyloxy-2-trifluoromethyl-phenyl)-acetic acid ethyl ester.

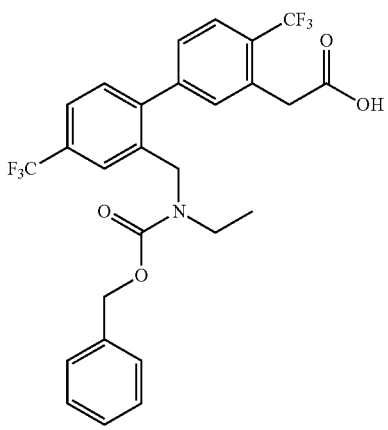

Step 6: {2'-[(Benzyloxycarbonyl-ethyl-amino)-methyl]-4,4'-bis-trifluoromethyl-biphenyl-3-yl}-acetic acid Prepared according to the procedure described in Example 185, Step 6, using the following starting material: {2'-[(benzyloxycarbonyl-ethyl-amino)-methyl]-4,4'-bis-trifluoromethyl-biphenyl-3-yl}-acetic acid ethyl ester. M+H is 540.

Example 190

Synthesis of {2'-[(Benzyloxycarbonyl-ethyl-amino)-methyl]-5-fluoro-4'-trifluoromethyl-biphenyl-3-yl}-acetic acid (Compound 1-126)

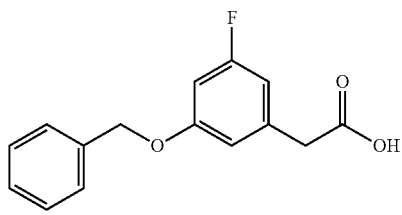 [SMILES: O=C(O)Cc1cc(F)cc(OCc2ccccc2)c1]

Step 1: (3-Benzyloxy-5-fluoro-phenyl)-acetic acid

To benzyl alcohol (1.4 g, 12.8 mmol) in NMP (30 mL) was added sodium hydride (60% in mineral oil; 0.5 g, 12.8 mmol), and the mixture was stirred for 20 minutes. 3,5-Difluorophenylacetic acid (1.0 g, 5.8 mmol) was added, and the reaction was stirred at 100° C. for 2 hours, and then 60° C. overnight. The mixture was worked-up to give the title compound, plus ~30% of benzyl alcohol impurity.

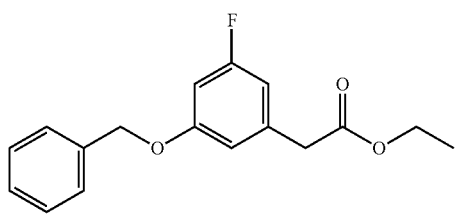 [SMILES: CCOC(=O)Cc1cc(F)cc(OCc2ccccc2)c1]

Step 2: (3-Benzyloxy-5-fluoro-phenyl)-acetic acid ethyl ester

Prepared according to the procedure described in Example 185, Step 2, using the following starting material: (3-benzyloxy-5-fluoro-phenyl)-acetic acid.

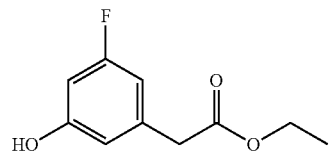

Step 3: (3-Fluoro-5-hydroxy-phenyl)-acetic acid ethyl ester

Prepared according to the procedure described in Example 185, Step 3, using the following starting material: (3-benzyloxy-5-fluoro-phenyl)-acetic acid ethyl ester.

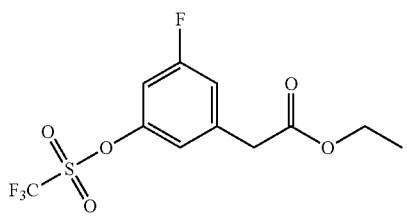 [SMILES: CCOC(=O)Cc1cc(F)cc(OS(=O)(=O)C(F)(F)F)c1]

Step 4: (3-Fluoro-5-trifluoromethanesulfonyloxy-phenyl)-acetic acid ethyl ester

Prepared according to the procedure described in Example 185, Step 4, using the following starting materials: (3-fluoro-5-hydroxy-phenyl)-acetic acid ethyl ester and N-phenyl-bis(trifluoromethanesulfonimide).

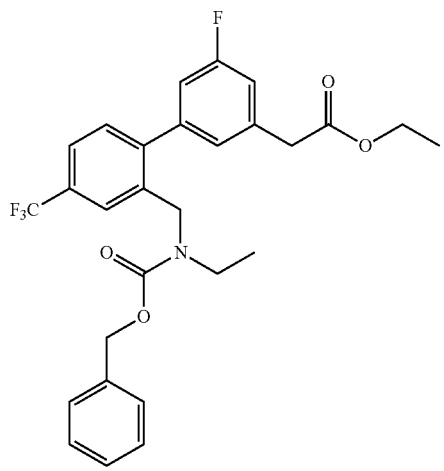 [SMILES: CCOC(=O)Cc1cc(F)cc(-c2ccc(C(F)(F)F)cc2CN(CC)C(=O)OCc2ccccc2)c1]

Step 5: {2'-[(Benzyloxycarbonyl-ethyl-amino)-methyl]-5-fluoro-4'-trifluoromethyl-biphenyl-3-yl}-acetic acid ethyl ester Prepared according to the procedure described in Example 1, Step 4, using the following starting materials: ethyl-[2-(4, 4,5,5-tetramethyl-[1,3,2]dioxaborolan-2-yl)-5-trifluoromethyl-benzyl]-carbamic acid benzyl ester and (3-fluoro-5-trifluoromethanesulfonyloxy-phenyl)-acetic acid ethyl ester.

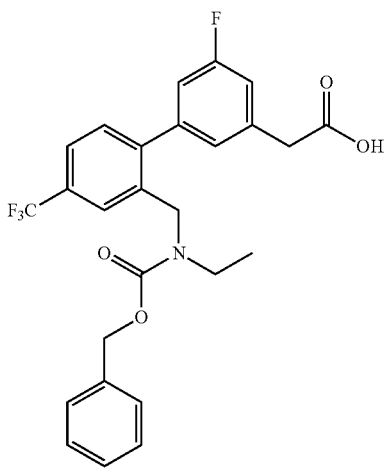 [SMILES: CCN(Cc1cc(C(F)(F)F)ccc1-c1cc(F)cc(CC(=O)O)c1)C(=O)OCc1ccccc1]

Step 6: {2'-[(Benzyloxycarbonyl-ethyl-amino)-methyl]-5-fluoro-4'-trifluoromethyl-biphenyl-3-yl}-acetic acid Prepared according to the procedure described in Example 185, Step 6, using the following starting material: {2'-[(benzyloxycarbonyl-ethyl-amino)-methyl]-5-fluoro-4'-trifluoromethyl-biphenyl-3-yl}-acetic acid ethyl ester. M+H is 490.

Example 191

Synthesis of {2'-[(Benzyloxycarbonyl-ethyl-amino)-methyl]-4-fluoro-4'-trifluoromethyl-biphenyl-3-yl}-acetic acid (Compound 1-127)

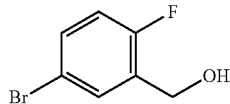

Step 1: (5-Bromo-2-fluoro-phenyl)-methanol

To a solution of 5-bromo-2-fluorobenzaldehyde (1.3 g, 6.4 mmol) in MeOH (10 mL) was added sodium borohydride (0.29 g, 7.7 mmol), and the reaction was stirred at room temperature for 5 minutes. After aqueous work-up, the residue was purified by silica gel chromatography to give the title compound.

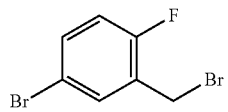

Step 2: 4-Bromo-2-bromomethyl-1-fluoro-benzene

To (5-bromo-2-fluoro-phenyl)-methanol (1.2 g, 5.9 mmol) in DME (20 mL) was added phosphorus tribromide (0.83 mL, 8.8 mmol), and the reaction was stirred at room temperature for 6 hours. The mixture was cooled to 0° C. and adjusted to pH 6 with saturated aqueous NaHCO₃. The solution was extracted with EtOAc, and the combined organic layers were dried, concentrated, and purified by silica gel chromatography to give the title compound.

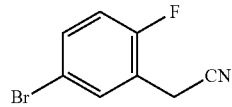

Step 3: (5-Bromo-2-fluoro-phenyl)-acetonitrile

4-Bromo-2-bromomethyl-1-fluoro-benzene (1.2 g, 3.7 mmol) and sodium cyanide (2.0 g, 4.1 mmol) were combined in DMSO (15 mL) and stirred at 90° C. for 2 hours. Once no starting material was seen by analytical tlc, the mixture was worked-up with EtOAc and H₂O to give the title compound.

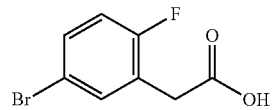 [SMILES: O=C(O)Cc1cc(Br)ccc1F]

Step 4: (5-Bromo-2-fluoro-phenyl)-acetic acid (5-Bromo-2-fluoro-phenyl)-acetonitrile (0.5 g, 2.3 mmol) was treated with acetic acid (2 mL) and sulfuric acid (2 mL) in H₂O (2 mL) at 95° C. for 5 hours. Aqueous worked-up afforded the title compound.

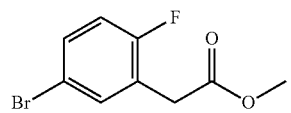

Step 5: (5-Bromo-2-fluoro-phenyl)-acetic acid methyl ester

To a solution of (5-bromo-2-fluoro-phenyl)-acetic acid (2.3 mmol) in MeOH (15 mL) was added 4N HCl in 1,4-dioxane (2 mL), and the reaction was stirred at 90° C. for 2 hours. The mixture was concentrated, and the residue was purified by silica gel chromatography to give the title compound.

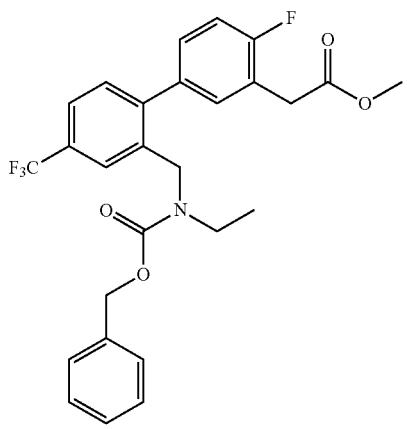 [SMILES: CCN(Cc1cc(C(F)(F)F)ccc1-c1ccc(F)c(CC(=O)OC)c1)C(=O)OCc1ccccc1]

Step 6: {2'-[(Benzyloxycarbonyl-ethyl-amino)-methyl]-4-fluoro-4'-trifluoromethyl-biphenyl-3-yl}-acetic acid methyl ester Prepared according to the procedure described in Example 1, Step 4, using the following starting materials: ethyl-[2-(4,4,5,5-tetramethyl-[1,3,2]dioxaborolan-2-yl)-5-trifluoromethyl-benzyl]-carbamic acid benzyl ester and (5-bromo-2-fluoro-phenyl)-acetic acid methyl ester.

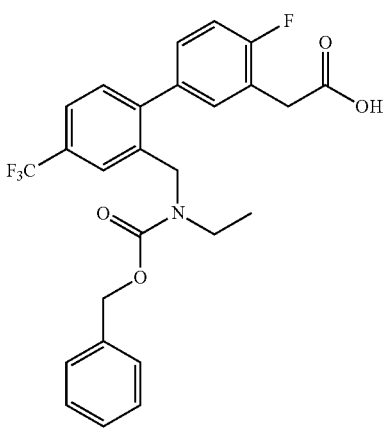 [SMILES: CCN(Cc1cc(C(F)(F)F)ccc1-c1ccc(F)c(CC(=O)O)c1)C(=O)OCc1ccccc1]

Step 7: {2'-[(Benzyloxycarbonyl-ethyl-amino)-methyl]-4-fluoro-4'-trifluoromethyl-biphenyl-3-yl}-acetic acid Prepared according to the procedure described in Example 185, Step 6, using the following starting material: {2'-[(benzyloxycarbonyl-ethyl-amino)-methyl]-4-fluoro-4'-trifluoromethyl-biphenyl-3-yl}-acetic acid methyl ester. M+H is 490.

Example 192

Synthesis of {5-Chloro-2'-[(cyclopropanecarbonyl-ethyl-amino)-methyl]-4'-trifluoromethyl-biphenyl-3-yl}-acetic acid (Compound 1-135)

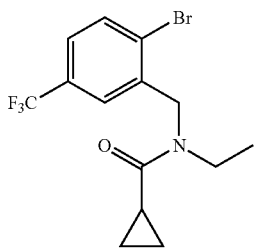 [SMILES: CCN(Cc1cc(C(F)(F)F)ccc1Br)C(=O)C1CC1]

Step 1: Cyclopropanecarboxylic acid (2-bromo-5-trifluoromethyl-benzyl)-ethyl-amide Prepared according to the procedure described in Example 1, Step 6, using the following starting materials: (2-bromo-5-trifluoromethyl-benzyl)-ethyl-amine and cyclopropanecarbonyl chloride.

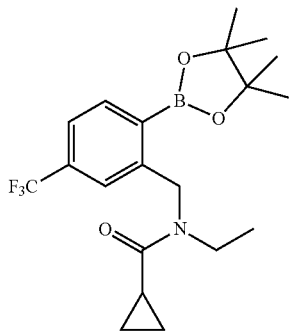 [SMILES: CCN(Cc1cc(C(F)(F)F)ccc1B1OC(C)(C)C(C)(C)O1)C(=O)C1CC1]

Step 2: Cyclopropanecarboxylic acid ethyl-[2-(4,4,5,5-tetramethyl-[1,3,2]dioxaborolan-2-yl)-5-trifluoromethyl-benzyl]-amide Prepared according to the procedure described in Example 33, Step 2, using the following starting materials: cyclopropanecarboxylic acid (2-bromo-5-trifluoromethyl-benzyl)-ethyl-amide and bis(pinacolato)diboron.

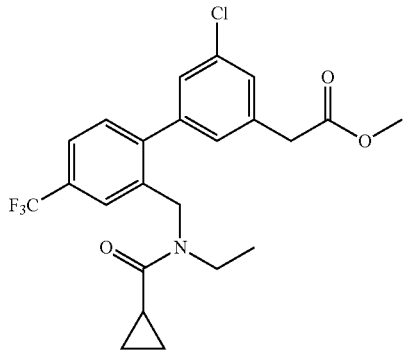 [SMILES: CCN(Cc1cc(C(F)(F)F)ccc1-c1cc(Cl)cc(CC(=O)OC)c1)C(=O)C1CC1]

Step 3: {5-Chloro-2'-[(cyclopropanecarbonyl-ethyl-amino)-methyl]-4'-trifluoromethyl-biphenyl-3-yl}-acetic acid methyl ester Prepared according to the procedure described in Example 1, Step 4, using the following starting materials: cyclopropanecarboxylic acid ethyl-[2-(4,4,5,5-tetramethyl-[1,3,2]dioxaborolan-2-yl)-5-trifluoromethyl-benzyl]-amide and (3-bromo-5-chloro-phenyl)-acetic acid methyl ester.

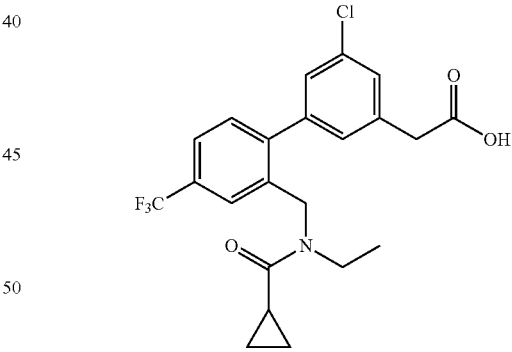

Step 4: {5-Chloro-2'-[(cyclopropanecarbonyl-ethyl-amino)-methyl]-4'-trifluoromethyl-biphenyl-3-yl}-acetic acid Prepared according to the procedure described in Example 185, Step 6, using the following starting material: {5-chloro-2'-[(cyclopropanecarbonyl-ethyl-amino)-methyl]-4'-trifluoromethyl-biphenyl-3-yl}-acetic acid methyl ester. M+H is 440.

Example 193

Synthesis of {2'-[(Cyclopropanecarbonyl-ethyl-amino)-methyl]-5,4'-bis-trifluoromethyl-biphenyl-3-yl}-acetic acid (Compound 1-136)

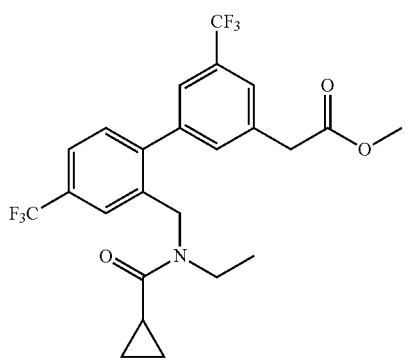 [SMILES: CCN(Cc1cc(C(F)(F)F)ccc1-c1cc(CC(=O)OC)cc(C(F)(F)F)c1)C(=O)C1CC1]

Step 1: {2'-[(Cyclopropanecarbonyl-ethyl-amino)-methyl]-5,4'-bis-trifluoromethyl-biphenyl-3-yl}-acetic acid methyl ester Prepared according to the procedure described in Example 1, Step 4, using the following starting materials: cyclopropanecarboxylic acid ethyl-[2-(4,4,5,5-tetramethyl-[1,3,2]dioxaborolan-2-yl)-5-trifluoromethyl-benzyl]-amide and (3-trifluoromethanesulfonyloxy-5-trifluoromethyl-phenyl)-acetic acid methyl ester.

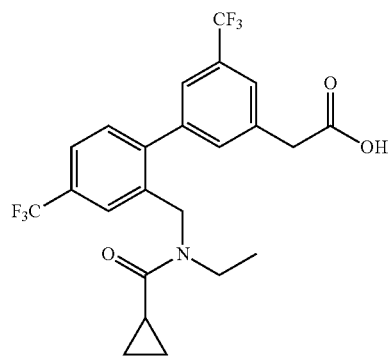 [SMILES: CCN(Cc1cc(C(F)(F)F)ccc1-c1cc(CC(=O)O)cc(C(F)(F)F)c1)C(=O)C1CC1]

Step 2: {2'-[(Cyclopropanecarbonyl-ethyl-amino)-methyl]-5,4'-bis-trifluoromethyl-biphenyl-3-yl}-acetic acid Prepared according to the procedure described in Example 185, Step 6, using the following starting material: {2'-[(cyclopropanecarbonyl-ethyl-amino)-methyl]-5,4'-bis-trifluoromethyl-biphenyl-3-yl}-acetic acid methyl ester. M+H is 474.

Example 194

Synthesis of {2'-[(Acetyl-ethyl-amino)-methyl]-5-chloro-4'-trifluoromethyl-biphenyl-3-yl}-acetic acid (Compound 1-137)

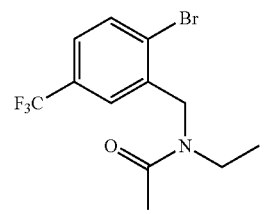 [SMILES: CCN(Cc1cc(C(F)(F)F)ccc1Br)C(C)=O]

Step 1: N-(2-Bromo-5-trifluoromethyl-benzyl)-N-ethyl-acetamide

Prepared according to the procedure described in Example 1, Step 6, using the following starting materials: (2-bromo-5-trifluoromethyl-benzyl)-ethyl-amine and acetyl chloride.

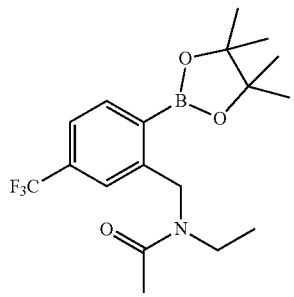 [SMILES: CCN(Cc1cc(C(F)(F)F)ccc1B1OC(C)(C)C(C)(C)O1)C(C)=O]

Step 2: N-Ethyl-N-[2-(4,4,5,5-tetramethyl-[1,3,2]dioxaborolan-2-yl)-5-trifluoromethyl-benzyl]-acetamide Prepared according to the procedure described in Example 33, Step 2, using the following starting materials: N-(2-Bromo-5-trifluoromethyl-benzyl)-N-ethyl-acetamide and bis(pinacolato)diboron.

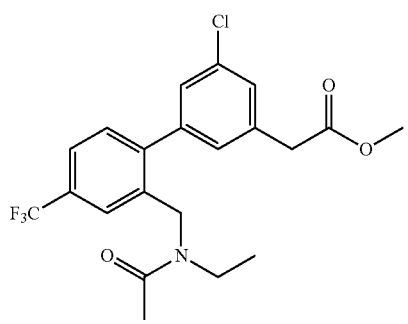 [SMILES: CCN(Cc1cc(C(F)(F)F)ccc1-c1cc(Cl)cc(CC(=O)OC)c1)C(C)=O]

Step 3: {2'-[(Acetyl-ethyl-amino)-methyl]-5-chloro-4'-trifluoromethyl-biphenyl-3-yl}-acetic acid methyl ester Prepared according to the procedure described in Example 1, Step 4, using the following starting materials: N-ethyl-N-

[2-(4,4,5,5-tetramethyl-[1,3,2]dioxaborolan-2-yl)-5-trifluoromethyl-benzyl]-acetamide and (3-bromo-5-chloro-phenyl)-acetic acid methyl ester.

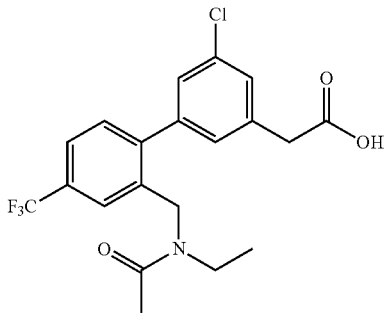 [SMILES: CCN(Cc1cc(C(F)(F)F)ccc1-c1cc(Cl)cc(CC(=O)O)c1)C(C)=O]

Step 4: {2'-[(Acetyl-ethyl-amino)-methyl]-5-chloro-4'-trifluoromethyl-biphenyl-3-yl}-acetic acid Prepared according to the procedure described in Example 185, Step 6, using the following starting material: {2'-[(acetyl-ethyl-amino)-methyl]-5-chloro-4'-trifluoromethyl-biphenyl-3-yl}-acetic acid methyl ester. M+H is 414.

Example 195

Synthesis of {2'-[(Acetyl-ethyl-amino)-methyl]-5,4'-bis-trifluoromethyl-biphenyl-3-yl}-acetic acid (Compound 1-138)

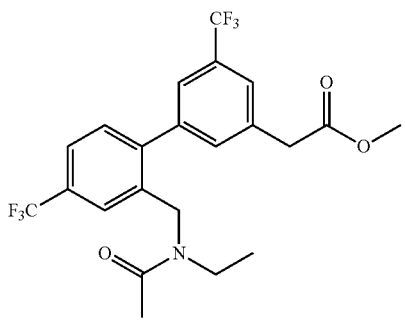 [SMILES: CCN(Cc1cc(C(F)(F)F)ccc1-c1cc(CC(=O)OC)cc(C(F)(F)F)c1)C(C)=O]

Step 1: {2'-[(Acetyl-ethyl-amino)-methyl]-5,4'-bis-trifluoromethyl-biphenyl-3-yl}-acetic acid methyl ester Prepared according to the procedure described in Example 1, Step 4, using the following starting materials: N-ethyl-N-[2-(4,4,5,5-tetramethyl-[1,3,2]dioxaborolan-2-yl)-5-trifluoromethyl-benzyl]-acetamide and (3-trifluoromethanesulfonyloxy-5-trifluoromethyl-phenyl)-acetic acid methyl ester.

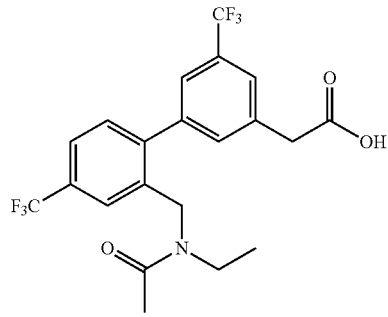

Step 2: {2'-[(Acetyl-ethyl-amino)-methyl]-5,4'-bis-trifluoromethyl-biphenyl-3-yl}-acetic acid Prepared according to the procedure described in Example 185, Step 6, using the following starting material: {2'-[(acetyl-ethyl-amino)-methyl]-5,4'-bis-trifluoromethyl-biphenyl-3-yl}-acetic acid methyl ester. M+H is 448.

Example 196

Synthesis of [2'-(3-Benzyl-1-ethyl-ureidomethyl)-5-chloro-4'-trifluoromethyl-biphenyl-3-yl]-acetic acid (Compound 1-157)

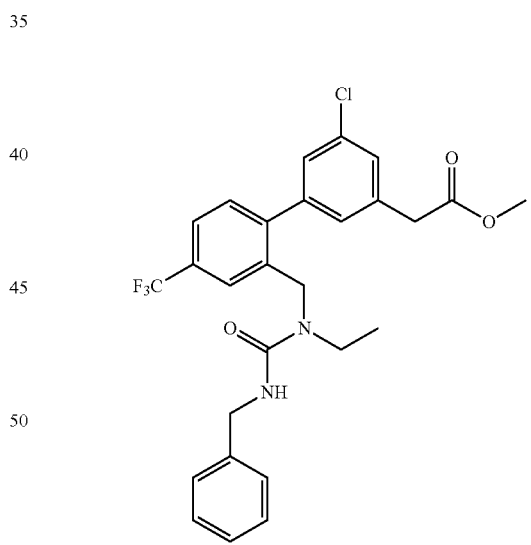

Step 1: [2'-(3-Benzyl-1-ethyl-ureidomethyl)-5-chloro-4'-trifluoromethyl-biphenyl-3-yl]-acetic acid methyl ester Prepared according to the procedure described in Example 1, Step 4, using the following starting materials: 3-benzyl-1-ethyl-1-[2-(4,4,5,5-tetramethyl-[1,3,2]dioxaborolan-2-yl)-5-trifluoromethyl-benzyl]-urea and (3-bromo-5-chloro-phenyl)-acetic acid methyl ester.

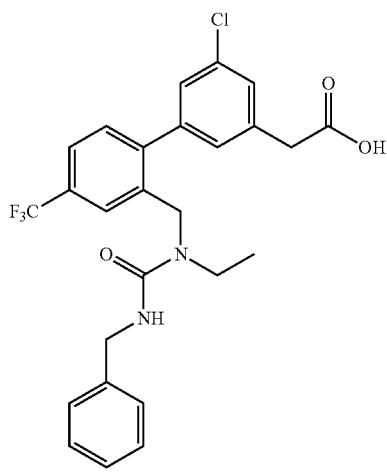

Step 2: [2'-(3-Benzyl-1-ethyl-ureidomethyl)-5-chloro-4'-trifluoromethyl-biphenyl-3-yl]-acetic acid Prepared according to the procedure described in Example 185, Step 6, using the following starting material: [2'-(3-benzyl-1-ethyl-ureidomethyl)-5-chloro-4'-trifluoromethyl-biphenyl-3-yl]-acetic acid methyl ester. M+H is 505.

Example 197

Synthesis of [2'-(3-Benzyl-1-ethyl-ureidomethyl)-5,4'-bis-trifluoromethyl-biphenyl-3-yl]-acetic acid (Compound 1-158)

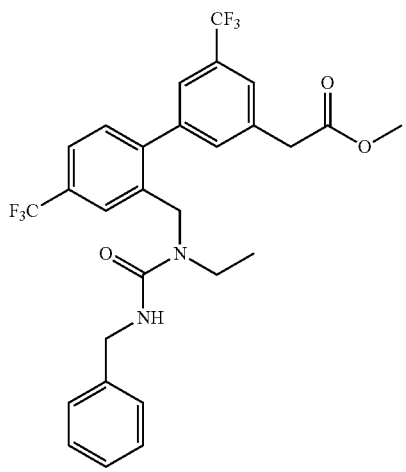 [SMILES: CCN(Cc1cc(C(F)(F)F)ccc1-c1cc(CC(=O)OC)cc(C(F)(F)F)c1)C(=O)NCc1ccccc1]

Step 1: [2'-(3-Benzyl-1-ethyl-ureidomethyl)-5,4'-bis-trifluoromethyl-biphenyl-3-yl]-acetic acid methyl ester Prepared according to the procedure described in Example 1, Step 4, using the following starting materials: 3-benzyl-1-ethyl-1-[2-(4,4,5,5-tetramethyl-[1,3,2]dioxaborolan-2-yl)-5-trifluoromethyl-benzyl]-urea and (3-trifluoromethane-sulfonyloxy-5-trifluoromethyl-phenyl)-acetic acid methyl ester.

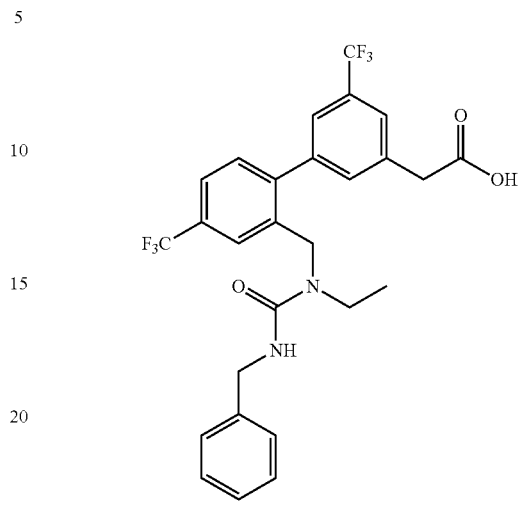

Step 2: [2'-(3-Benzyl-1-ethyl-ureidomethyl)-5,4'-bis-trifluoromethyl-biphenyl-3-yl]-acetic acid Prepared according to the procedure described in Example 185, Step 6, using the following starting material: [2'-(3-benzyl-1-ethyl-ureidomethyl)-5,4'-bis-trifluoromethyl-biphenyl-3-yl]-acetic acid methyl ester. M+H is 539.

Example 198

Synthesis of (2'-Ethylaminomethyl-5-fluoro-4'-trifluoromethyl-biphenyl-3-yl)-acetic acid (Compound 1-162)

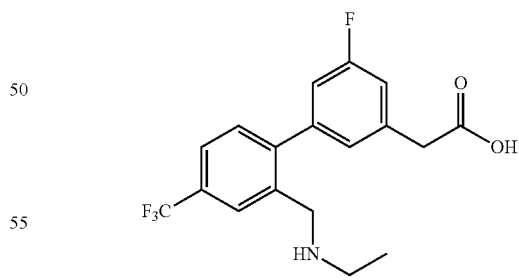

A solution of {2'-[(benzyloxycarbonyl-ethyl-amino)-methyl]-5-fluoro-4'-trifluoromethyl-biphenyl-3-yl}-acetic acid (0.025 g, 0.05 mmol) and 10% palladium on carbon (catalytic) in MeOH was hydrogenated under a balloon of $H_2$ at room temperature for 2 hours. The mixture was filtered through a pad of Celite, and the filtrate was concentrated to give the title compound. M+H is 382.

Example 199

Synthesis of [2'-(3-Benzyl-1-ethyl-ureidomethyl)-5-fluoro-4'-trifluoromethyl-biphenyl-3-yl]-acetic acid (Compound 1-159)

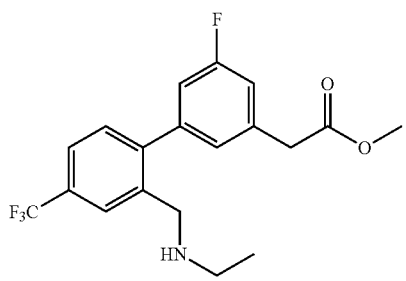 [SMILES: CCNCc1cc(C(F)(F)F)ccc1-c1cc(F)cc(CC(=O)OC)c1]

Step 1: (2'-Ethylaminomethyl-5-fluoro-4'-trifluoromethyl-biphenyl-3-yl)-acetic acid methyl ester Prepared according to the procedure described in Example 184, Step 1, using the following starting material: (2'-ethylaminomethyl-5-fluoro-4'-trifluoromethyl-biphenyl-3-yl)-acetic acid.

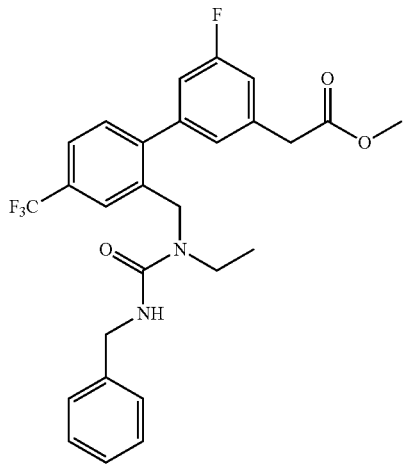 [SMILES: CCN(Cc1cc(C(F)(F)F)ccc1-c1cc(F)cc(CC(=O)OC)c1)C(=O)NCc1ccccc1]

Step 2: [2'-(3-Benzyl-1-ethyl-ureidomethyl)-5-fluoro-4'-trifluoromethyl-biphenyl-3-yl]-acetic acid methyl ester Prepared according to the procedure described in Example 95, Step 1, using the following starting materials: (2'-ethylaminomethyl-5-fluoro-4'-trifluoromethyl-biphenyl-3-yl)-acetic acid methyl ester and benzyl isocyanate.

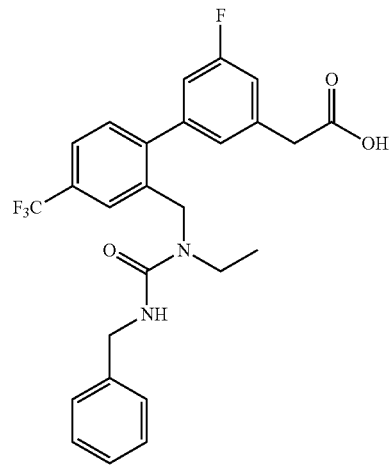 [SMILES: CCN(Cc1cc(C(F)(F)F)ccc1-c1cc(F)cc(CC(=O)O)c1)C(=O)NCc1ccccc1]

Step 3: [2'-(3-Benzyl-1-ethyl-ureidomethyl)-5-fluoro-4'-trifluoromethyl-biphenyl-3-yl]-acetic acid Prepared according to the procedure described in Example 185, Step 6, using the following starting material: [2'-(3-benzyl-1-ethyl-ureidomethyl)-5-fluoro-4'-trifluoromethyl-biphenyl-3-yl]-acetic acid methyl ester. M+H is 489.

Example 200

Synthesis of (5-Chloro-2'-ethylaminomethyl-4'-trifluoromethyl-biphenyl-3-yl)-acetic acid (Compound 1-160)

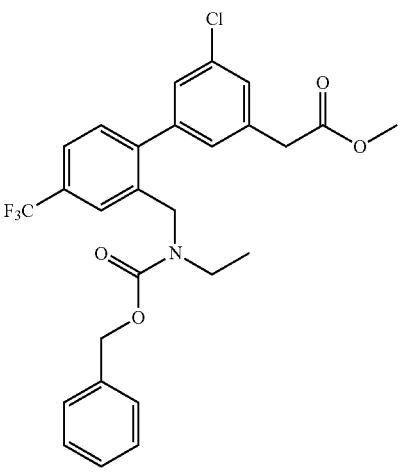 [SMILES: CCN(Cc1cc(C(F)(F)F)ccc1-c1cc(Cl)cc(CC(=O)OC)c1)C(=O)OCc1ccccc1]

Step 1: {2'-[(Benzyloxycarbonyl-ethyl-amino)-methyl]-5-chloro-4'-trifluoromethyl-biphenyl-3-yl}-acetic acid methyl ester Prepared according to the procedure described in Example 1, Step 4, using the following starting materials: ethyl-[2-(4,4,5,5-tetramethyl-[1,3,2]dioxaborolan-2-yl)-5-trifluoromethyl-benzyl]-carbamic acid benzyl ester and (3-bromo-5-chloro-phenyl)acetic acid methyl ester.

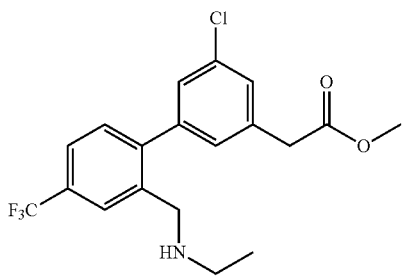

Step 2: (5-Chloro-2'-ethylaminomethyl-4'-trifluoromethyl-biphenyl-3-yl)-acetic acid methyl ester Prepared according to the procedure described in Example 198, Step 1, using the following starting material: {2'-[(benzyloxycarbonyl-ethyl-amino)-methyl]-5-chloro-4'-trifluoromethyl-biphenyl-3-yl}-acetic acid methyl ester.

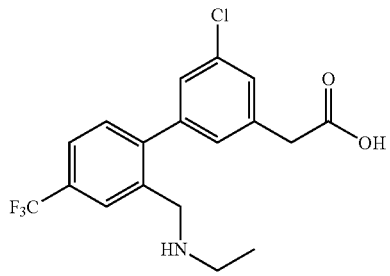

Step 3: (5-Chloro-2'-ethylaminomethyl-4'-trifluoromethyl-biphenyl-3-yl)-acetic acid (5-Chloro-2'-ethylaminomethyl-4'-trifluoromethyl-biphenyl-3-yl)-acetic acid methyl ester (0.010 g, 0.03 mmol) in 1,4-dioxane (2 mL) was treated with 1N aqueous LiOH (1 mL) at room temperature for 1 hour. The solution was neutralized to pH 6 and extracted with EtOAc, and the combined organic layers were concentrated and purified by preparative HPLC to give the title compound.

Example 201

Synthesis of (2'-Ethylaminomethyl-5,4'-bis-trifluoromethyl-biphenyl-3-yl)-acetic acid (Compound 1-161)

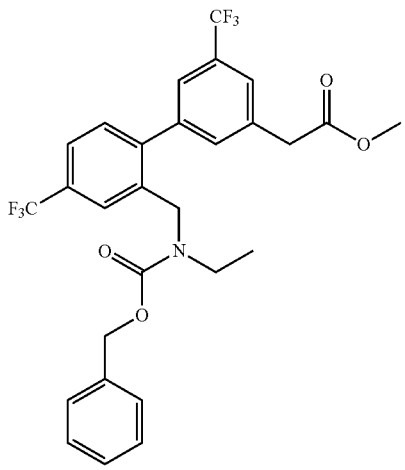 [SMILES: CCN(Cc1cc(C(F)(F)F)ccc1-c1cc(CC(=O)OC)cc(C(F)(F)F)c1)C(=O)OCc1ccccc1]

Step 1: {2'-[(Benzyloxycarbonyl-ethyl-amino)-methyl]-5,4'-bis-trifluoromethyl-biphenyl-3-yl}-acetic acid methyl ester Prepared according to the procedure described in Example 1, Step 4, using the following starting materials: ethyl-[2-(4,4,5,5-tetramethyl-[1,3,2]dioxaborolan-2-yl)-5-trifluoromethyl-benzyl]-carbamic acid benzyl ester and (3-trifluoromethanesulfonyloxy-5-trifluoromethyl-phenyl)-acetic acid methyl ester.

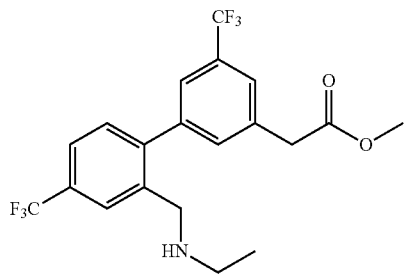 [SMILES: CCNCc1cc(C(F)(F)F)ccc1-c1cc(CC(=O)OC)cc(C(F)(F)F)c1]

Step 2: (2'-Ethylaminomethyl-5,4'-bis-trifluoromethyl-biphenyl-3-yl)-acetic acid methyl ester Prepared according to the procedure described in Example 198, Step 1, using the following starting material: {2'-[(benzyloxycarbonyl-ethyl-amino)-methyl]-5,4'-bis-trifluoromethyl-biphenyl-3-yl}-acetic acid methyl ester.

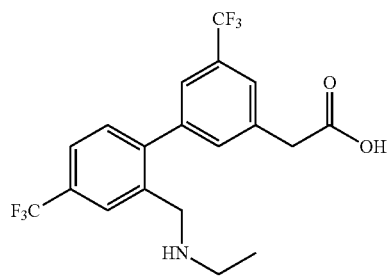

Step 3: (2'-Ethylaminomethyl-5,4'-bis-trifluoromethyl-biphenyl-3-yl)-acetic acid Prepared according to the procedure described in Example 201, Step 3, using the following starting material: (2'-ethylaminomethyl-5,4'-bis-trifluoromethyl-biphenyl-3-yl)-acetic acid methyl ester.

Example 202

Synthesis of {2'-[(Ethyl-methoxycarbonyl-amino)-methyl]-5,4'-bis-trifluoromethyl-biphenyl-3-yl}-acetic acid (Compound 1-163)

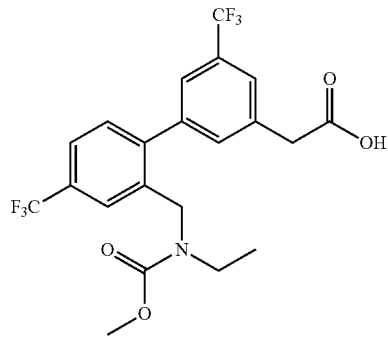 [SMILES: CCN(Cc1cc(C(F)(F)F)ccc1-c1cc(CC(=O)O)cc(C(F)(F)F)c1)C(=O)OC]

To a solution of (2'-ethylaminomethyl-5,4'-bis-trifluoromethyl-biphenyl-3-yl)-acetic acid methyl ester (0.110 g, 0.26 mmol) in $CH_2Cl_2$ at 0° C. was added diisopropylethylamine (0.11 mL, 0.66 mmol), followed by phosgene (1.9M in toluene; 0.20 mL, 0.39 mmol), and the mixture was stirred for 2 hours. Triethylamine (0.06 mL, 0.52 mmol) was added, followed by methylamine (2M in THF; 0.20 mL, 0.39 mmol), and the reaction was stirred at room temperature for 2 hours. Urea formation did not occur, so the mixture was worked-up with $CH_2Cl_2$ and $H_2O$, and the residue was purified by silica gel chromatography to give the carbamoyl chloride intermediate, which was treated with 1N aqueous LiOH in MeOH and THF to give the title compound. M+H is 464.

Example 203

Synthesis of {5-Chloro-2'-[(ethyl-methoxycarbonyl-amino)-methyl]-4'-trifluoromethyl-biphenyl-3-yl}-acetic acid (Compound 1-164)

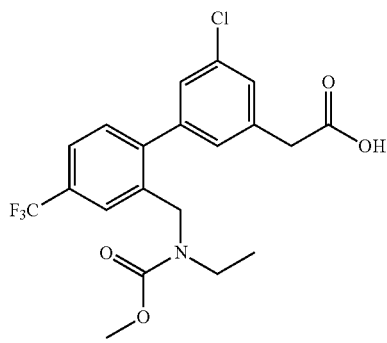 [SMILES: CCN(Cc1cc(C(F)(F)F)ccc1-c1cc(Cl)cc(CC(=O)O)c1)C(=O)OC]

Prepared according to the procedure described in Example 202, Step 1, using the following starting material: (5-chloro-2'-ethylaminomethyl-4'-trifluoromethyl-biphenyl-3-yl)-acetic acid methyl ester. M+H is 430.

Example 204

Synthesis of (5-Chloro-2'-{[(4-chloro-benzyloxycarbonyl)-ethyl-amino]-methyl}-4'-trifluoromethyl-biphenyl-3-yl)-acetic acid (Compound 1-188)

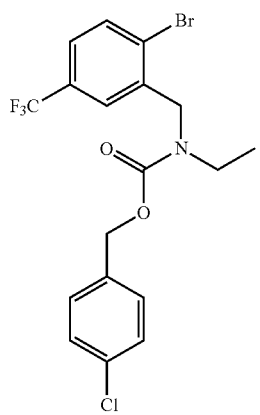 [SMILES: CCN(Cc1cc(C(F)(F)F)ccc1Br)C(=O)OCc1ccc(Cl)cc1]

Step 1: (2-Bromo-5-trifluoromethyl-benzyl)-ethyl-carbamic acid 4-chloro-benzyl ester Prepared according to the procedure described in Example 56, Step 2, using the following starting materials: (2-bromo-5-trifluoromethyl-benzyl)-ethyl-amine and 4-chlorobenzyl chloroformate.

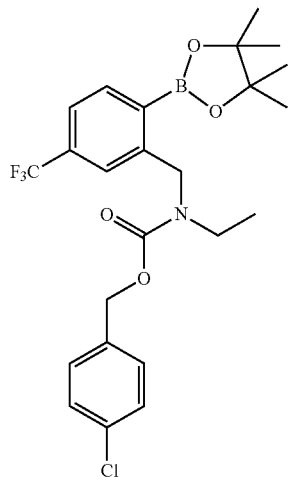 [SMILES: CCN(Cc1cc(C(F)(F)F)ccc1B1OC(C)(C)C(C)(C)O1)C(=O)OCc1ccc(Cl)cc1]

Step 2: Ethyl-[2-(4,4,5,5-tetramethyl-[1,3,2]dioxaborolan-2-yl)-5-trifluoromethyl-benzyl]-carbamic acid 4-chloro-benzyl ester Prepared according to the procedure described in Example 33, Step 2, using the following starting materials: (2-Bromo-5-trifluoromethyl-benzyl)-ethyl-carbamic acid 4-chloro-benzyl ester and bis(pinacolato)diboron.

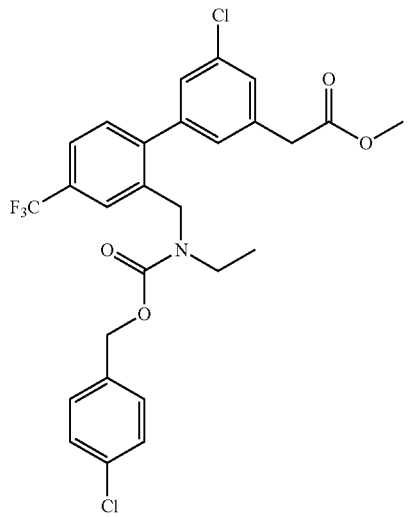 [SMILES: CCN(Cc1cc(C(F)(F)F)ccc1-c1cc(Cl)cc(CC(=O)OC)c1)C(=O)OCc1ccc(Cl)cc1]

Step 3: (5-Chloro-2'-{[(4-chloro-benzyloxycarbonyl)-ethyl-amino]-methyl}-4'-trifluoromethyl-biphenyl-3-yl)-acetic acid methyl ester Prepared according to the procedure described in Example 1, Step 4, using the following starting materials: ethyl-[2-(4, 4,5,5-tetramethyl-[1,3,2]dioxaborolan-2-yl)-5-trifluoromethyl-benzyl]-carbamic acid 4-chloro-benzyl ester and (3-bromo-5-chloro-phenyl)-acetic acid methyl ester.

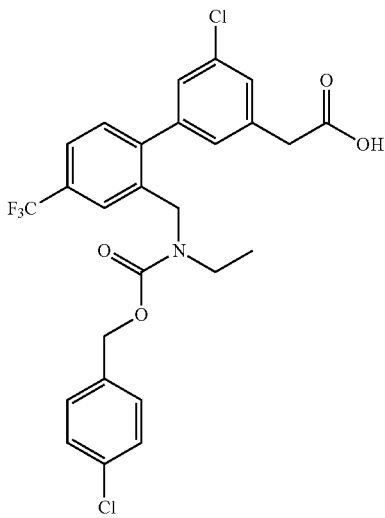 [SMILES: CCN(Cc1cc(C(F)(F)F)ccc1-c1cc(Cl)cc(CC(=O)O)c1)C(=O)OCc1ccc(Cl)cc1]

Step 4: (5-Chloro-2'-{[(4-chloro-benzyloxycarbonyl)-ethyl-amino]-methyl}-4'-trifluoromethyl-biphenyl-3-yl)-acetic acid Prepared according to the procedure described in Example 185, Step 6, using the following starting material: (5-chloro-2'-{[(4-chloro-benzyloxycarbonyl)-ethyl-amino]-methyl}-4'-trifluoromethyl-biphenyl-3-yl)-acetic acid methyl ester. M+H is 540.

Example 205

Synthesis of (2'-{[(4-Chloro-benzyloxycarbonyl)-ethyl-amino]-methyl}-5,4'-bis-trifluoromethyl-biphenyl-3-yl)-acetic acid (Compound 1-189)

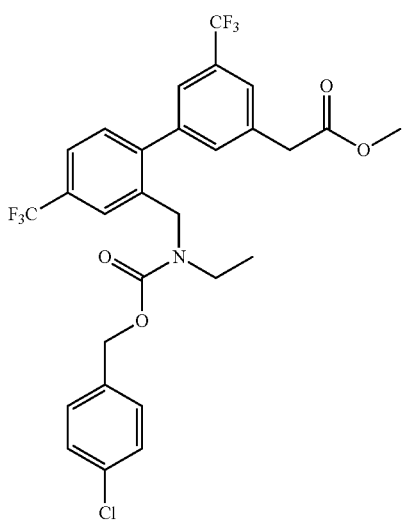

Step 1: (2'-{[(4-Chloro-benzyloxycarbonyl)-ethyl-amino]-methyl}-5,4'-bis-trifluoromethyl-biphenyl-3-yl)-acetic acid methyl ester Prepared according to the procedure described in Example 1, Step 4, using the following starting materials: ethyl-[2-(4,4,5,5-tetramethyl-[1,3,2]dioxaborolan-2-yl)-5-trifluoromethyl-benzyl]-carbamic acid 4-chloro-benzyl ester and (3-trifluoromethanesulfonyloxy-5-trifluoromethyl-phenyl)-acetic acid methyl ester.

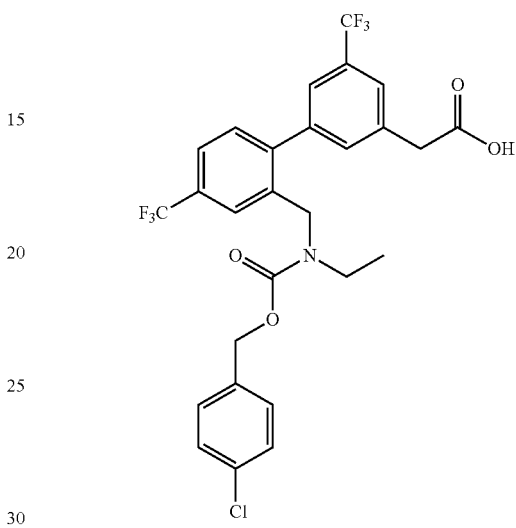

Step 2: (2'-{[(4-Chloro-benzyloxycarbonyl)-ethyl-amino]-methyl}-5,4'-bis-trifluoromethyl-biphenyl-3-yl)-acetic acid Prepared according to the procedure described in Example 185, Step 6, using the following starting material: (2'-{[(4-chloro-benzyloxycarbonyl)-ethyl-amino]-methyl}-5,4'-bis-trifluoromethyl-biphenyl-3-yl)-acetic acid methyl ester. M+H is 574.

Example 206

Synthesis of (5-Chloro-2'-{[ethyl-(4-fluoro-benzyloxycarbonyl)-amino]-methyl}-4'-trifluoromethyl-biphenyl-3-yl)-acetic acid (Compound 1-190)

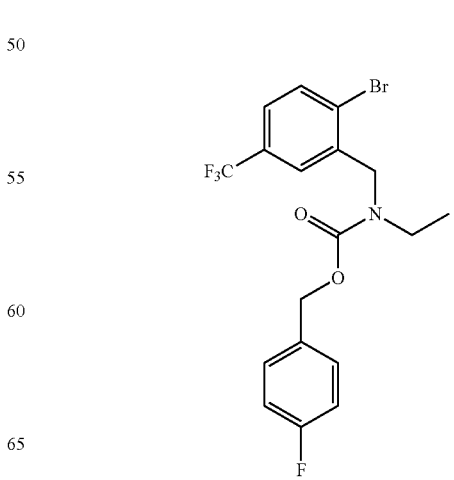

Step 1: (2-Bromo-5-trifluoromethyl-benzyl)-ethyl-carbamic acid 4-fluoro-benzyl ester Prepared according to the procedure described in Example 56, Step 2, using the following starting materials: (2-bromo-5-trifluoromethyl-benzyl)-ethyl-amine and 4-fluorobenzyl chloroformate.

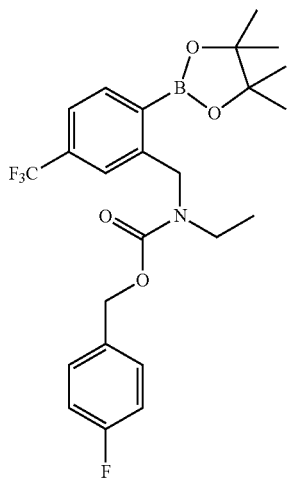 [SMILES: CCN(Cc1cc(C(F)(F)F)ccc1B1OC(C)(C)C(C)(C)O1)C(=O)OCc1ccc(F)cc1]

Step 2: Ethyl-[2-(4,4,5,5-tetramethyl-[1,3,2]dioxaborolan-2-yl)-5-trifluoromethyl-benzyl]-carbamic acid 4-fluoro-benzyl ester Prepared according to the procedure described in Example 33, Step 2, using the following starting materials: (2-bromo-5-trifluoromethyl-benzyl)-ethyl-carbamic acid 4-fluoro-benzyl ester and bis(pinacolato)diboron.

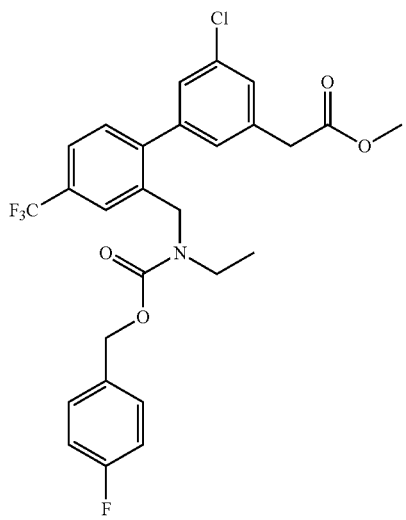 [SMILES: CCN(Cc1cc(C(F)(F)F)ccc1-c1cc(Cl)cc(CC(=O)OC)c1)C(=O)OCc1ccc(F)cc1]

Step 3: (5-Chloro-2'-{[ethyl-(4-fluoro-benzyloxycarbonyl)-amino]-methyl}-4'-trifluoromethyl-biphenyl-3-yl)-acetic acid methyl ester Prepared according to the procedure described in Example 1, Step 6, using the following starting materials: ethyl-[2-(4, 4,5,5-tetramethyl-[1,3,2]dioxaborolan-2-yl)-5-trifluoromethyl-benzyl]-carbamic acid 4-fluoro-benzyl ester and (3-bromo-5-chloro-phenyl)-acetic acid methyl ester.

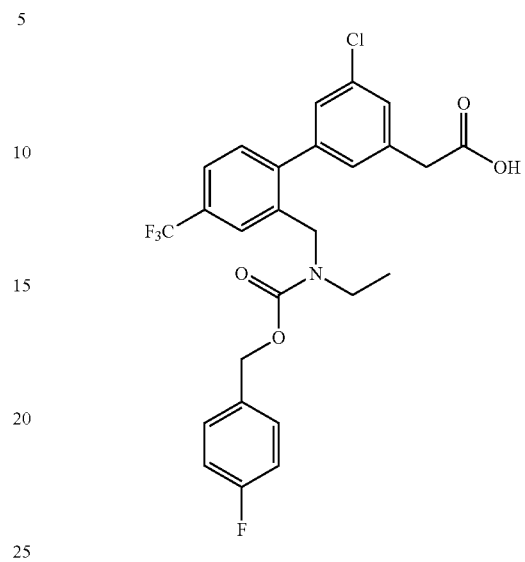

Step 4: (5-Chloro-2'-{[ethyl-(4-fluoro-benzyloxycarbonyl)-amino]-methyl}-4'-trifluoromethyl-biphenyl-3-yl)-acetic acid Prepared according to the procedure described in Example 185, Step 6, using the following starting material: (5-chloro-2'-{[ethyl-(4-fluoro-benzyloxycarbonyl)-amino]-methyl}-4'-trifluoromethyl-biphenyl-3-yl)-acetic acid methyl ester. M+H is 524.

Example 207

Synthesis of (2'-{[Ethyl-(4-fluoro-benzyloxycarbonyl)-amino]-methyl}-5,4'-bis-trifluoromethyl-biphenyl-3-yl)-acetic acid (Compound 1-191)

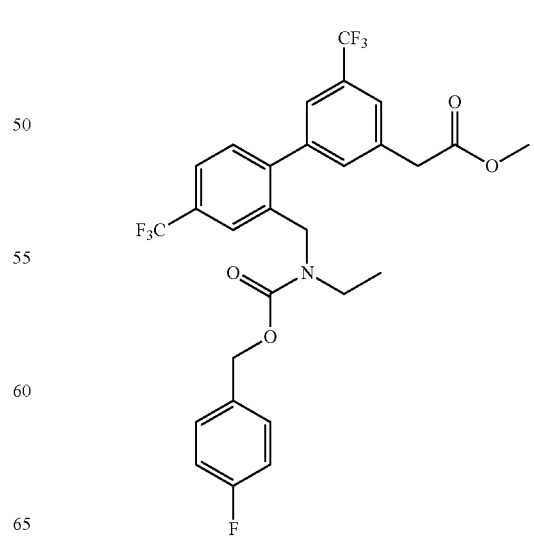

Step 1: (2'-{[Ethyl-(4-fluoro-benzyloxycarbonyl)-amino]-methyl}-5,4'-bis-trifluoromethyl-biphenyl-3-yl)-acetic acid methyl ester Prepared according to the procedure described in Example 1, Step 4, using the following starting materials: ethyl-[2-(4,4,5,5-tetramethyl-[1,3,2]dioxaborolan-2-yl)-5-trifluoromethyl-benzyl]-carbamic acid 4-fluoro-benzyl ester and (3-trifluoromethanesulfonyloxy-5-trifluoromethyl-phenyl)-acetic acid methyl ester.

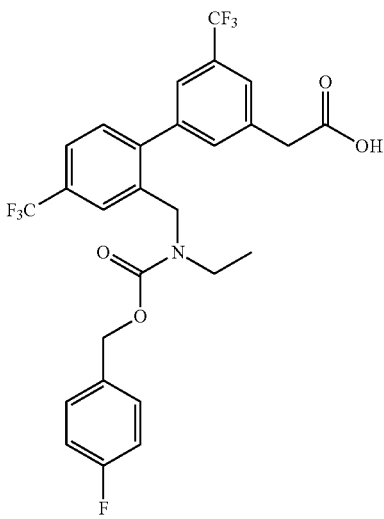 [SMILES: CCN(Cc1cc(C(F)(F)F)ccc1-c1cc(CC(=O)O)cc(C(F)(F)F)c1)C(=O)OCc1ccc(F)cc1]

Step 2: (2'-{[Ethyl-(4-fluoro-benzyloxycarbonyl)-amino]-methyl}-5,4'-bis-trifluoromethyl-biphenyl-3-yl)-acetic acid Prepared according to the procedure described in Example 185, Step 6, using the following starting material: (2'-{[ethyl-(4-fluoro-benzyloxycarbonyl)-amino]-methyl}-5,4'-bis-trifluoromethyl-biphenyl-3-yl)-acetic acid methyl ester. M+H is 558.

Example 208

Synthesis of {5-Chloro-2'-[3-(4-chloro-benzyl)-1-ethyl-ureidomethyl]-4'-trifluoromethyl-biphenyl-3-yl}-acetic acid (Compound 1-192)

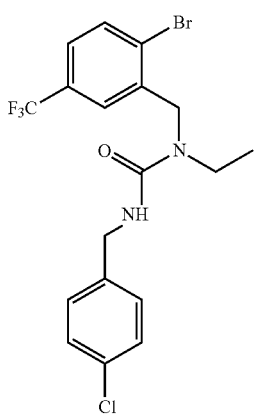 [SMILES: CCN(Cc1cc(C(F)(F)F)ccc1Br)C(=O)NCc1ccc(Cl)cc1]

Step 1: 1-(2-Bromo-5-trifluoromethyl-benzyl)-3-(4-chloro-benzyl)-1-ethyl-urea Prepared according to the procedure described in Example 95, Step 1, using the following starting materials: (2-bromo-5-trifluoromethyl-benzyl)-ethyl-amine and 4-chlorobenzyl isocyanate.

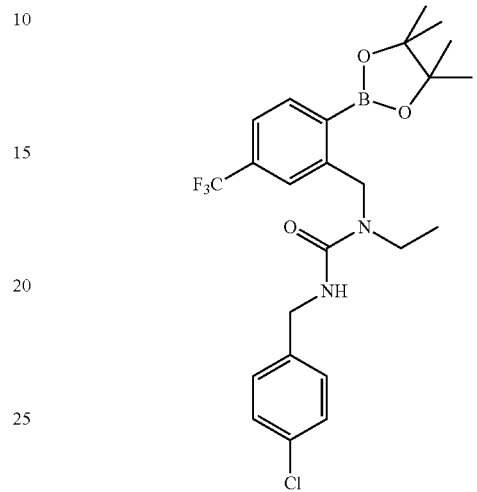

Step 2: 3-(4-Chloro-benzyl)-1-ethyl-1-[2-(4,4,5,5-tetramethyl-[1,3,2]dioxaborolan-2-yl)-5-trifluoromethyl-benzyl]-urea Prepared according to the procedure described in Example 33, Step 2, using the following starting materials: 1-(2-bromo-5-trifluoromethyl-benzyl)-3-(4-chloro-benzyl)-1-ethyl-urea and bis(pinacolato)diboron.

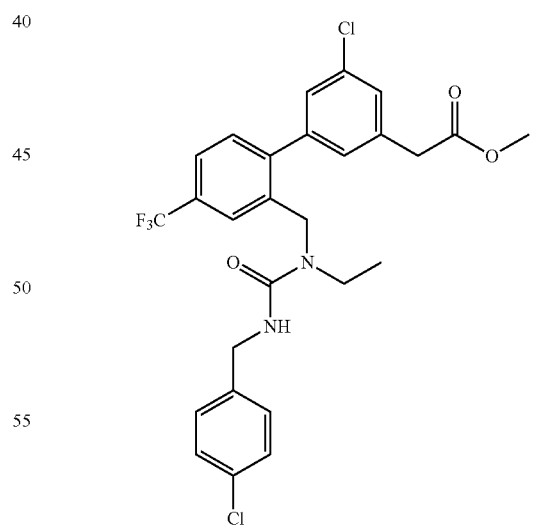

Step 3: {5-Chloro-2'-[3-(4-chloro-benzyl)-1-ethyl-ureidomethyl]-4'-trifluoromethyl-biphenyl-3-yl}-acetic acid methyl ester Prepared according to the procedure described in Example 1, Step 4, using the following starting materials: 3-(4-chlorobenzyl)-1-ethyl-1-[2-(4,4,5,5-tetramethyl-[1,3,2]dioxaboro-lan-2-yl)-5-trifluoromethyl-benzyl]-urea and (3-bromo-5-chloro-phenyl)-acetic acid methyl ester.

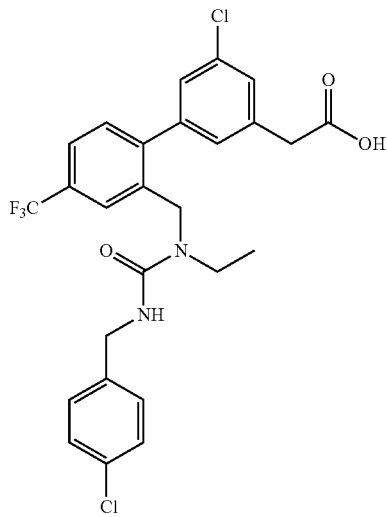 [SMILES: CCN(Cc1cc(C(F)(F)F)ccc1-c1cc(Cl)cc(CC(=O)O)c1)C(=O)NCc1ccc(Cl)cc1]

Step 4: {5-Chloro-2'-[3-(4-chloro-benzyl)-1-ethyl-ureidomethyl]-4'-trifluoromethyl-biphenyl-3-yl}-acetic acid Prepared according to the procedure described in Example 185, Step 6, using the following starting material: {5-chloro-2'-[3-(4-chloro-benzyl)-1-ethyl-ureidomethyl]-4'-trifluoromethyl-biphenyl-3-yl}-acetic acid methyl ester. M+H is 539.

Example 209

Synthesis of {2'-[3-(4-Chloro-Benzyl)-1-ethyl-ureidomethyl]-5,4'-bis-trifluoromethyl-biphenyl-3-yl}-acetic acid (Compound 1-193)

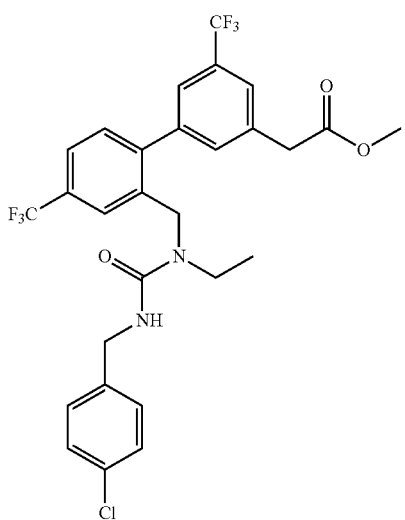

Step 1: {2'-[3-(4-Chloro-benzyl)-1-ethyl-ureidomethyl]-5,4'-bis-trifluoromethyl-biphenyl-3-yl}-acetic acid methyl ester Prepared according to the procedure described in Example 1, Step 4, using the following starting materials: 3-(4-chloro-benzyl)-1-ethyl-1-[2-(4,4,5,5-tetramethyl-[1,3,2]dioxaboro-lan-2-yl)-5-trifluoromethyl-benzyl]-urea and (3-trifluo-romethanesulfonyloxy-5-trifluoromethyl-phenyl)-acetic acid methyl ester.

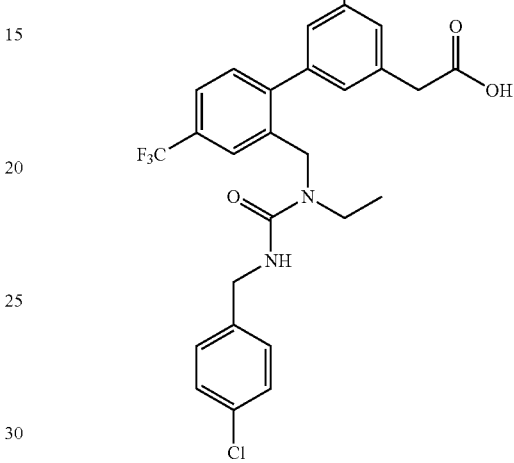

Step 2: {2'-[3-(4-Chloro-benzyl)-1-ethyl-ureidomethyl]-5,4'-bis-trifluoromethyl-biphenyl-3-yl}-acetic acid Prepared according to the procedure described in Example 185, Step 6, using the following starting material: {2'-[3-(4-chloro-benzyl)-1-ethyl-ureidomethyl]-5,4'-bis-trifluorom-ethyl-biphenyl-3-yl}-acetic acid methyl ester. M+H is 573.

Example 210

Synthesis of [5-Chloro-2'-(1-ethyl-3-methyl-ureidomethyl)-4'-trifluoromethyl-biphenyl-3-yl]-acetic acid (Compound 1-201)

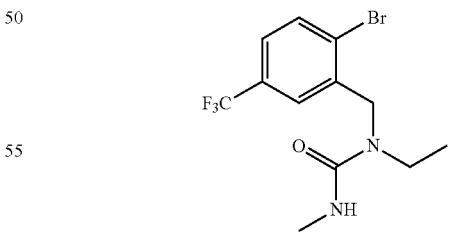

Step 1: 1-(2-Bromo-5-trifluoromethyl-benzyl)-1-ethyl-3-methyl-urea

Prepared according to the procedure described in Example 95, Step 1, using the following starting materials: (2-bromo-5-trifluoromethyl-benzyl)-ethyl-amine and methyl isocyanate.

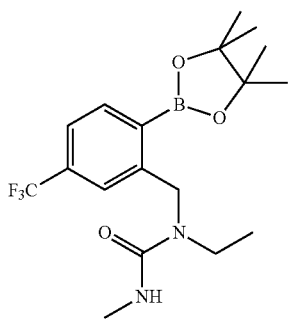 [SMILES: CCN(Cc1cc(C(F)(F)F)ccc1B1OC(C)(C)C(C)(C)O1)C(=O)NC]

Step 2: 1-Ethyl-3-methyl-1-[2-(4,4,5,5-tetramethyl-[1,3,2]dioxaborolan-2-yl)-5-trifluoromethyl-benzyl]-urea Prepared according to the procedure described in Example 33, Step 2, using the following starting materials: 1-(2-Bromo-5-trifluoromethyl-benzyl)-1-ethyl-3-methyl-urea and bis(pinacolato)diboron.

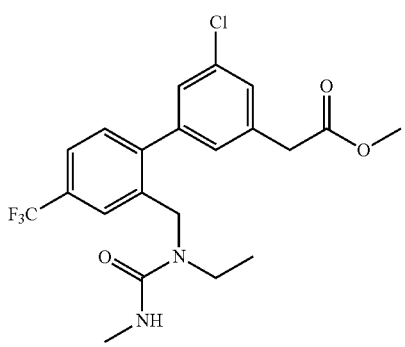 [SMILES: CCN(Cc1cc(C(F)(F)F)ccc1-c1cc(Cl)cc(CC(=O)OC)c1)C(=O)NC]

Step 3: [5-Chloro-2'-(1-ethyl-3-methyl-ureidomethyl)-4'-trifluoromethyl-biphenyl-3-yl]-acetic acid methyl ester Prepared according to the procedure described in Example 1, Step 4, using the following starting materials: 1-ethyl-3-methyl-1-[2-(4,4,5,5-tetramethyl-[1,3,2]dioxaborolan-2-yl)-5-trifluoromethyl-benzyl]-urea and (3-bromo-5-chloro-phenyl)-acetic acid methyl ester.

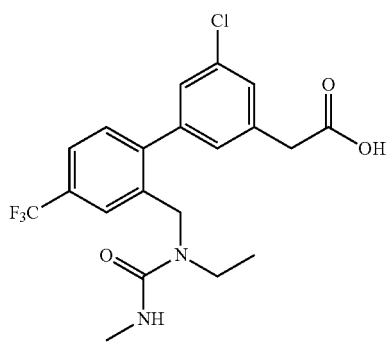 [SMILES: CCN(Cc1cc(C(F)(F)F)ccc1-c1cc(Cl)cc(CC(=O)O)c1)C(=O)NC]

Step 4: [5-Chloro-2'-(1-ethyl-3-methyl-ureidomethyl)-4'-trifluoromethyl-biphenyl-3-yl]-acetic acid Prepared according to the procedure described in Example 185, Step 6, using the following starting material: [5-chloro-2'-(1-ethyl-3-methyl-ureidomethyl)-4'-trifluoromethyl-biphenyl-3-yl]-acetic acid methyl ester. M+H is 429.

Example 211

Synthesis of {2'-[(Benzoyl-ethyl-amino)-methyl]-5-chloro-4'-trifluoromethyl-biphenyl-3-yl}-acetic acid (Compound 1-203)

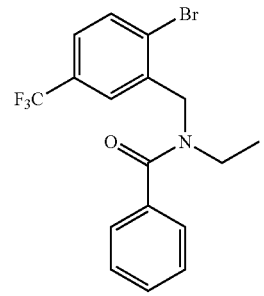 [SMILES: CCN(Cc1cc(C(F)(F)F)ccc1Br)C(=O)c1ccccc1]

Step 1: N-(2-Bromo-5-trifluoromethyl-benzyl)-N-ethyl-benzamide

Prepared according to the procedure described in Example 1, Step 6, using the following starting materials: (2-bromo-5-trifluoromethyl-benzyl)-ethyl-amine and benzoyl chloride.

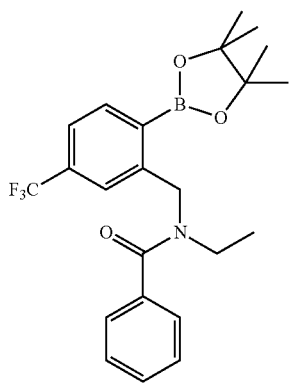 [SMILES: CCN(Cc1cc(C(F)(F)F)ccc1B1OC(C)(C)C(C)(C)O1)C(=O)c1ccccc1]

Step 2: N-Ethyl-N-[2-(4,4,5,5-tetramethyl-[1,3,2]dioxaborolan-2-yl)-5-trifluoromethyl-benzyl]-benzamide Prepared according to the procedure described in Example 33, Step 2, using the following starting materials: N-(2-bromo-5-trifluoromethyl-benzyl)-N-ethyl-benzamide and bis(pinacolato)diboron.

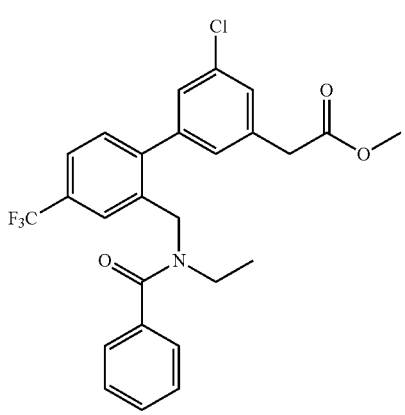 [SMILES: CCN(Cc1cc(C(F)(F)F)ccc1-c1cc(Cl)cc(CC(=O)OC)c1)C(=O)c1ccccc1]

Step 3: {2'-[(Benzoyl-ethyl-amino)-methyl]-5-chloro-4'-trifluoromethyl-biphenyl-3-yl}-acetic acid methyl ester Prepared according to the procedure described in Example 1, Step 4, using the following starting materials: N-ethyl-N-[2-(4,4,5,5-tetramethyl-[1,3,2]dioxaborolan-2-yl)-5-trifluoromethyl-benzyl]-benzamide and (3-bromo-5-chloro-phenyl)-acetic acid methyl ester.

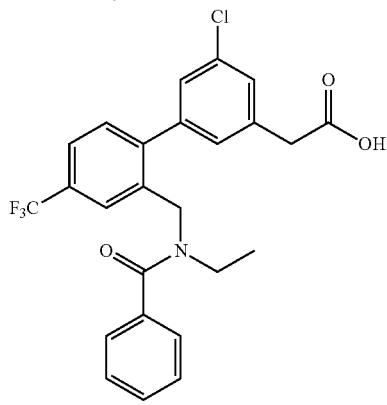 [SMILES: CCN(Cc1cc(C(F)(F)F)ccc1-c1cc(Cl)cc(CC(=O)O)c1)C(=O)c1ccccc1]

Step 4: {2'-[(Benzoyl-ethyl-amino)-methyl]-5-chloro-4'-trifluoromethyl-biphenyl-3-yl}-acetic acid Prepared according to the procedure described in Example 185, Step 6, using the following starting material: {2'-[(benzoyl-ethyl-amino)-methyl]-5-chloro-4'-trifluoromethyl-biphenyl-3-yl}-acetic acid methyl ester. M+H is 476.

Example 212

Synthesis of {2'-[(Benzoyl-ethyl-amino)-methyl]-5,4'-bis-trifluoromethyl-biphenyl-3-yl}-acetic acid (Compound 1-204)

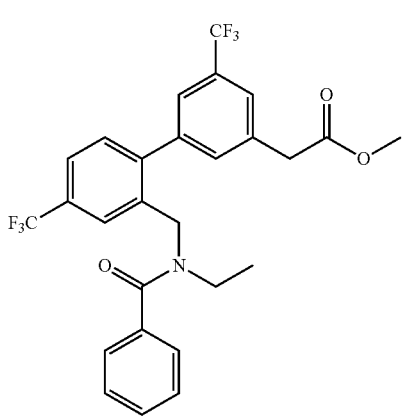 [SMILES: CCN(Cc1cc(C(F)(F)F)ccc1-c1cc(CC(=O)OC)cc(C(F)(F)F)c1)C(=O)c1ccccc1]

Step 1: {2'-[(Benzoyl-ethyl-amino)-methyl]-5,4'-bis-trifluoromethyl-biphenyl-3-yl}-acetic acid methyl ester Prepared according to the procedure described in Example 1, Step 4, using the following starting materials: N-ethyl-N-[2-(4,4,5,5-tetramethyl-[1,3,2]dioxaborolan-2-yl)-5-trifluoromethyl-benzyl]-benzamide and (3-trifluoromethanesulfonyloxy-5-trifluoromethyl-phenyl)-acetic acid methyl ester.

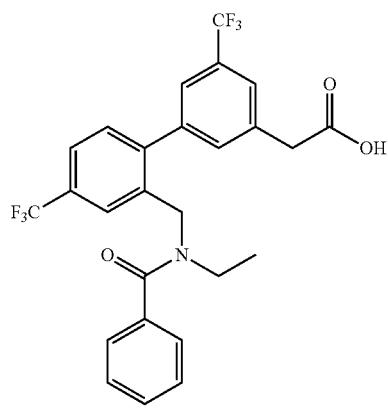

Step 2: {2'-[(Benzoyl-ethyl-amino)-methyl]-5,4'-bis-trifluoromethyl-biphenyl-3-yl}-acetic acid Prepared according to the procedure described in Example 185, Step 6, using the following starting material: {2'-[(benzoyl-ethyl-amino)-methyl]-5,4'-bis-trifluoromethyl-biphenyl-3-yl}-acetic acid methyl ester. M+H is 510.

Example 213

Synthesis of 2-{2'-[(Acetyl-ethyl-amino)-methyl]-5-chloro-4'-trifluoromethyl-biphenyl-3-yl}-propionic acid (Compound 1-211)

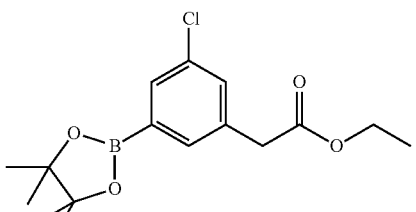

Step 1: [3-Chloro-5-(4,4,5,5-tetramethyl-[1,3,2]dioxaborolan-2-yl)-phenyl]-acetic acid ethyl ester Prepared according to the procedure described in Example 33, Step 2, using the following starting materials: (3-bromo-5-chloro-phenyl)-acetic acid ethyl ester and bis(pinacolato)diboron.

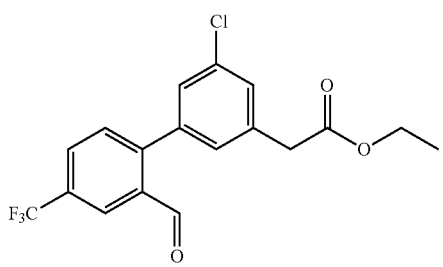 [SMILES: CCOC(=O)Cc1cc(Cl)cc(-c2ccc(C(F)(F)F)cc2C=O)c1]

Step 2: (5-Chloro-2'-formyl-4'-trifluoromethyl-biphenyl-3-yl)-acetic acid ethyl ester Prepared according to the procedure described in Example 1, Step 4, using the following starting materials: [3-chloro-5-(4,4,5,5-tetramethyl-[1,3,2]dioxaborolan-2-yl)-phenyl]-acetic acid ethyl ester and 2-bromo-5-(trifluoromethyl)benzaldehyde.

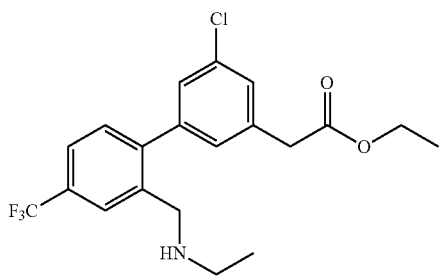 [SMILES: CCNCc1cc(C(F)(F)F)ccc1-c1cc(Cl)cc(CC(=O)OCC)c1]

Step 3: (5-Chloro-2'-ethylaminomethyl-4'-trifluoromethyl-biphenyl-3-yl)-acetic acid ethyl ester Prepared according to the procedure described in Example 33, Step 4, using the following starting materials: (5-chloro-2'-formyl-4'-trifluoromethyl-biphenyl-3-yl)-acetic acid ethyl ester and ethylamine (2M in THF).

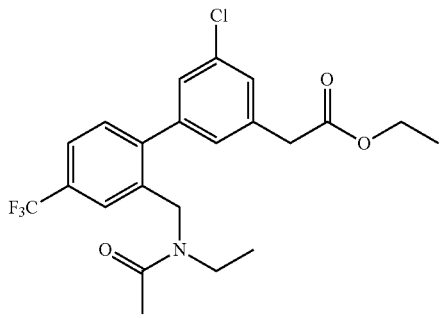 [SMILES: CCOC(=O)Cc1cc(Cl)cc(-c2ccc(C(F)(F)F)cc2CN(CC)C(C)=O)c1]

Step 4: {2'-[(Acetyl-ethyl-amino)-methyl]-5-chloro-4'-trifluoromethyl-biphenyl-3-yl}-acetic acid ethyl ester Prepared according to the procedure described in Example 1, Step 6, using the following starting materials: (5-chloro-2'-ethylaminomethyl-4'-trifluoromethyl-biphenyl-3-yl)-acetic acid ethyl ester and acetyl chloride.

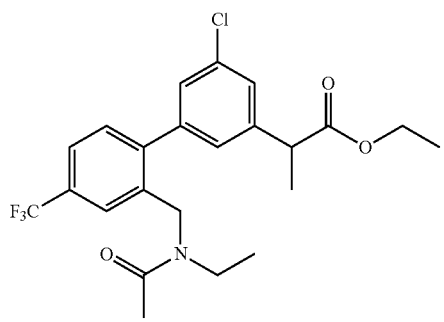 [SMILES: CCOC(=O)C(C)c1cc(Cl)cc(-c2ccc(C(F)(F)F)cc2CN(CC)C(C)=O)c1]

Step 5: 2-{2'-[(Acetyl-ethyl-amino)-methyl]-5-chloro-4'-trifluoromethyl-biphenyl-3-yl}-propionic acid ethyl ester To a solution of {2'-[(acetyl-ethyl-amino)-methyl]-5-chloro-4'-trifluoromethyl-biphenyl-3-yl}-acetic acid ethyl ester (0.070 g, 0.17 mmol) in THF at −78° C. under $N_2$ was added sodium hexamethyldisilazide (1M in THF; 0.20 mL, 0.20 mmol), and the mixture was stirred for 5 minutes. Iodomethane (0.01 mL, 0.20 mmol) was then added, and the reaction was stirred at −78° C. for 30 minutes. Once no starting material was seen by analytical LCMS, the mixture was worked-up with EtOAc and $H_2O$, and the crude material was purified by silica gel chromatography to give the title compound.

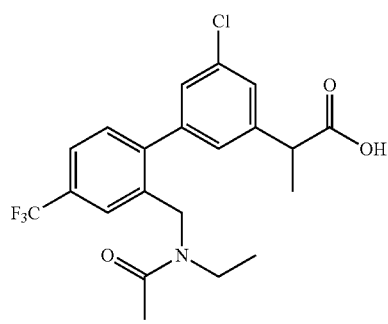 [SMILES: CCN(Cc1cc(C(F)(F)F)ccc1-c1cc(Cl)cc(C(C)C(=O)O)c1)C(C)=O]

Step 6: 2-{2'-[(Acetyl-ethyl-amino)-methyl]-5-chloro-4'-trifluoromethyl-biphenyl-3-yl}-propionic acid Prepared according to the procedure described in Example 185, Step 6, using the following starting material: 2-{2'-[(acetyl-ethyl-amino)-methyl]-5-chloro-4'-trifluoromethyl-biphenyl-3-yl}-propionic acid ethyl ester. M+H is 428.

Example 214

Synthesis of 2-{5-Chloro-2'-[(cyclopropanecarbonyl-ethyl-amino)-methyl]-4'-trifluoromethyl-biphenyl-3-yl}-propionic acid (Compound 1-212)

Step 1: {5-Chloro-2'-[(cyclopropanecarbonyl-ethyl-amino)-methyl]-4'-trifluoromethyl-biphenyl-3-yl}-acetic acid ethyl ester

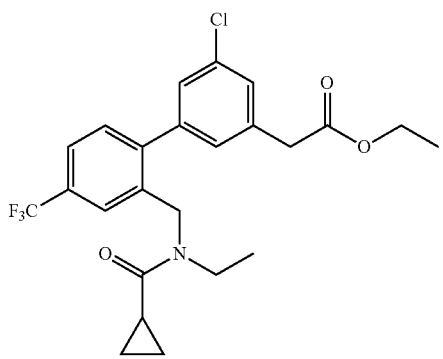 [SMILES: CCOC(=O)Cc1cc(Cl)cc(-c2ccc(C(F)(F)F)cc2CN(CC)C(=O)C2CC2)c1]

Prepared according to the procedure described in Example 1, Step 6, using the following starting materials: (5-chloro-2'-ethylaminomethyl-4'-trifluoromethyl-biphenyl-3-yl)-acetic acid ethyl ester and cyclopropanecarbonyl chloride.

Step 2: 2-{5-Chloro-2'-[(cyclopropanecarbonyl-ethyl-amino)-methyl]-4'-trifluoromethyl-biphenyl-3-yl}-propionic acid ethyl ester

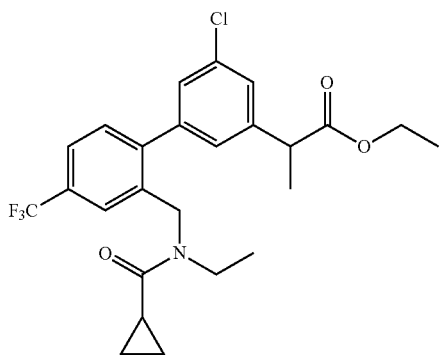 [SMILES: CCOC(=O)C(C)c1cc(Cl)cc(-c2ccc(C(F)(F)F)cc2CN(CC)C(=O)C2CC2)c1]

Prepared according to the procedure described in Example 213, Step 5, using the following starting materials: {5-chloro-2'-[(cyclopropanecarbonyl-ethyl-amino)-methyl]-4'-trifluoromethyl-biphenyl-3-yl}-acetic acid ethyl ester and iodomethane.

Step 3: 2-{5-Chloro-2'-[(cyclopropanecarbonyl-ethyl-amino)-methyl]-4'-trifluoromethyl-biphenyl-3-yl}-propionic acid

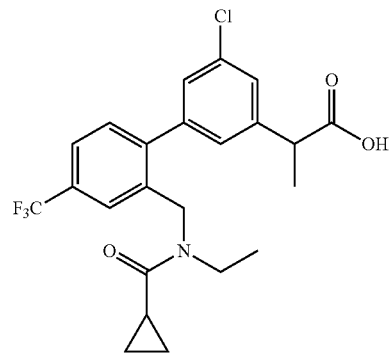 [SMILES: CCN(Cc1cc(C(F)(F)F)ccc1-c1cc(Cl)cc(C(C)C(=O)O)c1)C(=O)C1CC1]

Prepared according to the procedure described in Example 185, Step 6, using the following starting material: 2-{5-chloro-2'-[(cyclopropanecarbonyl-ethyl-amino)-methyl]-4'-trifluoromethyl-biphenyl-3-yl}-propionic acid ethyl ester. M+H is 454.

Example 215

Synthesis of 2-{2'-[(Acetyl-ethyl-amino)-methyl]-5,4'-bis-trifluoromethyl-biphenyl-3-yl}-propionic acid (Compound 1-213)

Step 1: {2'-[(Acetyl-ethyl-amino)-methyl]-5,4'-bis-trifluoromethyl-biphenyl-3-yl}-acetic acid ethyl ester

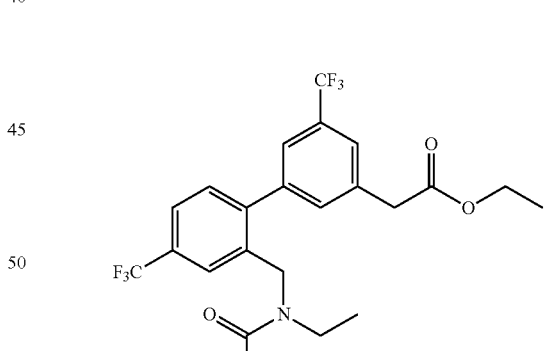

Prepared according to the procedure described in Example 184, Step 1, using the following starting material: {2'-[(acetyl-ethyl-amino)-methyl]-5,4'-bis-trifluoromethyl-biphenyl-3-yl}-acetic acid.

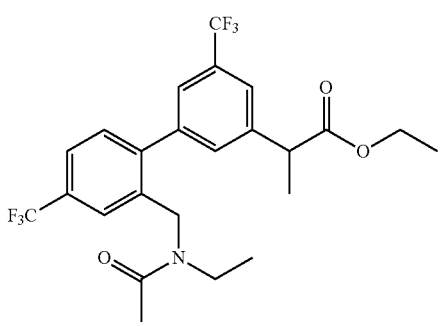 [SMILES: CCOC(=O)C(C)c1cc(-c2ccc(C(F)(F)F)cc2CN(CC)C(C)=O)cc(C(F)(F)F)c1]

Step 2: 2-{2'-[(Acetyl-ethyl-amino)-methyl]-5,4'-bis-trifluoromethyl-biphenyl-3-yl}-propionic acid ethyl ester Prepared according to the procedure described in Example 213, Step 5, using the following starting materials: {2'-[(acetyl-ethyl-amino)-methyl]-5,4'-bis-trifluoromethyl-biphenyl-3-yl}-acetic acid ethyl ester and iodomethane.

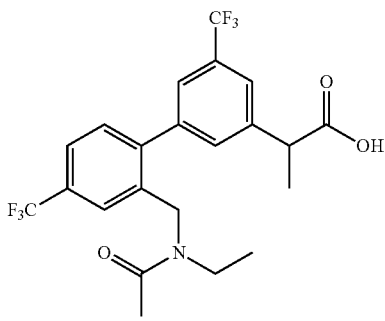

Step 3: 2-{2'-[(Acetyl-ethyl-amino)-methyl]-5,4'-bis-trifluoromethyl-biphenyl-3-yl}-propionic acid Prepared according to the procedure described in Example 185, Step 6, using the following starting material: 2-{2'-[(acetyl-ethyl-amino)-methyl]-5,4'-bis-trifluoromethyl-biphenyl-3-yl}-propionic acid ethyl ester. M+H is 462.

Example 216

Synthesis of 2-{2'-[(Cyclopropanecarbonyl-ethyl-amino)-methyl]-5,4'-bis-trifluoromethyl-biphenyl-3-yl}-propionic acid (Compound 1-214)

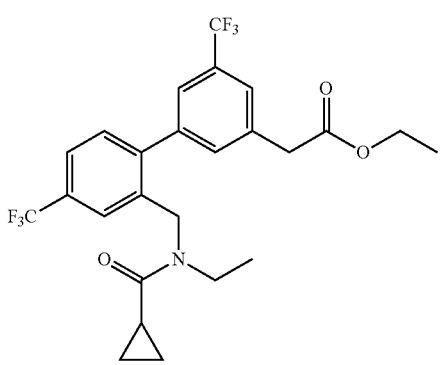 [SMILES: CCOC(=O)Cc1cc(-c2ccc(C(F)(F)F)cc2CN(CC)C(=O)C2CC2)cc(C(F)(F)F)c1]

Step 1: {2'-[(Cyclopropanecarbonyl-ethyl-amino)-methyl]-5,4'-bis-trifluoromethyl-biphenyl-3-yl}-acetic acid ethyl ester Prepared according to the procedure described in Example 184, Step 1, using the following starting material: {2'-[(cyclopropanecarbonyl-ethyl-amino)-methyl]-5,4'-bis-trifluoromethyl-biphenyl-3-yl}-acetic acid.

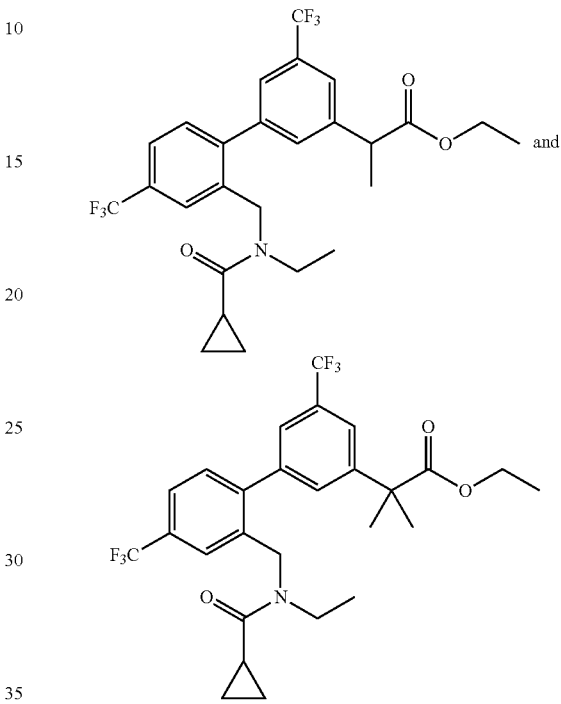

Step 2: 2-{2'-[(Cyclopropanecarbonyl-ethyl-amino)-methyl]-5,4'-bis-trifluoromethyl-biphenyl-3-yl}-propionic acid ethyl ester and 2-{2'-[(Cyclopropanecarbonyl-ethyl-amino)-methyl]-5,4'-bis-trifluoromethyl-biphenyl-3-yl}-2-methyl-propionic acid ethyl ester Prepared according to the procedure described in Example 213, Step 5, using the following starting materials: {2'-[(cyclopropanecarbonyl-ethyl-amino)-methyl]-5,4'-bis-trifluoromethyl-biphenyl-3-yl}-acetic acid ethyl ester and iodomethane; both the mono-alkylated and di-alkylated products were produced, and were separated via silica gel chromatography to give the title compounds.

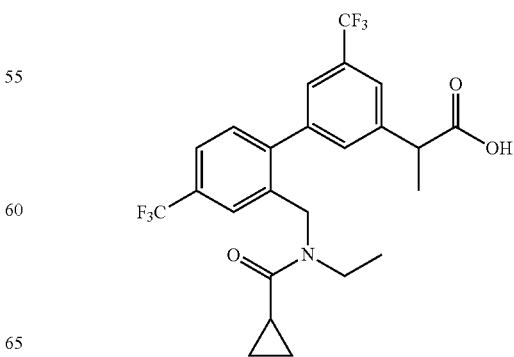

Step 3: 2-{2'-[(Cyclopropanecarbonyl-ethyl-amino)-methyl]-5,4'-bis-trifluoromethyl-biphenyl-3-yl}-propionic acid Prepared according to the procedure described in Example 185, Step 6, using the following starting material: 2-{2'-[(cyclopropanecarbonyl-ethyl-amino)-methyl]-5,4'-bis-trifluoromethyl-biphenyl-3-yl}-propionic acid ethyl ester. M+H is 488.

Example 217

Synthesis of 2-{2'-[(Cyclopropanecarbonyl-ethyl-amino)-methyl]-5,4'-bis-trifluoromethyl-biphenyl-3-yl}-2-methyl-propionic acid (Compound 1-236)

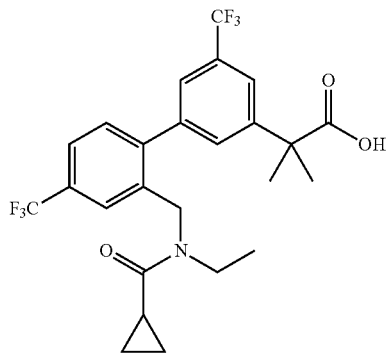 [SMILES: CCN(Cc1cc(C(F)(F)F)ccc1-c1cc(C(F)(F)F)cc(C(C)(C)C(=O)O)c1)C(=O)C1CC1]

Prepared according to the procedure described in Example 185, Step 6, using the following starting material: 2-{2'-[(cyclopropanecarbonyl-ethyl-amino)-methyl]-5,4'-bis-trifluoromethyl-biphenyl-3-yl}-2-methyl-propionic acid ethyl ester. M+H is 502.

Example 218

Synthesis of 2-[2'-(3-Benzyl-1-ethyl-ureidomethyl)-5-chloro-4'-trifluoromethyl-biphenyl-3-yl]-propionic acid (Compound 1-223)

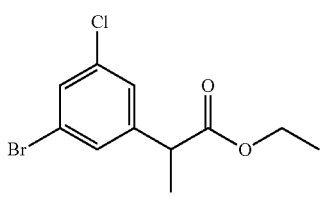

Step 1: 2-(3-Bromo-5-chloro-phenyl)-propionic acid ethyl ester

To a solution of (3-bromo-5-chloro-phenyl)-acetic acid ethyl ester (5.0 g, 18.0 mmol) in DMF (50 mL) at 0° C. under N₂ was added sodium hydride (60% in mineral oil; 0.8 g, 19.8 mmol), and the mixture was warmed to room temperature over 15 minutes. Iodomethane (1.3 mL, 19.8 mmol) was added, and the reaction was monitored by analytical LCMS. Once the reaction was complete, the mixture was worked-up with EtOAc and H₂O, and the crude material was purified by silica gel chromatography to give the title compound.

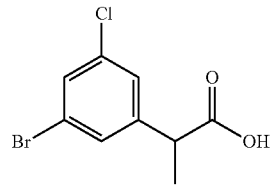

Step 2: 2-(3-Bromo-5-chloro-phenyl)-propionic acid 2-(3-Bromo-5-chloro-phenyl)-propionic acid ethyl ester (2.0 g, 6.9 mmol) in 2:2:1 MeOH:THF:H₂O was treated with 1N aqueous LiOH (3 mL) and stirred at room temperature overnight. The mixture was acidified with 10% aqueous HCl (10 mL) and extracted three times with EtOAc. The combined organic layers were concentrated, and the residue was purified by silica gel chromatography to give the title compound.

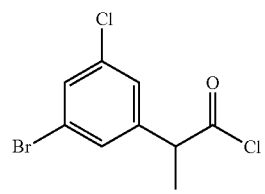

Step 3: 2-(3-Bromo-5-chloro-phenyl)-propionyl chloride

To a solution of 2-(3-bromo-5-chloro-phenyl)-propionic acid (0.87 g, 3.3 mmol) in CH₂Cl₂ (10 mL) was added oxalyl chloride (0.63 mL, 6.6 mmol) and DMF (2 drops), and the reaction was stirred for 15 minutes and then concentrated to give the title compound.

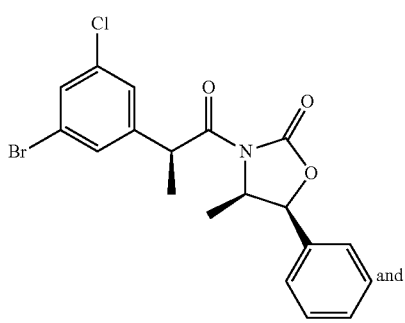

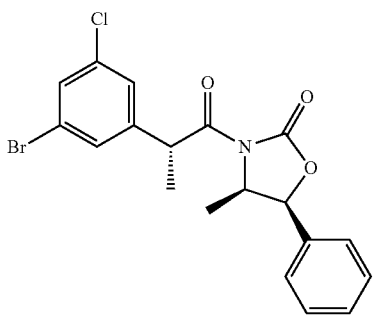

Step 4: (4R,5S)-3-[(S)-2-(3-Bromo-5-chloro-phenyl)-propionyl]-4-methyl-5-phenyl-oxazolidin-2-one and (4R,5S)-3-[(R)-2-(3-Bromo-5-chloro-phenyl)-propionyl]-4-methyl-5-phenyl-oxazolidin-2-one To a solution of (4R,5S)-(−)-4-methyl-5-phenyl-2-oxazolidinone (0.645 g, 3.6 mmol) in THF (10 mL) at −78° C. was added n-butyllithium (2.5M in THF; 1.5 mL, 3.0 mmol), and the mixture was stirred for 1 hour at −78° C. 2-(3-Bromo-5-chloro-phenyl)-propionyl chloride (3.3 mmol) in THF was added, and the reaction was warmed to room temperature. Aqueous work-up gave the title compounds, which were separated by silica gel chromatography.

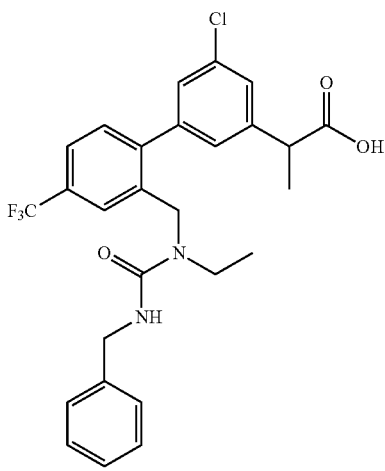

Step 5: 2-[2'-(3-Benzyl-1-ethyl-ureidomethyl)-5-chloro-4'-trifluoromethyl-biphenyl-3-yl]-propionic acid Prepared according to the procedure described in Example 1, Step 4, using the following starting materials: 3-benzyl-1-ethyl-1-[2-(4,4,5,5-tetramethyl-[1,3,2]dioxaborolan-2-yl)-5-trifluoromethyl-benzyl]-urea and (4R,5S)-3-[(S)-2-(3-bromo-5-chloro-phenyl)-propionyl]-4-methyl-5-phenyl-oxazolidin-2-one; under the coupling conditions, the oxazolidinone was hydrolyzed to the acid and the stereocenter racemized. M+H is 519.

Example 219

Synthesis of Cyclopropanecarboxylic acid ethyl-{3'-[(R)-1-methyl-2-((4R,5S)-4-methyl-2-oxo-5-phenyl-oxazolidin-3-yl)-2-oxo-ethyl]-4,5'-bis-trifluoromethyl-biphenyl-2-ylmethyl}-amide (Compound 2-15) and Cyclopropanecarboxylic acid ethyl-{3'-[(S)-1-methyl-2-((4R,5S)-4-methyl-2-oxo-5-phenyl-oxazolidin-3-yl)-2-oxo-ethyl]-4,5'-bis-trifluoromethyl-biphenyl-2-ylmethyl}-amide (Compound 2-16)

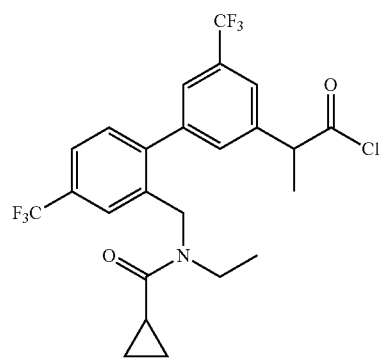 [SMILES: CCN(Cc1cc(C(F)(F)F)ccc1-c1cc(C(C)C(=O)Cl)cc(C(F)(F)F)c1)C(=O)C1CC1]

Step 1: 2-{2'-[(Cyclopropanecarbonyl-ethyl-amino)-methyl]-5,4'-bis-trifluoromethyl-biphenyl-3-yl}-propionyl chloride Prepared according to the procedure described in Example 218, Step 3, using the following starting materials: 2-{2'-[(cyclopropanecarbonyl-ethyl-amino)-methyl]-5,4'-bis-trifluoromethyl-biphenyl-3-yl}-propionic acid and oxalyl chloride.

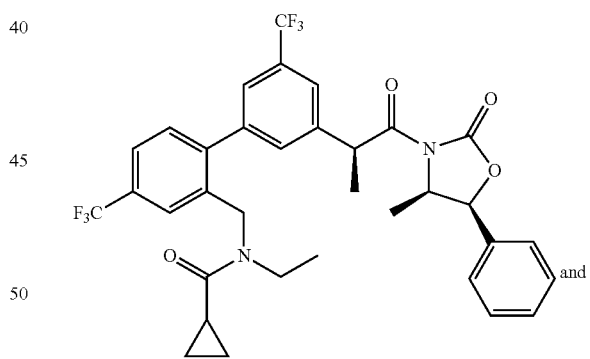

and

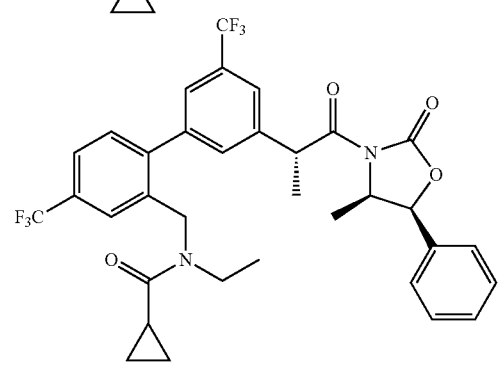

Step 2: Cyclopropanecarboxylic acid ethyl-{3'-[(S)-1-methyl-2-((4R,5S)-4-methyl-2-oxo-5-phenyl-oxazolidin-3-yl)-2-oxo-ethyl]-4,5'-bis-trifluoromethyl-biphenyl-2-ylmethyl}-amide and Cyclopropanecarboxylic acid ethyl-{3'-[(R)-1-methyl-2-((4R,5S)-4-methyl-2-oxo-5-phenyl-oxazolidin-3-yl)-2-oxo-ethyl]-4,5'-bis-trifluoromethyl-biphenyl-2-ylmethyl}-amide Prepared according to the procedure described in Example 218, Step 4, using the following starting materials: 2-{2'-[(cyclopropanecarbonyl-ethyl-amino)-methyl]-5,4'-bis-trifluoromethyl-biphenyl-3-yl}-propionyl chloride and (4R,5S)-4-methyl-5-phenyl-2-oxazolidinone; the title compounds were separated by silica gel chromatography. M+H is 647.

Example 220

Synthesis of (R)-2-{2'-[(Cyclopropanecarbonyl-ethyl-amino)-methyl]-5,4'-bis-trifluoromethyl-biphenyl-3-yl}-propionic acid (Compound 1-237)

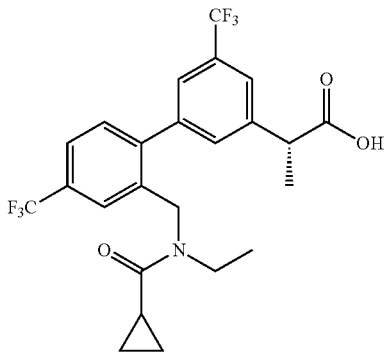 [SMILES: CCN(Cc1cc(C(F)(F)F)ccc1-c1cc([C@@H](C)C(=O)O)cc(C(F)(F)F)c1)C(=O)C1CC1]

To a solution of cyclopropanecarboxylic acid ethyl-{3'-[(R)-1-methyl-2-((4R,5S)-4-methyl-2-oxo-5-phenyl-oxazolidin-3-yl)-2-oxo-ethyl]-4,5'-bis-trifluoromethyl-biphenyl-2-ylmethyl}-amide (0.036 g, 0.06 mmol) in THF (1 mL) and H$_2$O (1 mL) was added lithium hydroxide (0.005 g, 0.11 mmol) and hydrogen peroxide (29%; 0.01 mL, 0.11 mmol), and the reaction was stirred at room temperature overnight. The mixture was acidified to pH 5 with 10% aqueous HCl are extracted with EtOAc. The crude material was purified by preparative HPLC to give the title compound. M+H is 488.

Example 221

Synthesis of (S)-2-{2'-[(Cyclopropanecarbonyl-ethyl-amino)-methyl]-5,4'-bis-trifluoromethyl-biphenyl-3-yl}-propionic acid (Compound 1-238)

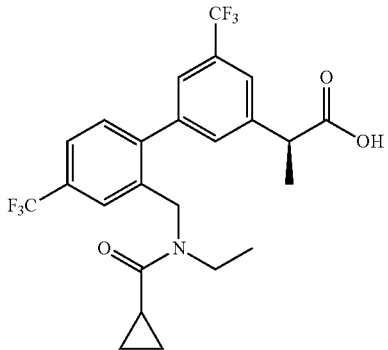 [SMILES: CCN(Cc1cc(C(F)(F)F)ccc1-c1cc([C@H](C)C(=O)O)cc(C(F)(F)F)c1)C(=O)C1CC1]

Prepared according to the procedure described in Example 220, Step 1, using the following starting material: cyclopropanecarboxylic acid ethyl-{3'-[(S)-1-methyl-2-((4R,5S)-4-methyl-2-oxo-5-phenyl-oxazolidin-3-yl)-2-oxo-ethyl]-4,5'-bis-trifluoromethyl-biphenyl-2-ylmethyl}-amide. M+H is 488.

Example 222

Synthesis of N-Ethyl-N-[5'-(2-hydroxy-2-methyl-propyl)-2'-methoxy-4-trifluoromethyl-biphenyl-2-ylmethyl]-acetamide (Compound 2-2)

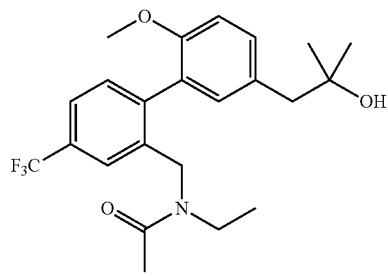 [SMILES: CCN(Cc1cc(C(F)(F)F)ccc1-c1cc(CC(C)(C)O)ccc1OC)C(C)=O]

To {2'-[(acetyl-ethyl-amino)-methyl]-6-methoxy-4'-trifluoromethyl-biphenyl-3-yl}-acetic acid ethyl ester (0.143 g, 0.33 mmol) in THF (1.5 mL) at 0° C. was added methylmagnesium iodide (3M in diethyl ether; 0.65 mL, 1.96 mmol), and the reaction was stirred for 1 hour. The mixture was diluted with CH$_2$Cl$_2$ and saturated aqueous NH$_4$Cl, and the aqueous layer was extracted with CH$_2$Cl$_2$. The combined organic layers were dried over MgSO$_4$, filtered, and concentrated, and the residue was purified by silica gel chromatography (0-100% EtOAc in hexanes). The isolated material was repurified by preparative HPLC to give the title compound. M+H is 424.

Example 223

Synthesis of Ethyl-[2'-methoxy-5'-(2H-tetrazol-5-ylmethyl)-4-trifluoromethyl-biphenyl-2-ylmethyl]-carbamic acid benzyl ester (Compound 2-5)

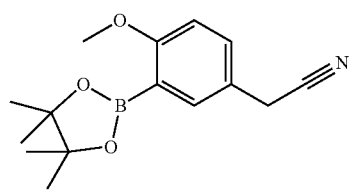 [SMILES: COc1ccc(CC#N)cc1B1OC(C)(C)C(C)(C)O1]

Step 1: [4-Methoxy-3-(4,4,5,5-tetramethyl-[1,3,2]dioxaborolan-2-yl)-phenyl]-acetonitrile Prepared according to the procedure described in Example 33, Step 2, using the following starting materials: 3-bromo-4-methoxyphenylacetonitrile and bis(pinacolato)diboron.

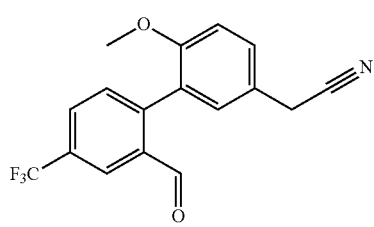 [SMILES: COc1ccc(CC#N)cc1-c1ccc(C(F)(F)F)cc1C=O]

Step 2: (2'-Formyl-6-methoxy-4'-trifluoromethyl-biphenyl-3-yl)-acetonitrile

Prepared according to the procedure described in Example 1, Step 4, using the following starting materials: 2-bromo-5-(trifluoromethyl)benzaldehyde and [4-methoxy-3-(4,4,5,5-tetramethyl-[1,3,2]dioxaborolan-2-yl)-phenyl]-acetonitrile.

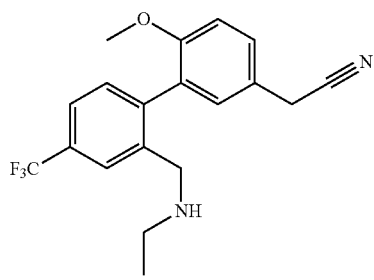 [SMILES: CCNCc1cc(C(F)(F)F)ccc1-c1cc(CC#N)ccc1OC]

Step 3: (2'-Ethylaminomethyl-6-methoxy-4'-trifluoromethyl-biphenyl-3-yl)-acetonitrile Prepared according to the procedure described in Example 1, Step 5, using the following starting materials: (2'-formyl-6-methoxy-4'-trifluoromethyl-biphenyl-3-yl)-acetonitrile and ethylamine (2M in MeOH).

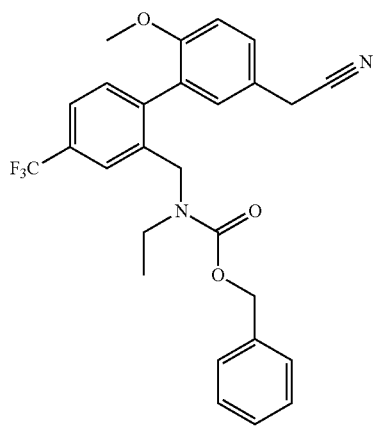 [SMILES: CCN(Cc1cc(C(F)(F)F)ccc1-c1cc(CC#N)ccc1OC)C(=O)OCc1ccccc1]

Step 4: (5'-Cyanomethyl-2'-methoxy-4-trifluoromethyl-biphenyl-2-ylmethyl)-ethyl-carbamic acid benzyl ester Prepared according to the procedure described in Example 1, Step 6, using the following starting materials: (2'-ethylaminomethyl-6-methoxy-4'-trifluoromethyl-biphenyl-3-yl)-acetonitrile and benzyl chloroformate.

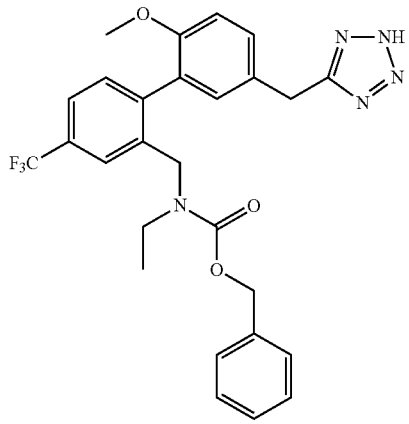 [SMILES: CCN(Cc1cc(C(F)(F)F)ccc1-c1cc(Cc2nn[nH]n2)ccc1OC)C(=O)OCc1ccccc1]

Step 5: Ethyl-[2'-methoxy-5'-(2H-tetrazol-5-ylmethyl)-4-trifluoromethyl-biphenyl-2-ylmethyl]-carbamic acid benzyl ester (5'-Cyanomethyl-2'-methoxy-4-trifluoromethyl-biphenyl-2-ylmethyl)-ethyl-carbamic acid benzyl ester (0.209 g, 0.43 mmol), azidotrimethylsilane (0.07 mL, 0.52 mmol), and dibutyltin oxide (0.015 g, 0.04 mmol) were combined in toluene (2.1 mL) and stirred at 110° C. overnight Analytical LCMS indicated that the reaction wasn't proceeding, so additional azidotrimethylsilane (0.04 mL, 0.26 mmol), and dibutyltin oxide (catalytic) was added, and the reaction was stirred at 100° C. overnight. The mixture was cooled to room temperature and concentrated, and the residue was purified by silica gel chromatography (0-100% EtOAc in hexanes) to give the title compound. M+H is 526.

Example 224

Synthesis of Cyclopropanecarboxylic acid (5'-cyanomethyl-2'-methoxy-4-trifluoromethyl-biphenyl-2-ylmethyl)-ethyl-amide (Compound 2-3)

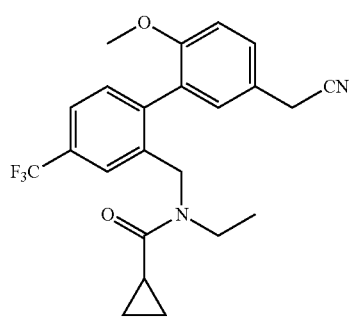 [SMILES: CCN(Cc1cc(C(F)(F)F)ccc1-c1cc(CC#N)ccc1OC)C(=O)C1CC1]

Prepared according to the procedure described in Example 1, Step 6, using the following starting materials: (2'-ethylaminomethyl-6-methoxy-4'-trifluoromethyl-biphenyl-3-yl)-acetonitrile and cyclopropanecarbonyl chloride. M+H is 417.

Example 225

Synthesis of Cyclopropanecarboxylic acid ethyl-[2'-methoxy-5'-(2H-tetrazol-5-ylmethyl)-4-trifluoromethyl-biphenyl-2-ylmethyl]-amide (Compound 2-7)

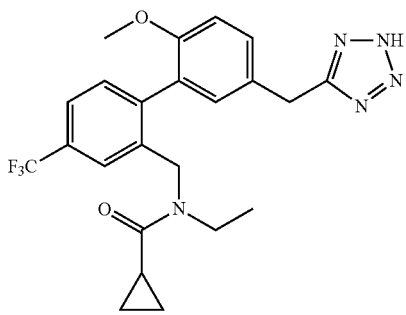 [SMILES: CCN(Cc1cc(C(F)(F)F)ccc1-c1cc(Cc2nn[nH]n2)ccc1OC)C(=O)C1CC1]

Prepared according to the procedure described in Example 223, Step 5, using the following starting material: cyclopropanecarboxylic acid (5'-cyanomethyl-2'-methoxy-4-trifluoromethyl-biphenyl-2-ylmethyl)-ethyl-amide. M+H is 460.

Example 226

Synthesis of Cyclopropanecarboxylic acid (5'-carbamoylmethyl-2'-methoxy-4-trifluoromethyl-biphenyl-2-ylmethyl)-ethyl-amide (Compound 2-8)

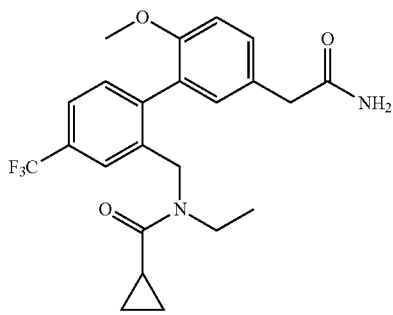 [SMILES: CCN(Cc1cc(C(F)(F)F)ccc1-c1cc(CC(N)=O)ccc1OC)C(=O)C1CC1]

To a solution of cyclopropanecarboxylic acid (5'-cyanomethyl-2'-methoxy-4-trifluoromethyl-biphenyl-2-ylmethyl)-ethyl-amide (0.064 g, 0.15 mmol) and potassium carbonate (0.064 g, 0.46 mmol) in DMSO (1 mL) at 0° C. was added hydrogen peroxide (30%; 0.44 mL), and the reaction was warmed to room temperature and stirred for 3 hours. The mixture was partitioned between EtOAc and aqueous $Na_2S_2O_4$, and the aqueous layer was extracted with EtOAc. The combined organic layers were dried over $MgSO_4$, filtered, and concentrated to give the title compound. M+H is 435.

Example 227

Synthesis of (5'-Cyanomethyl-2'-methoxy-4-trifluoromethyl-biphenyl-2-ylmethyl)-ethyl-carbamic acid benzyl ester (Compound 2-4)

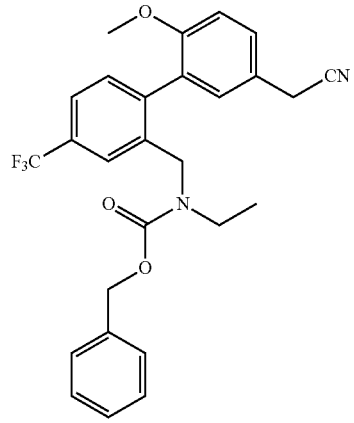 [SMILES: CCN(Cc1cc(C(F)(F)F)ccc1-c1cc(CC#N)ccc1OC)C(=O)OCc1ccccc1]

Prepared according to the procedure described in Example 1, Step 6, using the following starting materials: (2'-ethylaminomethyl-6-methoxy-4'-trifluoromethyl-biphenyl-3-yl)-acetonitrile and benzyl chloroformate. M+H is 483.

Example 228

Synthesis of (5'-Carbamoylmethyl-2'-methoxy-4-trifluoromethyl-biphenyl-2-ylmethyl)-ethyl-carbamic acid benzyl ester (Compound 2-6)

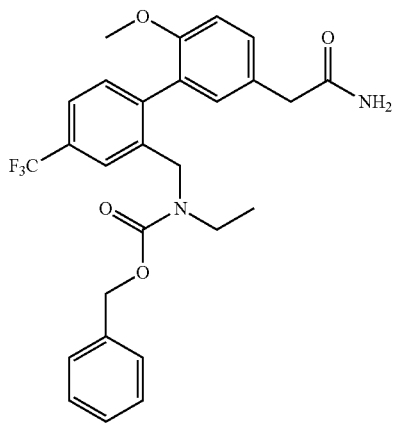 [SMILES: CCN(Cc1cc(C(F)(F)F)ccc1-c1cc(CC(N)=O)ccc1OC)C(=O)OCc1ccccc1]

Prepared according to the procedure described in Example 226, Step 1, using the following starting material: (5'-cyanomethyl-2'-methoxy-4-trifluoromethyl-biphenyl-2-ylmethyl)-ethyl-carbamic acid benzyl ester. M+H is 501.

Example 229

Synthesis of (2S,3S,4S,5R,6S)-6-{2-[2'-(3-Benzyl-1-ethyl-ureidomethyl)-6-methoxy-4'-trifluoromethyl-biphenyl-3-yl]-acetoxy}-3,4,5-trihydroxy-tetrahydro-pyran-2-carboxylic acid (Compound 2-17)

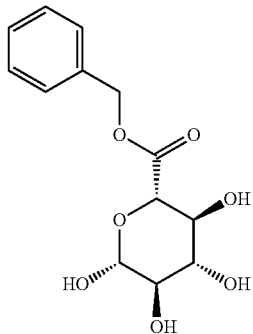 [SMILES: O=C(OCc1ccccc1)[C@H]1O[C@@H](O)[C@H](O)[C@@H](O)[C@@H]1O]

Step 1: (2S,3S,4S,5R,6R)-3,4,5,6-Tetrahydroxy-tetrahydro-pyran-2-carboxylic acid benzyl ester Prepared according to the procedure described in Tetrahedron, 2007, p 7596, using the following starting material: D-glucuronic acid.

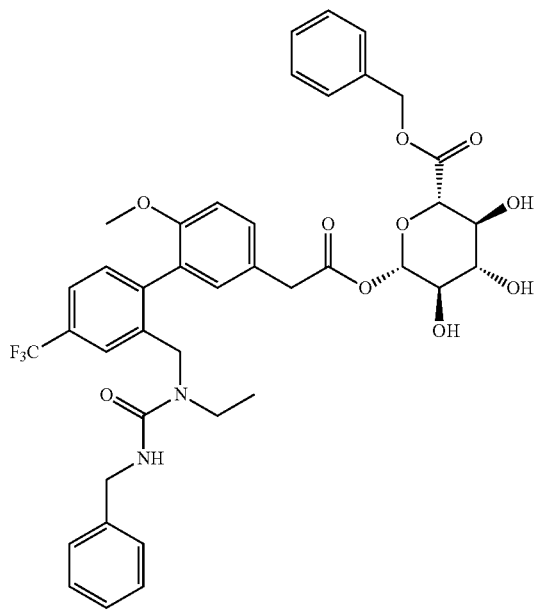 [SMILES: CCN(Cc1cc(C(F)(F)F)ccc1-c1cc(CC(=O)O[C@@H]2O[C@H](C(=O)OCc3ccccc3)[C@@H](O)[C@H](O)[C@H]2O)ccc1OC)C(=O)NCc1ccccc1]

Step 2: (2S,3S,4S,5R,6S)-6-{2-[2'-(3-Benzyl-1-ethyl-ureidomethyl)-6-methoxy-4'-trifluoromethyl-biphenyl-3-yl]-acetoxy}-3,4,5-trihydroxy-tetrahydro-pyran-2-carboxylic acid benzyl ester

[2'-(3-Benzyl-1-ethyl-ureidomethyl)-6-methoxy-4'-trifluoromethyl-biphenyl-3-yl]-acetic acid (0.110 g, 0.2 mmol), (2S,3S,4S,5R,6R)-3,4,5,6-tetrahydroxy-tetrahydro-pyran-2-carboxylic acid benzyl ester (0.060 g, 0.2 mmol), HATU (0.026 g, 0.2 mmol), and N-methylmorpholine-N-oxide (0.05 mL, 0.4 mmol) were combined in MeCN (2 mL) and stirred for 2 days at room temperature. The mixture was concentrated, and the residue was purified by preparative HPLC to give the title compound.

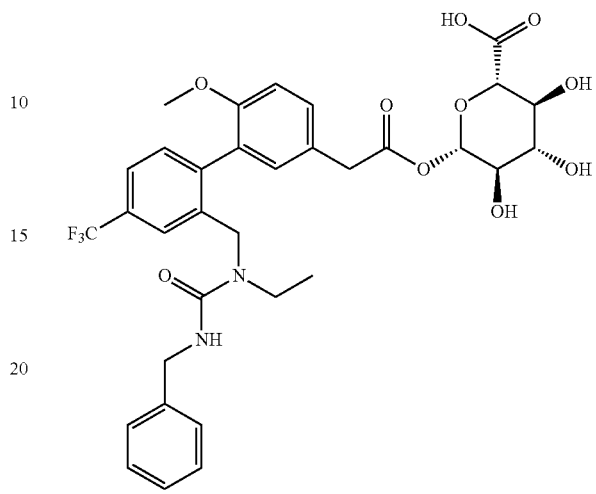

Step 3: (2S,3S,4S,5R,6S)-6-{2-[2'-(3-Benzyl-1-ethyl-ureidomethyl)-6-methoxy-4'-trifluoromethyl-biphenyl-3-yl]-acetoxy}-3,4,5-trihydroxy-tetrahydro-pyran-2-carboxylic acid (2S,3S,4S,5R,6S)-6-{2-[2'-(3-Benzyl-1-ethyl-ureidomethyl)-6-methoxy-4'-trifluoromethyl-biphenyl-3-yl]-acetoxy}-3,4,5-trihydroxy-tetrahydro-pyran-2-carboxylic acid benzyl ester (0.2 mmol) in EtOAc was treated with 10% palladium on carbon (catalytic) and hydrogenated under a balloon of $H_2$. The solution was filtered over a pad of Celite, and the filtrate was concentrated and purified by preparative HPLC to give the title compound.

Example 230

CRTH2 Assays

Example 230a

$DP_2$/CRTH2 Binding Assay

The ability of a compound to bind to the human $DP_2$ receptor is assessed via a radioligand binding assay using [$^3$H]$PGD_2$. HEK293 cells stably expressing recombinant human $DP_2$ are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol to approximately 5 mg protein/ml. Membranes (2-10 µg protein/well) are incubated in 96-well plates with 1 nM [$^3$H] $PGD_2$ and test compound in Assay Buffer (50 mM Hepes, 10 mM $MnCl_2$, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polythylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried.

Scintillant is then added to the plates and the radioactivity retained on the filters is determined on a Packard TopCount (Perkin Elmer). Specific binding is determined as total radioactive binding minus non-specific binding in the presence of 10 µM PGD$_2$. IC$_{50}$s were determined using GraphPad prism analysis of drug titration curves. Compounds in Table 1 and Table 2 that were tested had an IC$_{50}$ of less than 30 micromolar in this assay, unless otherwise noted.

Example 230b

GTPγS Binding Assay

The ability of a compound to inhibit binding of GTP to DP$_2$ is assessed via a membrane GTPγS assay. CHO cells stably expressing the recombinant human CRTH2 receptor are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol. Membranes (~12.5 µg per well) are incubated in 96-well plates with 0.05 nM [$^{35}$S]-GTPγS, 80 nM PGD$_2$, 5 µM GDP, and test compound in Assay Buffer (50 mM Hepes, pH 7.4, 100 mM NaCl, 5 mM MgCl$_2$ and 0.2% human serum albumin) for 60 minutes at 30° C. The reactions are terminated by rapid filtration through Whatman GF/B glass fibre filter plates. The filter plates are washed 3 times with 1 ml cold Assay Buffer and dried. Scintillant is then added to the plates and the radioactivity retained on the filters is determined on a Packard TopCount (Perkin Elmer). Specific binding is determined as total radioactive binding minus non-specific binding in the absence of the ligand (80 nM PGD$_2$). IC$_{50}$s were determined using Graphpad prism analysis of drug titration curves.

Example 230c

Whole Blood Esoinophil Shape Change Assay

Blood is drawn from consenting human volunteers in EDTA vacutainer tubes and used within 1 hr of draw. A 98 µl aliquot of blood is mixed with 2 µl of test compound (in 50% DMSO) in 1.2 ml polypropylene tubes. The blood is vortexed and incubated at 37° C. for 15 minutes. 5 µl of 1 µM PGD$_2$ in PBS is added for a final concentration of 50 nM and the tubes briefly vortexed. The reactions are incubated for exactly 5 minutes at 37° C. and then terminated by placing the tubes on ice and immediately adding 250 µl of ice-cold 1:4 diluted Cytofix (BD Biosciences). The reactions are transferred to 12×75 mM polystyrene round bottom tubes and the red blood cells lysed by the addition of 3 ml ammonium chloride lysing solution (150 mM NH$_4$Cl, 10 mM KHCO$_3$, 0.1 mM EDTA disodium salt) and incubation at room temperature for 15 minutes. The cells are pelleted by spinning at 1300 rpm for 5 minutes at 4° C. and washed once with 3 ml ice-cold PBS. The cells are resuspended in 0.2 ml of ice-cold 1:4 diluted Cytofix (BD Biosciences) and analyzed on a FACSCalibur (BD Biosciences) within 2 hours. Eosinophils were gated on the basis of autofluorescence in the FL2 channel and shape change on 500 eosinophils was assayed by forward scatter and side scatter analysis. The specific change in shape induced by PGD$_2$ was calculated as the difference between the percentage of high forward scatter eosinophils in the presence and absence of PGD$_2$. IC$_{50}$s were determined using Graphpad Prism® analysis of drug titration curves.

Example 230d

DP$_1$ Binding Assay

The ability of a compound to bind to the human DP1 receptor was evaluated via a radioligand membrane binding assay using the DP$_1$ selective synthetic ligand [$^3$H] BWA868C. Packed human platelets (Biological Specialty Corporation), were resuspended in 6 volumes of Hepes/HBSS buffer (10 mM Hepes, 1 mM DTT in Hanks Balanced Salt Solution (HBSS)), lysed and centrifuged at 75,000×g to pellet the membranes. Membranes were resuspended in Hepes/HBSS buffer to approximately 12 mg protein/ml. Membranes (20 µg protein/well) are incubated in 96-well plates with 2 nM [$^3$H]BWA868C and test compound in Assay Buffer (50 mM Hepes, 10 mM MnCl$_2$, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polethylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried. Scintillant is then added to the plates and the radioactivity retained on the filters is determined on a Packard TopCount (Perkin Elmer). Specific binding is determined as total radioactive binding minus non-specific binding in the presence of 10 µM BW A868C. IC$_{50}$s were determined using GraphPad prism analysis of drug titration curves.

Example 231

In vivo Assays

Mouse Allergic Rhinitis Model

The compounds ability to inhibit allergen-induced sneezing and nasal rubbing is assessed using a mouse model of allergic rhinitis. Methods were adapted from those detailed in Nakaya, M., et al. 2006. Noninvasive system for evaluating allergen-induced nasal hypersensitivity in murine allergic rhinitis. *Laboratory Investigation*, 86:917-926. Female BALB/c mice (20-25 g) are immunized by an intraperitoneal injection (i.p.) of 2 µg ovalbumin (OVA) complexed with alum in a volume 0.2 ml on days 0 and 14. Seven days later (day 21) mice are challenged intranasally with 20 µl of a 10 mg/ml solution of OVA. The challenge period occurs daily from days 21 to day 25. Mice (5-7/group) are randomly assigned to receive either compound or vehicle and are treated by oral gavage 1-2 hour prior to each OVA challenge. The number of sneezes and nasal rubs are counted by an independent blind observe during a period of 8 minutes immediately following OVA challenge on days 21, 23 and 25. A significant increase in allergen-induced sneezing and nasal rubbing occurs over the 5-day challenge period. Inhibition of this effect by select compounds is determined statistically using Graphpad prism.

Example 232

Guinea Pig IV-DKPGD2-Induced Peripheral Blood Leukocyte Influx

The compounds ability to inhibit leukocyte migration in vivo was assessed using intravenous injection of 13,14-dihydro-15-keto-prostaglandin D2 (DK-PGD2). Methods were adapted from those detailed Shichijo et al., 2003, Chemoattractant receptor-homologous molecule expressed on Th2 cells activation in vivo increases blood leukocyte counts and its blockade abrogates 13,14-dihydro-15-keto-prostaglandin D2-induced eosinophilia in rats. *Journal of Pharmacology and Experimental Therapeutics*, 307:518-525. Male Hartley guinea pigs were immunized with ovalbumin (OVA) on day 0 by intraperitoneal (IP) injection of 1 ml of a 100 µg/ml solution in Imject Alum. They were then used in the DK-PGD2 procedure between days 14 and 21. Subjects were randomly assigned to receive either vehicle (0.5% methyl cellulose, 4 ml/kg, oral (PO)) or one of three to four doses of test compound. Two hours or eighteen hours after dosing, animals were anesthetized with ketamine and challenged with DK-PGD2 (1 mg/kg, IV). Thirty minutes after IV administration, blood was collected via the marginal ear vein into EDTA tubes for cell analysis. 10 µl blood was lysed in 190 µl water followed by a further 20-fold dilution in PBS. A 10 µl fraction was mixed with equal parts trypan blue and loaded on a hemocytometer. Cells were visualized at a magnification of 40× using a LabPro light microscope and totals counted and recorded. Cells are expressed as total cells×$10^8$ per ml of blood. Inhibition of this effect by select compounds is determined statistically using Graphpad prism.

The compounds that were tested in Table 1 and Table 2 had $IC_{50}$ below 30 µM in the CRTH2 binding assay, unless otherwise noted.

TABLE 4

Representative Biological Data

| Compound # | hDP2 µM | hDP1 µM | hDP2 GTPγS µM (+HSA) |
|---|---|---|---|
| Compound 1-1 | A | C | A |
| Compound 1-2 | A | C | A |
| Compound 1-3 | A | C | A |
| Compound 1-4 | A | C | A |
| Compound 1-5 | A | C | B |
| Compound 1-6 | A | C | A |
| Compound 1-7 | B | C | B |
| Compound 1-8 | C | C | C |
| Compound 1-9 | B | C | B |
| Compound 1-10 | A | C | A |
| Compound 1-11 | A | C | A |
| Compound 1-12 | A | C | A |
| Compound 1-13 | B | A | B |
| Compound 1-14 | A | C | A |
| Compound 1-15 | C | C | — |
| Compound 1-16 | C | C | — |
| Compound 1-17 | A | C | A |
| Compound 1-18 | B | C | B |
| Compound 1-19 | A | C | A |
| Compound 1-20 | A | C | A |
| Compound 1-21 | A | C | A |
| Compound 1-22 | C | C | — |
| Compound 1-23 | A | C | A |
| Compound 1-24 | A | C | A |
| Compound 1-25 | A | C | A |
| Compound 1-26 | A | C | A |
| Compound 1-27 | A | C | A |
| Compound 1-28 | A | C | A |
| Compound 1-29 | A | C | A |
| Compound 1-30 | A | C | A |
| Compound 1-31 | A | C | A |
| Compound 1-32 | A | C | A |
| Compound 1-33 | A | C | A |
| Compound 1-34 | A | C | A |
| Compound 1-35 | A | B | A |
| Compound 1-36 | A | C | A |
| Compound 1-37 | C | C | — |
| Compound 1-38 | A | C | A |
| Compound 1-39 | A | C | A |
| Compound 1-40 | A | C | A |
| Compound 1-41 | A | C | A |
| Compound 1-42 | A | C | A |
| Compound 1-43 | A | C | A |
| Compound 1-44 | A | C | A |
| Compound 1-45 | A | C | A |
| Compound 1-46 | A | C | A |
| Compound 1-47 | A | C | A |
| Compound 1-48 | A | C | A |
| Compound 1-49 | C | C | — |
| Compound 1-80 | A | — | — |
| Compound 1-91 | C | C | — |
| Compound 1-92 | A | C | A |
| Compound 1-93 | A | C | A |
| Compound 1-94 | A | C | A |
| Compound 1-96 | A | C | A |
| Compound 1-97 | A | C | A |
| Compound 1-98 | A | C | A |
| Compound 1-99 | A | C | B |
| Compound 1-100 | A | C | C |
| Compound 1-101 | C | C | — |
| Compound 1-104 | C | C | — |
| Compound 1-107 | A | C | A |
| Compound 1-108 | A | C | A |
| Compound 1-109 | A | C | A |
| Compound 1-110 | A | C | A |
| Compound 1-111 | A | C | A |
| Compound 1-112 | A | C | A |
| Compound 1-113 | A | C | A |
| Compound 1-114 | A | C | A |
| Compound 1-115 | D | C | — |
| Compound 1-116 | B | C | — |
| Compound 1-117 | A | C | A |
| Compound 1-118 | A | C | A |
| Compound 1-119 | A | C | A |
| Compound 1-120 | A | C | A |
| Compound 1-121 | A | C | A |
| Compound 1-122 | A | B | C |
| Compound 1-123 | A | B | B |
| Compound 1-124 | B | B | — |
| Compound 1-125 | A | B | B |
| Compound 1-126 | A | B | A |
| Compound 1-127 | A | B | A |
| Compound 1-128 | A | B | A |
| Compound 1-129 | A | C | A |
| Compound 1-130 | A | C | A |
| Compound 1-131 | A | C | A |
| Compound 1-132 | C | C | — |
| Compound 1-135 | A | C | — |
| Compound 1-136 | A | C | A |
| Compound 1-137 | A | C | — |
| Compound 1-138 | A | C | — |
| Compound 1-139 | A | C | — |
| Compound 1-140 | A | C | — |
| Compound 1-143 | A | B | — |
| Compound 1-144 | A | B | — |
| Compound 1-145 | A | C | — |
| Compound 1-146 | A | C | — |
| Compound 1-147 | A | C | — |
| Compound 1-148 | A | C | — |
| Compound 1-149 | A | C | — |
| Compound 1-150 | B | C | — |
| Compound 1-151 | C | C | — |
| Compound 1-152 | A | C | — |
| Compound 1-153 | A | C | — |
| Compound 1-154 | A | C | — |
| Compound 1-155 | A | C | — |
| Compound 1-156 | A | C | — |
| Compound 1-157 | A | C | — |
| Compound 1-158 | A | C | — |
| Compound 1-159 | A | C | — |
| Compound 1-163 | A | C | — |
| Compound 1-164 | A | C | — |
| Compound 1-165 | A | C- | — |
| Compound 1-168 | A | B | — |

TABLE 4-continued

Representative Biological Data

| Compound # | hDP2 μM | hDP1 μM | hDP2 GTPγS μM (+HSA) |
|---|---|---|---|
| Compound 1-169 | A | C | — |
| Compound 1-170 | A | C | — |
| Compound 1-171 | A | C | — |
| Compound 1-172 | A | C | — |
| Compound 1-173 | A | C | — |
| Compound 1-174 | A | B | — |
| Compound 1-175 | A | B | — |
| Compound 1-176 | A | C | — |
| Compound 1-177 | A | C | — |
| Compound 1-178 | A | C | — |
| Compound 1-179 | A | C | — |
| Compound 1-180 | A | C | — |
| Compound 1-181 | A | C | — |
| Compound 1-182 | A | C | — |
| Compound 1-183 | A | C | — |
| Compound 1-184 | A | C | — |
| Compound 1-185 | A | C | — |
| Compound 1-186 | A | C | A |
| Compound 1-187 | A | C | — |
| Compound 1-188 | A | — | — |
| Compound 1-189 | A | — | — |
| Compound 1-190 | A | — | — |
| Compound 1-191 | A | — | — |
| Compound 1-192 | A | — | — |
| Compound 1-193 | A | — | — |
| Compound 1-194 | A | — | — |
| Compound 1-195 | A | — | — |
| Compound 1-196 | A | — | — |
| Compound 1-197 | A | — | — |
| Compound 1-198 | A | — | — |
| Compound 1-199 | A | — | — |
| Compound 1-200 | A | — | — |
| Compound 1-201 | A | — | — |
| Compound 1-202 | A | — | — |
| Compound 1-203 | A | — | — |
| Compound 1-204 | A | — | — |
| Compound 1-206 | A | — | — |
| Compound 1-207 | A | — | — |
| Compound 1-208 | A | — | — |
| Compound 1-209 | A | — | — |
| Compound 1-210 | A | — | — |
| Compound 1-211 | A | — | — |
| Compound 1-212 | A | — | — |
| Compound 1-213 | A | — | — |
| Compound 1-214 | A | — | — |
| Compound 1-215 | A | — | — |
| Compound 1-216 | A | — | — |
| Compound 1-217 | A | — | — |
| Compound 1-218 | A | — | — |
| Compound 1-219 | A | — | — |
| Compound 1-220 | A | — | A |
| Compound 1-221 | A | — | — |
| Compound 1-222 | A | — | A |
| Compound 1-223 | A | — | — |
| Compound 1-224 | A | — | A |
| Compound 1-225 | C | — | — |
| Compound 1-226 | A | — | — |
| Compound 1-227 | A | C | A |
| Compound 1-228 | A | — | A |
| Compound 1-229 | A | — | — |
| Compound 1-230 | A | — | — |
| Compound 1-231 | A | — | — |
| Compound 1-232 | A | — | — |
| Compound 1-233 | A | — | A |
| Compound 1-234 | A | — | A |
| Compound 1-236 | B | — | — |
| Compound 1-237 | A | — | A |
| Compound 1-238 | A | — | — |
| Compound 1-239 | A | — | — |
| Compound 1-240 | A | — | — |
| Compound 1-241 | A | — | — |
| Compound 1-242 | A | — | — |
| Compound 1-243 | A | — | — |
| Compound 1-244 | A | — | — |
| Compound 1-245 | C | — | — |
| Compound 1-246 | A | — | A |
| Compound 1-247 | A | — | — |
| Compound 1-249 | A | — | — |
| Compound 1-250 | A | — | — |
| Compound 1-252 | A | — | — |
| Compound 1-253 | A | — | — |
| Compound 1-254 | A | — | — |
| Compound 1-255 | A | — | — |
| Compound 1-256 | A | — | — |
| Compound 1-257 | A | — | — |
| Compound 2-2 | C | C | — |
| Compound 2-3 | D | C | — |
| Compound 2-4 | D | C | — |
| Compound 2-5 | A | A | — |
| Compound 2-6 | C | C | — |
| Compound 2-7 | C | C | — |
| Compound 2-8 | C | C | — |
| Compound 2-10 | D | — | — |
| Compound 2-11 | A | — | — |
| Compound 2-12 | D | — | — |
| Compound 2-13 | C | — | — |
| Compound 2-14 | C | — | — |
| Compound 2-15 | C | — | — |
| Compound 2-16 | C | — | — |
| Compound 2-17 | B | — | — |
| Ramatroban | B | C | B |

A = less than 0.3 μM
B = greater than 0.3 μM and less than 1 μM
C = greater than 1 μM and less than 30 μM
D = greater than 30 μM Example 233

Clinical Trials in Humans

Study 1: Clinical Trial Evaluating Effect of Compound of Formula (I) on ex vivo PGD2-Induced Blood Eosinophil Shape Change In this double-blind, randomized, placebo-controlled, single ascending dose study of Compound of Formula (I) in healthy volunteers the inhibition of ex vivo PGD2-induced blood eosinophil shape change is determined to show proof of biochemical mechanism of DP2 receptor antagonism. Eight subjects (6 active, 2 placebo) per dose level are used. Pre dose blood is drawn and challenged with PGD2 to determine baseline shape change as described above in Example 230. At varying times after dosing blood is drawn for both pharmacokinetic analyses of drug concentration in blood, and also for PGD2 challenge and eosinophil shape change determination. The extent of receptor blockage is determined from the relationship between drug blood concentration and percentage inhibition of eosinophil shape change.

Study 2: Clinical Trial Evaluating Effect of Compound of Formula (I) on Allergen-Induced Nasal Symptoms and Inflammatory and Allergic Biomarkers In this double-blind, randomized, placebo-controlled study of Compound of Formula (I) in individuals with allergic rhinitis the inhibition of nasal symptoms and allergic biomarkers is determined following nasal challenge with appropriate allergen. Fifteen subjects (10 active, 5 placebo) are used. Subjects are dosed for 7 days with either placebo or an amount of compound of formula (I) that results in complete DP2 receptor block in an ex vivo PGD2-induced blood eosinophil shape change pharmacodynamic study as described above. On day 7 subjects undergo nasal allergen challenge (2 hours post-dose) and early allergic response (0.25-1.0 hr) and late allergic response (4-24 hr) are evaluated as an increase from baseline for treated vs placebo. In addition changes in inflammatory cell differentials, TH2 cytokines and other inflammatory markers are determined as increase from baseline for treated vs placebo.

Compound of Formula (I) Assay

The plasma concentrations of compound of Formula (I) are determined by gas chromatography, giving a detection limit of 1 ng·ml-1 (Ritter W. Determination of BAY u 3405, a novel thromboxane antagonist, in plasma and urine by HPLC and GC. In: Reid E, Wilson I D, eds. Bioanalytical Approaches for Drugs, Including Anti-asthmatics and Metabolites. Methodological Surveys in Biochemistry and Analysis, 1992; 22: 211-216).

Example 234a

Parenteral Composition

To prepare a parenteral pharmaceutical composition suitable for administration by injection, 100 mg of a water-soluble salt of a compound of Formula (I) is dissolved in DMSO and then mixed with 10 mL of 0.9% sterile saline. The mixture is incorporated into a dosage unit form suitable for administration by injection.

Example 234b

Oral Composition

To prepare a pharmaceutical composition for oral delivery, 100 mg of a compound of Formula (I) is mixed with 750 mg of starch. The mixture is incorporated into an oral dosage unit for, such as a hard gelatin capsule, which is suitable for oral administration, Example 234c Sublingual (Hard Lozenge) Composition To prepare a pharmaceutical composition for buccal delivery, such as a hard lozenge, mix 100 mg of a compound of Formula (I) with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 234d

Fast-Disintegrating Sublingual Tablet

A fast-disintegrating sublingual tablet is prepared by mixing 48.5% by weigh of a compound of Formula (I), 44.5% by weight of microcrystalline cellulose (KG-802), 5% by weight of low-substituted hydroxypropyl cellulose (50 µm), and 2% by weight of magnesium stearate. Tablets are prepared by direct compression (*AAPS Pharm Sci Tech*. 2006; 7(2):E41). The total weight of the compressed tablets is maintained at 150 mg. The formulation is prepared by mixing the amount of compound of Formula (I) with the total quantity of microcrystalline cellulose (MCC) and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Example 234e

Inhalation Composition

To prepare a pharmaceutical composition for inhalation delivery, 20 mg of a compound of Formula (I) is mixed with 50 mg of anhydrous citric acid and 100 mL of 0.9% sodium chloride solution. The mixture is incorporated into an inhalation delivery unit, such as a nebulizer, which is suitable for inhalation administration.

Example 234f

Rectal Gel Composition

To prepare a pharmaceutical composition for rectal delivery, 100 mg of a compound of Formula (I) is mixed with 2.5 g of methylcellulose (1500 mPa), 100 mg of methylparapen, 5 g of glycerin and 100 mL of purified water. The resulting gel mixture is then incorporated into rectal delivery units, such as syringes, which are suitable for rectal administration.

Example 234g

Topical Gel Composition

To prepare a pharmaceutical topical gel composition, 100 mg of a compound of Formula (I) is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example 234h

Ophthalmic Solution Composition

To prepare a pharmaceutical opthalmic solution composition, 100 mg of a compound of Formula (I) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 234i

Nasal Spray Solution

To prepare a pharmaceutical nasal spray solution, 10 g of a compound of Formula (I) is mixed with 30 mL of a 0.05M phosphate buffer solution (pH 4.4). The solution is placed in a nasal administrator designed to deliver 100 µl of spray for each application.

The examples and embodiments described herein are for illustrative purposes only and various modifications or changes suggested to persons skilled in the art are to be included within the spirit and purview of this application and scope of the appended claims.

What is claimed is:

1. A method for treating chronic obstructive pulmonary disease (COPD) in a mammal comprising administering to the mammal a therapeutically effective amount of a compound having the structure of Formula (I), or a pharmaceutically acceptable salt thereof:

Formula (I)

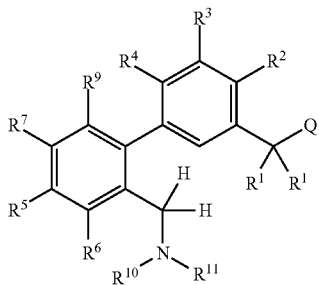

wherein,
Q is tetrazolyl or —C(=O)-Q$^1$;
Q$^1$ is —OH, —O(C$_1$-C$_4$alkyl), —NHSO$_2$R$^{12}$, —N(R$^{13}$)$_2$, —NH—OH, or —NH—CN;
each R$^1$ is independently selected from H, F, and —CH$_3$;
each of R$^2$, R$^3$, R$^4$, R$^5$, R$^6$, R$^7$ and R$^9$ is independently H, halogen, —CN, —NO$_2$, —OH, —OR$^{13}$, —SR$^{12}$, —S(=O)R$^{12}$, —S(=O)$_2$R$^{12}$, —NHS(=O)$_2$R$^{12}$, —C(=O)R$^{12}$, —OC(=O)R$^{12}$, —CO$_2$R$^{13}$, —OCO$_2$R$^{13}$, —CH(R$^{13}$)$_2$, —N(R$^{13}$)$_2$, —NHCH$_2$CO$_2$R$^{13}$, —OCH$_2$CO$_2$R$^{13}$, —SCH$_2$CO$_2$R$^{13}$, —C(=O)N(R$^{13}$)$_2$, —OC(=O)N(R$^{13}$)$_2$, —NHC(=O)NH(R$^{13}$), —NHC(=O)R$^{12}$, —NHC(=O)OR$^{12}$, —C(OH)(R$^{13}$)$_2$, C$_1$-C$_6$alkyl, C$_1$-C$_6$-fluoroalkyl, C$_1$-C$_6$-fluoroalkoxy, C$_1$-C$_6$alkoxy, C$_1$-C$_6$heteroalkyl, C$_3$-C$_{10}$cycloalkyl, a substituted or unsubstituted C$_2$-C$_{10}$heterocycloalkyl, a substituted or unsubstituted phenyl, a substituted or unsubstituted naphthyl, a substituted or unsubstituted monocyclic heteroaryl, a substituted or unsubstituted bicyclic heteroaryl, —OCH$_2$—(C$_3$-C$_6$cycloalkyl), —OCH$_2$-(substituted or unsubstituted phenyl), or —OCH$_2$-(substituted or unsubstituted monocyclic heteroaryl);
R$^{10}$ is —C(=O)R$^{14}$, —C(=O)OR$^{15}$, —C(=O)N(R$^{16}$)$_2$, —C(=NR$^{19}$)N(R$^{16}$)$_2$, —S(=O)$_2$N(R$^{16}$)$_2$ or —S(=O)$_2$R$^{15}$;
R$^{14}$ is C$_1$-C$_6$alkyl, C$_1$-C$_6$-fluoroalkyl, C$_1$-C$_6$heteroalkyl, C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_4$alkyl-(C$_3$-C$_{10}$cycloalkyl), —C$_1$-C$_4$alkyl-(a substituted or unsubstituted C$_2$-C$_{10}$heterocycloalkyl), —C$_1$-C$_4$alkyl-(a substituted or unsubstituted aryl), or —C$_1$-C$_4$alkyl-(a substituted or unsubstituted heteroaryl); or
R$^{14}$ is L$^3$-X$^3$-Q$^3$;
L$^3$ is a C$_1$-C$_4$alkylene;
X$^3$ is a bond, —O—, —S—, —S(=O)—, —S(=O)$_2$—, or —NR$^{13}$—;
Q$^3$ is C$_1$-C$_6$alkyl, C$_1$-C$_6$-fluoroalkyl, C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_4$alkyl-C$_3$-C$_{10}$cycloalkyl, —C$_1$-C$_4$alkyl-(a substituted or unsubstituted C$_2$-C$_{10}$heterocycloalkyl), —C$_1$-C$_4$alkyl-(a substituted or unsubstituted aryl), or —C$_1$-C$_4$alkyl-(a substituted or unsubstituted heteroaryl);
R$^{15}$ is C$_1$-C$_6$alkyl, C$_1$-C$_6$-fluoroalkyl, C$_1$-C$_6$heteroalkyl, C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_4$alkyl-C$_3$-C$_{10}$cycloalkyl, —C$_1$-C$_4$alkyl-(substituted or unsubstituted C$_2$-C$_{10}$heterocycloalkyl), —C$_1$-C$_4$alkyl-(substituted or unsubstituted aryl), or —C$_1$-C$_4$alkyl-(substituted or unsubstituted heteroaryl);
each R$^{16}$ is independently H, —CN, C$_1$-C$_6$alkyl, C$_1$-C$_6$-fluoroalkyl, C$_1$-C$_6$heteroalkyl, C$_3$-C$_{10}$cycloalkyl, substituted or unsubstituted C$_2$-C$_{10}$heterocycloalkyl, substituted or unsubstituted aryl, substituted or unsubstituted heteroaryl, —C$_1$-C$_4$alkyl-C$_3$-C$_{10}$cycloalkyl, —C$_1$-C$_4$alkyl-(substituted or unsubstituted C$_2$-C$_{10}$heterocycloalkyl), —C$_1$-C$_4$alkyl-(substituted or unsubstituted aryl), or —C$_1$-C$_4$alkyl-(substituted or unsubstituted heteroaryl); or
two R$^{16}$ groups attached to the same N atom are taken together with the N atom to which they are attached to form a substituted or unsubstituted heterocycloalkyl;
R$^{19}$ is selected from among H, —S(=O)$_2$R$^{12}$, —S(=O)$_2$NH$_2$, —C(=O)R$^{12}$, —CN, and —NO$_2$;
R$^{11}$ is C$_1$-C$_6$alkyl, C$_1$-C$_6$heteroalkyl, C$_1$-C$_6$haloalkyl, C$_3$-C$_6$cycloalkyl, —C$_1$-C$_6$alkylene-OH, —C$_1$-C$_6$alkylene-O—(C$_1$-C$_4$alkyl), —C$_1$-C$_6$alkylene-S—(C$_1$-C$_4$alkyl), —C$_1$-C$_6$alkylene-S(=O)—(C$_1$-C$_4$alkyl), —C$_1$-C$_6$alkylene-S(=O)$_2$—(C$_1$-C$_4$alkyl), —C$_1$-C$_6$alkylene-NH$_2$, —C$_1$-C$_6$alkylene-N(CH$_3$)$_2$, —C$_1$-C$_6$alkylene-C(=O)—(C$_1$-C$_4$alkyl), —C$_1$-C$_6$alkylene-C(=O)OH, —C$_1$-C$_6$alkylene-C(=O)O(C$_1$-C$_4$alkyl), or —C$_1$-C$_6$alkylene-C(=O)NH$_2$;
R$^{12}$ is C$_1$-C$_6$alkyl, C$_1$-C$_6$heteroalkyl, C$_1$-C$_6$-fluoroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted benzyl, a substituted or unsubstituted heteroaryl, —C$_1$-C$_4$alkyl-(substituted or unsubstituted C$_3$-C$_{10}$cycloalkyl), —C$_1$-C$_4$alkyl-(substituted or unsubstituted C$_2$-C$_{10}$heterocycloalkyl), —C$_1$-C$_4$alkyl-(substituted or unsubstituted aryl), or —C$_1$-C$_4$alkyl-(substituted or unsubstituted heteroaryl);
each R$^{13}$ is independently selected from H, C$_1$-C$_6$alkyl, C$_1$-C$_6$heteroalkyl, C$_1$-C$_6$-fluoroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted benzyl, a substituted or unsubstituted heteroaryl, —C$_1$-C$_4$alkyl-(substituted or unsubstituted C$_3$-C$_{10}$cycloalkyl), —C$_1$-C$_4$alkyl-(substituted or unsubstituted C$_2$-C$_{10}$heterocycloalkyl), —C$_1$-C$_4$alkyl-(substituted or unsubstituted aryl), and —C$_1$-C$_4$alkyl-(substituted or unsubstituted heteroaryl); or
two R$^{13}$ groups attached to the same N atom are taken together with the N atom to which they are attached to form an optionally substituted C$_2$-C$_{10}$heterocycloalkyl.

2. The method of claim 1, wherein:
Q is —C(=O)-Q';
Q$^1$ is —OH, or —O(C$_1$-C$_4$alkyl);
at least one of R$^2$ and R$^3$ is H;
at least two of R$^6$, R$^7$ and R$^9$ is H; and
R$^{11}$ is C$_1$-C$_6$alkyl, C$_1$-C$_6$heteroalkyl, C$_1$-C$_6$haloalkyl, C$_3$-C$_6$cycloalkyl, —C$_1$-C$_6$alkylene-C(=O)OH, —C$_1$-C$_6$alkylene-C(=O)O(C$_1$-C$_4$alkyl), or —C$_1$-C$_6$alkylene-C(=O)NH$_2$.

3. The method of claim 2, wherein:
each R$^1$ is H;
each of R$^2$ and R$^3$ is independently selected from H, halogen, —OH, C$_1$-C$_4$alkyl, C$_1$-C$_4$alkoxy, and C$_1$-C$_4$-fluoroalkyl;
R$^4$ is H, F, Cl, Br, I, —CN, —OH, —C$_1$-C$_6$alkyl, C$_1$-C$_6$-fluoroalkyl, C$_1$-C$_6$-fluoroalkoxy, C$_1$-C$_6$alkoxy, C$_1$-C$_6$heteroalkyl, —OCH$_2$—CO$_2$R$^{13}$, —OCH$_2$—C$_3$-C$_6$cycloalkyl, or —OCH$_2$-(substituted or unsubstituted phenyl);
R$^5$ is H, halogen, —CN, —NO$_2$, —OH, —OR$^{13}$, —SR$^{12}$, —S(=O)R$^{12}$, —S(=O)$_2$R$^{12}$, —NHS(=O)$_2$R$^{12}$, —C(=O)R$^{12}$, —OC(=O)R$^{12}$, —CO$_2$R$^{13}$, OCO$_2$R$^{13}$, —CH(R$^{13}$)$_2$, —N(R$^{13}$)$_2$, —NHCH$_2$CO$_2$R$^{13}$, —OCH$_2$CO$_2$R$^{13}$, —SCH$_2$CO$_2$R$^{13}$, —C(=O)N(R$^{13}$)$_2$, —OC(=O)N(R$^{13}$)$_2$, —NHC(=O)NH(R$^{13}$), —NHC(=O)R$^{12}$, —NHC(=O)OR$^{12}$, —C(OH)(R$^{13}$)$_2$, —C$_1$-C$_6$alkyl, C$_1$-C$_6$-fluoroalkyl, C$_3$-C$_{10}$cycloalkyl, substituted or unsubstituted C$_2$-C$_{10}$heterocycloalkyl, C$_1$-C$_6$-fluoroalkoxy, C$_1$-C$_6$alkoxy, C$_1$-C$_6$heteroalkyl, substituted or unsubstituted phenyl, substituted or unsubstituted naphthyl, substituted or unsubstituted monocyclic heteroaryl, substituted or unsubstituted bicyclic heteroaryl;

each of R$^6$, R$^7$ and R$^9$ are H;

R$^{10}$ is —C(=O)R$^{14}$, —C(=O)OR$^{15}$, or —C(=O)N(R$^{16}$)$_2$;

R$^{14}$ is C$_1$-C$_6$alkyl, C$_1$-C$_6$-fluoroalkyl, C$_1$-C$_6$heteroalkyl, or C$_3$-C$_6$cycloalkyl; or R$^{14}$ is L$^3$-X$^3$-Q$^3$;
  L$^3$ is —CH$_2$—, —CH(CH$_3$)—, or —C(CH$_3$)$_2$—;
  X$^3$ is a —O—, —S—, —S(=O)—, —S(=O)$_2$—, or —NR$^{13}$—;
  Q$^3$ is C$_1$-C$_6$alkyl, C$_1$-C$_6$-fluoroalkyl, C$_3$-C$_6$cycloalkyl, a substituted or unsubstituted phenyl, a substituted or unsubstituted monocyclic heteroaryl, —CH$_2$-(a substituted or unsubstituted phenyl), or —CH$_2$-(a substituted or unsubstituted monocyclic heteroaryl);

R$^{15}$ is C$_1$-C$_6$alkyl, C$_1$-C$_6$-fluoroalkyl, C$_1$-C$_6$heteroalkyl, C$_3$-C$_6$cycloalkyl, a substituted or unsubstituted phenyl, a substituted or unsubstituted monocyclic heteroaryl, —CH$_2$—C$_3$-C$_6$cycloalkyl, —CH$_2$-(substituted or unsubstituted phenyl), —CH(CH$_3$)-(substituted or unsubstituted phenyl), —CH$_2$-(substituted or unsubstituted monocyclic heteroaryl) or —CH(CH$_3$)-(substituted or unsubstituted monocyclic heteroaryl); and each R$^{16}$ is independently H, C$_1$-C$_6$alkyl, C$_1$-C$_6$-fluoroalkyl, C$_1$-C$_6$heteroalkyl, C$_3$-C$_6$cycloalkyl, a substituted or unsubstituted phenyl, a substituted or unsubstituted monocyclic heteroaryl, —CH$_2$—(C$_3$-C$_6$cycloalkyl), —CH$_2$-(a substituted or unsubstituted phenyl), —CH(CH$_3$)-(a substituted or unsubstituted phenyl), —CH$_2$-(a substituted or unsubstituted monocyclic heteroaryl), or —CH(CH$_3$)-(a substituted or unsubstituted monocyclic heteroaryl).

4. The method of claim 3, wherein the compound has the structure of Formula (III), or a pharmaceutically acceptable salt thereof:

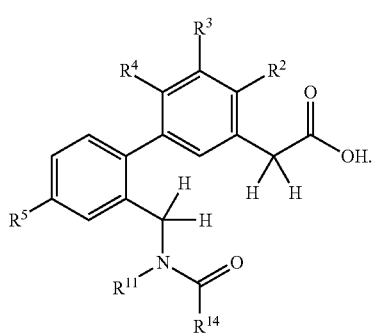

Formula (III)

5. The method of claim 4, wherein
R$^2$ and R$^3$ are H;
R$^4$ is H, F, Cl, Br, —OH, —CH$_3$, —OCH$_3$, —CF$_3$, or —OCF$_3$;

R$^5$ is a substituted or unsubstituted group selected from pyrrolyl, oxazolyl, thiazolyl, imidazolyl, pyrazolyl, isoxazolyl, isothiazolyl, pyridinyl, pyridazinyl, pyrazinyl, pyrimidinyl, quinolinyl, and isoquinolinyl;

R$^{11}$ is —CH$_3$, —CH$_2$CH$_3$, or —CH$_2$CF$_3$; and

R$^{14}$ is C$_1$-C$_6$alkyl, C$_1$-C$_6$-fluoroalkyl, or C$_3$-C$_6$cycloalkyl.

6. The method of claim 3, wherein the compound has the structure of Formula (IV), or a pharmaceutically acceptable salt thereof:

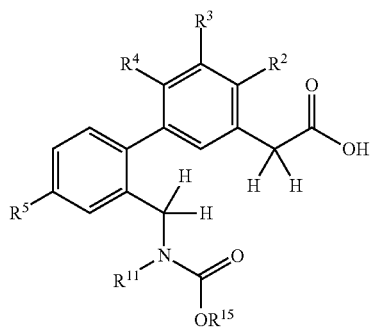

Formula (IV)

wherein:
R$^{15}$ is C$_1$-C$_6$alkyl, —CH$_2$-(substituted or unsubstituted phenyl), —CH(CH$_3$)-(substituted or unsubstituted phenyl), —CH$_2$-(substituted or unsubstituted monocyclic heteroaryl) or —CH(CH$_3$)-(substituted or unsubstituted monocyclic heteroaryl); and R$^{11}$ is C$_1$-C$_6$alkyl, C$_1$-C$_6$haloalkyl, or C$_3$-C$_6$cycloalkyl.

7. The method of claim 3, wherein the compound has the structure of Formula (V), or a pharmaceutically acceptable salt thereof:

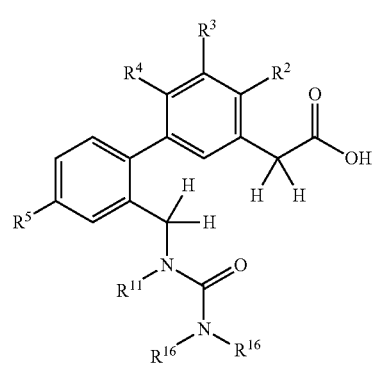

Formula (V)

wherein:
one R$^{16}$ is H and the other R$^{16}$ is —CH$_2$-(a substituted or unsubstituted phenyl), —CH(CH$_3$)-(a substituted or unsubstituted phenyl), —CH$_2$-(a substituted or unsubstituted monocyclic heteroaryl), or —CH(CH$_3$)-(a substituted or unsubstituted monocyclic heteroaryl); and R$^{11}$ is C$_1$-C$_6$alkyl, C$_1$-C$_6$haloalkyl, or C$_3$-C$_6$cycloalkyl.

8. The method of claim 7, wherein:
R$^2$ and R$^3$ are H;
R$^4$ is H, F, Cl, Br, —OH, —CH$_3$, —OCH$_3$, —CF$_3$, or —OCF$_3$;
R$^5$ is F, Cl, Br, —OH, —CH$_3$, —CF$_3$, —OCH$_3$, or —OCF$_3$;
R$^{11}$ is —CH$_3$, —CH$_2$CH$_3$, or —CH$_2$CF$_3$; and one R$^{16}$ is H and the other R$^{16}$ is —CH$_2$-(a substituted or unsubstituted phenyl).

9. A method for treating chronic obstructive pulmonary disease (COPD) in a mammal comprising administering to the mammal a therapeutically effective amount of a compound that is:

{2'-[(Acetyl-methyl-amino)-methyl]-6-methoxy-4'-trifluoromethyl-biphenyl-3-yl}-acetic acid; {2'-[(Acetyl-ethyl-amino)-methyl]-6-methoxy-4'-trifluoromethyl-biphenyl-3-yl}-acetic acid; (2'-{[Acetyl-(2,2-dimethyl-propyl)-amino]-methyl}-6-methoxy-4'-trifluoromethyl-biphenyl-3-yl)-acetic acid; (2'-{[Acetyl-(2,2,2-trifluoro-ethyl)-amino]-methyl}-6-methoxy-4'-trifluoromethyl-biphenyl-3-yl)-acetic acid; (2'-{[Acetyl-(2-hydroxy-ethyl)-amino]-methyl}-6-methoxy-4'-trifluoromethyl-biphenyl-3-yl)-acetic acid; (2'-{[Acetyl-(2-methoxy-ethyl)-amino]-methyl}-6-methoxy-4'-trifluoromethyl-biphenyl-3-yl)-acetic acid; (2'-{[Acetyl-(2-dimethylamino-ethyl)-amino]-methyl}-6-methoxy-4'-trifluoromethyl-biphenyl-3-yl)-acetic acid; {2'-[(Acetyl-carboxymethyl-amino)-methyl]-6-methoxy-4'-trifluoromethyl-biphenyl-3-yl}-acetic acid; {2'-[(Acetyl-carbamoylmethyl-amino)-methyl]-6-methoxy-4'-trifluoromethyl-biphenyl-3-yl}-acetic acid; {2'-[(Acetyl-ethyl-amino)-methyl]-6-fluoro-4'-trifluoromethyl-biphenyl-3-yl}-acetic acid; (2'-{[Acetyl-(2,2,2-trifluoro-ethyl)-amino]-methyl}-6-fluoro-4'-trifluoromethyl-biphenyl-3-yl)-acetic acid; {2'-[(Acetyl-cyclopropyl-amino)-methyl]-6-methoxy-4'-trifluoromethyl-biphenyl-3-yl}-acetic acid; {2'-[((S)-Acetyl-indan-1-yl-amino)-methyl]-6-methoxy-4'-trifluoromethyl-biphenyl-3-yl}-acetic acid; {2'-[((R)-Acetyl-indan-1-yl-amino)-methyl]-6-methoxy-4'-trifluoromethyl-biphenyl-3-yl}-acetic acid; (2'-{[Acetyl-((1R,2S)-2-hydroxy-indan-1-yl)-amino]-methyl}-6-methoxy-4'-trifluoromethyl-biphenyl-3-yl)-acetic acid; (2'-{[Acetyl-((1R,2S)-2-methoxy-indan-1-yl)-amino]-methyl}-6-methoxy-4'-trifluoromethyl-biphenyl-3-yl)-acetic acid; {2'-[(Acetyl-indan-2-yl-amino)-methyl]-6-methoxy-4'-trifluoromethyl-biphenyl-3-yl}-acetic acid; {2'-[(Acetyl-phenyl-amino)-methyl]-6-methoxy-4'-trifluoromethyl-biphenyl-3-yl}-acetic acid; {2'-[(Acetyl-benzyl-amino)-methyl]-6-methoxy-4'-trifluoromethyl-biphenyl-3-yl}-acetic acid; {2'-[(Acetyl-phenethyl-amino)-methyl]-6-methoxy-4'-trifluoromethyl-biphenyl-3-yl}-acetic acid; 2-{2'-[(Acetyl-ethyl-amino)-methyl]-6-methoxy-4'-trifluoromethyl-biphenyl-3-yl}-propionic acid; {2'-[1-(Acetyl-ethyl-amino)-ethyl]-6-methoxy-4'-trifluoromethyl-biphenyl-3-yl}-acetic acid; {2'-[(Ethyl-methoxycarbonyl-amino)-methyl]-6-methoxy-4'-trifluoromethyl-biphenyl-3-yl}-acetic acid; {2'-[(Benzyl-methoxycarbonyl-amino)-methyl]-6-methoxy-4'-trifluoromethyl-biphenyl-3-yl}-acetic acid; {6-Methoxy-2'-[(methoxycarbonyl-phenethyl-amino)-methyl]-4'-trifluoromethyl-biphenyl-3-yl}-acetic acid; {2'-[(Indan-2-yl-methoxycarbonyl-amino)-methyl]-6-methoxy-4'-trifluoromethyl-biphenyl-3-yl}-acetic acid; {2'-[(Benzyloxycarbonyl-methyl-amino)-methyl]-6-methoxy-4'-trifluoromethyl-biphenyl-3-yl}-acetic acid; {2'-[(Benzyloxycarbonyl-ethyl-amino)-methyl]-6-methoxy-4'-trifluoromethyl-biphenyl-3-yl}-acetic acid; {2'-[(Benzyloxycarbonyl-ethyl-amino)-methyl]-6-fluoro-4'-trifluoromethyl-biphenyl-3-yl}-acetic acid; {2'-[(Acetyl-cyclobutyl-amino)-methyl]-6-methoxy-4'-trifluoromethyl-biphenyl-3-yl}-acetic acid; {2'-[(Acetyl-cyclopentyl-amino)-methyl]-6-methoxy-4'-trifluoromethyl-biphenyl-3-yl}-acetic acid; (2'-{[Ethyl-(2,2,2-trifluoro-acetyl)-amino]-methyl}-6-methoxy-4'-trifluoromethyl-biphenyl-3-yl)-acetic acid; {2'-[(Cyclopropanecarbonyl-ethyl-amino)-methyl]-6-methoxy-4'-trifluoromethyl-biphenyl-3-yl]-acetic acid; {2'-[(Benzyloxycarbonyl-cyclobutyl-amino)-methyl]-6-methoxy-4'-trifluoromethyl-biphenyl-3-yl}-acetic acid; {2'-[(Benzyloxycarbonyl-cyclopentyl-amino)-methyl]-6-methoxy-4'-trifluoromethyl-biphenyl-3-yl}-acetic acid; {2'-[(Benzyloxycarbonyl-cyclopropyl-amino)-methyl]-6-methoxy-4'-trifluoromethyl-biphenyl-3-yl}-acetic acid; 2-{[Acetyl-(2,2,2-trifluoro-ethyl)-amino]-methyl}-5'-carboxymethyl-2'-methoxy-biphenyl-4-carboxylic acid; (2'-{[(3,5-Dichloro-benzyloxycarbonyl)-ethyl-amino]-methyl}-6-methoxy-4'-trifluoromethyl-biphenyl-3-yl)-acetic acid; (2'-{[(2-Chloro-benzyloxycarbonyl)-ethyl-amino]-methyl}-6-methoxy-4'-trifluoromethyl-biphenyl-3-yl)-acetic acid; (2'-{[(3,5-Difluoro-benzyloxycarbonyl)-ethyl-amino]-methyl}-6-methoxy-4'-trifluoromethyl-biphenyl-3-yl)-acetic acid; (2'-{[Ethyl-(4-fluoro-benzyloxycarbonyl)-amino]-methyl}-6-methoxy-4'-trifluoromethyl-biphenyl-3-yl)-acetic acid; (2'-{[(4-Chloro-benzyloxycarbonyl)-ethyl-amino}-methyl]-6-methoxy-4'-trifluoromethyl-biphenyl-3-yl)-acetic acid; (2'-{[(3-Chloro-benzyloxycarbonyl)-ethyl-amino]-methyl}-6-methoxy-4'-trifluoromethyl-biphenyl-3-yl)-acetic acid; [2'-({[1-(4-Chloro-phenyl)-ethoxycarbonyl]-ethyl-amino}-methyl)-6-methoxy-4'-trifluoromethyl-biphenyl-3-yl]-acetic acid; (2'-{[Ethyl-(2-phenoxy-propionyl)-amino]-methyl}-6-methoxy-4'-trifluoromethyl-biphenyl-3-yl)-acetic acid; (2'-{[Ethyl-(2-methoxy-acetyl)-amino]-methyl}-6-methoxy-4'-trifluoromethyl-biphenyl-3-yl)-acetic acid; {2'-[3-(2-Bromo-phenyl)-1-ethyl-ureidomethyl]-6-methoxy-4'-trifluoromethyl-biphenyl-3-yl}-acetic acid; (2'-{[Ethyl-(2-phenoxy-acetyl)-amino]-methyl}-6-methoxy-4'-trifluoromethyl-biphenyl-3-yl)-acetic acid; (2'-{[Benzyloxycarbonyl-(2,2,2-trifluoro-ethyl)-amino]-methyl}-6-fluoro-4'-trifluoromethyl-biphenyl-3-yl)-acetic acid; {2'-[(Acetyl-ethyl-amino)-methyl]-4'-bromo-6-methoxy-biphenyl-3-yl}-acetic acid; {4'-Acetylamino-2'-[(acetyl-ethyl-amino)-methyl]-6-methoxy-biphenyl-3-yl}-acetic acid; {2'-[(Acetyl-ethyl-amino)-methyl]-6-methoxy-4'-pyrazol-1-yl-biphenyl-3-yl}-acetic acid; {2'-[(Acetyl-o-tolyl-amino)-methyl]-6-methoxy-4'-trifluoromethyl-biphenyl-3-yl}-acetic acid; {2'-[(Acetyl-thiazol-2-yl-amino)-methyl]-6-methoxy-4'-trifluoromethyl-biphenyl-3-yl}-acetic acid; (2'-{[Acetyl-(2-methyl-pyrimidin-4-yl)-amino]-methyl}-6-methoxy-4'-trifluoromethyl-biphenyl-3-yl)-acetic acid; {2'-[(Acetyl-ethyl-amino)-methyl]-6-methyl-4'-trifluoromethyl-biphenyl-3-yl}-acetic acid; {2'-[(Acetyl-ethyl-amino)-methyl]-4-methoxy-4'-trifluoromethyl-biphenyl-3-yl}-acetic acid; {2'-[(Acetyl-methyl-amino)-methyl]-6-fluoro-4'-trifluoromethyl-biphenyl-3-yl}-acetic acid; {2'-[(Acetyl-methyl-amino)-methyl]-6-methyl-4'-trifluoromethyl-biphenyl-3-yl}-acetic acid; {2'-[(Acetyl-ethyl-amino)-methyl]-6-cyclopropyl-4'-trifluoromethyl-biphenyl-3-yl}-acetic acid; {2'-[(Acetyl-ethyl-amino)-methyl]-6,4'-bis-trifluoromethyl-biphenyl-3-yl}-acetic acid; {2'-[(Acetyl-ethyl-amino)-methyl]-4-methyl-4'-trifluoromethyl-biphenyl-3-yl}-acetic acid; {2'-

[(Acetyl-methyl-amino)-methyl]-4'-bromo-6-methoxy-biphenyl-3-yl}-acetic acid; {4'-Acetylamino-2'-[(acetyl-methyl-amino)-methyl]-6-methoxy-biphenyl-3-yl}-acetic acid; {2'-[(Acetyl-ethyl-amino)-methyl]-6-methoxy-4'-methoxycarbonylamino-biphenyl-3-yl}-acetic acid; {2'-[(Acetyl-ethyl-amino)-methyl]-4'-methanesulfonylamino-6-methoxy-biphenyl-3-yl}-acetic acid; {2'-[(Acetyl-ethyl-amino)-methyl]-4'-methanesulfonyl-6-methoxy-biphenyl-3-yl}-acetic acid; {2'-[(Acetyl-ethyl-amino)-methyl]-6-methoxy-4'-pyrrolidin-1-yl-biphenyl-3-yl}-acetic acid; {2'-[(Acetyl-methyl-amino)-methyl]-6-methoxy-4'-pyrazol-1-yl-biphenyl-3-yl}-acetic acid; {2'-[(Acetyl-ethyl-amino)-methyl]-4'-cyclopropyl-6-methoxy-biphenyl-3-yl}-acetic acid; {2'-[(Acetyl-ethyl-amino)-methyl]-6-methoxy-[1,1';4',1'']terphenyl-3-yl}-acetic acid; {2'-[(Acetyl-ethyl-amino)-methyl]-6-methoxy-4'-oxazol-2-yl-biphenyl-3-yl}-acetic acid; [2'-[(Acetyl-ethyl-amino)-methyl]-6-methoxy-4'-(1H-pyrazol-4-yl)-biphenyl-3-yl]-acetic acid; {2'-[(Acetyl-ethyl-amino)-methyl]-6-methoxy-4'-pyridin-2-yl-biphenyl-3-yl}-acetic acid; {2'-[(Cyclopropoxycarbonyl-ethyl-amino)-methyl]-6-methoxy-4'-trifluoromethyl-biphenyl-3-yl}-acetic acid; [2'-(1-Ethyl-3-methyl-ureidomethyl)-6-methoxy-4'-trifluoromethyl-biphenyl-3-yl]-acetic acid; {2'-[(Cyclopropanecarbonyl-methyl-amino)-methyl]-6-methoxy-4'-trifluoromethyl-biphenyl-3-yl}-acetic acid; {2'-[(Cyclopentanecarbonyl-ethyl-amino)-methyl]-6-methoxy-4'-trifluoromethyl-biphenyl-3-yl}-acetic acid; {2'-[(Acetyl-ethyl-amino)-methyl]-6-chloro-4'-trifluoromethyl-biphenyl-3-yl}-acetic acid; {2'-[(Benzoyl-ethyl-amino)-methyl]-6-methoxy-4'-trifluoromethyl-biphenyl-3-yl}-acetic acid; (2'-{[Ethyl-(pyridine-2-carbonyl)-amino]-methyl}-6-methoxy-4'-trifluoromethyl-biphenyl-3-yl)-acetic acid; (2'-{[Ethyl-(pyrazine-2-carbonyl)-amino]-methyl}-6-methoxy-4'-trifluoromethyl-biphenyl-3-yl)-acetic acid; (2'-{[Ethyl-(1-methyl-1H-pyrazole-3-carbonyl)-amino]-methyl}-6-methoxy-4'-trifluoromethyl-biphenyl-3-yl)-acetic acid; {2'-[(Acetyl-ethyl-amino)-methyl]-5'-bromo-6-methoxy-biphenyl-3-yl}-acetic acid; {5'-Acetylamino-2'-[(acetyl-ethyl-amino)-methyl]-6-methoxy-biphenyl-3-yl}-acetic acid; {2'-[(Acetyl-ethyl-amino)-methyl]-6-methoxy-5'-methoxycarbonylamino-biphenyl-3-yl}-acetic acid; {2'-[(Acetyl-ethyl-amino)-methyl]-5'-methanesulfonylamino-6-methoxy-biphenyl-3-yl}-acetic acid; {2'-[(Acetyl-ethyl-amino)-methyl]-6-methoxy-5'-pyrrolidin-1-yl-biphenyl-3-yl}-acetic acid; {2'-[(Acetyl-ethyl-amino)-methyl]-6-methoxy-5'-pyrazol-1-yl-biphenyl-3-yl}-acetic acid; {2'-[(Acetyl-ethyl-amino)-methyl]-3'-methanesulfonyl-6-methoxy-biphenyl-3-yl}-acetic acid; {2'-[(Acetyl-ethyl-amino)-methyl]-6-methoxy-4'-trifluoromethyl-biphenyl-3-yl}-difluoro-acetic acid; (2'-{[(2-Benzyloxy-acetyl)-ethyl-amino]-methyl}-6-methoxy-4'-trifluoromethyl-biphenyl-3-yl)-acetic acid; [2'-({2-(4-Chloro-phenoxy)-acetyl]-ethyl-amino}-methyl)-6-methoxy-4'-trifluoromethyl-biphenyl-3-yl]-acetic acid; [2'-(3-Benzyl-1,3-diethyl-ureidomethyl)-6methoxy-4'-trifluoromethyl-biphenyl-3-yl]-acetic acid; [2'-(3-Benzyl-1-ethyl-ureidomethyl)-6-methoxy-4'-trifluoromethyl-biphenyl-3-yl]-acetic acid; (2'-{[Ethyl-(pyrrolidine-1-carbonyl)-amino]-methyl}-6-methoxy-4'-trifluoromethyl-biphenyl-3-yl)-acetic acid; 2-{2'-[(Benzyloxycarbonyl-ethyl-amino)-methyl]-6-methoxy-4'-trifluoromethyl-biphenyl-3-yl}-propionic acid; [2'-(3-Cyano-1-ethyl-ureidomethyl)-6-methoxy-4'-trifluoromethyl-biphenyl-3-yl]-acetic acid; (2'-{[(4-Chloro-benzenesulfonyl)-ethyl-amino]-methyl}-6-methoxy-4'-trifluoromethyl-biphenyl-3-yl)-acetic acid; {2'-[(Methanesulfonyl-phenethyl-amino)-methyl]-6-methoxy-4'-trifluoromethyl-biphenyl-3-yl}-acetic acid; (2'-{[Acetyl-((1S,2R)-2-hydroxy-1-methyl-2-phenyl-ethyl)-amino]-methyl}-6-methoxy-4'-trifluoromethyl-biphenyl-3-yl)-acetic acid; {2'-[(Benzyloxycarbonyl-ethyl-amino)-methyl]-4-methoxy-4'-trifluoromethyl-biphenyl-3-yl}-acetic acid; {2'-[(Benzyloxycarbonyl-ethyl-amino)-methyl]-5-chloro-4'-trifluoromethyl-biphenyl-3-yl}-acetic acid; {2'-[(Benzyloxycarbonyl-ethyl-amino)-methyl]-5,4'-bis-trifluoromethyl-biphenyl-3-yl}-acetic acid; {2'-[(Benzyloxycarbonyl-ethyl-amino)-methyl]-6-chloro-4'-trifluoromethyl-biphenyl-3-yl}-acetic acid; [2'-(N'-Benzyl-N''-cyano-N-ethyl-guanidinomethyl)-6-methoxy-4'-trifluoromethyl-biphenyl-3-yl]-acetic acid; [2'-(N'-Cyano-N'''-cyclohexylmethyl-N-ethyl-guanidinomethyl)-6-methoxy-4'-trifluoromethyl-biphenyl-3-yl]-acetic acid; {2'-[N'-Cyano-N''-(2,2-dimethyl-propyl)-N-ethyl-guanidinomethyl]-6-methoxy-4'-trifluoromethyl-biphenyl-3-yl}-acetic acid; {2'[N'-Cyano-N-ethyl-N''-(4-methoxy-benzyl)-guanidinomethyl]-6-methoxy-4'-trifluoromethyl-biphenyl-3-yl}-acetic acid; 2-{2'-[(Acetyl-ethyl-amino)-methyl]-6-methoxy-4'-trifluoromethyl-biphenyl-3-yl}-2-methyl-propionic acid; 2-{2'-[(Benzyloxycarbonyl-ethyl-amino)-methyl]-6-methoxy-4'-trifluoromethyl-biphenyl-3-yl}-2-methyl-propionic acid; (2'-{[Ethyl-(2-phenylsulfanyl-acetyl)-amino]-methyl}-6-methoxy-4'-trifluoromethyl-biphenyl-3-yl)-acetic acid; [2'-({[2-(4-Chloro-phenoxy)-2-methyl-propionyl]-ethyl-amino}-methyl)-6-methoxy-4'-trifluoromethyl-biphenyl-3-yl]-acetic acid; (2'-{[(2-Benzenesulfinyl-acetyl)-ethyl-amino]-methyl}-6-methoxy-4'-trifluoromethyl-biphenyl-3-yl)-acetic acid; (2'-{[(2-Benzenesulfonyl-acetyl)-ethyl-amino]-methyl}-6-methoxy-4'-trifluoromethyl-biphenyl-3-yl)-acetic acid; [2'-(1-Ethyl-3-phenyl-ureidomethyl)-6-methoxy-4'-trifluoromethyl-biphenyl-3-yl]-acetic acid; {2'-[(Benzyloxycarbonyl-ethyl-amino)-methyl]-6'-methoxy-biphenyl-3-yl}-acetic acid; (2'{[(3,5-Difluoro-benzyloxycarbonyl)-ethyl-amino]-methyl}-6'-methoxy-biphenyl-3-yl)-acetic acid; {2'-[(Benzyloxycarbonyl-ethyl-amino)-methyl]-4,4'-bis-trifluoromethyl-biphenyl-3-yl}-acetic acid; {2'-[(Benzyloxycarbonyl-ethyl-amino)-methyl]-4-chloro-4'-trifluoromethyl-biphenyl-3-yl}-acetic acid; {2'-[(Benzyloxycarbonyl-ethyl-amino)-methyl]-5-fluoro-4'-trifluoromethyl-biphenyl-3-yl}-acetic acid; {2'-[(Benzyloxycarbonyl-ethyl-amino)-methyl]-4-fluoro-4'-trifluoromethyl-biphenyl-3-yl}-acetic acid; {6-Benzyloxy-2'-[(benzyloxycarbonyl-ethyl-amino)-methyl]-4'-trifluoromethyl-biphenyl-3-yl}-acetic acid; {2'-[(Benzyloxycarbonyl-ethyl-amino)-methyl]-6-ethoxy-4'-trifluoromethyl-biphenyl-3-yl}-acetic acid; {2'-[(Benzyloxycarbonyl-ethyl-amino)-methyl]-6-cyclopropylmethoxy-4'-trifluoromethyl-biphenyl-3-yl}-acetic acid; [2'-({[1-(2,4-Dichloro-phenyl)-cyclopropanecarbonyl]-ethyl-amino}-methyl)-6-methoxy-4'-trifluoromethyl-biphenyl-3-yl]-acetic acid; {2'-[(Benzyloxycarbonyl-ethyl-amino)-methyl]-6-methoxy-4'-trifluoromethyl-biphenyl-3-yl}-difluoro-acetic acid; {5-Chloro-2'-[(cyclopropanecarbonyl-ethyl-amino)-methyl]-4'-trifluoromethyl-biphenyl-3-yl}-acetic acid; {2'-[((Cyclopropanecarbonyl-ethylamino)-methyl]-5,4'-bis-trifluoromethyl-biphenyl-3-yl}-acetic acid; {2'-[(Acetyl-ethyl-amino)-methyl]-5-chloro-4'-trifluoromethyl-biphenyl-3-yl}-acetic acid; {2'-[(Acetyl-ethyl-amino)-methyl]-5,4'-bis-trifluoromethyl-biphenyl-3-yl}-acetic acid; [2'-(1-Ethyl-3-pyridin-2-ylmethyl-ureidomethyl)-6-methoxy-4'-trifluoromethyl-biphenyl-3-yl]-acetic acid; {2'-[3-(4-Chloro-benzyl)-1-ethyl-ureidomethyl]-6-methoxy-4'-trifluoromethyl-biphenyl-3-yl}-acetic acid; {2'-[(Benzyloxycarbonyl-ethyl-amino)-methyl]-4'-trifluoromethyl-biphenyl-3-yl}-acetic acid; {2''-[(Benzyloxycarbonyl-ethyl-amino)-methyl]-4''-trifluoromethyl-[1,1';2',1]terphenyl-4'-yl]-acetic acid; [2'-(N'-Cyano-N-ethyl-N''-propyl-guanidinomethyl)-6-methoxy-4'-trifluoromethyl-biphenyl-3-yl]-acetic acid; [2'-(N'-Cyano-N''-cyclopropylmethyl-N-ethyl-guanidinomethyl)-6-methoxy-4'-trifluoromethyl-biphenyl-3-yl]-acetic acid; [2'-(N'-Cyano-N-ethyl-N''-pyridin-2-ylmethyl-guanidinomethyl)-6-methoxy-4'-trifluoromethyl-biphenyl-3-yl]-acetic acid; (2'-{[Ethyl-(2-pyrazol-1-yl-acetyl)-amino]-methyl}-6-methoxy-4'-trifluoromethyl-biphenyl-3-yl)-acetic acid; [2'-({Ethyl-[2-(2-methyl-imidazol-1-yl)-acetyl]-amino}-methyl)-6-methoxy-4'-trifluoromethyl-biphenyl-3-yl]-acetic acid; (2'-{[Ethyl-(2-[1,2,4]triazol-1-yl-acetyl)-amino]-methyl}-6-methoxy-4'-trifluoromethyl-biphenyl-3-yl)-acetic acid; (2'-{[Ethyl-(2-pyrrolidin-1-yl-acetyl)-amino]-methyl}-6-methoxy-4'-trifluoromethyl-biphenyl-3-yl)-acetic acid; {2'-[3-(3,4-Dichloro-benzyl)-1-ethyl-ureidomethyl]-6-methoxy-4'-trifluoromethyl-biphenyl-3-yl}-acetic acid; {4'-Acetylamino-2'-[(benzyloxycarbonyl-ethyl-amino)-methyl]-6-methoxy-biphenyl-3-yl}-acetic acid; [2'-[(Benzyloxycarbonyl-ethyl-amino)-methyl]-4'-(4-chloro-benzoylamino)-6-methoxy-biphenyl-3-yl]-acetic acid; {2'-[(Benzyloxycarbonyl-ethyl-amino)-methyl]-4'-methanesulfonylamino-6-methoxy-biphenyl-3-yl}-acetic acid; [2'-[(Benzyloxycarbonyl-ethyl-amino)-methyl]-4'-(4-chloro-benzenesulfonylamino)-6-methoxy-biphenyl-3-yl]-acetic acid; [2'-(3-Benzyl-1-ethyl-ureidomethyl)-5-chloro-4'-trifluoromethyl-biphenyl-3-yl]-acetic acid; [2'-(3-Benzyl-1-ethyl-ureidomethyl)-5,4'-bis-trifluoromethyl-biphenyl-3-yl]-acetic acid; [2'-(3-Benzyl-1-ethyl-ureidomethyl)-5-fluoro-4'-trifluoromethyl-biphenyl-3-yl]-acetic acid; {2'-[(Ethyl-methoxycarbonyl-amino)-methyl]-5,4'-bis-trifluoromethyl-biphenyl-3-yl}-acetic acid; {5-Chloro-2'-[(ethyl-methoxycarbonyl-amino)-methyl]-4'-trifluoromethyl-biphenyl-3-yl}-acetic acid; {2'3-[3-(3,5-Dichloro-benzyl)-1-ethyl-ureidomethyl]-6-methoxy-4'-trifluoromethyl-biphenyl-3-yl}-acetic acid; (2'-{[Ethyl-(4-fluoro-benzyloxycarbonyl)-amino]-methyl}-6-methoxy-5'-trifluoromethyl-biphenyl-3-yl)-acetic acid; (2'-{[Ethyl-(4-fluoro-benzyloxycarbonyl)-amino]-methyl}-6-methoxy-5'-methyl-biphenyl-3-yl)-acetic acid; {2'-[(Cyclopropanecarbonyl-ethyl-amino)-methyl]-6-methoxy-5'-trifluoromethyl-biphenyl-3-yl}-acetic acid; {2'-[(Cyclopropanecarbonyl-ethyl-amino)-methyl]-6-methoxy-5'-methyl-biphenyl-3-yl}-acetic acid; [2'-(3-Benzyl-1-ethyl-ureidomethyl)-6-methoxy-5'-trifluoromethyl-biphenyl-3-yl]-acetic acid; [2'-(3-Benzyl-1-ethyl-ureidomethyl)-6-methoxy-5'-methyl-biphenyl-3-yl]-acetic acid; (2'-{[(4-Chloro-benzyloxycarbonyl)-ethyl-amino]-methyl}-6-methoxy-5'-trifluoromethyl-biphenyl-3-yl)-acetic acid; (2'-{[(4-Chloro-benzyloxycarbonyl)-ethyl-amino]-methyl}-6-methoxy-5'-methyl-biphenyl-3-yl)-acetic acid; {2'-[1-Ethyl-3-(4-fluoro-benzyl)-ureidomethyl]-6-methoxy-4'-trifluoromethyl-biphenyl-3-yl}1-acetic acid; {2'-[3-(3-Chloro-benzyl)-1-ethyl-ureidomethyl]-6-methoxy-4'-trifluoromethyl-biphenyl-3-yl}-acetic acid; {2'-[3-(3,5-Difluoro-benzyl)-1-ethyl-ureidomethyl]-6-methoxy-4'-trifluoromethyl-biphenyl-3-yl}-acetic acid; (2'-{3-[(R)-1-(4-Chloro-phenyl)-ethyl]-1-ethyl-ureidomethyl}-6-methoxy-4'-trifluoromethyl-biphenyl-3-yl)-acetic acid; (2'-{3-[(S)-1-(4-Chloro-phenyl)-ethyl]-1-ethyl-ureidomethyl}-6-methoxy-4'-trifluoromethyl-biphenyl-3-yl)-acetic acid; [2'-(1,3-Diethyl-ureidomethyl)-6-methoxy-4'-trifluoromethyl-biphenyl-3-yl]-acetic acid; [2'-(3-Cyclopropyl-1-ethyl-ureidomethyl)-6-methoxy-4'-trifluoromethyl-biphenyl-3-yl]-acetic acid; {2'-[(Benzyloxycarbonyl-ethyl-amino)-methyl]-4'-fluoro-6-methoxy-biphenyl-3-yl}-acetic acid; {2'-[(Acetyl-ethyl-amino)-methyl]-4'-fluoro-6-methoxy-biphenyl-3-yl}-acetic acid; {2'-[3-(4-Chloro-benzyl)-1-ethyl-ureidomethyl]-4'-fluoro-6-methoxy-biphenyl-3-yl}-acetic acid; {2'-[(Cyclopropanecarbonyl-ethyl-amino)-methyl]-4'-fluoro-6-methoxy-biphenyl-3-yl}-acetic acid; [2'-(3-Benzyl-1-ethyl-ureidomethyl)-4'-fluoro-6-methoxy-biphenyl-3-yl]-acetic acid; (5-Chloro-2'-{[(4-chloro-benzyloxycarbonyl)-ethyl-amino]-methyl}-4'-trifluoromethyl-biphenyl-3-yl)-acetic acid; (2'-{[(4-Chloro-benzyloxycarbonyl)-ethyl-amino]-methyl}-5,4'-bis-trifluoromethyl-biphenyl-3-yl)-acetic acid; (5-Chloro-2'-{[ethyl-(4-fluoro-benzyloxycarbonyl)-amino]-methyl}-4'-trifluoromethyl-biphenyl-3-yl)-acetic acid; (2'-{[Ethyl-(4-fluoro-benzyloxycarbonyl)-amino]-methyl}-5,4'-bis-trifluoromethyl-biphenyl-3-yl)-acetic acid; {5-Chloro-2'-[3-(4-chloro-benzyl)-1-ethyl-ureidomethyl]-4'-trifluoromethyl-biphenyl-3-yl}-acetic acid; {2'-[3-(4-Chloro-benzyl)-1-ethyl-ureidomethyl]-5,4'-bis-trifluoromethyl-biphenyl-3-yl}-acetic acid; (2'-[Ethyl-(4-fluoro-benzyloxycarbonyl)-amino]-methyl)-6,5'-dimethoxy-biphenyl-3-yl)-acetic acid; (2'-{[(4-Chloro-benzyloxycarbonyl)-ethyl-amino]-methyl}-6,5'-dimethoxy-biphenyl-3-yl)-acetic acid; {2'-[(Cyclopropanecarbonyl-ethyl-amino)-methyl]-6,5'-dimethoxy-biphenyl-3-yl}-acetic acid; [2'-(3-Benzyl-1-ethyl-ureidomethyl)-6,5'-dimethoxy-biphenyl-3-yl]-acetic acid; [2'-(1-Ethyl-3-pyridin-3-ylmethyl-ureidomethyl)-6-methoxy-4'-trifluoromethyl-biphenyl-3-yl]-acetic acid; [2'-(1-Ethyl-3-pyridin-4-ylmethyl-ureidomethyl)-6-methoxy-4'-trifluoromethyl-biphenyl-3-yl]-acetic acid; {2'-[3-(6-Chloro-pyridin-3-ylmethyl)-1-ethyl-ureidomethyl]-6-methoxy-4'-trifluoromethyl-biphenyl-3-yl}-acetic acid; [5-Chloro-2'-(1-ethyl-3-methyl-ureidomethyl)-4'-trifluoromethyl-biphenyl-3-yl]-acetic acid; [2'-(1-Ethyl-3-methyl-ureidomethyl)-5,4'-bis-trifluoromethyl-biphenyl-3-yl]-acetic acid; {2'-[(Benzoyl-ethyl-amino)-methyl]-5-chloro-4'-trifluoromethyl-biphenyl-3-yl}-acetic acid; {2'-[(Benzoyl-ethyl-amino)-methyl]-5,4'-bis-trifluoromethyl-biphenyl-3-yl}-acetic acid; {2'-[(Cyclobutanecarbonyl-ethyl-amino)-methyl]-6-methoxy-4'-trifluoromethyl-biphenyl-3-yl}acetic acid; {2'-[(Ethyl-phenylacetyl-amino)-methyl]-6-methoxy-4'-trifluoromethyl-biphenyl-3-yl}-acetic acid; (2'-{[Ethyl-(3-phenyl-propionyl)-amino]-methyl}-6-methoxy-4'-trifluoromethyl-biphenyl-3-yl)-acetic acid; (2'-{[Ethyl-(1-hydroxy-cyclopropanecarbonyl)-amino]-methyl}-6-methoxy-4'-trifluoromethyl-biphenyl-3-yl)-acetic acid; {2'-[(1-Ethyl-ureido)-methyl]-6-methoxy-4'-trifluoromethyl-biphenyl-3-yl}-acetic acid; 2-{2'-[(Acetyl-ethyl-amino)-methyl]-5-chloro-4'-trifluoromethyl-biphenyl-3-yl}-propionic acid; 2-{5-Chloro-2'-[(cyclopropanecarbonyl-ethyl-amino)-methyl]-4'-trifluoromethyl-biphenyl-3-yl}-propionic acid; 2-{2'-[(Acetyl-ethyl-amino)-methyl]-5,4'-bis-trifluoromethyl-biphenyl-3-yl}-propionic acid; 2-{2'-[(Cyclopropanecarbonyl-ethyl-amino)-methyl]-5,4'-bis-trifluoromethyl-biphenyl-3-yl}-propionic acid; {2'-[(Benzyloxycarbonyl-ethyl-amino)-methyl]-4'-methanesulfonyl-6-methoxy-biphenyl-3-yl}-acetic acid; [2'-[(Benzyloxycarbonyl-ethyl-amino)-methyl]-4'-(1-hydroxy-1-methyl-ethyl)-6-methoxy-biphenyl-3-yl]-acetic acid; 2-{2'-[(Cyclopropanecarbonyl-ethyl-amino)-methyl]-6-methoxy-4'-trifluoromethyl-biphenyl-3-yl}-propionic acid; {5-Chloro-2'-[(cyclopropanecarbonyl-ethyl-amino)-methyl]-5'-methoxy-biphenyl-3-yl}-acetic acid; [2'-(3-Benzyl-1-ethyl-ureidomethyl)-5-chloro-5'-methoxy-biphenyl-3-yl]-acetic acid; [2'-(3-Benzyl-1-ethyl-ureidomethyl)-6-hydroxy-4'-trifluoromethyl-biphenyl-3-yl]-acetic acid; [5-Chloro-2'-({[2-(4-chloro-phenoxy)-acetyl]-ethyl-amino}-methyl)-5'-methoxy-biphenyl-3-yl]-acetic acid; 2-[2'-(3-Benzyl-1-ethyl-ureidomethyl)-6-methoxy-4'-trifluoromethyl-biphenyl-3-yl]-propionic acid; 2-[2'-(3-Benzyl-1-ethyl-ureidomethyl)-5-chloro-4'-trifluoromethyl-biphenyl-3-yl]-propionic acid; (R)-2-{2'-[(Cyclopropanecarbonyl-ethyl-amino)-methyl]-6-methoxy-4'-trifluoromethyl-biphenyl-3-yl}-propionic acid; (S)-2-{2'-[(Cyclopropanecarbonyl-ethyl-amino)-methyl]-6-methoxy-4'-trifluoromethyl-biphenyl-3-yl}-propionic acid; 2-[(Benzyloxycarbonyl-ethyl-amino)-methyl]-5'-carboxymethyl-2'-methoxy-biphenyl-4-carboxylic acid; [2'-[(Cyclopropanecarbonyl-ethyl-amino)-methyl]-4'-(6-ethoxy-pyridin-3-yl)-6-methoxy-biphenyl-3-yl]-acetic acid; 2-[2'-(3-Benzyl-1-ethyl-ureidomethyl)-4'-(6-ethoxy-pyridin-3-yl)-6-methoxy-biphenyl-3-yl]-acetic acid; [2'-({[2-(4-Chloro-phenoxy)-acetyl]-ethyl-amino}-methyl)-4'-(6-ethoxy-pyridin-3-yl)-6-methoxy-biphenyl-3-yl]-acetic acid; {2'-[(Cyclopropanecarbonyl-ethyl-amino)-methyl]-6-methoxy-4'-quinolin-7-yl-biphenyl-3-yl}-acetic acid; [2'-(3-Benzyl-1-ethyl-ureidomethyl)-6-methoxy-4'-quinolin-7-yl-biphenyl-3-yl]-acetic acid; [2'-({[2-(4-Chloro-phenoxy)-acetyl]-ethyl-amino}-methyl)-6-methoxy-4'-quinolin-7-yl-biphenyl-3-yl]-acetic acid; [2'-[(Cyclopropanecarbonyl-ethyl-amino)-methyl]-6-methoxy-4'-(1-methyl-1H-pyrazol-4-yl)-biphenyl-3-yl]-acetic acid; {2'-(3-Benzyl-1-ethyl-ureidomethyl)-6-methoxy-4'-(1-methyl-1H-pyrazol-4-yl)-biphenyl-3-yl}-acetic acid; 2-{2'-[(Cyclopropanecarbonyl-ethyl-amino)-methyl]-5,4'-bis-trifluoromethyl-biphenyl-3-yl}-2-methyl-propionic acid; (R)-2-[2'-[(Cyclopropanecarbonyl-ethyl-amino)-methyl]-5,4'-bis-trifluoromethyl-biphenyl-3-yl]-propionic acid; (S)-2-{2'-[(Cyclopropanecarbonyl-ethyl-amino)-methyl]-5,4'-bis-trifluoromethyl-biphenyl-3-yl}-propionic acid; (R)-2-[2'-(3-Benzyl-1-ethyl-ureidomethyl)-5,4'-bis-trifluoromethyl-biphenyl-3-yl]-propionic acid; (S)-2-[2'-(3-Benzyl-1-ethyl-ureidomethyl)-5,4'-bis-trifluoromethyl-biphenyl-3-yl]-propionic acid; {2'-[(Cyclopropanecarbonyl-ethyl-amino)-methyl]-6-methoxy-4'-methylsulfanyl-biphenyl-3-yl}-acetic acid; {5-Chloro-2'-[(cyclopropanecarbonyl-ethyl-amino)-methyl]-4'-methylsulfanyl-biphenyl-3-yl}-acetic acid; 2-[2'-(3-Cyclopropyl-1-ethyl-ureidomethyl)-6-methoxy-4'-trifluoromethyl-biphenyl-3-yl]-propionic acid; {2'-[(Cyclopropanecarbonyl-ethyl-amino)-methyl]-4'-trifluoromethyl-biphenyl-3-yl}-acetic acid; (2'-{[(2,2-Dimethyl-propionyl)-ethyl-amino]-methyl}-6-methoxy-4'-trifluoromethyl-biphenyl-3-yl)-acetic acid; {2'-[(Ethyl-isobutyryl-amino)-methyl]-6-methoxy-4'-trifluoromethyl-biphenyl-3-yl}-acetic acid; {4'-Bromo-2'-[(cyclopropanecarbonyl-ethyl-amino)-methyl]-6-methoxy-biphenyl-3-yl}-acetic acid; [2'-[(Cyclopropanecarbonyl-ethyl-amino)-methyl]-4'-(5-fluoro-pyridin-2-yl)-6-methoxy-biphenyl-3-yl]-acetic acid; [2'-[(Cyclopropanecarbonyl-ethyl-amino)-methyl]-6-methoxy-4'-(5-methoxy-pyrimidin-2-yl)-biphenyl-3-yl]-acetic acid; {2'-[1-Ethyl-3-(4-hydroxy-benzyl)-ureidomethyl]-6-methoxy-4'-trifluoromethyl-biphenyl-3-yl}-acetic acid; {2'-[1-Ethyl-3-(2-hydroxy-benzyl)-ureidomethyl]-6-methoxy-4'-trifluoromethyl-biphenyl-3-yl}-acetic acid; [2'-[(Benzoyl-ethyl-amino)-methyl]-4'-(6-ethoxy-pyridin-3-yl)-6-methoxy-biphenyl-3-yl]-acetic acid; {4'-(6-Ethoxy-pyridin-3-yl)-2'-[(ethyl-phenylacetyl-amino)-methyl]-6-methoxy-biphenyl-3-yl}-acetic acid; (4'-(6-Ethoxy-pyridin-3-yl)-2'-{[ethyl-(3-phenyl-propionyl)-amino]-methyl}-6-methoxy-biphenyl-3-yl)-acetic acid; {2'-[1-Ethyl-3-(3-hydroxy-benzyl)-ureidomethyl]-6-methoxy-4'-trifluoromethyl-biphenyl-3-yl}-acetic acid; N-Ethyl-N-[5'-(2-methanesulfonylamino-2-oxo-ethyl)-2'-methoxy-4-trifluoromethyl-biphenyl-2-ylmethyl]-acetamide; N-Ethyl-N-[5'-(2-hydroxy-2-methyl-propyl)-2'-methoxy-4-trifluoromethyl-biphenyl-2-ylmethyl]-acetamide; Cyclopropanecarboxylic acid (5'-cyanomethyl-2'-methoxy-4-trifluoromethyl-biphenyl-2-ylmethyl)-ethyl-amide; (5'-Cyanomethyl-2'-methoxy-4-trifluoromethyl-biphenyl-2-ylmethyl)-ethyl-carbamic acid benzyl ester; Ethyl-[2'-methoxy-5'-(2H-tetrazol-5-ylmethyl)-4-trifluoromethyl-biphenyl-2-ylmethyl]-carbamic acid benzyl ester; (5'-Carbamoylmethyl-2'-methoxy-4-trifluoromethyl-biphenyl-2-ylmethyl)-ethyl-carbamic acid benzyl ester; Cyclopropanecarboxylic acid ethyl-[2'-methoxy-5'-(2H-tetrazol-5-ylmethyl)-4-trifluoromethyl-biphenyl-2-ylmethyl]-amide; Cyclopropanecarboxylic acid (5'-carbamoylmethyl-T-methoxy-4-trifluoromethyl-biphenyl-2-ylmethyl)-ethyl-amide; [2'-(3-Benzyl-1-ethyl-ureidomethyl)-6-hydroxy-4'-trifluoromethyl-biphenyl-3-yl]-acetic acid ethyl ester; (R)-2-[2'-(3-Benzyl-1-ethyl-ureidomethyl)-5,4'-bis-trifluoromethyl-biphenyl-3-yl]-N-((R)-1-methyl-2-phenyl-ethyl)-propionamide; (S)-2-[2'-(3-Benzyl-1-ethyl-ureidomethyl)-5,4'-bis-trifluoromethyl-biphenyl-3-yl]-N—((R)-1-methyl-2-phenyl-ethyl)-propionamide; Cyclopropanecarboxylic acid ethyl-{2'-methoxy-5'-[(R)-1-methyl-2-((4R,5S)-4-methyl-2-oxo-5-phenyl-oxazolidin-3-yl)-2-oxo-ethyl]-4-trifluoromethyl-biphenyl-2-ylmethyl}-amide; Cyclopropanecarboxylic acid ethyl-{2'-methoxy-5'-[(S)-1-methyl-2-((4R,5S)-4-methyl-2-oxo-5-phenyl-oxazolidin-3-yl)-2-oxo-ethyl]-4-trifluoromethyl-biphenyl-2-ylmethyl}-amide; 2-[(Benzyloxycarbonyl-ethyl-amino)-methyl]-5'-ethoxycarbonylmethyl-2'-methoxy-biphenyl-4-carboxylic acid; Cyclopropanecarboxylic acid ethyl-{3'-[(R)-1-methyl-2-((4R,5S)-4-methyl-2-oxo-5-phenyl-oxazolidin-3-yl)-2-oxo-ethyl]-4,5'-bis-trifluoromethyl-biphenyl-2-ylmethyl}-amide; or Cyclopropanecarboxylic acid ethyl-{3'-[(S)-1-methyl-2-((4R,5S)-4-methyl-2-oxo-5-phenyl-oxazolidin-3-yl)-2-oxo-ethyl]-4,5'-bis-trifluoromethyl-biphenyl-2-ylmethyl}-amide; or a pharmaceutically acceptable salt thereof.

10. The method of claim 1, wherein the compound has the following structure:

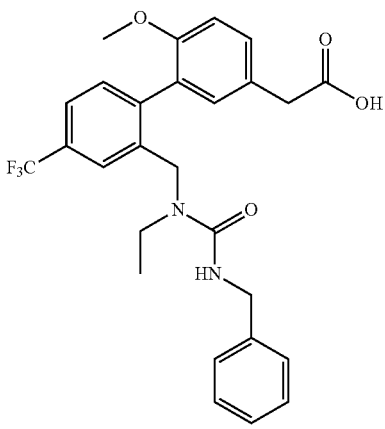 [SMILES: CCN(Cc1cc(C(F)(F)F)ccc1-c1cc(CC(=O)O)ccc1OC)C(=O)NCc1ccccc1]

or is a pharmaceutically acceptable salt thereof.

11. The method of claim 10, wherein the pharmaceutically acceptable salt is a sodium salt.

12. The method of claim 1, wherein the compound has the following structure:

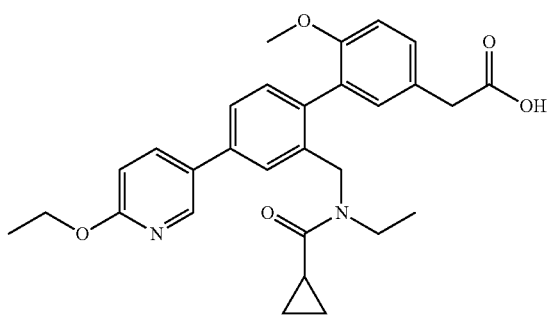 [SMILES: CCOc1ccc(-c2ccc(-c3cc(CC(=O)O)ccc3OC)c(CN(CC)C(=O)C3CC3)c2)cn1]

or is a pharmaceutically acceptable salt thereof.

13. The method of claim 12, wherein the pharmaceutically acceptable salt is a sodium salt.

14. The method of claim 1, 9, 10 or 12, wherein the mammal is a human and the chronic obstructive pulmonary disease includes chronic bronchitis, emphysema, or chronic bronchitis and emphysema.

15. The method of claim 1, wherein the mammal is a human and the therapeutically effective amount of the compound, or a pharmaceutically acceptable salt thereof, is systemically administered to the human.

16. The method of claim 1, 9, 10 or 12, wherein the mammal is a human and the therapeutically effective amount of the compound, or a pharmaceutically acceptable salt thereof, is orally administered to the human.

17. The method of claim 16, wherein the mammal is a human and the therapeutically effective amount of the compound, or a pharmaceutically acceptable salt thereof, is orally administered to the human in the form of a tablet, a pill, a capsule, or a liquid.

18. The method of claim 1, wherein the mammal is a human and the therapeutically effective amount of the compound, or a pharmaceutically acceptable salt thereof, is administered to the human by inhalation or by nasal administration.

19. The method of claim 1, 9, 10 or 12, wherein the mammal is a human and the method comprises preventing increased mucosal secretion in the human.

20. The method of claim 1, 9, 10 or 12, wherein the mammal is a human and the method comprises preventing or treating eosinophil and/or basophil and/or dendritic cell and/or neutrophil and/or monocyte and/or T-cell recruitment in the human.

21. The method of claim 1, 9, 10 or 12, wherein the method further comprises administering to the mammal a second therapeutic agent selected from 5-lipoxygenase-activating protein inhibitors, 5-lipoxygenase inhibitors, CYSLTR1 antagonists, CYSLTR2 antagonists, BLT1 antagonists, BLT2 antagonists, thromboxane antagonists, DP1 receptor antagonists, DP1 receptor, agonists, IP receptor agonists, anti-IgE, chemokine receptor antagonists, IL5 antibody, bronchodilators, theophylline, leukotriene receptor antagonists, leukotriene formation inhibitors, decongestants, antihistamines, mucolytics, corticosteroids, glucocorticoids, anticholinergics, antitussives, analgesics, expectorants, and β-2 agonists.

* * * * *